US012611418B2

(12) United States Patent
Londesbrough et al.

(10) Patent No.: US 12,611,418 B2
(45) Date of Patent: *Apr. 28, 2026

(54) METHODS FOR TREATING ANXIETY DISORDERS, HEADACHE DISORDERS, AND EATING DISORDERS WITH PSILOCYBIN

(71) Applicant: Compass Pathfinder Limited, Altrincham (GB)

(72) Inventors: Derek John Londesbrough, Hartlepool (GB); Christopher Brown, Gateshead (GB); Julian Scott Northen, South Shields (GB); Gillian Moore, Sedgefield (GB); David E. Nichols, Chapel Hill, NC (US); Hans Åke Eriksson, Altrincham (GB); George Goldsmith, Altrincham (GB); Ekaterina Malievskaia, Altrincham (GB); Manon Cecile Elisabeth Veraart, Altrincham (GB); Lars Christian Wilde, Altrincham (GB)

(73) Assignee: Compass Pathfinder Limited, Altrincham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/296,581

(22) Filed: Aug. 11, 2025

(65) Prior Publication Data

US 2025/0367223 A1 Dec. 4, 2025

Related U.S. Application Data

(63) Continuation of application No. 17/604,619, filed as application No. PCT/IB2020/053687 on Apr. 17, 2020, now Pat. No. 12,433,904.

(60) Provisional application No. 62/946,159, filed on Dec. 10, 2019, provisional application No. 62/893,611, filed on Aug. 29, 2019, provisional application No. 62/893,110, filed on Aug. 28, 2019, provisional application No. 62/835,485, filed on Apr. 17, 2019, provisional application No. 62/835,484, filed on Apr. 17, 2019, provisional application No. 62/835,482, filed on Apr. 17, 2019, provisional application No. 62/835,481, filed on Apr. 17, 2019, provisional application No. 62/835,480, filed on Apr. 17, 2019, provisional application No. 62/835,479, filed on Apr. 17, 2019, provisional application No. 62/835,478, filed on Apr. 17, 2019, provisional application No. 62/835,477, filed on Apr. 17, 2019, provisional application No. 62/835,476, filed on Apr. 17, 2019, provisional application No. 62/835,474, filed on Apr. 17, 2019, provisional application No. 62/835,472, filed on Apr. 17, 2019, provisional application No. 62/835,465, filed on Apr. 17, 2019, provisional application No. 62/835,464, filed on Apr. 17, 2019, (Continued)

(51) Int. Cl.

| | |
|---|---|
| A61K 31/675 | (2006.01) |
| A61K 9/00 | (2006.01) |
| A61K 9/20 | (2006.01) |
| A61K 9/48 | (2006.01) |
| A61K 31/661 | (2006.01) |
| A61P 25/00 | (2006.01) |
| A61P 25/04 | (2006.01) |
| A61P 25/08 | (2006.01) |
| A61P 25/16 | (2006.01) |
| A61P 25/20 | (2006.01) |
| A61P 25/22 | (2006.01) |
| A61P 25/24 | (2006.01) |
| A61P 25/28 | (2006.01) |
| C07F 9/572 | (2006.01) |

(52) U.S. Cl.
CPC .......... *A61K 31/675* (2013.01); *A61K 9/0053* (2013.01); *A61K 9/20* (2013.01); *A61K 9/48* (2013.01); *A61K 31/661* (2013.01); *A61P 25/00* (2018.01); *A61P 25/04* (2018.01); *A61P 25/08* (2018.01); *A61P 25/16* (2018.01); *A61P 25/20* (2018.01); *A61P 25/22* (2018.01); *A61P 25/24* (2018.01); *A61P 25/28* (2018.01); *C07F 9/5728* (2013.01); *C07B 2200/13* (2013.01)

(58) Field of Classification Search
CPC .................................................. A61K 31/675
See application file for complete search history.

(56) References Cited

U.S. PATENT DOCUMENTS

| | | | |
|---|---|---|---|
| 3,075,992 A | 1/1963 | Albert et al. | |
| 3,183,172 A | 5/1965 | Roger et al. | |

(Continued)

FOREIGN PATENT DOCUMENTS

| | | |
|---|---|---|
| AU | 2016208412 A1 | 8/2016 |
| AU | 2018203524 A1 | 6/2018 |

(Continued)

OTHER PUBLICATIONS

Aaron, M. (2017) "Open Your Mind: Merging Psychedelic Therapy with Sex Therapy" Psychology Today [online]. Retrieved from: https://www.psychologytoday.com/us/blog/standard-deviations/201710/open-your-mind-merging-psychedelic-therapy-sex-therapy, retrieved Oct. 24, 2017, 4 pages.

(Continued)

*Primary Examiner* — Yong S. Chong
(74) *Attorney, Agent, or Firm* — COOLEY LLP

(57) ABSTRACT

The disclosure provides methods for treating a subject in need thereof comprising administering to the subject a therapeutically-effective dose of psilocybin. The methods described herein may be used to treat a variety of diseases, disorders, and conditions. For example, the methods may be used to treat anxiety disorders, eating disorders, and headache disorders.

16 Claims, 65 Drawing Sheets

Related U.S. Application Data provisional application No. 62/835,460, filed on Apr. 17, 2019, provisional application No. 62/835,458, filed on Apr. 17, 2019, provisional application No. 62/835,450, filed on Apr. 17, 2019, provisional application No. 62/835,449, filed on Apr. 17, 2019.

(56) References Cited

U.S. PATENT DOCUMENTS

| | | | |
|---|---|---|---|
| 3,192,111 A | 6/1965 | Albert et al. |
| 4,499,096 A | 2/1985 | Lotsof |
| 4,587,243 A | 5/1986 | Lotsof |
| 4,721,612 A | 1/1988 | Janoff et al. |
| 5,145,677 A | 9/1992 | Von Eichborn et al. |
| 5,264,443 A | 11/1993 | Jarreau et al. |
| 5,468,486 A | 11/1995 | Reddick et al. |
| 5,482,706 A | 1/1996 | Igari et al. |
| 5,545,617 A | 8/1996 | Dartt et al. |
| 5,573,776 A | 11/1996 | Harrison et al. |
| 5,626,863 A | 5/1997 | Hubbell et al. |
| 5,629,307 A | 5/1997 | Olney |
| 5,643,586 A | 7/1997 | Perricone |
| 5,696,125 A | 12/1997 | Altura et al. |
| 5,725,871 A | 3/1998 | Illum |
| 5,736,161 A | 4/1998 | Garces et al. |
| 5,785,989 A | 7/1998 | Stanley et al. |
| 5,804,592 A | 9/1998 | Volicer |
| 5,827,819 A | 10/1998 | Yatvin et al. |
| 5,871,710 A | 2/1999 | Bogdanov et al. |
| 5,874,477 A | 2/1999 | McConnell et al. |
| 5,879,690 A | 3/1999 | Perricone |
| 5,902,815 A | 5/1999 | Olney et al. |
| 5,914,129 A | 6/1999 | Mauskop |
| 5,922,341 A | 7/1999 | Smith et al. |
| 5,925,634 A | 7/1999 | Olney |
| 5,935,925 A | 8/1999 | Weinshank et al. |
| 5,942,241 A | 8/1999 | Chasin et al. |
| 5,942,503 A | 8/1999 | Jung et al. |
| 5,958,919 A | 9/1999 | Olney et al. |
| 6,037,346 A | 3/2000 | Doherty, Jr. et al. |
| 6,121,264 A | 9/2000 | Sakamoto et al. |
| 6,126,924 A | 10/2000 | Scales-Medeiros et al. |
| 6,204,245 B1 | 3/2001 | Siegel et al. |
| 6,217,904 B1 | 4/2001 | Midha et al. |
| 6,228,864 B1 | 5/2001 | Smith et al. |
| 6,294,550 B1 | 9/2001 | Place et al. |
| 6,323,236 B2 | 11/2001 | McElroy |
| 6,348,456 B1 | 2/2002 | Mash et al. |
| 6,380,176 B2 | 4/2002 | Takahashi et al. |
| 6,383,471 B1 | 5/2002 | Chen et al. |
| 6,444,665 B1 | 9/2002 | Helton et al. |
| 6,479,074 B2 | 11/2002 | Murdock et al. |
| 6,489,341 B1 | 12/2002 | Jerussi |
| 6,495,154 B1 | 12/2002 | Tam et al. |
| 6,495,498 B2 | 12/2002 | Niemiec et al. |
| 6,500,459 B1 | 12/2002 | Chhabra et al. |
| 6,541,043 B2 | 4/2003 | Lang |
| 6,544,998 B2 | 4/2003 | Mylari |
| 6,592,901 B2 | 7/2003 | Durig et al. |
| 6,604,698 B2 | 8/2003 | Verhoff et al. |
| 6,635,279 B2 | 10/2003 | Kolter et al. |
| 6,693,135 B2 | 2/2004 | Yeager et al. |
| 6,720,348 B2 | 4/2004 | Mylari |
| 6,814,976 B1 | 11/2004 | Hille et al. |
| 6,893,662 B2 | 5/2005 | Dittmar et al. |
| 6,913,768 B2 | 7/2005 | Couch et al. |
| 6,962,717 B1 | 11/2005 | Huber et al. |
| 6,977,070 B2 | 12/2005 | Dugger, III |
| 6,979,447 B2 | 12/2005 | Jameson et al. |
| 7,045,543 B2 | 5/2006 | Yatvin et al. |
| 7,084,156 B2 | 8/2006 | DeVita et al. |
| 7,186,293 B2 | 3/2007 | Cunningham |
| 7,220,737 B1 | 5/2007 | Mash |
| 7,229,784 B2 | 6/2007 | Holtzman et al. |
| 7,241,797 B2 | 7/2007 | Horseman |
| 7,294,649 B2 | 11/2007 | Hui et al. |
| 7,384,651 B2 | 6/2008 | Hille et al. |
| 7,517,900 B2 | 4/2009 | Pendri et al. |
| 7,638,651 B2 | 12/2009 | Gant et al. |
| 7,666,877 B2 | 2/2010 | Baenteli et al. |
| 7,670,627 B2 | 3/2010 | Shefer et al. |
| 7,671,030 B2 | 3/2010 | Mickle et al. |
| 7,678,770 B2 | 3/2010 | Mickle et al. |
| 7,754,710 B2 | 7/2010 | Mash |
| 7,772,222 B2 | 8/2010 | Mickle |
| 7,799,337 B2 | 9/2010 | Levin |
| 7,833,546 B2 | 11/2010 | Petereit et al. |
| 7,838,034 B2 | 11/2010 | Kugelmann et al. |
| 7,981,441 B2 | 7/2011 | Pantelidis et al. |
| 8,008,285 B2 | 8/2011 | Roberts et al. |
| 8,067,028 B2 | 11/2011 | Bennett |
| 8,101,661 B2 | 1/2012 | Mickle |
| 8,263,561 B2 | 9/2012 | Saeed |
| 8,318,210 B2 | 11/2012 | Tengler et al. |
| 8,318,813 B2 | 11/2012 | Sanfilippo |
| 8,329,663 B2 | 12/2012 | Griffin |
| 8,362,007 B1 | 1/2013 | Mash et al. |
| 8,445,016 B2 | 5/2013 | Santerre et al. |
| 8,512,751 B2 | 8/2013 | Rariy et al. |
| 8,574,604 B2 | 11/2013 | Esfand et al. |
| 8,617,607 B2 | 12/2013 | Moses et al. |
| 8,673,351 B2 | 3/2014 | Andrysek et al. |
| 8,742,096 B2 | 6/2014 | Moriarty et al. |
| 8,747,832 B2 | 6/2014 | Uhrich et al. |
| 8,754,119 B2 | 6/2014 | Scheller et al. |
| 8,784,835 B2 | 7/2014 | Austin |
| 8,785,500 B2 | 7/2014 | Charney et al. |
| 8,846,100 B2 | 9/2014 | Shojaei et al. |
| 8,852,638 B2 | 10/2014 | Luk et al. |
| 8,859,579 B2 | 10/2014 | Sewell |
| 8,859,622 B1 | 10/2014 | Bristol et al. |
| 8,906,413 B2 | 12/2014 | Chang et al. |
| 8,906,847 B2 | 12/2014 | Cleemann et al. |
| 8,921,393 B2 | 12/2014 | Weiner et al. |
| 8,962,697 B2 | 2/2015 | Laronde et al. |
| 8,980,308 B2 | 3/2015 | Horstmann et al. |
| 8,980,880 B1 | 3/2015 | King et al. |
| 9,737,759 B2 | 8/2017 | Mrowka et al. |
| 9,878,138 B2 | 1/2018 | Altschul et al. |
| 10,058,253 B2 | 8/2018 | Parton et al. |
| 10,058,584 B2 | 8/2018 | Young et al. |
| 10,064,856 B2 | 9/2018 | Bosse et al. |
| 10,085,994 B2 | 10/2018 | Lozinsky et al. |
| 10,148,534 B2 | 12/2018 | Lazarescu et al. |
| 10,183,001 B1 | 1/2019 | King et al. |
| 10,231,651 B2 | 3/2019 | Deng et al. |
| 10,254,298 B1 | 4/2019 | Koh |
| 10,519,175 B2 | 12/2019 | Londesbrough et al. |
| 10,596,378 B2 | 3/2020 | Rustick |
| 10,729,706 B2 | 8/2020 | Küçüksen et al. |
| 10,738,268 B2 | 8/2020 | Leo |
| 10,947,257 B2 | 3/2021 | Londesbrough et al. |
| 10,954,259 B1 | 3/2021 | Londesbrough et al. |
| 11,149,044 B2 | 10/2021 | Londesbrough et al. |
| 11,180,517 B2 | 11/2021 | Londesbrough et al. |
| 11,447,510 B2 | 9/2022 | Londesbrough et al. |
| 11,505,564 B2 | 11/2022 | Londesbrough et al. |
| 11,564,935 B2 | 1/2023 | Londesbrough et al. |
| 11,629,159 B2 | 4/2023 | Londesbrough et al. |
| 11,738,035 B2 | 8/2023 | Londesbrough et al. |
| 11,851,451 B2 | 12/2023 | Londesbrough et al. |
| 11,865,126 B2 | 1/2024 | Londesbrough et al. |
| 11,939,346 B2 | 3/2024 | Londesbrough et al. |
| 12,312,375 B2 | 5/2025 | Londesbrough et al. |
| 12,377,112 B2 | 8/2025 | Londesbrough et al. |
| 2001/0004644 A1 | 6/2001 | Levin |
| 2002/0015730 A1 | 2/2002 | Hoffmann et al. |
| 2002/0019421 A1 | 2/2002 | Biberman |
| 2002/0044962 A1 | 4/2002 | Cherukuri et al. |
| 2002/0137785 A1 | 9/2002 | Kindness et al. |
| 2003/0013689 A1 | 1/2003 | Helton et al. |
| 2003/0049308 A1 | 3/2003 | Theobald et al. |
| 2003/0051728 A1 | 3/2003 | Lloyd et al. |
| 2003/0082225 A1 | 5/2003 | Mason |

(56) References Cited

U.S. PATENT DOCUMENTS

| | | |
|---|---|---|
| 2003/0096831 A1 | 5/2003 | Stone et al. |
| 2003/0099711 A1 | 5/2003 | Meadows et al. |
| 2003/0114512 A1 | 6/2003 | Collier et al. |
| 2003/0119884 A1 | 6/2003 | Epstein et al. |
| 2003/0135202 A1 | 7/2003 | Harper et al. |
| 2003/0144220 A1 | 7/2003 | Obach |
| 2003/0153552 A1 | 8/2003 | Mash et al. |
| 2003/0171435 A1 | 9/2003 | Pouletty et al. |
| 2003/0180357 A1 | 9/2003 | Martino et al. |
| 2003/0203912 A1 | 10/2003 | May et al. |
| 2003/0224057 A1 | 12/2003 | Martin-Letellier et al. |
| 2003/0235617 A1 | 12/2003 | Martino et al. |
| 2004/0006043 A1 | 1/2004 | Margalit et al. |
| 2004/0023952 A1 | 2/2004 | Leventhal |
| 2004/0024038 A1 | 2/2004 | Ebert et al. |
| 2004/0029860 A1 | 2/2004 | Gil-Ad et al. |
| 2004/0077540 A1 | 4/2004 | Quay |
| 2004/0132780 A1 | 7/2004 | Allen et al. |
| 2004/0186155 A1 | 9/2004 | Dayno et al. |
| 2004/0214215 A1 | 10/2004 | Yu et al. |
| 2004/0224942 A1 | 11/2004 | Weiner et al. |
| 2005/0009815 A1 | 1/2005 | DeVita et al. |
| 2005/0014786 A1 | 1/2005 | Sun et al. |
| 2005/0026842 A1 | 2/2005 | Simon |
| 2005/0070501 A1 | 3/2005 | Neurath et al. |
| 2005/0096396 A1 | 5/2005 | Davis et al. |
| 2005/0106220 A1 | 5/2005 | Inagawa et al. |
| 2005/0148673 A1 | 7/2005 | Harbut et al. |
| 2005/0176790 A1 | 8/2005 | Bartholomaus et al. |
| 2005/0203011 A1 | 9/2005 | Ron |
| 2005/0209218 A1 | 9/2005 | Meyerson et al. |
| 2005/0215521 A1 | 9/2005 | Lalji et al. |
| 2005/0215571 A1 | 9/2005 | Romano |
| 2005/0222270 A1 | 10/2005 | Olney et al. |
| 2005/0233010 A1 | 10/2005 | Satow |
| 2005/0245460 A1 | 11/2005 | Meyerson et al. |
| 2005/0245617 A1 | 11/2005 | Meyerson et al. |
| 2005/0255091 A1 | 11/2005 | Loomis |
| 2005/0260258 A1 | 11/2005 | Ficht et al. |
| 2005/0261278 A1 | 11/2005 | Weiner et al. |
| 2005/0265955 A1 | 12/2005 | Raman et al. |
| 2005/0288375 A1 | 12/2005 | Hobden et al. |
| 2006/0019963 A1 | 1/2006 | Barnette et al. |
| 2006/0025387 A1 | 2/2006 | Hochman |
| 2006/0030625 A1 | 2/2006 | Hart et al. |
| 2006/0034872 A1 | 2/2006 | Woolf |
| 2006/0045865 A1 | 3/2006 | Jacob et al. |
| 2006/0051408 A1 | 3/2006 | Parente Duena et al. |
| 2006/0067937 A1 | 3/2006 | Karumanchi et al. |
| 2006/0093679 A1 | 5/2006 | Mayer et al. |
| 2006/0110327 A1 | 5/2006 | Emigh et al. |
| 2006/0135403 A1 | 6/2006 | Gervais et al. |
| 2006/0183744 A1 | 8/2006 | Rohrer et al. |
| 2006/0229293 A1 | 10/2006 | Lotsof |
| 2006/0240014 A1 | 10/2006 | Sukhatme |
| 2006/0240043 A1 | 10/2006 | Meyerson et al. |
| 2006/0241172 A1 | 10/2006 | Zhou et al. |
| 2006/0264508 A1 | 11/2006 | Stone |
| 2006/0270592 A1 | 11/2006 | Ousler et al. |
| 2007/0053954 A1 | 3/2007 | Rowe et al. |
| 2007/0059367 A1 | 3/2007 | Cherukuri |
| 2007/0065463 A1 | 3/2007 | Aung-Din |
| 2007/0066996 A1 | 3/2007 | Katzman et al. |
| 2007/0092586 A1 | 4/2007 | Cutler |
| 2007/0099977 A1 | 5/2007 | Nudelman et al. |
| 2007/0100000 A1 | 5/2007 | Epstein et al. |
| 2007/0190130 A1 | 8/2007 | Mark et al. |
| 2007/0190142 A1 | 8/2007 | Breitenbach et al. |
| 2007/0203216 A1 | 8/2007 | Ebert et al. |
| 2007/0207222 A1 | 9/2007 | Yu et al. |
| 2007/0213394 A1 | 9/2007 | Beguin et al. |
| 2008/0015181 A1 | 1/2008 | Roberts et al. |
| 2008/0026014 A1 | 1/2008 | Michel |
| 2008/0026189 A1 | 1/2008 | Lin et al. |
| 2008/0066741 A1 | 3/2008 | LeMahieu et al. |
| 2008/0075789 A1 | 3/2008 | Vawter et al. |
| 2008/0103127 A1 | 5/2008 | Haas |
| 2008/0103165 A1 | 5/2008 | Barlow et al. |
| 2008/0103179 A1 | 5/2008 | Tam et al. |
| 2008/0103199 A1 | 5/2008 | Haas |
| 2008/0193540 A1 | 8/2008 | Soula et al. |
| 2008/0207600 A1 | 8/2008 | Goldstein et al. |
| 2008/0226715 A1 | 9/2008 | Cha et al. |
| 2008/0233201 A1 | 9/2008 | Royere et al. |
| 2008/0241255 A1 | 10/2008 | Rose et al. |
| 2008/0255096 A1 | 10/2008 | Knipper-Breer et al. |
| 2008/0260844 A1 | 10/2008 | Soula et al. |
| 2009/0036468 A1 | 2/2009 | Samoriski et al. |
| 2009/0041838 A1 | 2/2009 | Guimberteau et al. |
| 2009/0069308 A1 | 3/2009 | Deregnaucourt et al. |
| 2009/0105222 A1 | 4/2009 | Kranzler et al. |
| 2009/0143435 A1 | 6/2009 | Ebert et al. |
| 2009/0156581 A1 | 6/2009 | Dillon et al. |
| 2009/0169566 A1 | 7/2009 | Rawlin et al. |
| 2009/0176792 A1 | 7/2009 | Gant et al. |
| 2009/0186099 A1 | 7/2009 | Dugger, III |
| 2009/0198145 A1 | 8/2009 | Chow |
| 2009/0232898 A1 | 9/2009 | Pettersson et al. |
| 2009/0252786 A1 | 10/2009 | Hanz |
| 2009/0259039 A1 | 10/2009 | Bristol et al. |
| 2009/0285916 A1 | 11/2009 | Haritou |
| 2009/0291137 A1 | 11/2009 | Guimberteau et al. |
| 2009/0298814 A1 | 12/2009 | Nudelman et al. |
| 2010/0016280 A1 | 1/2010 | Nichols et al. |
| 2010/0098722 A1 | 4/2010 | Bachmann et al. |
| 2010/0152108 A1 | 6/2010 | Hung et al. |
| 2010/0166889 A1 | 7/2010 | Sanfilippo |
| 2010/0179221 A1 | 7/2010 | Nagel et al. |
| 2010/0189818 A1 | 7/2010 | Tsai |
| 2010/0216964 A1 | 8/2010 | Zech et al. |
| 2010/0255094 A1 | 10/2010 | Jackson et al. |
| 2010/0266701 A1 | 10/2010 | Guimberteau et al. |
| 2010/0303903 A1 | 12/2010 | Hackett |
| 2011/0038915 A1 | 2/2011 | Gonzalez |
| 2011/0053859 A1 | 3/2011 | Deadwyler et al. |
| 2011/0077239 A1 | 3/2011 | Knipper et al. |
| 2011/0091508 A1 | 4/2011 | Esfand et al. |
| 2011/0111029 A1 | 5/2011 | Schmitz et al. |
| 2011/0118189 A1 | 5/2011 | Farr et al. |
| 2011/0144209 A1 | 6/2011 | Zachar |
| 2011/0207718 A1 | 8/2011 | Bird |
| 2011/0217289 A1 | 9/2011 | Kolter et al. |
| 2011/0245261 A1 | 10/2011 | Lagarde et al. |
| 2011/0274634 A1 | 11/2011 | Rieth et al. |
| 2011/0306596 A1 | 12/2011 | Rao et al. |
| 2012/0058125 A1 | 3/2012 | Strittmatter et al. |
| 2012/0059066 A1 | 3/2012 | Bartholomäus et al. |
| 2012/0108510 A1 | 5/2012 | Young et al. |
| 2012/0129834 A1 | 5/2012 | Hughes et al. |
| 2012/0135960 A2 | 5/2012 | Mouthon et al. |
| 2012/0159656 A1 | 6/2012 | Gerber et al. |
| 2012/0282255 A1 | 11/2012 | Plucinski |
| 2012/0302590 A1 | 11/2012 | Bhide et al. |
| 2012/0302592 A1 | 11/2012 | Johnson et al. |
| 2013/0045979 A1 | 2/2013 | Sanfilippo |
| 2013/0116215 A1 | 5/2013 | Coma et al. |
| 2013/0276799 A1 | 10/2013 | Davidson et al. |
| 2013/0281401 A1 | 10/2013 | Turner |
| 2013/0295170 A1 | 11/2013 | Dordunoo |
| 2014/0093577 A1 | 4/2014 | Tengler et al. |
| 2014/0099336 A1 | 4/2014 | Woiwode et al. |
| 2014/0100282 A1 | 4/2014 | Wong |
| 2014/0148491 A1 | 5/2014 | Valia et al. |
| 2014/0178480 A1 | 6/2014 | King et al. |
| 2014/0187655 A1 | 7/2014 | Mash et al. |
| 2014/0220150 A1 | 8/2014 | Stamets |
| 2014/0255522 A1 | 9/2014 | Lozinsky et al. |
| 2014/0288056 A1 | 9/2014 | Friedhoff |
| 2014/0294923 A1 | 10/2014 | Cartt et al. |
| 2014/0315837 A1 | 10/2014 | Mash et al. |
| 2014/0356428 A1 | 12/2014 | Barnscheid et al. |
| 2014/0364367 A1 | 12/2014 | Cotter |
| 2015/0011644 A1 | 1/2015 | Leech |
| 2015/0094466 A1 | 4/2015 | Moriarty |

(56) References Cited

U.S. PATENT DOCUMENTS

| | | |
|---|---|---|
| 2015/0099741 A1 | 4/2015 | Li et al. |
| 2015/0118301 A1 | 4/2015 | Haswani et al. |
| 2015/0118327 A1 | 4/2015 | Sewell |
| 2015/0196533 A1 | 7/2015 | Mao et al. |
| 2015/0216799 A1 | 8/2015 | Farber |
| 2015/0231300 A1 | 8/2015 | Lozinsky et al. |
| 2015/0258114 A1 | 9/2015 | Friedhoff |
| 2016/0051476 A1 | 2/2016 | Pilgaonkar et al. |
| 2016/0331725 A1 | 11/2016 | Gillessen et al. |
| 2016/0338945 A1 | 11/2016 | Knight |
| 2016/0340334 A1 | 11/2016 | Knight |
| 2017/0086727 A1 | 3/2017 | Dagum |
| 2017/0258382 A1 | 9/2017 | Dagum |
| 2017/0258383 A1 | 9/2017 | Dagum |
| 2017/0276676 A1 | 9/2017 | Slotman |
| 2017/0287348 A1 | 10/2017 | Mosher et al. |
| 2017/0348303 A1 | 12/2017 | Bosse et al. |
| 2018/0021326 A1 | 1/2018 | Stamets |
| 2018/0036303 A1 | 2/2018 | Raz |
| 2018/0104490 A1 | 4/2018 | Rustick |
| 2018/0147142 A1 | 5/2018 | Knight |
| 2018/0221396 A1 | 8/2018 | Chadeayne |
| 2018/0343812 A1 | 12/2018 | Leo |
| 2018/0344743 A1 | 12/2018 | Lozinsky et al. |
| 2018/0353434 A1 | 12/2018 | Hatanaka et al. |
| 2018/0354995 A1 | 12/2018 | Gudkov et al. |
| 2019/0105313 A1 | 4/2019 | Stamets |
| 2019/0142851 A1 | 5/2019 | Chadeayne |
| 2019/0187163 A1 | 6/2019 | Koh |
| 2019/0192498 A1 | 6/2019 | Stamets |
| 2019/0246591 A1 | 8/2019 | Leo |
| 2020/0078368 A1 | 3/2020 | Lehmann et al. |
| 2020/0093416 A1 | 3/2020 | Rogers et al. |
| 2020/0101041 A1 | 4/2020 | Kleidon |
| 2020/0147038 A1 | 5/2020 | Russ et al. |
| 2020/0215297 A1 | 7/2020 | Rabin et al. |
| 2020/0375967 A1 | 12/2020 | Stamets |
| 2021/0015738 A1 | 1/2021 | LaRosa et al. |
| 2021/0015833 A1 | 1/2021 | LaRosa et al. |
| 2021/0069170 A1 | 3/2021 | Stamets |
| 2021/0267966 A1 | 9/2021 | Petcavich |
| 2022/0088041 A1 | 3/2022 | Londesbrough et al. |
| 2022/0169668 A1 | 6/2022 | Londesbrough et al. |
| 2022/0402949 A1 | 12/2022 | Londesbrough et al. |
| 2023/0000883 A1 | 1/2023 | Londesbrough et al. |
| 2023/0023092 A1 | 1/2023 | Londesbrough et al. |
| 2023/0119714 A1 | 4/2023 | Londesbrough et al. |
| 2023/0124137 A1 | 4/2023 | Londesbrough et al. |
| 2023/0277568 A1 | 9/2023 | Bridges et al. |
| 2024/0197758 A1 | 6/2024 | Elder et al. |
| 2024/0199660 A1 | 6/2024 | Londesbrough et al. |
| 2024/0252521 A1 | 8/2024 | Londesbrough et al. |
| 2024/0360162 A1 | 10/2024 | Londesbrough et al. |
| 2025/0000881 A1 | 1/2025 | Mill |
| 2025/0122232 A1 | 4/2025 | Londesbrough et al. |

FOREIGN PATENT DOCUMENTS

| | | | |
|---|---|---|---|
| CA | 672478 A | 10/1963 | |
| CA | 2338326 A1 | 2/2000 | |
| CA | 2416650 A1 | 1/2002 | |
| CA | 2422730 A1 | 3/2002 | |
| CA | 2492823 A1 | 3/2003 | |
| CA | 2492826 A1 | 3/2003 | |
| CA | 2487849 A1 | 1/2004 | |
| CA | 2489410 A1 | 1/2004 | |
| CA | 2498938 A1 | 4/2004 | |
| CA | 2517675 A1 | 10/2004 | |
| CA | 2541090 A1 | 5/2005 | |
| CA | 2594451 A1 | 6/2007 | |
| CA | 3050679 A1 | 7/2018 | |
| CN | 103535561 A | 1/2014 | |
| CN | 103549133 A | 2/2014 | |
| CN | 103751943 A | 4/2014 | |
| CN | 103773056 A | 5/2014 | |
| CN | 107252080 A | 10/2017 | |
| CN | 108619214 A | 10/2018 | |
| EP | 0152379 A2 | 8/1985 | |
| EP | 0218479 A2 | 4/1987 | |
| EP | 0493380 B1 | 10/1997 | |
| EP | 0628042 B1 | 8/2001 | |
| EP | 0554352 B1 | 3/2003 | |
| EP | 0932416 B1 | 6/2005 | |
| EP | 1944017 A2 | 7/2008 | |
| EP | 2106799 A1 | 10/2009 | |
| EP | 1774968 B1 | 12/2011 | |
| EP | 1861427 B1 | 8/2012 | |
| EP | 2142185 B1 | 8/2012 | |
| EP | 2525226 A1 | 11/2012 | |
| EP | 2649989 A1 | 10/2013 | |
| EP | 2053919 B1 | 12/2013 | |
| EP | 2183227 B1 | 9/2014 | |
| EP | 2023900 B1 | 12/2014 | |
| EP | 2818177 A1 | 12/2014 | |
| EP | 2481740 B1 | 11/2015 | |
| EP | 3151906 B1 | 12/2019 | |
| ES | 2693502 T3 | 12/2018 | |
| FI | 20176142 A1 | 6/2019 | |
| FI | 20185254 A1 | 9/2019 | |
| GB | 911946 A | 12/1962 | |
| GB | 912714 A | 12/1962 | |
| HR | P20050421 A2 | 12/2005 | |
| IE | 24138 L | 8/1959 | |
| JP | S5576859 A | 6/1980 | |
| JP | S5728046 A | 2/1982 | |
| JP | 4174016 B2 | 10/2008 | |
| JP | 2013233437 A | 11/2013 | |
| MX | 2014005372 A | 7/2014 | |
| TW | 201605856 A | 2/2016 | |
| WO | WO-9728798 A1 | 8/1997 | |
| WO | WO-9728799 A1 | 8/1997 | |
| WO | WO-9728800 A1 | 8/1997 | |
| WO | WO-9729121 A1 | 8/1997 | |
| WO | WO-9747285 A1 | 12/1997 | |
| WO | WO-9850027 A1 | 11/1998 | |
| WO | WO-9859234 A1 | 12/1998 | |
| WO | WO-9903458 A1 | 1/1999 | |
| WO | WO-9909828 A1 | 3/1999 | |
| WO | WO-9948501 A1 | 9/1999 | |
| WO | WO-9966909 A2 | 12/1999 | |
| WO | WO-0003679 A2 | 1/2000 | |
| WO | WO-0003701 A1 | 1/2000 | |
| WO | WO-0003746 A2 | 1/2000 | |
| WO | WO-0006139 A2 | 2/2000 | |
| WO | WO-0056403 A1 | 9/2000 | |
| WO | WO-0113935 A2 | 3/2001 | |
| WO | WO-0126642 A2 | 4/2001 | |
| WO | WO-0152832 A1 | 7/2001 | |
| WO | WO-0167890 A2 | 9/2001 | |
| WO | WO-0172839 A2 | 10/2001 | |
| WO | WO-0182915 A2 | 11/2001 | |
| WO | WO-0205851 A2 | 1/2002 | |
| WO | WO-0224865 A2 | 3/2002 | |
| WO | WO-03016903 A2 | 2/2003 | |
| WO | WO-03024480 A2 | 3/2003 | |
| WO | WO-03024481 A2 | 3/2003 | |
| WO | WO-03026564 A2 | 4/2003 | |
| WO | WO-03041645 A2 | 5/2003 | |
| WO | WO-03045353 A1 | 6/2003 | |
| WO | WO-03047551 A1 | 6/2003 | |
| WO | WO-03066030 A2 | 8/2003 | |
| WO | WO-2004000275 A2 | 12/2003 | |
| WO | WO-2004007538 A2 | 1/2004 | |
| WO | WO-2004009116 A2 | 1/2004 | |
| WO | WO-2004014429 A1 | 2/2004 | |
| WO | WO-2004025268 A2 | 3/2004 | |
| WO | WO-2004032900 A2 | 4/2004 | |
| WO | WO-2004071431 A2 | 8/2004 | |
| WO | WO-2004084940 A1 | 10/2004 | |
| WO | WO-2004111185 A2 | 12/2004 | |
| WO | WO-2005039502 A2 | 5/2005 | |
| WO | WO-2005039546 A2 | 5/2005 | |
| WO | WO-2005058319 A1 | 6/2005 | |
| WO | WO-2005067930 A2 | 7/2005 | |

(56) References Cited

FOREIGN PATENT DOCUMENTS

| | | |
|---|---|---|
| WO | WO-2005102390 A2 | 11/2005 |
| WO | WO-2006006858 A1 | 1/2006 |
| WO | WO-2006047032 A2 | 5/2006 |
| WO | WO-2006079999 A2 | 8/2006 |
| WO | WO-2006121552 A2 | 11/2006 |
| WO | WO-2006127418 A1 | 11/2006 |
| WO | WO-2007050697 A2 | 5/2007 |
| WO | WO-2007066240 A2 | 6/2007 |
| WO | WO-2007067519 A2 | 6/2007 |
| WO | WO-2007085898 A2 | 8/2007 |
| WO | WO-2007092043 A2 | 8/2007 |
| WO | WO-2007101884 A1 | 9/2007 |
| WO | WO-2008009125 A1 | 1/2008 |
| WO | WO-2008010223 A2 | 1/2008 |
| WO | WO-2008023261 A1 | 2/2008 |
| WO | WO-2008026046 A1 | 3/2008 |
| WO | WO-2008038291 A1 | 4/2008 |
| WO | WO-2008039179 A1 | 4/2008 |
| WO | WO-2008119097 A1 | 10/2008 |
| WO | WO-2008122990 A1 | 10/2008 |
| WO | WO-2008130638 A2 | 10/2008 |
| WO | WO-2009018338 A2 | 2/2009 |
| WO | WO-2009021055 A1 | 2/2009 |
| WO | WO-2009050354 A1 | 4/2009 |
| WO | WO-2009055001 A2 | 4/2009 |
| WO | WO-2009061436 A1 | 5/2009 |
| WO | WO-2009079765 A1 | 7/2009 |
| WO | WO-2009091605 A2 | 7/2009 |
| WO | WO-2009097596 A1 | 8/2009 |
| WO | WO-2009102805 A1 | 8/2009 |
| WO | WO-2009109428 A2 | 9/2009 |
| WO | WO-2009118179 A1 | 10/2009 |
| WO | WO-2009118763 A1 | 10/2009 |
| WO | WO-2009149252 A1 | 12/2009 |
| WO | WO-2010099522 A1 | 9/2010 |
| WO | WO-2010123577 A2 | 10/2010 |
| WO | WO-2010124089 A2 | 10/2010 |
| WO | WO-2011027060 A2 | 3/2011 |
| WO | WO-2011028875 A1 | 3/2011 |
| WO | WO-2011045443 A1 | 4/2011 |
| WO | WO-2011045769 A1 | 4/2011 |
| WO | WO-2011048494 A2 | 4/2011 |
| WO | WO-2011072398 A1 | 6/2011 |
| WO | WO-2011097269 A1 | 8/2011 |
| WO | WO-2011109809 A2 | 9/2011 |
| WO | WO-2011116189 A1 | 9/2011 |
| WO | WO-2011138142 A1 | 11/2011 |
| WO | WO-2011143254 A2 | 11/2011 |
| WO | WO-2011158964 A1 | 12/2011 |
| WO | WO-2012012764 A1 | 1/2012 |
| WO | WO-2012019989 A2 | 2/2012 |
| WO | WO-2012022928 A2 | 2/2012 |
| WO | WO-2012031125 A2 | 3/2012 |
| WO | WO-2012039660 A1 | 3/2012 |
| WO | WO-2012045118 A1 | 4/2012 |
| WO | WO-2012054815 A1 | 4/2012 |
| WO | WO-2012063257 A2 | 5/2012 |
| WO | WO-2012066537 A2 | 5/2012 |
| WO | WO-2012074588 A2 | 6/2012 |
| WO | WO-2012077110 A2 | 6/2012 |
| WO | WO-2012085919 A2 | 6/2012 |
| WO | WO-2012110537 A1 | 8/2012 |
| WO | WO-2012134436 A1 | 10/2012 |
| WO | WO-2012137971 A1 | 10/2012 |
| WO | WO-2012158892 A2 | 11/2012 |
| WO | WO-2012177962 A1 | 12/2012 |
| WO | WO-2013004999 A1 | 1/2013 |
| WO | WO-2013040471 A1 | 3/2013 |
| WO | WO-2013068949 A1 | 5/2013 |
| WO | WO-2013083710 A1 | 6/2013 |
| WO | WO-2013085849 A2 | 6/2013 |
| WO | WO-2013085850 A2 | 6/2013 |
| WO | WO-2013085922 A1 | 6/2013 |
| WO | WO-2013091900 A1 | 6/2013 |
| WO | WO-2013097947 A1 | 7/2013 |
| WO | WO-2013112163 A1 | 8/2013 |
| WO | WO-2013112757 A1 | 8/2013 |
| WO | WO-2013169355 A1 | 11/2013 |
| WO | WO-2014015993 A1 | 1/2014 |
| WO | WO-2014031958 A1 | 2/2014 |
| WO | WO-2014035473 A1 | 3/2014 |
| WO | WO-2014064703 A1 | 5/2014 |
| WO | WO-2014078857 A1 | 5/2014 |
| WO | WO-2014093277 A1 | 6/2014 |
| WO | WO-2014098877 A1 | 6/2014 |
| WO | WO-2014117089 A1 | 7/2014 |
| WO | WO-2014140925 A2 | 9/2014 |
| WO | WO-2014143085 A1 | 9/2014 |
| WO | WO-2014145126 A2 | 9/2014 |
| WO | WO-2014146082 A1 | 9/2014 |
| WO | WO-2014153099 A2 | 9/2014 |
| WO | WO-2014176556 A1 | 10/2014 |
| WO | WO-2014186623 A2 | 11/2014 |
| WO | WO-2014190440 A1 | 12/2014 |
| WO | WO-2014195872 A1 | 12/2014 |
| WO | WO-2015004245 A1 | 1/2015 |
| WO | WO-2015006315 A1 | 1/2015 |
| WO | WO-2015034846 A1 | 3/2015 |
| WO | WO-2015061125 A1 | 4/2015 |
| WO | WO-2015065546 A2 | 5/2015 |
| WO | WO-2015066344 A1 | 5/2015 |
| WO | WO-2015112168 A2 | 7/2015 |
| WO | WO-2015134405 A1 | 9/2015 |
| WO | WO-2015187289 A1 | 12/2015 |
| WO | WO-2016161138 A1 | 10/2016 |
| WO | WO-2016176177 A1 | 11/2016 |
| WO | WO-2016178053 A1 | 11/2016 |
| WO | WO-2017023679 A1 | 2/2017 |
| WO | WO-2018035477 A1 | 2/2018 |
| WO | WO-2018135943 A1 | 7/2018 |
| WO | WO-2018141063 A1 | 8/2018 |
| WO | WO-2018145219 A1 | 8/2018 |
| WO | WO-2018148605 A1 | 8/2018 |
| WO | WO-2018184206 A1 | 10/2018 |
| WO | WO-2018195455 A1 | 10/2018 |
| WO | WO-2018223044 A1 | 12/2018 |
| WO | WO-2019073379 A1 | 4/2019 |
| WO | WO-2019079742 A1 | 4/2019 |
| WO | WO-2019081764 A1 | 5/2019 |
| WO | WO-2019099745 A1 | 5/2019 |
| WO | WO-2019109124 A1 | 6/2019 |
| WO | WO-2019122525 A1 | 6/2019 |
| WO | WO-2019144140 A1 | 7/2019 |
| WO | WO-2019161050 A1 | 8/2019 |
| WO | WO-2019173797 A1 | 9/2019 |
| WO | WO-2019180309 A1 | 9/2019 |
| WO | WO-2019213551 A1 | 11/2019 |
| WO | WO-2019246532 A1 | 12/2019 |
| WO | WO-2020024060 A1 | 2/2020 |
| WO | WO-2020041329 A1 | 2/2020 |
| WO | WO-2020053196 A1 | 3/2020 |
| WO | WO-2020142259 A1 | 7/2020 |
| WO | WO-2020157569 A1 | 8/2020 |
| WO | WO-2020169850 A1 | 8/2020 |
| WO | WO-2020212948 A1 | 10/2020 |
| WO | WO-2020212951 A1 | 10/2020 |
| WO | WO-2020212952 A1 | 10/2020 |
| WO | WO-2022207746 A1 | 10/2022 |
| WO | WO-2024026573 A1 | 2/2024 |

OTHER PUBLICATIONS

Abramovitch, A. et al. (Jul./Aug. 2015). Comorbidity Between Attention Deficit/Hyperactivity Disorder and Obsessive-Compulsive Disorder Across the Lifespan: A Systematic and Critical Review. Harvard Review of Psychiatry, 23(4):245-262.

Adams, K.S. et al., (2014). Melatonin agonists in the management of sleep disorders: A focus on ramelteon and tasimelteon. Ment Health Clin, 4:59-64. https://doi.org/10.9740/mhc.n190087.

Adams, T.G. et al. (Apr. 2017). Intranasal ketamine and cognitive-behavioral therapy for treatment-refractory obsessive-compulsive disorder. Journal of Clinical Psychopharmacology, 37(2):269-271.

(56)            References Cited

OTHER PUBLICATIONS

HHS Public Access Author Manuscript; available in PMC Apr. 1, 2018, 4 pages.

Adelow, C. et al. (Jan. 2012). Hospitalization for psychiatric disorders before and after onset of unprovoked seizures/epilepsy. Neurology, 78(6), 396-401. https://doi.org/10.1212/WNL.0b013e318245f461.

Advokat, C. et al., (May 2013). Attention-deficit hyperactivity disorder (ADHD) stimulant medications as cognitive enhancers. Front Neurosci, 7:Article 92, 8 pages.

Agh, T. et al. (Jan. 2015). Epidemiology, health-related quality of life and economic burden of binge eating disorder: a systematic literature review. Eating and Weight Disorders, 20:1-12.

Agin-Liebes, G.I. et al. (2020). Long-term follow-up of psilocybin-assisted psychotherapy for psychiatric and existential distress in patients with life-threatening cancer. J Psychopharmacol [online]; retrieved from: https://doi.org/10.1177/0269881119897615, 12 pages.

Aguglia, A., Signorelli, M. S., Albert, U., & Maina, G. (Mar. 2018). The impact of general medical conditions in obsessive-compulsive disorder. Psychiatry Investigation, 15(3):246-253. https://doi.org/10.30773/pi.2017.06.17.2.

Alayadhi, L.Y. et al. (Dec. 2016). High-resolution SNP genotyping platform identified recurrent and novel CNVs in autism multiplex families. Neuroscience, 339:561-570.

Albelda, N., & Joel, D. (Jun. 2012). Current animal models of obsessive compulsive disorder: An update. Neuroscience, 211:83-106. https://doi.org/10.1016/j.neuroscience.2011.08.070.

Alcaro, A., and J. Panksepp (Oct. 2011). The Seeking mind: Primal neuro-affective substrates for appetitive incentive states and their pathological dynamics in addictions and depression. Neurosci Biobehav Rev, 35:1805-1820. https://doi.org/10.1016/j.neubiorev.2011.03.002.

Alderson, R.M. et al. (May 2013) Attention-deficit/hyperactivity disorder (ADHD) and working memory in adults: A meta-analytic review. Neuropsychology, 27(3):287-302.

Allam, J.S., Collop, N., 2018. Central Sleep Apnea Syndrome (Idiopathic CSA, Cheyne-Stokes Respiration, CSA due to a drug or substance, High-altitude Periodic breathing, CSA due to a medical condition other than Cheyne-Stokes). Pulmonology Advisor (2018): pp. 1-14. Retrieved from: https://www.pulmonologyadvisor.com/home/decision-support-in-medicine/pulmonary-medicine/central-sleep-apnea-syndrome-idiopathic-csa-cheyne-stokes-respiration-csa-due-to-a-drug-or-substance-high-altitude-periodic-breathing-csa-due-to-a-medical-condition-ot (accessed Jul. 30, 2020).

Allen, G. and E. Courchesne (Jan. 1, 2001). Attention function and dysfunction in autism. Frontiers in Bioscience, 6:d105-119.

Alonso, P., Lopez-Sola, C., Real, E., Segalas, C., & Menchon, J. M. (Aug. 2015). Animal models of obsessive-compulsive disorder: Utility and limitations. In Neuropsychiatric Disease and Treatment, 11:1939-1955. https://doi.org/10.2147/NDT.S62785.

Alvarez, A.J. et al. (2009) "Polymorph Screening: Comparing a Semi-Automated Approach with a High Throughput Method" Crystal Growth and Design, 9:4181-4188.

Alzheimer's Association (2019). Alzheimer's Disease Facts and Figures. Alzheimers Dement, 15(3):321-387, with Appendices, 90 total pages.

Alzheimer's Association (2019). FDA-approved treatments for Alzheimer's. TS-0087. 5 pages.

American Parkinson Disease Association. (2019). Medications for Parkinson's. Retrieved from https://www.apdaparkinson.org/what-is-parkinsons/treatment-medication/medication/; retrieved on Jul. 30, 2020, 18 pages.

American Psychiatric Association (2013) Binge-eating disorder. In: Diagnostic and Statistical Manual of Mental Disorders. 5th ed. Arlington, VA: American Psychiatric Association; p. 350-353.

American Psychiatric Association (2013). Diagnostic and statistical manual of mental disorders (5th ed.). American Journal of Psychiatry. https://doi.org/10.1176/appi.books.9780890425596.744053, 970 pages.

American Psychiatric Association (2013). Sleep-Wake Disorders. In: Diagnostic and Statistical Manual of Mental Disorders. 5th Edition. [online]. Retrieved from: https://doi.org/10.1176/appi.books.9780890425596.dsm12, 2 pages.

Amiri, S. et al. (Jan. 2008) Modafinil as a treatment for Attention-Deficit/Hyperactivity Disorder in children and adolescents: A double blind, randomized clinical trial. Prog Neuro-Psychopharmacol Biol Psychiatry. 32(1):145-149.

Amodeo, D.A. et al. (Feb. 2012). Differences in BTBR T+ tf/J and C57BL/6J mice on probabilistic reversal learning and stereotyped behaviors. Behavioural Brain Research,227(1):64-72. NIH Public Access Author Manuscript, available Mar. 1, 2012, 19 pages.

Andermann, F. (Jul. 1987). Migraine-epilepsy relationships. Epilepsy Research, 1(4):213-226. https://doi.org/10.1016/0920-1211(87)90028-3.

Andersson et al., "Psychoactive substances as a last resort—a qualitative study of self-treatment of migraine and cluster headaches." Harm Reduct J. Sep. 5, 2017; 14(1):60. 11 pages.

Andres-Pepina, S. et al. (2019). Long-term outcome and psychiatric comorbidity of adolescent-onset anorexia nervosa. Clinical Child Psychology and Psychiatry [online]. Retrieved from: https://doi.org/10.1177/1359104519827629, 12 pages.

Angst, J., Gamma, A., Endrass, J., Goodwin, R., Ajdacic, V., Eich, D., & Rossler, W. (Jun. 2004). Obsessive-compulsive severity spectrum in the community: Prevalence, comorbidity, and course. European Archives of Psychiatry and Clinical Neuroscience, 254(3):156-164. https://doi.org/10.1007/s00406-004-0459-4.

Anonymous: "Compass Pathways announces positive outcome of 25mg COMP360 psilocybin therapy as adjunct to SRI antidepressants on open-label treatment-resistant depression study," Dec. 13, 2021 (Dec. 13, 2021), XP093033918, Retrieved from the Internet: URL:https://compasspathways.com/positive-outcome-25mg-comp360-psilocybin-therapy-adjunct-ssri-antidepressants-open-label-treatment-resistant-depression-study/ [retrieved on Mar. 22, 2023], 7 pages.

Anonymous: "Psilocybin in Depression Resistant to Standard Treatments—Full Text View—ClinicalTrials.gov", Jul. 13, 2021 (Jul. 13, 2021), XPO93024023, Retrieved from the Internet: URL:https://clinicaltrials.gov/ct2/show/NCT04959253?term=depression&cond=psilocyb in&draw=2&rank=11 [retrieved on Feb. 15, 2023], 5 pages.

Anonymous: "Record History I ver. 1: Aug. 8, 2019 I NCT04052568 ClinicalTrials.gov Effects of Psilocybin in Anorexia Nervosa", Aug. 8, 2019, pp. 1-13, Retrieved May 12, 2024 from the Internet: URL:https://clinicaltrials.gov/study/NCT04052568?tab=history&a=1#version-content-panel.

Anwar, M.A. et al. (2013). Negative regulatory approaches to the attenuation of Toll-like receptor signaling. Experimental & Molecular Medicine, 45(2):e11, 14 pages. https://doi.org/10.1038/emm.2013.28.

Ara, A. et al. (2016). Sleep disturbances and substance use disorders: A bi-directional relationship. Psychiatr Ann, 46(7):408-412.

Arcelus, J., Mitchell, A. J., Wales, J., & Nielsen, S. (Jul. 2011). Mortality rates in patients with anorexia nervosa and other eating disorders. A meta-analysis of 36 studies. Archives of General Psychiatry, 68(7):724-731. https://doi.org/10.1001/archgenpsychiatry.2011.74.

Armstrong, M.J. and M.S. Okun (2020). Diagnosis and Treatment of Parkinson Disease. A Review. JAMA, 323(6):548-560.

Arzt, E. et al. (1991). Serotonin inhibition of tumor necrosis factor-α synthesis by human monocytes. Life Sciences, 48(26):2557-2562.

Asnis, G.M. et al. (2016). Pharmacotherapy treatment options for insomnia: A primer for clinicians. Int J Mol Sci, 17:50, 11 pages. https://doi.org/10.3390/ijms17010050.

Attia, E., Kaplan, A. S., Walsh, B. T., Gershkovich, M., Yilmaz, Z., Musante, D., & Wang, Y. (Oct. 2011). Olanzapine versus placebo for out-patients with anorexia nervosa. Psychological Medicine, 41(10):2177-2182. https://doi.org/10.1017/S0033291711000390.

Auger, R.R. et al. (Jun. 2005). Risks of high-dose stimulants in the treatment of disorders of excessive somnolence: A case-control study. Sleep, 28(6):667-672.

Avidan, A.Y. (2012). Comorbidities of central nervous system hypersomnia. Sleep Med Clin, 7:291-302.

(56) References Cited

OTHER PUBLICATIONS

Ayaz, G. et al. (Feb. 2017). Evaluation of 5-HT7 Receptor Trafficking on In Vivo and In Vitro Model of Lipopolysaccharide (LPS)-Induced Inflammatory Cell Injury in Rats and LPS-Treated A549 Cells. Biochemical Genetics, 55(1):34-47.

Babu, C.S. et al. (Oct. 2009). Co-morbidities in people living with epilepsy: Hospital based case-control study from a resource-poor setting. Epilepsy Research, 86(2-3):146-152.

Baglioni, C. et al. (Sep. 2016). Sleep and mental disorders: A meta-analysis of polysomnographic research. Psychol Bull, 142:969-990. HHS Public Access Author Manuscript, available Sep. 1, 2017, 56 pages.

Bahi Camile: II Antidepressants and Psychedelics—What Do We Know and What Could Be the Risks?, Mind Foundation, (Sep. 11, 2020), Retrieved from the Internet: URL:https://mind-foundation.org/psychedelicantidepressant-interactions/[retrieved on Jan. 20, 2022], 12 pages.

Bai, D. et al. (Jul. 17, 2019). Association of Genetic and Environmental Factors With Autism in a 5-Country Cohort. JAMA Psychiatry, 76(10):1035-1043.

Baio, J. (Mar. 30, 2012). Prevalence of autism spectrum disorders—Autism and developmental disabilities monitoring network, 14 sites, United States, 2008. Morbidity and Mortality Weekly Report (MMWR), 61(3):1-24.

Baker, L.A. et al. (2006) Behavioral Genetics: The Science of Antisocial Behavior. Law Contemp Probl, 69(1-2):7-46. NIH Public Access Author Manuscript, 37 pages.

Bandeen-Roche, K. et al. (Dec. 2009). Measuring Systemic Inflammatory Regulation in Older Adults: Evidence and Utility. Rejuvenation Research, 12(6):403-410.

Bandelow et al., "Epidemiology of anxiety disorders in the 21st century", Dialogues in Clinical Neuroscience (2015); 17(3): 327-335. doi: 10.31887/DCNS.2015.17.3/bbandelow.

Banks, W.A. et al. (Sep. 1994). Penetration of interleukin-6 across the murine blood-brain barrier. Neuroscience Letters, 179(1-2):53-56.

Barnes, D.T. (Dec. 1970). The uses and abuses of L.S.D. and other hallucinogenic drugs. The Australian and New Zealand Journal of Psychiatry, 4(4):170-173.

Barnes, P. J. (Jun. 2006). How corticosteroids control inflammation: Quintiles Prize Lecture 2005. British Journal of Pharmacology, 148(3):245-254.

Barnes, T.R.E. (May 1989) A Rating Scale for Drug-Induced Akathisia. Br J Psychiatry, 154:672-676.

Baron-Cohen, S. et al. (May 2000) The amygdala theory of autism. Neurosci Biobehav Rev, 24(3):355-364.

Barrett et al., "Validation of the revised Mystical Experience Questionnaire in experimental sessions with psilocybin", Journal of Psychopharmacology (2015); 29(11): 1182-1190. doi: 10.1177/0269881115609019. Epub Oct. 6, 2015.

Barrett, F.S. et al. (Dec. 2016) The Challenging Experience Questionnaire: Characterization of challenging experiences with psilocybin mushrooms. Journal of Psychopharmacology, 30(12):1279-1295. HHS Public Access Author Manuscript, 42 pages.

Barrett, F.S. et al. (Nov. 2018) Serotonin 2A Receptor Signaling Underlies LSD-Induced Alteration of the Neural Response to Dynamic Changes in Music. Cerebral Cortex, 28:3939-3950.

Basetti and Aldrich, "Idiopathic hypersomnia. A series of 42 patients," Brain, (Aug. 1997) 120(8): 1423-1435.

Bateman, R.J. et al. (Aug. 30, 2012). Clinical and biomarker changes in dominantly inherited Alzheimer's disease. The New England Journal of Medicine, 367(9):795-804.

Bech, P. et al. (Jun. 1978) The mania rating scale: scale construction and inter-observer agreement. Neuropharmacology. 17(6):430-431.

Becker, D. and Grilo, C. (2015). Comorbidity of mood and substance use disorders in patients with binge-eating disorder: Associations with personality disorder and eating disorder pathology. Journal of Psychosomatic Research, 79(2), pp. 159-164.

Becker et al., "Acute effects of psilocybin after escitalopram or placebo pretreatment in a randomized, double-blind, placebo-controlled, crossover study in healthy subjects", Clinical Pharmacology & Therapeutics (2022); 111(4): 886-895. doi: 10.1002/cpt.2487. Epub Nov. 22, 2021.

Becker, P.M. (Dec. 2006). Insomnia: Prevalence, Impact, Pathogenesis, Differential Diagnosis, and Evaluation. Psychiatr Clin North Am, 26:855-870.

Bell, R.F. and E.A. Kalso (2018) Ketamine for pain management. Pain Reports, 3:e674, 8 pages.

Belli, H. et al. (Oct. 2012). Dissociative symptoms and dissociative disorder comorbidity in patients with obsessive-compulsive disorder. Comprehensive Psychiatry, 53(7):975-980.

Bello, N. and Yeomans, B. (2018). Safety of pharmacotherapy options for bulimia nervosa and binge eating disorder. Expert Opinion on Drug Safety, 17(1), pp. 17-23.

Belzeaux, R. et al. (Feb. 2018). Focusing on the Opioid System for Addiction Biomarker Discovery. Trends in Molecular Medicine, 24(2), pp. 206-220.

Benzon, H.T. et al. (2013) Preface. Practical Management of Pain, 5th Edition. Philadelphia, PA: Elsevier Mosby; 13 total pages.

Berg, A.T. (Jan. 2011). Epilepsy, cognition, and behavior: The clinical picture. Epilepsia, 52(Suppl 1):7-12. NIH Public Access Author Manuscript, available Jan. 1, 2012, 8 pages.

Berg, A.T. et al. (Aug. 2008). Residual cognitive effects of uncomplicated idiopathic and cryptogenic epilepsy. Epilepsy & Behavior, 13(4):614-619.

Berg, D. et al. (Nov. 12, 2015). MDS research criteria for prodromal Parkinson's disease. Movement Disorders, 30(12):1600-1609.

Berlin, H.A. et al. (May 2011). Double-blind, placebo-controlled trial of topiramate augmentation in treatment-resistant obsessive-compulsive disorder. Journal of Clinical Psychiatry, 72(5):716-721. https://doi.org/10.4088/JCP.09m05266gre.

Berthold-Losleben, M. & H. Himmerich (Sep. 2008). The TNF-alpha System: Functional Aspects in Depression, Narcolepsy and Psychopharmacology. Current Neuropharmacology, 6(3):193-202.

Besnard, J. et al. (Dec. 13, 2012) Automated design of ligands to polypharmacological profiles. Nature, 492(7428):215-220. https://doi.org/10.1038/nature11691.

Bhidayasiri, R. & P. Martinez-Martin, "Clinical Assessments in Parkinson's Disease: Scales and Monitoring," International Review of Neurobiology 132:129-182 (Feb. 2017).

Billiard, M. & Bentley, A. (Jun. 2004). Is insomnia best categorized as a symptom or a disease? Sleep Med. 5(Suppl 1):S35-S40. https://doi.org/10.1016/S1389-9457(04)90006-8.

Billiard, M. (Jun. 2008). Narcolepsy: Current treatment options and future approaches. Neuropsychiatr Dis Treat, 4(3):557-566.

Binukumar, B.K. et al. (Sep. 2015). Peptide TFP5/TP5 derived from Cdk5 activator P35 provides neuroprotection in the MPTP model of Parkinson's disease. Molecular Biology of the Cell, 26(24):4478-4491. https://doi.org/10.1091/mbc.E15-06-0415.

Bird, A.D., et al., (Jun. 4, 2019). Dissecting Sholl Analysis into Its Functional Components. Cell Reports, 27(10):3081-3096.

Bison, S. et al. (2009). Differential behavioral, physiological, and hormonal sensitivity to LPS challenge in rats. International Journal of Interferon, Cytokine and Mediator Research, 1:1-13. https://doi.org/10.2147/IJICMR.S4273.

Black, D.W. (Jul. 2015) The Natural History of Antisocial Personality Disorder. The Canadian Journal of Psychiatry. 60(7):309-314.

Blair et al., "Effect of ring fluorination on the pharmacology of hallucinogenic tryptamines", Journal of Medicinal Chemistry (2000); 43(24): 4701-4710. doi: 10.1021/jm000339w.

Blasio, A. et al. (Jul. 2014). Opioid system in the medial prefrontal cortex mediates binge-like eating. Addiction Biology, 19(4), pp. 652-662.

Blum, A. (May 2014). HMG-CoA reductase inhibitors (statins), inflammation, and endothelial progenitor cells—New mechanistic insights of atherosclerosis. BioFactors, 40(3), 295-302. https://doi.org/10.1002/biof.1157.

Bonnet, M.H. et al. (Feb. 1990). The effect of triazolam on arousal and respiration in central sleep apnea patients. Sleep, 13:31-41.

Borovcanin, M.M. et al. (Nov. 6, 2017). Interleukin-6 in Schizophrenia—Is There a Therapeutic Relevance? Frontiers in Psychiatry, 8:Article 221, 10 pages. https://doi.org/10.3389/fpsyt.2017.00221.

(56)  References Cited

OTHER PUBLICATIONS

Bortolato, B. et al. (2015). The Involvement of TNF-alpha in Cognitive Dysfunction Associated with Major Depressive Disorder: An Opportunity for Domain Specific Treatments. Current Neuropharmacology, 13(5):558-576.

Bosanac, P. et al. (Mar. 2005). Serotonergic and dopaminergic systems in anorexia nervosa: a role for atypical antipsychotics? Australian and New Zealand Journal of Psychiatry, 39(3):146-153.

Bossers, K. et al. (Jan. 2009). Analysis of gene expression in Parkinson's disease: possible involvement of neurotrophic support and axon guidance in dopaminergic cell death. Brain Pathology, 19(1):91-107.

Boszormenyi, Z. (1961) Psilocybin and diethyltryptamine: Two tryptamine hallucinogens. In: Rothlin E (ed) neuropsychopharmacology, vol. II. Elsevier, Amsterdam, pp. 226-229.

Braak, H. et al. (Apr. 2003). Staging of brain pathology related to sporadic Parkinson's disease. Neurobiology of Aging, 24(2):197-211.

Bradley, T.D. and Phillipson, E.A. (1992). Central sleep apnea. Clin. Chest Med, 13(3):493-505 (1 page abstract only provided).

Bradley, T.D. et al. (Aug. 1986). Clinical and physiologic heterogeneity of the central sleep apnea syndrome. Am. Rev. Respir. Dis., 134:217-221.

Braga, R.J. et al. (Nov. 2013). Anxiety comorbidity in schizophrenia. Psychiatry Res, 210:1-7.

Brakoulias, V. et al. (Jul. 2017). Comorbidity, age of onset and suicidality in obsessive-compulsive disorder (OCD): An international collaboration. Comprehensive Psychiatry, 76:79-86.

Brandt, C. & Mula, M. (Jun. 2016). Anxiety disorders in people with epilepsy. Epilepsy Behav., 59:87-91. https://doi.org/10.1016/j.yebeh.2016.03.020.

Brandt, R.B. et al. (Feb. 2020) Pharmacotherapy for Cluster Headache. CNS Drugs, 34:171-184, doi.org/10.1007/s40263-019-00696-2.

Brasure, M. et al. (2015). Management of Insomnia Disorder. Comparative Effectiveness Review No. 159. (Prepared by the Minnesota Evidence-based Practice Center under Contract No. 290-2012-00016-I). AHRQ Publication No. 15(16)-EHC027-EF. Rockville, MD: Agency for Healthcare Research and Quality. Dec. 2015 [online]. Retrieved from: www.effectivehealthcare.ahrq.gov/reports/final.cfm, 288 pages.

Bratland-Sanda, S. et al. (Apr. 2019). Defining compulsive exercise in eating disorders: Acknowledging the exercise paradox and exercise obsessions. Journal of Eating Disorders, 7(1):8, https://doi.org/10.1186/s40337-019-0238-2, 3 pages.

Brawman-Mintzer, O. et al. (Aug. 1993). Psychiatric comorbidity in patients with generalized anxiety disorder. Am. J. Psychiatry, 150:1216-1218.

Brockmeyer, T. et al. (Sep. 2017) Advances in the treatment of anorexia nervosa: A review of established and emerging interventions. Psychological Medicine, 48(8):1228-1256. Cambridge University Press. https://doi.org/10.1017/S0033291717002604.

Brown, C. M., & Stokes, M.A. (Apr. 2020). Intersection of Eating Disorders and the Female Profile of Autism. Child and Adolescent Psychiatric Clinics of North America, 29:409-417.

Brown et al., "Pharmacokinetics of escalating doses of oral psilocybin in healthy adults", Clinical Pharmacokinetics (2017); 56: 1543-1554. doi: 10.1007/s40262-017-0540-6.

Brown, T.A. et al. (Nov. 2001). Current and Lifetime Comorbidity of the DSM-IV Anxiety and Mood Disorders in a Large Clinical Sample. J. Abnorm. Psychol., 110:585-599.

Brownley, K. et al. (Sep. 2016). Binge-Eating Disorder in Adults. Annals of Internal Medicine, 165(6):409-420.

Bruce, S.E. et al. (Jun. 2005). Influence of psychiatric comorbidity on recovery and recurrence in generalized anxiety disorder, social phobia, and panic disorder: A 12-year prospective study. Am. J. Psychiatry, 162:1179-1187. NIH Public Access Author Manuscript, available in PMC Feb. 6, 2012, 16 pages.

Buescher, A.V. S. et al. (Aug. 2014). Costs of autism spectrum disorders in the United Kingdom and the United States. JAMA Pediatrics, 168(8):721-728.

Bulik, C.M. et al. (Aug. 1997). Eating disorders and antecedent anxiety disorders: a controlled study. Acta Psychiatr. Scand. 96, 101-107. https://doi.org/10.1111/j.1600-0447.1997.tb09913.x.

Burgess, E. et al. (Oct. 2016). Effects of transcranial direct current stimulation (tDCS) on binge-eating disorder. International Journal of Eating Disorders, 49(10), pp. 930-936.

Burt, D.R. et al. (Jul. 1976). Binding interactions of lysergic acid diethylamide and related agents with dopamine receptors in the brain. Molecular Pharmacology, 12(4):631-638.

Buscemi, N. et al. (Jun. 2005). Manifestations and management of chronic insomnia in adults: summary. In: AHRQ Evidence Report Summaries. Rockville (MD): Agency for Healthcare Research and Quality (US); 1998-2005. 125. https://doi.org/10.1037/e439752005-001, 11 pages.

Buxbaum, J.D., & Hof, P.R. (2013). Introduction. In the Neuroscience of Autism Spectrum Disorders. Elsevier, 7 pages. https://doi.org/10.1016/C2011-0-04170-4.

Buysse et al., "The Pittsburgh Sleep Quality Index: a new instrument for psychiatric practice and research", Psychiatry Research (1989); 28(2): 193-213. doi: 10.1016/0165-1781(89)90047-4.

Cabarkapa S. et al. (Aug. 13, 2019) Co-morbid obsessive-compulsive disorder and attention deficit hyperactivity disorder: Neurobiological commonalities and treatment implications. Front Psychiatry, 10:Article 557, 4 pages.

Cahill, C.M., & Rogers, J.T. (Sep. 19, 2008). Interleukin (IL) 1β Induction of IL-6 Is Mediated by a Novel Phosphatidylinositol 3-Kinase-dependent AKT/IκB Kinase α Pathway Targeting Activator Protein-1. Journal of Biological Chemistry, 283(38):25900-25912.

Caira, M.R., "Crystalline Polymorphism of Organic Compounds," in: Weber, E., et al. Design of Organic Solids. Topics in Current Chemistry 1998, vol. 198. Springer, Berlin, Heidelberg, pp. 163-208.

Callahan, P. M., & Appel, J.B. (Sep. 1988). Differences in the stimulus properties of 3,4-methylenedioxyamphetamine and 3,4-methylenedioxymethamphetamine in animals trained to discriminate hallucinogens from saline. J Pharmacol Exp Ther, 246(3):866-870.

Calvin, A.D. et al. (Apr. 2010). Advanced heart failure and nocturnal hypoxaemia due to central sleep apnoea are associated with increased serum erythropoietin. Eur. J. Heart Fail., 12:354-359. https://doi.org/10.1093/eurjhf/hfq005.

Campolongo, M. et al. (Jun. 2018) Sociability deficits after prenatal exposure to valproic acid are rescued by early social enrichment. Molecular Autism, 9:36, https://doi.org/10.1186/s13229-018-0221-9, 17 pages.

Canellas, F. et al. (Sep. 2014). Dual cases of type 1 narcolepsy with schizophrenia and other psychotic disorders. J. Clin. Sleep Med., 10(9):1011-1018. https://doi.org/10.5664/jcsm.4040.

Carhart-Harris et al., "Psilocybin with psychological support for treatment-resistant depression: six-month follow-up", Psychopharmacology (2018); 235: 399-408. doi: 10.1007/s00213-017-4771-x. Epub Nov. 8, 2017.

Carhart-Harris, "Psilocybin for treatment-resistant depression: fMRI-measured brain mechanisms." Sci Rep. Oct. 13, 2017; 7(1): 13187. doi: 10.1038/s41598-017-13282-7. 11 pages.

Carhart-Harris, R. et al. (Mar. 2012). Implications for psychedelic-assisted psychotherapy: functional magnetic resonance imaging study with psilocybin. British Journal of Psychiatry, 200(3):238-244.

Carhart-Harris, R., et al., "Psilocybin with psychological support for treatment-resistant depression: an open-label feasibility study", The Lancet Psychiatry (2016); 3(7): 619-627. doi: 10.1016/S2215-0366(16)30065-7. Epub May 17, 2016.

Carlsson, T. et al. (Jun. 2011). Systemic administration of neuregulin-1β1 protects dopaminergic neurons in a mouse model of Parkinson's disease. Journal of Neurochemistry, 117(6), 1066-1074. https://doi.org/10.1111/j.1471-4159.2011.07284.x.

(56)            References Cited

OTHER PUBLICATIONS

Carosi, J. M., & Sargeant, T. J. (Aug. 2019). Rapamycin and Alzheimer disease: a double-edged sword? Autophagy, 15(8):1460-1462. https://doi.org/10.1080/15548627.2019.1615823.

Carter et al., "Using psilocybin to investigate the relationship between attention, working memory, and the serotonin 1A and 2A receptors", Journal of Cognitive Neuroscience (2005); 17(10): 1497-1508. doi: 10.1162/089892905774597191.

Cashman, J.N. (1996). The mechanisms of action of NSAIDs in analgesia. Drugs, 52(Suppl. 5):13-23. https://doi.org/10.2165/00003495-199600525-00004.

Cassano, G.B. et al. (Sep. 2002). Psychopharmacology of anxiety disorders. Dialogues Clin. Neurosci., 4(3):271-285.

Cavalli, E et al. (Dec. 2019). The neuropathic pain: An overview of the current treatment and future therapeutic approaches. Intl J Immunopathol Pharmacol, 33:1-10; DOI: 10.1177/2058738419838383.

Chang, A. et al. (Jun. 3, 2020). Capsaicin. StatPearls. NCBI Bookshelf [online]. Retrieved from: https://www.ncbi.nlm.nih.gov/books/NBK459168/?report=printable; retrieved on Jul. 30, 2020, 4 pages.

Chang, S. et al. (Oct. 2015). Disease monitoring in inflammatory bowel disease. World Journal of Gastroenterology, 21(40):11246-11259.

Chang, T.-T. and Yen, Y.-C. (2010). Cytokines and Major Psychiatric Disorders. Taiwanese Journal of Psychiatry, 24(4):257-268.

Chang, Y.C. et al. (May 2017). Behavioral phenotyping for autism spectrum disorders in mice. Current Protocols in Toxicology. 72:11.22.1-11.22.21, doi: 10.1002/cptx.19.

Charles, P. et al. (Aug. 1999). Regulation of Cytokines, Cytokine Inhibitors, and Acute-Phase Proteins Following Anti-TNF-α Therapy in Rheumatoid Arthritis. The Journal of Immunology, 163(3):1521-1528. http://www.jimmunol.org/content/163/3/1521.

Chelminski, P.R. et al. (Jan. 2005) A primary care, multi-disciplinary disease management program for opioid-treated patients with chronic non-cancer pain and a high burden of psychiatric comorbidity. BMC Health Serv Res, 5:3, doi:10.1186/1472-6963-5-3, 13 pages.

Chen et al., "Attention-deficit hyperactivity disorder comorbidity and antidepressant resistance among patients with major depression: A nationwide longitudinal study". Eur Neuropsychopharmacol. Nov. 2016;26(11): 1760-1767.

Cheng, Z. et al. (Jan. 2019). Ethnic differences in eating disorder prevalence, risk factors, and predictive effects of risk factors among young women. Eating Behaviors, 32, pp. 23-30.

Chieffi, S. et al. (May 2017). Orexin system: The key for a healthy life. Front. Physiol., 8:357, doi: 10.3389/fphys.2017.00357, 9 pages.

Choi, G.B. et al. (Feb. 2016). The maternal interleukin-17a pathway in mice promotes autism-like phenotypes in offspring. Science, 351(6276):933-939.

Chrem, Mendez, P. et al. (2019). Biomarkers for Alzheimer's disease. Where we stand and where we are headed. Medicina (Buenos Aires), 79:546-551.

Citrome, L. (Aug. 2019). Binge eating disorder revisited: what's new, what's different, what's next. CNS Spectrums, 24, pp. 4-12.

Citrome, L. (Dec. 2014). Suvorexant for insomnia: A systematic review of the efficacy and safety profile for this newly approved hypnotic—What is the number needed to treat, number needed to harm and likelihood to be helped or harmed? Int. J. Clin. Pract., 68(12):1429-1441. https://doi.org/10.1111/ijcp.12568.

Ciz, M. et al. (Dec. 2007). Serotonin modulates the oxidative burst of human phagocytes via various mechanisms. Platelets, 18(8):583-590. https://doi.org/10.1080/09537100701471865.

Clark, B. (1968). Some early observations on the use of psilocybin in psychiatric patients. Brit. J. Soc. Psychiatry, 2:21-25.

Clemmensen, C. et al. (May 2012). The microtubule-associated protein 1A (MAP1A) is an early molecular target of soluble Aβ-peptide. Cellular and Molecular Neurobiology, 32(4):561-566.

Cleveland Clinic: "Bipolar Disorder" [Online]. Published on Apr. 12, 2022. Retrieved from Internet on Jun. 13, 2025. URL: https://my.clevelandclinic.org/health/diseases/9294-bipolar-disorder, 16 pages.

ClinicalTrials.gov, "Effects of Psilocybin in Major Depressive Disorder", NCT03181529, First posted Jun. 8, 2017, pp. 1-6.

clinicaltrials.gov, "Effects of SERT Inhibition on the Subjective Response to Psilocybin in Healthy Subjects", Study NCT03912974, Submitted Feb. 28, 2020. Retrieved from the Internet: URL:https://www.clinicaltrials.gov/ct2/history/NCT03912974?V_4=View#StudyPageTop [retrieved on Jan. 21, 2022]; 7 printed pages.

Cloez-Tayarani, I. et al. (Feb. 2003). Differential effect of serotonin on cytokine production in lipopolysaccharide-stimulated human peripheral blood mononuclear cells: Involvement of 5-hydroxytryptamine$_{2a}$ receptors. International Immunology, 15(2), 233-240. https://doi.org/10.1093/intimm/dxg027.

Coley, A.A., & Gao, W.J. (Jul. 2019). PSD-95 deficiency disrupts PFC-associated function and behavior during neurodevelopment. Scientific Reports, 9:9486, https://doi.org/10.1038/s41598-019-45971-w, 13 pages.

Collins, K.L. Et al. (Jun. 2018). A review of current theories and treatments for phantom limb pain. J Clin Invest, 128(6):2168-2176. https://doi.org/10.1172/JCI94003.

Colloca, L. et al. (Feb. 2017) Neuropathic pain. Nat Rev Dis Primers, 3:17002, doi:10.1038/nrdp.2017.2, 45 pages.

Connolly, J. et al. (Sep. 2015). ADHD & Pharmacotherapy: Past, Present and Future. Ther Innoc Regul Sci., 49(5):632-642. HHS Public Access, available in PMC Sep. 1, 2016, 19 pages.

Cooper, C.M. et al. (May 2015) Tianeptine in an experimental medicine model of antidepressant action. Journal of Psychopharmacology, 29(5):582-590.

Coric, V. et al. (Sep. 2005). Riluzole augmentation in treatment-resistant obsessive-compulsive disorder: An open-label trial. Biological Psychiatry, 58(5):424-428. https://doi.org/10.1016/j.biopsych.2005.04.043.

Cornillie, F. et al. (Apr. 2001) Infliximab induces potent anti-inflammatory and local immunomodulatory activity but no systemic immune suppression in patients with Crohn's disease. Alimentary Pharmacology and Therapeutics, 15(4), 463-473. https://doi.org/10.1046/j.1365-2036.2001.00956.x.

Cossrow, N. et al. (Aug. 2016). Estimating the Prevalence of Binge Eating Disorder in a Community Sample From the United States: Comparing DSM-IV-TR and DSM-5 Criteria. The Journal of Clinical Psychiatry, 77(8), pp. e968-e974.

Costa-Mattioli, M., & Monteggia, L.M. (Nov. 2013). mTOR complexes in neurodevelopmental and neuropsychiatric disorders. Nature Neuroscience, 16(11):1537-1543.

Cowie, M.R. et al. (Sep. 2015) Adaptive servo-ventilation for central sleep apnea in systolic heart failure. N. Engl. J. Med., 373:1095-1105. doi.org/10.1056/NEJMoa1506459.

Croall, I.D. et al. (Jun. 2020). Cognitive Deficit and White Matter Changes in Persons with Celiac Disease: a Population-Based Study. Gastroenterology. 158:2112-2122.

Crow, S.J. et al. (Dec. 2009). Increased mortality in bulimia nervosa and other eating disorders. American Journal of Psychiatry, 166(12):1342-1346.

Crowson, C. S. et al. (Aug. 2009). Which Measure of Inflammation to Use? A Comparison of Erythrocyte Sedimentation Rate and C-Reactive Protein Measurements from Randomized Clinical Trials of Golimumab in Rheumatoid Arthritis. The Journal of Rheumatology, 36(8):1606-1610. https://doi.org/10.3899/jrheum.081188.

Cruccu, G. (Dec. 2017) A Review of Neuropathic Pain: From Guidelines to Clinical Practice. Pain Ther, 6(Suppl 1):S35-S42.

Cryan, J.F. & Sweeney, F.F. (Oct. 2011). The age of anxiety: Role of animal models of anxiolytic action in drug discovery. British Journal of Pharmacology, 164:1129-1161.

Csicsvari, J. et al. (Jan. 2003). Mechanisms of gamma oscillations in the hippocampus of the behaving rat. Neuron, 37:311-322.

Culbert, K.M. et al. (Nov. 2015). Research Review: What we have learned about the causes of eating disorders—A synthesis of socio-cultural, psychological, and biological research. Journal of Child Psychology and Psychiatry, 56:11, pp. 1141-1164. https://doi.org/10.1111/jcpp.12441.

Curatolo, P. et al. (Dec. 2010) The neurobiological basis of ADHD. Ital J Pediatr, 36:79, http://www.ijponline.net/content/36/1/79, 7 pages.

(56)            References Cited

OTHER PUBLICATIONS

Cuthbert, P.C. et al. (Mar. 2007). Synapse-associated protein 102/dlgh3 couples the NMDA receptor to specific plasticity pathways and learning strategies. Journal of Neuroscience, 27(10):2673-2682. https://doi.org/10.1523/JNEUROSCI.4457-06.2007.

Da Silveira, D.X. et al. (Jun. 2005). Ayahuasca in adolescence: A preliminary psychiatric assessment. Journal of Psychoactive Drugs, 37:2, 129-133. https://doi.org/10.1080/02791072.2005.10399792.

Dahan, A. et al. (Oct. 2014) Comorbidities and the Complexities of Chronic Pain. Anesthesiology, 121(4):675-677.

Dalic, L., & Cook, M. (Oct. 2016). Managing drug-resistant epilepsy: challenges and solutions. Neuropsychiatric Disease and Treatment, vol. 12, p. 2605-2616. https://doi.org/10.2147/NDT.S84852.

Damasio A.R., "Alzheimer's Disease and Related Dementias," Cecil Textbook of Medicine, 20th Edition, vol. 2, 1996, pp. 1992-1996.

Dansie, E.J. & Turk, D.C. (Jul. 2013) Assessment of patients with chronic pain. Br J Anaesth. 111(1):19-25.

Darveaux, J., & Busse, W. W. (Apr. 2015). Biologics in Asthma—The Next Step Toward Personalized Treatment. J Allergy Clin Immunol Pract, 3(2), 152-160. https://doi.org/10.1016/j.jaip.2014.09.014.

Dash, S. (2019). The impact of genetic and cultural factors on anorexia and bulimia. Life Research, 2(2), 71-79. https://doi.org/10.12032/life2019-0425-004.

Dauer, W., & Przedborski, S. (Sep. 2003). Parkinson's Disease: Mechanisms and Models. Neuron, 39(6), 889-909. https://doi.org/10.1016/S0896-6273(03)00568-3.

Dauvilliers, Y. & Barateau, L. (Aug. 2017). Narcolepsy and Other Central Hypersomnias. Continyyn (Minneap Minn), 23(4):989-1004. https://doi.org/10.1212/CON.0000000000000492.

Dauvilliers, Y. et al. (Feb. 2007). Narcolepsy with cataplexy. Lancet 369, 499-511. https://doi.org/10.1016/S0140-6736(07)60237-2.

Dauvilliers, Y. et al (Jun. 2009). Psychological health in central hypersomnias: The French Harmony study. J. Neurol. Neurosurg. Psychiatry, 80, 636-641. https://doi.org/10.1136/jnnp.2008.161588.

Davila Gonzalez, I. et al. (Apr. 2019). Benralizumab: A New Approach for the Treatment of Severe Eosinophilic Asthma. Journal of Investigational Allergology and Clinical Immunology, 29(2), 84-93. https://doi.org/10.18176/jiaci.0385.

Davis, C. (Dec. 2015). The epidemiology and genetics of binge eating disorder (BED). CNS Spectrums, 20(6), pp. 522-529.

Davis et al., "Effects of psilocybin-assisted therapy on major depressive disorder: a randomized clinical trial," JAMA Psychiatry 78(5):481-489 (2021). doi: 10.1001/jamapsychiatry.2020.3285. Erratum in: JAMA Psychiatry. Feb. 10, 2021:569. doi: 10.1001/jamapsychiatry.2020.4714. (52 total pages).

Davis, H., & Attia, E. (Nov. 2017). Pharmacotherapy of eating disorders. Current Opinion in Psychiatry, 30(6), 452-457. https://doi.org/10.1097/YCO.0000000000000358.

De Heer et al., The Association of Depression and Anxiety with Pain: A Study from Nesda. PLOS ONE 9(10): e106907 pp. 1-11 (2014).

De Veen, B.T.H. et al. (Feb. 2017) "Psilocybin for treating substance use disorders?" Exp Rev Neurotherapeutics, 17(2):203-212; DOI: 10.1080/14737175.2016.1220834.

Deacon, R.M.J. & Rawlins, J.N.P. (2006) T-maze alternation in the rodent. Nat Protoc, 1(1):7-12. Available from: http://www.ncbi.nlm.nih.gov/pubmed/17406205.

Debacker, W.A. et al. (Jan. 1995). Central apnea index decreases after prolonged treatment with acetazolamide. Am. J. Respir. Crit. Care Med., 151:87-91, https://doi.org/10.1164/ajrccm.151.1.7812578.

Debotton, N. and A. Dahan (Jan. 2017) Applications of Polymers as Pharmaceutical Excipients in Solid Oral Dosage Forms. Med Res Rev, 37(1):52-97.

Decaluwe, V. and Braet, C. (2003). Prevalence of binge-eating disorder in obese children and adolescents seeking weight-loss treatment. International Journal of Obesity, 27(3), pp. 404-409.

Dejong, H. et al. (Nov. 2013). Quality of life in anorexia nervosa, bulimia nervosa and eating disorder not-otherwise-specified. Journal of Eating Disorders, 1:43, http://www.jeatdisord.com/content/1/1/43, 8 pages.

Delisi, M. et al. (Jul. 2019) The etiology of antisocial personality disorder: The differential roles of adverse childhood experiences and childhood psychopathology. Compr Psychiatry, 92:1-6.

Dell'Osso, B. et al. (Feb. 2018). Prevalence of suicide attempt and clinical characteristics of suicide attempters with obsessive-compulsive disorder: A report from the International College of Obsessive-Compulsive Spectrum Disorders (ICOCS). CNS Spectrums, 23(1), 59-66. https://doi.org/10.1017/S1092852917000177.

Depboylu, C. et al. (May 2015). Systemically administered neuregulin-1β1 rescues nigral dopaminergic neurons via the ErbB4 receptor tyrosine kinase in MPTP mouse models of Parkinson's disease. Journal of Neurochemistry, 133(4), 590-597. https://doi.org/10.1111/jnc.13026.

Di Lodovico, L., & Gorwood, P. (Feb. 2020). The relationship between moderate to vigorous physical activity and cognitive rigidity in anorexia nervosa. Psychiatry Research, 284:112703, https://doi.org/10.1016/j.psychres.2019.112703, 9 pages.

Dijkstra, P.U. et al. (Dec. 2002) Phantom pain and risk factors: A multivariate analysis. J Pain Symptom Manage. 24(6):578-585.

Diniz, J.B. et al. (Mar. 2010) "Quetiapine versus clomipramine in the augmentation of selective serotonin reuptake inhibitors for the treatment of obsessive-compulsive disorder: A randomized, open-label trial" Journal of Psychopharmacology, 24(3):297-307.

Dodick D W, et al., "Assessing Clinically Meaningful Treatment Effects in Controlled Trials: Chronic Migraine as an example," The Journal of pain, Feb. 2015;16(2):164-75.

Dold, M. et al. (Feb. 2015) "Second-Generation Antipsychotic Drugs in Anorexia Nervosa: A Meta-Analysis of Randomized Controlled Trials" Psychotherapy and Psychosomatics, 84(2):110-116. https://doi.org/10.1159/000369978.

Dold, M. et al. (May 2015). Antipsychotic Augmentation of Serotonin Reuptake Inhibitors in Treatment-Resistant Obsessive-Compulsive Disorder: An Update Meta-Analysis of Double-Blind, Randomized, Placebo-Controlled Trials. The International Journal of Neuropsychopharmacology, 1-11, https://doi.org/10.1093/ijnp/pyv047.

Dotterer, H.L. et al. (Apr. 2017) Amygdala reactivity predicts adolescent antisocial behavior but not callous-unemotional traits. Dev Cogn Neurosci, 24:84-92.

Drakatos, P. et al (Jul. 2017). Safety and efficacy of long-term use of sodium oxybate for narcolepsy with cataplexy in routine clinical practice. Sleep Med, 35:80-84. https://doi.org/10.1016/j.sleep.2017.03.028.

Droogleever Fortuyn, H.A. et al. (Aug. 2011). Narcolepsy and psychiatry: An evolving association of increasing interest. Sleep Med. 12, 714-719. https://doi.org/10.1016/j.sleep.2011.01.013.

Drover, D.R., 2004. Comparative pharmacokinetics and pharmacodynamics of short-acting hypnosedatives: Zaleplon, zolpidem and zopiclone. Clin. Pharmacokinet. 423(4):227-238. https://doi.org/10.2165/00003088-200443040-00002.

drugs.com (2014) Venlafaxine. Drugs.com, Web Archives [online]. Retrieved from: https://web.archive.org/web/20140502180823/https://www.drugs.com/venlafaxine.html; on May 2, 2014; 5 pages.

Dunning, C.J.R. et al. (May 2016). Multisite tyrosine phosphorylation of the N-terminus of Mint1/X11α by Src kinase regulates the trafficking of amyloid precursor protein. Journal of Neurochemistry, 137(4), 518-527. https://doi.org/10.1111/jnc.13571.

Durk, T. et al. (May 2005). 5-Hydroxytryptamine modulates cytokine and chemokine production in LPS-primed human monocytes via stimulation of different 5-HTR subtypes. International Immunology, 17(5), 599-606. https://doi.org/10.1093/intimm/dxh242.

Earle, W. J. (2014) "DSM-5" The Philosophical Forum [online]. Retrieved from: https://doi.org/10.1111/phil.12034; pp. 179-196.

Eckert, D.J. et al. (Feb. 2007). Central sleep apnea: Pathophysiology and treatment. Chest, 131:595-607. NIH Public Access Author Manuscript, available Apr. 3, 2008, 22 pages.

(56)  References Cited

OTHER PUBLICATIONS

Edfawy, M. et al. (Mar. 2019). Abnormal mGluR-mediated synaptic plasticity and autism-like behaviours in Gprasp2 mutant mice. Nature Communications. 10:1431, https://doi.org/10.1038/s41467-019-09382-9, 15 pages.
Edwards, A. (Jun. 2010) Book Review: Handbook of Depression (2nd ed.). Gotlib, I.H., Hammen, C.L. (Eds.), The Guilford Press: New York, 2009. Psychology Medicine, 40:1051-1052.
Eijk, S. et al. (Jul. 2018). Autism Spectrum Disorder in an Unselected Cohort of Children with Neurofibromatosis Type 1 (NF1). Journal of Autism and Developmental Disorders, 15:2278-2285. https://doi.org/10.1007/s10803-018-3478-0.
Ekbom, K. et al. (Mar. 2002) Age at onset and sex ratio in cluster headache: Observations over three decades. Cephalalgia, 22(2):94-100.
Elbassuoni, E. A., & Ahmed, R. F. (Dec. 2019). Mechanism of the neuroprotective effect of GLP-1 in a rat model of Parkinson's with pre-existing diabetes. Neurochemistry International, 131, 104583. https://doi.org/10.1016/j.neuint.2019.104583, 8 pages.
El-Emshaty, H. M., Nasif, W. A., & Mohamed, I. E. (Dec. 2015). Serum Cytokine of IL-10 and IL-12 in Chronic Liver Disease: The Immune and Inflammatory Response. Disease Markers, https://doi.org/10.1155/2015/707254, 7 pages.
El-Gabalawy, H., Guenther, L. C., & Bernstein, C. N. (May 2010). Epidemiology of Immune-Mediated Inflammatory Diseases: Incidence, Prevalence, Natural History, and Comorbidities. The Journal of Rheumatology Supplement, 85, 2-10. https://doi.org/10.3899/jrheum.091461.
Epstein JN, Loren Rea. (Oct. 2013) Changes in the definition of ADHD in DSM-5: Subtle but important. Neuropsychiatry, 3(5):455-8.
Erdur, L. et al. (Feb. 2012). Somatic comorbidity in anorexia nervosa: First results of a 21-year follow-up study on female inpatients. BioPsychoSocial Medicine, 6:4, https://doi.org/10.1186/1751-0759-6-4, 6 pages.
Erskine, H. and Whiteford, H.(Nov. 2018). Epidemiology of binge eating disorder. Current Opinion in Psychiatry, 31(6), pp. 462-470.
Essau, C.A. et al. (Jul. 2014). Anxiety disorders in adolescents and psychosocial outcomes at age 30. J. Affect. Disord. 163, 125-132. https://doi.org/10.1016/j.jad.2013.12.033. NIH Public Access Author Manuscript, 19 pages.
Evans, M.M. et al. (Jun. 2016) Ego-dissolution and psychedelics: Validation of the Ego-Dissolution Inventory (EDI). Front Human Neurosci, 10:269, doi: 10.3389/fnhum.2016.00269, 13 pages.
Everitt, H. et al. (May 2018). Antidepressants for insomnia in adults (Review). Cochrane Database Syst. Rev., Issue 5, Art. No. CD010753, https://doi.org/10.1002/14651858.CD010753.pub2, 117 pages.
Fadiman, J. & Korb, S. (Mar. 2019) Might Microdosing Psychedelics Be Safe and Beneficial? An Initial Exploration. J Psychoactive Drugs, 51(2):118-22. Available from: https://doi.org/10.1080/02791072.2019.1593561.
Fan, L.Y. et al. (Oct. 2018) Visual processing as a potential endophenotype in youths with attention-deficit/hyperactivity disorder: A sibling study design using the counting Stroop functional MRI. Hum Brain Mapp, 39(10):3827-35. Available from: http://www.ncbi.nlm.nih.gov/pubmed/29749060.
Fayaz, A. et al. (2016) Prevalence of chronic pain in the UK: a systematic review and meta-analysis of population studies. BMJ Open [Internet]. 6:e010364, doi:10.1136/bmjopen-2015-010364, 12 pages.
FDA mulls drug to slow late-stage Alzheimer's [Sep. 24, 2003] [online], [retrieved on Sep. 24, 2003]. Retrieved from the internet, http;//www.cnn/com/2003/HEALTH/conditions/09/24/alzheimers.drug.ap/index.html. pp. 1-3.
Feinstein, A.R. (Dec. 1970). The pre-therapeutic classification of co-morbidity in chronic disease. Journal of Chronic Diseases, 23(7), 455-468. https://doi.org/10.1016/0021-9681(70)90054-8.
Fekadu et al., "Standardisation framework for the Maudsley staging method for treatment resistance in depression," BMC Psychiatry (Apr. 11, 2018) 18:100, 13 pages.

Ferguson, S.A. et al. (Feb. 2010). Melatonin agonists and insomnia. Expert Rev. Neurother., 10(2):305-318. https://doi.org/10.1586/ern.10.1.
Fernandez, B. A., & Scherer, S.W. (Dec. 2017). Syndromic autism spectrum disorders: Moving from a clinically defined to a molecularly defined approach. Dialogues in Clinical Neuroscience, 19:353-371.
Feyder, M. et al. (Dec. 2010). Association of mouse Dlg4 (PSD-95) gene deletion and human DLG4 gene variation with phenotypes relevant to autism spectrum disorders and Williams' syndrome. American Journal of Psychiatry, 167:1508-1517. https://doi.org/10.1176/appi.ajp.2010.10040484.
Fiebich, B.L. et al. (2004). Antiinflammatory effects of 5-HT3 receptor antagonists in lipopolysaccharide-stimulated primary human monocytes. Scandinavian Journal of Rheumatology. 33:28-32. https://doi.org/15515409.
Fisher, G. (1970). The psycholytic treatment of a childhood schizophrenic girl. International Journal of Social Psychiatry. 16(2):112-130. https://doi.org/10.1177/002076407001600204.
Fisher, K.A & Hany, M. (Jun. 24, 2020) Antisocial Personality Disorder. StatPearls [Internet]. NCBI Bookshelf. Retrieved from: http://www.ncbi.nlm.nih.gov/pubmed/31536279, 6 printed pages.
Fisher, R.S. et al. (Apr. 2005). Epileptic Seizures and Epilepsy: Definitions Proposed by the International League Against Epilepsy (ILAE) and the International Bureau for Epilepsy (IBE). Epilepsia, 46(4), 470-472. https://doi.org/10.1111/j.0013-9580.2005.66104.x.
Flament, M.F. et al. (Mar. 2012) Evidence-based pharmacotherapy of eating disorders. The International Journal of Neuropsychopharmacology, 15(02), 189-207. https://doi.org/10.1017/S1461145711000381.
Flanagan, T.W. et al. (Nov. 2019). 5-HT2 receptor activation alleviates airway inflammation and structural remodeling in a chronic mouse asthma model. Life Sciences, 236:116790, https://doi.org/10.1016/j.lfs.2019.116790, 9 pages.
FMC Product Overview (2017) Avicel® SMCC HD 50 Silicified Microcrystalline cellulose NF. Product Specifications, 2 pages.
FMC Product Overview (2017) Avicel® SMCC HD 90 Silicified Microcrystalline cellulose NF. Product Specifications, 2 pages.
Folen, V. (Apr. 1975) X-ray powder diffraction data for some drugs, excipients, and adulterants in illicit samples. Journal of Forensic Science. 1975, 20, 348-372.
Fond, G. et al. (Dec. 2014). Anxiety and depression comorbidities in irritable bowel syndrome (IBS): a systematic review and meta-analysis. Eur. Arch. Psychiatry Clin. Neurosci. 264, 651-660. https://doi.org/10.1007/s00406-014-0502-z.
Fornasari, D. (Dec. 2017) Pharmacotherapy for Neuropathic Pain: A Review. Pain Ther, 6(Suppl 1):S25-S33.
Fortuyn, H.A.D. et al. (Feb. 2010). Anxiety and mood disorders in narcolepsy: a case-control study. Gen. Hosp. Psychiatry, 32:49-56. https://doi.org/10.1016/j.genhosppsych.2009.08.007.
Fortuyn, H.A.D. et al. (Mar. 2008). High Prevalence of Eating Disorders in Narcolepsy with Cataplexy: A Case-Control Study. Sleep 31, 335-341. https://doi.org/10.1093/sleep/31.3.335.
*Freedom to Operate, Inc.* v. *Compass Pathways Limited.* Case PGR2022-00012, U.S. Pat. No. 10,947,257. and *Freedom to Operate, Inc.* v. *Compass Pathways Limited.* Case PGR2022-00018, U.S. Pat. No. 10,954,259; Order that the requests for POP review are denied and original panel maintains authority over all matters, including considering the submitted rehearing requests, dated Feb. 10, 2023, 3 pages.
*Freedom to Operate, Inc.* v. *Compass Pathways Limited.* Case PGR2022-00012, U.S. Pat. No. 10,947,257. and *Freedom to Operate, Inc.* v. *Compass Pathways Limited.* Case PGR2022-00018,U.S. Pat. No. 10,954,259; Paper No. 21, Order Denying Petitioners Request on Rehearing, dated May 23, 2023, 9 pages.
*Freedom to Operate, Inc.* v. *Compass Pathways Limited.* Case PGR2022-00012, U.S. Pat. No. 10,947,257. Exhibit 1006: Declaration of Sven Lidin, Ph.D. (PTAB Dec. 15, 2021), 68 pages.
*Freedom to Operate, Inc.* v. *Compass Pathways Limited.* U.S. Pat. No. 10,947,257. Exhibit 1007: Curriculum Vitae—Sven Lidin, Ph.D. (PTAB Dec. 15, 2021), 2 pages.
*Freedom to Operate, Inc.* v. *Compass Pathways Limited.* Case PGR2022-00012, U.S. Pat. No. 10,947,257. Exhibit 1008: Declaration of James A. Kaduk, Ph.D. (PTAB Dec. 15, 2021), 25 pages.

(56) References Cited

OTHER PUBLICATIONS

*Freedom to Operate, Inc.* v. *Compass Pathways Limited.* Case PGR2022-00012, U.S. Pat. No. 10,947,257. Exhibit 1009: Curriculum Vitae—James A. Kaduk, Ph.D. (PTAB Dec. 15, 2021), 3 pages.
*Freedom to Operate, Inc.* v. *Compass Pathways Limited.* Case PGR2022-00012, U.S. Pat. No. 10,947,257. Exhibit 1010: Declaration of Raj Suryanarayanan, Ph.D. (PTAB Dec. 15, 2021), 23 pages.
*Freedom to Operate, Inc.* v. *Compass Pathways Limited.* Case PGR2022-00012, U.S. Pat. No. 10,947,257. Exhibit 1011: Curriculum Vitae—Raj Suryanarayanan, Ph.D. (PTAB Dec. 15, 2021), 53 pages.
*Freedom to Operate, Inc.* v. *Compass Pathways Limited.* Case PGR2022-00012, U.S. Pat. No. 10,947,257. Exhibit 1012: Declaration of Charles L. Raison, M.D. (PTAB Dec. 15, 2021), 6 pages.
*Freedom to Operate, Inc.* v. *Compass Pathways Limited.* Case PGR2022-00012, U.S. Pat. No. 10,947,257. Exhibit 1014: Arlin, J.B. et al. Experimental Crystal Structure Determination, pp. 1-3, 2021 (PTAB Dec. 15, 2021).
*Freedom to Operate, Inc.* v. *Compass Pathways Limited.* Case PGR2022-00012, U.S. Pat. No. 10,947,257. Exhibit 1015: Bernstein J. Polymorphism in Molecular Crystals, International Union of Crystallography, Oxford, 2002 (PTAB Dec. 15, 2021), 429 pages.
*Freedom to Operate, Inc.* v. *Compass Pathways Limited.* Case PGR2022-00012, U.S. Pat. No. 10,947,257. Exhibit 1016: Boratto, M. H. Semiconducting and Insulating Oxides Applied to Electronic Devices. Thesis Ph.D. UNESP, School of Science, Bauru, 2018. (PTAB Dec. 15, 2021), 117 pages.
*Freedom to Operate, Inc.* v. *Compass Pathways Limited.* Case PGR2022-00012, U.S. Pat. No. 10,947,257. Exhibit 1017: D.E. Nichols, Synthesis of High Purity Psilocybin: Lot 10415-25, Nov. 1, 2009. (PTAB Dec. 15, 2021), 43 pages.
*Freedom to Operate, Inc.* v. *Compass Pathways Limited.* Case PGR2022-00012, U.S. Pat. No. 10,947,257. Exhibit 1018: Jun. 6, 2012 Letter from D. Nichols to R. Griffiths. (PTAB Dec. 15, 2021), 7 pages.
*Freedom to Operate, Inc.* v. *Compass Pathways Limited.* Case PGR2022-00012, U.S. Pat. No. 10,947,257. Exhibit 1019: Apr. 15, 2014 Letter from C. Kim to E. Elder. (PTAB Dec. 15, 2021), 4 pages.
*Freedom to Operate, Inc.* v. *Compass Pathways Limited.* Case PGR2022-00012, U.S. Pat. No. 10,947,257. Exhibit 1020: Declaration of Brett D. Bobzien. (PTAB Dec. 15, 2021), 5 pages.
*Freedom to Operate, Inc.* v. *Compass Pathways Limited.* Case PGR2022-00012, U.S. Pat. No. 10,947,257. Exhibit 1021: Triclinic Labs Report, Characterization of Psilocybin, Dec. 2, 2021. (PTAB Dec. 15, 2021), 11 pages.
*Freedom to Operate, Inc.* v. *Compass Pathways Limited.* Case PGR2022-00012, U.S. Pat. No. 10,947,257. Exhibit 1023: USP35-(941) Physical Tests/X-Ray Powder Diffraction. (PTAB Dec. 15, 2021), 7 pages.
*Freedom to Operate, Inc.* v. *Compass Pathways Limited.* Case PGR2022-00012, U.S. Pat. No. 10,947,257. Exhibit 1024: Ottoboni S. et al. Understanding API Static Drying with Hot Gas Flow: Design and Test of a Drying Rig Prototype and Drying Modeling Development. Org. Process Res. Dev. 2020, 24, 2505-2520. (PTAB Dec. 15, 2021).
*Freedom to Operate, Inc.* v. *Compass Pathways Limited.* Case PGR2022-00012, U.S. Pat. No. 10,947,257. Exhibit 1025: Airaksinen S. et al. Comparison of the effects of two drying methods on polymorphism of theophylline. International Journal of Pharmaceutics 276 (2004) 129-141. (PTAB Dec. 15, 2021).
*Freedom to Operate, Inc.* v. *Compass Pathways Limited.* Case PGR2022-00012, U.S. Pat. No. 10,947,257. Exhibit 1026: Lim, H.L. et al., Understanding and preventing agglomeration in a filter drying process. Powder Technology, 300 (2016) 146-156. (PTAB Dec. 15, 2021).
*Freedom to Operate, Inc.* v. *Compass Pathways Limited.* Case PGR2022-00012, U.S. Pat. No. 10,947,257. Exhibit 1028: Curriculum Vitae—Charles L. Raison, M.D. (PTAB Dec. 15, 2021), 59 pages.
*Freedom to Operate, Inc.* v. *Compass Pathways Limited.* Case PGR2022-00012, U.S. Pat. No. 10,947,257. Exhibit 1029: Excerpt from Diagnostic and Statistical Manual of Mental Disorders, Fifth Edition, DSM-5. Am. Psychiatric Assn., 2013; pp. 160-168. (PTAB Dec. 15, 2021).
*Freedom to Operate, Inc.* v. *Compass Pathways Limited.* Case PGR2022-00012, U.S. Pat. No. 10,947,257. Exhibit 1030: Declaration of Roland R. Griffiths, Ph.D. (PTAB Dec. 15, 2021), 6 pages.
*Freedom to Operate, Inc.* v. *Compass Pathways Limited.* Case PGR2022-00012, U.S. Pat. No. 10,947,257. Exhibit 1031: Excerpt from A. Dictionary of Chemistry, 6th Edition. John Daintith (Ed.) Oxford University Press; p. 428 (PTAB Dec. 15, 2021), 3 pages.
*Freedom to Operate, Inc.* v. *Compass Pathways Limited.* Case PGR2022-00012, U.S. Pat. No. 10,947,257. Exhibit 1032: *Astrazeneca AB* v. *Reddy's Laboratories, Inc.,* Civil Action No. 11-2317 (May 1, 2013). 2013 U.S. Dist. Lexis 62149; Dec. 13, 2021. (PTAB Dec. 15, 2021), 17 pages.
*Freedom to Operate, Inc.* v. *Compass Pathways Limited.* Case PGR2022-00012, U.S. Pat. No. 10,947,257. Exhibit 1033: Baker R.W. et al. Molecular Structures of Hallucinogenic Substances: Lysergic Acid Diethylamide, Psilocybin, and 2,4,5-Trimethoxyamphetamine. Molecular Pharmacology, 9, 1973, 23-32. (PTAB Dec. 15, 2021).
*Freedom to Operate, Inc.* v. *Compass Pathways Limited.* Case PGR2022-00012, U.S. Pat. No. 10,947,257. Exhibit 1034: Petcher, T.J. and Weber, H.P. Crystal Structures of the Teonanacatl Hallucinogens. J. Chem Soc. Perkins Trans., 2, 8, 946-948, 1974. (PTAB Dec. 15, 2021).
*Freedom to Operate, Inc.* v. *Compass Pathways Limited.* Case PGR2022-00012, U.S. Pat. No. 10,947,257. Exhibit 1041: Sherwood A.M. et al. an Improved, Practical, and Scalable Five-Step Synthesis of Psilocybin. Synthesis 2020, 52, 688-694 (PTAB Dec. 15, 2021).
*Freedom to Operate, Inc.* v. *Compass Pathways Limited.* Case PGR2022-00012, U.S. Pat. No. 10,947,257. Exhibit 1042: dos Santos, R.G. et al. Antidepressive, anxiolytic, and antiaddictive effects of ayahuasca, psilocybin and lysergic acid diethylamide (LSD): a systematic review of clinical trials published in the last 25 years. Ther Adv Psychopharmacol, 2016, vol. 6(3), 193-213. (PTAB Dec. 15, 2021).
*Freedom to Operate, Inc.* v. *Compass Pathways Limited.* Case PGR2022-00012, U.S. Pat. No. 10,947,257. Exhibit 1043: Hill, R.J. Expanded Use of the Rietveld Method in Studies of Phase Abundance in Multiphase Mixtures. Powder Diffraction, Jun. 1991, vol. 6, No. 2, pp. 74-77. (PTAB Dec. 15, 2021).
*Freedom to Operate, Inc.* v. *Compass Pathways Limited.* Case PGR2022-00012, U.S. Pat. No. 10,947,257. Exhibit 1044: Groom, C.R. et al. The Cambridge Structural Database. Acta Cryst. (2016). B72, 171-179. (PTAB Dec. 15, 2021).
*Freedom to Operate, Inc.* v. *Compass Pathways Limited.* Case PGR2022-00012, U.S. Pat. No. 10,947,257. Exhibit 1045: Lee, P.L. et al. A twelve-analyzer detector system for high-resolution powder diffraction. J Synchrotron Rad. (2008). 15, 427-432. (PTAB Dec. 15, 2021).
*Freedom to Operate, Inc.* v. *Compass Pathways Limited.* Case PGR2022-00012, U.S. Pat. No. 10,947,257. Exhibit 1046: Wang, J. et al. A dedicated powder diffraction beamline at the Advanced Photon Source: Commissioning and early operational results. Review of Scientific Instruments, 79, 085105 (2008). (PTAB Dec. 15, 2021), 8 pages.
*Freedom to Operate, Inc.* v. *Compass Pathways Limited.* Case PGR2022-00012, U.S. Pat. No. 10,947,257. Exhibit 1047: Antao, S.M. et al. State-of-the-Art High-Resolution Powder X-Ray Diffraction (HRPXRD) Illustrated With Rietveld Structure Refinement of Quartz, Sodalite, Tremolite, and Meionite. The Canadian Mineralogist, vol. 46, pp. 1501-1509 (2008). (PTAB Dec. 15, 2021).
*Freedom to Operate, Inc.* v. *Compass Pathways Limited.* Case PGR2022-00012, U.S. Pat. No. 10,947,257. Exhibit 1048: Toby B.H. and Von Dreele, B. GSAS-II: The genesis of a modern

(56) References Cited

OTHER PUBLICATIONS open-source all purpose crystallography software package. J Appl Cryst, (2013) 46, 544-549. (PTAB Dec. 15, 2021).

*Freedom to Operate, Inc. v. Compass Pathways Limited.* Case PGR2022-00012, U.S. Pat. No. 10,947,257. Exhibit 1049: Sykes, R.A. et al. New software for statistical analysis of Cambridge Structural Database data. J Appl Cryst, (2011) vol. 44, pp. 882-886. (PTAB Dec. 15, 2021).

*Freedom to Operate, Inc. v. Compass Pathways Limited.* Case PGR2022-00012, U.S. Pat. No. 10,947,257. Exhibit 1050: Bruno, I.J. et al. Retrieval of Crystallographically-Derived Molecular Geometry Information, J Chem Inf Comput Sci (2004) vol. 44, pp. 2133-2144. (PTAB Dec. 15, 2021).

*Freedom to Operate, Inc. v. Compass Pathways Limited.* Case PGR2022-00012, U.S. Pat. No. 10,947,257. Exhibit 1051: Kresse, G. and Furthmüller, J. Efficiency of ab-initio total energy calculations for metals and semiconductors using a plane-wave basis set. Computational Materials Science (1996) vol. 6, pp. 15-50. (PTAB Dec. 15, 2021).

*Freedom to Operate, Inc. v. Compass Pathways Limited.* Case PGR2022-00012, U.S. Pat. No. 10,947,257. Exhibit 1052: Dovesi, R. et al. Quantum-mechanical condensed matter simulations with Crystal. WIREs Comput Mol Sci (2018) e1360, pp. 1-36. (PTAB Dec. 15, 2021).

*Freedom to Operate, Inc. v. Compass Pathways Limited.* Case PGR2022-00012, U.S. Pat. No. 10,947,257. Exhibit 1053: Gatti, C. et al. Crystal field effects on the topological properties of the electron density in molecular crystals: The case of urea. J Chem Phys (1994) vol. 101, 10686. (PTAB Dec. 15, 2021), 12 pages.

*Freedom to Operate, Inc. v. Compass Pathways Limited.* Case PGR2022-00012, U.S. Pat. No. 10,947,257. Exhibit 1054: Peintinger, M.F. et al. Consistent Gaussian Basis Sets of Triple-Zeta Valence with Polarization Quality for Solid-State Calculations. Journal of Computational Chemistry (2012) 1-9. (PTAB Dec. 15, 2021).

*Freedom to Operate, Inc. v. Compass Pathways Limited.* Case PGR2022-00012, U.S. Pat. No. 10,947,257. Exhibit 1055: Louër, D. and Boultif, A. Some further considerations in powder diffraction pattern indexing with the dichotomy method. Powder Diffraction, 29(S2), S7-S12, Dec. 2014. (PTAB Dec. 15, 2021).

*Freedom to Operate, Inc. v. Compass Pathways Limited.* Case PGR2022-00012, U.S. Pat. No. 10,947,257. Exhibit 1056: Kourkoumelis, K. Powdl: a Reusable .net Component for Interconverting Powder Diffraction Data. Recent Developments. Powder Diffr., vol. 28, No. 2, Jun. 2013, pp. 137-148. (PTAB Dec. 15, 2021).

*Freedom to Operate, Inc. v. Compass Pathways Limited.* Case PGR2022-00012, U.S. Pat. No. 10,947,257. Exhibit 1057: Curriculum Vitae—Roland R. Griffiths. (PTAB Dec. 15, 2021), 64 pages.

*Freedom to Operate, Inc. v. Compass Pathways Limited.* Case PGR2022-00012, U.S. Pat. No. 10,947,257. Exhibit 1058: Zeeh Pharmaceutical Experiment Station, University of Wisconsin—Madison School of Pharmacy. Certificate of Analysis for Lot No. 10415-25. (PTAB Dec. 15, 2021), 1 page.

*Freedom to Operate, Inc. v. Compass Pathways Limited.* Case PGR2022-00012, U.S. Pat. No. 10,947,257. Exhibit 1059: Barrett, F.S. et al. Double-blind comparison of the two hallucinogens psilocybin and dextromethorphan: Effects on cognition. Psychopharmacology (Berl), Oct. 2018; 235(10): 2915-2927. HHS Public Access Author Manuscript. (PTAB Dec. 15, 2021).

*Freedom to Operate, Inc. v. Compass Pathways Limited.* Case PGR2022-00012, U.S. Pat. No. 10,947,257. Exhibit 1060: Non-Final Office Action, Aug. 13, 2020 (PTAB Dec. 15, 2021), 9 pages.

*Freedom to Operate, Inc. v. Compass Pathways Limited.* Case PGR2022-00012, U.S. Pat. No. 10,947,257. Exhibit 1061: Applicant-Initiated Interview Summary, filed Oct. 14, 2020 (PTAB Dec. 15, 2021), 3 pages.

*Freedom to Operate, Inc. v. Compass Pathways Limited.* Case PGR2022-00012, U.S. Pat. No. 10,947,257. Exhibit 1062: Amendment/Response to Non-Final Office Action, filed Nov. 13, 2020 (PTAB Dec. 15, 2021), 8 pages.

*Freedom to Operate, Inc. v. Compass Pathways Limited.* Case PGR2022-00012, U.S. Pat. No. 10,947,257. Exhibit 1063: Lakshmana Prabhu, S. and Suriyaprakash, T.N.K. Impurities and Its Importance in Pharmacy. Int Journal of Pharmaceutical Sciences Review and Research, vol. 3, Issue 2, Jul.-Aug. 2010, Article 012, pp. 66-71. (PTAB Dec. 15, 2021).

*Freedom to Operate, Inc. v. Compass Pathways Limited.* Case PGR2022-00012, U.S. Pat. No. 10,947,257. Exhibit 1064: ICH Topic Q 3 A (R2) Impurities in New Drug Substances, 2006. (PTAB Dec. 15, 2021), 15 pages.

*Freedom to Operate, Inc. v. Compass Pathways Limited.* Case PGR2022-00012, U.S. Pat. No. 10,947,257. Exhibit 1065: Excerpts of Handbook of Pharma Excipients, Sixth Edition. Rowe, R.C. et al. (Eds.) London, UK: Pharmaceutical Press, 2011; pp. 129-133, 139-141 (PTAB Dec. 15, 2021).

*Freedom to Operate, Inc. v. Compass Pathways Limited.* Case PGR2022-00012, U.S. Pat. No. 10,947,257. Exhibit 1066: Martin's Physical Pharmacy and Pharmaceutical Sciences, Sixth Edition. P.J. Sinko (Ed.) Lippincott Williams & Wilkins, 2011; p. 564 (PTAB Dec. 15, 2021), 4 total pages.

*Freedom to Operate, Inc. v. Compass Pathways Limited.* Case PGR2022-00012, U.S. Pat. No. 10,947,257. Exhibit 1067: Supplemental Amendment, filed Nov. 19, 2020 (PTAB Dec. 15, 2021), 7 pages.

*Freedom to Operate, Inc. v. Compass Pathways Limited.* Case PGR2022-00012, U.S. Pat. No. 10,947,257. Exhibit 1068: The Manufacturing Process. Solid Dose Experts Techceuticals, vol. 15. (2015). (PTAB Dec. 15, 2021), 12 pages.

*Freedom to Operate, Inc. v. Compass Pathways Limited.* Case PGR2022-00012, U.S. Pat. No. 10,947,257. Exhibit 1069: Documentation of shipment of sample from Johns Hopkins University Batch to Triclinic Labs, Jul. 21, 2021. (PTAB Dec. 15, 2021), 3 pages.

*Freedom to Operate, Inc. v. Compass Pathways Limited.* Case PGR2022-00012, U.S. Pat. No. 10,947,257. Exhibit 1070: USP 24|NF 19. The Official Compendia of Standards, U.S. Pharmacopeia, 2000; pp. 738-739, 865-866. (PTAB Dec. 15, 2021).

*Freedom to Operate, Inc. v. Compass Pathways Limited.* Case PGR2022-00012, U.S. Pat. No. 10,947,257. Exhibit 1071: Sixsmith, D. The effect of compression on some physical properties of microcrystalline cellulose powders. J Pharm Pharmac, 1977, 29, 33-36. (PTAB Dec. 15, 2021).

*Freedom to Operate, Inc. v. Compass Pathways Limited.* Case PGR2022-00012, U.S. Pat. No. 10,947,257. Exhibit 1072: Curriculum Vitae—Brett D. Bobzien. (PTAB Dec. 15, 2021), 2 pages.

*Freedom to Operate, Inc. v. Compass Pathways Limited.* Case PGR2022-00012, U.S. Pat. No. 10,947,257. Exhibit 1073: Documentation of shipment of sample from Johns Hopkins University Batch to Triclinic Labs, Jul. 21, 2021. (PTAB Dec. 15, 2021), 3 pages.

*Freedom to Operate, Inc. v. Compass Pathways Limited.* Case PGR2022-00012, U.S. Pat. No. 10,947,257. Exhibit 1074: Altomare, A. et al. Expo2013: A kit of tools for phasing crystal structures from powder data. Journal of Applied Crystallography (2013) 46, 1231-1235. (PTAB Dec. 15, 2021).

*Freedom to Operate, Inc. v. Compass Pathways Limited.* Case PGR2022-00012, U.S. Pat. No. 10,947,257. Exhibit 1078: Petzoldt, C. et al. An example of how to handle amorphous fractions in API during early pharmaceutical development: SAR114137—A successful approach. European Journal of Pharmaceutics and Biopharmaceutics, 86 (2014) 337-350. (PTAB Dec. 15, 2021).

*Freedom to Operate, Inc. v. Compass Pathways Limited.* Case PGR2022-00012, U.S. Pat. No. 10,947,257. Exhibit 1079: Sivén, M. et al. Challenge of paediatric compounding to solid dosage forms sachets and hard capsules—Finnish perspective. Journal of Pharmacy and Pharmacol (2017) vol. 69, pp. 593-602 (PTAB Dec. 15, 2021).

*Freedom to Operate, Inc. v. Compass Pathways Limited.* Case PGR2022-00012, U.S. Pat. No. 10,947,257. Exhibit 1080: Tobyn, M. et al. (1998) Physicochemical comparison between microcrystalline cellulose and silicified microcrystalline cellulose. International Journal of Pharmaceutics, 169 (1998) 183-194. (PTAB Dec. 15, 2021).

(56) References Cited

OTHER PUBLICATIONS

*Freedom to Operate, Inc.* v. *Compass Pathways Limited.* Case PGR2022-00012, U.S. Pat. No. 10,947,257. Exhibit 1081: Packing Slip, Johns Hopkins BPRU Pharmacy to Triclinic Laboratories, Inc., Jul. 21, 2021. (PTAB Dec. 15, 2021), 2 pages.

*Freedom to Operate, Inc.* v. *Compass Pathways Limited.* Case PGR2022-00012, U.S. Pat. No. 10,947,257. Exhibit 1082: Triclinic Labs Inc., Standard Operating Procedure. Controlled Substances, No. G026.10 (PTAB Dec. 15, 2021), 11 pages.

*Freedom to Operate, Inc.* v. *Compass Pathways Limited.* Case PGR2022-00012, U.S. Pat. No. 10,947,257. Exhibit 1085: Sherwood, A.M. et al. Psilocybin: crystal structure solutions enable phase analysis of prior art and recently patented examples. Acta Cryst. (2022) C78, pp. 1-20. (PTAB Dec. 15, 2021).

*Freedom to Operate, Inc.* v. *Compass Pathways Limited.* Case PGR2022-00012, U.S. Pat. No. 10,947,257. Paper No. 18: Decision Denying Institution of Post-Grant Review (PTAB Jun. 22, 2022); 25 pages.

*Freedom to Operate, Inc.* v. *Compass Pathways Limited.* Case PGR2022-00012, U.S. Pat. No. 10,947,257. Paper No. 2: Petition for Post-Grant Review (PTAB Dec. 15, 2021), 68 pages.

*Freedom to Operate, Inc.* v. *Compass Pathways Limited.* Case PGR2022-00012, U.S. Pat. No. 10,947,257: Petitioner's Request for Rehearing Under 37 C.F.R. § 42.71 (PTAB Jul. 22, 2022); 17 pages.

*Freedom to Operate, Inc.* v. *Compass Pathways Limited.* Case PGR2022-00018, U.S. Pat. No. 10,954,259. Exhibit 1106: Declaration of Sven Lidin, Ph.D. (PTAB Dec. 22, 2021), 69 pages.

*Freedom to Operate, Inc.* v. *Compass Pathways Limited.* Case PGR2022-00018, U.S. Pat. No. 10,954,259. Exhibit 1108: Declaration of James A. Kaduk, Ph.D. (PTAB Dec. 22, 2021), 25 pages.

*Freedom to Operate, Inc.* v. *Compass Pathways Limited.* Case PGR2022-00018, U.S. Pat. No. 10,954,259. Exhibit 1110: Declaration of Raj Suryanarayanan, Ph.D. (PTAB Dec. 22, 2021), 23 pages.

*Freedom to Operate, Inc.* v. *Compass Pathways Limited.* Case PGR2022-00018, U.S. Pat. No. 10,954,259. Exhibit 1112: Declaration of Charles L. Raison, M.D. (PTAB Dec. 22, 2021), 6 pages.

*Freedom to Operate, Inc.* v. *Compass Pathways Limited.* Case PGR2022-00018, U.S. Pat. No. 10,954,259. Exhibit 1113: Roy, J. An Introduction to Pharmaceutical Sciences, Biohealthcare, UK (2011) (PTAB Dec. 22, 2021), 37 pages.

*Freedom to Operate, Inc.* v. *Compass Pathways Limited.* Case PGR2022-00018, U.S. Pat. No. 10,954,259. Exhibit 1120: Declaration of Brett D. Bobzien. (PTAB Dec. 22, 2021), 5 pages.

*Freedom to Operate, Inc.* v. *Compass Pathways Limited.* Case PGR2022-00018, U.S. Pat. No. 10,954,259. Exhibit 1130: Declaration of Roland R. Griffiths, Ph.D. (PTAB Dec. 22, 2021), 6 pages.

*Freedom to Operate, Inc.* v. *Compass Pathways Limited.* Case PGR2022-00018, U.S. Pat. No. 10,954,259. Exhibit 1160: Claims of '739 Application as Filed and Preliminary Amendment filed Dec. 9, 2020. (PTAB Dec. 22, 2021), 10 pages.

*Freedom to Operate, Inc.* v. *Compass Pathways Limited.* Case PGR2022-00018, U.S. Pat. No. 10,954,259. Exhibit 1161: Terminal Disclaimer. (PTAB Dec. 22, 2021), 3 pages.

*Freedom to Operate, Inc.* v. *Compass Pathways Limited.* Case PGR2022-00018, U.S. Pat. No. 10,954,259. Paper No. 16: Decision Denying Institution of Post-Grant Review (PTAB Jun. 22, 2022); 25 pages.

*Freedom to Operate, Inc.* v. *Compass Pathways Limited.* Case PGR2022-00018, U.S. Pat. No. 10,954,259. Paper No. 2: Petition for Post-Grant Review (PTAB Dec. 22, 2021), 67 pages.

*Freedom to Operate, Inc.* v. *Compass Pathways Limited.* Case PGR2022-00018, U.S. Pat. No. 10,954,259: Petitioner's Request for Rehearing Under 37 C.F.R. § 42.71 (PTAB Jul. 22, 2022); 17 pages.

Freudenberg, F., Alttoa, A., & Reif, A. (Jan. 2015). Neuronal nitric oxide synthase (NOS1) and its adaptor, NOS1AP, as a genetic risk factors for psychiatric disorders. Genes, Brain and Behavior, 14(1), 46-63. https://doi.org/10.1111/gbb.12193.

Fuchs, X. et al. (Jun. 2018) Psychological factors associated with phantom limb pain: A review of recent findings. Pain Res Manag, 2018:5080123, http://doi.org/10.1155/2018/5080123, 12 pages.

Funk, C. D., & Fitzgerald, G. A. (Nov. 2007). COX-2 Inhibitors and Cardiovascular Risk. Journal of Cardiovascular Pharmacology, 50(5), 470-479. https://doi.org/10.1097/FJC.0b013e318157f72d.

Galbiati, A. et al. (Feb. 2019). The risk of neurodegeneration in REM sleep behavior disorder: A systematic review and meta-analysis of longitudinal studies. Sleep Medicine Reviews, 43, 37-46. https://doi.org/10.1016/j.smrv.2018.09.008.

Galimberti, D. et al. (Sep. 2008). Association of a NOS1 promoter repeat with Alzheimer's disease. Neurobiology of Aging, 29(9), 1359-1365. https://doi.org/10.1016/j.neurobiolaging.2007.03.003.

Galmiche, M. et al. (May 2019). Prevalence of eating disorders over the 2000-2018 period: a systematic literature review. The American Journal of Clinical Nutrition, 109(5), pp. 1402-1413.

Gamez, W. et al. (Mar. 2014) The Brief Experiential Avoidance Questionnaire: Development and Initial Validation. Psychological Assessment. 26:35-45.

Gan, W., Mohamad, N. and Law, L. (2018). Factors Associated with Binge Eating Behavior among Malaysian Adolescents. Nutrients, 10:66, doi:10.3390/nu10010066, 12 pages.

Gandal, M. J. et al. (Feb. 2018). Shared molecular neuropathology across major psychiatric disorders parallels polygenic overlap. Science, 359:693-697. https://doi.org/10.1126/science.aad6469.

Gandy, M. et al. (Jan. 2013). Rates of DSM-IV mood, anxiety disorders, and suicidality in Australian adult epilepsy outpatients: A comparison of well-controlled versus refractory epilepsy. Epilepsy Behav. 26, 29-35. https://doi.org/10.1016/j.yebeh.2012.10.023.

Ganesan, H. et al. (Jun. 2019). mTOR signalling pathway—A root cause for idiopathic autism? BMB Reports, 52(7):424-433.

Garcia-Rayado, G., Navarro, M., & Lanas, A. (Oct. 2018). NSAID induced gastrointestinal damage and designing GI-sparing NSAIDs. Expert Review of Clinical Pharmacology, 11(10), 1031-1043. https://doi.org/10.1080/17512433.2018.1516143.

Garcia-Romeu et al., "Psilocybin-occasioned mystical experiences in the treatment of tobacco addiction", Current Drug Abuse Reviews (2014); 7(3): 157-164. doi: 10.2174/1874473708666150107121331.

Gasior, M. et al (Jun. 2017). A Phase 3, Multicenter, Open-Label, 12-Month Extension Safety and Tolerability Trial of Lisdexamfetamine Dimesylate in Adults With Binge Eating Disorder. Journal of Clinical Psychopharmacology, 37(3), pp. 315-322.

Gau, S.S.-F. & Huang, W.L. (Jan. 2014) Rapid visual information processing as a cognitive endophenotype of attention deficit hyper-activity disorder. Psychol Med, 44(2):435-446.

Gaul, C. et al. (Aug. 2011) Cluster Headache—Clinical Features and Therapeutic Options. Deutsches Arzteblatt International, 108(33):543-549.

GBD 2016 Parkinson's Disease Collaborators. (2018). Global, regional, and national burden of Parkinson's disease, 1990-2016: a systematic analysis for the Global Burden of Disease Study 2016. The Lancet. Neurology, 17(11), 939-953. https://doi.org/10.1016/S1474-4422(18)30295-3.

Gessner, P.K. et al. (Oct. 1960) The relationship between the metabolic fate and pharmacological actions of serotonin, bufotenine and psilocybin. J. Pharmacol. Exp. Ther., 130:126-133.

Ghanizadeh, A. (May 2015 ) A systematic review of reboxetine for treating patients with attention deficit hyperactivity disorder. Nord J Psychiatry. 69(4):241-8.

Gibb, A. & Deeks, E.D.(Jan. 2014). Vortioxetine: First global approval. Drugs 74:135-145, https://doi.org/10.1007/s40265-013-0161-9, 11 pages.

Gilon Mann, T. et al. (Jul. 2018). Different attention bias patterns in anorexia nervosa restricting and binge/purge types. European Eating Disorders Review, 26(4):293-301. https://doi.org/10.1002/erv.2593.

Giovinazzo, S. et al. (Apr. 2019). Anorexia nervosa and heart disease: a systematic review. Eating and Weight Disorders—Studies on Anorexia, Bulimia and Obesity, vol. 24, Issue 2, pp. 199-207. https://doi.org/10.1007/s40519-018-0567-1.

Glaesmer, H. et al. (May 2012) Psychometric properties and population-based norms of the Life Orientation Test Revised (LOT-R). British Journal of Health Psychology, 17:432-445.

(56)            References Cited

OTHER PUBLICATIONS

Glashouwer, K. A., Van Der Veer, R. M. L., Adipatria, F., De Jong, P. J., & Vocks, S. (Dec. 2019). The role of body image disturbance in the onset, maintenance, and relapse of anorexia nervosa: A systematic review. Clinical Psychology Review, 74:101771; DOI:10.1016/j.cpr.2019.101771, 21 pages.
Glenn, A.L. et al. (Dec. 2013) Antisocial personality disorder: A current review. Current Psychiatry Reports, 15:427, DOI: 10.1007/s11920-013-0427-7, 9 pages.
Global Burden of Disease Study Aug. 2013 Collaborators. (2015). Global, regional, and national incidence, prevalence, and years lived with disability for 301 acute and chronic diseases and injuries in 188 countries, 1990-2013: a systematic analysis for the Global Burden of Disease Study 2013. Lancet (London, England), 386(9995), 743-800. https://doi.org/10.1016/S0140-6736(15)60692-4.
Golden, E.C. & Lipford, M.C. (Dec. 2018). Narcolepsy: Diagnosis and management. Cleveland Clin. J. Med., 85(12):959-969. https://doi.org/10.3949/ccjm.85a.17086.
Goldstein-Piekarski, A.N. et al. (Jun. 2016). A trans-diagnostic review of anxiety disorder comorbidity and the impact of multiple exclusion criteria on studying clinical outcomes in anxiety disorders. Transl. Psychiatry, 6:e847, doi.org/10.1038/tp.2016.108, 9 pages.
Golyala, A., & Kwan, P. (Jan. 2017). Drug development for refractory epilepsy: The past 25 years and beyond. Seizure, 44, 147-156. https://doi.org/10.1016/j.seizure.2016.11.022.
Golzari, S.E.J. et al. Lidocaine and pain management in the emergency department: A review article. Anesthesiol Pain Med. (Feb. 2014); 4(1):1-6.
Gong, D. et al. (Jun. 2012). TGFβ signaling plays a critical role in promoting alternative macrophage activation. BMC Immunology, 13:31, https://doi.org/10.1186/1471-2172-13-31, 10 pages.
Gonzalez-Maeso J. et al. (Mar. 24, 2008) "Identification of a serotonin/glutamate receptor complex implicated in psychosis" Nature, 452(7183):93-7. Available from: http://www.nature.com/articles/nature06612.
González-Maeso et al., "Hallucinogens recruit specific cortical 5-HT2A receptor-mediated signaling pathways to affect behavior", Neuron (2007); 53(3): 439-452. doi: 10.1016/j.neuron.2007.01.008.
Gooriah, R. et al. (Nov. 2015) Evidence-based treatments for cluster headache. Ther Clin Risk Manag, 11:1687-1696. Available from: http://dx.doi.org/10.2147/TCRM.S94193.
Gorla, K., & Mathews, M. (Jun. 2005). Pharmacological treatment of eating disorders. Psychiatry, 2(6), 43-48. http://www.ncbi.nlm.nih.gov/pubmed/21152155.
Gotvaldova et al., "Stability of psilocybin and its four analogs in the biomass of the psychotropic mushroom Psilocybe cubensis," Drug Test Anal. Feb. 2021;13(2):439-446. Epub Nov. 4, 2020.
Gouzoulis-Mayfrank, E. et al (2002). Effects of the hallucinogen psilocybin on covert orienting of visual attention in humans. Neuropsychobiology, 45(4):205-212. Available from: http://www.ncbi.nlm.nih.gov/pubmed/12097810.
Grant, A.M. et al. (2002) The Self-Reflection and Insight Scale: A New Measure of Private Self-Consciousness. Social Behavior and Personality, 30(8), 821-836.
Grant, J. et al. (Jul. 2019). A double-blind, placebo-controlled study of vortioxetine in the treatment of binge-eating disorder. International Journal of Eating Disorders, 52(7), pp. 786-794.
Greenan, C. et al (Feb. 13, 2020) "Preparation and Characterization of Novel Crystalline Solvates and Polymorphs of Psilocybin and Identification of Solid Forms Suitable for Clinical Development" Preprint [online]. Retrieved from ResearchGate: https://www.researchgate.net/publication/339238710, 29 printed pages.
Greten, F.R. et al. (Sep. 2007). NF-κB Is a Negative Regulator of IL-1β Secretion as Revealed by Genetic and Pharmacological Inhibition of IKKβ. Cell, 130(5), 918-931. https://doi.org/10.1016/j.cell.2007.07.009.
Greyson, B., The Near-Death Experience Scale, The Journal of Nervous and Mental Disease, 171:369-375 (1983).

Grieco, M et al. (Oct. 2019). Glucagon-Like Peptide-1: A Focus on Neurodegenerative Diseases. Frontiers in Neuroscience, 13, Article 1112, 7 pages. https://doi.org/10.3389/fnins.2019.01112.
Grieshaber, A. F., Moore, K. A., & Levine, B. (May 2001). The detection of psilocin in human urine. Journal of Forensic Sciences, 46(3), 627-630. http://www.ncbi.nlm.nih.gov/pubmed/11373000.
Griffin, C.E. et al. (2013). Benzodiazepine pharmacology and central nervous system-mediated effects. Ochsner J. 13, 214-223.
Griffiths et al., "Psilocybin occasioned mystical-type experiences: immediate and persisting dose-related effects", Psychopharmacology (2011); 218: 649-665. doi: 10.1007/s00213-011-2358-5. Epub Jun. 15, 2011.
Griffiths et al., "Psilocybin produces substantial and sustained decreases in depression and anxiety in patients with life-threatening cancer: a randomized double-blind trial", Journal of Psychopharmacology (2016); 30: 1181-1197. doi: 10.1177/0269881116675513.
Griffiths, K. (Jul. 2019). Understanding the neural mechanisms of lisdexamfetamine dimesylate (LDX) pharmacotherapy in Binge Eating Disorder (BED): a study protocol. Journal of Eating Disorders, 7:23, https://doi.org/10.1186/s40337-019-0253-3, 10 pages.
Griffiths, K.R. et al. (2017). "Sustained attention and heart rate variability in children and adolescents with ADHD." Biol Psychol [Internet]. 124:11-20. Available from: http://www.ncbi.nlm.nih.gov/pubmed/28099875.
Griffiths, R.R. et al. (Aug. 2006) Psilocybin can occasion mystical-type experiences having substantial and sustained meaning and spiritual significance. Psychopharmacol (Berl), 187(3):268-283.
Griffiths, S. (Oct. 2019). "The Vulnerability Experiences Quotient (VEQ): A Study of Vulnerability, Mental Health and Life Satisfaction in Autistic Adults." Autism Research. (10):1516-28. https://doi.org/10.1002/aur.2162.
Grilo, C. et al. (Dec. 2012). 12-month follow-up of fluoxetine and cognitive behavioral therapy for binge eating disorder. Journal of Consulting and Clinical Psychology, 80(6), pp. 1108-1113.
Grilo, C., Reas, D. and Mitchell, J. (2016). Combining Pharmacological and Psychological Treatments for Binge Eating Disorder: Current Status, Limitations, and Future Directions. Current Psychiatry Reports, 18:55, doi:10.1007/s11920-016-0696-z, 11 pages.
Grob, C.S. et al. (2013) Chapter 17: Use of the Classic Hallucinogen Psilocybin for Treatment of Existential Distress Associated with Cancer. In B.I. Carr and J. Steel (Eds.) Psychological Aspsects of Cancer. Springer Science + Business Media; p. 291-308.
Grob et al., "Pilot study of psilocybin treatment for anxiety in patients with advanced-stage cancer", Archives of General Psychiatry (2011); 68(1): 71-78. doi: 10.1001/archgenpsychiatry.2010.116. Epub Sep. 6, 2010.
Guerdjikova, A. et al. (Apr. 2016). Novel pharmacologic treatment in acute binge eating disorder—role of lisdexamfetamine. Neuropsychiatric Disease and Treatment, 12:833-841.
Guerreiro, R. et al. (Oct. 2015). "The age factor in Alzheimer's disease." Genome Medicine, 7:106, https://doi.org/10.1186/s13073-015-0232-5, 3 pages.
Guo, M. et al. (2003) "Potential Application of Silicified Microcrystalline Cellulose in Direct-Fill Formulations for Automatic Capsule-Filling Machines," Pharmaceutical Development and Technology, vol. 8, No. 1, pp. 47-59.
Gupta, S. P. et al. (Jul. 2016). "Association of Polymorphism of Neuronal Nitric Oxide Synthase Gene with Risk to Parkinson's Disease." Molecular Neurobiology, 53(5), 3309-3314. https://doi.org/10.1007/s12035-015-9274-3.
Guze, S.B. , Diagnostic and Statistical Manual of Mental Disorders, 4th ed. (DSM-IV). Am. J. Psychiatry, 152, p. 1228 (1995).
Hajihosseini, A. et al. (Apr. 2012). "The role of beta-gamma oscillations in unexpected rewards processing." Neuroimage. 60(3):1678-85. https://doi.org/10.1016/j.neuroimage.2012.01.125.
Halberstadt, A. L. et al. (Jan. 2011). "Multiple receptors contribute to the behavioral effects of indoleamine hallucinogens." Neuropharmacology, 61(3):364-381, https://doi.org/10.1016/j.neuropharm.2011.01.017.
Halberstadt et al., "Correlation between the potency of hallucinogens in the mouse head-twitch response assay and their behavioral

(56)        References Cited

OTHER PUBLICATIONS and subjective effects in other species." Neuropharmacology. May 1, 2020: 167: 107933. doi: 10.1016/j.neuropharm.2019.107933. Epub Jan. 7, 2020, 12 pages.

Hall N. et al. (2018). "Phantom limb pain: a review of pharmacological management." Br J Pain [Internet]. 12(4):202-7. Available from: https://doi.org/10.1177/2049463717747307.

Halpern, J.H. (Oct. 2003) Hallucinogens: An Update. Current Psychiatry Reports, 5:347-354.

Hama, Y. et al. (2015). "Level of plasma neuregulin-1 SMDF is reduced in patients with idiopathic Parkinson's disease." Neuroscience Letters, 587, 17-21. https://doi.org/10.1016/j.neulet.2014.12.024.

Hamadjida, A. et al. (Jun. 2020). "The highly selective mGlu2 receptor positive allosteric modulator LY-487,379 alleviates l-DOPA-induced dyskinesia in the 6-OHDA-lesioned rat model of Parkinson's disease." The European Journal of Neuroscience. 51(12): 2412-2422. https://doi.org/10.1111/ejn.14679.

Hamilton. "A rating scale for depression", Journal of Neurology, Neurosurgery, and Psychiatry (1960); 23(1): 56-62. doi: 10.1136/jnnp.23.1.56.

Hancock et al., "Characteristics and significance of the amorphous state in pharmaceutical systems", Journal of Pharmaceutical Sciences (Jan. 1997); 86(1): 1-12.

Hanes, K.R. (Apr. 1996). "Serotonin, Psilocybin, and Body Dysmorphic Disorder." Journal of Clinical Psychopharmacology, 16(2), pp. 188-189.

Hanyu-Deutmeyer, A.A. et al. (Sep. 12, 2020) Phantom Limb Pain. StatPearls. StatPearls Publishing. [online]. Available from NCBI Bookshelf: http://www.ncbi.nlm.nih.gov/pubmed/28846343, 6 pages.

Haroon, E. et al. (May 2018). Antidepressant treatment resistance is associated with increased inflammatory markers in patients with major depressive disorder. Psychoneuroendocrinology, 95:43-49. https://doi.org/10.1016/j.psyneuen.2018.05.026.

Hasler et al., "Acute psychological and physiological effects of psilocybin in healthy humans: a double-blind, placebo-controlled dose-effect study", Psychopharmacology (2004); 172: 145-156. doi: 10.1007/s00213-003-1640-6. Epub Nov. 13, 2003.

Hasler et al., "Determination of psilocin and 4-hydroxyindole-3-acetic acid in plasma by HPLC-ECD and pharmacokinetic profiles of oral and intravenous psilocybin in man", Pharmaceutica Acta Helvetiae (1997); 72(3): 175-184. doi: 10.1016/s0031-6865(97)00014-9.

Hasler et al., "Renal excretion profiles of psilocin following oral administration of psilocybin: a controlled study in man", Journal of Pharmaceutical and Biomedical Analysis (2002); 30(2): 331-339. doi: 10.1016/s0731-7085(02)00278-9.

Heal, D. et al. (Jun. 2017). Dopamine and μ-opioid receptor dysregulation in the brains of binge-eating female rats—possible relevance in the psychopathology and treatment of binge-eating disorder. Journal of Psychopharmacology, 31(6), pp. 770-783.

Hebert, L.E. et al. (May 2013). "Alzheimer disease in the United States (2010-2050) estimated using the 2010 census." Neurology, 80(19), 1778-1783. https://doi.org/10.1212/WNL.0b013e31828726f5.

Heim, R. et al. (Mar. 3, 1958) "Mycologie—Determinisme de la formation des carpophores et des sclerotes dans la culture du Psilocybe mexicana Heim, Agaric hallucinogene du Mexique, et mise en evidence de la psilocybine et de la psilocine [Mycology—Determinism in the formation of carpophores and sclerotia in the cultivation of Psilocybe mexicana Heim, an hallucinogenic Agaric of Mexico, and isolation of psilocybin and psilocyn]" Comptes Rendus Hebdomadaires des Seances de L'Academie des Sciences [Weekly Reports of the Sessions of the Academy of Sciences], 246(9):1346-1351, 19 pages total.

Herr, N. et al. (Jul. 2017). "The Effects of Serotonin in Immune Cells." Frontiers in Cardiovascular Medicine, 4, Article 48, 11 pages. https://doi.org/10.3389/fcvm.2017.00048.

Herring, W.J. et al. (Dec. 2012). "Orexin receptor antagonism for treatment of insomnia: A randomized clinical trial of suvorexant." Neurology 79, 2265-2274. https://doi.org/10.1212/WNL.0b013e31827688ee.

Hibicke, M. et al. (Apr. 1, 2019). "Psychedelics Improve the Mental Health of Rats." FASEB J., 33(S1):666.1; https://doi.org/10.1096/fasebj.2019.33.1_supplement.666.1, 3 pages.

Hilbert, A. et al. (Jan. 2019). Meta-analysis of the efficacy of psychological and medical treatments for binge-eating disorder. Journal of Consulting and Clinical Psychology, 87(1), pp. 91-105.

Hilfiker, Polymorphism: In the Pharmaceutical Industry. Wiley-VCH Vrlag GmbH & Co. KGaA, Weinheim. (2.7 Crystallization of Polymorphs; 8.3 Statistical Aspects and Frequency of Solvates, 18 pages (2016). retrieved at https://onlinelibrary.wiley.com/doi/epdf/10.1002/3527607889.fmatter.

Hill, L.S. et al. (May 2010) Scoff, the development of an eating disorder screening questionnaire. International Journal of Eating Disorders, 43(4):344-351. https://doi.org/10.1002/eat.20679.

Himmerich, H. et al. (Apr. 2019). "Psychiatric comorbidity as a risk factor for mortality in people with anorexia nervosa." European Archives of Psychiatry and Clinical Neuroscience, 269(3), 351-359. https://doi.org/10.1007/s00406-018-0937-8.

Hoek, H. et al. (Dec. 2003). "Review of the Prevalence and Incidence of Eating Disorders." International Journal of Eating Disorders, vol. 34, Issue 4, pp. 383-396. https://doi.org/10.1002/eat.10222.

Hofmann, A. et al. (Mar. 15, 1958) "Psilocybin, ein psychotroper Wirkstoff aus dem mexikanischen Rauschpilz Psilocybe mexicana Heim [Psilocybin, a psychotropic substance from Mexican magic mushrooms Psilocybe mexicana Heim]" Experientia, 14(3):107-109, with English translation (3 pages).

Hofmann, A. et al. (1959) "Psilocybin und Psilocin, zwei psychotrope Wirkstoffe aus mexikanischen Rauschpilzen [Psilocybin and Psilocin, two psychotropic active substances from Mexican magic mushrooms" Helvetica Chimica Acta, vol. XLII, Issue v, No. 168, pp. 1557-1572, with English translation (17 pages).

Hofmann, A. et al. (Nov. 1958) "Konstitutionsaufklärung und Synthese von Psilocybin [Constitutional elucidation and synthesis of psilocybin]" Experientia, 14(11):397-399, with English translation (3 pages).

Holtkamp, K. et al. (May 2005). "A retrospective study of SSRI treatment in adolescent anorexia nervosa: Insufficient evidence for efficacy." Journal of Psychiatric Research, 39(3), 303-310. https://doi.org/10.1016/j.jpsychires.2004.08.001.

Hood, S.D. et al. (Feb. 2014). "Benzodiazepine dependence and its treatment with low dose flumazenil." Br. J. Clin. Pharmacol. 77, 285-294. https://doi.org/10.1111/bcp.12023.

Howell, M. J. et al. (Jun. 2015). "Rapid Eye Movement Sleep Behavior Disorder and Neurodegenerative Disease." JAMA Neurology, 72(6), 707-712. https://doi.org/10.1001/jamaneurol.2014.4563.

Hoyer, D. et al. (1985). "Molecular pharmacology of 5-HT1 and 5-HT2 recognition sites in rat and pig brain membranes: Radioligand binding studies with [3H]5-HT, [3H]8-OH-DPAT, (−)[125I]iodocyanopindolol, [3H]mesulergine and [3H]Ketanserin." Eur J Pharmacol. 118(1-2):13-23.

Hsu, E. et al. (Feb. 2013). "Postamputation pain: Epidemiology, mechanisms, and treatment." J Pain Res, 6:121-136. http://dx.doi.org/10.2147/JPR.S32299.

Huang, H. et al. (Oct. 2016). "Genetic association of NOS1 exon18, NOS1 exon29, ABCB1 1236C/T, and ABCB1 3435C/T polymorphisms with the risk of Parkinson's disease: A meta-analysis." Medicine, 95(40), e4982, pp. 1-9. https://doi.org/10.1097/MD.0000000000004982.

Hudson, C.C. et al. (Jan. 2019). "Prevalence of Depressive Disorders in Individuals with Autism Spectrum Disorder: a Meta-Analysis." Journal of Abnormal Child Psychology. 47(1):165-75. https://doi.org/10.1007/s10802-018-0402-1.

Hudson, J.I. et al. (Feb. 2007). "The Prevalence and Correlates of Eating Disorders in the National Comorbidity Survey Replication." Biological Psychiatry, 61(3), 348-358. https://doi.org/10.1016/j.biopsych.2006.03.040.

Hudson, J.I. et al. (May 1992). "Polysomnographic Characteristics of Young Manic Patients: Comparison with Unipolar Depressed

(56)        References Cited

OTHER PUBLICATIONS

Patients and Normal Control Subjects." Arch. Gen. Psychiatry 49, 378-383. https://doi.org/10.1001/archpsyc.1992.01820050042006.

Huecker, M. et al. (2020). Bupropion. StatPearls. NCBI Bookshelf [online]. Retrieved from: https://www.ncbi.nlm.nih.gov/books/NBK470212/; retrieved on Jul. 30, 2020, 4 pages.

Huedo-Medina, T.B. et al. (Dec. 2012). "Effectiveness of non-benzodiazepine hypnotics in treatment of adult insomnia: Meta-analysis of data submitted to the Food and Drug Administration." BMJ, 345:e8343,. https://doi.org/10.1136/bmj.e8343, 13 pages.

Huff et al. (2020) Neuroanatomy, Cranial Nerve 5 (Trigeminal). StatPearls. StatPearls Publishing; Available from NCBI Bookshelf: http://www.ncbi.nlm.nih.gov/pubmed/29489263, pp. 1-8.

Hughes, J.R. (Jul. 2008). "Gamma, fast, and ultrafast waves of the brain: Their relationships with epilepsy and behavior." Epilepsy Behav. 13(1):25-31. https://doi.org/10.1016/j.yebeh.2008.01.011.

Hussman, J.P. et al. (Jan. 2011). "A noise-reduction GWAS analysis implicates altered regulation of neurite outgrowth and guidance in autism." Molecular Autism. 2, 1, pp. 1-16. https://doi.org/10.1186/2040-2392-2-1.

Hutson, P., Balodis, I. and Potenza, M. (Feb. 2018). Binge-eating disorder: Clinical and therapeutic Advances. Pharmacology & Therapeutics, 182:15-27.

Hutten, N.R.P.W. et al. (2019). "Self-Rated Effectiveness of Microdosing With Psychedelics for Mental and Physical Health Problems Among Microdosers." Front Psychiatry [Internet]. 10:672, pp. 1-9. Available from: http://www.ncbi.nlm.nih.gov/pubmed/31572246.

Huysmans, S. et al. (2019). "Melatonin and sleep disorders: Overview of literature and testing in psychiatric practice." Tijdschr. Psychiatr. 61, 854-861.

Hvolby, A. (Aug. 2014). "Associations of sleep disturbance with ADHD: implications for treatment." ADHD Atten. Deficit Hyperact. Disord. 7(1):1-8. https://doi.org/10.1007/s12402-014-0151-0.

Hwang, J.Y. et al. (2008) The development of the Santa Clara brief compassion scale: An abbreviation of Sprecher and Fehr's compassionate love scale. Pastoral Psychology, 56(4):421-428.

ICH (Jun. 2017) Q3C—Tables and List Guidance for Industry. U.S. Department of Health and Human Services, Food and Drug Administration, Center for Drug Evaluation and Research (CDER), Center for Biologics Evaluation and Research (CBER) Revision 3, 10 pages.

Infliximab Side Effects. (2019). Drugs.Com [online]. Retrieved Sep. 12, 2020 from: https://www.drugs.com/sfx/infliximab-side-effects.html, 11 pages.

Institute for Quality and Efficiency in Health Care (IQWIG) (Oct. 2017). Treatment options for generalized anxiety disorder [online]. InformedHealth.org. Retrieved from: https://www.ncbi.nlm.nih.gov/books/NBK279594/?report=printable; retrieved on Jul. 30, 2020, 3 pages.

Institute for Quality and Efficiency in Health Care (IQWiG) (Feb. 2018). What is an inflammation? [online]. Retrieved from: https://www.ncbi.nlm.nih.gov/books/NBK279298/; retrieved on Jul. 30, 2020, 1 page.

International Search Report and Written Opinion for PCT/IB2018/057811 mailed on Mar. 11, 2019, 10 pages.

International Search Report and Written Opinion issued in International Patent Application No. PCT/IB2020/053684, mailed Aug. 26, 2020, with Notification of Transmittal; 24 total pages.

International Search Report and Written Opinion issued in International Patent Application No. PCT/IB2020/053687, mailed Aug. 26, 2020, with Notification of Transmittal; 22 total pages.

International Search Report and Written Opinion issued in International Patent Application No. PCT/IB2020/053688, mailed Aug. 26, 2020, with Notification of Transmittal; 30 total pages.

Isaacson, R.S. et al. (Dec. 2018). "The clinical practice of risk reduction for Alzheimer's disease: A precision medicine approach." Alzheimer's & Dementia : The Journal of the Alzheimer's Association, 14(12), 1663-1673. https://doi.org/10.1016/j.jalz.2018.08.004.

Isooka, N. et al. (Jan. 2020) "Dopaminergic neuroprotective effects of rotigotine via 5-HT1A receptors: Possibly involvement of metal-lothionein expression in astrocytes." Neurochemistry International, 132:104608, https://doi.org/10.1016/j.neuint.2019.104608, 13 pages.

Ivarsson, M. et al. (Oct. 2005). "Antidepressants and REM sleep in Wistar-Kyoto and Sprague-Dawley rats" Eur. J. Pharmacol., 522(1-3):63-71. https://doi.org/10.1016/j.ejphar.2005.08.050.

Jack, C. R. et al. (Apr. 2018). "NIA-AA Research Framework: Toward a biological definition of Alzheimer's disease." Alzheimer's & Dementia : The Journal of the Alzheimer's Association, 14(4), 535-562. https://doi.org/10.1016/j.jalz.2018.02.018.

Jacobs H, et al., "Medical Comorbidities in Pediatric Headache," Seminars in Pediatric Neurology, 23(1):60-7, 2016, Epub Feb. 3, 2016.

Jaeger and Domingo, "The Digit Symbol Substitution Test (DSST): Psychometric properties and clinical utility in major depressive disorder," Poster presented at the 29th ECNP Congress, Sep. 17-20, 2016, 1 page. Vienna, Austria. Retrieved from ResearchGate [online], http://www.researchgate.net/publication/309602300.

Jafarian, S. et al. (2008). "High-altitude sleep disturbance: Results of the Groningen Sleep Quality Questionnaire survey." Sleep Med. 9, 446-449. https://doi.org/10.1016/j.sleep.2007.06.017.

Jagielska et al. (Apr. 2017). "Outcome, comorbidity and prognosis in anorexia nervosa." Psychiatr. Pol, 51(2), 205-218. https://doi.org/10.12740/PP/64580.

Jagmag, S.A. et al. (Jan. 2016). "Evaluation of Models of Parkinson's Disease." Frontiers in Neuroscience, 9: 503, pp. 1-13. https://doi.org/10.3389/fnins.2015.00503.

Jankovic. "Parkinson's disease: clinical features and diagnosis", Journal of Neurology, Neurosurgery & Psychiatry (2008); 79(4): 368-376. doi: 10.1136/jnnp.2007.131045.

Jansen, C. et al. (Nov. 2018). "Interictal psychiatric comorbidities of drug-resistant focal epilepsy: Prevalence and influence of the localization of the epilepsy." Epilepsy Behav. 94, 288-296. https://doi.org/10.1016/j.yebeh.2018.06.046.

Javaheri, S. et al. (Aug. 1996). "Effect of theophylline on sleep-disordered breathing in heart failure." N. Engl. J. Med. 335, 562-567. https://doi.org/10.1056/NEJM199608223350805.

Javaheri, S. (Oct. 2005). "Acetazolamide improves central sleep apnea in heart failure: a double-blind, prospective study." Am. J. Respir. Crit. Care Med. 173, 234-237.

Jayakumar, A.R. & Norenberg, M.D. (2016). Glutamine Synthetase: Role in Neurological Disorders. The Glutamate/GABA-Glutamine Cycle. A. Schousboe, R. Sonnewald (eds.), Springer International Publishing. Advances in Neurobiology, vol. 13, https://doi.org/10.1007/978-3-319-45096-4_13; pp. 327-350.

Jendrzejewska I. et al., Application of X-ray powder diffraction and differential scanning calorimetry for identification of counterfeit drugs, Monatsh Chern.vol. 149(5): 977-985. (2018).

Jennings, K. M. et al. (Dec. 2017). "Eating Disorder Examination-Questionnaire (EDE-Q): Norms for Clinical Sample of Female Adolescents with Anorexia Nervosa." Archives of Psychiatric Nursing, 31(6), 578-581. https://doi.org/10.1016/j.apnu.2017.08.002.

Jiang, H.-R. et al. (Nov. 2002). "Secretion of interleukin-10 or interleukin-12 by LPS-activated dendritic cells is critically dependent on time of stimulus relative to initiation of purified DC culture" Journal of Leukocyte Biology, 72(5):978-985.

Jiao, J.-J. et al. (2017). "GLP-1/GIP/Gcg receptor Triagonist improves the cognitive behaviors in triple-transgenic mice of Alzheimer's disease." Sheng Li Xue Bao : [Acta Physiologica Sinica], 69(2), 135-145. Retrieved from http://www.ncbi.nlm.nih.gov/pubmed/28435972.

Jin, L. et al. (May 2019). "Antidepressants for the treatment of narcolepsy: A prospective study of 148 patients in northern China." J. Clin. Neurosci. 63, 27-31. https://doi.org/10.1016/j.jocn.2019.02.014.

Johanson, M. et al. (Feb. 2020) A Systematic Literature Review of Neuroimaging of Psychopathic Traits. Front Psychiatry. 10:1027, doi: 10.3389/fpsyt.2019.01027, 20 pages.

John, O. P., & Srivastava, S. (1999). The Big-Five trait taxonomy: History, measurement, and theoretical perspectives. In L. A. Pervin & O. P. John (Eds.), Handbook of personality: Theory and Research (vol. 2, pp. 102-138). New York: Guilford Press.

(56)           References Cited

OTHER PUBLICATIONS

Johns, M. (1991). "New Method for Measuring Daytime Sleepiness: The Epworth Sleepiness Scale." Sleep. 14(6):540-5 [online]. Retrieved from:https://academic.oup.com/sleep/article/14/6/540/2742871 (accessed Mar. 26, 2020).

Johnson et al., "Human hallucinogen research: guidelines for safety", Journal of Psychopharmacology (2008); 22(6): 603-620. doi: 10.1177/0269881108093587. Epub Jul. 1, 2008.

Johnson et al., "Long-term follow-up of psilocybin-facilitated smoking cessation", The American Journal of Drug and Alcohol Abuse (2017); 43(1): 55-60. doi: 10.3109/00952990.2016.1170135. Epub Jul. 21, 2016. Erratum in: Am J Drug Alcohol Abuse. Jan. 2017;43(1):127. doi: 10.1080/00952990.2016.1277105, 7 pages total.

Johnson et al., "Pilot study of the 5-HT2AR agonist psilocybin in the treatment of tobacco addiction", Journal of Psychopharmacology (2014); 28(11): 983-992. doi: 10.1177/0269881114548296. Epub Sep. 11, 2014.

Johnson et al., "Potential therapeutic effects of psilocybin", Neurotherapeutics (2017); 14: 734-740. doi: 10.1007/s13311-017-0542-y.

Johnstad, P.G. (Feb. 2018). "Powerful substances in tiny amounts: An interview study of psychedelic microdosing" Nord Stud Alcohol Drugs, 35(1):39-51.

Jones, S.A.V., et al., "Psychedelics as a Treatment for Alzheimer's Disease Dementia," Frontiers in Synaptic Neuroscience, Aug. 21, 2020, vol. 12, Article 34, pp. 1-6.

Jyonouchi, H. (2013). "Immunological abnormalities in autism spectrum disorders." Advances in Neuroimmune Biology. vol. 4, No. 3, pp. 141-159. https://doi.org/10.3233/NIB-130061.

Kaelen et al., "LSD enhances emotional response to music", Psychopharmacology (Aug. 2015); 232(19): 3607-3614. doi: 10.1007/s00213-015-4014-y. Epub Aug. 11, 2015.

Kaelen, M. et al. (Feb. 2018) "The hidden therapist: evidence for a central role of music in psychedelic therapy" Psycopharmacology, 235:505-519.

Kaladjian, A. et al. (2014). "Troubles affectifs et comorbidités anxieuses." Encephale 40, S18-S22. https://doi.org/10.1016/S0013-7006(14)70126-5.

Kalliolias, G. D. et al. (Jan. 2016). "TNF biology, pathogenic mechanisms and emerging therapeutic strategies." Nature Reviews Rheumatology, 12(1), 49-62. https://doi.org/10.1038/nrrheum.2015.169.

Kandel, S.A. and Mandiga P. (2020) Cluster Headache. StatPearls. StatPearls Publishing [Internet]. Available from NCI Bookshelf: http://www.ncbi.nlm.nih.gov/pubmed/31334961, 6 pages.

Kandil, E. et al. (Jan. 2017). "Lidocaine Infusion: A Promising Therapeutic Approach for Chronic Pain." J Anesth Clin Res. 08(01): 697, pp. 1-29.

Kandratavicius, L. et al. (Sep. 2014). Animal models of epilepsy: use and limitations. Neuropsychiatric Disease and Treatment, 1693. https://doi.org/10.2147/NDT.S50371, pp. 1-13.

Kang, D. W. et al. (Apr. 2019). "Long-term benefit of Microbiota Transfer Therapy on autism symptoms and gut microbiota." Scientific Reports. 9(1):1-9. https://doi.org/10.1038/s41598-019-42183-0.

Kang Y. et al. (Oct. 2017). "Self-report pain assessment tools for cognitively intact older adults: Integrative review." International journal of older people nursing. 13(2):e12170, pp. 1-29.

Kanner, A.M. (May 2011). "Anxiety disorders in epilepsy: The forgotten psychiatric comorbidity." Epilepsy Curr. 11(3):90-91. https://doi.org/10.5698/1535-7511-11.3.90.

Kantojarvi, K.et al. (Jun. 2011). "Fine mapping of Xq11.1-q21.33 and mutation screening of RPS6KA6, ZNF711, ACSL4, DLG3, and IL1RAPL2 for autism spectrum disorders (ASD)." Autism Research. 4(3):228-33. https://doi.org/10.1002/aur.187.

Kargbo et al., "Direct phosphorylation of psilocin enables optimized cGMP kilogram-scale manufacture of psilocybin", ACS Omega (2020) 5(27): 16959-16966; 25 pages with Supporting Information. doi: 10.1021/acsomega.0c02387.

Karimi, P. et al. (Feb. 2017). Environmental factors influencing the risk of autism. J Res Med Sci. 22:27, https://doi.org/10.4103/1735-1995.200272, 12 pages.

Kasper LJ et al. (Jul. 2012). "Moderators of Working Memory deficits in Children with Attention-deficit/hyperactivity Disorder (ADHD): A meta-analytic Review." Clinical Psychology Review. vol. 32, p. 605-17.

Kasper, S. et al. (Mar. 2009). "Efficacy of pregabalin and venlafaxine-XR in generalized anxiety disorder: Results of a double-blind, placebo-controlled 8-week trial." Int. Clin. Psychopharmacol. 24, 87-96. https://doi.org/10.1097/YIC.0b013e32831d7980.

Katzman, M.A. et al. (Aug. 2017). "Adult ADHD and comorbid disorders: Clinical implications of a dimensional approach." BMC Psychiatry. 17(1):1-15.

Kaur A et al. (Dec. 2018). "Phantom limb pain: A literature review." Chinese Journal of Tramatology, 21(6):366-8. https://doi.org/10.1016/j.cjtee.2018.04.006.

Kaur, H. et al. (2018). Chronic Insomnia. StatPearls. NLM Bookshelf [online]. Retrieved from: https://www.ncbi.nih.gov/books/NBK526136/?report=reader; retrieved on Jul. 30, 2002; 5 pages.

Keezer, M. R. et al. (Nov. 2015). "Comorbidities of epilepsy: current concepts and future perspectives." The Lancet Neurology, 15(1), 106-115. https://doi.org/10.1016/S1474-4422(15)00225-2.

Kelly, W.E. et al. (2019). "A brief self-report measure for frequent distressing nightmares: The Nightmare Experience Scale (NExS)." Dreaming 29, 180-195. https://doi.org/10.1037/drm0000106.

Kelton, M.C. et al. (Jun.-Aug. 2000). The effects of nicotine on Parkinson's disease. Brain and Cognition, 43(1-3):274-282 (abstract). Retrieved from http://www.ncbi.nlm.nih.gov/pubmed/10857708, 1 page.

Kessler, R. et al. (Apr. 2016). The neurobiological basis of binge-eating disorder. Neuroscience & Biobehavioral Reviews, 63, pp. 223-238.

Kessler, R.C. et al. (Jan. 2013). The prevalence and correlates of binge eating disorder in the World Health Organization World Mental Health Surveys. Biological Psychiatry, 73(9):904-914.

Khajehpour, H. et al. (Dec. 2019). "Disrupted resting-state brain functional network in methamphetamine abusers: A brain source space study by EEG." PLoS One 14, e0226249, pp. 1-20. https://doi.org/10.1371/journal.pone.0226249.

Khalifa, N. et al. (Aug. 2010) Pharmacological interventions for antisocial personality disorder. Cochrane Database Syst Rev. (8):CD007667, doi: 10.1002/14651858.CD007667.pub2. Europe PMC Funders Group Author Manuscript, 83 pages.

Khemka, S. et al. (Jul. 2017). "Dissecting the function of hippocampal oscillations in a human anxiety model." J. Neurosci. 37, 6869-6876.

Khurshid KA., "Comorbid insomnia and psychiatric disorders: an update." Innovations in Clinical Neuroscience. 15(3-4):28-32 (2018).

Kim, J.W. et al. (Aug. 2014). "Subchronic treatment of donepezil rescues impaired social, hyperactive, and stereotypic behavior in valproic acid-induced animal model of autism." PLoS One. 9(8):e104927, pp. 2-23.

Kim, Y. E., & Jeon, B. S. (2014). Clinical Implication of REM Sleep Behavior Disorder in Parkinson's Disease. Journal of Parkinson's Disease, 4(2), 237-244. https://doi.org/10.3233/JPD-130293.

Kinnaird, E. et al. (Jun. 2019). Same behaviours, different reasons: what do patients with co-occurring anorexia and autism want from treatment? International Review of Psychiatry, 31(4), 308-317. https://doi.org/10.1080/09540261.2018.1531831.

Kirsh, K.L. (Mar. 2010). "Differentiating and Managing Common Psychiatric Comorbidities Seen in Chronic Pain Patients." J Pain Palliat Care Pharmacother, 24(1):39-47. Available from: https://www.tandfonline.com/action/journalInformation?journalCode=ippc20.

Kishi, T. et al. (Jun. 2012). Are Antipsychotics Effective for Anorexia Nervosa? Are Antipsychotics Effective for the Treatment of Anorexia Nervosa? Results From a Systematic Review and Meta-Analysis. J Clin Psychiatry, 73(6), 757-766. https://doi.org/10.4088/JCP.12r07691.

Kishi, T. et al. (Aug. 2015). "Suvorexant for primary insomnia: A systematic review and meta-analysis of randomized placebo-

(56)        References Cited

OTHER PUBLICATIONS

Closely Resemble Parkinson's Disease." The Journal of Neuroscience : The Official Journal of the Society for Neuroscience, 37(39), 9361-9379. https://doi.org/10.1523/JNEUROSCI.0084-17.2017.

Kornum, B.R. et al. (Feb. 2017). "Narcolepsy." Nat. Rev. Dis. Prim. 3(1):1-9. https://doi.org/10.1038/nrdp.2016.100.

Kothare, S.V. et al. (Apr. 2008) "Zonisamide: review of pharmacology, clinical efficacy, tolerability, and safety." Expert Opinion on Drug Metabolism & Toxicology, 4(4), 493-506. https://doi.org/10.1517/17425255.4.4.493.

Kotov, S.B. Bellman, and D.B. Watson (2004) Multidimensional Iowa Suggestibility Scale (MISS) Brief Manual. [online] Retrieved from: https://renaissance.stonybrookmedicine.edu/sites/default/files/MISSBriefManual.pdf, 16 pages.

Kouli, A. et al. (Dec. 2018). Parkinson's Disease: Etiology, Neuropathology, and Pathogenesis. In Parkinson's Disease: Pathogenesis and Clinical Aspects. Thomas B. Stoker & Julia C. Greenland (Eds.) Codon Publications, pp. 3-26. Retrieved from http://www.ncbi.nlm.nih.gov/pubmed/30702842.

Kountza, M. et al. (Nov. 2018). "La comorbidité psychiatrique de l'anorexie mentale : une étude comparative chez une population de patients anorexiques français et grecs." L'Encéphale, 44(5), 429-434. https://doi.org/10.1016/j.encep.2017.07.005. English abstract on p. 429.

Kryzhanovskii, G.N. et al. (1992). [The antiepileptic effects of sodium valproate and the calcium antagonist riodipine when used jointly in a model of generalized korazol-induced epileptic activity]. Biulleten' Eksperimental'noi Biologii i Meditsiny, 114(10), 376-378 [Abstract]. Retrieved from http://www.ncbi.nlm.nih.gov/pubmed/1288691, 1 page.

Krzyszkowiak, W. et al. (Aug. 2019) "Treatment of obsessive-compulsive disorders (OCD) and obsessive-compulsive-related disorders (OCRD)" Psychiatr Pol, 53(4):825-843; DOI: https://doi.org/10.12740/PP/105130.

Kubera, M. et al. (Apr. 2005). Effects of serotonin and serotonergic agonists and antagonists on the production of tumor necrosis factor α and interleukin-6. Psychiatry Research, 134(3), 251-258. https://doi.org/10.1016/j.psychres.2004.01.014.

Kuhnert, M. et al. (Aug. 1976) "Polymorphe Modifikationen und Solvate von Psilocin und Psilocybin [Polymorphic Modifications and Solvates of Psilocin and Psilocybin]" Archiv der Pharmazie, 309:625-631, with English translation from Google Translate (14 total pages).

Kurrasch-Orbaugh et al., "Serotonin 5-hydroxytryptamine2A receptor-coupled phospholipase C and phospholipase A2 signaling pathways have different receptor reserves", The Journal of Pharmacology and Experimental Therapeutics (2003); 304(1): 229-237. doi: 10.1124/jpet.102.042184.

Kwan, P., & Brodie, M. J. (Jan. 2001). Neuropsychological effects of epilepsy and antiepileptic drugs. The Lancet, 357(9251), 216-222. https://doi.org/10.1016/S0140-6736(00)03600-X.

Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.

Lader, M., 2015. Generalized Anxiety Disorder BT—Encyclopedia of Psychopharmacology, in: Stolerman, I.P., Price, L.H. (Eds.). Springer Berlin Heidelberg, pp. 699-702. https://doi.org/10.1007/978-3-642-36172-2_317.

Lahdenpaa et al., "Direct compression with silicified and non-silicified microcrystalline cellulose: study of some properties of powders and tablets," S.T.P. Pharma Sciences, 2001; 11(2):129-135. Supplied by the British Library Oct. 12, 2019, 8 pages.

Lahey, B.B. et al. (Jun. 2005) Predicting Future Antisocial Personality Disorder in Males From a Clinical Assessment in Childhood. J Consult Clin Psychol, 73(3):389-399.

Lahmame, A. et al. (Oct. 1997). "Are Wistar-Kyoto rats a genetic animal model of depression resistant to antidepressants?" Eur. J. Pharmacol. 337(2-3):115-23. https://doi.org/10.1016/S0014-2999(97)01276-4.

Lai, M.C. et al. (Oct. 2019). "Prevalence of co-occurring mental health diagnoses in the autism population: a systematic review and meta-analysis." The Lancet Psychiatry. 6(10):819-29. https://doi.org/10.1016/S2215-0366(19)30289-5.

Landau, A.M. et al. (Sep. 2005). "Defective Fas expression exacerbates neurotoxicity in a model of Parkinson's disease." The Journal of Experimental Medicine, 202(5), 575-581. https://doi.org/10.1084/jem.20050163.

Larrosa, O. et al. (May 2001). "Stimulant and Anticataplectic Effects of Reboxetine in Patients with Narcolepsy: A Pilot Study." Sleep. 24(3):282-5.

Layzer, R., "Section 5—Degenerative Diseases of the Nervous System," Cecil Textbook of Medicine, Eds. J. Claude Bennett, MD and Fred Plum, 20th edition (1996), vol. 2, pp. 2050-2057.

Lecavalier, L. (Nov. 2006). "Behavioral and emotional problems in young people with pervasive developmental disorders: Relative prevalence, effects of subject characteristics, and empirical classification." Journal of Autism and Developmental Disorders. 36(8):1101-14. https://doi.org/10.1007/s10803-006-0147-5.

Lecendreux, M. et al. (Aug. 2015). Attention-Deficit/Hyperactivity Disorder (ADHD) Symptoms in Pediatric Narcolepsy: A Cross-Sectional Study. Sleep 38, 1285-1295. https://doi.org/10.5665/sleep.4910.

Leclerc, S. et al. (Jun. 2015). "Pharmacological therapies for autism spectrum disorder: A review." Pharmacy and Therapeutics. 40(6):389-397.

Ledonne, A., & Mercuri, N. B. (Dec. 2019). On the modulatory roles of neuregulins/ErbB signaling on synaptic plasticity. International Journal of Molecular Sciences, 21:275, 23 pages. https://doi.org/10.3390/ijms21010275.

Lee, P. H. et al. (Dec. 2019). "Genomic Relationships, Novel Loci, and Pleiotropic Mechanisms across Eight Psychiatric Disorders." Cell. 179(1469-1482):e11. https://doi.org/10.1016/j.cell.2019.11.020.

Lee, R.M. and Robbins, S.B. (1995) Measuring belongingness: the social connectedness and the social assurance scales Journal of Counseling Psychology. 42:232-241.

Lee, T. J. et al. (Mar. 2017). "Repeated adolescent activity-based anorexia influences central estrogen signaling and adulthood anxiety-like behaviors in rats." Physiology and Behavior, 171, 199-206. https://doi.org/10.1016/j.physbeh.2016.12.039.

Lee, Y.C. et al. (Dec. 2010). "A review of SSRIs and SNRIs in neuropathic pain." Expert Opin Pharmacother. 11(17):2813-25.

Leigh, J. P. et al. (Dec. 2015). "Brief Report: Forecasting the Economic Burden of Autism in 2015 and 2025 in the United States." Journal of Autism and Developmental Disorders. 45(12):4135-9. https://doi.org/10.1007/s10803-015-2521-7.

Leonard, H.L., & Rapoport, J.L. (Sep. 1987) "Letter to the Editor: Relief of obsessive-compulsive symptoms by LSD and psilocin" American Journal of Psychiatry, 144(9):1239-1240.

Leonard, "What is the link between anxiety and ADHD?," https://www.medicalnewstoday.com/articles/315303 May 15, 2017 , 19 pages.

Leroux, E. and Ducros, A. (2008) Cluster headache. Orphanet J Rare Dis, 3:20, doi: 10.1186/1750-1172-3-20, 11 pages.

Levin, E. D., & Rezvani, A. H. (Mar. 2000). Development of nicotinic drug therapy for cognitive disorders. European Journal of Pharmacology, 393(1-3), 141-146. https://doi.org/10.1016/s0014-2999(99)00885-7.

Leysen, J.E. et al. (1982). [$^3$H]Ketanserin (R 41 468), a selective $^3$H-ligand for serotonin$_2$ receptor binding sites. Binding properties, brain distribution, and functional role. Molecular Pharmacology, 21(2), 301-314.

Li, T. et al. (Nov. 2016). A scored human protein-protein interaction network to catalyze genomic interpretation. Nature Methods, 14(1), 61-64. https://doi.org/10.1038/nmeth.4083.

(56)    References Cited

OTHER PUBLICATIONS

Li, Y. et al. (Aug. 2011) "Quantification of polymorphic impurity in an enantiotropic polymorph system using differential scanning calorimetry, X-ray powder diffraction and Raman spectroscopy" Intl J Pharma, 415:110-118.

Liang, H. et al. (2019). Mammalian Target of Rapamycin at the Crossroad Between Alzheimer's Disease and Diabetes. In Diabetes Mellitus. A Risk Factor for Alzheimer's Disease. Advances in Experimental Medicine and Biology, 1128, 185-225. https://doi.org/10.1007/978-981-13-3540-2_10.

Limakatso K et al. (2019). "The prevalence of phantom limb pain and associated risk factors in people with amputations: A systematic review protocol." Syst Rev. 8:17, 5 pages. https://doi.org/10.1186/s13643-018-0938-8.

Lindenblatt et al., "Quantitation of psilocin in human plasma by high-performance liquid chromatography and electrochemical detection: comparison of liquid-liquid extraction with automated on-line solid-phase extraction", Journal of Chromatography B: Biomedical Sciences and Applications (1998); 709(2): 255-263. doi: 10.1016/s0378-4347(98)00067-x.

Liu, L. et al. (Jul. 2018). "Deficiency of Sustained Attention in ADHD and Its Potential Genetic Contributor MAOA" J Atten Disord, 22(9):878-885.

Liu, P.-P. et al. (Aug. 2019). "History and progress of hypotheses and clinical trials for Alzheimer's disease." Signal Transduction and Targeted Therapy, 4:29, https://doi.org/10.1038/s41392-019-0063-8, 22 pages.

Lopez-Castejon, G. et al. (Aug. 2011). "Understanding the mechanism of IL-1β secretion." Cytokine & Growth Factor Reviews, 22(4), 189-195. https://doi.org/10.1016/j.cytogfr.2011.10.001.

Loth, E. et al. (Jan. 2018). "Facial expression recognition as a candidate marker for autism spectrum disorder: how frequent and severe are deficits?" Molecular Autism, 9:7, https://doi.org/10.1186/s13229-018-0187-7, 11 pages.

Lu, T.-T., Wan, C., Yang, W., & Cai, Z. (2019). Role of Cdk5 in Amyloid-beta Pathology of Alzheimer's Disease. Current Alzheimer Research, 16(13), 1206-1215. https://doi.org/10.2174/1567205016666191210094435.

Lucchina, L. et al. (Oct. 2013). "Altered Peripheral and Central Inflammatory Responses in a Mouse Model of Autism." Autism Research. 7(2):273-89. https://doi.org/10.1002/aur.1338.

Lucza, T. et al. (May 2015). "Screening Mild and Major Neurocognitive Disorders in Parkinson's Disease." Behavioural Neurology, 2015, Article ID 983606, 10 pages. https://doi.org/10.1155/2015/983606.

Lugli, S.M. et al. (Feb. 1997). "Tumor Necrosis Factor α Enhances the Expression of the Interleukin (IL)-4 Receptor α-Chain on Endothelial Cells Increasing IL-4 or IL-13-induced Stat6 Activation." Journal of Biological Chemistry, 272(9), 5487-5494. https://doi.org/10.1074/jbc.272.9.5487.

Lynch ME et al. (2006). "The pharmacotherapy of chronic pain: A review." Pain Res Manag. 11(1):11-38.

Lyons, "More Realistic Forecasting of Future Life Events After Psilocybin for Treatment-Resistant Depression" Frontiers in Psychology, vol. 9(1721): 1-11 (2018).

Lyons, T and R.L. Carhart-Harris (Jul. 2018) Increased nature relatedness and decreased authoritarian political views after psilocybin for treatment-resistant depression. Journal of Psychopharmacology, 32(7):811-819.

Mabunga, D.F.N. et al. (Dec. 2015). "Exploring the Validity of Valproic Acid Animal Model of Autism." Experimental Neurobiology. 24(4):285-300. https://doi.org/10.5607/en.2015.24.4.285.

Macy, A.S. et al. (Jan. 2013) "Quality of life in obsessive compulsive disorder" CNS Spectrums, 18(1):21-33.

Magnuson K M, et al., "Characterization of depression in children with autism spectrum disorders," Journal of developmental and Behavioral Pediatrics, May 2011; 32(4):332-40.

Mahapatra et al., "Role of psilocybin in the treatment of depression," Ther Adv Psychopharmacol, Jan. 2017; 7(1): 54-56.

Mahfoud, Y. et al. (Sep. 2009). Sleep disorders in substance abusers: How common are they? Psychiatry, 6(9):38-42.

Mahone EM et al. (2017). "Attention-Deficit/Hyperactivity Disorder: A Historical Neuropsychological Perspective." J Int Neuropsychol Soc [Internet]. 23:916-29. Available from: http://www.rmtcnet.com/resources/Phenylbutazone_Review-Dr._Lawrence_R._Soma.pdf.

Maiano, C. et al. (Jul. 2019). Psychometric Properties of the Body Checking Questionnaire (BCQ) and of the Body Checking Cognitions Scale (BCCS): A Bifactor-Exploratory Structural Equation Modeling Approach. Assessment, 1-15, https://doi.org/10.1177/1073191119858411.

Maimoun, L. et al. (Jun. 2018). Effects of the two types of anorexia nervosa (binge eating/purging and restrictive) on bone metabolism in female patients. Clinical Endocrinology, 88(6):863-872. https://doi.org/10.1111/cen.13610.

Maina, G. et al. (Jan. 2003) "Antipsychotic augmentation for treatment resistant obsessive-compulsive disorder: What if antipsychotic is discontinued?" International Clinical Psychopharmacology, 18(1):23-28; DOI: 10.1097/01.yic.0000047784.24295.2b.

Manavalan, A. et al. (Sep. 2013). Brain site-specific proteome changes in aging-related dementia. Experimental & Molecular Medicine. 45:e39, 17 pages. https://doi.org/10.1038/emm.2013.76.

Marras, C. et al. (Jul. 2018). Prevalence of Parkinson's disease across North America. npjParkinson's Disease. 4:21, https://doi.org/10.1038/s41531-018-0058-0, 7 pages.

Martin, W., Vaupel, D., Nozaki, M. and Bright, L. (1978). The identification of LSD-like hallucinogens using the chronic spinal dog. Drug and Alcohol Dependence, 3(2), pp. 113-123.

Martins, G.R. et al. (Feb. 2016). Proinflammatory and Anti-Inflammatory Cytokines Mediated by NF-κ B Factor as Prognostic Markers in Mammary Tumors. Mediators of Inflammation, 2016:1-10. https://doi.org/10.1155/2016/9512743.

Martinussen R. et al. (Apr. 2005). A meta-analysis of working memory impairments in children with attention-deficit/hyperactivity disorder. J Am Acad Child Adolesc Psychiatry, 44(4):377-84.

Marvanova, M. & Gramith, K. (Apr. 2018). Role of antidepressants in the treatment of adults with anorexia nervosa. Ment Health Clin [Internet] 8(3):127-37. DOI: 10.9740/mhc.2018.05.127.

Mason, N.L. et al. (Jun. 2019). Sub-Acute Effects of Psilocybin on Empathy, Creative Thinking, and Subjective Well-Being. Journal of Psychoactive Drugs, https://doi.org/10.1080/02791072.2019.1580804, 13 pages.

Mathes, B.M. et al. (Apr. 2019). Epidemiological and Clinical Gender Differences in OCD. In Current Psychiatry Reports (vol. 21, Issue 5, pp. 1-7). Curr Psychiatry Rep, 21:36, 7 pages, https://doi.org/10.1007/s11920-019-1015-2.

Matheson, E. & Hainer, B.L. (Jul. 2017) Insomnia: Pharmacologic Therapy—American Family Physician. Am Fam Physician, 96(1):29-35.

Matsushima, Y. et al. (Aug. 2009). Effects of Psilocybe argentipes on Marble-Burying Behavior in Mice. Bioscience Biotechnology and Biochemistry, 73(8):1866-1868. https://doi.org/10.1271/bbb.90095.

Mattingly, G. et al. (May 2012). Attention deficit hyperactivity disorder subtypes and symptom response in adults treated with lisdexamfetamine dimesylate. Innov Clin Neurosci, 9(5-6):22-30.

Maxwell, C.R. et al. (Feb. 2015). Atypical Laterality of Resting Gamma Oscillations in Autism Spectrum Disorders, 45(2):292-297, doi:10.1007/s10803-013-1842-7.

Mayhew A. & Argaez, C. (Jan. 2018). Intravenous lidocaine for chronic pain: a review of the clinical effectiveness and guidelines. Ottawa: CADTH; Jan. 2018 (CADTH rapid response report: summary with critical appraisal), 22 pages.

Mazza M, Marano G, Janiri L. (Aug. 2016) An update on pharmacotherapy for personality disorders. Expert Opinion on Pharmacotherapy. 17:(15):1977-1979.

Mccarberg, B. & Billington, R. (Jun. 2006). Consequences of neuropathic pain: Quality-of-life issues and associated costs. Am J Manag Care, 12(Suppl. 9):S263-8.

Mccuen-Wurst, C. et al. (Jan. 2018). Disordered eating and obesity: associations between binge-eating disorder, night-eating syndrome,

(56)                    References Cited

OTHER PUBLICATIONS and weight-related comorbidities. Annals of the New York Academy of Sciences, 1411(1), pp. 96-105.
Mccullough et al, "The Grateful Disposition: A Conceptual and Empirical Topography," Journal of Personality and Social Psychology, 82:112-127 (2002).
Mcelroy, S. et al. (Feb. 2013). A placebo-controlled pilot study of the novel opioid receptor antagonist ALKS-33 in binge eating disorder. International Journal of Eating Disorders, 46(3), pp. 239-245.
Mcelroy, S. et al. (Mar. 2015). Efficacy and Safety of Lisdexamfetamine for Treatment of Adults With Moderate to Severe Binge-Eating Disorder. JAMA Psychiatry, 72(3), p. 235-246.
Mcelroy, S. et al. (May 2012). Pharmacological management of binge eating disorder: current and emerging treatment options. Therapeutics and Clinical Risk Management, 8:219-241.
Mcguire-Snieckus, R. et al. (Nov. 2006) A new scale to assess the therapeutic relationship in community mental health care: STAR. Psychological Medicine. 37:85-95.
Nall, "What to know about Parkinson's dementia," R, Medical News Today (Jan. 15, 2019. Retrieved Jul. 30, 2020 from https://www.medicalnewstoday.com/articles/314486, 14 pages.
Medzhitov, R. (Jul. 2008). Origin and physiological roles of inflammation. Nature, 454(7203):428-435. https://doi.org/10.1038/nature07201.
Mei, L., & Nave, K.-A. (2014). Neuregulin-ERBB signaling in the nervous system and neuropsychiatric diseases. In Neuron, 83:27-49, https://doi.org/10.1016/j.neuron.2014.06.007.
Meier, S.M. et al. (Mar. 2016). Mortality among persons with obsessive-compulsive disorder in Denmark. JAMA Psychiatry, 73(3):268-274. https://doi.org/10.1001/jamapsychiatry.2015.3105.
Meinzer M C, et al., "ADHD and the Development of Depression: Commentary on the Prevalence, Proposed Mechanisms, and Promising Interventions," Current developmental disorders reports, Mar. 2017;4(1):1-4, Epub Feb. 27, 2017.
Meldrum, B.S. & Naquet, R. (Sep. 1970). Effects of psilocybin, dimethyltryptamine and various lysergic acid derivatives on photically-induced epilepsy in the baboon (Papio papio). British Journal of Pharmacology, 40(1):144P-145P. Retrieved from http://www.ncbi.nlm.nih.gov/pubmed/4992165.
Mertens, L.J., et al., "Therapeutic mechanisms of psilocybin: Changes in amygdala and prefrontal functional connectivity during emotional processing after psilocybin for treatment-resistant depression," Journal of Psychopharmacology, Feb. 2020, vol. 34 (2), pp. 167-180.
Meyer, A.-C. et al. (Sep. 2009). Global disparities in the epilepsy treatment gap: a systematic review. Bulletin of the World Health Organization, 88(4):260-266. https://doi.org/10.2471/BLT.09.064147.
Miller, A.H., & Raison, C. L. (Jan. 2016). Role of inflammation in depression from evolutionary imperative to modern treatment target. Nat Rev Immunol, 16(1):22-34. https://doi.org/10.1038/nri.2015.5.
Mills, S.E.E. et al. (Aug. 2019). Chronic pain: a review of its epidemiology and associated factors in population-based studies. Br J Anaesth. 123(2):273-83.
Milos, G. et al. (Apr. 2002). Comorbidity of obsessive-compulsive disorders and duration of eating disorders. International Journal of Eating Disorders, 31(3):284-289. https://doi.org/10.1002/eat.10013.
Min, S.S. et al. (Nov. 2011). Neuregulin-1 prevents amyloid β-induced impairment of long-term potentiation in hippocampal slices via ErbB4. Neuroscience Letters, 505(1):6-9. https://doi.org/10.1016/j.neulet.2011.05.246.
Minen, M.T. et al. (Jan. 2016). Migraine and its psychiatric comorbidities. J. Neurol. Neurosurg. Psychiatry, 87:741-749. https://doi.org/10.1136/jnnp-2015-312233.
Miniati, M. et al. (Apr. 2016). Psychopharmacological options for adult patients with anorexia nervosa. CNS Spectrums, 21:134-142. https://doi.org/10.1017/S1092852914000790.

Mitsuyama, F. et al. (Sep. 2009). Amyloid beta: a putative intra-spinal microtubule-depolymerizer to induce synapse-loss or dentritic spine shortening in Alzheimer's disease. Italian Journal of Anatomy and Embryology, 114(2-3), 109-120. [Abstract]. Retrieved Dec. 9, 2020 from http://www.ncbi.nlm.nih.gov/pubmed/20198823, 1 page.
Molero, P. et al. (May 2018). Antidepressant Efficacy and Tolerability of Ketamine and Esketamine: A Critical Review. CNS Drugs 32:411-420. https://doi.org/10.1007/s40263-018-0519-3.
Montejo, A.L. et al. (2008) Psychometric Properties of the Psychotropic-Related Sexual Dysfunction Questionnaire (PRSexDQ-SALSEX) in Patients with Schizophrenia and Other Psychotic Disorders. Journal of Sex Marital Therapy. 34(3):227-39.
Montigny, C. (Jun. 1989). Cholecystokinin Tetrapeptide Induces Panic-like Attacks in Healthy Volunteers: Preliminary Findings. Archives of General Psychiatry, 46:511-517. https://doi.org/10.1001/archpsyc.1989.01810060031006.
Moran, P. et al. (Sep. 2003) Standardised Assessment of Personality—Abbreviated Scale (SAPAS): preliminary validation of a brief screen for personality disorder. The British Journal of Psychiatry, 183(3):228-232.
Moreno et al., "Safety, tolerability, and efficacy of psilocybin in 9 patients with obsessive-compulsive disorder", Journal of Clinical Psychiatry (Nov. 2006); 67(11): 1735-1740. doi: 10.4088/jcp.v67n1110.
Moreno, F. A., & Delgado, P. L. (Jul. 1997). Hallucinogen-induced relief of obsessions and compulsions. American Journal of Psychiatry, vol. 154, Issue 7, pp. 1037-1038. https://doi.org/10.1176/ajp.154.7.1037b.
Morgan, C. et al. (Feb. 2017). Tripping up addiction: the use of psychedelic drugs in the treatment of problematic drug and alcohol use. Current Opinion in Behavioral Sciences, 13, pp. 71-76.
Morilak, D.A. et al. (Oct. 2005). Role of brain norepinephrine in the behavioral response to stress. Prog. Neuro-Psychopharmacology Biol. Psychiatry, 29:1214-1224. https://doi.org/10.1016/j.pnpbp.2005.08.007.
Moscovich, M. et al. (Aug. 2017). Death certificate data and causes of death in patients with parkinsonism. Parkinsonism & Related Disorders, 41:99-103. https://doi.org/10.1016/j.parkreldis.2017.05.022.
Moser, P.C. et al. (Jul. 7, 1988) "The effect of benzodiazepines on the 5-HT agonist-induced head-twitch response in mice", Eur J. Pharmacol, 151(2): 223-231.
Mukherjee, S. et al. (Jul. 2009). Lipopolysaccharide-driven Th2 Cytokine Production in Macrophages Is Regulated by Both MyD88 and TRAM. Journal of Biological Chemistry, 284(43):29391-29398. https://doi.org/10.1074/jbc.M109.005272.
Mula, M. et al. (Dec. 2006). Psychopharmacology of topiramate: From epilepsy to bipolar disorder. Neuropsychiatric Disease and Treatment, 2(4):475-488. https://doi.org/10.2147/nedt.2006.2.4.475.
Mulvey, M.R. (Oct. 2017) Neuropathic pain in cancer: systematic review, performance of screening tools and analysis of symptom profiles. British Journal of Anaesthesia, 119(4):765-774.
Municio, C. et al. (May 2018). Methotrexate limits inflammation through an A20-dependent cross-tolerance mechanism. Annals of the Rheumatic Diseases, 77(5):752-759. https://doi.org/10.1136/annrheumdis-2017-212537.
Murphy-Beiner, A. & Soar, K. (Apr. 2020). Ayahuasca's 'after-glow': improved mindfulness and cognitive flexibility in ayahuasca drinkers. Psychopharmacology, published online, https://doi.org/10.1007/s00213-019-05445-3, 9 pages.
Murrough, J.W. et al. (Sep. 2015). Emerging drugs for the treatment of anxiety. Expert Opin. Emerg. Drugs, 20(3):393-406. https://doi.org/10.1517/14728214.2015.1049996.
Nam, H. et al. (Apr. 2014). Learned helplessness and social avoidance in the Wistar-Kyoto rat. Front. Behav. Neurosci., 8(109), https://doi.org/10.3389/fnbeh.2014.00109, 18 pages.
National Institute for Health and Care Excellence (NICE) (Jan. 28, 2019) Antisocial Personality Disorder: Prevention and Management. Clinical guidance CG77 [online]. Available from www.nice.org.uk/guidance/cg77, 35 pages.
National Institute of Mental Health (NIMH) (Nov. 2017) Eating Disorders. Mental Health Information—Statistics (online). Retrieved

(56)         References Cited

OTHER PUBLICATIONS

Mar. 5, 2020, from https://www.nimh.nih.gov/health/statistics/eating-disorders.shtml#part_155063, 14 pages.

Nau, F. et al. (Jan. 2015). Serotonin 5-HT$_2$ receptor activation prevents allergic asthma in a mouse model. American Journal of Physiology. Lung Cellular and Molecular Physiology, 308(2), L191-8. https://doi.org/10.1152/ajplung.00138.2013.

Nau, F., Yu, B., Martin, D., & Nichols, C. D. (2013). Serotonin 5-HT$_{2a}$ Receptor Activation Blocks TNF-α Mediated Inflammation In Vivo. PLoS One, 8(10):2-9. https://doi.org/10.1371/journal.pone.0075426.

Naulls, S. and Bunn, S., "Psychedelic drugs to treat post-traumatic stress disorder (PTSD)," UK Parliament [online], Published Monday Apr. 22, 2024, 11 pages. Available from: https://post.parliament.uk/psychedelic-drugs-to-treat-post-traumatic-stress-disorder-ptsd/ [Accessed Jun. 18, 2025].

Naviaux, J.C. et al. (Jun. 2014). Reversal of autism-like behaviors and metabolism in adult mice with single-dose antipurinergic therapy. Translational Psychiatry, 4:e400, 11 pages. https://doi.org/10.1038/tp.2014.33.

Nechita, D. et al. (2018). A review of the influence the anxiety exerts on human life. Rom. J. Morphol. Embryol., 59(4):1045-1051.

Nelis, S.M. et al. (May 2019). The impact of co-morbidity on the quality of life of people with dementia: findings from the IDEAL study. Age and Ageing, 48(3):361-367. https://doi.org/10.1093/ageing/afy155.

Nelson, R. J. et al. (Apr. 2005). Pleiotropic contributions of nitric oxide to aggressive behavior. Neuroscience and Biobehavioral Reviews, 30(3):346-355. https://doi.org/10.1016/j.neubiorev.2005.02.002.

Newman-Tancredi, A. et al. (Mar. 2018). Effects of the Serotonin 5-HT1A Receptor Biased Agonists, F13714 and F15599, on Striatal Neurotransmitter Levels Following L-DOPA Administration in Hemi-Parkinsonian Rats. Neurochemical Research, 43(5):1035-1046. https://doi.org/10.1007/s11064-018-2514-y.

Ngugi, A.K. et al. (May 2010). Estimation of the burden of active and life-time epilepsy: A meta-analytic approach. Epilepsia, 51(5): 883-890. https://doi.org/10.1111/j.1528-1167.2009.02481.x.

Ni, H.C. et al. (Oct. 2013) A head-to-head randomized clinical trial of methylphenidate and atomoxetine treatment for executive function in adults with attention-deficit hyperactivity disorder. Int J Neuropsychopharmacol, 16(9):1959-1973.

Nichols et al., "Improvements to the synthesis of psilocybin and a facile method for preparing the O-acetyl prodrug of psilocin", Synthesis (1999); 1999(06): 935-938.

Nichols. "Hallucinogens", Pharmacology & Therapeutics (2004); 101(2): 131-181. doi: 10.1016/j.pharmthera.2003.11.002.

Nichols. "Psychedelics." Pharmacological Reviews. Apr. 2016;68(2):264-355. doi: 10.1124/pr.115.011478.

Nicholson, B. & Verma S. (Mar. 2004). Comorbidities in chronic neuropathic pain. Pain Medicine. 5(S1):S9-25. Retrieved from: https://academic.oup.com/painmedicine/article-abstract/5/suppl_1/S9/1884243, on Jul. 30, 2020.

Nicolini, C. et al. (Jan. 2015). Decreased mTOR signaling pathway in human idiopathic autism and in rats exposed to valproic acid. Acta Neuropathologica Communications, 3:3, 13 pages, https://doi.org/10.1186/s40478-015-0184-4.

Niederhofer, H. (Sep. 2005). Atomoxetine Also Effective in Patients Suffering From Narcolepsy? Sleep, 28(9):1189, 1 page. https://www.researchgate.net/publication/7500498_Atomoxetine_Also_Effective_in_Patients_Suffering_From_Narcolepsy (accessed Mar. 26, 2020).

Nielsen, S. (2017). Benzodiazepines. Curr. Top. Behav. Neurosci. 34:141-159. https://doi.org/10.1007/7854_2015_425.

Nimmo-Smith, V. et al. (Jan. 2020). Anxiety Disorders in Adults with Autism Spectrum Disorder: A Population-Based Study. Journal of Autism and Developmental Disorders, 50:308-318. https://doi.org/10.1007/s10803-019-04234-3.

Nisbet, E. et al. (Sep. 2009) The nature relatedness scale. Linking individuals' connection with nature to environmental concern and behavior. Environment and Behavior 41(5):715-740.

Norris, M.L. et al. (Jun. 2011). Olanzapine Use for the Adjunctive Treatment of Adolescents with Anorexia Nervosa. Journal of Child and Adolescent Psychopharmacology, 21(3):213-220. https://doi.org/10.1089/cap.2010.0131.

Nour, M.M. et al. (Jun. 2016) Ego-Dissolution and Psychedelics: Validation of the Ego-Dissolution Inventory (EDI) Frontiers in Human Neuroscience, 10:269, doi: 10.3389/fnhum.2016.00269, 13 pages.

Nour, M.M. et al. (Apr. 2017) Psychedelics, Personality and Political Perspectives. Journal of Psychoactive Drugs, 49(3):182-191.

Nowacka, A. & Borczyk, M. (Oct. 2019). Ketamine applications beyond anesthesia—A literature review. European Journal of Pharmacology, 860, 172547, 14 pages. https://doi.org/10.1016/j.ejphar.2019.172547.

Nutt, "5HT2a Receptors—a New Target for Depression?" European Psychiatry, vol. 30, Supplement 1, Mar. 28-31, 2015, p. 35, 1 page total.

Nutt, D. et al. (Apr. 2, 2020) "Psychedelic Psychiatry's Brave New World", Cell, 181(1, 2):24-28.

Oerbeck, B. et al. (Jan. 2017) ADHD, comorbid disorders and psychosocial functioning: How representative is a child cohort study? Findings from a national patient registry. BMC Psychiatry, 17:23, 9 pages. Available from: http://dx.doi.org/10.1186/s12888-017-1204-7.

Olguin, P. et al. (Mar. 2017). Medical comorbidity of binge eating disorder. Eat Weight Disord 22, 13-26.

Onakpoya et al., "Benefits and harms of pregabalin in the management of neuropathic pain: A rapid review and meta-analysis of randomised clinical trials," BMJ Open 9, e023600, 19 pages (Jan. 2019).

Opbroek, A. et al. (Jun. 2002) Emotional blunting associated with SSRI-induced sexual dysfunction. Do SSRIs inhibit emotional responses? International Journal of Neuropsychopharmacology, 5:147-151.

Orekhova, E.V. et al. (Mar. 2008). Sensory gating in young children with autism: Relation to age, IQ, and EEG gamma oscillations. Neurosci. Lett., 434:218-223. https://doi.org/10.1016/j.neulet.2008.01.066.

Osland, S. et al. (Oct. 2018). The prevalence of diagnosed obsessive compulsive disorder and associated comorbidities: A population-based Canadian study. Psychiatry Research, 268:137-142. https://doi.org/10.1016/j.psychres.2018.07.018.

Ottman, R. et al.(Feb. 2011). Comorbidities of epilepsy: results from the Epilepsy Comorbidities and Health (EPIC) survey. Epilepsia, 52(2):308-315. https://doi.org/10.1111/j.1528-1167.2010.02927.x.

Otto, M.W. et al. (Dec. 2001). An effect-size analysis of the relative efficacy and tolerability of serotonin selective reuptake inhibitors for panic disorder. Am. J. Psychiatry 158:1989-1992. https://doi.org/10.1176/appi.ajp.158.12.1989.

Page, J. & Henry, D. (Mar. 2000). Consumption of NSAIDs and the Development of Congestive Heart Failure in Elderly Patients. Archives of Internal Medicine, 160(6):777-784. https://doi.org/10.1001/archinte.160.6.777.

Pahwa, R. et al. (2020). Chronic Inflammation. Statpearls [Internet]. NCBI Bookshelf. Retrieved from: https://www.ncbi.nlm.nih.gov/books/NBK493173/, 9 printed pages.

Palsson-Mcdermott, E. M. & O'Neill, L. A. J. (Oct. 2004). Signal transduction by the lipopolysaccharide receptor, Toll-like receptor-4. Immunology, 113(2):153-162. https://doi.org/10.1111/j.1365-2567.2004.01976.x.

Papakostas, G.I. et al. (2006) "The combination of duloxetine and bupropion for treatment-resistant major depressive disorder" Depression and Anxiety, 23:178-181.

Parameswaran, N. & Patial, S. (2010). Tumor necrosis factor-α signaling in macrophages. Critical Reviews in Eukaryotic Gene Expression, 20(2):87-103. https://doi.org/10.1615/critreveukargeneexpr.v20.i2.10.

Park, A. (Dec. 2021) Characterization of Psilocybin. Freedom to Operate, LLC. Triclinic Labs Report No. R2021638.01, 11 pages.

Park, J.H. & Park, H.J. (Aug. 2017) Botulinum toxin for the treatment of neuropathic pain. Toxins. 9:290, doi:10.3390/toxins9090260, 15 pages.

(56)        References Cited

OTHER PUBLICATIONS

Parkinson's Foundation (2020). Prescription Medications for Parkinson Disease. Retrieved from https://www.parkinson.org/Understanding-Parkinsons/Treatment/Prescription-Medications; retrieved on Jul. 30, 2020; 6 pages.

Parkinson's Foundation, P. (2020). Stages of Parkinson's disease. Retrieved from https://www.parkinson.org/Understanding-Parkinsons/What-is-Parkinsons/Stages-of-Parkinsons, 8 pages.

Parnas, J. et al. (Sep. 2005) EASE: Examination of Anomalous Self-Experience. Psychopathology. 38:236-258.

Passie et al., "The pharmacology of psilocybin", Addiction Biology (2002); 7(4): 357-364. doi: 10.1080/1355621021000005937.

Patra, S. (Dec. 2016) "Return of the psychedelics: Psilocybin for treatment resistant depression," Asian Journal of Psychiatry, vol. 24, p. 51-52.

Patton, J.H. (Nov. 1995) Factor structure of the Barratt Impulsiveness Scale. Journal of Clinical Psychology. 51:768-774.

Pauli, D. et al. (Apr. 2017). Motivation to change, coping, and self-esteem in adolescent anorexia nervosa: A validation study of the Anorexia Nervosa Stages of Change Questionnaire (ANSOCQ). Journal of Eating Disorders, 5(1):11, 11 pages. https://doi.org/10.1186/s40337-016-0125-z.

Pecina, S., & Berridge, K.C. (Dec. 2005). Hedonic hot spot in nucleus accumbens shell: Where do μ opioids cause increased hedonic impact of sweetness? The Journal of Neuroscience, 25(50):11777-11786.

Pelletier, M. & Siegel, R. M. (Dec. 2009). Wishing away inflammation? New links between serotonin and TNF signaling. Molecular Interventions, 9(6):299-301. https://doi.org/10.1124/mi.9.6.5.

Pennington, S. et al. (Aug. 2010). The cause of death in idiopathic Parkinson's disease. Parkinsonism & Related Disorders, 16(7):434-437. https://doi.org/10.1016/j.parkreldis.2010.04.010.

Perez-Carbonell, L. et al. (Jun. 2020). Adherence to wakefulness promoting medication in patients with narcolepsy. Sleep Med. 70:50-54. https://doi.org/10.1016/j.sleep.2020.02.013.

Perini, G. I. et al. (Dec. 1996). Interictal mood and personality disorders in temporal lobe epilepsy and juvenile myoclonic epilepsy. Journal of Neurology, Neurosurgery & Psychiatry, 61(6):601-605. https://doi.org/10.1136/jnnp.61.6.601.

Perlis, M.L. et al. (Feb. 2001). Beta/Gamma EEG Activity in Patients with Primary and Secondary Insomnia and Good Sleeper Controls. Sleep, 24(1):110-117.

Persson, S. A. (Aug. 1978). LSD and related drugs as DA antagonists: receptor-mediated effects on the synthesis and turnover of DA. Life Sciences, 23(5):523-526. https://doi.org/10.1016/0024-3205(78)90165-0.

Peters, E. et al. (2004) Measuring Delusional Ideation: the 21-item Peters et al. Delusions Inventory (PDI). Schizophrenia Bulletin, 30(4):1005-1022.

Piedmont, R.L. (1999) Does spirituality represent the sixth factor of personality? Spiritual transcendence and the five-factor model. Journal of Personality. 67:985-1013.

Piton A. et al. (2011). Systematic resequencing of X-chromosome synaptic genes in autism spectrum disorder and schizophrenia. Molecular Psychiatry, 16(8):867-880. https://doi.org/10.1038/mp.2010.54.

Pittenger, C. et al. (Sep. 2014). Pharmacological treatment of obsessive-compulsive disorder. In Psychiatric Clinics of North America, 37(3):375-391. https://doi.org/10.1016/j.psc.2014.05.006.

Polat, G. et al. (Feb. 2017). Sepsis and Septic Shock: Current Treatment Strategies and New Approaches. Eurasian Journal of Medicine, 49(1):53-58. https://doi.org/10.5152/eurasianjmed.2017.17062.

Polito et al., "A systematic study of microdosing psychedelics", PloS One (2019); 14(2): e0211023; 26 pages. doi: 10.1371/journal.pone.0211023.

Postal, M. et al. (Jan. 2016). Depressive symptoms are associated with tumor necrosis factor alpha in systemic lupus erythematosus. Journal of Neuroinflammation, 13(1):5. https://doi.org/10.1186/s12974-015-0471-9, 7 pages.

Price, J. et al. (2012) The Oxford Questionnaire on the Emotional Side-effects of Antidepressants (OQuESA): Development, validity, reliability and sensitivity to change. Journal of Affective Disorders. 140:66-74.

Prince J. (2008) Catecholamine dysfunction in attention-deficit/hyperactivity disorder. An update. Journal of Clinical Psychopharmacology. 28(3 Suppl 2):39-45.

Prochazkova, L. et al. (Dec. 2018). Exploring the effect of microdosing psychedelics on creativity in an open-label natural setting. Psychopharmacology, 235(12):3401-3413. https://doi.org/10.1007/s00213-018-5049-7.

Prosolv® SMCC (2022). Retrieved from Web Archive, Reset https://web.archive.org/web/20160318071326/http://www.jrspharma.com/pharmaen/productsservices/excipients/hfe/prosolvs-mcc.php Retrieved Mar. 18, 2016, 3 pages.

Pryor, T. et al. (May 1996). Clinical correlates of anorexia nervosa subtypes. The International Journal of Eating Disorders, 19(4):371-379. http://www.ncbi.nlm.nih.gov/pubmed/9156690.

Psilocybin for the Treatment of Cluster Headache. ClinicalTrials.gov [Internet]. Identifier: NCT02981173. Retrieved from: https://clinicaltrials.gov/ct2/show/NCT02981173, 8 pages (2016).

Psilocybin Patent Tracker. Psilocybin Alpha, 2020 [online]. Retrieved from: https://psilocybinalpha.com/data/psilocybin-patent-tracker; retrieved on Oct. 1, 2020, 2 printed pages.

Pugazhenthi, S. et al. (Jul. 2013). Induction of an Inflammatory Loop by Interleukin-1β and Tumor Necrosis Factor-α Involves NF-κB and STAT-1 in Differentiated Human Neuroprogenitor Cells. PLOS ONE, 8(7):1-12. https://doi.org/10.1371/journal.pone.0069585.

Pulikkan, J. et al. (2019). Role of the Gut Microbiome in Autism Spectrum Disorders. In Advances in Experimental Medicine and Biology, 1118:253-269. https://doi.org/10.1007/978-3-030-05542-4_13.

Quadri, S. et al. (Apr. 2009). Improvement of idiopathic central sleep apnea with zolpidem. J. Clin. Sleep Med. 5:122-129. https://doi.org/10.5664/jcsm.27439.

Quan, Q. et al. (2019). CDK5 Participates in Amyloid-β Production by Regulating PPARγ Phosphorylation in Primary Rat Hippocampal Neurons. Journal of Alzheimer's Disease : JAD, 71(2):443-460. https://doi.org/10.3233/JAD-190026.

Quan, X. et al. (2020). Related Network and Differential Expression Analyses Identify Nuclear Genes and Pathways in the Hippocampus of Alzheimer Disease. Medical Science Monitor : International Medical Journal of Experimental and Clinical Research, 26:e919311, 11 pages. https://doi.org/10.12659/MSM.919311.

Quintero J. et al. (2010). Reboxetine for ADHD in children non-responders or with poor tolerance to methylphenidate: A prospective long-term open-label study. ADHD Atten Deficit Hyperact Disord., 2(3):107-113.

Raffaeli, W. & Arnaudo, E. (Aug. 2017). Pain as a disease: An overview. J Pain Res., 10:2003-2008.

Rai, D. et al. (Jan. 2012). Epilepsy and psychiatric comorbidity: A nationally representative population-based study. Epilepsia 53:1095-1103. https://doi.org/10.1111/j.1528-1167.2012.03500.x.

Ramachandran, V. et al. (2018). Relief from intractable phantom pain by combining psilocybin and mirror visual-feedback (MVF). Neurocase, 24(2):105-110. Available from: https://doi.org/10.1080/13554794.2018.1468469 Ramachandran.

Ramadan, M.I. et al. (2006). Protect against drug-drug interactions with anxiolytics. Current Psychiatry, 5(5):16-28.

Ramos, A.A. et al. (2019). A meta-analysis on verbal working memory in children and adolescents with ADHD. Clinical Neuropsychologist, 34(5):873-898.

Rastam, M., et al. (2003). Outcome of teenage-onset anorexia nervosa in a Swedish community-based sample. European Child and Adolescent Psychiatry, 12(Suppl. 1):78-90. https://doi.org/10.1007/s00787-003-1111-y.

Rautiainen, M-R. et al. (2016) Genome-wide association study of antisocial personality disorder. Transl Psychiatry. 6:e883, doi:10.1038/tp.2016.155, 10 pages.

(56)　　　　　References Cited

OTHER PUBLICATIONS

Raval et al., "Silicified Microcrystalline Cellulose as a Multifunctional Pharmaceutical Excipient," Drug Delivery Technology, 2009;9(4):28 and 30-32. Supplied by the British Library Oct. 12, 2019, 6 pages.
Ravindran, L.N. & Stein, M.B. (2010). The pharmacologic treatment of anxiety disorders: A review of progress. J. Clin. Psychiatry. 71(7):839-854. https://doi.org/10.4088/JCP.10r06218blu.
Reas, D. and Grilo, C. (Mar. 2014). Current and emerging drug treatments for binge eating disorder. Expert Opinion on Emerging Drugs, 19(1), pp. 99-142.
Registry No. 1026609-93-7, File Registry on STN, entered STN Jun. 8, 2008, 3 pages.
Reimherr, F.W. et al. (2017). ADHD and Anxiety: Clinical Significance and Treatment Implications. Curr. Psychiatry Rep., 19:109, 10 pages. https://doi.org/10.1007/s11920-017-0859-6.
Reitz, C. & Mayeux, R. (Apr. 2014). Alzheimer disease: Epidemiology, diagnostic criteria, risk factors and biomarkers. Biochemical Pharmacology, 88(4):640-651. https://doi.org/10.1016/j.bcp.2013. 12.024.
Remes, O. et al. (2016). A systematic review of reviews on the prevalence of anxiety disorders in adult populations. Brain Behav. https://doi.org/10.1002/brb3.497, 33 pages.
Repke et al., Psilocin Analogs. 1. Synthesis of 3-[2-(Dialkylamino)ethyl]- and 3-[2-(Cycloalkylamino)ethyl] indol-4-ols, J. Heterocyclic Chem., 14, 71 (Feb. 1977), 4 pages.
Rickels. "Pregabalin for treatment of generalized anxiety disorder: A 4-week, multicenter, double-blind, placebo-controlled trial of pregabalin and alprazolam." Arch. Gen. Psychiatry, Sep. 2005; 62: 1022-1030. doi.org/10.1001/archpsyc.62.9.1022.
Riediger C. et al. (2017). Adverse effects of antidepressants for chronic pain: A systematic review and meta-analysis. Front. Neurol. 8:307, 23 pages. doi: 10.3389/fneur.2017.00307.
Rintala, H. et al. (2017). Register-based study of the incidence, comorbidities and demographics of obsessive-compulsive disorder in specialist healthcare. BMC Psychiatry, 17(1):64, 8 pages. https://doi.org/10.1186/s12888-017-1224-3.
Ripoll, L.H. et al., Evidence-based pharmacotherapy for personality disorders,: International Journal of Neuropsychopharmacology 14:1257-1288 (2011).
Robbins, M.S. (2013) The psychiatric comorbidities of cluster headache. Curr Pain Headache Rep, 17(2):313, DOI:10.1007/s11916-012-0313-8, 8 pages.
Robner, A. et al. (Sep. 2017). Cognitive Flexibility in Juvenile Anorexia Nervosain Relation to Comorbid Symptoms of Depression, Obsessive Compulsive Symptoms and Duration of Illness. Zeitschrift für Kinder- und Jugendpsychiatrie und Psychotherapie, 45 (5):371-380. https://doi.org/10.1024/1422-4917/a000493.
Rodriguez, C. et al. (2016). Attention deficit/hyperactivity disorder (ADHD) diagnosis: An activation-executive model. Front. Psychol. 7:1406, 13 pages. doi: 10.3389/fpsyg.2016.01406.
Rojas, D.C. & Wilson, L.B. (2014). γ-band abnormalities as markers of autism spectrum disorders. Biomark Med. Mar. 2014; 8(3):353-368. doi:10.2217/bmm.14.15.
Rosen, E. et al. (2017). Hepatic Complications of Anorexia Nervosa. Dig Dis Sci, 62:2977-2981. doi:10.1007/s10620-017-4766-9.
Rosenberg, M. (1965) Society and the adolescent self-image. Science, 148(3671):804, DOI:10.1126/science.148.3671.804, 2 pages.
Rosenblat, J.D. et al. (Aug. 2014). Inflamed moods: A review of the interactions between inflammation and mood disorders. Progress in Neuro-Psychopharmacology and Biological Psychiatry, 53:23-34. https://doi.org/10.1016/j.pnpbp.2014.01.013.
Ross et al., "Rapid and sustained symptom reduction following psilocybin treatment for anxiety and depression in patients with life-threatening cancer: a randomized controlled trial", Journal of Psychopharmacology (2016); 30: 1165-1180. doi: 10.1177/0269881116675512.
Rossi, P. and Whelan, J. (2016) What is cluster headache? Fact sheet for patients and their families. A publication to mark Cluster Headache Day 2016. Functional Neurology. 31(3):181-183.

Roth, T. et al. (2007). Insomnia: Definition, prevalence, etiology, and consequences. J. Clin. Sleep Med. Supplement to vol. 3, No. 5, https://doi.org/10.5664/jcsm.26929, 4 pages.
Roth, T. et al. (Nov. 2007). Efficacy and safety of doxepin 1 mg, 3 mg, and 6 mg in adults with primary insomnia. Sleep 30, 1555-61. https://doi.org/10.1093/sleep/30.11.1555.
Rucker, J. et al. (Dec. 25, 2017) "Psychiatry & the psychedelic drugs. Past, present & future," Neuropharmacol, 142:200-218.
Rucker, J. et al. (Dec. 2019) Psilocybin administration to healthy participants: safety and feasibility in a placebo-controlled study. Poster # W111, 1 page, presented at the 58th Annual Meeting of the American College of Neuropsychopharmacology, Orlando, FL, USA, Dec. 8-11, 2019.
Ruffolo, S. et al. (Jan. 2006). Comorbidity of body dysmorphic disorder and eating disorders: Severity of psychopathology and body image disturbance. International Journal of Eating Disorders, 39(1), pp. 11-19.
Rupprecht, R. et al. (2009). Translocator protein (18 kD) as target for anxiolytics without benzodiazepine-like side effects. Science, New Series, vol. 325, No. 5939, pp. 490-493. https://doi.org/10. 1126/science.1175055.
Ruscio, A. M. et al. (2010). The epidemiology of obsessive-compulsive disorder in the National Comorbidity Survey Replication. Molecular Psychiatry, 15(1), 53-63. https://doi.org/10.1038/mp.2008.94.
Rush, A.J. et al. (2003) The 16-Item Quick Inventory of Depressive Symptomatology (QIDS), Clinician Rating (QIDS-C), and Self-Report (QIDS-SR): A Psychometric Evaluation in Patients with Chronic Major Depression. Biol Psy, 54(5):573-583.
Russell, E.J. et al. (Apr. 2013). Risk of obsessive-compulsive disorder in pregnant and postpartum women: A meta-analysis. Journal of Clinical Psychiatry, 74(4), 377-385. https://doi.org/10. 4088/JCP.12r07917.
Russo, A.J. (2014). Increased Epidermal Growth Factor Receptor (EGFR) Associated with Hepatocyte Growth Factor (HGF) and Symptom Severity in Children with Autism Spectrum Disorders (ASDs). Journal of Central Nervous System Disease. 6:79-83. https://doi.org/10.4137/jonsd.s13767.
Ryder, S. & A, Stannard C.F. (2005). Treatment of chronic pain: Antidepressant, antiepileptic and antiarrhythmic drugs. Contin Educ Anaesthesia, Crit Care Pain. 5(1):18-21.
Rylander, M. et al. (2017). A comparison of the metabolic complications and hospital course of severe anorexia nervosa by binge-purge and restricting subtypes. Eating Disorders, 25(4), 345-357. https://doi.org/10.1080/10640266.2016.1269555.
Sagata, N. et al. (Oct. 2017). Dysregulated gene expressions of MEX3D, FOS and BCL2 in human induced-neuronal (iN) cells from NF1 patients: A pilot study. Scientific Reports. https://doi.org/10.1038/s41598-017-14440-7, 8 pages.
Sahu, A. & Gupta, R. (Dec. 2017). A study of psychiatric comorbidity after traumatic limb amputation: A neglected entity. Ind Psychiatry J. 26(6):228-32.
Saigal N., et al., "Microcrystalline Cellulose as a Versatile Excipient in Drug Research," Journal of Young Pharmacists, 2009, vol. 1, pp. 6-12.
Sakashita, Y. et al. (2015). Effect of Psilocin on Extracellular Dopamine and Serotonin Levels in the Mesoaccumbens and Mesocortical Pathway in Awake Rats. Biol. Pharm. Bull. 38, 134-138 (2015).
Salama, R. M. et al. (2020). Neuroprotective effect of crocin against rotenone-induced Parkinson's disease in rats: Interplay between PI3K/Akt/mTOR signaling pathway and enhanced expression of miRNA-7 and miRNA-221. Neuropharmacology, 164, 107900., 12 pages. https://doi.org/10.1016/j.neuropharm.2019.107900.
Salisbury-Afshar, E. (2018). Management of Insomnia Disorder in Adults—Implementing AHRQ Effective Health Care Reviews. Am Fam Physician. 98(5), 5 pages. https://www.aafp.org/afp/2018/0901/p319.html#afp20180901p319-b4.
Sandbank, M. et al. (2020). Project AIM: Autism intervention meta-analysis for studies of young children. Psychological Bulletin. 146(1):1-29. https://doi.org/10.1037/bul0000215.
Sandiego, C.M. et al. (Oct. 2015). Imaging robust microglial activation after lipopolysaccharide administration in humans with

(56)         References Cited

OTHER PUBLICATIONS

PET. Proceedings of the National Academy of Sciences, 112(40), 12468-12473. https://doi.org/10.1073/pnas.1511003112.

Santiago, J.A. et al. (2017). Biological and Clinical Implications of Comorbidities in Parkinson's Disease. Frontiers in Aging Neuroscience, 9, 16 pages. https://doi.org/10.3389/fnagi.2017.00394.

Santini, E. et al. (2013). Exaggerated translation causes synaptic and behavioural aberrations associated with autism. Nature, 493, https://doi.org/10.1038/nature11782, 6 pages.

Saraf, G. et al. (Mar. 2017). Bipolar disorder comorbidity in patients with a primary diagnosis of OCD, International Journal of Psychiatry in Clinical Practice, 21:1, 70-74, doi: 10.1080/13651501.2016.1233344.

Saraiva, M., & O'Garra, A. (Mar. 2010). The regulation of IL-10 production by immune cells. Nature Reviews Immunology, 10(3), 170-181. https://doi.org/10.1038/nri2711.

Sard et al., "SAR of psilocybin analogs: discovery of a selective 5-HT2C agonist", Bioorganic & Medicinal Chemistry Letters (2005); 15(20): 4555-4559. doi: 10.1016/j.bmcl.2005.06.104.

Saunders, A.M. et al. (Aug. 1993). Association of apolipoprotein E allele ε4 with late-onset familial and sporadic Alzheimer's disease. Neurology, 43(8):1467-1467. https://doi.org/10.1212/WNL.43.8.1467.

Savage. "Lysergic acid diethylamide (LSD-25) a clinical-psychological study", American Journal of Psychiatry (1952); 108(12): 896-900. doi: 10.1176/ajp.108.12.896.

Savioz, A., Leuba, G., & Vallet, P. G. (Sep. 2014). A framework to understand the variations of PSD-95 expression in brain aging and in Alzheimer's disease. Ageing Research Reviews, 18, 86-94. https://doi.org/10.1016/j.arr.2014.09.004.

Saxton, R. A. & Sabatini, D.M. (Mar. 2017). mTOR Signaling in Growth, Metabolism, and Disease. Cell, 168(6):960-976. https://doi.org/10.1016/j.cell.2017.02.004.

Sayal, K. et al. (Feb. 2018) ADHD in children and young people: prevalence, care pathways, and service provision. The Lancet Psychiatry, 5(2):175-186. Available from: http://dx.doi.org/10.1016/S2215-0366(17)30167-0cdc.gov.

Scammell, T.E. (2015) Narcolepsy. N. Engl. J. Med., 373:2654-2662. https://doi.org/10.1056/NEJMra1500587.

Schachter, M. & Parkes, J.D. (Feb. 1980). Fluvoxamine and clomipramine in the treatment of cataplexy. Journal of Neurology, Neurosurgery, and Psychiatry, 43:171-174.

Scheller, J. et al. (May 2011). The pro- and anti-inflammatory properties of the cytokine interleukin-6. Biochimica et Biophysica Acta, 1813(5):878-888. https://doi.org/10.1016/j.bbamcr.2011.01.034.

Schneider, T. et al. (Jul. 2008). Gender-specific behavioral and immunological alterations in an animal model of autism induced by prenatal exposure to valproic acid. Psychoneuroendocrinology, 33:728-740. https://doi.org/10.1016/j.psyneuen.2008.02.011.

Schulke, S. (Mar. 2018). Induction of Interleukin-10 Producing Dendritic Cells as a Tool to Suppress Allergen-Specific T Helper 2 Responses. Frontiers in Immunology, 9:455, https://doi.org/10.3389/fimmu.2018.00455, 18 pages.

Schwalberg, M.D. et al. (Nov. 1992). Comparison of Bulimics, Obese Binge Eaters, Social Phobics, and Individuals With Panic Disorder on Comorbidity Across DSM-III-R Anxiety Disorders. J. Abnorm. Psychol., 101:675-681. https://doi.org/10.1037/0021-843X.101.4.675.

Sedgwick, O. et al. (2017) Neuropsychology and emotion processing in violent individuals with antisocial personality disorder or schizophrenia: The same or different? A systematic review and meta-analysis. Australian and New Zealand Journal of Psychiatry, 51(12):1178-1197.

Sedley, W. & Cunningham, M.O. (2013). Do cortical gamma oscillations promote or suppress perception? An under-asked question with an over-assumed answer. Front. Hum. Neurosci., 7:595, https://doi.org/10.3389/fnhum.2013.00595, 17 pages.

Serrano-Pozo, A. et al. (2011). Neuropathological Alterations in Alzheimer Disease. Cold Spring Harbor Perspectives in Medicine, 1(1):a006189, https://doi.org/10.1101/cshperspect.a006189, 23 pages.

Sewell et al., "Response of cluster headache to psilocybin and LSD", Neurology (2006); 66(12): 1920-1922. doi: 10.1212/01.wnl.0000219761.05466.43.

Shah, K., & Lahiri, D.K. (Jun. 2014). Cdk5 activity in the brain—multiple paths of regulation. Journal of Cell Science, 127(11):2391-2400. https://doi.org/10.1242/jcs.147553.

Shannon, P. et al. (Nov. 2003). Cytoscape: a software environment for integrated models of biomolecular interaction networks. Genome Research, 13(11):2498-2504. https://doi.org/10.1101/gr.1239303.

Sharma, S.R. et al. (2018). Autism Spectrum Disorder: Classification, diagnosis and therapy. Pharmacology and Therapeutics, 190:91-104. https://doi.org/10.1016/j.pharmthera.2018.05.007.

Sheng et al, "The Link between Depression and Chronic Pain: Neural Mechanisms in the Brain," Neural Plast. 2:9724371, pp. 1-10 (2017); Epub 2017 Jun. 19, 2017.

Sherman, E.M.S. et al. (Mar. 2011). Neuropsychological outcomes after epilepsy surgery: Systematic review and pooled estimates. Epilepsia, 52(5):857-869. https://doi.org/10.1111/j.1528-1167.2011.03022.x.

Sherwood, A.M. et al. (2021) Psilocybin: crystal structure solutions enable phase analysis of prior art and recently patented examples. Acta Crystallographica, 78(1):1-20.

Shier, A.C. et al. (2013) Pharmacological Treatment of Attention Deficit Hyperactivity Disorder in Children and Adolescents: Clinical Strategies. J Cent Nerv Syst Dis, 5, doi: 10.4137/JCNSD.S6691, 17 pages.

Shirota et al., "Concise large-scale synthesis of psilocin and psilocybin, principal hallucinogenic constituents of "magic mushroom"", Journal of Natural Products (2003); 66(6): 885-887. doi: 10.1021/np030059u.

Shofty, B. et al. (Apr. 26, 2019). Loss of function in the autism and learning disabilities associated gene Nf1 disrupts corticocortical and corticostriatal functional connectivity in human and mouse. BioRxiv, preprint, https://doi.org/10.1101/618223, 35 pages.

Shoja Shafti, S., & Kaviani, H. (Feb. 2015). Aripiprazole versus quetiapine in treatment-resistant obsessive-compulsive disorder: A double-blind clinical trial. Therapeutic Advances in Psychopharmacology, 5(1):32-37. https://doi.org/10.1177/2045125314560739.

Shulgin et al., "Tihkal: The Continuation," Transform Press, 1997, pp. 468-473.

Sid-Otmane, L. et al. (Apr. 2020). Selective metabotropic glutamate receptor 2 positive allosteric modulation alleviates L-DOPA-induced psychosis-like behaviours and dyskinesia in the MPTP-lesioned marmoset. European Journal of Pharmacology, 873:172957, https://doi.org/10.1016/j.ejphar.2020.172957, 6 pages.

Siervo, M. et al. (Jun. 2005). Application of the Scoff, Eating Attitude Test 26 (EAT 26) and Eating Inventory (TFEQ) questionnaires in young women seeking diet-therapy. Eating and Weight Disorders, 10(2):76-82. https://doi.org/10.1007/BF03327528.

Sifferlin A., "What You Need to Know About Magic Mushrooms and Depression," Time, 4 pages (Dec. 1, 2016).

Silber, M.H. et al. (2002) The epidemiology of narcolepsy in Olmsted County, Minnesota: A population-based study. Sleep, 25(2):197-202. https://doi.org/10.1093/sleep/25.2.197.

Silva, N. et al. (Feb. 2014) Searching for a neurobiological basis for self-medication theory in ADHD comorbid with substance use disorders: An in vivo study of dopamine transporters using $^{99m}$Tc-TRODAT-1 SPECT. Clin Nucl Med, 39(2):e129-e134.

Simon, N.M. (2009) Generalized Anxiety Disorder and Psychiatric Comorbidities Such as Depression, Bipolar Disorder, and Substance Abuse. J Clin Psychiatry, 70(suppl 2):10-14.

Singh, A., & Trevick, S. (Nov. 2016). The Epidemiology of Global Epilepsy. Neurologic Clinics, 34(4):837-847. https://doi.org/10.1016/j.ncl.2016.06.015.

Siniscalco, D. et al. (Jun. 2018). Inflammation and neuro-immune dysregulations in autism spectrum disorders. Pharmaceuticals, 11:56, https://doi.org/10.3390/ph11020056, 14 pages.

Skapinakis, P. et al. (Aug. 2016) "Pharmacological and psychotherapeutic interventions for management of obsessive-compulsive

(56) References Cited

OTHER PUBLICATIONS disorder in adults: a systematic review and network meta-analysis" The Lancet Psychiatry, 3(8):730-739. https://doi.org/10.1016/S2215-0366(16)30069-4.

Smith, B.W. et al. (2008) The Brief Resilience Scale: Assessing the Ability to Bounce Back. International Journal of Behavioral Medicine. 15:194-200.

Smith, K.N. et al. (2019). Changes in meal-related anxiety predict treatment outcomes in an intensive family-based treatment program for adolescents with anorexia nervosa. Eating Disorders, DOI: 10.1080/10640266.2019.1688008, 13 pages.

Snaith, R.P. et al. (1995) A scale for the assessment of hedonic tone. The Snaith-Hamilton Pleasure Scale. The British Journal of Psychiatry, 167:99-103.

Soler, J. et al. (2018). Genetic variability in scaffolding proteins and risk for schizophrenia and autism-spectrum disorders: A systematic review. Journal of Psychiatry and Neuroscience, 43(4):223-244. https://doi.org/10.1503/jpn.170066.

Souery, D. et al. "Clinical factors associated with treatment resistance in major depressive disorder: results from a European multicenter study" J Clin Psychiatry (2007); 68(7):1062-1070.

Spangler, E.L., Rigby, P., & Ingram, D.K. (1986). Scopolamine impairs learning performance of rats in a 14-unit T-maze. Pharmacology, Biochemistry and Behavior, 25:673-679. https://doi.org/10.1016/0091-3057(86)90158-9.

Spielberger, C.D. (2020) State-Trait Anxiety Inventory for AdultsTM. STAI—Adult Manual. Mind Garden Inc., www.mindgarden.com, 87 pages.

Spowart-Manning L. et al. (May 2004) The T-maze continuous alternation task for assessing the effects of putative cognition enhancers in the mouse. Behav Brain Res, 151(1-2):37-46.

Srinivas, H.V. & Shah, U. (2017). Comorbidities of epilepsy. Neurology India, 65(Supplement):S18-S24. https://doi.org/10.4103/neuroindia.NI_922_16, 15 pages.

Srivastava, R.K. et al. (2011). Role of Donepezil in Autism: Its Conduciveness in Psychopharmacotherapy. Case Reports in Psychiatry, 2011:563204, https://doi.org/10.1155/2011/563204, 2 pages.

Stahl, S.M. (Dec. 1998) Mechanism of action of serotonin selective reuptake inhibitors. Serotonin receptors and pathways mediate therapeutic effects and side effects. J. Affect. Disord., 51:215-235. https://doi.org/10.1016/S0165-0327(98)00221-3.

Stancil, S. et al. (Nov. 2019). Naltrexone Reduces Binge Eating and Purging in Adolescents in an Eating Disorder Program. Journal of Child and Adolescent Psychopharmacology, 29(9):721-724.

Stancu, C., & Sima, A. (Dec. 2001). Statins: mechanism of action and effects. Journal of Cellular and Molecular Medicine, 5(4), 378-387. https://doi.org/10.1111/j.1582-4934.2001.tb00172.x.

Starr, M.S. (1996). The role of dopamine in epilepsy. Synapse. 22:159-194.

Stefano, S. et al. (Apr. 2008). Antidepressants in short-term treatment of binge eating disorder: Systematic review and meta-analysis. Eating Behaviors, 9(2), pp. 129-136.

Steger, M.F. et al. (2008) Understanding the serach for meaning in life: Personality, cognitive style, and the dynamic between seeking and experiencing meaning. Journal of Personality, 76:199-228.

Stein, D.J. et al. (Aug. 2019) "Obsessive-compulsive disorder" Nature Reviews Disease Primers, 5(1):52; doi: 10.1038/s41572-019-0102-3, 21 pages.

Stein, D.J. et al. (Jun. 2017). Epidemiology of anxiety disorders: From surveys to nosology and back. Dialogues Clin Neurosci, 19:127-135.

Stein, M.B. & Sareen, J. (2015). Generalized anxiety disorder. N. Engl. J. Med., 373:2059-2068. https://doi.org/10.1056/NEJMcp1502514.

Steinhausen, H-C. (Jan. 2009). Outcome of Eating Disorders. Child and Adolescent Psychiatric Clinics of North America, 18(Issue 1):225-242. https://doi.org/10.1016/j.chc.2008.07.013.

Stevenson, R.A. et al. (2019). Conjunctive visual processing appears abnormal in Autism. Frontiers in Psychology, 9:2668, https://doi.org/10.3389/fpsyg.2018.02668, 7 pages.

Stice, L. V., & Lavner, J. A. (Mar. 2019). Social Connectedness and Loneliness Mediate the Association Between Autistic Traits and Internalizing Symptoms Among Young Adults. Journal of Autism and Developmental Disorders, 49(3), 1096-1110. https://doi.org/10.1007/s10803-018-3812-6.

Sticht, G., & Kaferstein, H. (Sep. 2000). Detection of psilocin in body fluids. Forensic Science International, 113(1-3):403-407. https://doi.org/10.1016/S0379-0738(00)00213-9.

Stojanovic, A. et al. (Mar. 2014). Increased serum interleukin-6 levels in early stages of psychosis: Associations with at-risk mental states and the severity of psychotic symptoms. Psychoneuroendocrinology, 41, 23-32. https://doi.org/10.1016/j.psyneuen.2013.12.005.

Strawbridge, R. et al. (Mar. 2019). Inflammatory profiles of severe treatment-resistant depression. Journal of Affective Disorders, 246:42-51. https://doi.org/10.1016/j.jad.2018.12.037.

Strunk, D.R. et al. (Jun. 2006) Depressive symptoms are associated with unrealistic negative predictions of future life events. Behavior Research and Therapy, 44:861-882.

Studerus, E. et al. (2011) "Acute, subacute and long-term subjective effects of psilocybin in healthy humans: a pooled analysis of experimental studies" J Psychopharmacol, 25(11):1434-1452.

Studerus et al., "Psychometric evaluation of the altered states of consciousness rating scale (OAV)." PloS One. Aug. 2010;5(8):e12412; 19 pages. doi: 10.1371/journal.pone.0012412.

Su, H., Lei, C.-T., & Zhang, C. (Apr. 2017). Interleukin-6 Signaling Pathway and Its Role in Kidney Disease: An Update. Frontiers in Immunology, 8:405, https://doi.org/10.3389/fimmu.2017.00405, 10 pages.

Subedi, B. & Grossberg, G.T. (2011) Phantom limb pain: Mechanisms and treatment approaches. Pain Res Treat, 2011:864605, doi:10.155/2011/864605, 8 pages.

Substance Abuse and Mental Health Services Administration. (Jun. 2016) Table 3.35, DSM-IV to DSM-5 Hypersomnolence Disorder Comparison. In: Impact of the DSM-IV to DSM-5 Changes on the National Survey on Drug Use and Health [Internet]. Rockville (MD): Substance Abuse and Mental Health Services Administration (US). Retrieved from NCBI Bookshelf, https://www.ncbi.nlm.nih.gov/books/NBK519704/table/ch3 .t35/, on Jul. 30, 2020, 3 printed pages.

Suda, S. et al. (2011). Decreased expression of axon-guidance receptors in the anterior cingulate cortex in autism. Molecular Autism, 2:14, https://doi.org/10.1186/2040-2392-2-14, 5 pages.

Suto, F. et al. (2005). Plexin-A4 mediates axon-repulsive activities of both secreted and transmembrane semaphorins and plays roles in nerve fiber guidance. Journal of Neuroscience, 25(14):3628-3637. https://doi.org/10.1523/JNEUROSCI.4480-04.2005.

Swieboda, P. et al. (2013) Assessment of pain: types, mechanism and treatment. Ann Agric Environ Med, 1(1):2-7.

Sztainberg, Y. & Zoghbi, H. Y. (2016). Lessons learned from studying syndromic autism spectrum disorders. Nature Neuroscience, 19(11):1408-1418. https://doi.org/10.1038/nn.4420.

Tai, J. et al. (Jan. 2018). Neuroprotective effects of a triple GLP-1/GIP/glucagon receptor agonist in the APP/PS1 transgenic mouse model of Alzheimer's disease. Brain Research, 1678:64-74. https://doi.org/10.1016/j.brainres.2017.10.012.

Takamori, S. (Feb. 2016). Presynaptic Molecular Determinants of Quantal Size. Frontiers in Synaptic Neuroscience, 8:2, https://doi.org/10.3389/fnsyn.2016.00002, 9 pages.

Tan, L.L. et al. (2019). Gamma oscillations in somatosensory cortex recruit prefrontal and descending serotonergic pathways in aversion and nociception. Nat. Commun. 10:983, https://doi.org/10.1038/s41467-019-08873-z, 17 pages.

Tan, T. et al. (2018). Low-frequency r TMS ameliorates autistic-like behaviors in rats induced by neonatal isolation through regulating the synaptic gaba transmission. Frontiers in Cellular Neuroscience, 12:Article 46, https://doi.org/10.3389/fncel.2018.00046, 12 pages.

Tanaka, T. et al. (Sep. 2014). IL-6 in Inflammation, Immunity, and Disease. Cold Spring Harbor Perspectives in Biology, 6(10):a016295, https://doi.org/10.1101/cshperspect.a016295, 16 pages.

Tarpey, P. et al. (2004). Mutations in the DLG3 gene cause nonsyndromic X-linked mental retardation. American Journal of Human Genetics, 75:318-324. https://doi.org/10.1086/422703.

(56)          References Cited

OTHER PUBLICATIONS

Tatsumi, M. et al. (Dec. 1997). Pharmacological profile of antidepressants and related compounds at human monoamine transporters. Eur. J. Pharmacol., 340, 249-258. https://doi.org/10.1016/S0014-2999(97)01393-9.

Taylor, J.F. et al. (1994) Self-Report Assessment of Female Sexual Function: Psychometrie Evaluation of the Brief Index of Sexual Functioning for Women. Archives of Sexual Behavior. 23(6):627-643.

Tecott, L. et al. (1995). Eating disorder and epilepsy in mice lacking 5-HT2C serotonin receptors. Nature, 374(6522), pp. 542-546.

Tellegen, A. and Atkinson, G. (1974) Openness to Absorbing and Self-Altering Experiences ("Absorption"), a Trait Related to Hypnotic Susceptibility. Journal of Abnormal Psychology, 83:268-277.

Tennant, R. et al. (2007) The Warrwick-Edinburgh Mental Well-being Scale (WEMWBS): development and the UK validation. Health and Quality of Life Outcomes, 5:63 doi:10.1186/1477-7525-5-63, 14 pages.

Terrando, N. et al. (Nov. 2010). Tumor necrosis factor-α triggers a cytokine cascade yielding postoperative cognitive decline. Proceedings of the National Academy of Sciences, 107(47):20518-20522. https://doi.org/10.1073/pnas.1014557107.

Thamby, A., & Jaisoorya, T. S. (Jan. 2019) "Antipsychotic augmentation in the treatment of obsessive-compulsive disorder" Indian Journal of Psychiatry, 61(7):S51-S57. https://doi.org/10.4103/psychiatry.IndianJPsychiatry_519_18.

Thapar, A. et al. (Nov. 2005). Do depression symptoms predict seizure frequency—or vice versa? Journal of Psychosomatic Research, 59(5):269-274. https://doi.org/10.1016/j.jpsychores.2005.04.001.

Thase, M.E. (1999). Antidepressant treatment of the depressed patient with insomnia. Journal of Clinical Psychiatry, 60(suppl. 17):28-31.

Thomas, A. et al. (2009) "Marble burying reflects a repetitive and perseverative behavior more than novelty-induced anxiety" Psychopharmacology, 204(2):361-373. NIH Public Access Author Manuscript, available in PMC Jul. 8, 2010, 22 pages.

Tokudome, K. et al. (Jun. 2016). Synaptic vesicle glycoprotein 2A (SV2A) regulates kindling epileptogenesis via GABAergic neurotransmission. Scientific Reports, 6(1):27420. https://doi.org/10.1038/srep27420, 12 pages.

Tolba, R. et al. (2018) The opioid epidemic and pain medicine specialists: Where to begin and what is next? Ochsner J, 18(1):20-22.

Toronto Research Chemicals; Certificate of Analysis; Product available for sale (Catalog No. P839650); Test Date: Apr. 5, 2013, 1 page.

Torres, A.R. et al. (Nov. 2006) "Obsessive-compulsive disorder: Prevalence, Comorbidity, impact, and help-seeking in the British National Psychiatric Morbidity Survey of 2000" American Journal of Psychiatry, 163(11):1978-1985. https://doi.org/10.1176/ajp.2006.163.11.1978.

Tramutola, A. et al. (Jun. 2015). Alteration of mTOR signaling occurs early in the progression of Alzheimer disease (AD): analysis of brain from subjects with pre-clinical AD, amnestic mild cognitive impairment and late-stage AD. Journal of Neurochemistry, 133(5), 739-749. https://doi.org/10.1111/jnc.13037.

Treynor, W. et al. (Jun. 2003) Rumination Reconsidered: A Psychometric Analysis. Cognitive Therapy and Research, 27:247-259.

Trulson, M. E., Stark, A. D., & Jacobs, B. L. (Jul. 1977). Comparative effects of hallucinogenic drugs on rotational behavior in rats with unilateral 6-hydroxydopamine lesions. European Journal of Pharmacology, 44(2), 113-119. https://doi.org/10.1016/0014-2999(77)90097-8.

Trunko, M.E. et al. (Apr. 2011). Aripiprazole in anorexia nervosa and low-weight bulimia nervosa: Case reports. International Journal of Eating Disorders, 44(3):269-275. https://doi.org/10.1002/eat.20807.

Tsai, S.-J. (Oct. 2017). Effects of interleukin-1beta polymorphisms on brain function and behavior in healthy and psychiatric disease conditions. Cytokine & Growth Factor Reviews, 37:89-97. https://doi.org/10.1016/j.cytogfr.2017.06.001.

Tucha, L. et al. (Feb. 2017) Sustained attention in adult ADHD: time-on-task effects of various measures of attention. J Neural Transm, 124(Suppl. 1):S39-S53.

Tully, P.J. et al. (2016). Anxiety and Cardiovascular Disease Risk: a Review. Curr. Cardiol. Rep., 18:120, https://doi.org/10.1007/s11886-016-0800-3, 8 pages.

Tully, P.J. et al. (Dec. 2014). The anxious heart in whose mind? A systematic review and meta-regression of factors associated with anxiety disorder diagnosis, treatment and morbidity risk in coronary heart disease. J. Psychosom. Res., 77:439-448. https://doi.org/10.1016/j.jpsychores.2014.10.001.

Tumolo, J. (Sep. 2018) "Uncovering the Therapeutic Potential of Psychedelics" Retrieved from Psychiatry & Behavioral Health Learning Network [online]. Retrieved from: https://www.hmpgloballearningnetwork.com/site/pcn/article/uncovering-therapeutic-potential-psychedelics, 8 pages.

Tyrer, P. and Baldwin, D. (2006). Generalised anxiety disorder. Lancet, 368:2156-2166. https://doi.org/10.1016/S0140-6736(06)69865-6.

Ulfvebrand, S. et al. (Sep. 2015). Psychiatric comorbidity in women and men with eating disorders results from a large clinical database. Psychiatry Research, 230(2), 294-299. https://doi.org/10.1016/j.psychres.2015.09.008.

Unruh, K. E., Bodfish, J. W., & Gotham, K. O. (2018). Adults with Autism and Adults with Depression Show Similar Attentional Biases to Social-Affective Images. Journal of Autism and Developmental Disorders, 50:2336-2347. https://doi.org/10.1007/s10803-018-3627-5.

Uyeno, E.T. (Mar. 1967). Effects of mescaline and psilocybin on dominance behavior of the rat. Archives Internationales de Pharmacodynamie et de Therapie, 166(1), 60-64. http://www.ncbi.nlm.nih.gov/pubmed/6034329.

Valbrun, L. and Zvonarev, V. (Dec. 2020). The Opioid System and Food Intake: Use of Opiate Antagonists in Treatment of Binge Eating Disorder and Abnormal Eating Behavior. Journal of Clinical Medicine Research, 12(2), pp. 41-63.

Van Ameringen, M. et al. (Mar. 2014) "DSM-5 obsessive-compulsive and related disorders: Clinical implications of new criteria" Depression and Anxiety, 31(6):487-493. https://doi.org/10.1002/da.22259.

Van Den Beuken-Van Everdingen, M.H.J. et al. (Jun. 2006) Update on Prevalence of Pain in Patients with Cancer: Systematic Review and Meta-Analysis. Journal of Pain and Symptom Management. 51(6):1070-1090, with Appendix I, 1090:e1-e9.

Van Hecke, A.V. et al. (2013). Measuring the Plasticity of Social Approach: A Randomized Controlled Trial of the Effects of the Peers Intervention on EEG Asymmetry in Adolescents with Autism Spectrum Disorders. J. Autism Dev. Disord., 45(2):316-335. https://doi.org/10.1007/s10803-013-1883-y.

Van Spijker, B.A.J. et al. (2014) The Suicidal Ideation Attributes Scale (SIDAS): Community-Based Validation Study of a New Scale for the Measurement of Suicidal Ideation. Suicide and Life-Threatening Behavior, 44(4):408-419.

Varga, Z. et al. (2017). Cardiovascular Risk of Nonsteroidal Anti-Inflammatory Drugs: An Under-Recognized Public Health Issue. Cureus, 9(4):e1144, https://doi.org/10.7759/cureus.1144, 12 pages.

Vaupel, D. et al. (Jun. 1979). The inhibition of food intake in the dog by LSD, mescaline, psilocin, -amphetamine and phenylisopropylamine derivatives. Life Sciences, 24(26), pp. 2427-2431.

Veale, D. et al. (Nov. 2014) "Atypical antipsychotic augmentation in SSRI treatment refractory obsessive-compulsive disorder: A systematic review and meta-analysis" BMC Psychiatry, 14(1):317, https://doi.org/10.1186/s12888-014-0317-5, 13 pages.

Velikonja, T., Fett , A. K., & Velthorst, E. (2019). Patterns of Nonsocial and Social Cognitive Functioning in Adults with Autism Spectrum Disorder: A Systematic Review and Meta-analysis. JAMA Psychiatry, 76(2):135-151. https://doi.org/10.1001/jamapsychiatry.2018.3645.

Venlafaxine Hydrochloride (Sep. 23, 2020). Drugs.com (online). Retrieved from: https://www.drugs.com/monograph/venlafaxine-hydrochloride.html, 19 printed pages.

Verbeeck, W. et al. (Oct. 2017). Bupropion for attention deficit hyperactivity disorder (ADHD) in adults. Cochrane Database of

(56)                References Cited

OTHER PUBLICATIONS

Systematic Reviews, 2017, Issue 10, Art. No. CD009504, DOI: 10.1002/14651858.CD009504.pub2, 58 pages.

Verroust Vincent et al., "Psilocybin in the treatment of anorexia nervosa: The English transition of a French 1959 case study", Annales Medico-Psychologiques, Elsevier, Amsterdam, NL 179(8):777-781 (Sep. 28, 2021).

Vinik, A. et al. Diabetic Neuropathies. Table 7, Drugs Approved by the FDA for Treatment of Neuropathic Pain Syndromes. [Updated Feb. 5, 2018]. In: Feingold, K.R., Anawalt, B., Boyce, A. et al., editors. Endotext [Internet]. South Dartmouth (MA): MDText.com, Inc.; 2000-. Retrieved from: https://www.ncbi.nlm.nih.gov/books/NBK279175/table/diab-neuropathies.medication/, retrieved on Jul. 30, 2020, 2 printed pages.

Volkow, N.D. et al. (Aug. 2007) Depressed dopamine activity in caudate and preliminary evidence of limbic involvement in adults with attention-deficit/hyperactivity disorder. Arch Gen Psychiatry, 64(8):932-940.

Volkow, N.D. et al. (Feb. 1, 2007) Brain dopamine transporter levels in treatment and drug naïve adults with ADHD. Neuroimage [Internet]. 34(3):1182-90. Available from: http://www.ncbi.nlm.nih.gov/pubmed/17126039.

Vollenweider et al., "5-HT modulation of dopamine release in basal ganglia in psilocybin-induced psychosis in man—a PET study with [11C] raclopride", Neuropsychopharmacology (1999); 20(5): 424-433. doi: 10.1016/S0893-133X(98)00108-0.

Vollenweider et al., "The effects of the preferential 5-HT2A agonist psilocybin on prepulse inhibition of startle in healthy human volunteers depend on interstimulus interval", Neuropsychopharmacology (2007); 32(9): 1876-1887. doi: 10.1038/sj.npp.1301324. Epub Feb. 14, 2007.

Vollenweider et al. The neurobiology of psychedelic drugs: implications for the treatment of mood disorders. Nat Rev Neurosci 11:642-651 (2010).

Vollenweider, F. (Jul. 1998) Advances and Pathophysiological Models of Hallucinogenic Drug Actions in Humans: A Preamble to Schizophrenia Research. Pharmacopsychiatry, 31(Suppl):92-103. https://doi.org/10.1055/s-2007-979353.

Von Bernhardi, R. et al. (Oct. 28, 2015). Role of TGFβ signaling in the pathogenesis of Alzheimer's disease. Frontiers in Cellular Neuroscience, 9:426, https://doi.org/10.3389/fncel.2015.00426, 21 pages.

Voon, P. et al. (2017). Chronic pain and opioid misuse: a review of reviews. Substance Abuse Treatment, Prevention and Policy, 12:36, DOI 10.1186/s13011-017-0120-7, 9 pages.

Vossler, D.G. (Oct. 2016). Antiepileptic drugs. Are generics as effective as brand name? Neurology, 87(17):e211-e214. https://doi.org/10.1212/WVNL.0000000000003323.

Wade, A.G. et al. (Jan. 2011). Prolonged release melatonin in the treatment of primary insomnia: Evaluation of the age cut-off for short- and long-term response. Curr. Med. Res. Opin., 27:87-98. https://doi.org/10.1185/03007995.2010.537317.

Wagner, J. and Wagner, M.L. (2000). Non-benzodiazepines for the treatment of insomnia. Sleep Med. Rev., 4(6):551-581. https://doi.org/10.1053/smrv.2000.0126.

Wahlberg (2015) "UW-Madison tunes in to 'magic mushroom' medicine" Oct. 11, 2015; retrieved from Web Archive, https://web.archive.org/web/20181214181711/https://madison.com/wsi/news/local/heal th-med-fit/uw-madison-tunes-in-to-magic-mushroom-medicine/article5c229322-I 132-5328-90cl-017e917f0696.html, retrieved Dec. 14, 2018, 1 page.

Walia, K.S. et al. (Sep. 2004) Side Effects of Antiepileptics—A Review. Pain Pract, (3):194-203.

Walsh, B.T. et al. (Jun. 2006). Fluoxetine after weight restoration in anorexia nervosa: A randomized controlled trial. Journal of the American Medical Association, 295(22):2605-2612. https://doi.org/10.1001/jama.295.22.2605.

Wang, G. et al. (2017). Resveratrol mitigates lipopolysaccharide-mediated acute inflammation in rats by inhibiting the TLR4/NF-KBp65/MAPKs signaling cascade. Scientific Reports, 7:45006, https://doi.org/10.1038/srep45006, 13 pages.

Wang, J. et al. (2016). Enhanced Gamma oscillatory activity in rats with chronic inflammatory pain. Front. Neurosci. 10:489, https://doi.org/10.3389/fnins.2016.00489, 8 pages.

Wang, L. et al. (Sep. 2003). IL-6 Induces NF-κB Activation in the Intestinal Epithelia. The Journal of Immunology, 171(6):3194-3201. https://doi.org/10.4049/jimmunol.171.6.3194.

Wang, Q. et al. (May 2018). CDK5-Mediated Phosphorylation-Dependent Ubiquitination and Degradation of E3 Ubiquitin Ligases GP78 Accelerates Neuronal Death in Parkinson's Disease. Molecular Neurobiology, 55(5):3709-3717. https://doi.org/10.1007/s12035-017-0579-2.

Wang, X. et al. (2018). Gastrodin Rescues Autistic-Like Phenotypes in Valproic Acid-Induced Animal Model. Frontiers in Neurology, 9:1052, https://doi.org/10.3389/fneur.2018.01052, 10 pages.

Wang, Z.-J. et al. (Feb. 2020). A dual GLP-1 and Gcg receptor agonist rescues spatial memory and synaptic plasticity in APP/PS1 transgenic mice. Hormones and Behavior, 118:104640. https://doi.org/10.1016/j.yhbeh.2019.104640, 9 pages.

Washburn, J.J. et al. (Apr. 2007) Development of Antisocial Personality Disorder in Detained Youth: The Predictive Value of Mental Disorders. J Consult Clin Psychol, 75(2):221-231. NIH Public Access Author Manuscript, 20 pages.

Watson, J. et al. (Jul. 2019). Use of multiple inflammatory marker tests in primary care: using Clinical Practice Research Datalink to evaluate accuracy. British Journal of General Practice, 69(684), e462-e469. https://doi.org/10.3399/bjgp19X704309.

Weber, A. et al. (2010). Interleukin-1 (IL-1) Pathway. Science Signaling, 3(105):cm1, https://doi.org/10.1126/scisignal.3105cm1, 7 pages.

Weber, H.P., et al. (1974) "Crystal structures of the teonanacatl hallucinogens. Part 1. Psilocybin C12HI7N204P" J Chem Soc, Perkin Trans, 2:942-946.

Wegner, D.M. and Zanakos, S. (1994) Chronic Thought Suppression. Journal of Personality, 62:615-640.

Wei, D. Y-T. et al. (2018) Cluster headache: Epidemiology, pathophysiology, clinical features, and diagnosis. Annals of Indian Academy of Neurology, 21(5):3-8.

Weissman, A.N. (1979) The Dysfunctional Attitude Scale: A validation study. [Dissertation in Education, Doctor of Philosophy]. University of Pennsylvania. Publicly Accessible Penn Dissertations. 1182. https://repository.upenn.edu/edissertations/1185, 209 pages.

Welch, E. et al. (2016). Treatment-seeking patients with binge-eating disorder in the Swedish national registers: clinical course and psychiatric comorbidity. BMC Psychiatry, 16:163, doi:10.1186/s12888-016-0840-7, 8 pages.

Werner, K.B. et al. (Apr. 2015) Epidemiology, comorbidity, and behavioral genetics of antisocial personality disorder and psychopathy. Psychiatr Ann. 45(4):195-199. HHS Public Access Author Manuscript, 8 pages.

Westmoreland, P. et al. (Jul. 2016). Medical Complications of Anorexia Nervosa and Bulimia. The American Journal of Medicine, 129:30-37.

Whelan, A & Johnson, M, "Lysergic Acid Diethylamide and Psilocybin for the Management of Patients with Persistent Pain: a Potential Role?," Pain Management 8:217-229 (2018).

White, H. K., & Levin, E. D. (Apr. 1999). Four-week nicotine skin patch treatment effects on cognitive performance in Alzheimer's disease. Psychopharmacology, 143(2):158-165. https://doi.org/10.1007/s002130050931.

White S W, et al., "Anxiety in Children and Adolescents with Autism Spectrum Disorders," Clinical psychology review, 29(3):216-29, 2009, Epub Jan. 25, 2009.

Whitfield, D.R. et al. (Dec. 2014). Assessment of ZnT3 and PSD95 protein levels in Lewy body dementias and Alzheimer's disease: association with cognitive impairment. Neurobiology of Aging, 35(12):2836-2844. https://doi.org/10.1016/j.neurobiolaging.2014.06.015.

Whyatt, C., & Craig, C. (Jul. 18, 2013). Sensory-motor problems in autism. Frontiers in Integrative Neuroscience. 7:51, https://doi.org/10.3389/fnint.2013.00051, 12 pages.

(56)  References Cited

OTHER PUBLICATIONS

Wiedemann, K. et al. (2001). Anxiolyticlike effects of atrial natriuretic peptide on cholecystokinin tetrapeptide-induced panic attacks. Preliminary findings. Archives of General Psychiatry, 58:371-377. https://doi.org/10.1001/archpsyc.58.4.371.

Wikberg, "Comparison Between the Montgomery-Asberg Depression Rating Scale-Self (MADRS-S) and the Beck Depression Inventory II (BDI-11) in Primary Care" The Primary Care Companion for CNS Disorders, 17(3): 1-6 (2015).

Wilcox, J.A. (Nov. 2014) "Psilocybin and obsessive compulsive disorder" Journal of Psychoactive Drugs, 46(5):393-395: DOI: 10.1080/02791072.2014.963754.

Wilens, T.E. et al. (Oct. 2011) An update on the pharmacotherapy of attention-deficit/hyperactivity disorder in adults. Expert Rev Neurother, 11(10):1443-1465. NIH Public Access Author Manuscript; available in PMC Aug. 1, 2012, 34 pages.

Williams, J.M.G. et al. (1986) Autobiographical Memory in Suicide Attempters. Journal of Abnormal Psychology, 95:144-149.

Williams, K. et al. (2013). Selective serotonin reuptake inhibitors (SSRIs) for autism spectrum disorders (ASD). Cochrane Database of Systematic Reviews, 8:CD004677, https://doi.org/10.1002/14651858.CD004677.pub3, 46 pages.

Willoughby, J.O. et al. (2003). Persistent abnormality detected in the non-ictal electroencephalogram in primary generalised epilepsy. J. Neurol. Neurosurg. Psychiatry, 74:51-55. https://doi.org/10.1136/jnnp.74.1.51.

Wilson, S. et al. (Jul. 2017) Interpersonal dysfunction in personality disorders: A meta-analytic review. Psychol Bull, 143(7):677-734. HHS Public Access Author Manuscript, 120 pages.

Wingo A, Ghaemi S. (Nov. 2007) A systematic review of rates and diagnostic validity of comorbid adult attention-deficit/hyperactivity disorder and bipolar disorder. J Clin Psychiatry, 68(11):1775-1784.

Winkelman, J.W. et al. (Sep. 2011). Randomized polysomnography study of gabapentin enacarbil in subjects with restless legs syndrome. Mov. Disord., 26:2065-2072. https://doi.org/10.1002/mds.23771.

Winter et al., "Psilocybin-induced stimulus control in the rat", Pharmacology Biochemistry and Behavior (2007); 87(4): 472-480. doi: 10.1016/j.pbb.2007.06.003. Epub Jun. 22, 2007.

Witkin, J.M. (2008) "Animal models of obsessive-compulsive disorder" Current Protocols in Neuroscience. 45:9.30.1-9.30.9, 10 pages.

Wong, M. et al. (Feb. 2008). TNFα blockade in human diseases: Mechanisms and future directions. Clinical Immunology, 126(2):121-136. https://doi.org/10.1016/j.clim.2007.08.013.

World Health Organization (WHO) (2015). International statistical classification of diseases and related health problems (ICD-10), 10th revision, Fifth edition. vol. 1, Tabular List. Geneva, Switzerland: WHO Press, www.who.int; 1076 pages.

World Health Organization (WHO) (2019). Risk reduction of cognitive decline and dementia—WHO Guidelines. Foreward and Executive Summary, pp. 3-11.

World Health Organization (WHO) (Sep. 19, 2019). Dementia. Retrieved from https://www.who.int/news-room/fact-sheets/detail/dementia, 5 pages.

Worrell, G.A. et al. (Jul. 2004). High-frequency oscillations and seizure generation in neocortical epilepsy. Brain 127, 1496-1506. https://doi.org/10.1093/brain/awh149.

Wu, H. et al. (Sep. 2016). Field potential oscillations in the bed nucleus of the Stria terminalis correlate with compulsion in a rat model of obsessive-compulsive disorder. J. Neurosci. 36, 10050-10059.

Wultsch, T. et al. (2007) "Behavioural and expressional phenotyping of nitric oxide synthase-I knockdown animals" Journal of Neural Transmission, (Suppl 72):69-85. https://doi.org/10.1007/978-3-211-73574-9_10.

Xie, Z. et al. (May 2017). A review of sleep disorders and melatonin. Neurol. Res., 39:559-565. https://doi.org/10.1080/01616412.2017.1315864.

Xu, C. et al. ( Mar. 2019). Integrative analysis of shared genetic pathogenesis by obsessive-compulsive and eating disorders. Molecular Medicine Reports, 19(3):1761-1766. https://doi.org/10.3892/mmr.2018.9772.

Xu, P. et al. (Jun. 2016). Activation of serotonin 2C receptors in dopamine neurons inhibits binge-like eating in mice. Biological Psychiatry, 81, 737-747.

Yang et al. "Role of TNF-TNF receptor 2 signal in regulatory T cells and its therapeutic implications", Frontiers in Immunology, (2018); 9(784):1-11.

Yilmaz, Z. et al. (Mar. 2015). Genetics and epigenetics of eating disorders. Advances in Genomics and Genetics, 5:131-150. HHS Public Access Author Manuscript, 36 pages.

Ypsilantis, E. and Tang, T.Y. (2010) Pre-emptive analgesia for chronic limb pain after amputation for peripheral vascular disease: A systematic review. Annals of Vascular Surgery, 24:1139-1146.

Yu, B. et al. (Nov. 2008). Serotonin 5-hydroxytryptamine$_{2a}$ receptor activation suppresses tumor necrosis factor-alpha-induced inflammation with extraordinary potency. The Journal of Pharmacology and Experimental Therapeutics, 327(2):316-323.

Zammit, G. et al. (2007). Evaluation of the efficacy and safety of ramelteon in subjects with chronic insomnia. J. Clin. Sleep Med., 3:495-504. https://doi.org/10.5664/jcsm.26914.

Zetner, M. et al. (2008) Emotions evoked by the sound of music: Characterization, classification, and measurement. Emotion. 8:494-521.

Zhai, H. et al. (Dec. 2019). Baicalin attenuated substantia nigra neuronal apoptosis in Parkinson's disease rats via the mTOR/AKT/GSK-3β pathway. Journal of Integrative Neuroscience, 18(4), 423-429. https://doi.org/10.31083/j.jin.2019.04.192.

Zhang, J.-M., & An, J. (2007). Cytokines, Inflammation and Pain. Int Anesthesiol Clin., 69(2):482-489. NIH Public Access Author Manuscript, available in PMC Nov. 30, 2009, 10 pages.

Zhou, R. et al. (2018). Elevated Resting State Gamma Oscillatory Activities in Electroencephalogram of Patients With Post-herpetic Neuralgia. Front. Neurosci. 12, 750, 10 pages. https://doi.org/10.3389/fnins.2018.00750.

Zhou, Y. et al. (2017). Comorbid generalized anxiety disorder and its association with quality of life in patients with major depressive disorder. Sci. Rep. 7:40511, https://doi.org/10.1038/srep40511, 8 pages.

Ziani et al., "Drug repurposing and personalized treatment strategies for bipolar disorder using transcriptomics: an exploratory study". Braz J Psychiatry, 2024. vol. 46: 9 pages.

Zipfel, S. et al. (Dec. 2015). Anorexia nervosa: Aetiology, assessment, and treatment. The Lancet Psychiatry, vol. 2, Issue 12, pp. 1099-1111. https://doi.org/10.1016/S2215-0366(15)00356-9.

Zulauf, C.A. et al. (Mar. 2014). The complicated relationship between attention deficit/hyperactivity disorder and substance use disorders. Curr Psychiatry Rep, 16(3):436; doi:10.1007/s11920-013-0436-6. HHS Public Access Author Manuscript; available in PMC Apr. 29, 2015, 17 pages.

Psilocybin
$C_{12}H_{17}N_2O_4P$
Exact Mass: 284.09
Mol. Wt.: 284.25

FIG. 1

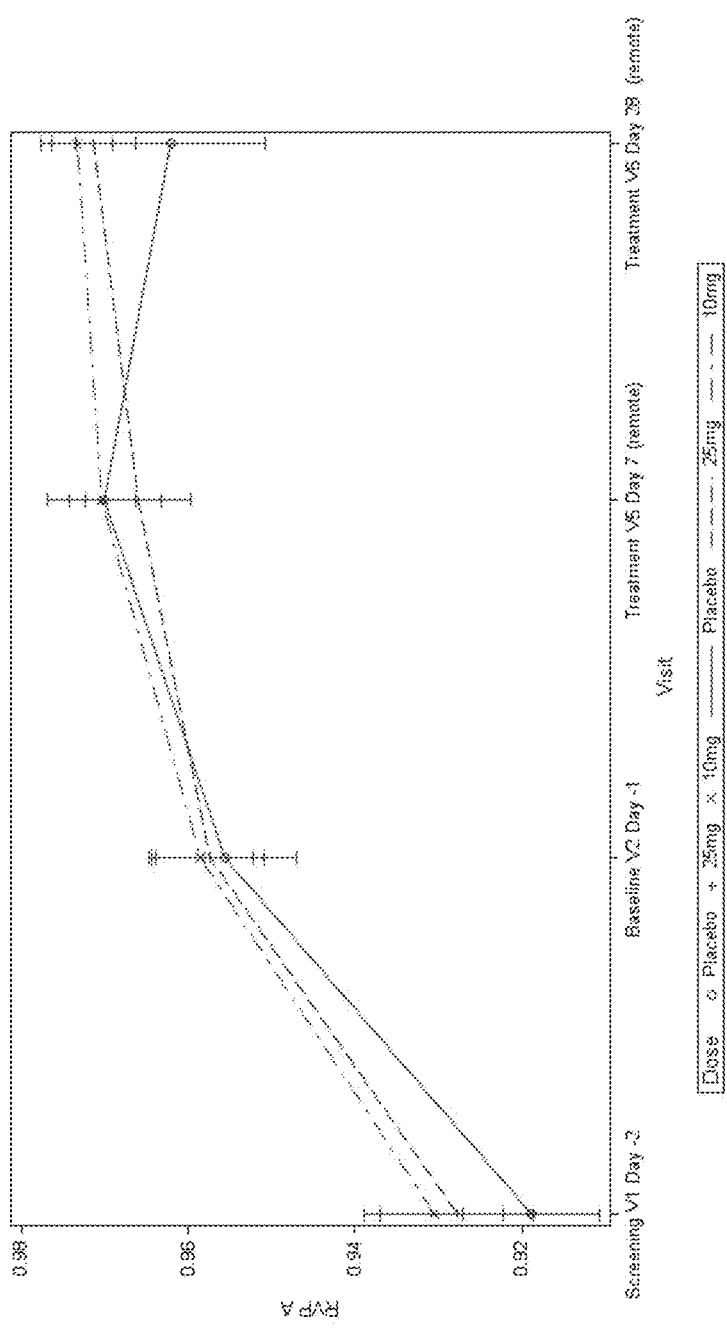
FIG. 9L

FIG. 16

FIG. 19
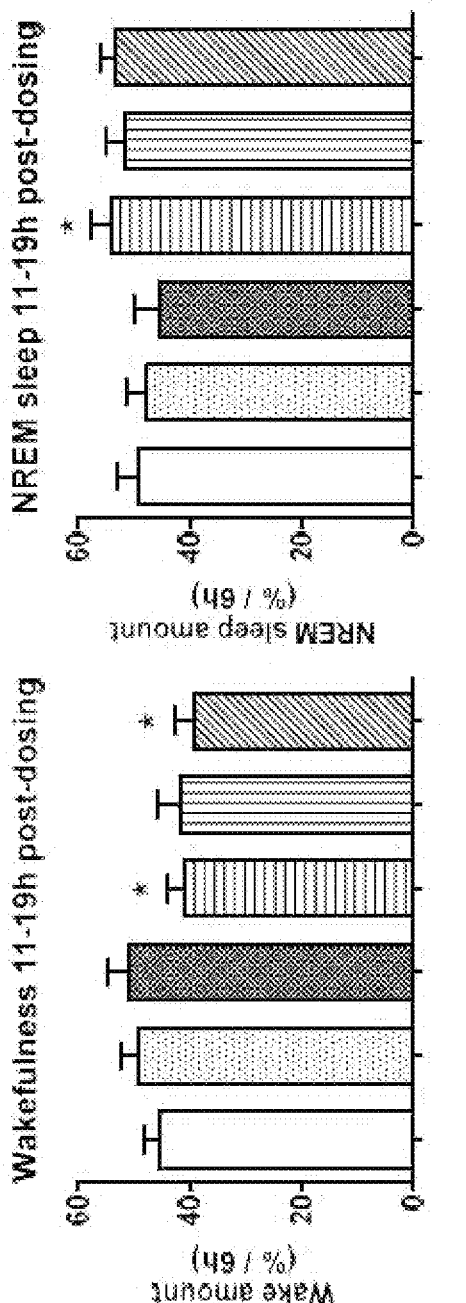
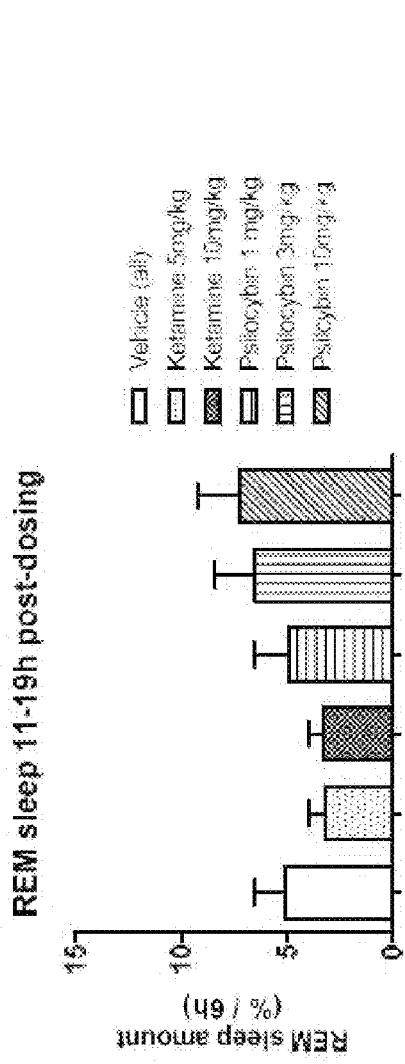

FIG. 20
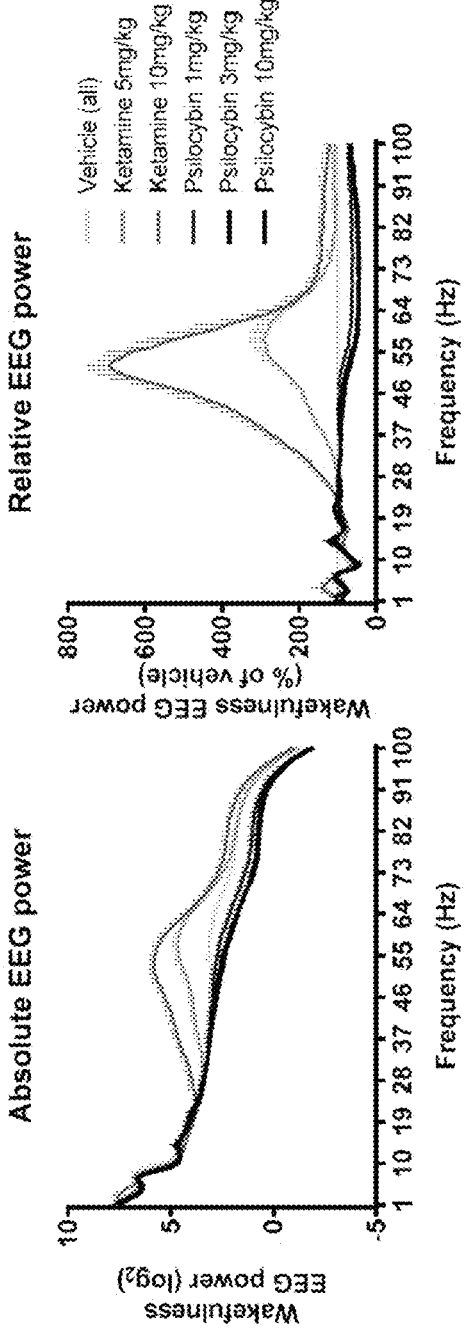
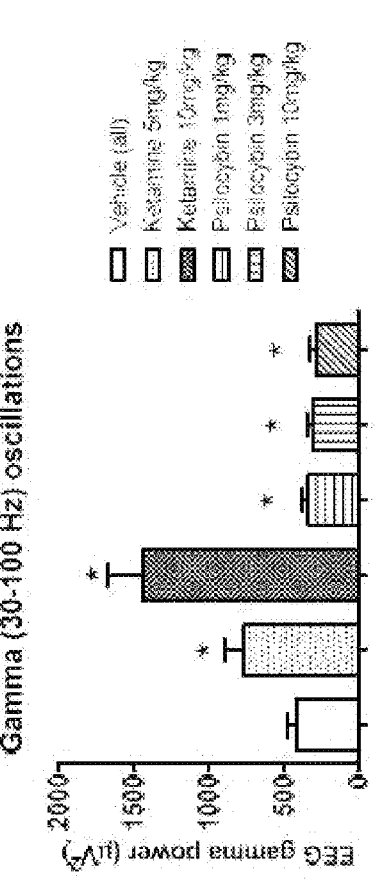

FIG. 22
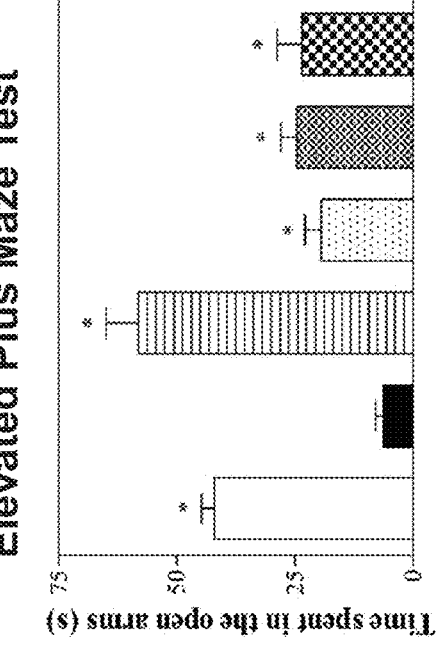
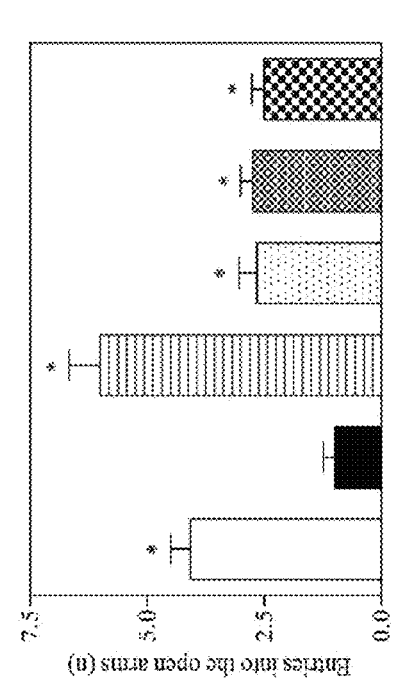

FIG. 23
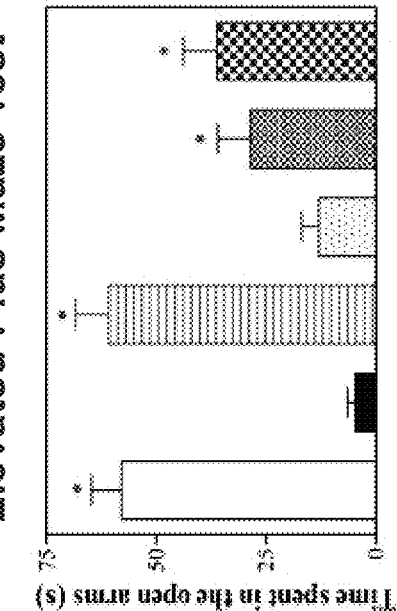
Elevated Plus Maze Test
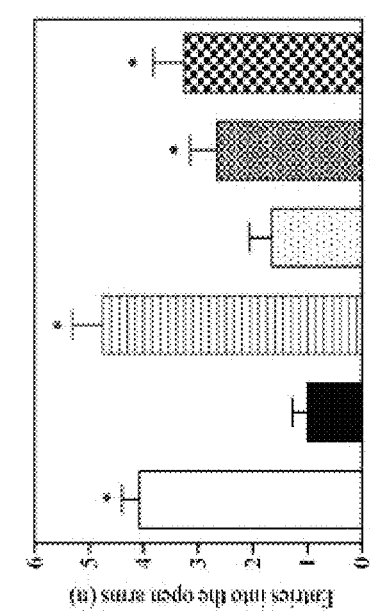
Elevated Plus Maze Test

FIG. 27

Recruitment, screening, two-week washout

Follow-up at 6 & 12 months

Headache log book

Baseline observation (4 weeks) | Week 1 | Week 2 | Week 3 | Week 4 | Week 5 | Week 6

MRI

Psi   Psi   Psi

MRI

Effect of psilocybin on the average 24 hour food intake

FIG. 34

Effect of psilocybin on body weight change

Overall body weight change (g)

Vehicle (po/ip) / no chocolate
Vehicle (po/ip) / Binge
Vehicle (po) / Psilocybin (1 mg/kg ip)
Vehicle (po) / Psilocybin (3 mg/kg ip)
Vehicle (po) / Psilocybin (10 mg/kg ip)
LDX (0.8 mg/kg, po) / Vehicle (ip)

METHODS FOR TREATING ANXIETY DISORDERS, HEADACHE DISORDERS, AND EATING DISORDERS WITH PSILOCYBIN

RELATED APPLICATIONS

This application is a continuation of U.S. application Ser. No. 17/604,619, filed Oct. 18, 2021, which is a U.S. National Stage Application under 35 U.S.C. § 371 of International Application No. PCT/IB2020/053687, filed Apr. 17, 2020, which claims priority to benefit of U.S. Application Serial Nos. 62/835,449; 62/835,450; 62/835,458; 62/835,460; 62/835,464; 62/835,465; 62/835,472; 62/835,474; 62/835,476; 62/835,477; 62/835,478; 62/835,479; 62/835,480; 62/835,481; 62/835,482; 62/835,484; and 62/835,485, all filed Apr. 17, 2019; U.S. Application Ser. No. 62/893,110, filed Aug. 28, 2019, U.S. Application Ser. No. 62/893,611, filed Aug. 29, 2019, and U.S. Application Ser. No. 62/946,159, filed Dec. 10, 2019, each of which is incorporated herein by reference in its entirety.

BACKGROUND

Psilocybin belongs to a class of drugs referred to as psychedelics ("mind-manifesting" drugs). Specifically, psilocybin is considered a 5-hydroxytryptaminergic (serotonergic) psychedelic, as distinguished from other tryptamines such as dimethyltryptamine (DMT), ergolines such as lysergic acid diethylamide (LSD), and phenethylamines such as mescaline. Psilocybin was first isolated from psilocybe mushrooms and later synthesized in a laboratory.

There are several common diseases, disorders, and conditions for which no adequate treatment, therapies or cure exist, including:

Anxiety Disorders: Anxiety disorders are a class of psychiatric disorders that involve extreme fear or worry. Oftentimes, anxiety disorders interfere with daily activities, such as job performance, school work, and relationships. Anxiety disorders have a variety of causes, including changes in the brain, environmental stress, and genetics. Examples of anxiety disorders include acute stress disorder, anxiety due to a medical condition, generalized anxiety disorder, panic disorder, panic attack, a phobia, post-traumatic stress disorder, obsessive-compulsive disorder, separation anxiety disorder, social anxiety disorder, substance-induced anxiety disorder, and selective mutism.

Headache Disorders: Headache disorders are characterized by recurrent headaches and are among the most common disorders of the nervous system. Headaches are a disabling feature of headache disorders, such as migraine, tension-type headache, and cluster headaches.

Eating Disorders: Eating disorders are characterized by irregular eating habits and severe distress or concern about body weight or shape. Eating disturbances may include inadequate or excessive food intake which can ultimately damage an individual's physical and/or psychological health. Examples of eating disorders include pica, anorexia nervosa, bulimia nervosa, rumination disorder, avoidant/restrictive food intake disorder, and binge-eating disorder.

There remains a need in the art for improved compositions and methods for treating subjects using psilocybin.

SUMMARY

Psilocybin may provide numerous clinical benefits, such as benefits in neural plasticity and cognitive function (as measured using e.g., Cambridge Neuropsychological Test Automated Battery (CANTAB) tests) with improvements in, for example, working memory and executive function, sustained attention, and episodic memory. These benefits have implications for psilocybin's use in the treatment of various diseases, disorders, and conditions, including both psychiatric and neurological aspects thereof.

In some embodiments, a method for treating one or more of anxiety disorders, eating disorders, and headache disorders, comprising administering to the subject an effective amount of psilocybin or an active metabolite thereof is disclosed herein.

Provided herein is a method for treating an anxiety disorder in a subject in need thereof, the method comprising administering to the subject a therapeutically effective amount of psilocybin or an active metabolite thereof.

Also provided herein is a method for treating an obsessive-compulsive and related disorder in a subject in need thereof, the method comprising administering to the subject a therapeutically effective amount of psilocybin or an active metabolite thereof.

Also provided herein is a method for treating post-traumatic stress disorder in a subject in need thereof, the method comprising administering to the subject a therapeutically effective amount of psilocybin or an active metabolite thereof.

Provided herein is a method for treating a headache disorder in a subject in need thereof, the method comprising administering to the subject a therapeutically effective amount of psilocybin or an active metabolite thereof.

Also provided herein is a method for treating a cluster headache in a subject in need thereof, the method comprising administering to the subject a therapeutically effective amount of psilocybin or an active metabolite thereof.

Also provided herein is a method for treating migraine in a subject in need thereof, the method comprising administering to the subject a therapeutically effective amount of psilocybin or an active metabolite thereof.

Provided herein is a method for treating an eating disorder in a subject in need thereof, the method comprising administering to the subject a therapeutically effective amount of psilocybin or an active metabolite thereof.

Also provided herein is a method for treating binge-eating disorder in a subject in need thereof, the method comprising administering to the subject a therapeutically effective amount of psilocybin or an active metabolite thereof.

Also provided herein is a method for treating anorexia nervosa in a subject in need thereof, the method comprising administering to the subject a therapeutically effective amount of psilocybin or an active metabolite thereof.

In some embodiments, the psilocybin is administered in a dosage form comprising a therapeutically effective amount of highly pure crystalline psilocybin in the form of Polymorph A, wherein the crystalline psilocybin comprises at least 90% by weight of Polymorph A. In some embodiments, the crystalline psilocybin comprises at least 95% by weight of Polymorph A. In some embodiments, the crystalline psilocybin has a chemical purity of greater than 97% by high performance liquid chromatography (HPLC), and no single impurity of greater than 1%.

In some embodiments, the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%. In some embodiments, the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%, further comprising a mixture of two silicified microcrystalline cellulose variants wherein the first variant has a particle size from about 45 to 80 microns and the second variant has a particle size of about 90 to 150 microns. In some embodiments, 30% or less of the microcrystalline cellulose is the first variant having a particle size from about 45 to 80 microns and about 70% or more of the microcrystalline cellulose is the second variant having a particle size of about 90 to 150 microns. In some embodiments, the psilocybin is administered in an oral dosage form. In some embodiments, the psilocybin is administered in a capsule. In some embodiments the psilocybin is administered in a tablet.

In some embodiments, at least one dose of psilocybin is administered to the subject. In some embodiments, the dose of psilocybin is in the range of about 0.1 mg to about 100 mg. In some embodiments, the dose of psilocybin is about 25 mg.

In some embodiments, the subject participates in at least one psychological support session before administration of the psilocybin. In some embodiments, the subject participates in at least one psychological support session after administration of the psilocybin. In some embodiments, a therapist provides psychological support to the subject for approximately 4-8 hours after administration of the psilocybin.

BRIEF DESCRIPTION OF THE DRAWINGS

FIG. 1 is a numbered structural formula of psilocybin.

4

Figure 9A:
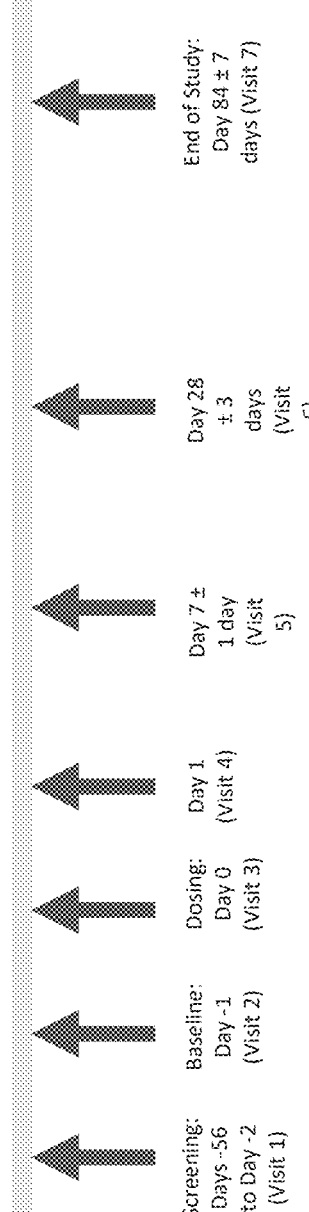
FIG. 9A shows a timeline of the Phase 1 exploratory study, which evaluated psilocybin treatment in healthy volunteer subjects.
Figure 9B:
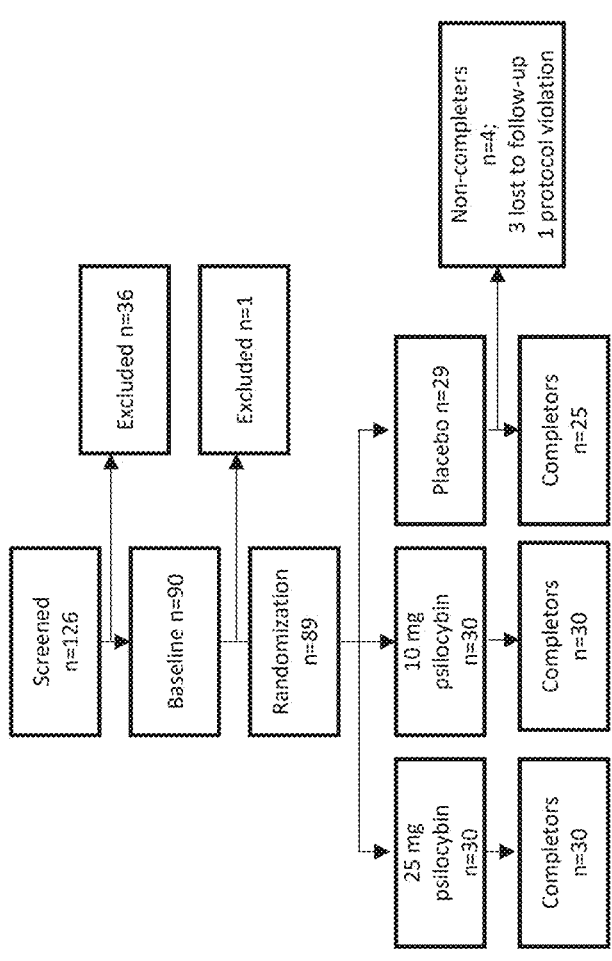
Figure 9C:
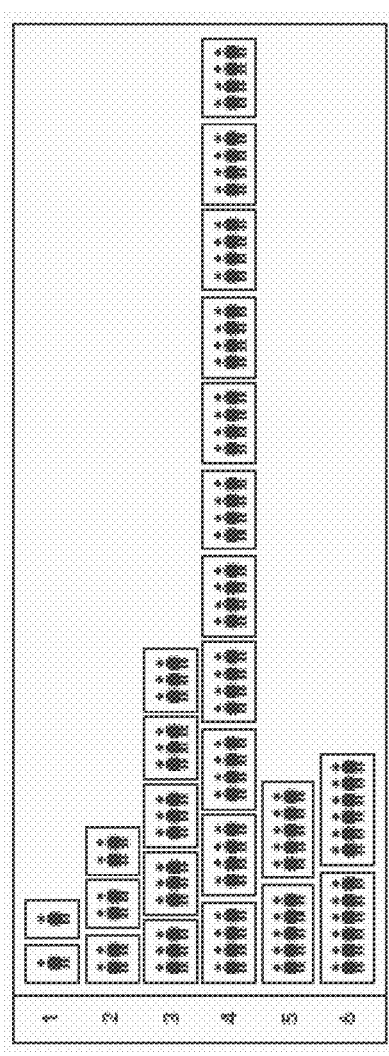
Figure 9D:
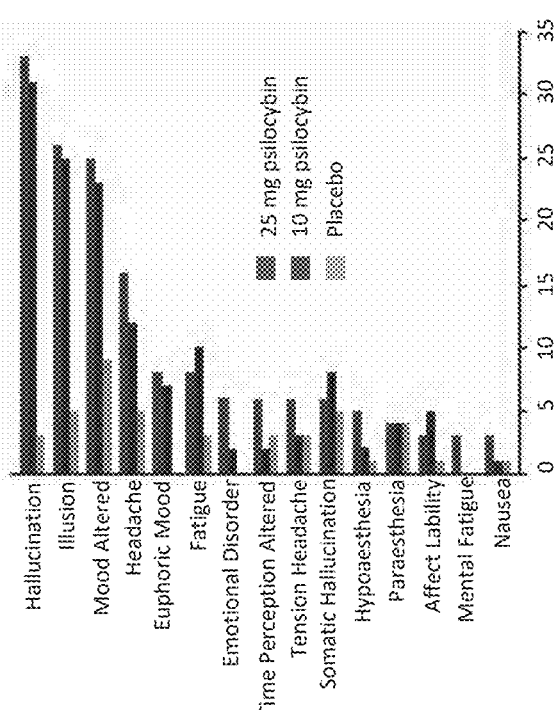
Figure 9E:
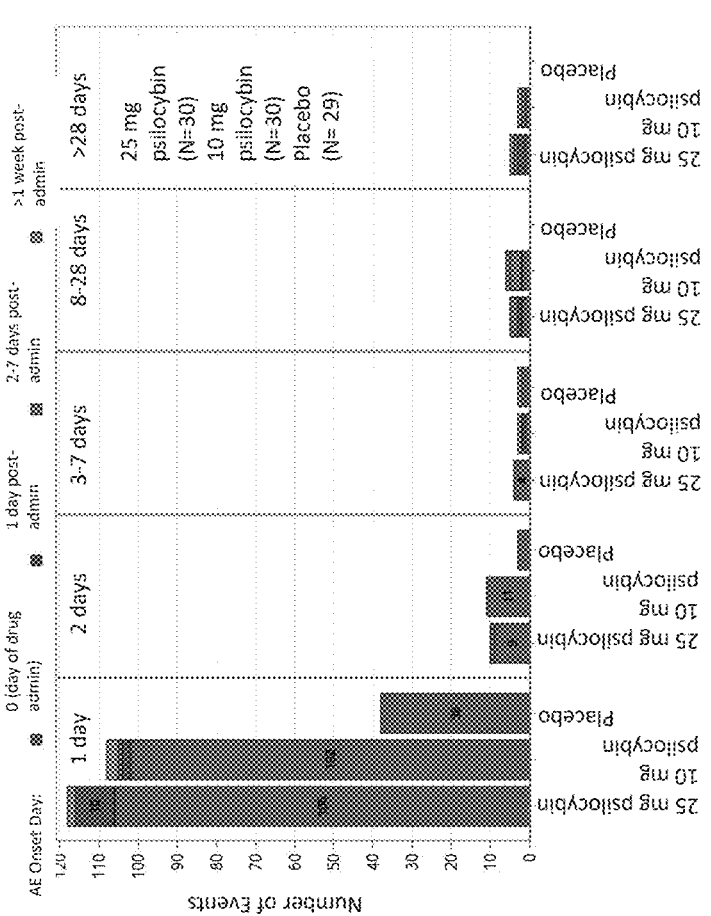
Figure 9F:
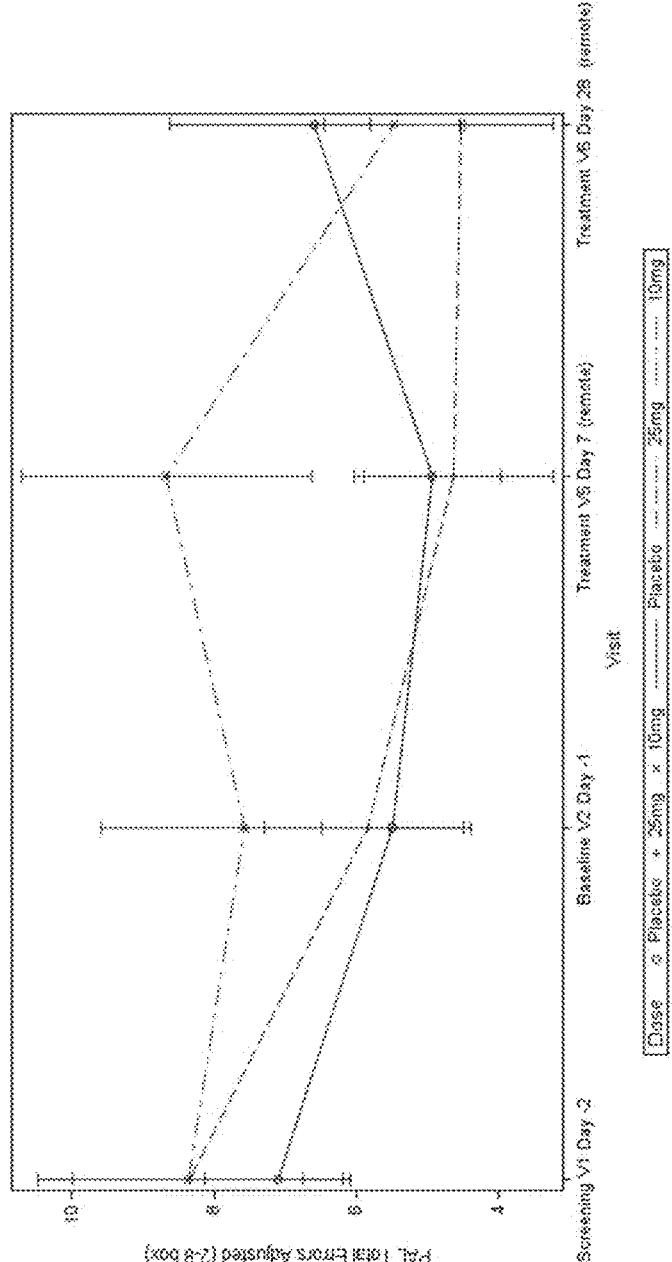
Figure 9G:
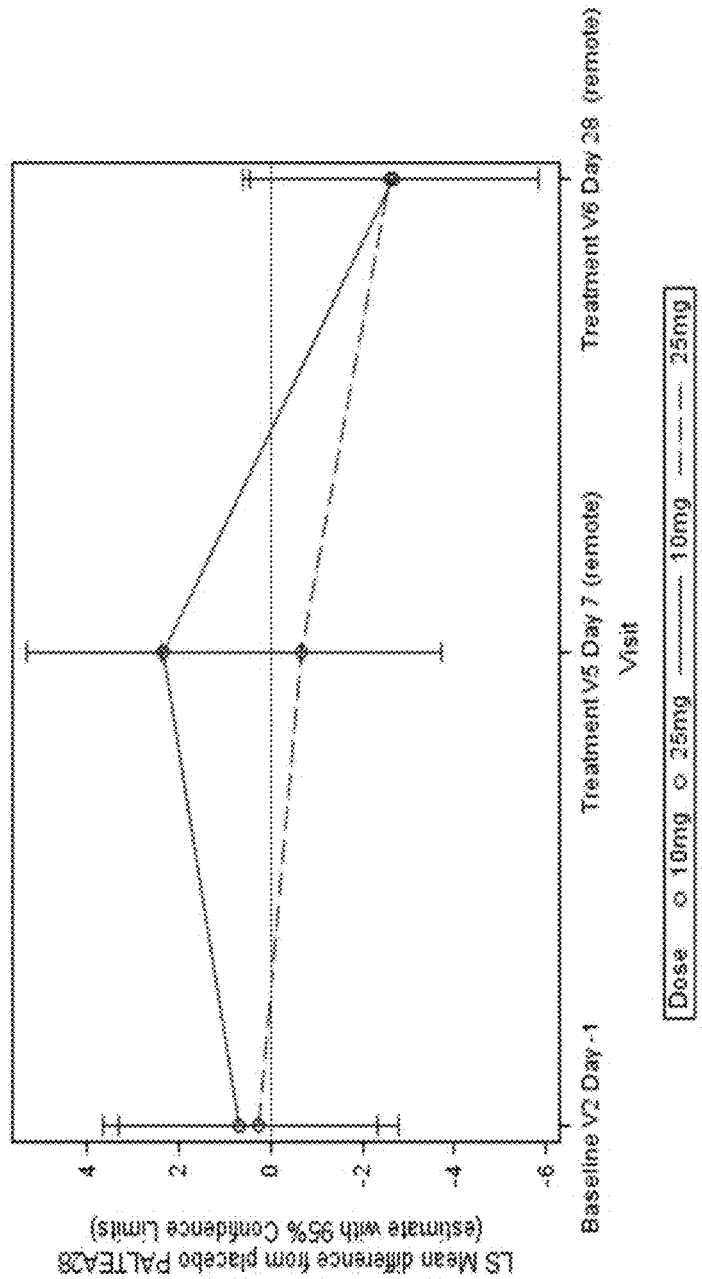
Figure 9H:
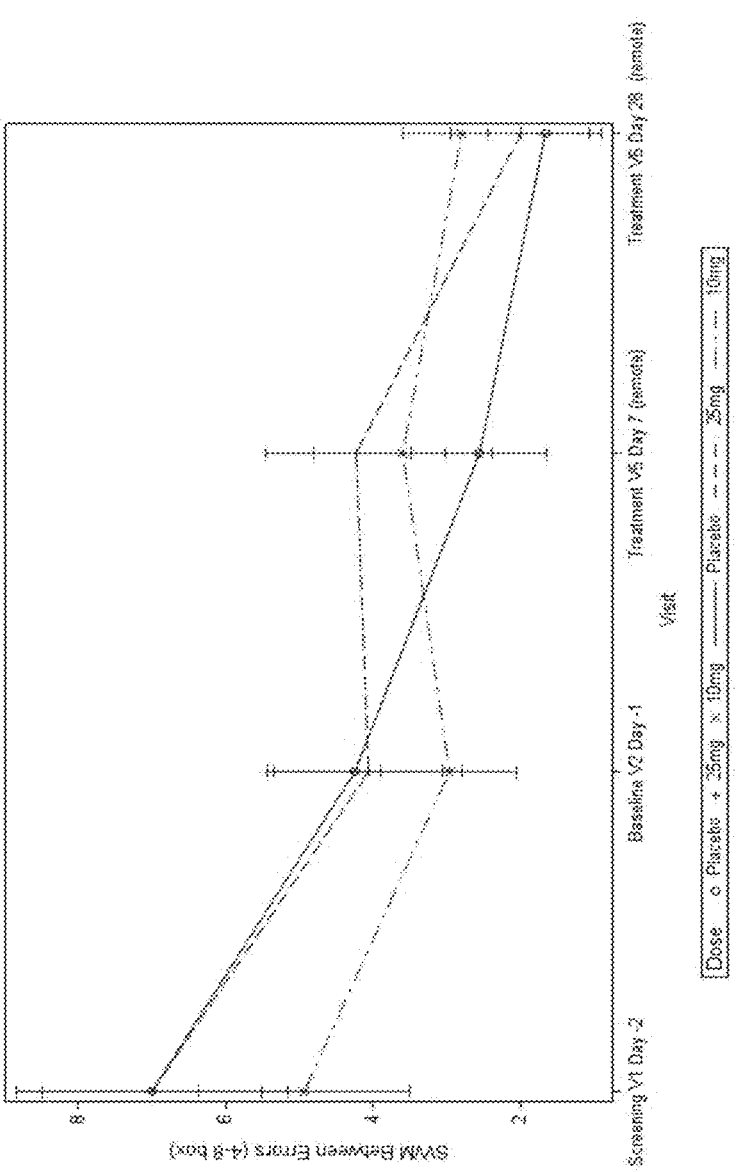
Figure 91:
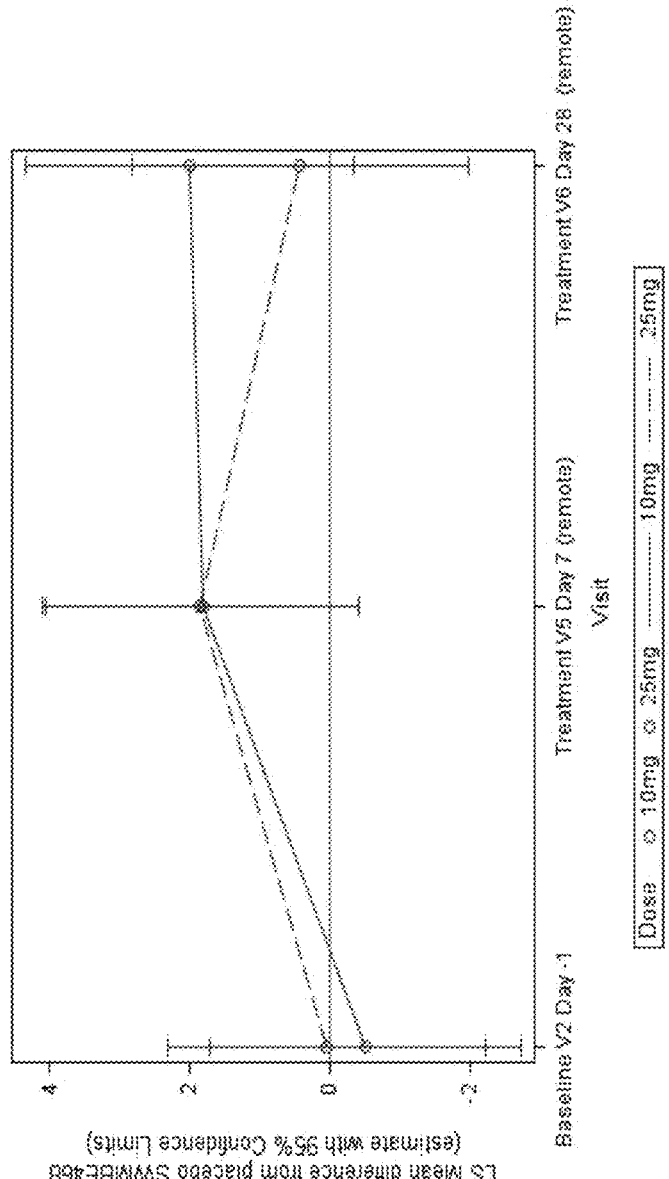
Figure 9J:
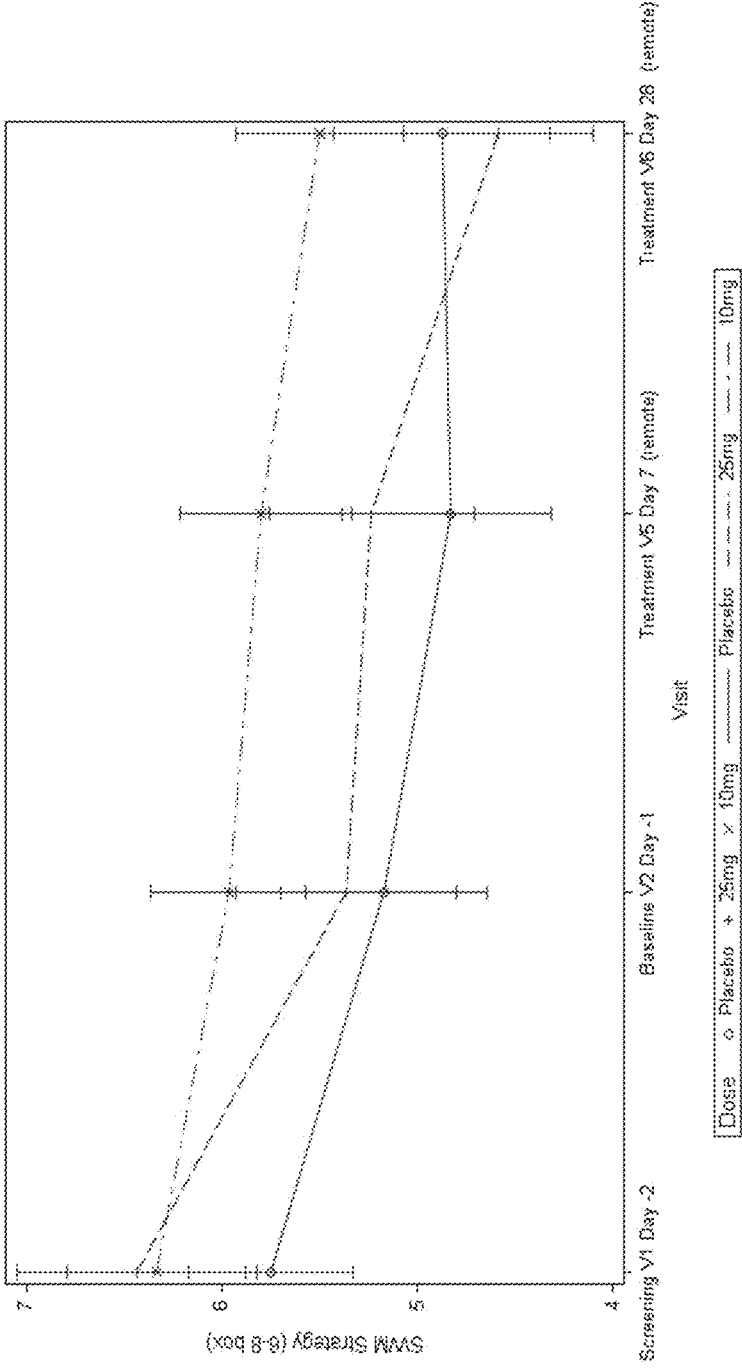
Figure 9K:
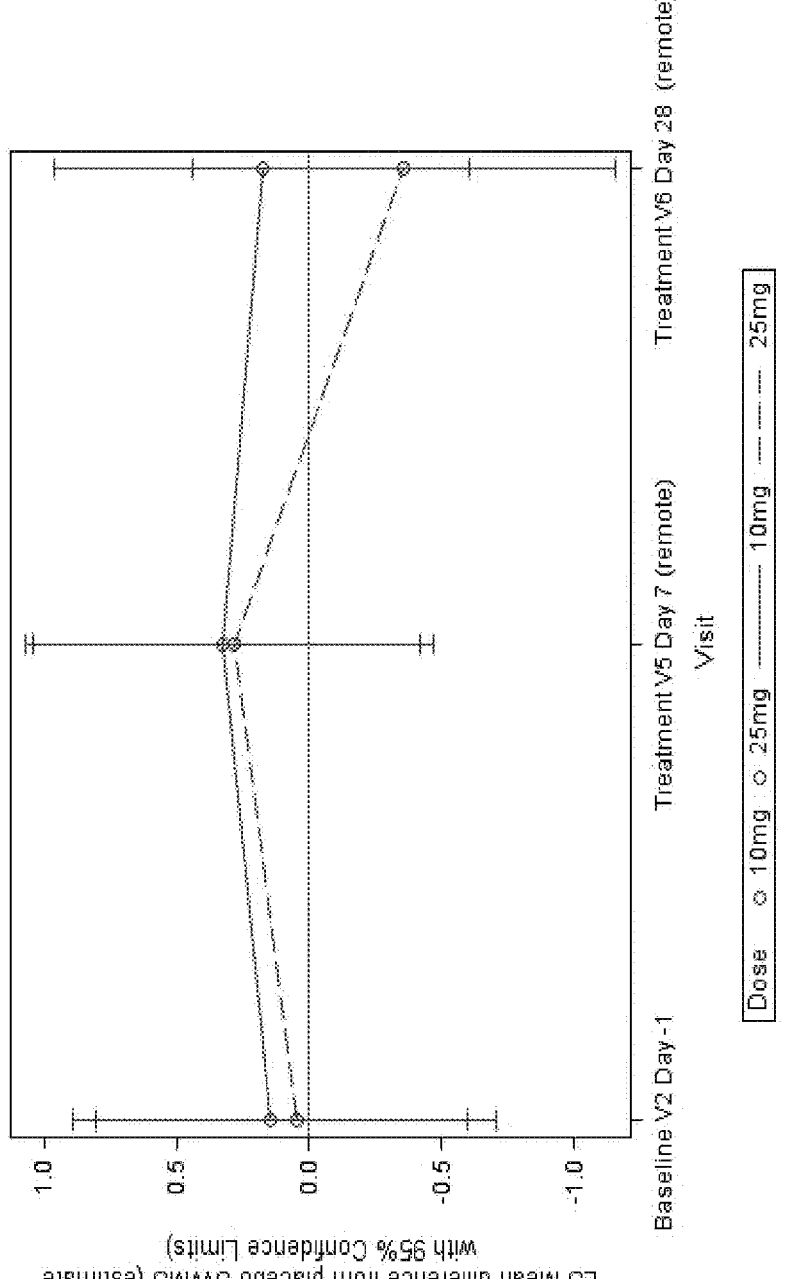
Figure 9M:
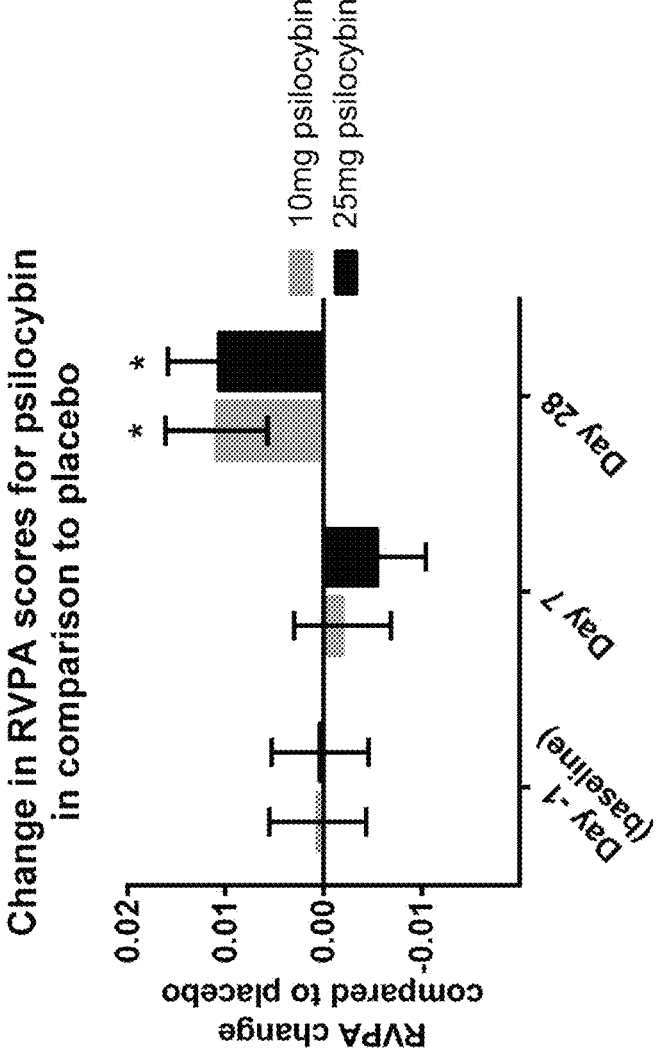
Figure 9N:
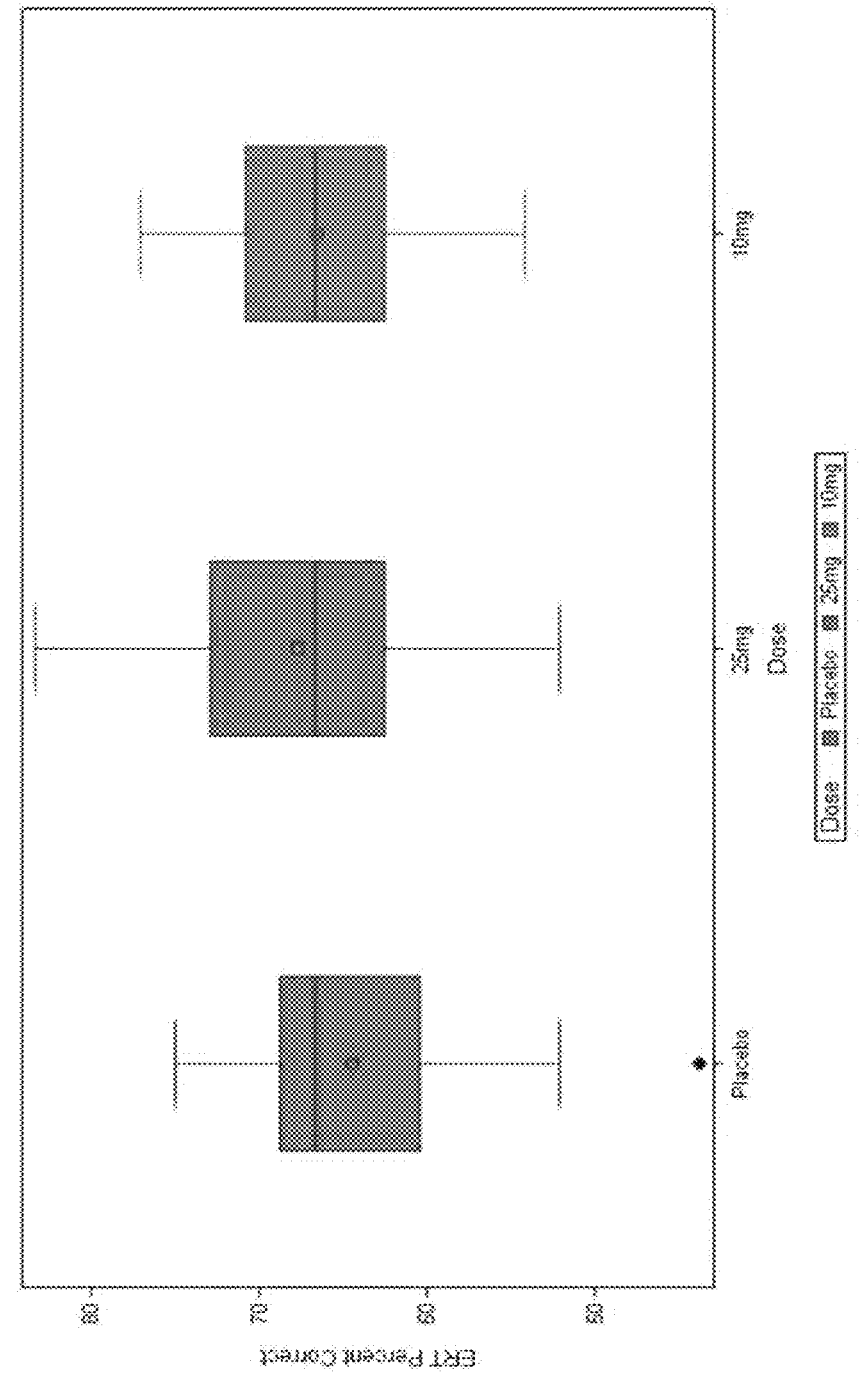
Figure 90:
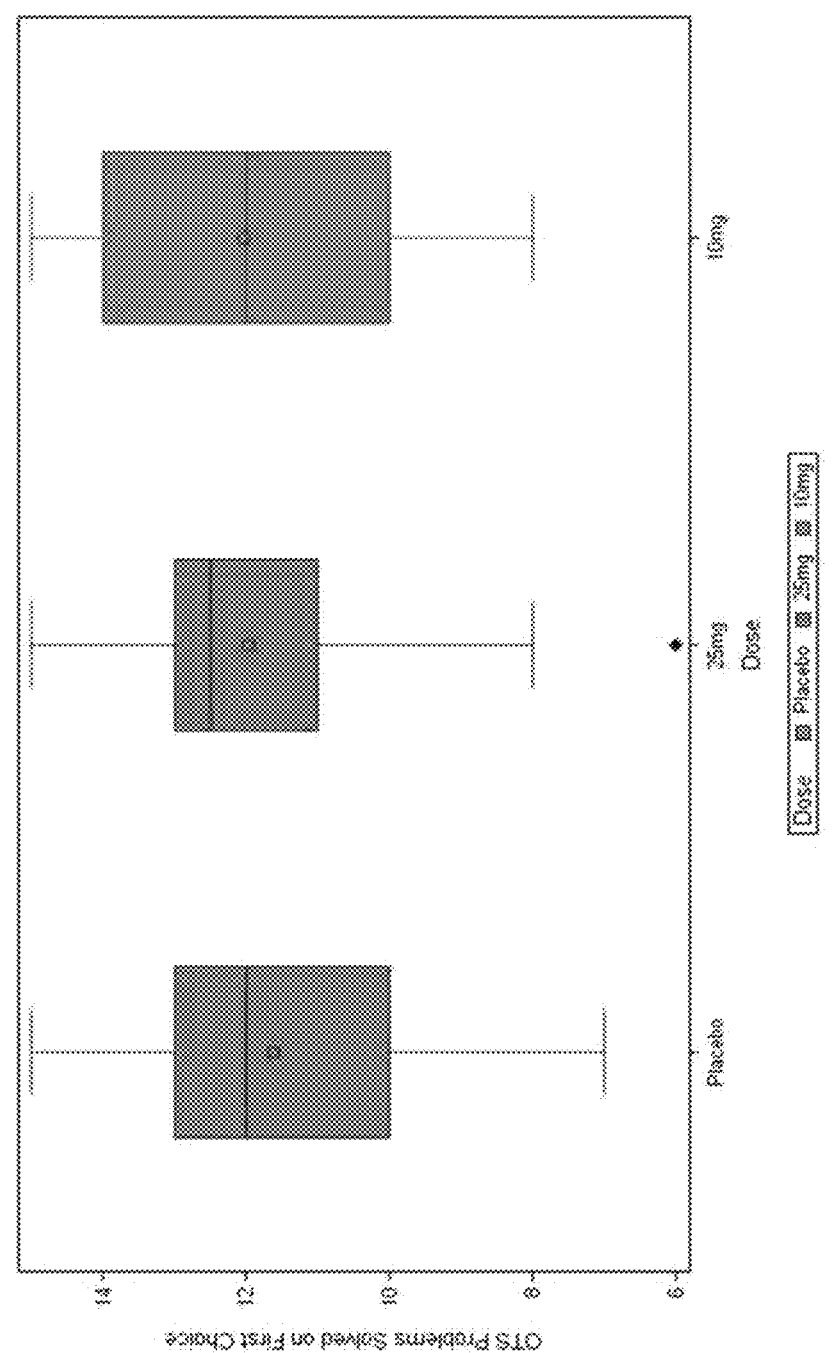
Figure 9P:
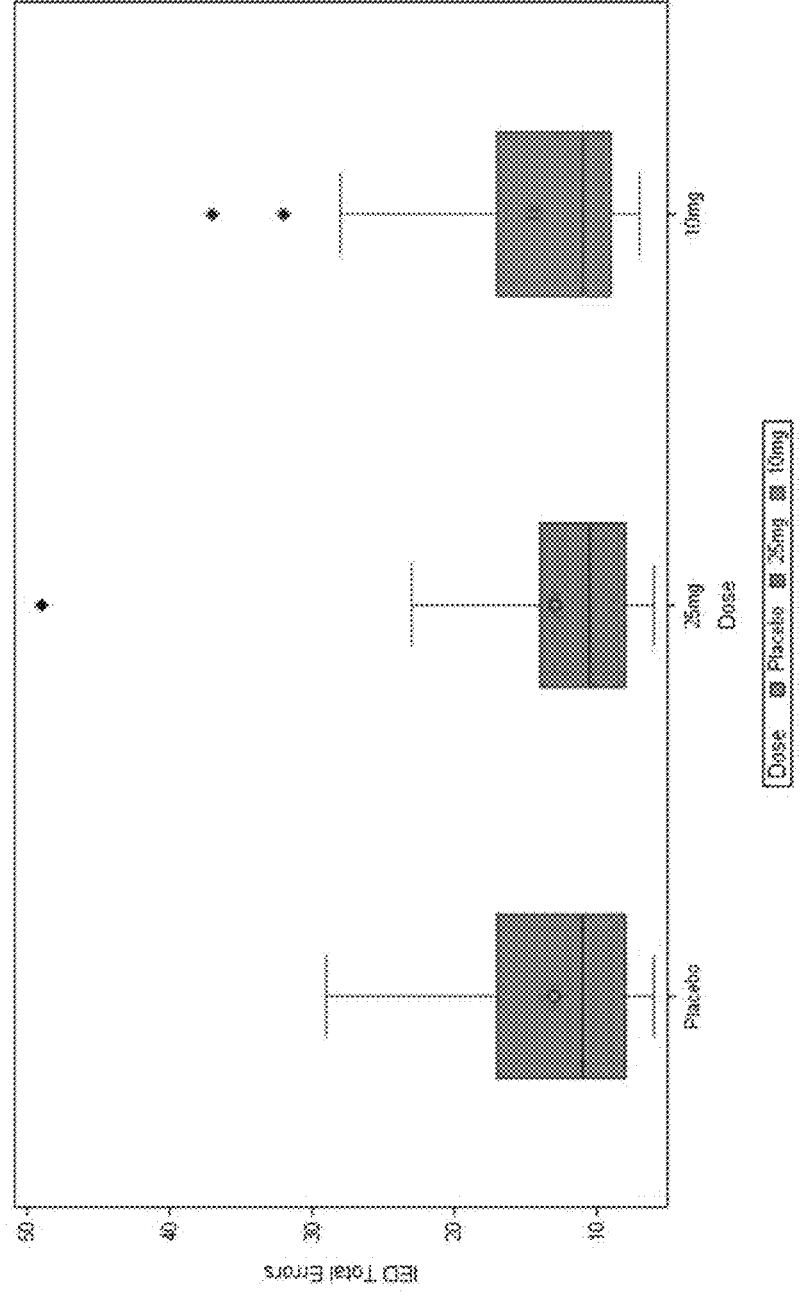
Figure 9Q:
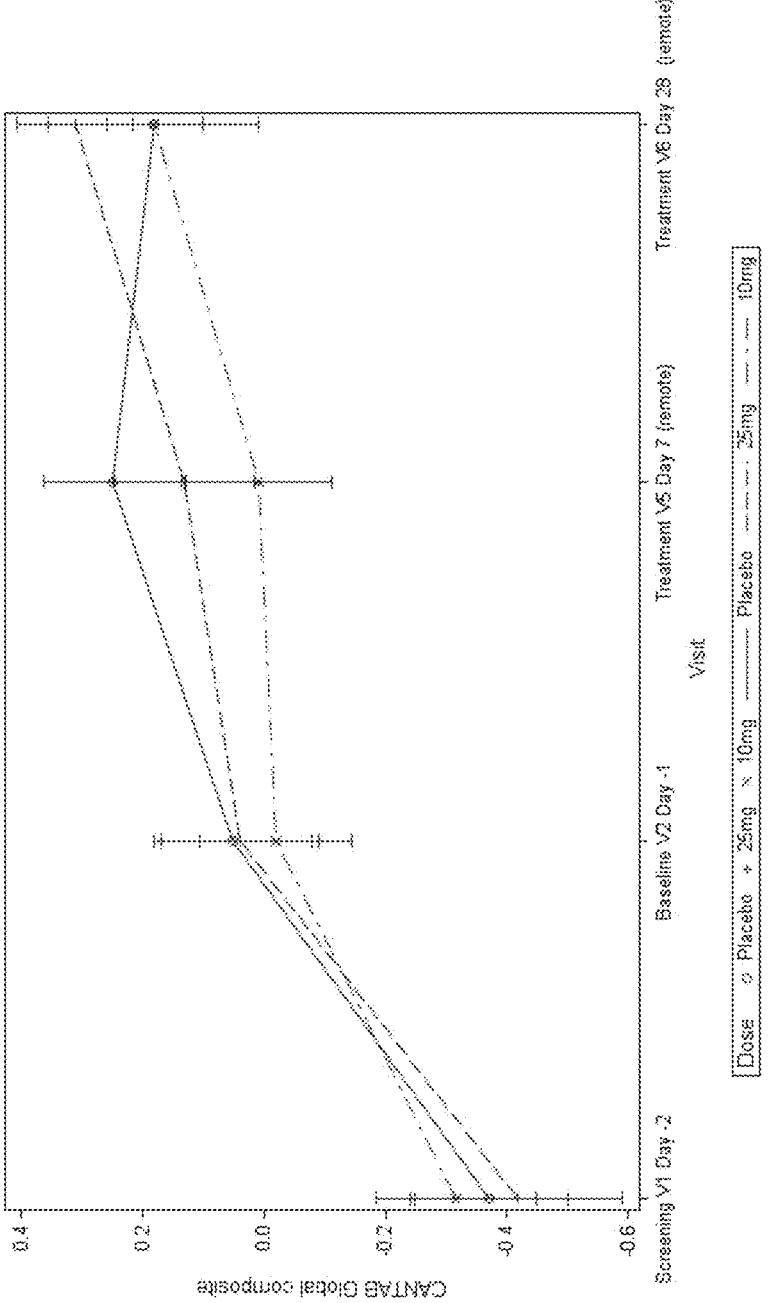
Figure 9R:
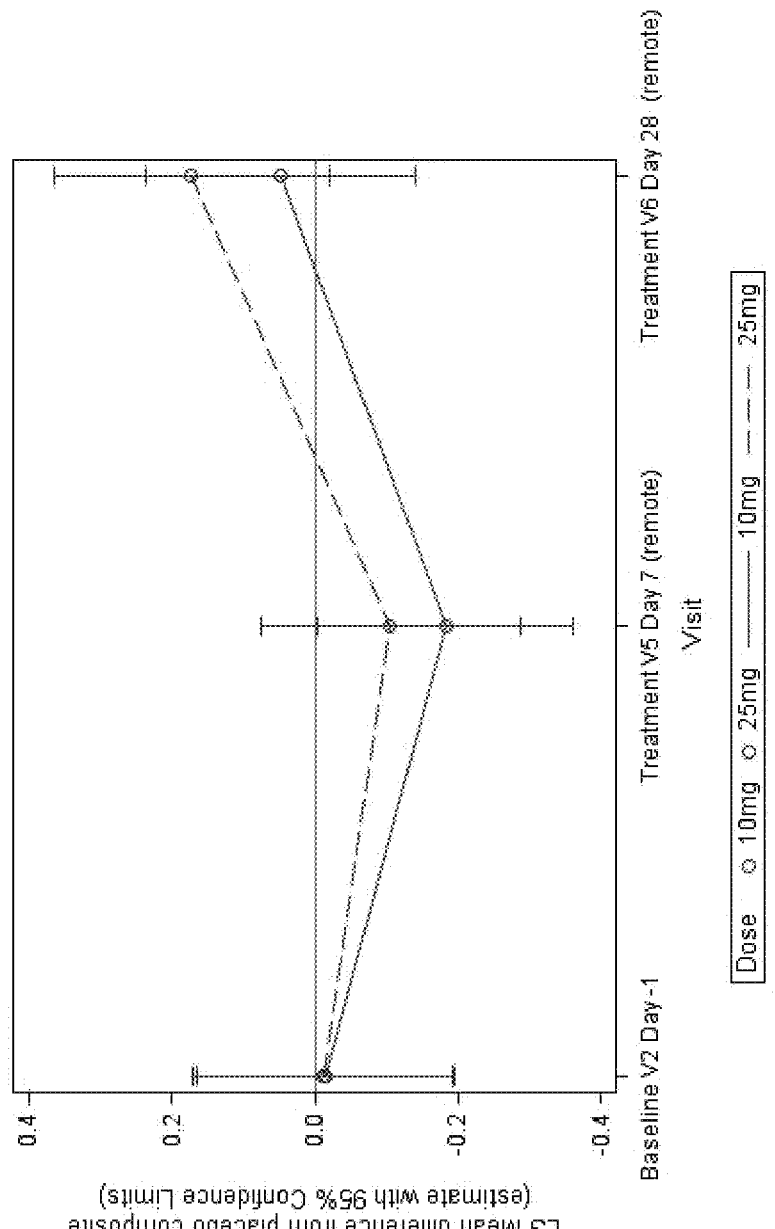

FIG. 9B shows the number of subjects that completed screening (Visit 1), baseline measurements (Visit 2), and drug administration (Visit 3) of the Phase 1 exploratory study.
FIG. 9C shows the group sizes of the dosing sessions of the Phase 1 exploratory study.
FIG. 9D shows the most frequently reported adverse events of the Phase 1 exploratory study.
FIG. 9E shows the duration of adverse events of the Phase 1 exploratory study.
FIG. 9F shows a graph of the Paired Associates Learning Total Errors Adjusted (PALTEA) score of the Cambridge Neuropsychological Test Automated Battery (CANTAB) over time for the psilocybin-treated and placebo-treated subjects of the Phase 1 exploratory study.
FIG. 9G shows a graph of the least squares (LS) mean difference from placebo for the PALTEA score of the CANTAB over time for the psilocybin-treated subjects of the Phase 1 exploratory study.
FIG. 9H shows a graph of the spatial working memory between errors (SWMBE) score of the CANTAB over time for the psilocybin-treated and placebo-treated subjects of the Phase 1 exploratory study.
FIG. 9I shows a graph of the least squares mean difference from placebo for the SWMBE score of the CANTAB over time for the psilocybin-treated subjects of the Phase 1 exploratory study.
FIG. 9J shows a graph of the spatial working memory strategy (SWM strategy) score of the CANTAB over time for the psilocybin-treated and placebo-treated subjects of the Phase 1 exploratory study.
FIG. 9K shows a graph of the least squares mean difference from placebo for the SWM strategy score of the CANTAB over time for the psilocybin-treated subjects of the Phase 1 exploratory study.
FIG. 9L shows a graph of the Rapid Visual Information Processing A Prime (RVPA) score of the CANTAB over time for the psilocybin-treated and placebo-treated subjects of the Phase 1 exploratory study.
FIG. 9M shows a graph of the least squares (LS) mean difference of psilocybin groups (10 mg and 25 mg) compared to placebo groups over time. Psilocybin was administered on Day 0. Data on Days 7 and Day 28 were collected remotely. Positive scores indicate psilocybin performed better than placebo. Negative scores indicate placebo performed better than psilocybin. LS means were calculated using repeated-measures ANOVA and compared with placebo. *p≤0.05. Data are expressed as LS mean±sem.
FIG. 9N shows a graph of the Emotional Recognition Task percent correct (ERTPC) of the CANTAB for the psilocybin-treated and placebo-treated subjects of the Phase 1 exploratory study.
FIG. 9O shows a graph of the One Touch Stockings Problems Solved on First Choice (OTSPSFC) of the CANTAB for the psilocybin-treated and placebo-treated subjects of the Phase 1 exploratory study.
FIG. 9P shows a graph of the intra-extra dimensional set shift total errors (IEDYERT) of the CANTAB for the psilocybin-treated and placebo-treated subjects of the Phase 1 exploratory study.
FIG. 9Q shows a graph of the CANTAB global composite score over time for the psilocybin-treated and placebo-treated subjects of the Phase 1 exploratory study.
FIG. 9R shows a graph of the least squares mean difference from placebo for the CANTAB global composite score over time for the psilocybin-treated subjects of the Phase 1 exploratory study.

Figure 9S:
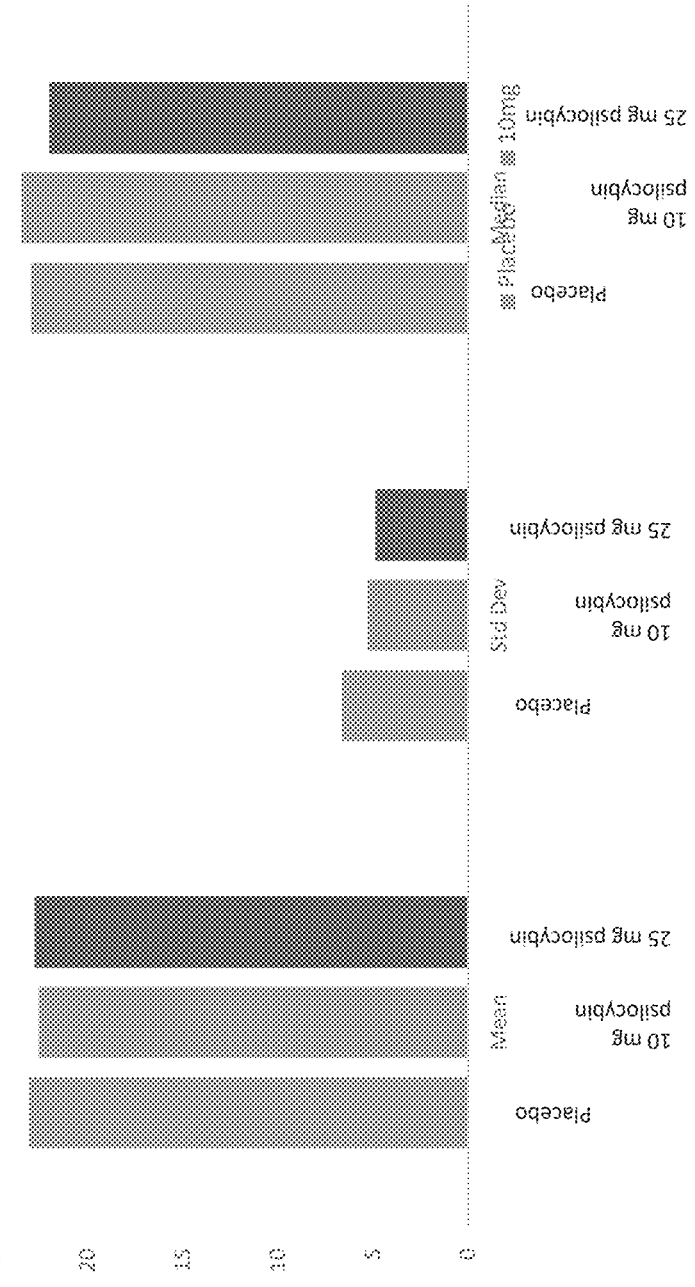

FIG. 9S shows a graph of the verbal fluency test for the psilocybin-treated and placebo-treated subjects of the Phase 1 exploratory study.

Figure 9T:
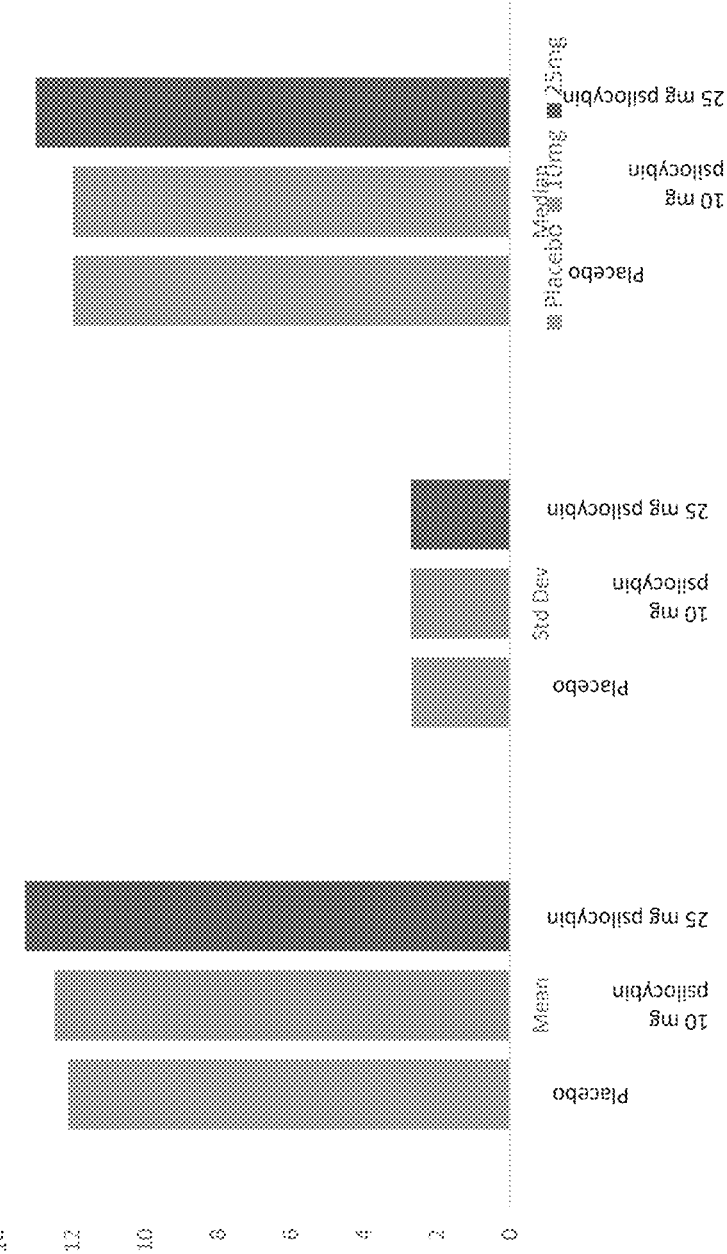

FIG. 9T shows a graph of the digit span forward test for the psilocybin-treated and placebo-treated subjects of the Phase 1 exploratory study.

Figure 9U:
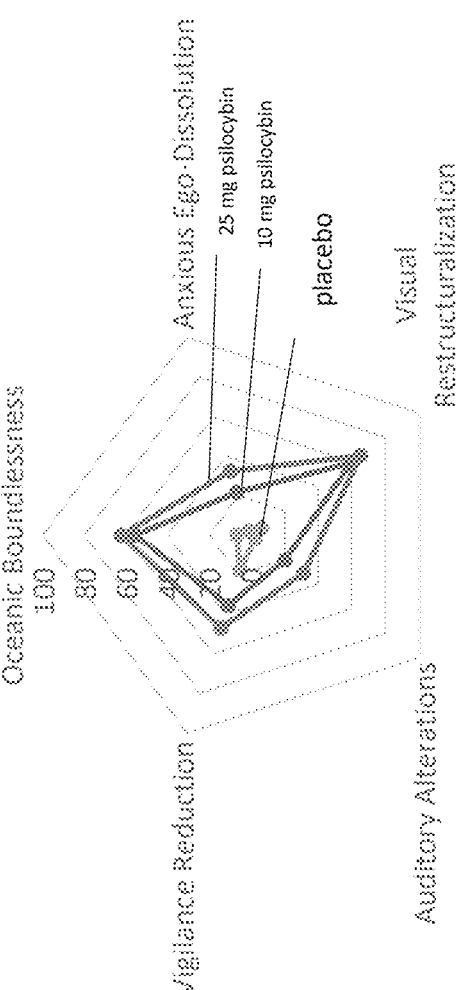

FIG. 9U shows a graph of the Five Dimensional-Altered States of Consciousness (5D-ASC), which measures alterations in mood, perception, and experience of self, after administration of psilocybin or placebo in the Phase 1 exploratory study.

Figure 9V:
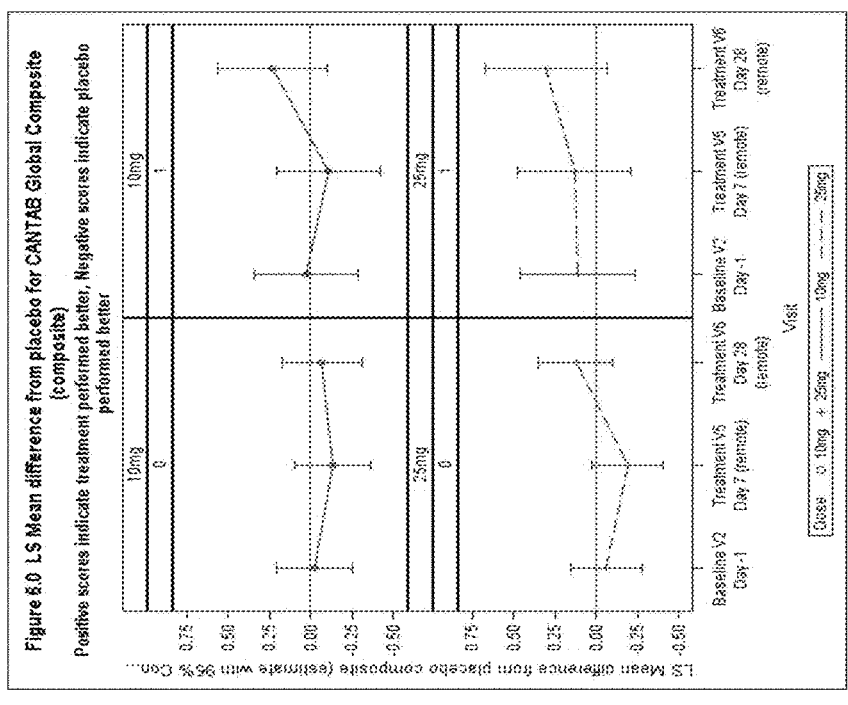

FIG. 9V shows the difference in CANTAB composite score between "psilocybin-naïve" (0, left-hand side) subjects and subjects with prior psilocybin experience (1, right-hand side).

Figure 10:
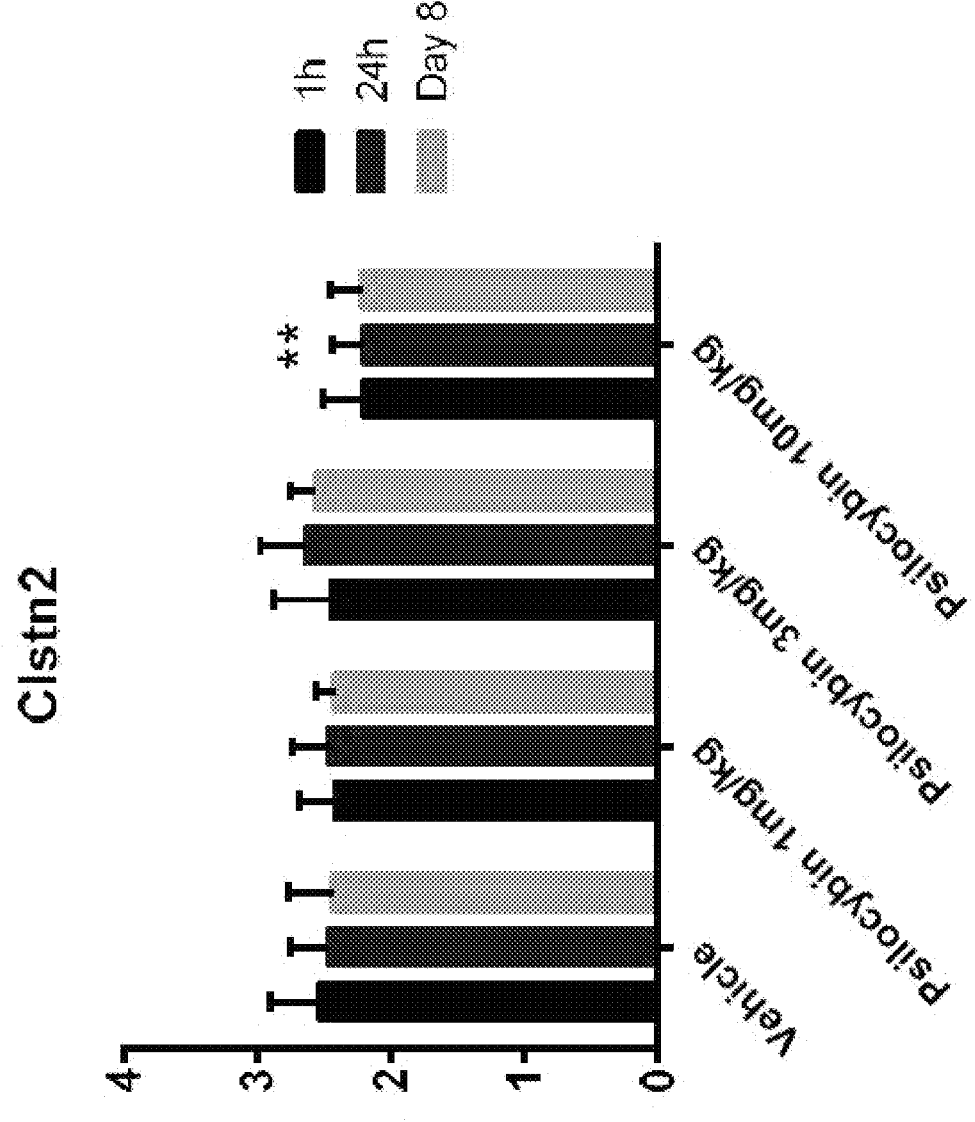

FIG. 10 shows the calsyntenin 2 (Clstn2) expression levels at 1 hour, 24 hours, and on Day 8 following a single administration of psilocybin in naïve mice compared to vehicle treated animals. Two-way ANOVA repeated measures followed by Bonferroni multiple comparison test, *<0.05, p<0.01, *p<0.001, ****p<0.0001. Data are expressed as mean±standard deviation (SD).

Figure 11:
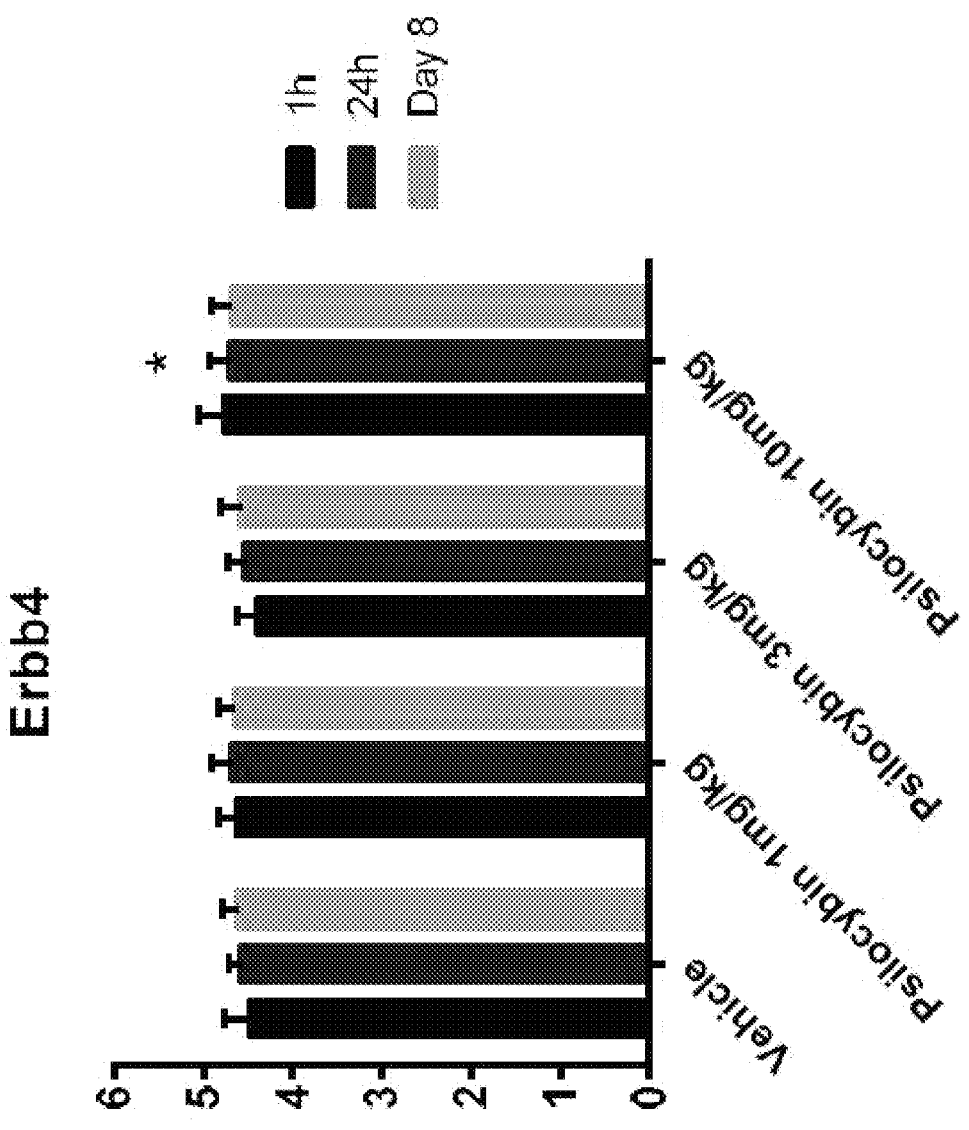

FIG. 11 shows the receptor tyrosine-protein kinase erbB-4 (Erbb4) expression levels at 1 hour, 24 hours, and on Day 8 following a single administration of psilocybin in naïve mice compared to vehicle treated animals. Two-way ANOVA repeated measures followed by Bonferroni multiple comparison test, *p<0.05, p<0.01, *p<0.001, ****p<0.0001. Data are expressed as mean±SD.

Figure 12:
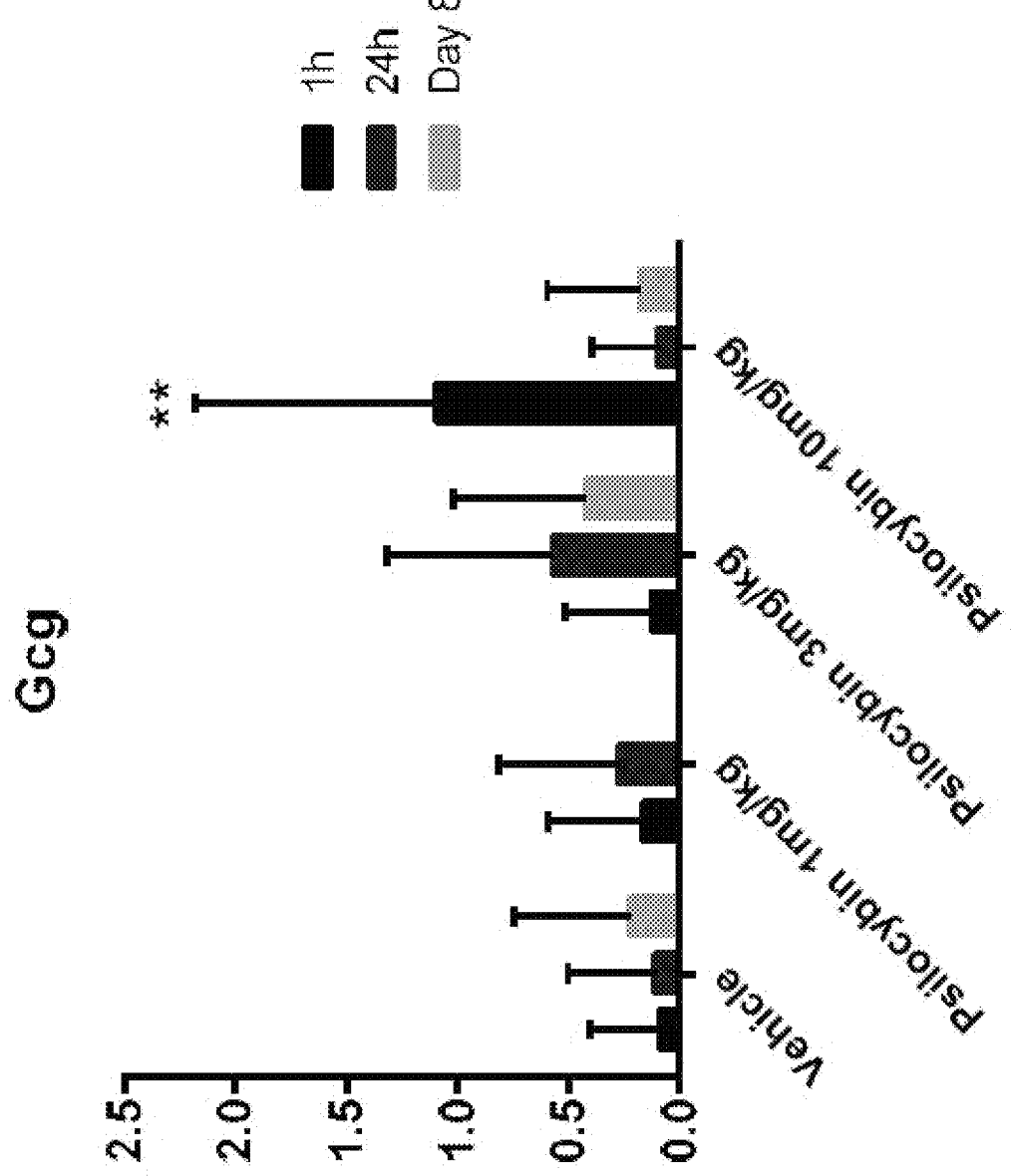

FIG. 12 shows glucagon (Gcg) expression levels at 1 hour, 24 hours, and on Day 8 following a single administration of psilocybin in naïve mice compared to vehicle treated animals. Two-way ANOVA repeated measures followed by Bonferroni multiple comparison test, *p<0.05, p<0.01, *p<0.001, ****p<0.0001. Data are expressed as mean±SD.

Figure 13:
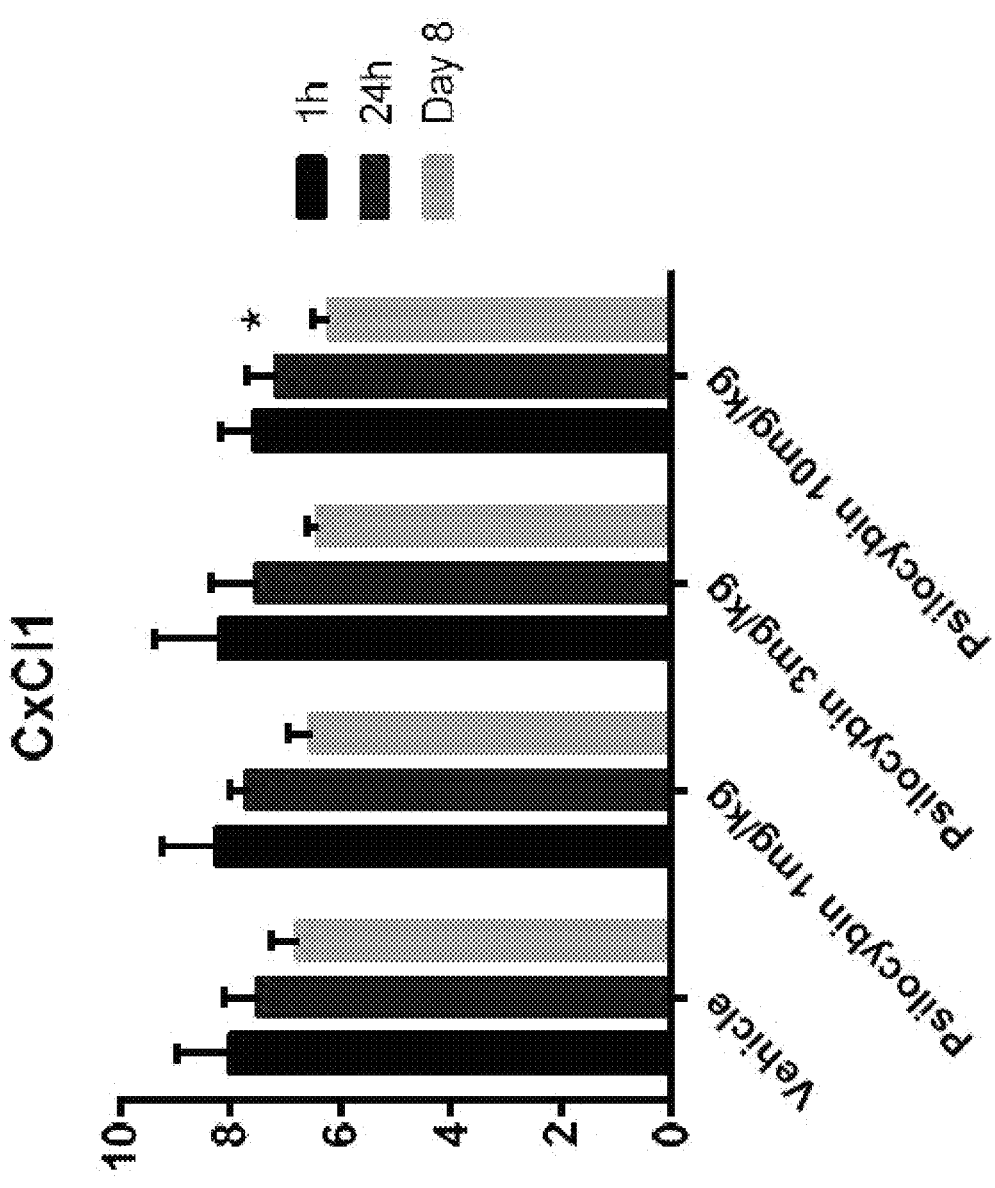

FIG. 13 shows chemokine ligand 1 (Cxcl1) expression levels at 1 hour, 24 hours, and on Day 8 following a single administration of psilocybin in naïve mice compared to vehicle treated animals. Two-way ANOVA repeated measures followed by Bonferroni multiple comparison test, *p<0.05, p<0.01, *p<0.001, ****p<0.0001. Data are expressed as mean±SD.

Figure 14:
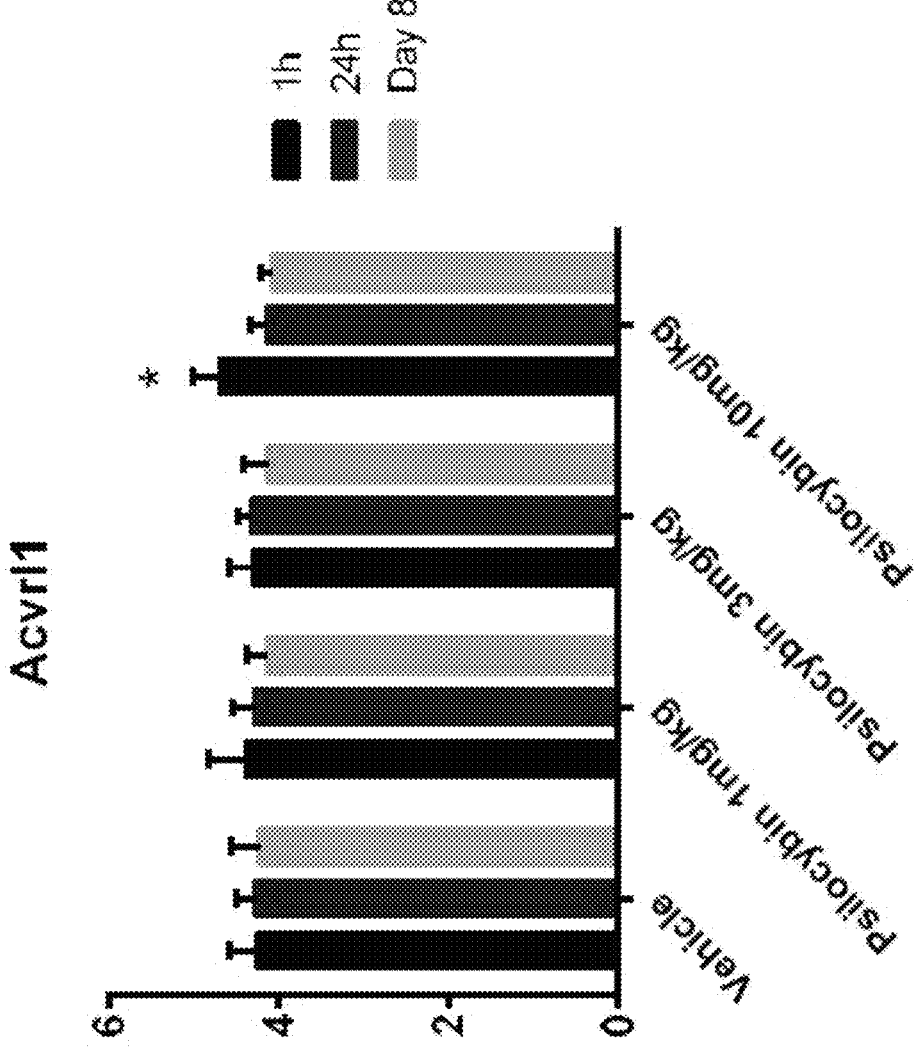

FIG. 14 shows Activin A Receptor Like Type1 (Acvrl1) expression levels at 1 hour, 24 hours, and on Day 8 following a single administration of psilocybin in naïve mice compared to vehicle treated animals. Two-way ANOVA repeated measures followed by Bonferroni multiple comparison test, *p<0.05, p<0.01, *p<0.001, ****p<0.0001. Data are expressed as mean±SD.

Figure 15:
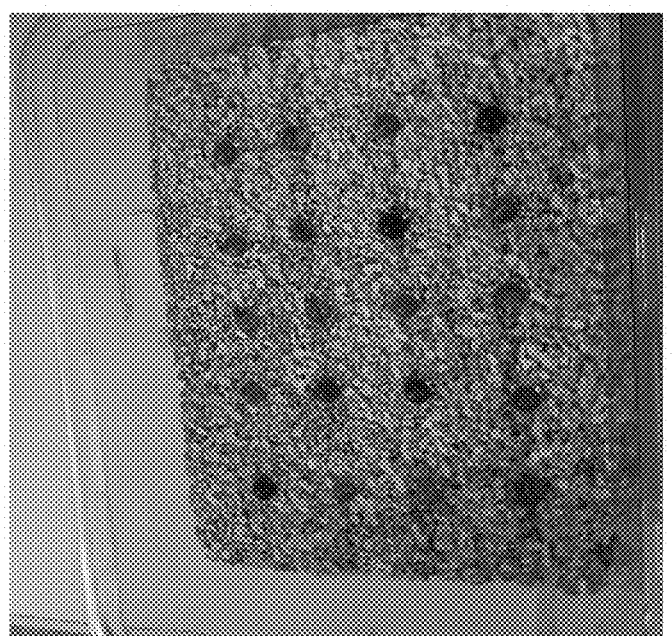

FIG. 15 illustrates the experimental conditions of the marble burying test.

Figure 16:
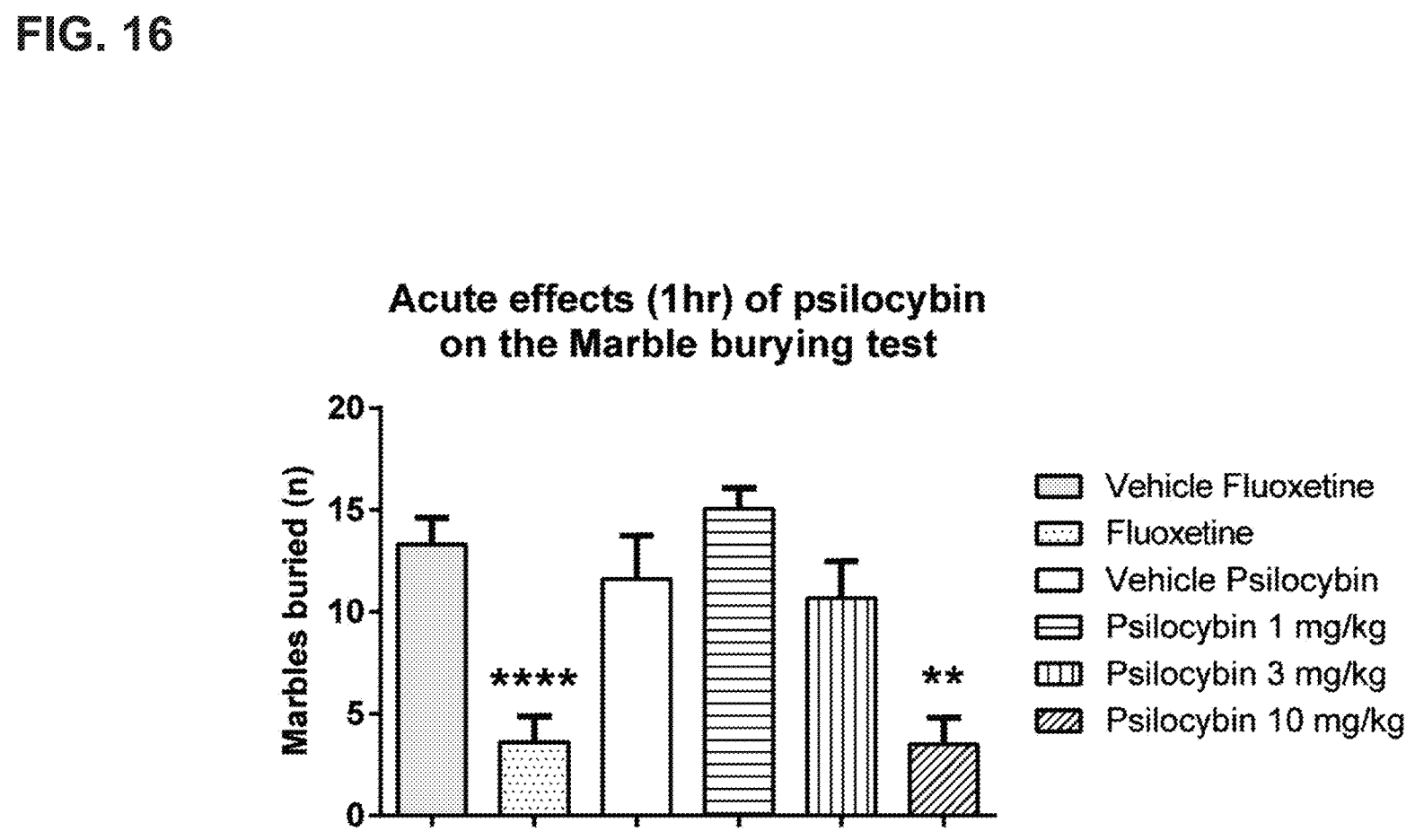

FIG. 16 shows the number of buried marbles 1 hour following psilocybin (PS) treatment. Fluoxetine (Fluox, 30 min pre-treatment) was used as a positive control. Data are expressed as mean±SEM. Statistical significance was determined using an unpaired t-test for vehicle FL and fluoxetine, **p<0.0001. Statistical significance was determined using one-way ANOVA and Tukey's correction test for vehicle PS and psilocybin, p<0.001. FL=fluoxetine; PS=psilocybin.

Figure 17:
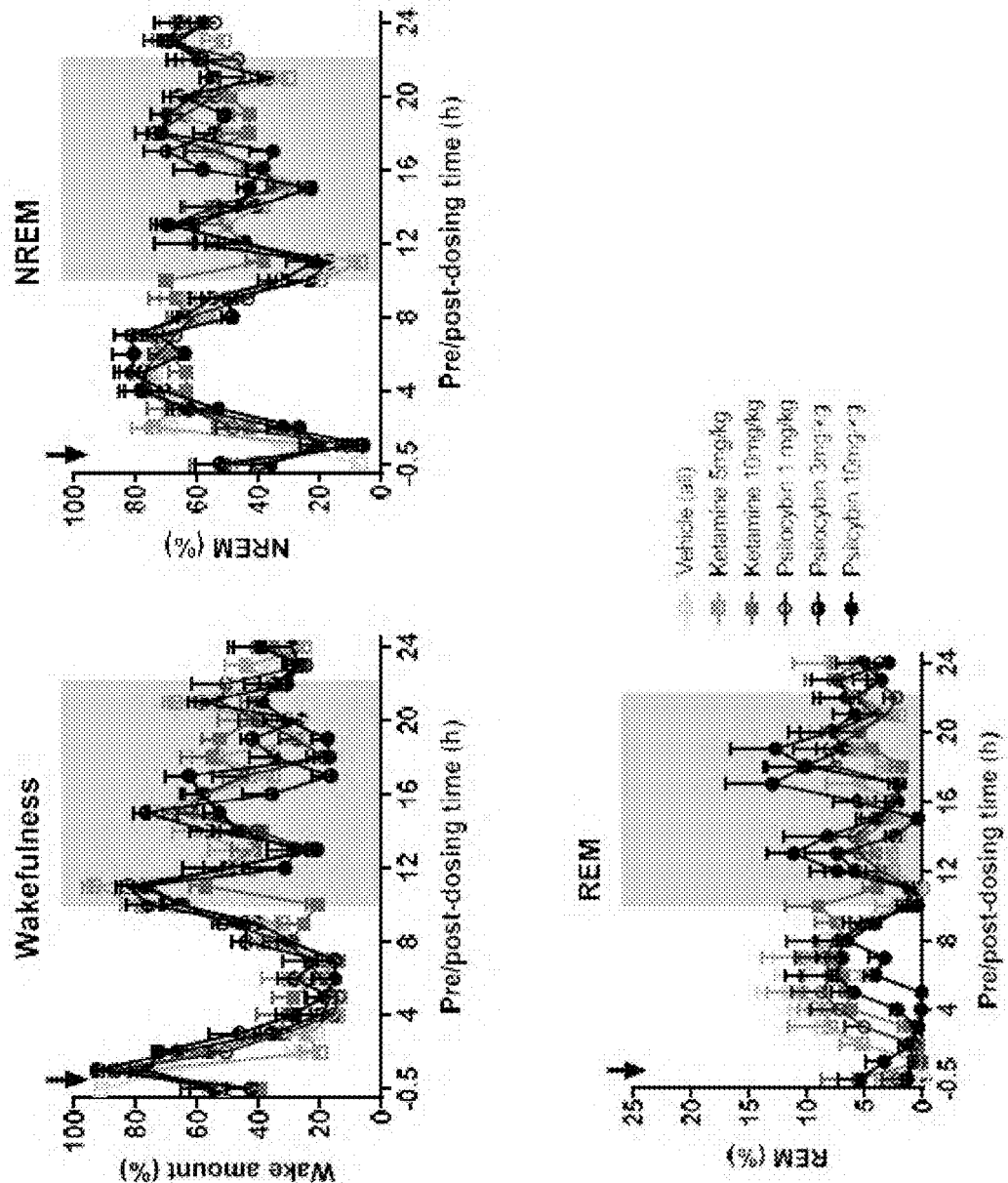

FIG. 17 is a graph showing the changes in amount of wakefulness, non-rapid eye movement (NREM) sleep and rapid eye movement (REM) sleep over 24 hours following psilocybin administration. Black arrow denotes dosing time. The grey background denotes dark phase (awake phase for rodents).

Figure 18:
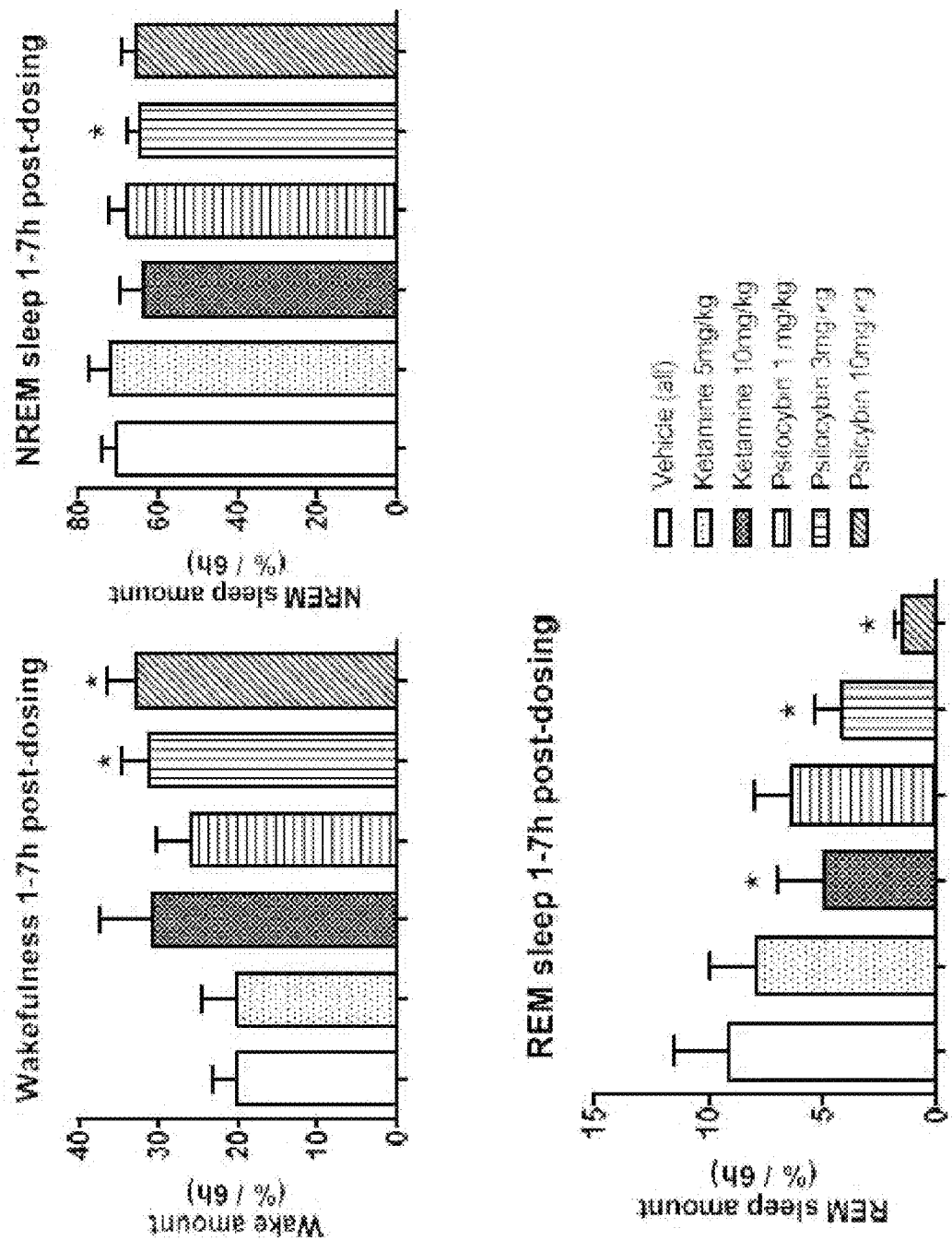

FIG. 18 is a graph showing the amount of wakefulness, NREM sleep and REM sleep 1-7 hours (light phase, sleep phase for rodents) post-dosing with psilocybin. Statistical analysis by repeated measures ANOVA, *p<0.05.

FIG. 19 is a graph showing the amount of wakefulness, NREM sleep and REM sleep 11-19 hours (dark phase) post-dosing with psilocybin. Statistical analysis by repeated measures ANOVA, *p<0.05.

FIG. 20 is a graph showing the changes in the absolute and relative wakefulness electroencephalogram (EEG) power with frequency, and the amount of gamma oscillations. Statistical analysis by repeated measures ANOVA, *p<0.05.

Figure 21:
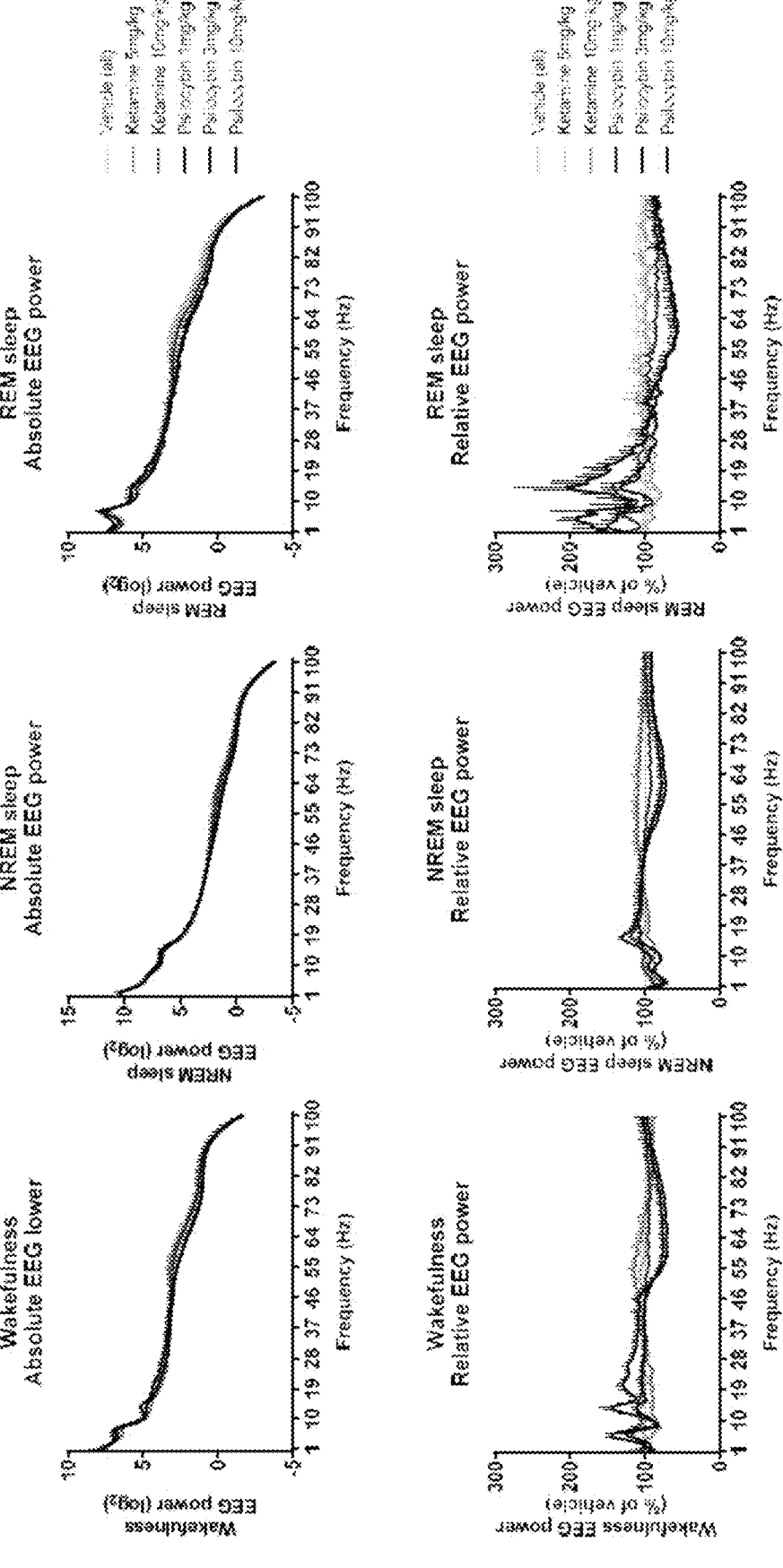

FIG. 21 is a graph showing the changes in the absolute and relative wakefulness, NREM and REM sleep EEG power with frequency.

FIG. 22 shows the number of entries into the open arms (left panel) and the time spent in open arms (right panel) 2 hours post-administration of psilocybin. Diazepam was used as a positive control. Data are expressed as mean±SEM. Statistical significance was determined using one-way ANOVA and Fisher's Least Significant Difference for pairwise comparison, *p≤0.05

FIG. 23 shows the number of entries into the open arms (left panel) and the time spent in open arms (right panel) 24 hours post-administration of psilocybin. Diazepam was used as a positive control.

Figure 24:
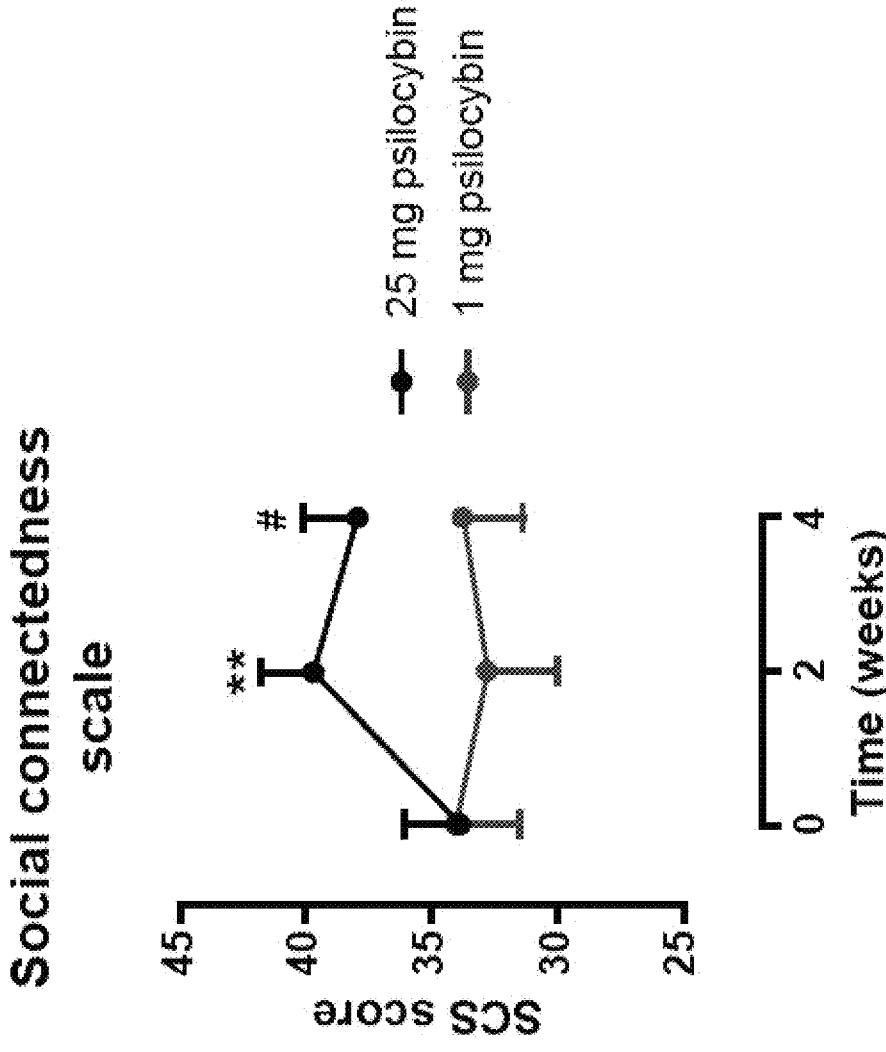

FIG. 24 shows the change in social connectedness scale score following administration of psilocybin to healthy human volunteers. Two-way ANOVA repeated measures with Bonferroni correction, **p<0.01, #<0.05. Data are expressed as mean±sem.

Figure 25:
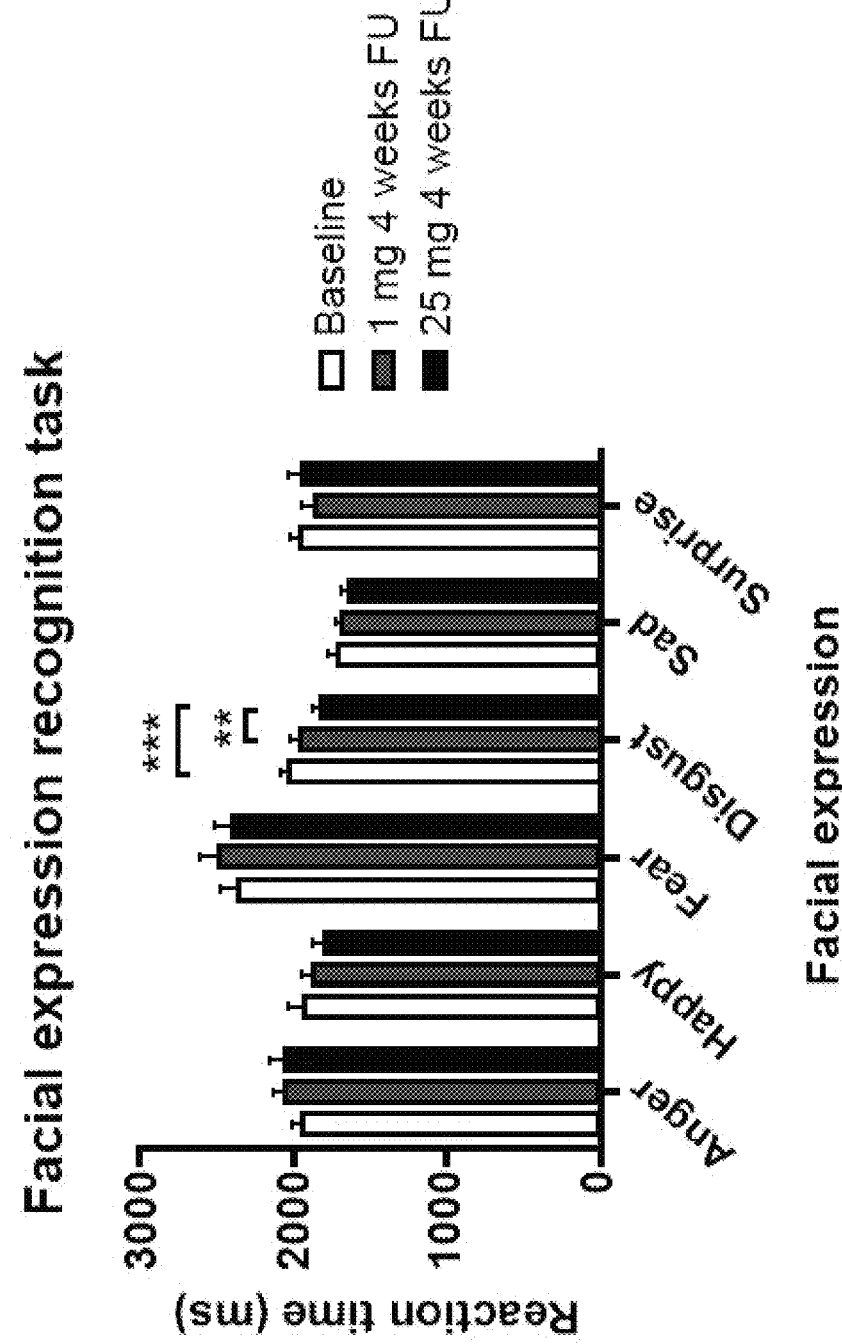

FIG. 25 shows the reaction time of healthy human volunteers in the facial expression recognition task following administration of psilocybin. One-way ANOVA repeated measures, *p<0.05, p<0.01, *p<0.001. Data are expressed as mean±sem.

Figure 26:
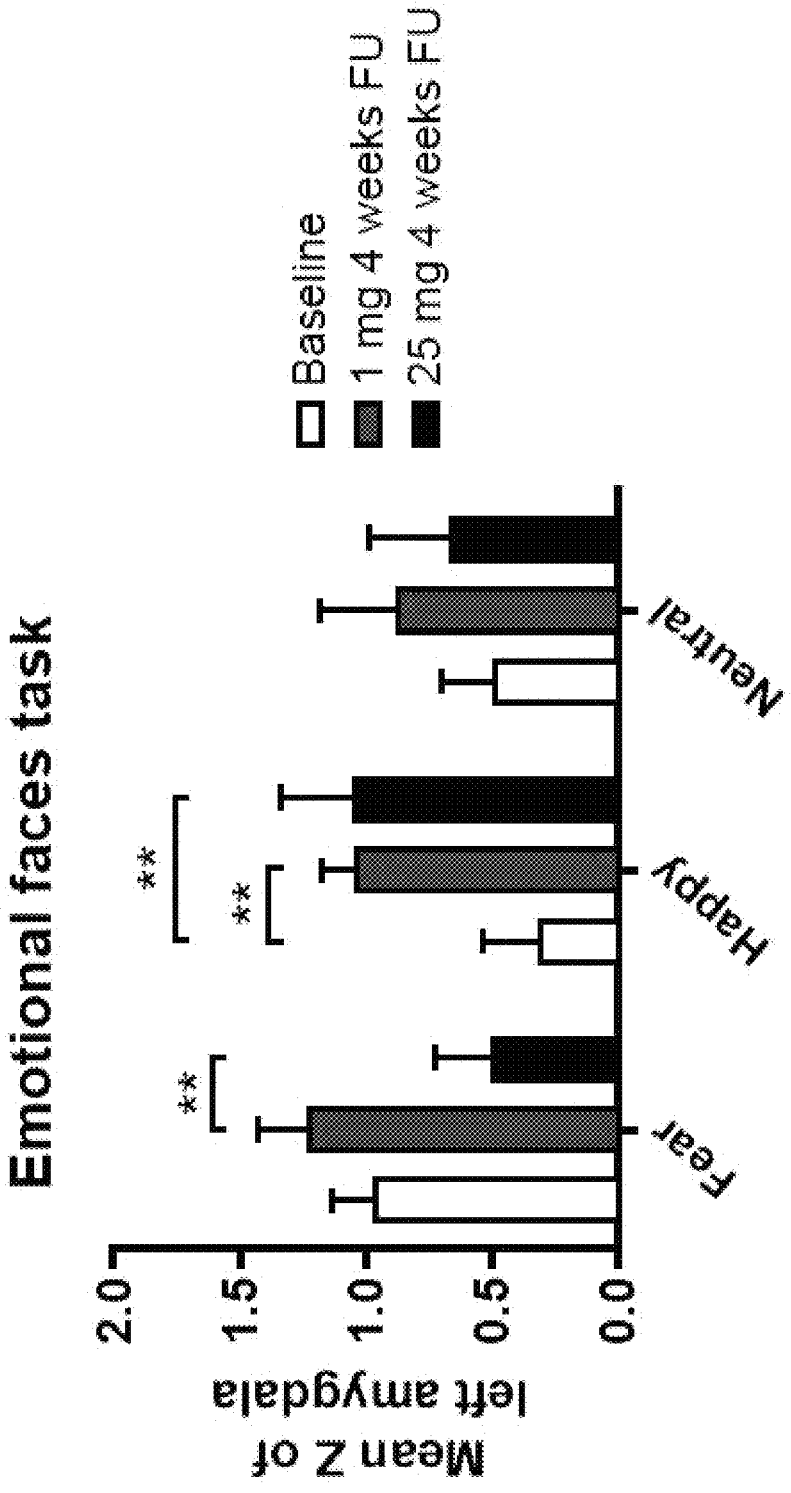

FIG. 26 shows the activation of the left amygdala as represented by the change of mean Z in the left amygdala in healthy volunteers following administration of psilocybin. One-way ANOVA repeated measures, *p<0.05, p<0.01, *p<0.001. Data are expressed as mean±sem.

FIG. 27 illustrates the timeline for the chronic cluster headaches study.

Figure 28:
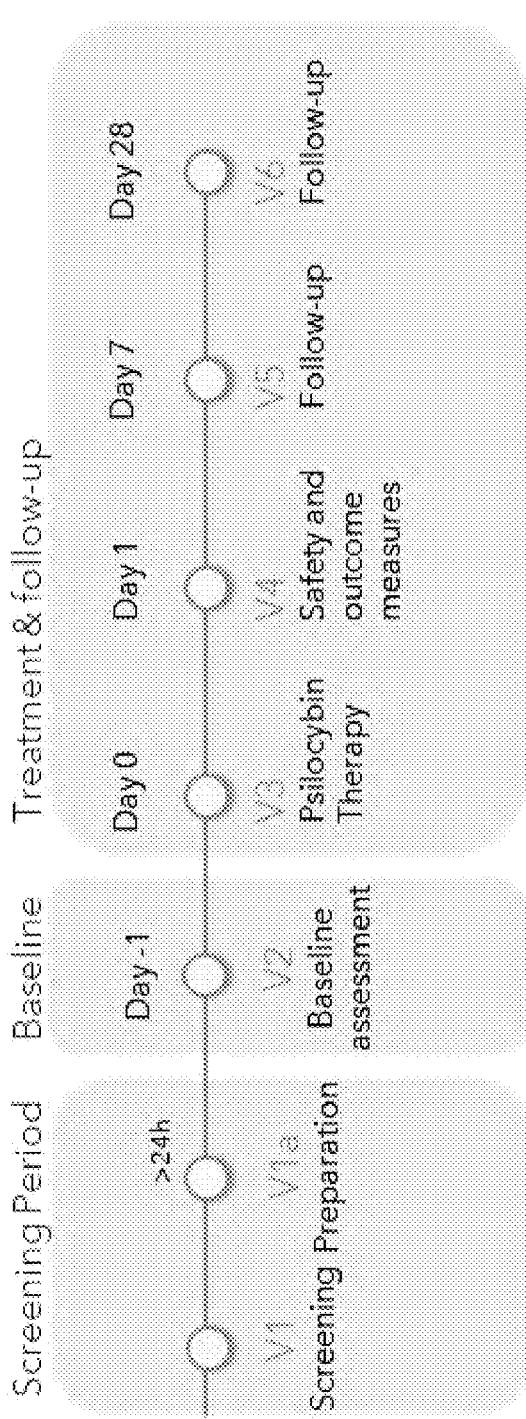

FIG. 28 shows a timeline of visits for a Phase 2 investigational trial for evaluating the use of psilocybin for the treatment of anorexia.

Figure 29:
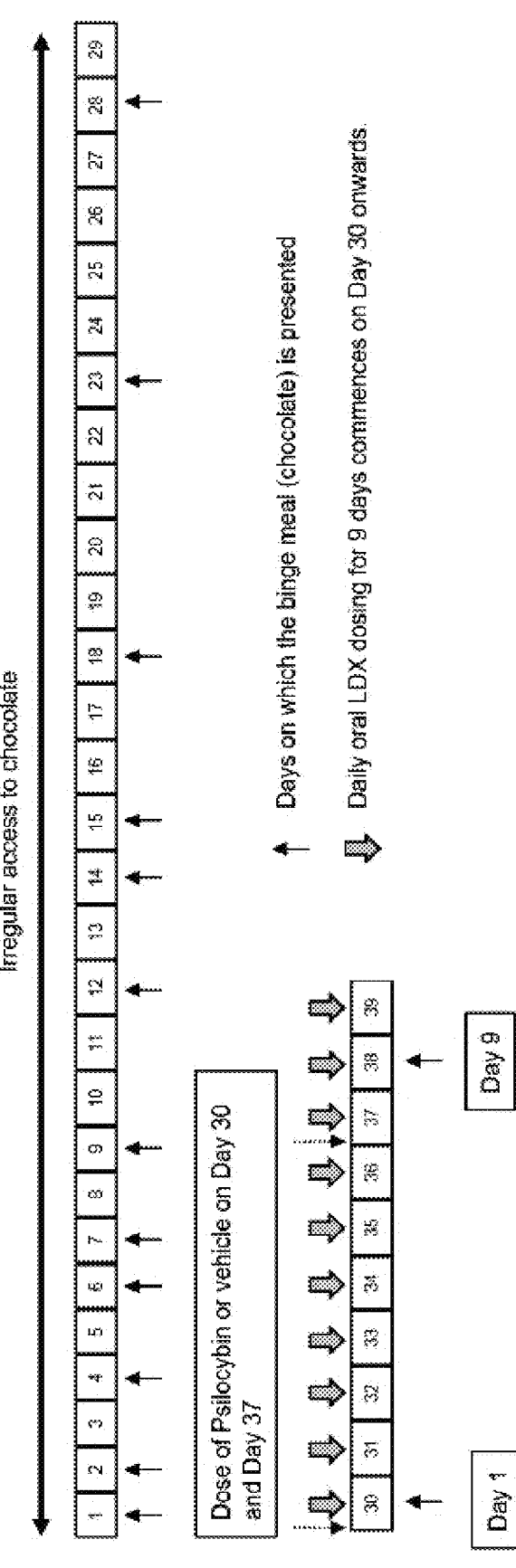

FIG. 29 shows a timeline of an in vivo study that evaluates the use of psilocybin for the treatment of binge eating.

Figure 30:
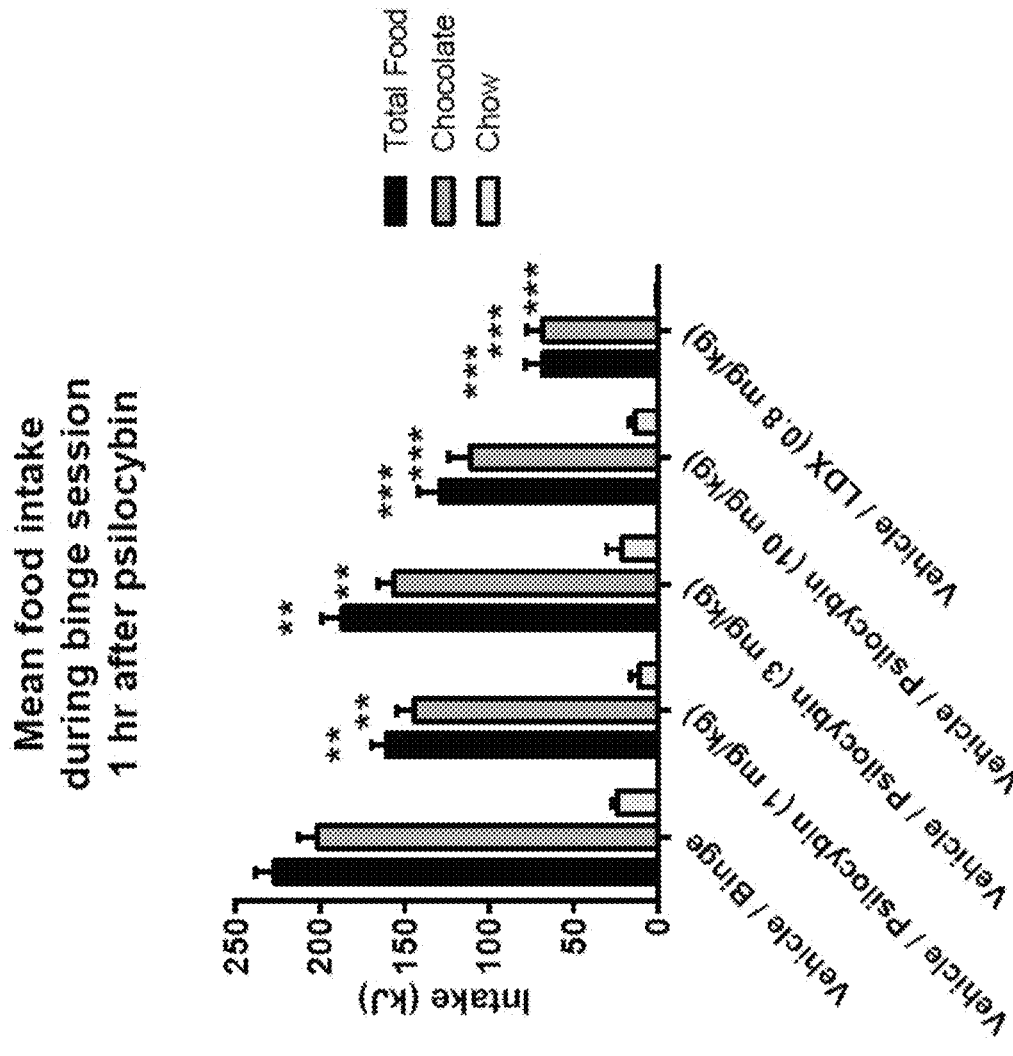

FIG. 30 shows the amount of chow, chocolate and total food that were consumed 1 hour following administration of 1 mg/kg psilocybin, 3 mg/kg psilocybin, 10 mg/kg psilocybin, saline vehicle, or lisdexamfetamine (LDX). Multiple comparisons against vehicle are by Williams' test for Psilocybin and the multiple t test for LDX. p<0.01, *p<0.001. Data are expressed as adjusted mean±sem.

Figure 31:
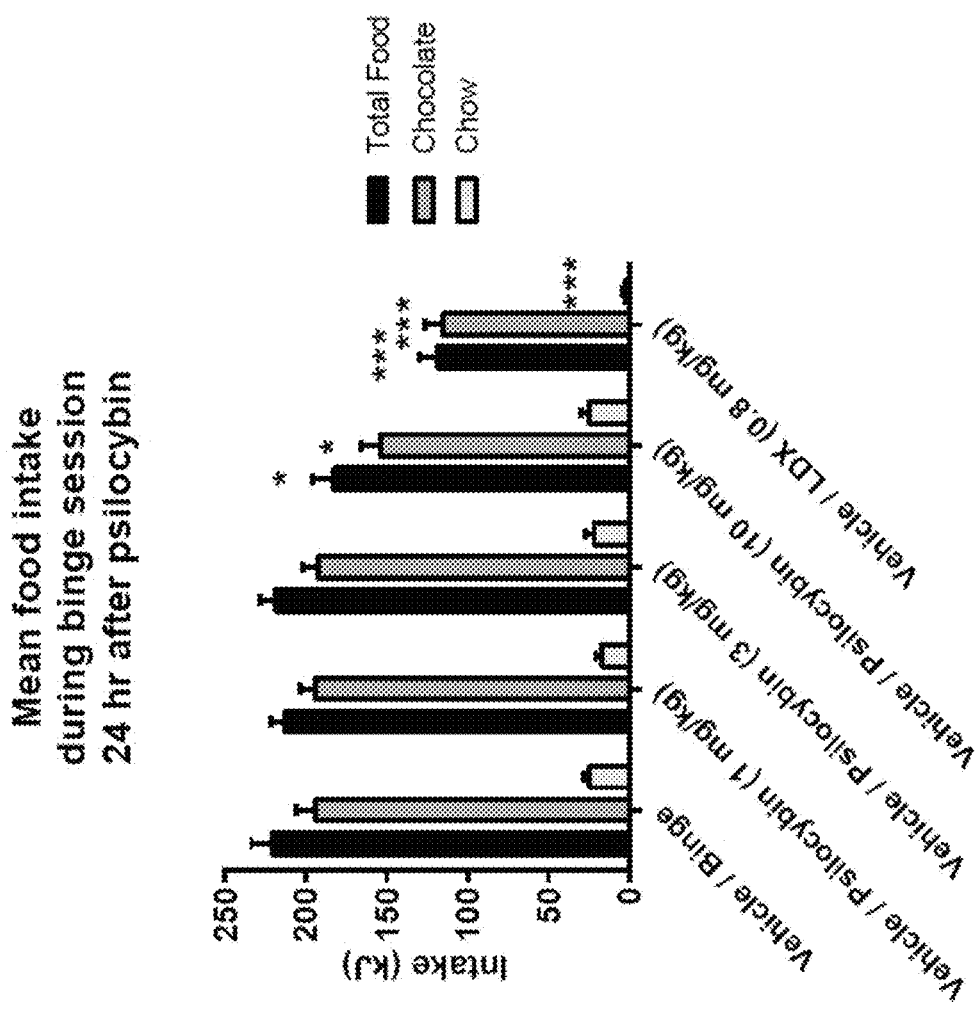

FIG. 31 shows the amount of chow, chocolate and total food consumed 24 hours following administration of 1 mg/kg psilocybin, 3 mg/kg psilocybin, 10 mg/kg psilocybin, saline vehicle, or LDX. Multiple comparisons against vehicle are by Williams' test for Psilocybin and the multiple t test for LDX. *p<0.05, ***p<0.001. Data are expressed as adjusted mean±sem.

Figure 32:
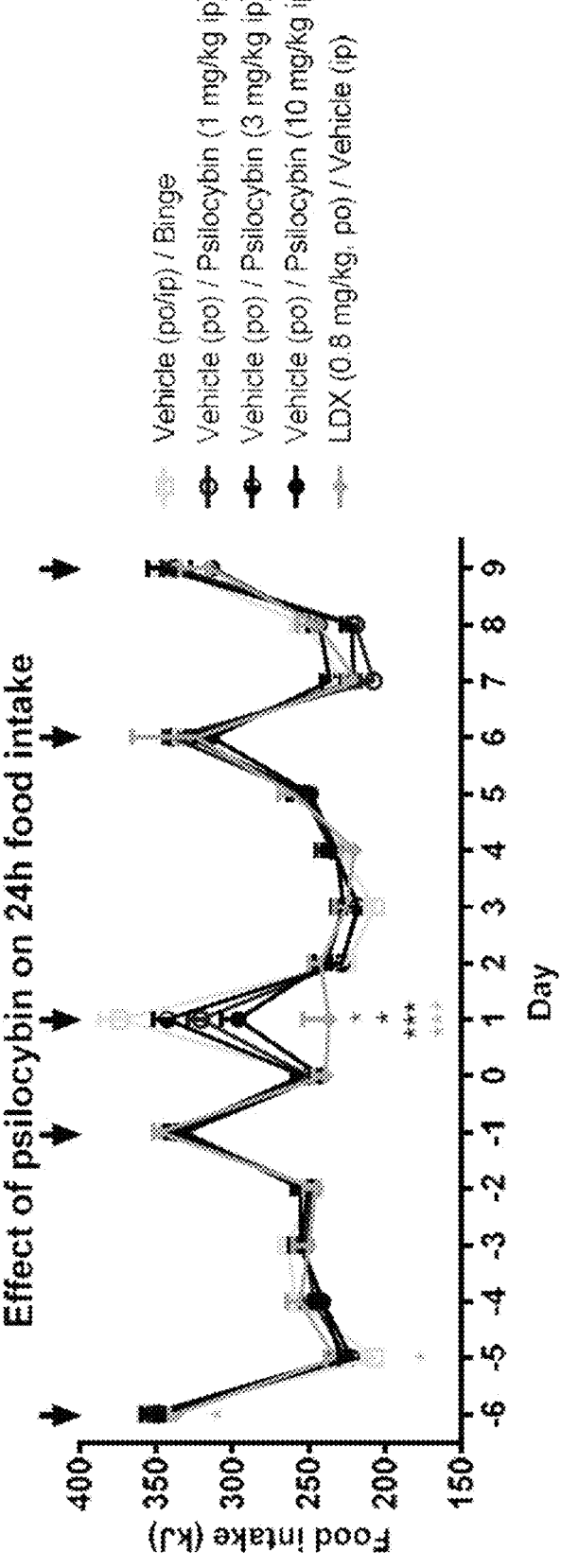

FIG. 32 shows effect of psilocybin on 24 hour food intake compared to vehicle/binge treated group. One-way ANOVA followed by Williams' test and multiple t-test for f or LDX,

*p<0.05, p<0.01, and *p<0.001. Data are expressed as adjusted mean±sem. Arrows indicate binge days.

Figure 33:
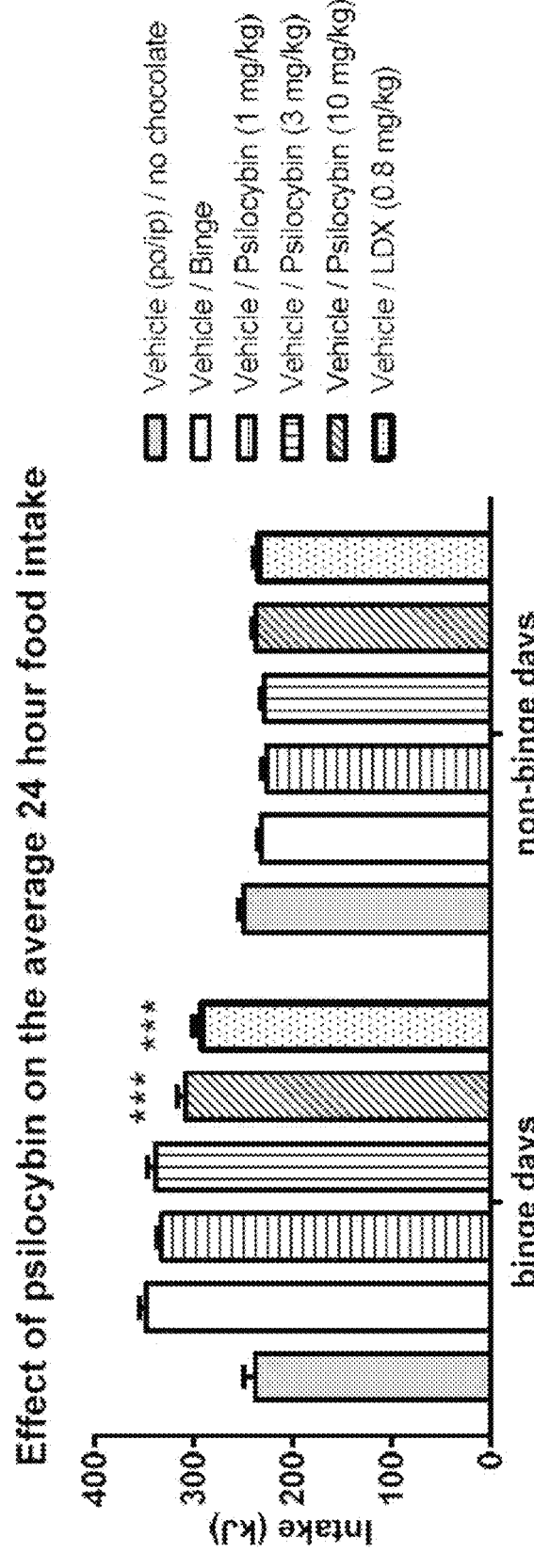

FIG. 33 shows the effect of psilocybin on average 24 hour food intake. One-way ANOVA followed by Williams' test and multiple t-test for f or LDX, *p<0.05, p<0.01, and *p<0.001. Data for vehicle/no chocolate expressed as mean±sem, all other groups are expressed as adjusted mean±sem.

FIG. 34 shows the effect of psilocybin on body weight change compared to vehicle/binge treated group. One-way ANOVA followed by Williams' test and multiple t-test for f or LDX, *p<0.05, p<0.01, and *p<0.001. Data for vehicle/no chocolate are expressed as mean±sem, all other groups are expressed as adjusted mean±sem.

Figure 35:
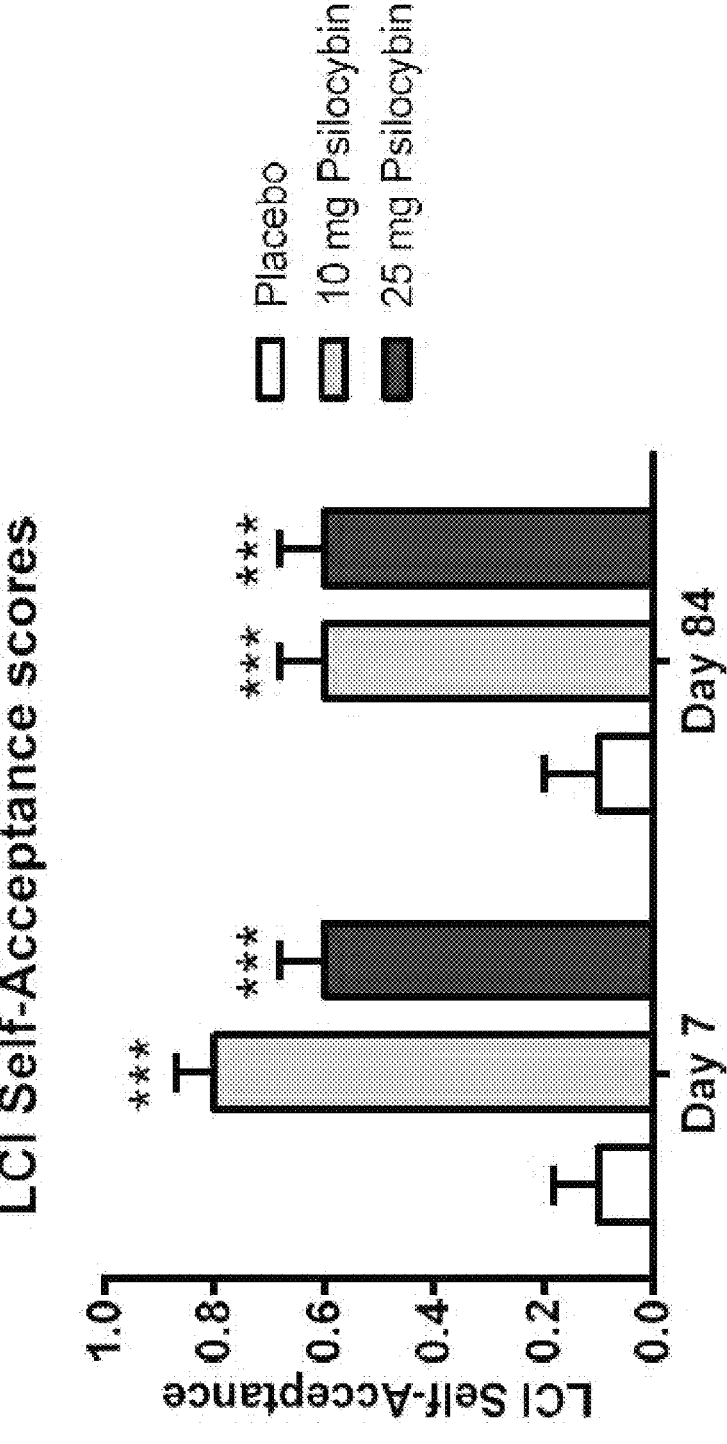

FIG. 35 shows the effect of psilocybin on the Life Changes Inventory Self-Acceptance Score in a healthy volunteer study. Mixed model for repeated measures was used to calculate least squares (LS) means, followed by pairwise comparison with placebo group. ***p<0.001. Data are presented as LS mean±sem.

DETAILED DESCRIPTION

Definitions

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

The singular forms "a," "an" and "the" are intended to include the plural forms as well, unless the context clearly indicates otherwise.

Furthermore, the term "about" as used herein when referring to a measurable value such as a dose, time, temperature, and the like, is meant to encompass variations of ±20%, ±10%, ±5%, ±1%, ±0.5%, or even ±0.1% of the specified amount.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless the context indicates otherwise, it is specifically intended that the various features described herein can be used in any combination.

As used herein, the terms "reduce," "decrease," "lessen" and similar terms mean a decrease of at least about 10%, about 15%, about 20%, about 25%, about 35%, about 50%, about 75%, about 80%, about 85%, about 90%, about 95%, about 97%, or more.

As used herein, the terms "improve," "increase," "enhance," and similar terms indicate an increase of at least about 10%, about 15%, about 20%, about 25%, about 50%, about 75%, about 100%, about 150%, about 200%, about 300%, about 400%, about 500%, or more.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

As used herein, "substantially absent" with reference to XRPD diffractogram peak means the peak has a relative intensity compared to a reference peak present in the diffractogram of less than about 5%, less than about 4%, less than about 3%, less than about 2%, or less than about 1% of the intensity of the reference peak, or that the peak is not detectable.

XRPD diffractograms and XRPD peak positions may be acquired using Cu Kα radiation.

DSC thermograms and TGA thermograms may be acquired using a heating rate of 20° C./min.

As used herein, the term "diffusion tensor imaging" or "DTI" refers to a technique that detects how water travels along the white matter tracts in the brain. In some embodiments, DTI is used to characterize microstructural changes associated with mental disorders (e.g., major depressive disorder) and/or the response to treatment in subjects with mental disorders.

All disease and disorders listed herein are defined as described in the Diagnostic and Statistical Manual of Mental Disorders (DSM-5), published by the American Psychiatric Association, or in International Classification of Diseases (ICD), published by the World Health Organization.

As used herein the term "subject" and "patient" are used interchangeably.

As used herein, "treating" and like terms refer to reducing the severity and/or frequency of one or more symptoms, eliminating one or more symptoms and/or the underlying cause of said symptoms, reducing the frequency or likelihood of one or more symptoms and/or their underlying cause, delaying, preventing and/or slowing the progression of diseases and/or disorders and improving or remediating damage caused, directly or indirectly, by the diseases and/or disorders.

As used herein, "therapeutically-effective dose" means a dose sufficient to achieve the intended therapeutic purpose, such as, to alleviate a sign or symptom of a disease or disorder in a subject.

As used herein a "precursor" and/or "derivative" of psilocybin includes, but is not limited to, prodrugs of psilocybin, prodrugs of an active metabolite of psilocybin, and an active metabolite of psilocybin.

As used herein, a subject that is "psilocybin-naïve" has not previously been exposed to psilocybin.

As used herein, the following Medical Dictionary for Regulatory Activities (MedDRA) terms are considered to be adverse events that are psychedelic in nature: altered mood, altered state of consciousness, autoscopy, delusional perception, disinhibition, dissociation, dissociative identity disorder, dreamy state, emotional disorder, euphoric mood, feeling abnormal, hallucination, hyperacusis, hyperaesthesia, hypoaesthesia, illusion, paranoia, parosmia, photophobia, sensory disturbance, time perception altered, thinking abnormal, synaesthesia, substance-induced psychotic distress, and somatic hallucination.

As used herein, the term "anxiety disorder" refers to a state of apprehension, uncertainty, and/or fear resulting from the anticipation of an event and/or situation. Non-limiting examples of anxiety disorders include acute stress disorder, anxiety due to a medical condition, generalized anxiety disorder, panic disorder, panic attack, a phobia, post-traumatic stress disorder, obsessive-compulsive disorder, separation anxiety disorder, social anxiety disorder, substance-induced anxiety disorder, or selective mutism.

As used herein, the term "post traumatic stress disorder" refers to a condition developed after experiencing and/or witnessing a traumatic event or learning that a traumatic event has happened to a loved one. Non-limiting examples of traumatic events include exposure to war, rape or sexual violence, a physical attack, disease, a mugging, childhood physical or sexual violence, kidnapping or being taken hostage, terrorist attacks, torture, nature disasters and/or severe accidents.

As used herein, an "obsessive-compulsive and related disorder" refers to a condition that involves obsessions or compulsions. Non-limiting examples of obsessive-compulsive and relating disorder is obsessive compulsive disorder, body dysmorphic disorder, hoarding disorder, dermatillomania, trichotillomania, excoriation, substance-induced obsessive compulsive and related disorder, or an obsessive-compulsive disorder due to another medical condition, or a combination thereof.

As used herein, the term "eating disorder" refers to any of a range of psychological disorders characterized by abnormal or disturbed eating habits. Non-limiting examples of eating disorders include pica, anorexia nervosa, bulimia nervosa, rumination disorder, avoidant/restrictive food intake disorder, binge-eating disorder, other specified feeding or eating disorder, unspecified feeding or eating disorder, or combinations thereof.

As used herein, the term "headache disorder" refers to a disorder characterized by recurrent headaches.

As used herein, an "antidepressant" refers to any drug used to alleviate depression. Non-limiting examples of antidepressants include In some embodiments, an antidepressant may include, but are not limited to, one or more of the following antidepressants: adatanserine hydrochloride; adinazolam; adinazolam mesylate; allaproclate; alletamine hydrochloride; amedalin hydrochloride; amitriptyline hydrochloride; amoxapine; aftazapine maleate; amitriptyline; azaroxane fumarate; azepindol; azipramine hydrochloride; bifenanol hydrochloride; bupropion hydrochloride; butacetin; butriftyline hydrochloride; caroxazone; cartazolate; cyclazindol; cydoxepin hydrochloride; cilobamin mesylate; citalipram; clodazone hydrochloride; clomipramine hydrochloride; cotinine fumarate; cyclindol; cyphenamine hydrochloride; cyproridol hydrochloride; cyproxymid; darledin tosylate; dapoxetine hydrochloride; dazadrol maleate; dazefinyl hydrochloride; desipramine hydrochloride; dexamidazole; deximaphene; dibenzepine hydrochloride; dioxadol hydrochloride; dothipine hydrochloride; doxepin hydrochloride; duloxetine hydrochloride; eclanamine maleate; encyclates; etoferidone hydrochloride; pantridone hydrochloride; femetosol hydrochloride; penmetamide; pezolamine fumarate; fluorothracene hydrochloride; fluoxetine; fluoxetine hydrochloride; fluparoxane hydrochloride; gamma pexin; guanoxyphen sulfate; imafen hydrochloride; imilox hydrochloride; imipramine hydrochloride; indeloxazine hydrochloride; intriptyline hydrochloride; ifrindol; isocacarazide; ketipramine fumarate; lofepramine hydrochloride; lortalamine; mapprotilin; mapprotiline hydrochloride; melitracene hydrochloride; milacemide hydrochloride; minarin hydrochloride; mirtazapine; moclobemide; modal sulphate; napaktadine hydrochloride; napamezol hydrochloride; nefazodone hydrochloride; nisoxetine; nitroputam hydrochloride; nomifensin maleate; nortriptyline hydrochloride; octriptyline phosphate; opipramol hydrochloride; oxaprotiline hydrochloride; oxypertin; paroxetine; phenelazine sulfate; pyrandamine hydrochloride; piezotiline; pridepine hydrochloride; prolinetane hydrochloride; protriptyline hydrochloride; quipazine maleate; rolycyrine; ceproxetine hydrochloride; sertraline hydrochloride; sibutramine hydrochloride; sulfides; hydrotosol; tamethalin hydrochloride; tampramine fumarate; tandamine hydrochloride; thiazime hydrochloride; tozalinone; geocetin hydrochloride; trazodone hydrochloride; trebenzomine hydrochloride; trimimipramine; trimimipramine maleate; venlafaxine hydrochloride; biloxazine hydrochloride; gimeldine hydrochloride; and zometapine.

Psilocybin

In some embodiments, a method of treatment comprises the administration of a therapeutically effective amount of psilocybin, a prodrug of psilocybin, an active metabolite of psilocybin, or a prodrug of an active metabolite of psilocybin to a subject in need thereof as described herein. In some embodiments, a method of treatment comprises the administration of a therapeutically effective amount of psilocybin as described herein. In some embodiments, a method of treatment comprises the administration of a therapeutically effective amount of psilocin as described herein. Some embodiments comprise psilocybin, a prodrug of psilocybin, an active metabolite of psilocybin, or a prodrug of an active metabolite of psilocybin for use in the treatment of an indication as described herein. Some embodiments comprise psilocybin for use in the treatment of an indication as described herein. Some embodiments comprise psilocin for use in the treatment of an indication as described herein. Some embodiments comprise the use of psilocybin, a prodrug of psilocybin, an active metabolite of psilocybin, or a prodrug of an active metabolite of psilocybin in the manufacture of a medicament for the treatment of an indication as described herein.

Figure 1:
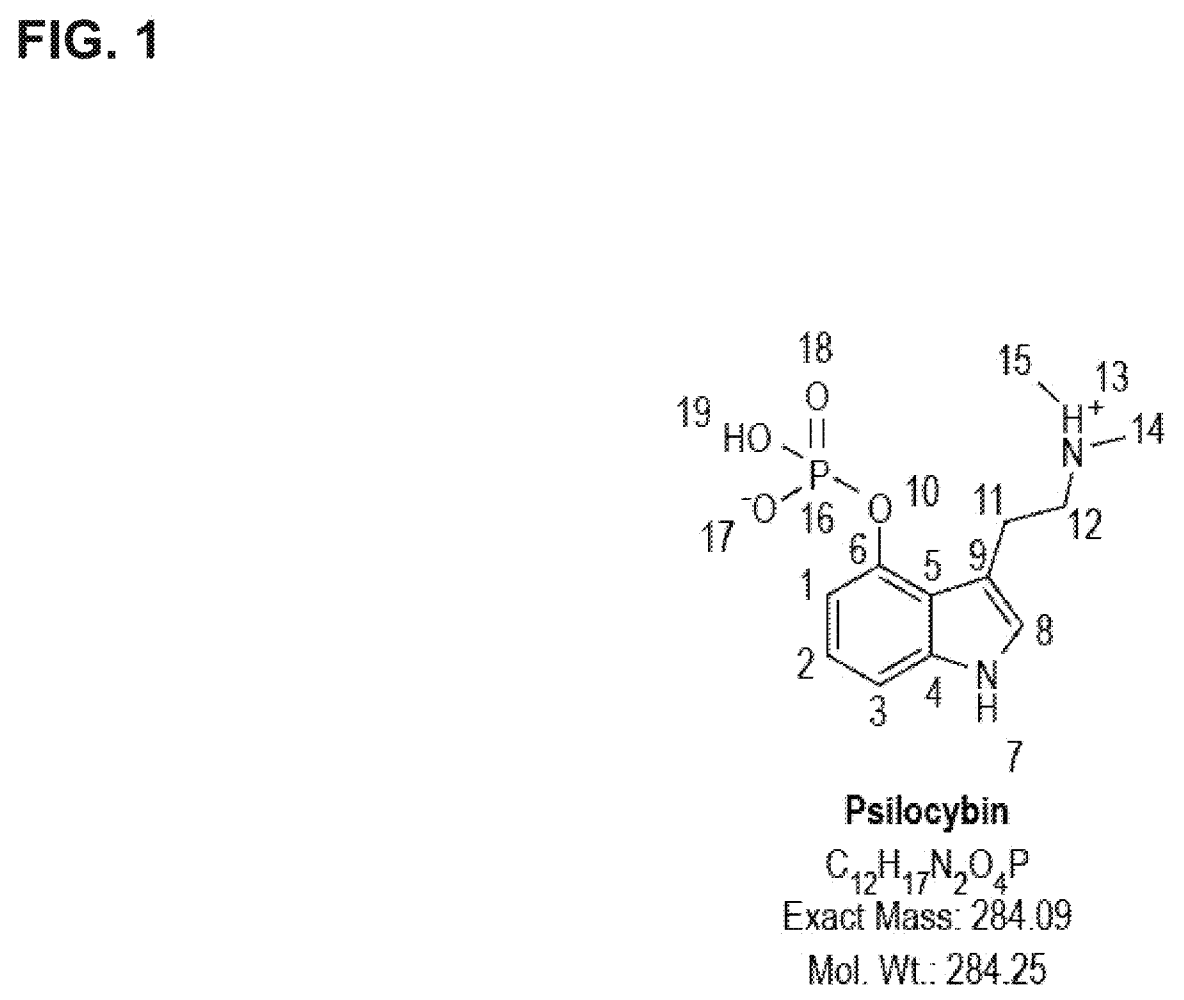

A numbered structural formula of psilocybin is shown in FIG. 1. Novel polymorphs and hydrates of psilocybin, along with the preparation and formulations thereof are disclosed in U.S. Application No. US2019/0119310 A1, which is incorporated by reference herein in its entirety. US2019/0119310 discloses a number of formulations and the challenges of formulating psilocybin due to e.g. its hygroscopicity and poor flow characteristics. US2019/0119310 also discloses the importance of a controlled aqueous crystallisation process.

In some embodiments, the psilocybin comprises crystalline psilocybin in the form Polymorph A or Polymorph A', as described herein, the crystalline psilocybin exhibits peaks in an X-ray powder diffraction (XRPD) diffractogram at 11.5, 12.0 and 14.5°2θ±0.1°2θ. In some embodiments, the crystalline psilocybin further exhibits at least one peak in the XRPD diffractogram at 19.7, 20.4, 22.2, 24.3 or 25.7°2θ±0.1°2θ. Illustrative XRPD diffractograms are provided as FIGS. 2A and 2B. In some embodiments, the crystalline psilocybin exhibits an endothermic event in a DSC thermogram having a first onset temperature of between 145° C. and 165° C. and a second onset temperature of between 205° C. and 220° C. Illustrative DSC thermograms are provided as FIGS. 3A and 3B.

Polymorph A

Figure 2A:
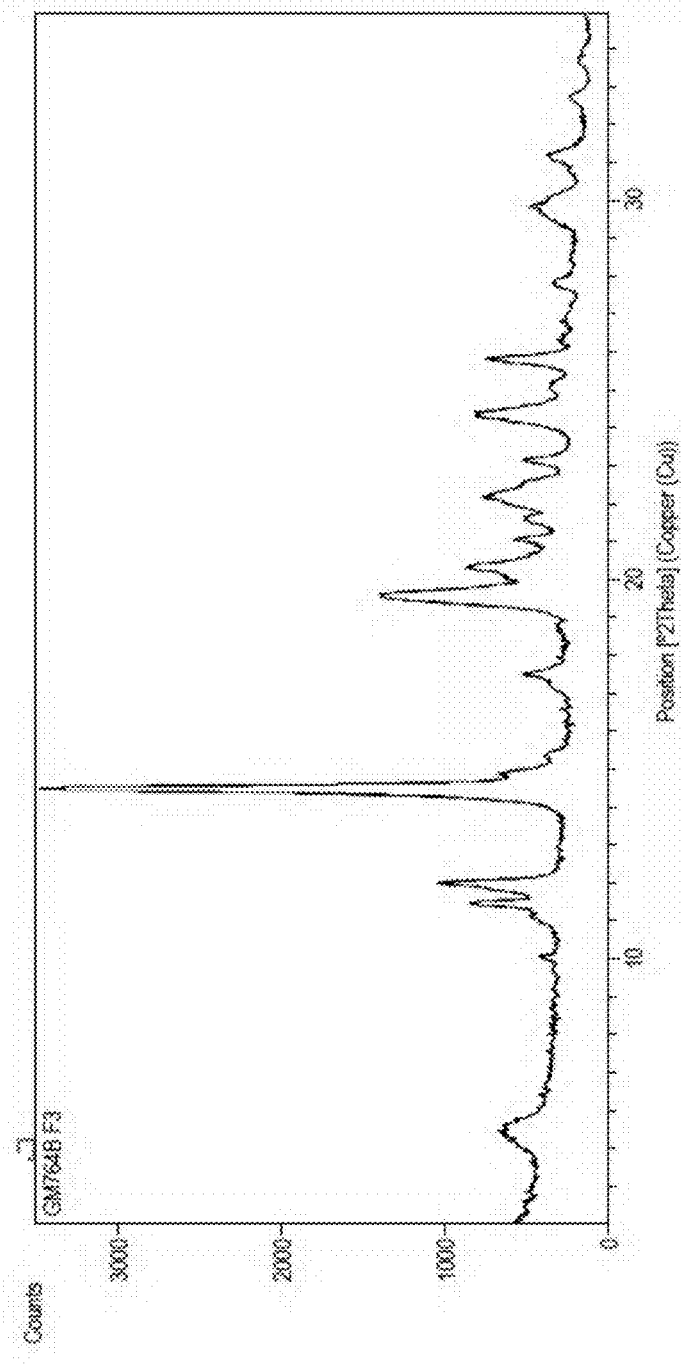
FIG. 2A is a XRPD diffractogram of Polymorph A (GM764B).
Figure 3A:
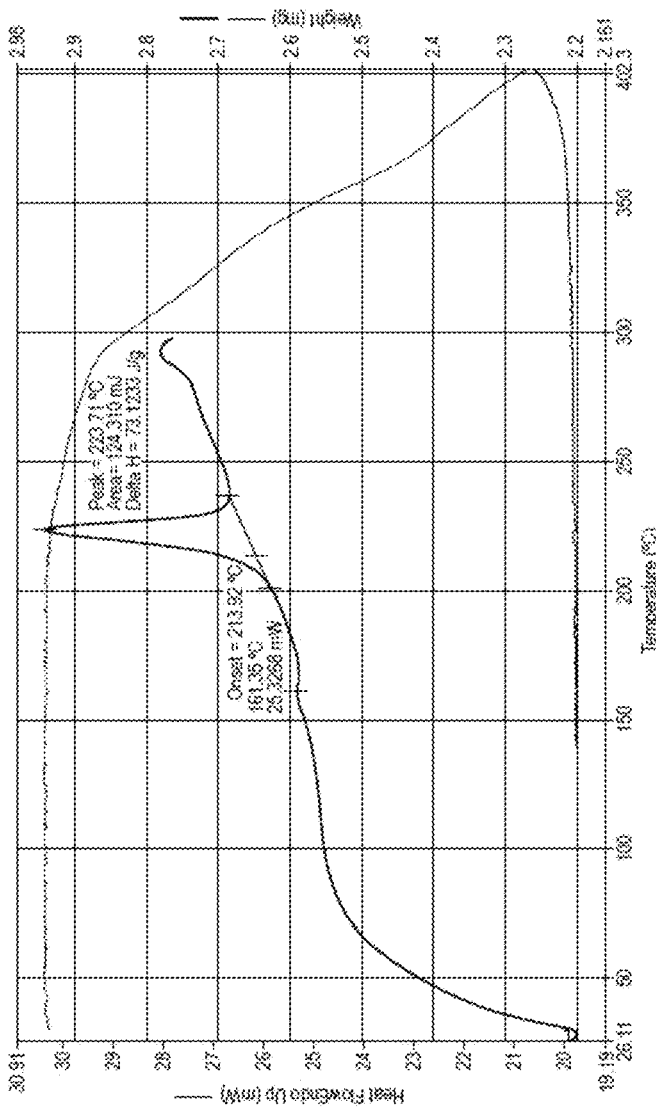
FIG. 3A is a DSC and TGA thermograph of Polymorph A (GM764B).

In some embodiments, the present disclosure provides crystalline psilocybin in the form Polymorph A, characterized by one or more of:

peaks in an XRPD diffractogram at 11.5, 12.0, 14.5, and 17.5, °2θ±0.1°2θ;

peaks in an XRPD diffractogram at 11.5, 12.0, 14.5 and 17.5, °2θ±0.1°2θ, further characterized by at least one further peak at 19.7, 20.4, 22.2, 24.3 or 25.7°2θ±0.1°2θ;

an XRPD diffractogram as substantially illustrated in FIG. 2A; or an endothermic event in a DSC thermogram having an endothermic event in a DSC thermogram having a first onset temperature of between 145° C. and 165° C. and a second onset temperature of between 205° C. and 220° C. substantially as illustrated in FIG. 3A.

In some embodiments, the peak at 17.5°2θ±0.1°2θ has a relative intensity compared to the peak at 14.5°2θ±0.1°2θ of at least 5%, at least 6%, at least 7%, at least 8%, at least 9%, or at least 10%.

In some embodiments, the present disclosure provides crystalline psilocybin in the form Polymorph A, characterized by one or more of:

peaks in an XRPD diffractogram at 11.5, 12.0, 14.5, and 17.5, °2θ±0.2°2θ;

peaks in an XRPD diffractogram at 11.5, 12.0, 14.5 and 17.5, °2θ±0.2°2θ, further characterized by at least one further peak at 19.7, 20.4, 22.2, 24.3 or 25.7°2θ±0.2°2θ;

an XRPD diffractogram as substantially illustrated in FIG. 2A; or an endothermic event in a DSC thermogram having an endothermic event in a DSC thermogram having a first onset temperature of between 145° C. and 165° C. and a second onset temperature of between 205° C. and 220° C. substantially as illustrated in FIG. 3A.

In some embodiments, the crystalline psilocybin of Polymorph A exhibits an XRPD diffractogram having at least 3, 4, 5, 6, 7, 8, 9, 10, 11, 12, 13, 14, 15, 16, or 17 of the peaks listed in Table 1, or equivalent peaks within about ±0.1°2θ of the peaks listed in Table 1. In some embodiments, the crystalline psilocybin of Polymorph A exhibits an XRPD diffractogram having at least 3, 4, 5, 6, 7, 8, 9, 10, 11, 12, 13, 14, 15, 16, or 17 of the peaks listed in Table 1, or equivalent peaks within about ±0.2°2θ of the peaks listed in Table 1. In some embodiments, Polymorph A exhibits a peak at 17.5°2θ±0.1°2θ that is substantially absent in Polymorph A'. In some embodiments, Polymorph A exhibits a peak at 17.5°2θ±0.2°2θ that is substantially absent in Polymorph A'.

TABLE 1

| XRPD peak positions for Polymorph A | |
| --- | --- |
| Position [°2Th.] | Relative Intensity [%] |
| 5.6 | 8.42 |
| 11.5 | 13.05 |
| 12.0 | 26.45 |
| 14.5 | 100.00 |
| 17.5 | 10.71 |
| 19.7 | 37.29 |
| 20.4 | 20.06 |
| 22.2 | 17.83 |
| 23.2 | 6.99 |
| 24.3 | 17.93 |
| 25.7 | 16.40 |
| 26.8 | 3.15 |
| 27.8 | 4.54 |
| 29.7 | 9.53 |
| 31.2 | 6.51 |
| 32.6 | 2.45 |
| 33.7 | 1.75 |

In some embodiments, crystalline psilocybin Polymorph A exhibits XRPD diffractogram peaks at 11.5, 12.0, 14.5, and 17.5°2θ±0.1°2θ. In some embodiments, crystalline psilocybin Polymorph A exhibits at least one additional peak appearing at 19.7, 20.4, 22.2, 24.3 or 25.7°2θ±0.1°2θ. In some embodiments, crystalline psilocybin Polymorph A exhibits at least two additional peaks appearing at 19.7, 20.4, 22.2, 24.3 or 25.7°2θ±0.1°2θ. In some embodiments, crystalline psilocybin Polymorph A exhibits at least three additional peaks appearing at 19.7, 20.4, 22.2, 24.3 or 25.7°2θ±0.1°2θ. In some embodiments, crystalline psilocybin Polymorph A exhibits an XRPD diffractogram substantially the same as the XRPD diffractogram shown in FIG. 2A.

In some embodiments, crystalline psilocybin Polymorph A is characterized by XRPD diffractogram peaks at 14.5 and 17.5°2θ±0.1°2θ with the peak at 17.5°2θ having an intensity which is at least about 5%, at least about 6%, at least about 7%, at least about 8%, at least about 9%, or at least about 10% of the intensity of the peak at 14.5°2θ.

In some embodiments, the crystalline psilocybin Polymorph A exhibits no peak at 10.1—that is, the peak at 10.1 is absent or substantially absent.

In some embodiments, crystalline psilocybin Polymorph A is characterized by an endothermic event in a DSC thermogram having a first onset temperature of between 145° C. and 165° C. such as between 145 and 160° C., or such as between 145 and 155° C. and a second onset temperature of between 205 and 220° C., such as between 210 and 220° C., such as between 210 and 218° C., or such as between 210 and 216° C. In some embodiments, crystalline psilocybin Polymorph A exhibits an endothermic event in a DSC thermogram having an onset temperature of between about 205 and about 220° C., between about 210 and about 220° C., between about 210 and about 218° C., or between about 210 and about 216° C. In some embodiments, crystalline psilocybin Polymorph A further exhibits an endothermic event in the DSC thermogram having an onset temperature of between about 145 and about 165° C., between about 145 and about 160° C., or between about 145 and about 155° C. In some embodiments, crystalline psilocybin Polymorph A exhibits an endothermic event having an onset temperature of between about 205 and about 220° C., between about 210 and about 220° C., between about 210 and about 218° C., or between about 210 and about 216° C.; and an endothermic event having an onset temperature of between about 145 and about 165° C., between about 145 and about 160° C., between about 145 and about 155° C., in a DSC thermogram. In some embodiments, crystalline psilocybin Polymorph A exhibits a DSC thermogram substantially the same as the DSC thermogram in FIG. 3A.

In some embodiments, crystalline psilocybin Polymorph A exhibits a water content of <0.5% w/w, <0.4% w/w, <0.3% w/w, <0.2% w/w, or <0.1% w/w. The water content of a crystalline compound can be determined by known methods, for example Karl Fischer Titration. In some embodiments, crystalline psilocybin Polymorph A exhibits <0.5% w/w loss, <0.4% w/w, <0.3% w/w, <0.2% w/w, or <0.1% w/w in the TGA thermogram between ambient temperature, e.g., about 25° C., and 200° C. In some embodiments, crystalline psilocybin Polymorph A loses less than 2% by weight, less than 1% by weight, or than 0.5% by weight in a loss on drying test, e.g., a loss on drying test performed at 70° C.

In some embodiments, crystalline psilocybin Polymorph A is a highly pure crystalline form of Polymorph A, for example, the in a loss on drying test psilocybin comprises at least 90%, at least 95%, at least 99%, or at least 99.5% by weight crystalline psilocybin of Polymorph A.

In some embodiments, crystalline psilocybin Polymorph A is a white to off-white solid.

In some embodiments, crystalline psilocybin Polymorph A is chemically pure, for example the psilocybin has a chemical purity of greater than 97%, 98%, or 99% by HPLC. In some embodiments, crystalline psilocybin Polymorph A has no single impurity of greater than 1%, greater than 0.5%, greater than 0.4%, greater than 0.3%, or greater than 0.2% e.g., the impurity phosphoric acid as measured by $^{31}$P NMR, or the impurity psilocin measured by HPLC. In some embodiments, crystalline psilocybin Polymorph A has a chemical purity of greater than 97 area %, greater than 98 area %, or greater than 99 area % by HPLC. In some embodiments, crystalline psilocybin Polymorph A has no single impurity greater than 1 area %, greater than 0.5 area %, greater than 0.4%, greater than 0.3%, or greater than 0.2% as measured by HPLC. In some embodiments, crystalline psilocybin Polymorph A does not contain psilocin at a level greater than 1 area %, greater than 0.5 area %, greater than 0.4%, greater than 0.3%, or greater than 0.2% as measured by HPLC. In some embodiments, crystalline psilocybin Polymorph A does not contain phosphoric acid at a level greater than 1 weight %, greater than 0.5 weight %, greater than 0.4 weight %, 0.3 weight %, or greater than 0.2 weight %, as measured by $^{31}$P NMR. In some embodiments, crystalline psilocybin Polymorph A has a chemical assay of at least 95 weight %, at least 96 weight %, or at least 98 weight %.

Methods of Manufacturing Crystalline Psilocybin Polymorph A.

In another embodiment, the disclosure provides a method for large scale manufacture of psilocybin characterized in that the method comprises subjecting psilocybin to a water crystallization step, with controlled drying, to produce crystalline psilocybin Polymorph A.

In another embodiment, the disclosure provides a method for large scale manufacture of psilocybin characterized in that the method comprises subjecting psilocybin to a water crystallization step, with controlled drying, to produced crystalline psilocybin Polymorph A with an XRPD diffractogram as illustrated in FIG. 2A and a DSC and TGA thermograph as illustrated in FIG. 3A. In another embodiment, the disclosure provides a method for large-scale manufacture of psilocybin characterized in that the method comprises subjecting psilocybin to a water crystallization step, with controlled drying, to produce a high purity crystalline psilocybin—Polymorph A with an XRPD diffractogram as illustrated in FIG. 2A and a DSC thermograph as illustrated in FIG. 3A.

In another embodiment of the disclosure, psilocybin is recrystallized in about 10-volumes of water, heated with agitation to a temperature of at least 70° C., polish filtered with a suitable cut off (typically, below 5 μm), seeded at a temperature of about 70° C., and cooled in a controlled manner to about 5° C. over a period of more than 2 hours.

In some embodiments, psilocybin recrystallization comprises controlled cooling which drops the temperature by about 5° C.-15° C. an hour, more preferably about 10° C. an hour. In certain embodiments, the polish filter step is done through an appropriately sized filter such as, but not limited to, a 1.2 μm in line filter.

In some embodiments, agitation is by stirring at about 400-500 rpm, typically about 450 rpm.

In some embodiments, the psilocybin is dissolved in water heated to no more than 90° C. In some embodiments the psilocybin is dissolved in water heated to no more than 85° C. Without being bound by any particular mechanism, this dissolution step is intended to solubilize psilocybin whilst also minimizing the formation of hydrolysis products.

In some embodiments, the psilocybin solution is stirred to speed the solubilization and reduce the time that the solution is at a high temperature, namely one at or around 80° C., or higher.

In some embodiments, the seed is psilocybin Hydrate A. In one embodiment, 0.1% weight or less of seed is added to the process.

In some embodiments, the psilocybin the crystalline psilocybin is isolated by vacuum filtration.

In some embodiments, the isolated crystals are dried in vacuo at a temperature of at least 30° C., such as between 3° and 50° C., or such as between 4° and 50° C. In some embodiment, the isolated crystals are dried in vacuo for at least 10 hours, such as between 12 and 18 hours, or such as about 30 hours. In some embodiments, the isolated crystals are dried in vacuo at a temperature of at least 30° C., such as between 3° and 50° C., or such as between 4° and 50° C., for at least 10 hours, such as between 12 and 18 hours, or such as about 30 hours. In some embodiments, the isolated crystals are dried until the isolated crystals lose less than 2% weight in a loss on drying test, such as less than 0.5% weight.

In some embodiments, the isolated crystals are washed, several times, in water and dried in vacuo at about 50° C. for at least 12 hours.

In some embodiments, the crystals obtained are typically relatively large (range 50 to 200 microns) and uniform when viewed under the microscope×10.

In contrast, crystals obtained without controlled cooling which are much smaller in size (typically 5 to 50 microns) when viewed under the microscope×10.

In some embodiments, there is provided Psilocybin obtained by the method of crystallization described herein.

In some embodiments, there is provided a pharmaceutical formulation comprising psilocybin polymorph A obtained by the method of crystallization described herein.

In some embodiments, psilocybin manufactured prior to crystallization may be produced using one of the following methods: synthetic or biological, e.g. by fermentation or obtained by extraction from mushrooms. In some embodiments, psilocybin manufactured prior to crystallization is manufactured according to all or some of the methods described in U.S. Application No. US2019/0119310 A1, which is incorporated by reference herein in its entirety.

Polymorph A'

Figure 2B:
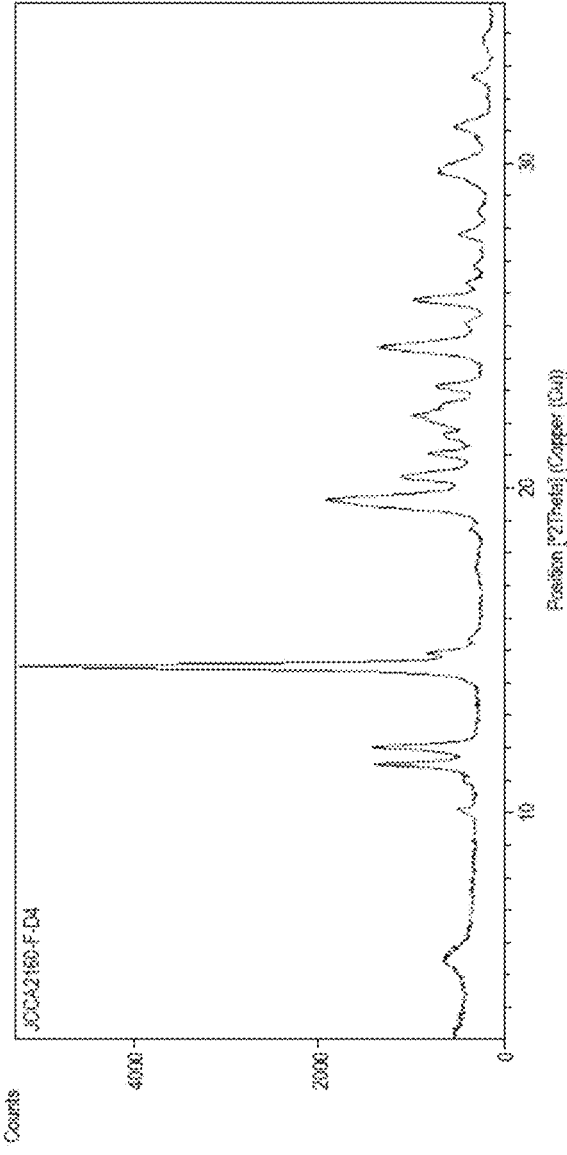
FIG. 2B is a XRPD diffractogram of Polymorph A' (JCCA2160F).
Figure 3B:
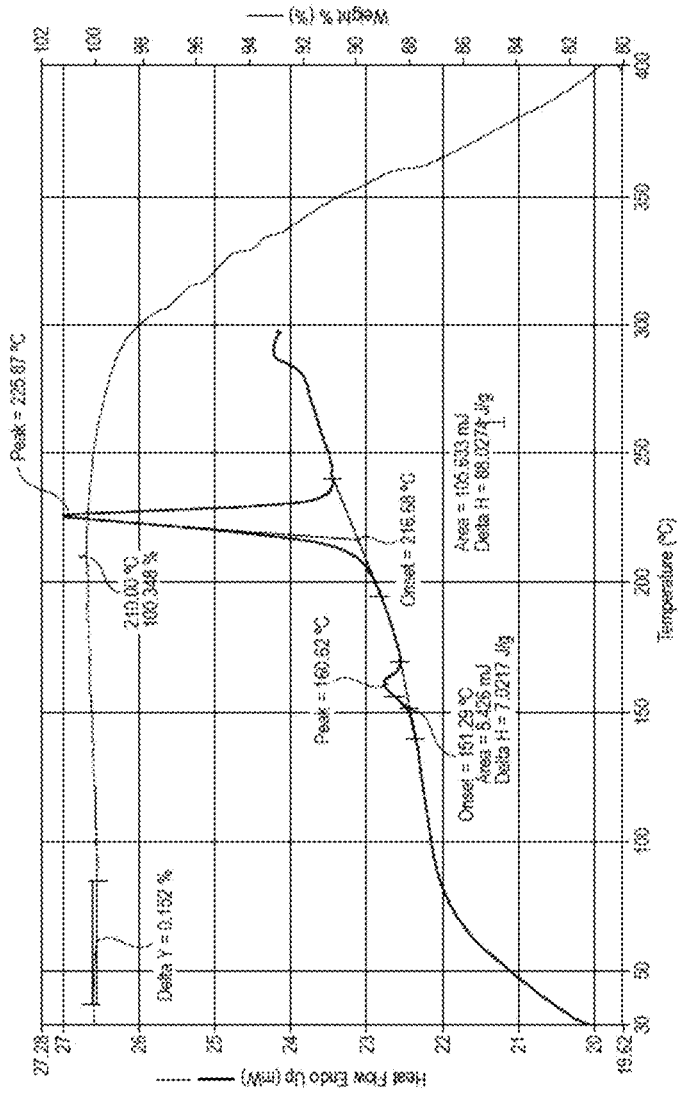
FIG. 3B is a DSC and TGA thermograph of Polymorph A' (JCCA2160F).

The present disclosure provides crystalline psilocybin in the form of Polymorph A', characterized by one or more of:

(i) peaks in an XRPD diffractogram at 11.5, 12.0 and 14.5°2θ±0.1°2θ, but absent or substantially absent of a peak at 17.5°2θ±0.1°2θ;

(ii) peaks in an XRPD diffractogram at 11.5, 12.0 and 14.5°2θ±0.1°2θ, but absent or substantially absent of a peak at 17.5°2θ±0.1°2θ, further characterized by at least one further peak at 19.7, 20.4, 22.2, 24.3 or 25.7°2θ±0.1°2θ;

(iii) an XRPD diffractogram as substantially illustrated in FIG. 2B; or (iv) an endothermic event in a DSC thermogram having a first onset temperature of between 145° C. and 165° C. and a second onset temperature of between 205° C. and 220° C. substantially as illustrated in FIG. 3B.

In some embodiments, the crystalline psilocybin comprises crystalline psilocybin Polymorph A'. Crystalline psilocybin Polymorph A' exhibits peaks in an XRPD diffractogram at 11.5, 12.0 and 14.5°2θ±0.1°2θ, but absent or substantially absent of a peak at 17.5°2θ±0.1°2θ. In some embodiments, crystalline psilocybin Polymorph A' further exhibits 1, 2, 3, 4, or 5 peaks selected from 19.7, 20.4, 22.2, 24.3 or 25.7°2θ±0.1°2θ. An illustrative XRPD diffractogram for Polymorph A' is provided as FIG. 2B. An illustrative DSC thermogram having an onset temperature of between 205 and 220° C. for Polymorph A' is provided as FIG. 3B.

In some embodiments, psilocybin Polymorph A' exhibits an XRPD diffractogram as summarized in Table 2. In some embodiments, crystalline psilocybin Polymorph A' exhibits at least 3, 4, 5, 6, 7, 8, 9, 10, 11, 12, 13, 14, 15, 16, 17, 18, 19, 20, 21, 22, 23, 24, or 25 peaks listed of Table B or equivalent peaks within about ±0.1°2θ, and absent or substantially absent peak at 17.5°2θ±0.1°2θ.

TABLE 2

| XRPD peak positions for Polymorph A' | |
| --- | --- |
| Position [°2Th.] | Relative Intensity [%] |
| 5.5 | 4.89 |
| 10.1 | 4.09 |
| 11.5 | 22.05 |
| 12.0 | 22.77 |
| 14.5 | 100.00 |
| 14.9 | 11.29 |
| 17.5 | 1.08 |
| 18.7 | 2.44 |
| 19.4 | 23.02 |
| 19.6 | 33.70 |
| 20.3 | 17.01 |
| 21.1 | 12.08 |
| 21.6 | 8.51 |
| 22.2 | 15.54 |
| 22.6 | 8.78 |
| 23.1 | 10.11 |
| 24.3 | 21.83 |
| 25.1 | 4.36 |
| 25.8 | 15.40 |
| 26.3 | 4.28 |
| 26.8 | 2.86 |
| 27.8 | 5.96 |
| 28.6 | 1.91 |
| 29.7 | 10.56 |
| 31.1 | 7.35 |
| 32.6 | 3.72 |
| 33.8 | 1.54 |

In some embodiments, crystalline psilocybin Polymorph A' exhibits XRPD diffractogram peaks at 11.5, 12.0, and 14.5°2θ±0.1°2θ but substantially absent of a peak at 17.5°2θ±0.1°2θ. In some embodiments, crystalline psilocybin Polymorph A' further exhibits at least one additional peak appearing at 19.7, 20.4, 22.2, 24.3, or 25.7°2θ±0.1°2θ. In some embodiments, crystalline psilocybin Polymorph A' exhibits at least two additional peaks appearing at 19.7, 20.4, 22.2, 24.3, or 25.7°2θ±0.1°2θ. In some embodiments, crystalline psilocybin Polymorph A' exhibits and is distinguished from Polymorph A by the presence of a peak appearing at 10.1°2θ±0.1°2θ. In yet a further embodiment, crystalline psilocybin Polymorph A' exhibits an XRPD diffractogram substantially the same as the XRPD diffractogram shown in FIG. 2B.

In some embodiments, crystalline psilocybin Polymorph A' exhibits XRPD diffractogram peaks at 14.5 and 17.5°2θ±0.1°2θ, wherein the intensity of the peak at 17.5°2θ is less than 5%, less than 4%, less than 3%, less than 2%, or less than 1% of the intensity of the peak at 14.5°2θ.

In some embodiments, crystalline psilocybin Polymorph A' exhibits XRPD diffractogram peaks at 10.1 and 14.5°2θ±0.1°2θ, wherein the intensity of the peak at 10.1°2θ is at least 1%, at least 2%, at least 3%, or at least 4% of the intensity of the peak at 14.5°2θ.

In some embodiments, crystalline psilocybin Polymorph A' is characterized by an endothermic event in a DSC thermogram having a first onset temperature of between 145° C. and 165° C. such as between 145 and 160° C., or such as between 145 and 155° C. and a second onset temperature of between 205 and 220° C., such as between 210 and 220° C., such as between 210 and 218° C., or such as between 210 and 216° C. In some embodiments, crystalline psilocybin Polymorph A' is characterized by an endothermic event in a DSC thermogram having an onset temperature of between about 205 and about 220° C., between about 210 and about 220° C., between about 210 and about 218° C., or between about 210 and about 216° C. In some embodiments, crystalline psilocybin Polymorph A' exhibits an endothermic event in the DSC thermogram having an onset temperature of between about 145 and about 165° C., between about 145 and about 160° C., or between about 145 and about 155° C. In some embodiments, crystalline psilocybin Polymorph A' exhibits an endothermic event having an onset temperature of between about 205 and about 220° C., between about 210 and about 220° C., between about 210 and about 218° C., or between about 210 and about 216° C., and an endothermic event having an onset temperature of between about 145 and about 165° C., between about 145 and about 160° C., or between about 145 and about 155° C., in a DSC thermogram. In some embodiments, crystalline psilocybin Polymorph A' exhibits a DSC thermogram substantially the same as the DSC thermogram in FIG. 3B.

In some embodiments, crystalline psilocybin Polymorph A' exhibits a water content of <0.5% w/w, <0.4% w/w, <0.3% w/w, <0.2% w/w, or <0.1% w/w. Methods to determine the water content of a crystalline compound are known, for example Karl Fischer Titration. In some embodiments, crystalline psilocybin Polymorph A' exhibits <0.5% w/w loss, <0.4% w/w, <0.3% w/w, <0.2% w/w, <0.1% w/w in the TGA thermogram between ambient temperature, e.g., 25° C., and 200° C. In some embodiments, crystalline psilocybin Polymorph A' loses less than 2% by weight, less than 1% by weight, or less than 0.5% by weight in a loss on drying test. In some embodiments, the loss on drying test is performed at 70° C.

In some embodiments, crystalline psilocybin Polymorph A' is a highly pure crystalline form of Polymorph A'. In some embodiments, the crystalline psilocybin comprises at least 90%, 95%, 99%, or 99.5% by weight of Polymorph A'.

In some embodiments, crystalline psilocybin Polymorph A's is a white to off white solid.

In some embodiments, crystalline psilocybin Polymorph A' is chemically pure, for example the psilocybin has a chemical purity of greater than 97%, greater than 98%, or than 99% by HPLC. In some embodiments, crystalline psilocybin Polymorph A' has no single impurity of greater than 1% or greater than 0.5%, e.g., the impurity phosphoric acid as measured by 31P NMR or the impurity psilocin as measured by HPLC. In some embodiments, crystalline psilocybin Polymorph A' has a chemical purity of greater than 97 area %, greater than 98 area %, or greater than 99 area % by HPLC. In some embodiments, crystalline psilocybin Polymorph A' has no single impurity greater than 1 area % or greater than 0.5 area %, e.g., as measured by HPLC. In some embodiments, crystalline psilocybin Polymorph A' does not contain psilocin at a level greater than 1 area % or greater than 0.5 area % as measured by HPLC. In some embodiments, crystalline psilocybin Polymorph A' does not contain phosphoric acid at a level greater than 1 weight % or greater than 0.5 weight % as measured by 31P NMR. In some embodiments, crystalline psilocybin Polymorph A' has a chemical assay of at least 95 weight %, at least 96 weight %, or at least 98 weight %.

In some embodiments, crystalline psilocybin Polymorph A' is chemically pure, for example the psilocybin has a chemical purity of greater than 97%, 98%, or 99% by HPLC. In some embodiments, crystalline psilocybin Polymorph A' has no single impurity of greater than 1%, greater than 0.5%, greater than 0.4%, greater than 0.3%, or greater than 0.2% e.g., the impurity phosphoric acid as measured by 31P NMR, or the impurity psilocin measured by HPLC. In some embodiments, crystalline psilocybin Polymorph A' has a chemical purity of greater than 97 area %, greater than 98 area %, or greater than 99 area % by HPLC. In some embodiments, crystalline psilocybin Polymorph A' has no single impurity greater than 1 area %, greater than 0.5 area %, greater than 0.4%, greater than 0.3%, or greater than 0.2% as measured by HPLC. In some embodiments, crystalline psilocybin Polymorph A' does not contain psilocin at a level greater than 1 area %, greater than 0.5 area %, greater than 0.4%, greater than 0.3%, or greater than 0.2% as measured by HPLC. In some embodiments, crystalline psilocybin Polymorph A' does not contain phosphoric acid at a level greater than 1 weight %, greater than 0.5 weight %, greater than 0.4 weight %, 0.3 weight %, or greater than 0.2 weight %, as measured by 31P NMR. In some embodiments, crystalline psilocybin Polymorph A' has a chemical assay of at least 95 weight %, at least 96 weight %, or at least 98 weight %.

Illustrative XRPD diffractograms for high purity crystalline psilocybin, Polymorph A or Polymorph A' are provided in FIGS. 2A and 2B. Illustrative DSC thermographs for high purity crystalline psilocybin, Polymorph A or Polymorph A' are provided in FIGS. 2A and 2B.

Figure 2C:
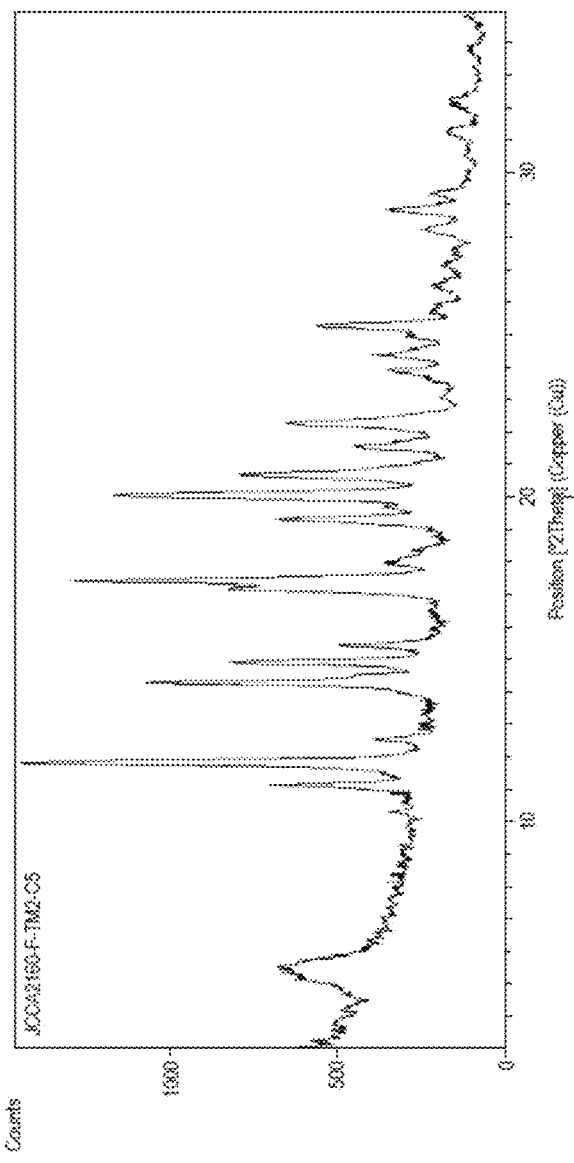
FIG. 2C is a XRPD diffractogram of Polymorph B (JCCA2160-F-TM2).
Figure 2D:
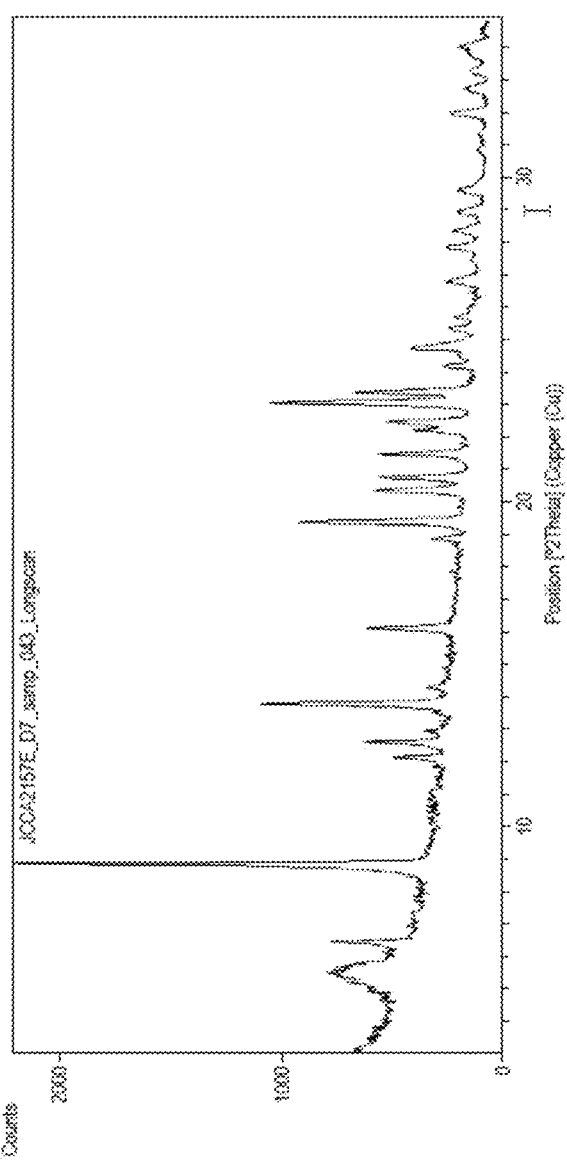
FIG. 2D is a XRPD diffractogram of a Hydrate A (JCCA2157E).
Figure 2E:
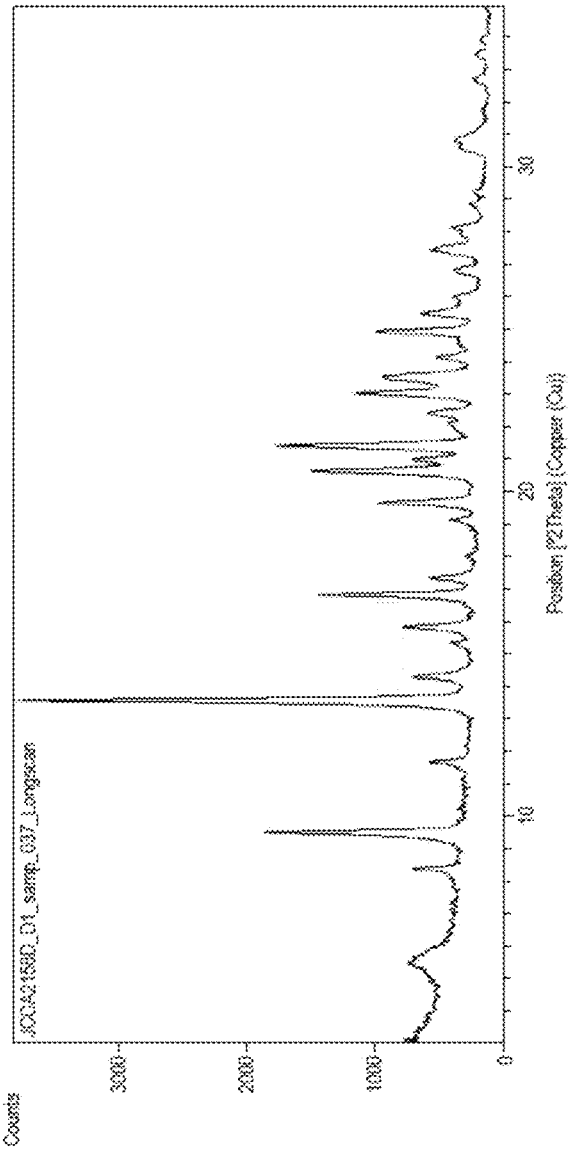
FIG. 2E is a XRPD diffractogram of an ethanol solvate (JCCA2158D).
Figure 2F:
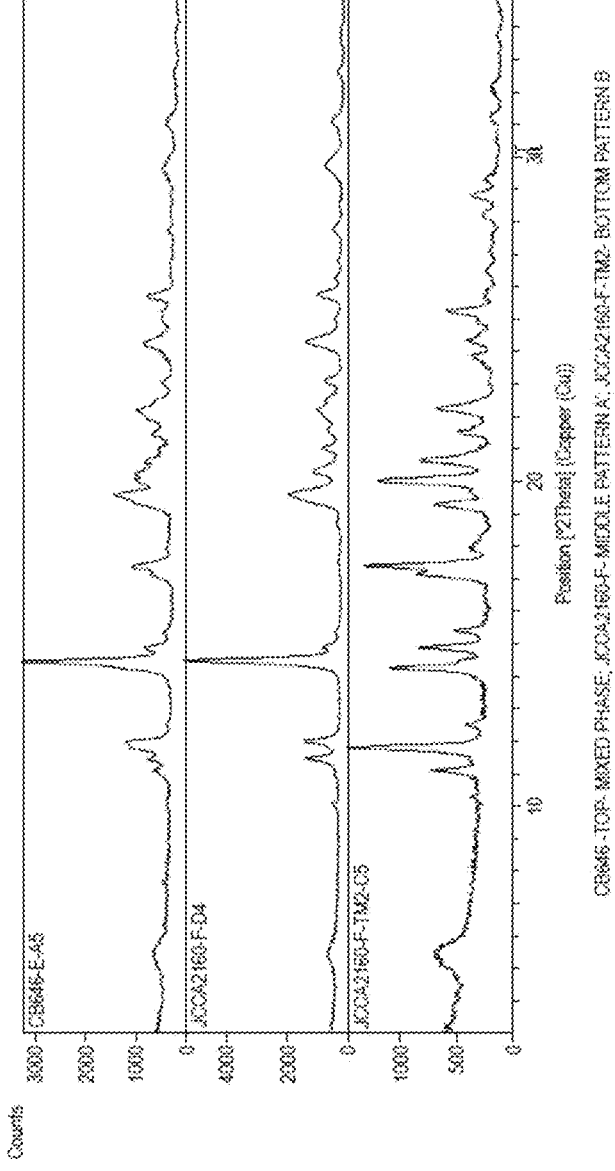
FIG. 2F is a XRPD diffractogram of product obtained during development of the process (CB646-E) (top)—compared to the diffractograms Polymorph A' (JCCA2160F) (middle) and Polymorph B (JCCA2160-TM2) (bottom).
Figure 4:
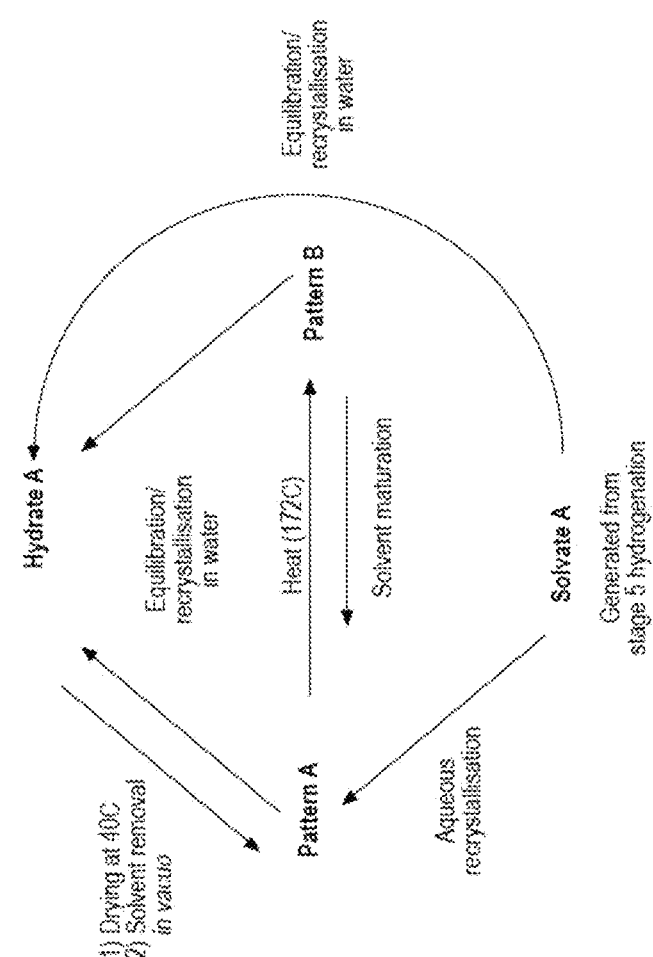
FIG. 4 is a form phase diagram showing the interrelationship of form in water-based systems.
Figure 5:
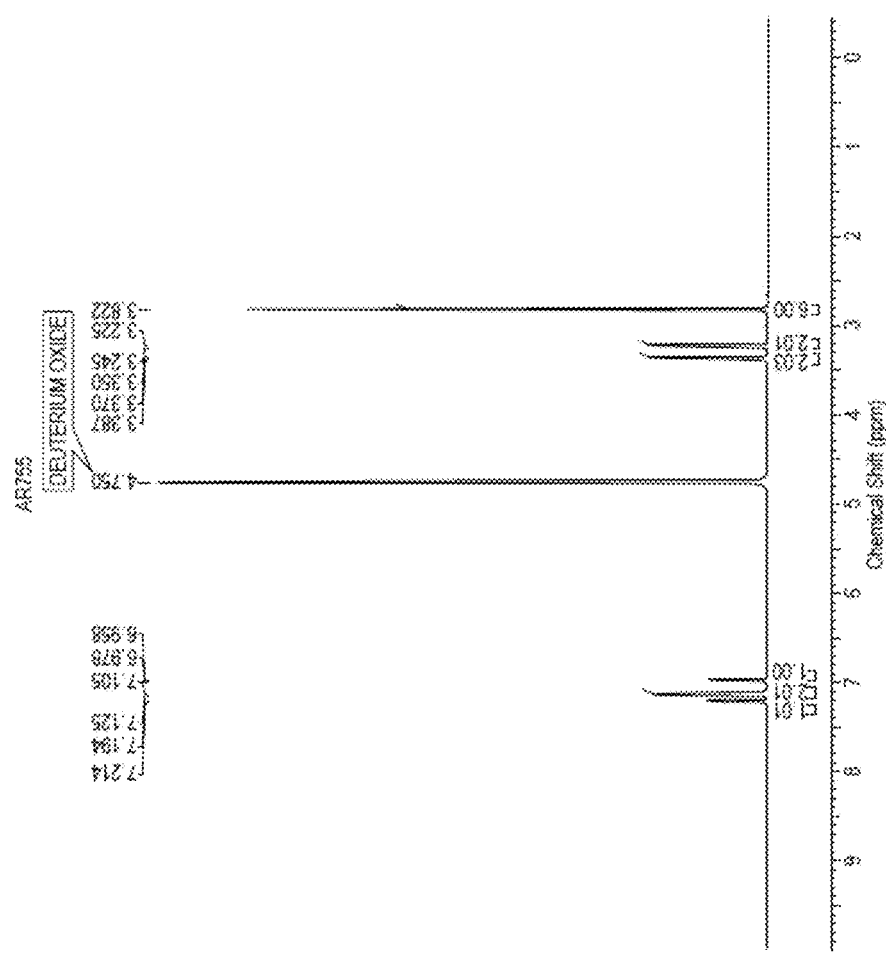
FIG. 5 is a 1H NMR (Nuclear Magnetic Resonance) spectrum of psilocybin.
Figure 6:
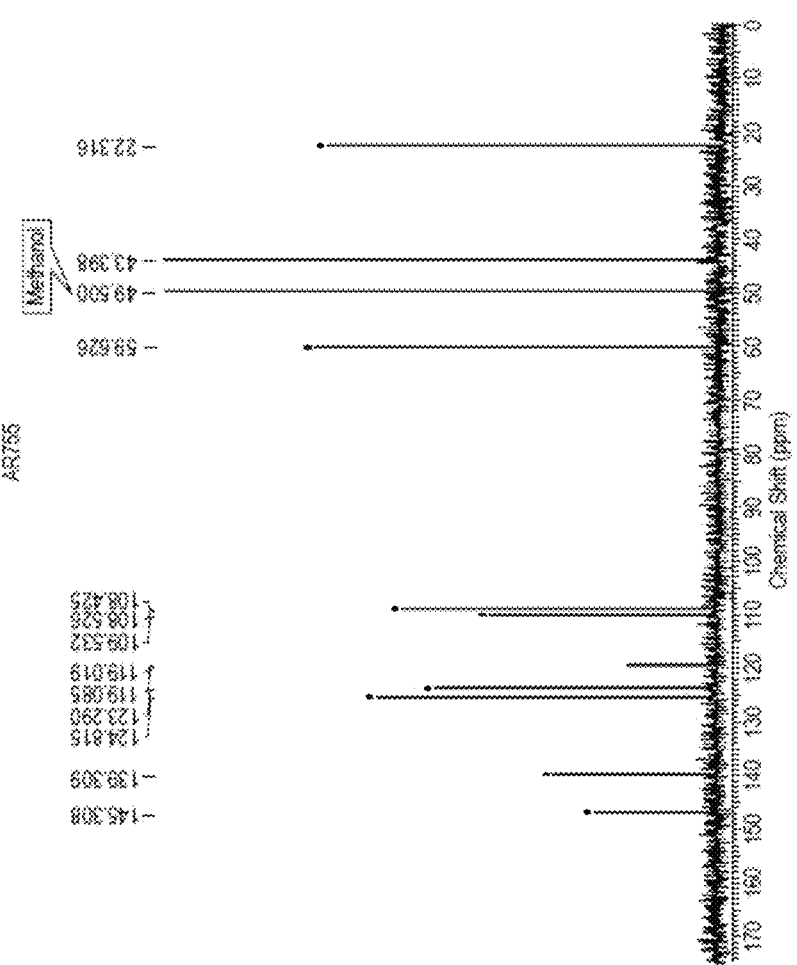
FIG. 6 is a 13C NMR spectrum of psilocybin.
Figure 7:
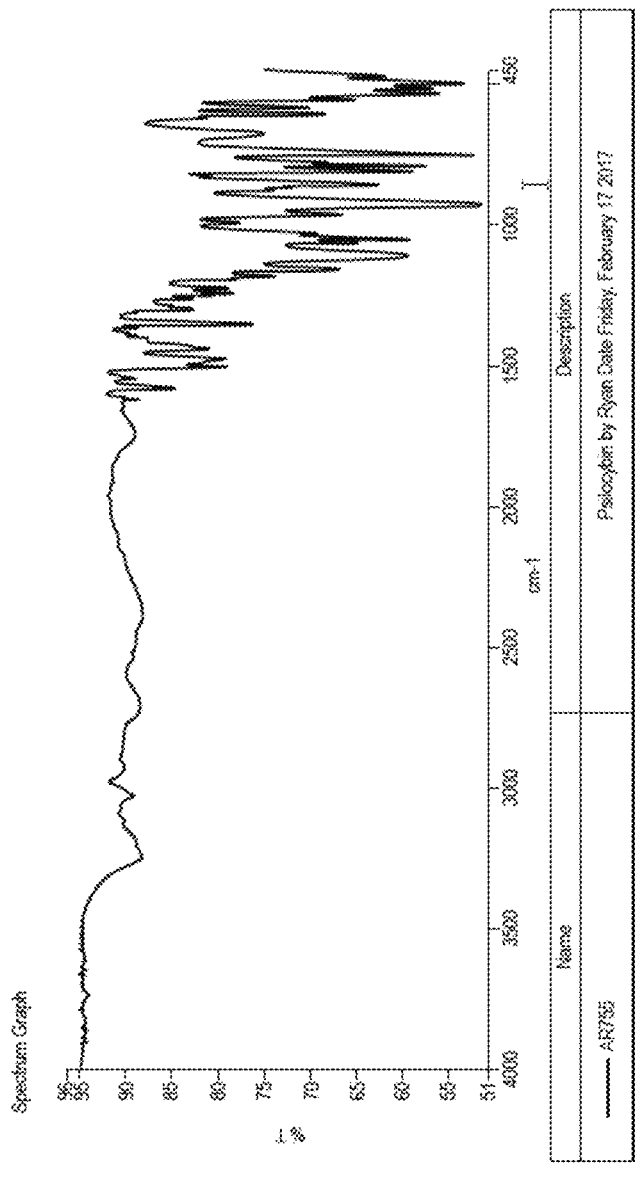
FIG. 7 is a FT-IR Spectrum of psilocybin.
Figure 8:
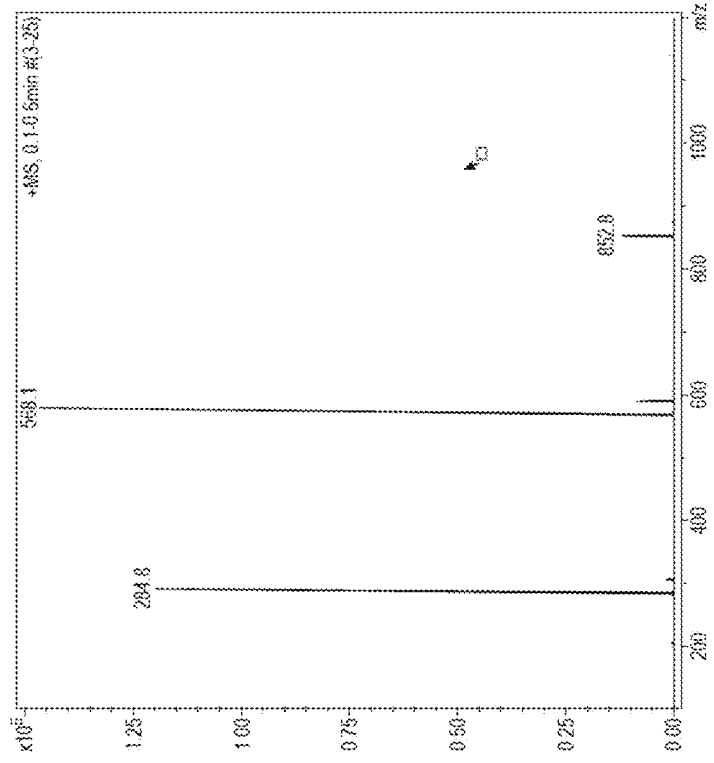
FIG. 8 is a Mass Spectrum of psilocybin.

Polymorph A (including its isostructural variant Polymorph A') (FIGS. 2A and 2B) differs from Polymorph B (FIG. 2C), the Hydrate A (FIG. 2D) and the ethanol solvate (FIG. 2E: Solvate A), and the relationship between some of the different forms is illustrated in FIG. 4.

In some embodiments, the crystalline psilocybin Polymorph A or Polymorph A' is a white to off white solid, and/or has a chemical purity of greater than 97%, 98%, or 99% by HPLC. In some embodiments, crystalline psilocybin Polymorph A or Polymorph A' has no single impurity of greater than 1%, greater than 0.5%, greater than 0.4%, greater than 0.3%, or greater than 0.2% e.g., the impurity phosphoric acid as measured by $^{31}$P NMR, or the impurity psilocin measured by HPLC. In some embodiments, crystalline psilocybin Polymorph A or Polymorph A' has a chemical purity of greater than 97 area %, greater than 98 area %, or greater than 99 area % by HPLC. In some embodiments, crystalline psilocybin Polymorph A or Polymorph A' has no single impurity greater than 1 area %, greater than 0.5 area %, greater than 0.4%, greater than 0.3%, or greater than 0.2% as measured by HPLC. In some embodiments, crystalline psilocybin Polymorph A or Polymorph A' does not contain psilocin at a level greater than 1 area %, greater than 0.5 area %, greater than 0.4%, greater than 0.3%, or greater than 0.2% as measured by HPLC. In some embodiments, crystalline psilocybin Polymorph A or Polymorph A' does not contain phosphoric acid at a level greater than 1 weight %, greater than 0.5 weight %, greater than 0.4 weight %, 0.3 weight %, or greater than 0.2 weight %, as measured by $^{31}$P NMR. In some embodiments, crystalline psilocybin Polymorph A or Polymorph A' has a chemical assay of at least 95 weight %, at least 96 weight %, or at least 98 weight %.

The heating of Polymorph A or A' results in an endothermic event having an onset temperature of circa 150° C. corresponding to solid-solid transition of Polymorph A or Polymorph A' to Polymorph B. Continued heating of the resulting solid, i.e., Polymorph B, results in a second endothermic event corresponding to a melting point having an onset temperature of between 205 and 220° C. (see FIGS. 3A and 3B).

Hydrate A

In some embodiments, the disclosure provides a crystalline form of psilocybin, Hydrate A. In some embodiments, crystalline psilocybin Hydrate A exhibits peaks in an XRPD diffractogram at 8.9, 12.6 and 13.8°2θ±0.1°2θ. In some embodiments, crystalline psilocybin Hydrate A further exhibits at least 1, 2, 3, 4, or 5 further peaks at 6.5, 12.2, 19.4, 20.4 or 20.8°2θ±0.1°2θ. An illustrative XRPD diffractogram is provided as FIG. 2D. In some embodiments, crystalline psilocybin Hydrate A further exhibits an endothermic event in a DSC thermogram having a first onset temperature of between 90° C. and 100° C., a second onset temperature of between 100° C. and 120° C. and a third onset temperature of between 210° C. and 220° C. An illustrative DSC thermogram is provided as FIG. 2D.

In some embodiments, psilocybin Hydrate A exhibits an XRPD diffractogram comprising at least 3, 4, 5, 6, 7, 8, 9, or 10 peaks listed in Table 3 or equivalent peaks within about ±0.1°2θ.

TABLE 3

| XRPD peak positions for Hydrate A | |
| --- | --- |
| Position [°2Th.] | Relative Intensity [%] |
| 5.6 | 14.40 |
| 6.5 | 18.84 |
| 8.9 | 100.00 |
| 12.2 | 11.51 |
| 12.6 | 18.65 |
| 13.8 | 44.22 |
| 16.2 | 21.22 |
| 18.9 | 6.62 |
| 19.4 | 38.68 |
| 20.4 | 21.32 |
| 20.8 | 19.73 |
| 21.5 | 20.75 |
| 22.3 | 12.80 |
| 22.5 | 19.38 |
| 23.1 | 47.53 |
| 23.5 | 25.79 |
| 24.3 | 5.62 |
| 24.8 | 14.62 |
| 25.4 | 5.27 |
| 26.9 | 6.53 |
| 27.9 | 7.82 |
| 28.4 | 5.78 |
| 29.0 | 5.09 |
| 29.7 | 4.83 |
| 32.1 | 8.27 |
| 32.8 | 4.81 |
| 33.4 | 3.74 |
| 34.2 | 5.96 |

In some embodiments, crystalline psilocybin Hydrate A exhibits XRPD diffractogram peaks at 8.9, 12.6 and 13.8°2θ±0.1°2θ. In some embodiments, crystalline psilocybin Hydrate A exhibits at least one peak appearing at 6.5, 12.2, 19.4, 20.4 or 20.8°2θ±0.1°2θ. In some embodiments, crystalline psilocybin Hydrate A exhibits at least two peaks appearing at 6.5, 12.2, 19.4, 20.4 or 20.8°2θ±0.1°2θ. In some embodiments, crystalline psilocybin Hydrate A exhibits an XRPD diffractogram substantially the same as the XRPD diffractogram shown in FIG. 2D.

Figure 3C:
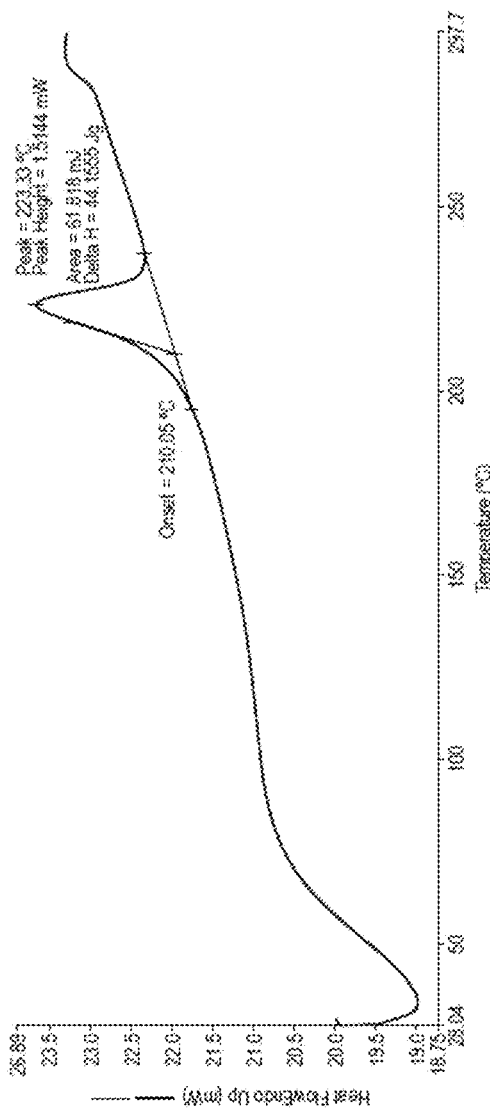
FIG. 3C is a DSC thermograph of Polymorph B (GM748A).
Figure 3D:
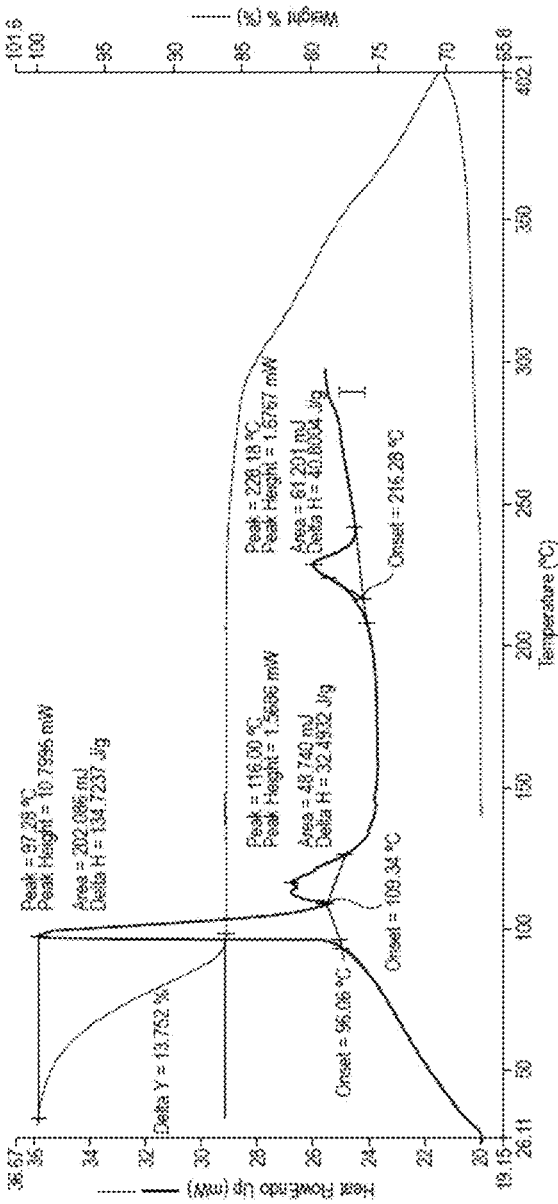
FIG. 3D is a DSC and TGA thermograph of Hydrate A (JCCA2157E).
Figure 3E:
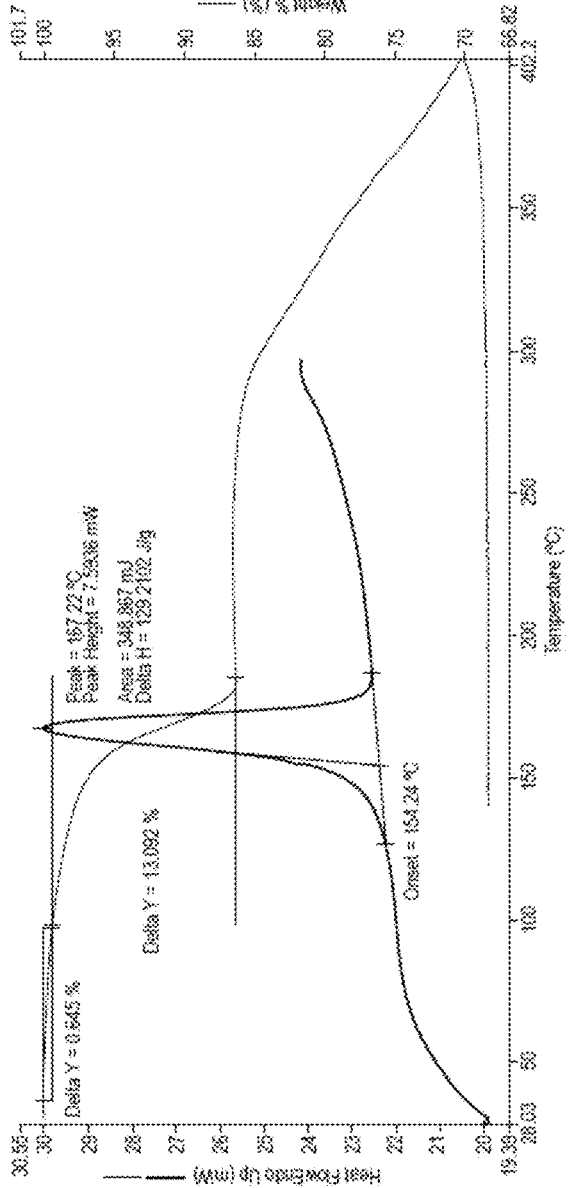
FIG. 3E is a DSC and TGA thermograph of ethanol solvate (JCCA2158D).

In certain embodiments, crystalline psilocybin Hydrate A is characterized by an endothermic event in a DSC thermogram having a first onset temperature of between 85° C. and 105° C., such as between 90° C. and 100° C. and most preferably at about 96° C., a second onset temperature of between 100° C. and 120° C. such as between 105° C. and 115° C., and most preferably at about 109° C. and a third onset temperature of between 205 and 220° C., such as between 210 and 220° C., such as between 210 and 218° C., or such as between 210 and 216° C., or about 216° C. In some embodiments, crystalline psilocybin Hydrate A exhibits an endothermic event in a DSC thermogram having an onset temperature of between about 205 and about 220° C., between about 210 and about 220° C., between about 210 and about 218° C., or between about 210 and about 216° C. In some embodiments, crystalline psilocybin Hydrate A exhibits an endothermic event in the DSC thermogram having an onset temperature of between about 85 and about 105° C., or between about 90 and about 100° C. In some embodiments, crystalline psilocybin Hydrate A exhibits an endothermic event having an onset temperature of between about 205 and about 220° C., between about 210 and about 220° C., between about 210 and about 218° C., or between about 210 and about 216° C., and an endothermic event having an onset temperature of between about 85 and about 105° C. or between about 90 and about 100° C., in a DSC thermogram. In some embodiments, crystalline psilocybin Hydrate A exhibits a DSC thermogram substantially the same as the DSC thermogram in FIG. 3D.

In some embodiments, crystalline psilocybin Hydrate A exhibits a water content of between about 10 and about 18%, between about 12 and about 16%, or about 13%. Methods to determine the water content of a crystalline compound are known, for example Karl Fischer Titration. In some embodiments, crystalline psilocybin Hydrate A exhibits a weight loss in the TGA thermogram of between about 10% and about 18%, between about 12% and about 16%, or about 13%, between ambient temperature, about 25° C., and 120° C.

In some embodiments, crystalline psilocybin Hydrate A is chemically pure, for example the psilocybin has a chemical purity of greater than 97%, 98%, or 99% by HPLC. In some embodiments, crystalline psilocybin Hydrate A has no single impurity of greater than 1%, greater than 0.5%, greater than 0.4%, greater than 0.3%, or greater than 0.2% e.g., the impurity phosphoric acid as measured by 31P NMR, or the impurity psilocin measured by HPLC. In some embodiments, crystalline psilocybin Hydrate A has a chemical purity of greater than 97 area %, greater than 98 area %, or greater than 99 area % by HPLC. In some embodiments, crystalline psilocybin Hydrate A has no single impurity greater than 1 area %, greater than 0.5 area %, greater than 0.4%, greater than 0.3%, or greater than 0.2% as measured by HPLC. In some embodiments, crystalline psilocybin Hydrate A does not contain psilocin at a level greater than 1 area %, greater than 0.5 area %, greater than 0.4%, greater than 0.3%, or greater than 0.2% as measured by HPLC. In some embodiments, crystalline psilocybin Hydrate A does not contain phosphoric acid at a level greater than 1 weight %, greater than 0.5 weight %, greater than 0.4 weight %, 0.3 weight %, or greater than 0.2 weight %, as measured by 31P NMR. In some embodiments, crystalline psilocybin Hydrate A has a chemical assay of at least 95 weight %, at least 96 weight %, or at least 98 weight %.

In some embodiments, crystalline psilocybin Hydrate A is a highly pure crystalline form of Hydrate A. In some embodiments, the crystalline psilocybin comprises at least 90%, at least 95%, at least 99%, or at least 99.5% by weight of Hydrate A.

Polymorph B

In some embodiments, the disclosure provides a crystalline form of psilocybin, Polymorph B. In some embodiments, crystalline psilocybin Polymorph B exhibits peaks in an XRPD diffractogram at 11.1, 11.8 and 14.3°2θ±0.1°2θ. In some embodiments, crystalline psilocybin Polymorph B exhibits at least 1, 2, 3, 4 or 5 peaks in an XRPD diffractogram at 14.9, 15.4, 19.3, 20.0 or 20.6°2θ±0.1°2θ. An illustrative XRPD diffractogram of crystalline psilocybin Polymorph B is provided as FIG. 2C. In some embodiments, crystalline psilocybin Polymorph B exhibits a single endothermic event in a DSC thermogram having an onset temperature of between about 205 and about 220° C. An illustrative DSC thermogram of crystalline psilocybin Polymorph B is provided as FIG. 3C.

In some embodiments, psilocybin Polymorph B exhibits an XRPD diffractogram comprising at least 3, 4, 5, 6, 7, 8, 9, or 10 peaks listed in Table 4 or equivalent peaks within about ±0.1°2θ.

TABLE 4

| XRPD peak positions for Polymorph B | |
| --- | --- |
| Position [°2Th.] | Relative Intensity [%] |
| 5.5 | 21.33 |
| 11.1 | 36.91 |
| 11.8 | 100.00 |
| 12.5 | 12.73 |
| 14.3 | 70.23 |
| 14.9 | 50.01 |
| 15.4 | 23.67 |
| 17.1 | 51.58 |
| 17.4 | 91.25 |
| 18.0 | 12.61 |
| 19.3 | 39.33 |
| 20.0 | 76.61 |
| 20.6 | 50.26 |
| 21.5 | 20.77 |
| 22.3 | 40.19 |
| 23.9 | 13.32 |
| 24.3 | 16.03 |
| 25.3 | 32.94 |
| 28.3 | 7.60 |
| 28.9 | 17.89 |
| 29.3 | 8.96 |
| 31.3 | 6.57 |
| 32.2 | 6.90 |
| 33.8 | 2.37 |

In some embodiments, crystalline psilocybin Polymorph B exhibits XRPD diffractogram peaks at 11.1, 11.8 and 14.3°2θ±0.1°2θ. In some embodiments, crystalline psilocybin Polymorph B exhibits at least one peak at 14.9, 15.4, 19.3, 20.0 or 20.6°2θ±0.1°2θ. In some embodiments, crystalline psilocybin Polymorph B exhibits at least two peaks appearing at 14.9, 15.4, 19.3, 20.0 or 20.6°2θ±0.1°2θ. In some embodiments, crystalline psilocybin Polymorph B exhibits an XRPD diffractogram substantially the same as the XRPD diffractogram shown in FIG. 2C.

In some embodiments, crystalline psilocybin Polymorph B is characterized by a single endothermic event in a DSC thermogram having an onset temperature of between about 205 and about 220° C., between about 210 and about 220° C., between about 210 and about 218° C., or between about 210 and about 216° C. In some embodiments, crystalline psilocybin Polymorph B exhibits a DSC thermogram substantially the same as the DSC thermogram in FIG. 3C.

In some embodiments, crystalline psilocybin Polymorph B exhibits a water content of <0.5% w/w, <0.4% w/w, <0.3% w/w, <0.2% w/w, or <0.1% w/w. Methods to determine the water content of a crystalline compound are known, for example Karl Fischer Titration. In some embodiments, crystalline psilocybin Polymorph B exhibits <0.5% w/w, <0.4% w/w, <0.3% w/w, <0.2% w/w, or <0.1% w/w loss in the TGA thermogram between ambient temperature, about 25° C., and 200° C. In some embodiments, crystalline psilocybin Polymorph B exhibits a loss of less than 2% by weight, less than 1% by weight, or less than 0.5% by weight in a loss on drying test. In some embodiments, the loss on drying test is performed at 70° C.

In some embodiments, crystalline psilocybin Polymorph B is a highly pure crystalline form of Polymorph B, for example, psilocybin comprises at least 90%, at least 95%, at least 99%, or at least 99.5% by weight of Polymorph B.

In some embodiments, crystalline psilocybin Polymorph B is chemically pure, for example the psilocybin has a chemical purity of greater than 97%, 98%, or 99% by HPLC. In some embodiments, crystalline psilocybin Polymorph B has no single impurity of greater than 1%, greater than 0.5%, greater than 0.4%, greater than 0.3%, or greater than 0.2% e.g., the impurity phosphoric acid as measured by 31P NMR, or the impurity psilocin measured by HPLC. In some embodiments, crystalline psilocybin Polymorph B has a chemical purity of greater than 97 area %, greater than 98 area %, or greater than 99 area % by HPLC. In some embodiments, crystalline psilocybin Polymorph B has no single impurity greater than 1 area %, greater than 0.5 area %, greater than 0.4%, greater than 0.3%, or greater than 0.2% as measured by HPLC. In some embodiments, crystalline psilocybin Polymorph B does not contain psilocin at a level greater than 1 area %, greater than 0.5 area %, greater than 0.4%, greater than 0.3%, or greater than 0.2% as measured by HPLC. In some embodiments, crystalline psilocybin Polymorph B does not contain phosphoric acid at a level greater than 1 weight %, greater than 0.5 weight %, greater than 0.4 weight %, 0.3 weight %, or greater than 0.2 weight %, as measured by 31P NMR. In some embodiments, crystalline psilocybin Polymorph B has a chemical assay of at least 95 weight %, at least 96 weight %, or at least 98 weight %.

In some embodiments, the psilocybin of the disclosure in the form Polymorph A or A' has the general properties illustrated in Table 5.

TABLE 5

| Appearance: | White to off-white solid |
| --- | --- |
| Major endothermic event in DSC (onset temperature) (corresponding to a melt): | 210-215° C. |
| Hygroscopicity: | Psilocybin forms Hydrate A at high humidity and when added to water but the water of hydration is lost rapidly on drying. The anhydrous form is therefore being developed. |
| Crystalline form: | Anhydrous Polymorph A and/or A' |
| pKa (calculated): | 1.74, 6.71, 9.75 |
| Solubility | approx. 15 mg/ml in Water |

In some embodiments, the psilocybin conforms to the spectra as set out in Table 6 and illustrated in the spectra of FIGS. 5-8.

TABLE 6

| Technique | Conclusions |
| --- | --- |
| Proton ($^1$H) and Carbon ($^{13}$C) NMR | Assignment of the proton (FIG. 5) and carbon spectra (FIG. 6) are concordant with Psilocybin. |
| FT-Infrared Spectroscopy (FT-IR) | Assignment of the FT-IR spectrum (FIG. 7) is concordant with Psilocybin. |
| Mass Spectroscopy (MS) | Assignment of the mass spectrum (FIG. 8) is concordant with Psilocybin. |

Alternatively, and independently, the crystalline psilocybin may take the form of Hydrate A or Polymorph B.

In some embodiments, the disclosure provides the crystalline psilocybin in the form Polymorph A or Polymorph A' for use in medicine. In some embodiments, the disclosure provides crystalline psilocybin Polymorph A for use in medicine. In some embodiments, the disclosure provides crystalline psilocybin Polymorph A' for use in medicine. In some embodiments, the disclosure provides a high purity crystalline psilocybin Polymorph A for use in medicine. In some embodiments, the disclosure provides a high purity crystalline psilocybin Polymorph A' for use in medicine. Alternatively, and independently, the crystalline psilocybin may take the form of Hydrate A or Polymorph B.

In some embodiments, the disclosure provides crystalline psilocybin in the form Polymorph A or Polymorph A' for use in treating a subject in need thereof. Alternatively, and independently, the crystalline psilocybin may take the form of Hydrate A or Polymorph B.

In some embodiments, the disclosure provides crystalline psilocybin, Polymorph A or Polymorph A', for use in treating a subject in need thereof. In some embodiments, the disclosure provides crystalline psilocybin, Polymorph A or Polymorph A', for use in treating a subject in need thereof. In some embodiments, the disclosure provides crystalline psilocybin Polymorph A for use in treating a subject in need thereof. In some embodiments, the disclosure provides crystalline psilocybin Polymorph A' for use in treating a subject in need thereof. In some embodiments, the disclosure provides a high purity crystalline psilocybin Polymorph A for use in treating a subject in need thereof. In some embodiments, the disclosure provides a high purity crystalline psilocybin Polymorph A' for use in treating a subject in need thereof.

Pharmaceutical Compositions and Formulations

In some embodiments, the disclosure provides a pharmaceutical composition comprising crystalline psilocybin and one or more pharmaceutically acceptable carriers or excipients.

In some embodiments, the disclosure provides a pharmaceutical formulation comprising high purity psilocybin and one or more pharmaceutically acceptable carriers or excipients. In some embodiments, the disclosure provides a pharmaceutical formulation comprising crystalline psilocybin Polymorph A and one or more pharmaceutically acceptable carriers or excipients. In some embodiments, the disclosure provides a pharmaceutical formulation comprising crystalline psilocybin Polymorph A' and one or more pharmaceutically carriers or excipients. In some embodiments, the disclosure provides a pharmaceutical formulation comprising high purity crystalline psilocybin, Polymorph A or Polymorph A', and one or more pharmaceutically acceptable carriers or excipients. In some embodiments, the disclosure provides a pharmaceutical formulation comprising high purity crystalline psilocybin Polymorph A and one or more pharmaceutically acceptable carriers or excipients. In some embodiments, the disclosure provides a pharmaceutical formulation comprising high purity crystalline psilocybin Polymorph A' and one or more pharmaceutically acceptable carriers or excipients.

Preferred pharmaceutical excipients for an oral formulation include: diluents, such as microcrystalline cellulose, starch, mannitol, calcium hydrogen phosphate anhydrous or co-mixtures of silicon dioxide, calcium carbonate, microcrystalline cellulose and talc; disintegrants, such as sodium starch glycolate or croscarmellose sodium; binders, such as povidone, co-povidone or hydroxyl propyl cellulose; lubricants, such as magnesium stearate or sodium stearyl fumurate; glidants, such as colloidal silicon dioxide; and film coats, such as Opadry II white or PVA based brown Opadry II.

In some embodiments, the oral dosage form also comprises a disintegrant, such as, but not limited to: starch glycolate, croscarmellose sodium, and/or mixtures thereof. In some embodiments, the oral dosage form comprises 3% or less by wt disintegrant, less than 3% by wt disintegrant and greater than 0.001% by wt disintegrant, about 2.5% by wt or less disintegrant; 2% by wt or less disintegrant; 1.5% by wt or less disintegrant; 1% by wt or less disintegrant; 0.7% by wt or less disintegrant; 0.5% by wt or less disintegrant, or 0.3% by wt or less disintegrant.

In some embodiments, the disintegrant is sodium starch glycolate. In some embodiments, the sodium starch glycolate is present at less than 3% wt. In Other embodiments, the sodium starch glycolate is present at about 2% by wt or less, about 2% by wt; about 1% by wt or less, about 1% by wt; about 0.7% by wt or less, about 0.7% by wt; about 0.5% by wt or less, or about 0.5% by wt. In still other embodiments, the sodium starch glycolate is present at about 0.5% to 1% by wt.

In some embodiments, the oral dosage form comprises 5 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 10 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 25 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5%.

In some embodiments there is provided the crystalline psilocybin in the form Polymorph A or Polymorph A' for use in medicine. In some embodiments, there is provided crystalline psilocybin Polymorph A for use in medicine. In some embodiments, there is provided crystalline psilocybin Polymorph A' for use in medicine. In some embodiments, there is provided a high purity crystalline psilocybin Polymorph A for use in medicine. In some embodiments, there is provided a high purity crystalline psilocybin Polymorph A' for use in medicine.

Alternatively, and independently, the crystalline psilocybin may take the form of Hydrate A or Polymorph B.

In some embodiments, there is provided crystalline psilocybin, particularly but not essentially in the form Polymorph A or Polymorph A' for use in treating central nervous disorders.

Alternatively, and independently, the crystalline psilocybin may take the form of Hydrate A or Polymorph B.

In some embodiments, the pharmaceutical formulation is a parenteral dosage form. In some embodiments, the pharmaceutical formulation is an oral dosage form. In some embodiments, the pharmaceutical composition comprises a tablet. In some embodiments, the pharmaceutical composition comprises a capsule. In some embodiments, the pharmaceutical composition comprises a dry powder. In some embodiments, the pharmaceutical composition comprises a solution. In some embodiments, more than one dosage form is administered to the subject at substantially the same time. In some embodiments, the subject may be administered the entire therapeutic dose in one tablet or capsule. In some embodiments, the therapeutic dose may be split among multiple tablets or capsules. For example, for a dose of 25 mg, the subject may be administered 5 tablets or capsules each comprising 25 mg of psilocybin. Alternatively, for a dose of 10 mg, the subject may be administered 2 tablets or capsules each comprising 5 mg of psilocybin.

In some embodiments, the oral dosage form comprises a functional filler. The functional filler may be a silicified filler, such as, but not limited to silicified microcrystalline cellulose (SMCC). In some embodiments, the oral dosage form comprises high compactability grades of SMCC with a particle size range of from about 45 to 150 microns. A mixture of two functional fillers having different particle size ranges may be used with the weight percentages of the two favoring the larger sized particles.

In some embodiments, the silicified microcrystalline filler may comprise a first filler, having a particle size range of from about 45 to 80 microns in an amount of up to 30%, up to 20%, up to 15%, or less by weight of filler, and a second filler, having a particle size range of from about 90 to 150 microns, in an amount of up to 70%, up to 80%, up to 85%, or more, by weight of filler.

In some embodiments, the oral dosage form may comprise silicified microcrystalline cellulose with a particle size range of from about 45 to 80 microns (SMCC 50), such as Prosolv 50; silicified microcrystalline cellulose with a particle size range of from about 90 to 150 microns (SMCC 90), such as Prosolv 90; or mixtures thereof. In other embodiments, the oral dosage form may comprise SMCC 50 and SMCC 90. In other embodiments, the oral dosage form may comprise SMCC 50 and SMCC 90, wherein the ratio of SMCC 50 to SMCC 90 is 1:5 to 1:8 wt %. In still other embodiments the ratio of SMCC 50 to SMCC 90 is 1:5-1:7; 1:6-1:7; 1:6-1:8; or 1.7-1.8. In still other embodiments the ratio of SMCC 50 to SMCC 90 is 1:6; 1:6.1; 1:6.2; 1:6.3; 1:6.4; 1:6.5; 1:6.6; 1.6.7; 1:6.8; 1.6.9; or 1:7. The formulation may further comprise or consist essentially of a disintegrant, including without limitation sodium starch glycolate; a glidant, including without limitation colloidal silicon dioxide; and a lubricant, including without limitation sodium stearyl fumarate.

In some embodiments, the oral dosage form may comprise a disintegrant such as sodium starch glycolate, at less than 3% (by wt), less than 2%, or 1% or less.

In some embodiments, the oral dosage form comprises 5 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 10 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 25 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate. In some embodiments, the tablet or capsule comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

In some embodiments, the oral dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate. In some embodiments, the tablet or capsule comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

In some embodiments, the tablet or capsule comprises one or more excipients. Non-limiting exemplary excipients include microcrystalline cellulose and starch, including without limitation silicified microcrystalline cellulose.

It should be noted that the formulations may comprise psilocybin in any form, not only the polymorphic forms disclosed herein.

As used herein, oral doses of psilocybin are classified follows: "very low doses" (about 0.045 mg/kg or less); "low doses" (between about 0.115 and about 0.125 mg/kg), "medium doses" (between about 0.115 to about 0.260 mg/kg), and "high doses" (about 0.315 mg/kg or more). See Studerus et al (2011) *J Psychopharmacol* 25(11) 1434-1452.

In some embodiments, the formulated dose of psilocybin comprises from about 0.01 mg/kg to about 1 mg/kg. In some embodiments, a human dose (for an adult weighing 60-80 kg) comprises between about 0.60 mg and about 80 mg.

In some embodiments, a formulated dose comprises between about 2 and about 50 mg of crystalline psilocybin.

In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin. In some embodiments, a formulated dose comprises about 1 mg, about 5 mg, about 10 mg, or about 25 mg of crystalline psilocybin.

In some embodiments, a formulated dose comprises between about 2 and about 50 mg of crystalline psilocybin Polymorph A or Polymorph A' or a mixture thereof. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Polymorph A or Polymorph A' or a mixture thereof. In some embodiments, a formulated dose comprises about 1 mg, about 5 mg, about 10 mg, or about 25 mg of crystalline psilocybin Polymorph A or Polymorph A' or a mixture thereof. In some embodiments, a formulated dose comprises about 5 mg of crystalline psilocybin Polymorph A or Polymorph A' or a mixture thereof.

In some embodiments, a formulated dose comprises between about 2 and about 50 mg of crystalline psilocybin Polymorph A. In some embodiments, a formulated dose comprises between 2 mg and 40 mg, between 2 mg and 10 mg, between 5 mg and 30 mg, between 5 mg and 15 mg, or between 20 and 30 mg of crystalline psilocybin Polymorph A. In some embodiments, a formulated dose comprises about 1 mg, about 5 mg, about 10 mg, or about 25 mg of crystalline psilocybin Polymorph A.

In some embodiments, a formulated dose comprises between about 2 mg and about 50 mg of crystalline psilocybin Polymorph A'. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Polymorph A'. In some embodiments, a formulated dose comprises about 1 mg, about 5 mg, about 10 mg, or about 25 mg of crystalline psilocybin Polymorph A'.

In some embodiments, a formulated dose comprises between about 2 mg and about 50 mg of crystalline psilocybin Polymorph B. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Polymorph B. In some embodiments, a formulated dose comprises about 1 mg, about 5 mg, about 10 mg, or about 25 mg of crystalline psilocybin Polymorph B.

In some embodiments, a formulated dose comprises between about 2 and about 50 mg of crystalline psilocybin Hydrate A. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Hydrate A. In some embodiments, a formulated dose comprises about 1 mg, about 5 mg, about 10 mg, or about 25 mg of crystalline psilocybin Hydrate A.

Dosing

In some embodiments, a therapeutically effective dose of psilocybin is administered to the subject. In some embodiments, each dose of psilocybin administered to the subject is a therapeutically effective dose.

In some embodiments, a dose of psilocybin may be in the range of about 1 mg to about 100 mg. For example, the dose may be about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In some embodiments, the dose of psilocybin is between about 0.1 mg to about 100 mg, about 1 mg to about 50 mg, or about 5 mg to about 30 mg. In some embodiments, the dose of psilocybin is about 1 mg, about 10 mg, or about 25 mg. In some embodiments, the dose of psilocybin is in the range of about 0.001 mg to about 1 mg. In some embodiments, the dose of psilocybin is in the rage of about 100 mg to about 250 mg. In some embodiments, the dose of psilocybin is about 25 mg. In some embodiments, the psilocybin is in the form of polymorph A.

In some embodiments, an adult oral dose comprises about 1 mg to about 40 mg, about 2 to about 30 mg, or about 15 to about 30 mg of crystalline psilocybin, for example about 1 mg, about 5 mg, about 10 mg, or about 25 mg of crystalline psilocybin. In some embodiments, an adult oral dose comprises about 25 mg of crystalline psilocybin. In some embodiments, the crystalline psilocybin is in the form of polymorph A.

In some embodiments, a "micro-dose" of psilocybin is administered to a subject. A micro-dose may comprise, for example, about 0.05 mg to about 2.5 mg of crystalline psilocybin, such as about 1.0 mg. In the case of micro-dosing the regime may comprise a regular, continuous regime of, for example, daily administration, every other day administration, or weekly, administration. Such dosing may be absent of psychological support.

In some embodiments, one dose of psilocybin is administered to the subject. In some embodiments, multiple doses of psilocybin are administered to the subject. For example, at least 2, at least 3, at least 4, at least 5, at least 6, at least 7, at least 8, at least 9, at least 10, at least 15, at least 20, at least 25, at least 30, or at least 50 doses of psilocybin may be administered to the subject. In some embodiments, the same dose of psilocybin is administered to a subject during each administration. In some embodiments, a different dose of psilocybin is administered to a subject during each administration. In some embodiments, the dose of psilocybin administered to the subject is increased over time. In some embodiments, the dose of psilocybin administered to the subject is decreased over time.

In some embodiments, the psilocybin is administered at therapeutically effective intervals. In some embodiments, a therapeutically effective interval may be about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In some embodiments, a therapeutically effective interval may be about 1 month, about 3 months, about 6 months, or about 12 months. In some embodiments, the psilocybin is administered once per day. In some embodiments, the psilocybin is administered at least once per week or at least twice per week. In some embodiments, the psilocybin is administered at least once per month or at least twice per month. In some embodiments, the psilocybin is administered at least once every three months, at least once every six months, or at least once every 12 months.

In some embodiments, a first dose and a second dose of psilocybin are administered to the subject. In some embodiments, the first dose is about 1 mg and the second dose is about 1 mg. In some embodiments, the first dose is about 10 mg and the second dose is about 10 mg. In some embodiments, the first dose is about 25 mg and the second dose is about 25 mg. In some embodiments, the first dose is about 10 mg and the second dose is about 25 mg. In some embodiments, the first dose is about 25 mg and the second dose is about 10 mg. In some embodiments, the first dose is about 1 mg and the second dose is about 10 mg. In some embodiments, the first dose is about 1 mg and the second dose is about 25 mg. In some embodiments, the first dose is about 10 mg and the second dose is about 1 mg. In some embodiments, the first dose is about 25 mg and the second dose is about 1 mg.

In some embodiments a second dose of psilocybin is administered from about one week to about 12 weeks after a first dose. In some embodiments, a second dose of psilocybin is administered about one week after a first dose. In some embodiments, a second dose of psilocybin is administered about two weeks after a first dose. In some embodiments, a second dose of psilocybin is administered about three weeks after a first dose. In some embodiments, a second dose of psilocybin is administered about four weeks after a first dose. In some embodiments, a second dose of psilocybin is administered about five weeks after a first dose. In some embodiments, a second dose of psilocybin is administered about six weeks after a first dose.

Administration Routes

Exemplary modes for administration of psilocybin include oral, parenteral (e.g., intravenous, subcutaneous, intradermal, intramuscular [including administration to skeletal, diaphragm and/or cardiac muscle], intradermal, intrapleural, intracerebral, and intra-articular), topical (e.g., to both skin and mucosal surfaces, including airway surfaces, and transdermal administration), inhalation (e.g., via an aerosol), rectal (e.g., via a suppository), transmucosal, intranasal, buccal (e.g., sublingual), vaginal, intrathecal, intraocular, transdermal, in utero (or in ovo), intralymphatic, and direct tissue or organ injection (e.g., to liver, skeletal muscle, cardiac muscle, diaphragm muscle or brain). In some embodiments, psilocybin is administered orally to the subject.

Methods of Treatment

It is to be understood by one of skill in the art that the methods of treatment comprising administering psilocybin, a prodrug of psilocybin, a metabolite of psilocybin, and/or a prodrug of a metabolite of psilocybin for the treatment of one or more indications as described herein also include: the use of psilocybin, a prodrug of psilocybin, a metabolite of psilocybin, and/or a prodrug of a metabolite of psilocybin in the manufacture of a medicament for the treatment of one or more indications as described herein; and the use of psilocybin, a prodrug of psilocybin, a metabolite of psilocybin, and/or a prodrug of a metabolite of psilocybin for the treatment of one or more indications as described herein.

In some embodiments, a method for treating a subject in need thereof comprises administering to the subject a therapeutically effective dose of psilocybin. In some embodiments, a method for treating a subject in need thereof comprises administering to the subject a therapeutically effective dose of psilocybin in a controlled environment, wherein the subject is provided with psychological support.

In some embodiments, a method for treating a subject in need thereof comprises at least one of the following:

(i) administering to the subject a therapeutically effective dose of psilocybin in a controlled environment, wherein the subject is provided with psychological support;

(ii) having the subject participate in one or more pre-administration psychological support session(s); and/or (ii) having the subject participate in one or more post-administration psychological support session(s).

After administration of the psilocybin, the subject may not feel the effects of the drug for about 30 minutes to about 90 minutes. In some embodiments, the subject may not feel the effects of the drug for about 60 minutes. This period after administration and before the onset of effects will be referred to herein as the initial stage of the psilocybin session. The time marked by the onset of the drug's effects will be referred to herein as the early stage of the psilocybin session.

In some embodiments, the subject will experience the peak of the psilocybin's effects at about 1.5 hours to about 3.5 hours after administration thereof. The time period marked by the peak psilocybin experience will be referred to herein as the peak stage of the psilocybin session.

In some embodiments, the effects of the psilocybin may substantially wear off from about 4 hours to about 6 hours after administration. This time period will be referred to as the late stage of the psilocybin session.

In some embodiments, the subject's ability to reach a non-dual state (e.g., a mystical experience), or a sense of unity, boundlessness, ego-dissolution or transcendence correlates with positive clinical outcome. Each of these terms may be commonly defined as the breakdown of the usual relationship between self and other, whereby the subject might feel a oneness and increased sense of connectedness to the surrounding environment and/or the world at large.

In some embodiments, low levels of emotional arousal—which could indicate avoidance, lack of involvement or intellectualization—might, in some embodiments, be correlated with little or no improvement in treatment outcomes.

Factors that may influence the subjective experience of psilocybin include, for example, (i) dose, (ii) the mindset of the participant prior to the session, (iii) the setting of the session, (iv) the subject's ability to focus and stay with the experience, and/or (v) the subject's prior experience with psychedelics. These, and other factors, will be described in more detail below, along with ways to maximize therapeutic benefit of the psilocybin session.

Pre-Administration Psychological Support Sessions

In some embodiments, the subject participates in at least one psychological support session before administration of the psilocybin ("pre-administration psychological support session"). In some embodiments, a pre-administration psychological support session may be held about 1 month prior to the psilocybin administration. In some embodiments, a pre-administration psychological support session may be held about 2 weeks prior to the psilocybin administration. In some embodiments, a pre-administration psychological support session may be held about 1 week prior to the psilocybin administration. In some embodiments, a pre-administration psychological support session may be held about 3 days prior to the psilocybin administration. In some embodiments, a pre-administration psychological support session may be held about 1 day prior to the psilocybin administration. In some embodiments, a pre-administration psychological support session may be held on the same day as and prior to psilocybin administration.

In some embodiments, the subject may participate in one, two, three, four, five, six, seven, or eight pre-administration psychological support sessions. In some embodiments, the subject may participate in at least two pre-administration psychological support sessions. In some embodiments, the subject may participate in at least three pre-administration psychological support sessions. In some embodiments, the subject may participate in pre-administration psychological support sessions at least once per week, for at least two or three weeks prior to the psilocybin session. In some embodiments, the subject may additionally participate in a pre-administration psychological support session the day before the psilocybin session.

The pre-administration psychological support sessions may be individual sessions, wherein a subject meets oneon-one with a therapist. In some embodiments, the psychological support sessions may be group sessions, wherein more than one subject meets with a single therapist, or more than one therapist. In some embodiments, one or more of the subject's family members or friends may be present at the pre-administration psychological support session(s).

In some embodiments, the goals of the pre-administration session may include (i) establishing therapeutic alliance between subject and therapist; (ii) answering the subject's questions and addressing any concerns; and/or (iii) demonstrating and practicing the skills of self-directed inquiry and experiential processing. In some embodiments, the pre-administration psychological support sessions focus on discussion of possible psilocybin effects, and/or preparing subjects for the dosing session by practicing relevant therapeutic techniques to reduce avoidance and anxiety, eliciting relevant therapeutic goals, building rapport, and/or establishing therapeutic alliance. During the psychological support session, skills of self-directed inquiry and experiential processing may be demonstrated and/or practiced.

In some embodiments, breathing exercises meant to promote calm and/or ease anxiety may be demonstrated and/or practiced. In some embodiments, the breathing exercise comprise instructing the subject to focus on their breath and/or sensations associated with the breath throughout the body. For example the subject may be instructed to breathe in for a count of four, to hold their breath for a moment, and then to breathe out for a count of eight. In some embodiments, the therapist and subject may discuss the most helpful ways to support in case of emotional distress during the psilocybin session. In some embodiments, the subject is given access (e.g., online access) to materials concerning the safety and mechanism of action of psilocybin.

In some embodiments, the pre-administration psychological support sessions will serve to establish a therapeutic goal for the psilocybin session. In some embodiments, the subject suggests the therapeutic goal for herself or himself. In some embodiments, the therapist suggests the therapeutic goal to the subject. In some embodiments, the subject is reminded of the therapeutic goal during the pre-administration psychological support session.

In some embodiments, the therapists are trained to counsel the subject before, during, and/or after the psilocybin sessions. In some embodiments, the therapist will have mental health training. In some embodiments, the therapist will be a clinical psychologist, a psychiatrist, a social worker, a doctor or a nurse. In some embodiments, the therapist will meet the following criteria:

Demonstrate independent clinical experience with direct subject care in areas that require counselling and psychotherapeutic skills;

Current unrestricted professional license and/or good professional standing with no history of suspension, professional misconduct or disciplinary actions; and/or High level of openness to learning new approaches and receiving feedback.

Psychological Support During Psilocybin Sessions

During the treatment session, the subject may be supervised by one or more trained therapists. The therapist supervising the subject during the psilocybin session may be the same therapist from the subject's pre-administration psychological support session(s), or may be a different therapist. The therapist(s) may provide psychological support to the subject as necessary. As used herein, the term "psychological support" refers to any measure(s) taken by the therapist during the subject's psilocybin session to ensure the safety of the subject and maximize the clinical effectiveness of the psilocybin session. For example, the psychological support may be anything done by the therapist to (1) to ensure psychological safety of the subject; (2) to allow the subject's subjective experience to unfold naturally within the boundaries of the therapeutic intention set at the preparation; (3) to maintain participant's attention and awareness on the experience of the present moment thus allowing exposure and processing of the challenging emotional states and personal memories; and/or (4) to generate insights and solutions for the resolution of challenging personal situations, conflicts and traumatic experiences. In some embodiments, support can be in the form of therapeutic touch, verbal reassurance, guided imagery and/or relaxation or breathing exercises. In some embodiments, the support may comprise reminders, encouragement, or active guiding. Typically, only one technique is applied at a time to allow for minimal intervention and interference with the subject's unique process.

In some embodiments, the main therapeutic goals of the therapist during the psilocybin session are to (i) minimize extreme anxiety, and (ii) provide appropriate support that enables the skills and processes of self-directed inquiry and experiential processing. In some embodiments, the therapist demonstrates genuine presence, patience, curiosity, and/or openness during the psilocybin session. "Presence" refers to being totally available and present with the subject during all stages of the psilocybin session, and exuding calmness at all times. "Curiosity" refers to interest and willingness to understand the subject's experience, without making assumptions. "Patience" means that the therapist facilitates the participant taking as much time as needed to explore their experiences without controlling the natural urge to help or direct the experience. "Openness" is the ability of the therapist to remain cognitively and experientially open, including a capacity to be curious about how the subject's mind may uniquely choreograph the unfolding content of a session. This includes welcoming all emotions and expressions that might occur.

In some embodiments, the psychological support may comprise curious questioning. In this technique, brief, but detailed, questioning of subjects is used to help the subjects shift and sustain their attention towards different levels of cognition and emotions ("How does that make you feel?") Due to the applicability across a range of mental states and within various settings, the technique of curious questioning can typically be used safely and consistently during the psilocybin session, regardless of the quality or intensity of the experience of each subject.

In some embodiments, the level of psychological support will vary during the various stages of the subject's psilocybin experience (e.g., the initial stage, the early stage, the peak stage, and the late stage). In some embodiments, the type of psychological support will vary during the various stages of the subject's psilocybin experience (e.g., the initial stage, the early stage, the peak stage, and the late stage). Because non-dual, ego-dissolution or "unitive" experiences have been shown to positively correlate with the magnitude and durability of the clinical response, the therapist will, in some embodiments, attend to such states with particular care.

In some embodiments, a subject may experience of a compromised sense of self during the subject's psilocybin experience. In some embodiments, this is interpreted from a psychoanalytic perspective as a disruption of ego-boundaries, which results in a blurring of the distinction between self-representation and object-representation, and precludes the synthesis of self-representations into a coherent whole.

In some embodiments, non-dual, ego-dissolution or "unitive" experiences refer to an altered state of consciousness in which there is a reduction in the self-referential awareness that defines normal waking consciousness, resulting in a compromised sense of "self" and instead only a undivided background awareness, often characterised by a sense of unity or "oneness" that exceeds sensory or cognitive apprehension. In some embodiments, a non-dual experience is state of consciousness in which the subject-object dichotomy in normal waking consciousness is substituted for a unified background awareness that is centreless and undivided. In some embodiments, an ego dissolution experience is a spontaneously occurring state of consciousness where there is a reduction in the self-referential awareness that defines normal waking consciousness, resulting in a compromised sense of "self". In some embodiments, a unitive experience is an experience characterised by a sense of unity or "oneness" that exceeds sensory or cognitive apprehension.

At the initial and early stage of the psilocybin session, psychological support may be used to reduce severe and/or prolonged anxiety. Anxiety prior to or during the onset of psilocybin effects is not uncommon, and the therapists may be specially trained to recognize and actively manage subjects through such periods of anxiety until the subject is comfortable enough to continue on their own. In some embodiments, therapists validate the subject's feelings of anxiety without providing interpretations of perceptual disturbances or guiding subjects towards a particular image or memory, other than encouraging them to stay relaxed and open to the emergent experiences. For example, in some embodiments, the therapist may help alleviate anxiety using a grounding exercise. In such an exercise, the subject may be encouraged to pay attention to the sounds around them or to sensations on their skin when touching the bed/couch, ground, or other objects.

At the initial and early stage of the psilocybin session, the therapist may encourage the subject to lie down, practice relaxation and breathing exercises, and/or listen to calming music. In some embodiments, the therapist may remind the subject of the intention for the treatment session. For example, the therapist may ask the subject "What does feeling better or recovery feel like?" or any number of similar questions. Such reminders prior to the onset of or at the onset of psilocybin effects provide an implicit direction for the subjective experience during the psilocybin session. In some embodiments, the therapist may remind the subject that their primary task during this session is to simply collect new and interesting experiences which can then be discussed with the therapist after the session. The therapist may remind the participant of the purpose of the psilocybin therapy and the role of experiential processing, namely allowing the participant to be open and curious to whatever arises and encountering thoughts and feelings previously unknown to them. In some embodiments, the therapist emphasizes that this process inherently requires letting go and a willing passivity to the psychedelic experience.

During the acute onset of action, the subject might experience perceptual changes in visual, auditory or olfactory modes, and a range of unusual physical sensations. These experiences could be anxiety-provoking. In some embodiments, the therapist may practice reassuring "arm holding". This is where, upon the subject's request, a therapist will place his or her hand on the subject's wrist, arm, hand, or shoulder, as a way of helping the subject feel secure during this phase. This exercise may have been previously practiced during the pre-administration psychological support session.

In some embodiments, the therapist may encourage the subject to put on an eye mask, such as a Mindfold eyeshade. In some embodiments, the therapist encourages the subject to put on the eye mask before, during, or after the onset of the psilocybin's effects.

In some embodiments, the therapist may encourage the subject to put on headphones and listen to music. In some embodiments, the headphones reduce outside noise (e.g., "noise-cancelling" headphones). In some embodiments, the music is calming music such as instrumental (e.g., classical) music. In some embodiments, the music comprises nature sounds and/or the sound of moving water (e.g., ocean sounds). In some embodiments, the music comprises isochronic tones. In some embodiments, the music comprises moments of silence. In some embodiments, the music is emotionally evocative. In some embodiments, the music comprises a playlist which mirrors the pharmacodynamics of a typical high-dose psilocybin session: the initial stage, the early stage, the peak stage, and the late stage. In some embodiments, listening to music helps the subject to focus on their internal experience.

In case of prolonged anxiety or distress, therapists may, in some embodiments, actively guide participants through such experiences without interpreting or judging the experiences or giving advice. Once participants are comfortable, the therapist may encourage them to again engage in introspection.

During the peak and late stages of the psilocybin session, the therapist may encourage subjects to face and explore their experience, including the challenging ones. Therapists may direct subjects to participate self-directed inquiry and experiential processing to develop a different perspective on their personal challenges and conflicts, and to generate their own solutions. Such self-generated insights are not only therapeutic because of the emotional resolution, but also empowering to subjects.

As used herein, the term "self-directed inquiry" refers to directing attention to internal states. Subjects are encouraged to be curious about experiences in the present moment, including foreground and background thoughts, emotions, and physical sensations. During the preparation and integration stages, this inquiry might mean asking specific and detailed questions to help direct attention to internal states. However, during the period of drug action, inquiry might simply mean an attitude of openness to inner experiences.

As used herein, "experiential processing" refers to a participant's ability to maintain full attention on the experiences that come into awareness through self-directed enquiry. This includes a willingness and ability to be with and/or move 'in and through' even uncomfortable or challenging thoughts, feelings, sensations or emotions, until discomfort is diminished or resolved.

In some embodiments, the therapist will employ a transdiagnostic therapy. In some embodiments, the transdiagnostic therapy is a Method of Levels (MOL) therapy. In still further embodiments, the MOL therapy comprises Self-Directed Enquiry and Experiential Processing. Typically, MOL uses brief, but detailed, curious questioning to help subjects shift and sustain their attention towards different levels of cognition and emotions (Carey, 2006; Carey, Mansell & Tai, 2015). The emphasis within MOL is on identifying and working with a subject's underlying distress as opposed to just their symptoms. Such MOL related methods and techniques can include: (1) Self-directed enquiry—directing attention to internal states. Participants are encouraged to be curious about experiences in the present moment, including foreground and background thoughts, emotions, and physical sensations; during the preparation and integration stages, such enquiry can mean asking specific and detailed questions to help direct attention to internal states, although for some embodiments, during the period of drug action, enquiry can refer to an attitude of openness to inner experiences; and (2) Experiential processing—sustained focus on the experience; refers to a participant's ability to maintain full attention on the experiences that come into awareness through self-directed enquiry. This includes a willingness and ability to be with and/or move 'in and through' even uncomfortable or challenging thoughts, feelings, sensations or emotions, until discomfort is diminished or resolved.

In some embodiments, the psychological support comprises mindfulness-based therapy or CBT cognitive behavioral therapy (CBT). In some embodiments, the psychological support is informed by a functional theory of human behavior called Perceptual Control Theory.

Occasionally, the subject will try to avoid emerging experiences or distract him/herself while trying to regain cognitive control over the unusual state of their mind. Such distractions may take different forms. For example, the subject might want to engage in a conversation or prematurely describe in detail their experience, visions or insights. When this occurs, the therapist may aim to remain as silent as possible, thereby enabling the subject and his/her inner experience to direct the course of the psilocybin session. In some embodiments, the therapist may use active listening skills paired with prompts to encourage the subject to continue focusing attention on present experiences, particularly if the participant engages the therapist in conversation. In another example, a subject might ask to go to the bathroom or have a drink of water. The sudden and urgent character of such requests might suggest that they are really trying to avoid emerging material. In such cases, the therapist may encourage the subject to stay with the experience by simply redirecting their attention. For example, the therapist may say something like, "We will take a bathroom break at the end of this piece of music" or "I will get you water in a little while. Why don't you put the eye shades back on and relax for a few minutes?" If the subject is trying to avoid a difficult experience, they might listen to the suggestion and relax.

In some embodiments, spontaneous movement such as shaking, stretching or dancing while engaging with the experience is accepted and often encouraged, unless the movement seems to be a way to distract oneself from the experience. In some embodiments, if the subject continues to move around a lot, reminders to periodically return to a lying down position and to actively focus inwards may be provided.

The therapist is not required to understand, support or even have an opinion about the nature or content of the subject's experiences, but the therapist may validate them and convey openness toward the subject's own view of them without dismissing or pathologizing any experience based on its unusual content. These experiences may provide the subject with a perspective that goes beyond identification with their personal narrative. In some embodiments, the therapist will validate one or more of the subject's experiences. In some embodiments, validation of the experiences simply means acknowledging the courage of opening up to the experience and the possibility that any experience will serve the intention of the session.

In some embodiments, a therapist provides psychological support for approximately 4-8 hours immediately after administration of the psilocybin. In some embodiments, the therapist uses guided imagery and/or breathing exercises to calm the subject and/or focus the subject's attention. In some embodiments, the therapist holds the hand, arm, or shoulder of the subject. In some embodiments, the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

In some embodiments, the therapist avoids initiating conversation with the subject, but responds if the subject initiates conversation. Typically, active intervention is kept to a minimum during the treatment experience. In some embodiments, the subject is encouraged to explore their own mental space, and simple guided imagery may be used to assist relaxation. "Guided imagery" refers to an exercise wherein the subject is asked to imagine a scene (e.g., "Invite a scene, perhaps a landscape, and tell me where you find yourself"; "Imagine a place that feels safe to you.")

Post-Administration Psychological Support Session

In some embodiments, subjects may be encouraged to engage in post-administration integration sessions with their therapist. Integration is a process that involves processing, or embodying, a psychedelic experience within a therapeutic context. The process initially begins by the subject verbalising and reflecting upon any experience from the psilocybin session, and discussing it openly with their therapist. Successful integration of a psilocybin experience accommodates for emotional changes and comprises of translating experiences into new insights, perspectives, and subsequently new behaviors that can be used to benefit the subject's quality of life. New perspectives might in turn influence the participant's current knowledge or values and lead to new ways of relating to cognitions, emotions, behaviors and physical experiences.

In some embodiments, the goals and supportive methods used by the therapist throughout integration sessions should remain consistent, regardless of the intensity or content of the subjective experience explored by the subject. That said, the methods of support used by the therapist should accommodate for the full range of experiences a subject might have faced.

The integration process is not one that should be limited to the sessions with the therapist, and is a process that will likely continue to unfold beyond the visits in clinic. The therapist might encourage the participant to use methods such as spending time in nature, exercise, or creative expression to help facilitate the process further. The subject might also be encouraged to discuss experiences with their friends, family, and/or support network. The role of the integration sessions is not to cover and work on every experience, but to empower the participant by building their capacity to experientially process information safely. This enables the participant to continue self-directed integration, even outside of study visits.

In some embodiments, the subject participates in at least one psychological support session after administration of the psilocybin ("post-administration psychological support session"). In some embodiments, a post-administration psychological support session may be held on the same day as the psilocybin session, after the effects of the psilocybin have substantially worn off. In some embodiments, a post-administration psychological support session may be held the day after the psilocybin session. In some embodiments, a post-administration psychological support session may be held two days after the psilocybin session. In some embodiments, a post-administration psychological support session may be held three days after the psilocybin session. In some embodiments, a post-administration psychological support session may be held about one week after the psilocybin session. In some embodiments, a post-administration psychological support session may be held about two weeks after the psilocybin session. In some embodiments, a post-administration psychological support session may be held about one month after the psilocybin session. In some embodiments, a post-administration psychological support session may be held about three months after the psilocybin session. In some embodiments, a post-administration psychological support session may be held about six months after the psilocybin session. In some embodiments, a post-administration psychological support session may be held about twelve months after the psilocybin session.

In some embodiments, the subject may participate in one, two, three, four, five, six, seven, or eight post-administration psychological support sessions. In some embodiments, the subject may participate in at least two, or at least three post-administration psychological support sessions.

The post-administration psychological support sessions may be individual sessions, wherein a subject meets one-on-one with a therapist. In some embodiments, the psychological support sessions may be group sessions, wherein more than one subject meets with a single therapist, or more than one therapist. In some embodiments, one or more of the subject's family members or friends may be present at the post-administration psychological support session(s).

In some embodiments, the post-administration psychological support session may focus on integration of the psilocybin experience. Integration may involve processing a psychedelic experience in a therapeutic context. Integration may comprise psychological and somatic processing of the experience and a successful assimilation of insights into the subject's life for the purpose of growth, healing and/or well-being. During an integration session, a subject may be encouraged to talk about and reflect upon their experiences during the psilocybin session. In some embodiments, integration may comprise an external expression of the psilocybin experience, such as choice of words, tone of voice, gestures, and/or particular physical activities (yoga, exercise, bodywork, etc.) In some embodiments, integration comprises creatively expressing any insights or experiences gained during a psilocybin experience, for example through poetry, art, music/singing, dance, writing or drawing.

In some embodiments, the subject may be encouraged to reflect on both the thoughts and the feelings that he or she underwent during the psilocybin session, as well as to express those ideas and emotions into a concrete form that can serve as a tool for continuing to remember and integrate those lessons into the future. In some embodiments, the subject may be encouraged to acknowledge and connect with the range of the emotional cognitive and physical experiences of the psilocybin session, and relate them to current experiences in their life situation. This may be accomplished, for example, by discussing them initially with their therapist, and perhaps later with their family, friends, and support circle. Integration helps accommodate changes in emotional states as new insights are generated and integrated. When further explored through oscillating attention between foreground and background thoughts and emotions, such insights may lead to natural and effortless changes in perspectives or behaviors. In some embodiments, the integration process is not limited to initial integration meetings with the therapist, but continues to unfold spontaneously through a participant's own processing and actions in everyday life.

In the case of a low-intensity experience, the integration process might focus on the mental content that emerged during the hours of relaxation and introspection. This might also include reactions to what might have been an unremarkable experience, such as feeling of disappointment, anger, relief etc.

Psychological Support Provided Remotely

In some embodiments, psychological support may be provided remotely to a subject. For example, a therapist providing psychological support may not be in the same room, the same building, or in the same facility as a subject. Remote psychological support may be provided, for example by telephone (i.e., by voice call), by video call or video conference, by text, or by email.

In some embodiments, a pre-administration therapy session is conducted remotely. In some embodiments, a post-administration therapy session (e.g., an integration session) is conducted remotely.

In some embodiments, psychological support is provided remotely during the subject's psilocybin session. For example, in some embodiments, the subject takes the psilocybin in his or her own home, and a therapist provides psychological support by voice call, video call, text, email, etc., for at least 4-8 hours after the subject has taken the drug. In some embodiments, the subject takes the psilocybin in an administration facility as described herein, and the therapist provides psychological support to the subject a therapist provides psychological support by voice call, video call, text, email, etc., for at least 4-8 hours after the subject has taken the drug In some embodiments, remote psychological support is provided to the subject using a digital or electronic system. In some embodiments, the digital or electronic system may comprise one or more of the following features:

The digital or electronic system securely connects patients with one or more therapists or physicians for "virtual visits." These virtual visits may be introductory or routine.

The digital or electronic system allows a subject to qualify, prequalify, or register for a psilocybin-based clinical trial, or a psilocybin-based psychological support session.

The digital or electronic system is configured to help therapists and/or physicians manage and interact with patients. For example, the electronic system may allow the therapist to share documents with subjects, keep notes about sessions, or schedule future sessions.

The digital or electronic system is configured to provide alerts for crisis intervention. For example, the digital or electronic system may allow the subject to contact the therapist if they are feeling anxiety or otherwise urgently need to talk to the therapist.

The digital or electronic system is configured to help prepare the subject for a visit with their therapist and/or physician. For example, the digital or electronic system may contain information regarding psilocybin, the therapeutic protocol, etc.

The digital or electronic system is configured to allow the therapist to provide psychological support during the subject's psilocybin session. For example, the system may comprise a video calling or chat feature.

The digital or electronic system is configured to allow the therapist to provide psychological support during a post-administration session (e.g., an integration session).

The digital or electronic system is configured to track the subject's adherence to the treatment regimen or goals.

The digital or electronic system is configured to assess one or more clinical endpoints in the subject. For example the system may comprise one or more questionnaires or exercises for the subject to complete. Results may be made available to the subject's physician and/or therapist.

In some embodiments, the digital or electronic system is an "app" for use on a mobile phone or a computer. In some embodiments, the digital or electronic system is a website. In some embodiments, the digital or electronic system comprises a "chat" feature which allows communication between the subject and the therapist in real time. In some embodiments, the website comprises a video calling feature, which allows for the therapist to communicate with the subject using video communication. In some embodiments, the digital or electronic system is configured to allow a single therapist to provide psychological support to one or more subjects at or around the same time.

In some embodiments, psychological support sessions may be pre-recorded (e.g., audio or video recording) and provided to the subject for use at the subject's convenience via the digital or electronic system.

Administration Facility, "Set and Setting"

As used herein, the term "set and setting" refers to the subject's mindset ("set") and the physical and social environment ("setting") in which the user has the psilocybin session. In some embodiments, the psilocybin may be administered in a particular set and setting. In some embodiments, the set and setting is controlled, to the extent possible, to maximize therapeutic benefit of the psilocybin session.

In some embodiments, the psilocybin is administered by in a facility specifically designed for psilocybin administration. Administration of the psilocybin to the subject in a facility where the subject feels safe and comfortable may help ease anxiety in the subject, and may facilitate maximum clinical benefit. Psilocybin may be administered to a subject, for example, in the subject's home or at a clinical facility.

In some embodiments, the psilocybin is administered to the subject in a facility (e.g., a room) with a substantially non-clinical appearance. For example, the psilocybin can be administered in a room that comprises soft furniture (e.g., plush couches, chairs, or pillows) and/or plants. In some embodiments, the room may be decorated using muted colors (e.g., greyed, dulled, or desaturated colors). In some embodiments, the light in the room is dimmed and/or light levels are kept or adjust to be relatively low. In some embodiments, the room lighting is adjusted for intensity and/or color. In some embodiments, a virtual reality or augmented reality system (e.g., computer with visual/graphical and auditory outputs) is used. In some embodiments, the room comprises a sound system, for example a high-resolution sound system. In some embodiments, the sound system can allow for simultaneous ambient and earphone listening. In some embodiments, the subject may bring meaningful photographs or objects into the administration room.

In some embodiments, the room comprises a couch. In some embodiments, the room comprises a bed. In some embodiments the room comprises more than one couch or bed, such as 2, 3, 4, 5, 6, 7, 8, 9, or 10 couches or beds. In some embodiments, the subject sits on or lies in the couch or bed for approximately 4-8 hours, or a substantial fraction thereof, immediately after administration of the psilocybin. In some embodiments, the subject listens to music for approximately 4-8 hours, or a substantial fraction thereof, immediately after administration of the psilocybin. In some embodiments, the subject wears an eye mask for approximately 4-8 hours, or a substantial fraction thereof, immediately after administration of the psilocybin. In some embodiments, the subject is provided with a weighted blanket.

In some embodiments, each subject is supervised by one therapist during the psilocybin session. In some embodiments, each subject is supervised by more than one therapist during the psilocybin session, such as two therapists, three therapists, four therapists, or five therapists. In some embodiments, one therapist multiple subjects, wherein each subject is participating in a psilocybin session. For example, one therapist may supervise two, three, four, five, six, seven, eight, nine, or ten subjects.

Embodiments of the disclosure include use of additional tools and/or technique(s) with dosage/administration, including various transcranial magnetic stimulation (TMS) methods and protocols, for example, prior or subsequent to one or more dosing(s), biofeedback devices, etc.

Some embodiments can be used with a digital health product or digital solution. Teachings of the disclosure include utilization of such digital health products and/or related digital biomarkers as diagnostic and/or prognostic tools for patient monitoring and management pre-treatment, during treatment, and/or post treatment. Digital biomarkers can include, by way of non-limiting example: Number of and/or time of phone calls/e-mails/texts; word length in text communication; Gestures used (taps, swipes, or other); Gyroscope derived information e.g. orientation of the phone; Acceleration of the phone; Keystroke patterns; Location derived information from GPS; facial expressions and/or microexpressions; voice or vocal markers; natural language processing; social media use; sleep patterns; specific words or emojis used or not used; and/or the like. For example, in one embodiment, a digital health product can be utilized to determine dosing amount and/or dosing frequency, indicator of a need for re-dosing, re-dosing amount, a warning or alert, as tracking of compliance, etc.

In some embodiments, methods of treatment can include providing a clearance time for a subject or patient, such one or more medications is not present or substantially cleared from the system of the subject/patient. For example, methods of treatment can be configured such that, upon administration, the subject is not taking other serotonergic medications such as: selective-serotonin reuptake inhibitors, selective norepinephrine reuptake inhibitors, tricyclic antidepressants, monoamine oxidase inhibitors and/or antipsychotics. In some embodiment, the method of treatment include treatment concurrently with one or more medications, including but not limited to selective-serotonin reuptake inhibitors, selective norepinephrine reuptake inhibitors, tricyclic antidepressants, and/or monoamine oxidase inhibitors. In some embodiments, the method include treatment such that subjects or patients take concomitant compounds or medications, including but not limited to benzodiazepines, cannabidiol (CBD) and/or other cannabinoids (e.g., THC (tetrahydrocannabinol); THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin); CBCV (cannabichromevarin); CBGV (cannabigerovarin); CBGM (cannabigerol monomethyl ether); CBE (cannabielsoin); CBT (cannabicitran); and/or the like) magnesium, Levomefolic acid, e.g., for a period of time prior to, just prior to, and/or at the same time as receiving psilocybin.

In some embodiments, the method includes treatment such that a subject has not taken one or more medications, particularly has not taken one or more serotonergic medications for at least 2 days, at least, 3 days, at least 4 days, at least 5 days, at least six days, at least 1 week, at least 2, 3, or 4 weeks before administration of the disclosed psilocybin compound.

In some embodiments, the method and/or treatment can comprise subperceptual-dosing (e.g., a dose of less than 3 mg, 2.5 mg, 2 mg, 1.5 mg, 1 mg, 0.9 mg, 0.8 mg, 0.7 mg, 0.6 mg, 0.5 mg, 0.4 mg, 0.3 mg, 0.2 mg, or 0.1 mg) prior to and/or following the administration of a relatively larger single dose or multiple doses (given a few days to a few weeks apart), where the relatively larger single dose or multiple doses is one or more of 5 mg or more, 10 mg or more, 15 mg or more, 20 mg or more, 25 mg or more, 30 mg or more, 35 mg or more, 40 mg or more, 45 mg or more, 50 mg or more.

Embodiments of the disclosure include method utilizing a digital biomarker, for example, as a diagnostic and/or prognostic tool for patient management pre-, during and/or post treatment with psilocybin wherein the digital biomarker is one or more biomarkers associated with executive function, cognitive control, working memory, processing speed, and/or emotional valence.

In some embodiments the digital biomarker is identified from patterns in smartphone use such as swipes, taps, and other touchscreen activities, and can be scientifically validated to provide measurements of subject status, such as cognition and mood, including, by way of non-limiting example, as disclosed in one or more of the following, each of which is herein expressly incorporated by reference for all purposes: US20170086727, US20170258382, US20170258383, US20170287348, U.S. Ser. No. 10/148, 534, U.S. Pat. No. 9,737,759, and/or U.S. Ser. No. 10/231, 651.

Biomarkers which may serve as a diagnostic and/or prognostic tool for patient management pre, during and/or post treatment may be identified using one or more of: Number of and/or time of phone calls/e-mails/texts; word length in text communication; Gestures used (taps, swipes, or other); Gyroscope derived information e.g. orientation of the phone; Acceleration of the phone; Keystroke patterns; Location derived information from GPS; facial expressions and/or microexpressions; voice or vocal markers; natural language processing; social media use; sleep patterns; specific words or emojis used or not used; and/or the like. In some embodiments, health components and/or connected biomonitors and/or smart devices/wearables can be utilized to collect information to be used in diagnostic and/or prognostic outputs. For example, in some embodiments, a heart rate monitor or similar device can collect a subject's data and heart rate variability (for example only, as disclosed in U.S. Ser. No. 10/058,253, the entirety of which is herein incorporated by reference) can be used to assess/determine a metric relating to the subject's current emotional state, relative change in emotional state, etc., which can be used in determining a new or follow-on treatment plan, adjusting a treatment plan, etc.

In accordance with a further aspect of the disclosure there is provided a method of assessing a subject pre, during and/or post treatment of a central nervous system disorder to determine whether to provide a psilocybin treatment or a further psilocybin treatment comprising monitoring one or more biomarkers associated with executive function, cognitive control, working memory, processing speed, and emotional valence, and determining the treatment based on an outcome. The method can further comprise the step of administering psilocybin for a first or a subsequent time.

In some embodiments, the biomarker is identified from patterns in smartphone use such as swipes, taps, and other touchscreen activities, and are scientifically validated to provide measurements of cognition and mood. For example, in some instances, the pattern is identified using one or more of: Number of and/or time of phone calls/e-mails/texts; word length in text communication; Gestures used (taps, swipes, or other); Gyroscope derived information e.g. orientation of the phone; Acceleration of the phone; Keystroke patterns; Location derived information from GPS; facial expressions and/or microexpressions; voice or vocal markers; natural language processing; social media use; sleep patterns; specific words or emojis used or not used; and/or the like.

Embodiments include a method of assessing a subject pre, during and/or post treatment of a central nervous system disorder to determine whether to provide a psilocybin treatment or a further psilocybin treatment comprising monitoring one or more biomarkers associated with executive function, cognitive control, working memory, processing speed, and emotional valence, and determining the treatment based on an outcome; the method can further comprise administering psilocybin for a first or a subsequent time.

In some embodiments, the disclosure provides for treating 2 or more subjects, the method comprising administering to each subject a therapeutically-effective dose of psilocybin at the same time or substantially the same time (e.g., dosed within several minutes of each other, within 5, 10, 15, 20, 25, or 30 min of each other), wherein each subject is aware of the other subject also receiving treatment. In some embodiments, the subjects are in the same room. In some embodiments, the subjects are in different rooms.

In some embodiments, the disclosure provides a method of treating a subject, the method comprising administering to the subject a therapeutically-effective dose of psilocybin, and providing a virtual reality/immersive reality digital tool. In some embodiments, the light in the room is dimmed and/or light levels are kept or adjusted to be relatively low. In some embodiments, darkened glasses or eye shades are provided. In some embodiments, the room lighting is adjusted for intensity and/or color. In some embodiments, a virtual reality or augmented reality system (e.g., computer with visual/graphical and auditory outputs) is used.

Subjects

In some embodiments, the subject is a male. In some embodiments, the subject is a female. In some embodiments, the female subject is pregnant or post-partum. In some embodiments, the subject is attempting to reduce or eliminate their use of a pharmaceutical agent, such as an antidepressant or an anti-epileptic drug. In some embodiments, the subject is attempting to reduce or eliminate their use of the pharmaceutical agent before becoming pregnant, having surgery or other medical procedure, or starting to use different pharmaceutical agent.

The subject may be a geriatric subject, a pediatric subject, a teenage subject, a young adult subject, or a middle aged subject. In some embodiments, the subject is less than about 18 years of age. In some embodiments, the subject is at least about 18 years of age. In some embodiments, the subject is about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 85-90, about 90-95, or about 95-100 years of age.

The subject may have a chronic disease or a terminal disease. In some embodiments, the subject may have a life-altering disease or condition (such as the loss of a limb or onset of blindness).

The subject may have recently been diagnosed with a disease, disorder, or condition. For example, the subject may have been diagnosed within 1 month, within 3 months, within 6 months, or within 1 year. In some embodiments, the subject may have been living with a disease, disorder, or condition for an extended period time, such as at least 6 months, at least 1 year, at least 3 years, at least 5 years, or at least 10 years.

In some embodiments, the subject may be a cancer patient, such as a Stage 4 or terminal cancer patient. In some embodiments, the subject may have been determined to have a limited time to live, such as less than 1 year, less than 6 months, or less than 3 months.

The subject may have previously taken a psychedelic drug, or may have never previously taken a psychedelic drug. For example, the subject may or may not have previously taken psilocybin, a psilocybin mushroom ("magic mushroom"), LSD (lysergic acid diethylamide or acid), mescaline, or DMT (N,N-Dimethyltryptamine).

In some embodiments, the subject may have previously taken one or more serotonergic antidepressants (e.g., selective serotonin reuptake inhibitors (SSRIs)). In some embodiments, the subject has never previously taken a serotonergic antidepressant. In some embodiments, the subject has not taken any serotonergic antidepressants for at least 2 weeks, at least 4 weeks, or at least 6 weeks prior to receiving psilocybin.

In some embodiments, the subject may have previously received electroconvulsive therapy (ECT). In some embodiments, the subject has not received any ECT for at least 2 weeks, at least 4 weeks, or at least 6 weeks prior to receiving psilocybin.

The subject may have a medical condition that prevents the subject from receiving a particular medical therapy (such as an SSRI or ECT). In some embodiments, the subject may have previously had an adverse reaction to a particular medical therapy (such as an SSRI or ECT). In some embodiments, a prior medical therapy (such as an SSRI or ECT) was not effective in treating a disease, disorder, or condition in the subject.

Diseases, Disorders, and/or Conditions to be Treated

Provided herein are methods of treating a subject in need thereof, the method comprising administering to the subject a therapeutically-effective dose of therapeutically effective amount of psilocybin, a prodrug of psilocybin, an active metabolite of psilocybin, or a prodrug of an active metabolite of psilocybin.

Anxiety Disorders

In some embodiments, a method for treating one or more anxiety disorders in a subject in need thereof comprising administering to the subject an effective amount of psilocybin or an active metabolite thereof is disclosed herein. In some embodiments, the active metabolite is psilocin.

As used herein, the term "anxiety disorder" refers to a state of apprehension, uncertainty, and/or fear resulting from the anticipation of an event and/or situation. Anxiety disorders cause physiological and psychological signs or symptoms. Non-limiting examples of physiological symptoms include muscle tension, heart palpitations, sweating, dizziness, shortness of breath, tachycardia, tremor, fatigue, worry, irritability, and disturbed sleep. Non-limiting examples of psychological symptoms include fear of dying, fear of embarrassment or humiliation, fear of an event occurring, etc. Anxiety disorders also impair a subject's cognition, information processing, stress levels, and immune response. In some embodiments, the methods disclosed herein treat chronic anxiety disorders. As used herein, a "chronic" anxiety disorder is recurring.

Anxiety disorders are thought to be the most prevalent class of psychiatric disorders, with over 60 million people in Europe affected each year. While, according to epidemiological surveys, it is estimated that one third of the population is affected by an anxiety disorder during their lifetime.

Non-limiting examples of anxiety disorders include acute stress disorder, anxiety due to a medical condition, generalized anxiety disorder, panic disorder, panic attack, a phobia, post-traumatic stress disorder, obsessive-compulsive disorder, separation anxiety disorder, social anxiety disorder, substance-induced anxiety disorder, or selective mutism.

In some embodiments, the subject in need thereof develops an anxiety disorder after experiencing the effects of a disease. The effects of a disease include diagnosis of an individual with said disease, diagnosis of an individual's loved ones with said disease, social isolation due to said disease, quarantine from said disease, or social distancing as a result of said disease. In some embodiments, an individual is quarantined to prevent the spread of the disease. In some embodiments, the disease is COVID-19, SARS, or MERS. In some embodiments, a subject develops an anxiety disorder after job loss, loss of housing, or fear of not finding employment.

In some embodiments, an anxiety disorder comprises a medical diagnosis based on the criteria and classification from Diagnostic and Statistical Manual of Medical Disorders, 5th Ed. In one embodiment, an anxiety disorder comprises a medical diagnosis based on an independent medical evaluation.

In some embodiments, a method for treating a generalized anxiety disorder in a subject in need thereof comprising administering to the subject an effective amount of psilocybin or an active metabolite thereof is disclosed herein. Generalized anxiety disorder is characterized by excessive anxiety and worry, fatigue, restlessness, increased muscle aches or soreness, impaired concentration, irritability, and/or difficulty sleeping. In some embodiments, a subject with generalized anxiety disorder does not have associated panic attacks.

In some embodiments, a method for treating a social anxiety disorder in a subject in need thereof comprising administering to the subject an effective amount of psilocybin or an active metabolite thereof is disclosed herein. As used herein, "social anxiety disorder" is a marked fear or anxiety about one or more social situations in which the individual is exposed to possible scrutiny by others. Non-limiting examples of situations which induce social anxiety include social interactions (e.g., having a conversation, meeting unfamiliar people), being observed (e.g., eating or drinking), and performing in front of others (e.g., giving a speech). In some embodiments, the social anxiety disorder is restricted to speaking or performing in public. In some embodiments, treating according to the methods of the disclosure reduces or ameliorates a symptom of social anxiety disorder. In some embodiments, the reduction/amelioration in a symptom of a social anxiety disorder can be measured using any one of the assessments described herein. In some embodiments, after treating the symptom is reduced compared to prior to treating by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, a method for treating panic disorder in a subject in need thereof comprising administering to the subject an effective amount of psilocybin or an active metabolite thereof is disclosed herein. A subject with panic disorder experiences panic attacks, which are sudden feelings of terror when there is no real danger. A subject experiencing a panic attack may feel as if he or she is losing control. In some embodiments, a subject with a panic disorder has physical symptoms, including but not limited to, a fast heartbeat, chest or stomach pain, breathing difficulty, weakness or dizziness, sweating, feeling hot or cold, tingly or numb hands. In some embodiments, treating according to the methods of the disclosure reduces the incidence of panic attacks compared to prior to said treatment. In some embodiments, treating according to the methods of the disclosure reduces the number of panic attacks per month by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, a method for treating a phobia in a subject in need thereof comprising administering to the subject an effective amount of psilocybin or an active metabolite thereof is disclosed herein. A phobia is an irrational fear of something that is unlikely to cause harm. Phobias cause anxiety, fear, and panic. In some embodiments, the phobia is agoraphobia, acrophobia, aerophobia, arachnophobia, astraphobia, autophobia, claustrophobia, homophobia, hydrophobia, ophidiophobia, zoophobia, alektorophobia, onomatophobia, pogonophobia, nephophobia, and cryophobia. In some embodiments, the subject has agoraphobia. In some embodiments, the phobia is a specific phobia. In some embodiments, the specific phobia is an animal phobia, natural environment phobia, blood-injection-injury phobia, or situational phobia. In some embodiments, after treating according to the disclosure, one or more symptoms of a phobia are reduced.

In some embodiments, a method for treating a post traumatic stress disorder (PTSD) in a subject in need thereof comprising administering to the subject an effective amount of psilocybin or an active metabolite thereof is disclosed herein. As used herein, the term "post traumatic stress disorder" refers to a condition developed after experiencing and/or witnessing a traumatic event or learning that a traumatic event has happened to a loved one. Non-limiting examples of traumatic events include exposure to war, rape or sexual violence, a physical attack, disease, a mugging, childhood physical or sexual violence, kidnapping or being taken hostage, terrorist attacks, torture, nature disasters and/or severe accidents. In some embodiments, the post-traumatic stress disorder is caused by trauma associated with a pandemic due to an infectious disease, such as, but not limited to COVID-19. For example, the trauma may be caused by a pandemic, such as COVID-19, a mandated quarantine, social isolation, damage to one's health, or damage to a family member's health as a result of the infectious disease. In some embodiments, trauma results from job loss. In some embodiments, trauma results from loss of housing. In some embodiments, trauma results from fear of not finding employment.

In some instances, a person shows symptoms of post traumatic stress disorder within a week of experiencing of the traumatic event. In some instances, a person shows symptoms of post traumatic stress disorder within a month of experiencing of the traumatic event. In some instances, a person shows symptoms of post traumatic stress disorder within a year of experiencing of the traumatic event. In some instances, a person shows symptoms of post traumatic stress disorder after a year or more of experiencing of the traumatic event. In some instances, post traumatic stress disorder comprises a person re-experiencing the trauma event through intrusive distressing recollections of the event, flashbacks, and/or nightmares. In some instances, a symptom of post traumatic stress disorder comprises emotional numbness and avoidance of places, people, and activities that are reminders of the trauma. In some instances, a symptom of post traumatic stress disorder comprises increased arousal such as difficulty sleeping and concentrating, feeling anxious, and being easily irritated and angered.

In some embodiments, a method for treating moral injury in a subject in need thereof comprising administering to the subject an effective amount of psilocybin or an active metabolite thereof is disclosed herein. Moral injury may occur in individuals/populations with PTSD or at risk of developing PTSD (e.g. veterans or physicians). Moral injury may result from when an individual transgresses their own moral boundaries, often in high-stakes situations and where pressure is applied by higher authorities.

In some embodiments, a method for treating acute stress disorder in a subject in need thereof comprising administering to the subject an effective amount of psilocybin or an active metabolite thereof is disclosed herein. A subject may be determined to have acute stress disorder if the subject exhibits PTSD symptoms that have been present for about three days to about 1 month.

In some embodiments, a method for treating adjustment disorder in a subject in need thereof comprising administering to the subject an effective amount of psilocybin or an active metabolite thereof is disclosed herein. A subject may be determined to have adjustment disorder when the traumatic event experienced by a subject and/or the subject's symptoms do not meet the criteria required for a diagnosis of PTSD.

In some embodiments, a method for treating an obsessive-compulsive and related disorder in a subject in need thereof comprising administering to the subject an effective amount of psilocybin or an active metabolite thereof is disclosed herein. In some embodiments, the obsessive-compulsive and relating disorder is obsessive compulsive disorder, body dysmorphic disorder, hoarding disorder, dermatillomania, trichotillomania, excoriation, substance-induced obsessive compulsive and related disorder, or an obsessive-compulsive disorder due to another medical condition, or a combination thereof.

In some embodiments, a method for treating obsessive-compulsive disorder (OCD) in a subject in need thereof comprising administering the subject an effective amount of psilocybin or an active metabolite thereof is disclosed herein. An estimated 2-4% of adults meet the DSM criteria for OCD. There are mixed findings regarding gender differences, but OCD appears to be more common in males in childhood and in females in adolescence and adulthood. Up to 15% of those diagnosed with OCD have a history of suicide attempts. Pregnant and postpartum women have been found to exhibit higher prevalence of OCD than general populations. The prevalence of OCD in those over the age of 15 in Canada is estimated to be 1 in 100 people, this diagnosis was associated with adverse childhood experiences and likelihood of having lower income. Mortality rate of those with OCD is significantly higher even after adjusting for somatic comorbidities. Quality of life is significantly lower in those with OCD.

OCD involves the presence of impulses or urges associated with anxiety (obsessions) and repetitive behaviors or mental acts that exist in response to obsessions (compulsions).

A subject is diagnosed with obsessive compulsive disorder if the obsessions and compulsions significantly impact daily life. In some embodiments, a subject with OCD does not realize that the obsessions and compulsions are excessive or unreasonable. As used herein, an "obsession" is an intrusive, repetitive, and/or persistent thought, urge, and/or image that causes distress. In some embodiments, obsessions cannot be suppressed or ignored. In some embodiments, a subject with OCD is unaware that these thoughts are not a real threat but are generated by their mind.

As used herein, a "compulsion" is excessive and repetitive ritualistic behaviour that must be performed to prevent something bad from happening. In some embodiments, a compulsion is performed by a subject to reduce anxiety caused by obsessive thoughts. In some embodiments, a subject with OCD treated according to the methods described herein, performing one or more compulsions takes up at least about 15 minutes to about 20 hours per day, for example, about 15 minutes per day, about 30 minutes per day, about 45 minutes per day, about 1 hour per day, about 1.5 hours per day, about 2 hours per day, about 2.5 hours per day, about 3 hours per day, about 3.5 hours per day, about 4 hours per day, about 4.5 hours per day, about 5 hours per day, about 5.5 hours per day, about 6.0 hours per day, about 6.5 hours per day, about 7 hours per day, about 7.5 hours per day, about 8 hours per day, about 8.5 hours per day, about 9 hours per day, about 9.5 hours per day, about 10 hours per day, about 10.5 hours per day, about 11 hours per day, about 11.5 hours per day, about 12 hours per day, about 12.5 hours per day, about 13 hours, about 13.5 hours, about 14 hours, about 14.5 hours, about 15 hours, about 15.5 hours per day, about 16 hours per day, about 16.5 hours per day, about 17 hours per day, about 17.5 hours per day, about 18 hours per day, about 18.5 hours per day, about 19 hours per day, about 19.5 hours per day, or about 20 hours per day. In some embodiments, after treating according to the methods of the disclosure, the length of time a subject spends performing compulsions compared to prior to said treating decreases by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

In some embodiments, the obsessive compulsive and related disorder is trichotillomania. Trichotillomania is a disorder that involves recurrent, irresistible urges to pull out hair from your scalp, eyebrows, or other areas of your body. In some embodiments, a subject with trichotillomania repeatedly attempts to decrease or stop the recurrent hair pulling. In some embodiments, a subject with trichotillomania has hair loss that may cause bald spots. In some embodiments, a subject with trichotillomania ingests the pulled hair or parts thereof. In some embodiments, a subject with trichotillomania that ingests the pulled hair or parts thereof develops a trichobezoar or a hairball in the intestines or stomach. In some embodiments, after treating according to the methods of the disclosure, a subject's trichotillomania improves compared to prior to said treatment.

In some embodiments, the subject with an anxiety disorder has one or more comorbidities. Non-limiting examples of comorbidities include endocrine and/or metabolic diseases, gastrointestinal diseases, cardiovascular diseases, psychiatric disorders, or a neuroses. In some embodiments, the comorbidity is anxiety disorder, depressive disorder, psychotic disorder, developmental disorder, eating disorder, attention-deficit hyperactivity disorder (ADHD), COVID-19, disorders associated with COVID-19, attention deficit disorder (ADD), autism spectrum disorder (ASD), tic disorder, bipolar disorder, conduct disorder, mental retardation, or a combination thereof. In some embodiments, the comorbidity is a mood disorder, major depressive disorder, bipolar disorder, schizophrenia, an eating disorder, attention deficit/hyperactivity disorder, epilepsy, cardiovascular disease, migraine, irritable bowel syndrome, dementia, Alzheimer's disease, Parkinson's disease, or combinations thereof. In some embodiments, the comorbidity is depression, generalized anxiety, agoraphobia, or panic disorder. In some embodiments, the comorbidity is major depression. In some embodiments, the comorbidity is an eating disorder. In some embodiments, the comorbidity is ADHD. In some embodiments, the comorbidity is ASD. In some embodiments, the comorbidity is COVID-19, disorders associated with COVID-19, or both. In some embodiments, the comorbidity is COVID-19. In some embodiments, the comorbidity is a disorder associated with COVID-19. Non-limiting examples of disorders associated with COVID-19 include post-traumatic stress disorder, anxiety disorder, acute stress disorder, adjustment disorder, or panic disorder. In some embodiments, the comorbidity is major depressive disorder, bipolar disorder, irritable bowel disease, or irritable bowel syndrome.

In some embodiments, no other treatment is administered to the subject to treat anxiety disorder after administration of psilocybin.

In some embodiments, the subject with anxiety disorder is administered at least one additional therapy and/or therapeutic. In some embodiments, administration of an additional therapy and/or therapeutic is prior to administration of psilocybin. In some embodiments, administration of an additional therapy and/or therapeutic is after administration of psilocybin. In some embodiments, administration of an additional therapy and/or therapeutic is concurrent with administration of psilocybin.

In some embodiments, the additional therapy is an antidepressant, an anticonvulsant, lisdexamfetamine dimesylate, an antipsychotic, an anxiolytic, an anti-inflammatory drug, a benzodiazepine, an analgesic drug, a cardiovascular drug, or combinations thereof.

In some embodiments, the additional therapy is a benzodiazepine. In some embodiments, the benzodiazepine is diazepam or alprazolam.

In some embodiments, the additional therapy is a N-methyl-D-aspartate (NMDA) receptor antagonist. In some embodiments, the NMDA receptor antagonist is ketamine.

In some embodiments, the additional therapy is an antidepressant. In some embodiments, an antidepressant indirectly affects a neurotransmitter receptor, e.g., via interactions affecting the reactivity of other molecules at a neurotransmitter receptor. In some embodiments, an antidepressant is an agonist. In one embodiment, an antidepressant is an antagonist. In some embodiments, an antidepressant acts (either directly or indirectly) at more than one type of neurotransmitter receptor. In some embodiments, an antidepressant is chosen from buproprion, citalopram, duloxetine, escitalopram, fluoxetine, fluvoxamine, milnacipran, mirtazapine, paroxetine, reboxetine, sertraline, and venlafaxine.

In some embodiments, the antidepressant is a tricyclic antidepressant ("TCA"), selective serotonin reuptake inhibitor ("SSRI"), serotonin and noradrenaline reuptake inhibitor ("SNRI"), dopamine reuptake inhibitor ("DRI"), noradrenaline reuptake Monoamine oxidase inhibitor ("MAOI"), including inhibitor ("NRU"), dopamine, serotonin and noradrenaline reuptake inhibitor ("DSNRI"), a reversible inhibitor of monoamine oxidase type A (RIMA), or combination thereof. In some embodiments, the antidepressant is a TCA. In some embodiments, the TCA is imipramine or clomipramine. In some embodiments, the anti-depressant is an SRI. In some embodiments, the SSRI is escitalopram, paroxetine, sertraline, fluvoxamine, fluoxetine, or combinations thereof. In some embodiments, the SNRI is venlafaxine. In some embodiments, the additional therapy is pregabalin.

In some embodiments, the additional therapeutic is an anticonvulsant. In some embodiments, the anticonvulsant is gabapentin, carbamazepine, ethosuximide, lamotrigin, felbamate, topiramate, zonisamide, tiagabine, oxcarbazepine, levetiracetam, divalproex sodium, phenytoin, fos-phyenytoin. In some embodiments, the anticonvulsant is topiramate.

In some embodiments, the additional therapeutic is an antipsychotic. In some embodiments, the antipsychotic is a phenothiazine, butryophenone, thioxanthene, clozapine, risperidone, olanzapine, or sertindole, quetiapine, aripiprazole, zotepine, perospirone, a neurokinin-3 antagonist, such as osanetant and talnetant, rimonabant, or a combination thereof.

In some embodiments, the additional therapeutic is an anti-inflammatory drug. In some embodiments, the anti-inflammatory drug is a nonsteroidal antiinflammatory drugs (NSAIDS), steroid, acetaminophen (COX-3 inhibitors), 5-lipoxygenase inhibitor, leukotriene receptor antagonist, leukotriene A4 hydrolase inhibitor, angiotensin converting enzyme antagonist, beta blocker, antihistaminic, histamine 2 receptor antagonist, phosphodiesterase-4 antagonist, cytokine antagonist, CD44 antagonist, antineoplastic agent, 3-hydroxy-3-methylglutaryl coenzyme A inhibitor (statins), estrogen, androgen, antiplatelet agent, antidepressant, *Helicobacter pylori* inhibitors, proton pump inhibitor, thiazolidinedione, dual-action compounds, or combination thereof.

In some embodiments, the additional therapeutic is an anti-anxiolytic. In one embodiment, an anxiolytic is chosen from alprazolam, an alpha blocker, an antihistamine, a barbiturate, a beta blocker, bromazepam, a carbamate, chlordiazepoxide, clonazepam, clorazepate, diazepam, flurazepam, lorazepam, an opioid, oxazepam, temazepam, or triazolam.

In some embodiments, the subject with anxiety disorder is administered at least one therapy. Non-limiting examples of therapies include transcranial magnetic stimulation, cognitive behavioral therapy, interpersonal psychotherapy, dialectical behavior therapy, mindfulness techniques, or acceptance, commitment therapy, or combinations thereof.

In some embodiments, at least one sign or symptom of an anxiety disorder is improved following the administration of the psilocybin or active metabolite thereof. In some embodiments, a sign or symptom of an anxiety disorder is measured according to a diary assessment, an assessment by a clinician or caregiver, or a clinical scale. In some embodiments, psilocybin treatment causes a demonstrated improvement in one or more of the following: State-Trait Anxiety Inventory (STAI), Beck Anxiety Inventory (BAI), Hospital Anxiety and Depression Scale (HADS), Generalized Anxiety Disorder questionnaire-IV (GADQ-IV), Hamilton Anxiety Rating Scale (HARS), Leibowitz Social Anxiety Scale (LSAS), Overall Anxiety Severity and Impairment Scale (OASIS), Hospital Anxiety and Depression Scale (HADS), Patient Health Questionnaire 4 (PHQ-4), Social Phobia Inventory (SPIN), Brief Trauma Questionnaire (BTQ), Combat Exposure Scale (CES), Mississippi Scale for Combat-Related PTSD (M-PTSD), Posttraumatic Maladaptive Beliefs Scale (PMBS), Perceived Threat Scale (DRRI-2 Section: G), PTSD Symptom Scale—Interview for DSM-5 (PSS-1-5), Structured Interview for PTSD (SI-PTSD), Davidson Trauma Scale (DTS), Impact of Event Scale-Revised (IES-R), Posttraumatic Diagnostic Scale (PDS-5), Potential Stressful Events Interview (PSEI), Stressful Life Events Screening Questionnaire (SLESQ), Spielberger's Trait and Anxiety, Generalized Anxiety Disorder 7-Item Scale, The Psychiatric Institute Trichotillomania Scale (PITS), The MGH Hairpulling Scale (MGH-HPS), The NIMH Trichotillomania Severity Scale (NIMH-TSS), The NIMH Trichotillomania Impairment Scale (NIMH-TIS), The Clinical Global Impression (CGI), the Brief Social Phobia Scale (BSPS), The Panic Attack Questionnaire (PAQ), Panic Disorder Severity Scale, Florida Obsessive-Compulsive Inventory (FOCI), The Leyton Obsessional Inventory Survey Form, The Vancouver Obsessional Compulsive Inventory (VOCI), The Schedule of Compulsions, Obsessions, and Pathological Impulses (SCOPI), Padua Inventory-Revised (PI-R), Quality of Life (QoL), The Clinical Global Improvement (CGI) scale, The Yale-Brown Obsessive-Compulsive Scale (Y-BOCS), The Yale-Brown Obsessive-Compulsive Scale Second Edition (Y-BOCS-II), The Dimensional Yale-Brown Obsessive-Compulsive Scale (DY-BOCS), The National Institute of Mental Health-Global Obsessive-Compulsive Scale (NIMH-GOCS), The Yale-Brown Obsessive-Compulsive Scale Self-Report (Y-BOCS-SR), The Obsessive-Compulsive Inventory-Revised (OCI-R), and the Dimensional Obsessive-Compulsive Scale (DOCS), or a combination thereof.

In some embodiments, after treating with psilocybin, a sign or symptom of OCD is improved as demonstrated on one of the following scales: Florida Obsessive-Compulsive Inventory (FOCI), The Leyton Obsessional Inventory Survey Form, The Vancouver Obsessional Compulsive Inventory (VOCI), Schedule of Compulsions, Obsessions, and Pathological Impulses (SCOPI), Padua Inventory-Revised (PI-R), Quality of Life (QoL), The Clinical Global Improvement (CGI) scale, The Yale-Brown Obsessive-Compulsive Scale (Y-BOCS), The Yale-Brown Obsessive-Compulsive Scale Second Edition (Y-BOCS-II), The Dimensional Yale-Brown Obsessive-Compulsive Scale (DY-BOCS), The National Institute of Mental Health-Global Obsessive-Compulsive Scale (NIMH-GOCS), The Yale-Brown Obsessive-Compulsive Scale Self-Report (Y-BOCS-SR), The Obsessive-Compulsive Inventory-Revised (OCI-R), and The Dimensional Obsessive-Compulsive Scale (DOCS).

In some embodiments, after treating with psilocybin, a sign or symptom of trichotillomania is improved as demonstrated on one of the following scales: the Psychiatric Institute Trichotillomania Scale (PITS), the Massachusetts General Hospital (MGH) Hairpulling Scale (MGH-HPS), the National Institute for Mental Health (NIMH) Trichotillomania Severity Scale (NIMH-TSS), the NIMH Trichotillomania Impairment Scale (NIMH-TIS).

In some embodiments, treating according to the methods of the disclosure results in an improvement in an anxiety disorder compared to pre-treatment of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, according to any one of the diary assessments, assessments by a clinical or caregiver, or clinical scales, described herein.

In some embodiments, treating according to the methods of the disclosure results in an improvement in an obsessive compulsive and related disorder compared to pre-treatment of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, according to any one of the diary assessments, assessments by a clinical or caregiver, or clinical scales, described herein.

In some embodiments, treating according to the methods of the disclosure results in an improvement in post-traumatic stress disorder compared to pre-treatment of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, according to any one of the diary assessments, assessments by a clinical or caregiver, or clinical scales, described herein.

In some embodiments, after administration of the psilocybin or active metabolite thereof, a subject has improved cognition, information processing, stress levels, immune system, or combinations thereof.

In some embodiments, after administration of psilocybin or active metabolite thereof, at least one symptom of anxiety disorder is alleviated for a period of at least about 5 minutes to at least about 1 year, for example, at least one symptom of anxiety is alleviated for a period of at least about 5 minutes, at least about 15 minutes, at least about 30 minutes, at least about 45 minutes, at least about 1 hour, at least about 2 hours, at least 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, at least one symptom of anxiety is alleviated for a period of at least 1 month after administration of psilocybin. In some embodiments, at least one symptom of anxiety is alleviated for a period of at least 3 months after administration of psilocybin. In some embodiments, at least one symptom of anxiety is alleviated for a period of at least 1 year after administration of psilocybin.

In some embodiments, after administration of psilocybin or active metabolite thereof, at least one symptom of anxiety disorder is alleviated within about 5 minutes to about 1 week, for example, about 5 minutes, about 15 minutes, about 30 minutes, about 45 minutes, about 1 hour, about 2 hours, at least 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days. In some embodiments, at least one symptom of anxiety is alleviated within 24 hours of administration of the psilocybin. In some embodiments, at least one symptom of anxiety is alleviated within 1 week of administration of the psilocybin.

Eating Disorders

In some embodiments, a method for treating one or more eating disorders in a subject in need thereof comprising administering to the subject an effective amount of psilocybin or an active metabolite thereof is disclosed herein. In some embodiments, the active metabolite is psilocin.

As used herein, the term "eating disorder" refers to any of a range of psychological disorders characterized by abnormal or disturbed eating habits. In some embodiments, the eating disorder is pica, anorexia nervosa, bulimia nervosa, rumination disorder, avoidant/restrictive food intake disorder, binge-eating disorder, or combinations thereof.

In some embodiments, the methods disclosed herein treat chronic eating disorders. As used herein, a "chronic" eating disorder is recurring.

In some embodiments, an eating disorder comprises a medical diagnosis based on the criteria and classification from the Diagnostic and Statistical Manual of Medical Disorders, 5th Ed. In one embodiment, an eating disorder comprises a medical diagnosis based on an independent medical evaluation.

In some embodiments, a method for treating pica in a subject in need thereof comprising administering to the subject an effective amount of psilocybin or an active metabolite thereof is disclosed herein. Pica is a disorder characterized by an appetite for substances that are largely non-nutritive. Individuals with the disorder pica compulsively eat non-nutritive items. Substances may include ice, hair, cigarette ashes, glue, paper, drywall, paint, sharp objects, metal, stone, soil, glass, feces, chalk, dirt, or dust. In some embodiments, an individual with pica also has an intellectual disability, schizophrenia, or OCD. In some embodiments, an individual with pica has a nutritional deficiency. In some embodiments, the nutritional deficiency, is low levels of zinc or iron.

In some embodiment, a subject with pica has experienced the disorder for at least 1 month, for example 1 month, 2 months, 3 months, 4 months, 5 months, 6 months, 7 months, 8 months, 9 months, 10 months, 11 months, 12 months, 1 years, 2 years, 3 years, 4 years, 5 years, 6 years, 7 years, 8 years, 9 years, 10 years, or more.

In some embodiments, after treating according to the methods of the disclosure, an individual with pica stops eating non-nutritive items for at least 1 day, at least 2 days, at least 3 days, at least 4 days, at least 5 days, at least 6 days, at least 7 days, at least 2 weeks, at least 3 weeks, at least 4 weeks, at least 5 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years, or more. In some embodiments, after treating according to the methods of the disclosure, an individual with pica stops eating non-nutritive items within about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days.

In some embodiments, a method for treating anorexia nervosa (AN) in a subject in need thereof comprising administering to the subject an effective amount of psilocybin or an active metabolite thereof is disclosed herein. AN is a disorder characterized by intense fear of gaining weight, abnormally low body weight, and a distorted perception of weight. Individuals with AN often severely restrict the amount of food they eat. They may control calorie intake by vomiting after eating or by misusing laxatives, diet aids, diuretics, or enemas. They may also try to lose weight by exercising excessively. In some embodiments, a subject with AN has signs and symptoms, including but not limited to, extreme weight loss or not making expected developmental weight gains, thin appearance, abnormal blood counts, fatigue, insomnia, dizziness or fainting, bluish discoloration of the fingers, thin hair that breaks or falls out, soft downy hair covering the body, absence of menstruation, constipation and abdominal pain, dry or yellowish skin, intolerance of cold, irregular heart rhythms, low blood pressure, dehydration, swelling of arms or legs, or eroded teeth and calluses on the knuckles from induced vomiting.

In some embodiments, after treating according to the methods of the disclosure, one or more symptoms of AN improve for at least 1 day, at least 2 days, at least 3 days, at least 4 days, at least 5 days, at least 6 days, at least 7 days, at least 2 weeks, at least 3 weeks, at least 4 weeks, at least 5 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years, or more.

In some embodiments, after treating according to the methods of the disclosure, one or more symptoms of AN improve within about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days.

In some embodiments, a method for treating bulimia nervosa (BN) in a subject in need thereof comprising administering to the subject an effective amount of psilocybin or an active metabolite thereof is disclosed herein. BN is a disorder characterized by distortion of body image and an obsessive desire to lose weight in which bouts of extreme overeating are followed by depression and self-induced vomiting, purging, use of laxatives, diuretics, or fasting. In some embodiments, the binge eating and inappropriate compensatory behaviors both occur on average at least once a week for three months. Signs and symptoms of BN include but are not limited to behaviors and attitudes that indicate that weight loss, dieting, and control of food are becoming primary concerns; evidence of binge eating, including disappearance of large amounts of food in short periods of time or lots of empty wrappers and containers indicating consumption of large amounts of food; evidence of purging behaviors, including frequent trips to the bathroom after meals, signs and/or smells of vomiting, presence of wrappers or packages of laxatives or diuretics; appears uncomfortable eating around others; develops food rituals (e.g. eats only a particular food or food group [e.g. condiments], excessive chewing, doesn't allow foods to touch); skips meals or takes small portions of food at regular meals; disappears after eating, often to the bathroom; any new practice with food or fad diets, including cutting out entire food groups (no sugar, no carbs, no dairy, vegetarianism/veganism); fear of eating in public or with others; steals or hoards food in strange places; drinks excessive amounts of water or non-caloric beverages; uses excessive amounts of mouthwash, mints, and gum; hides body with baggy clothes; maintains excessive, rigid exercise regimen—despite weather, fatigue, illness, or injury—due to the need to "burn off" calories; shows unusual swelling of the cheeks or jaw area; has calluses on the back of the hands and knuckles from self-induced vomiting; teeth are discolored, stained; creates lifestyle schedules or rituals to make time for binge-and-purge sessions; withdraws from usual friends and activities; looks bloated from fluid retention; frequently diets; shows extreme concern with body weight and shape; frequent checking in the mirror for perceived flaws in appearance; has secret recurring episodes of binge eating (eating in a discrete period of time an amount of food that is much larger than most individuals would eat under similar circumstances); feels lack of control over ability to stop eating; purges after a binge (e.g. self-induced vomiting, abuse of laxatives, diet pills and/or diuretics, excessive exercise, fasting); extreme mood swings; self-injury (cutting and other forms of self-harm without suicidal intention), substance abuse, impulsivity, diabulimia, noticeable fluctuations in weight, both up and down; body weight is typically within the normal weight range; may be overweight; stomach cramps, other non-specific gastrointestinal complaints (constipation, acid reflux, etc.); difficulties concentrating; abnormal laboratory findings (anemia, low thyroid and hormone levels, low potassium, low blood cell counts, slow heart rate); dizziness; fainting/syncope; feeling cold all the time; sleep problems; cuts and calluses across the top of finger joints (a result of inducing vomiting); dental problems, such as enamel erosion, cavities, and tooth sensitivity; dry skin; dry and brittle nails; swelling around area of salivary glands; fine hair on body; thinning of hair on head, dry and brittle hair (lanugo); cavities, or discoloration of teeth, from vomiting; muscle weakness; yellow skin (in context of eating large amounts of carrots); cold, mottled hands and feet or swelling of feet; menstrual irregularities—missing periods or only having a period while on hormonal contraceptives (this is not considered a "true" period); poor wound healing; or impaired immune functioning.

In some embodiments, after treating according to the methods of the disclosure, one or more symptoms of BN improve for at least 1 day, at least 2 days, at least 3 days, at least 4 days, at least 5 days, at least 6 days, at least 7 days, at least 2 weeks, at least 3 weeks, at least 4 weeks, at least 5 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years, or more.

In some embodiments, after treating according to the methods of the disclosure, one or more symptoms of BN improve within about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days.

In some embodiments, a method for treating binge-eating disorder (BED) in a subject in need thereof comprising administering to the subject an effective amount of psilocybin or an active metabolite thereof is disclosed herein. Binge-eating disorder (BED) is the most common eating disorder and is characterised by the uncontrolled consumption of large volumes of food over a short time-period, causing psychological distress. To meet diagnosis, these episodes must be recurrent, occur on average at least once a week for three months, and involve three of the following: consuming food faster than normal; consuming food until uncomfortably full; consuming large amounts of food when not hungry; consuming food alone due to embarrassment; feeling disgusted, depressed, or guilty after eating a large amount of food. Compensatory behaviour associated with bulimia nervosa should not be involved, and binging should not occur during an episode of bulimia nervosa or anorexia nervosa.

Many factors have been associated with the cause of BED. High levels of depressive symptoms, body dissatisfaction, poor family cohesion, and low self-esteem are significant predictors of binge eating behaviours.

The global pooled prevalence of BED is estimated as 0.9%. The prevalence is higher in women (1.4%) than in men (0.4%). An online survey of 22,397 adults with BED in the US found that only 3.2% reported receiving support from a healthcare provider.

The WHO mental health survey found lifetime prevalence estimates of BED to be 1.4% with median age of onset in the late teens to early 20's. No ethnic differences have been found in the prevalence of eating disorders or differences in the relation of risk factors for future ED onset. BED is more common in obese populations, as 20-50% of those seeking weight control treatment report binge-eating episodes. However, only 1-2% of this population meet the full DSM criteria for BED.

In some embodiments, treating according to the methods of the disclosure improves one or more symptom of BED. Symptoms of BED include eating unusually large amounts of food in a specific amount of time, feeling that eating behaviour is out of control, eating when full or not hungry, eating rapidly during binge episodes, eating until uncomfortably full, eating alone or in secret, feeling depressed, disgusted, ashamed, guilty, or upset about your eating, or frequently dieting, possibly without weight loss.

In some embodiments, after treating according to the methods of the disclosure, one or more symptoms of BED improve for at least 1 day, at least 2 days, at least 3 days, at least 4 days, at least 5 days, at least 6 days, at least 7 days, at least 2 weeks, at least 3 weeks, at least 4 weeks, at least 5 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years, or more.

In some embodiments, after treating according to the methods of the disclosure, one or more symptoms of BED improve within about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days.

In some embodiments, a method for treating rumination disorder in a subject in need thereof comprising administering to the subject an effective amount of psilocybin or an active metabolite thereof is disclosed herein. Rumination disorder is an eating disorder in which an individual regurgitates food that has been swallowed. In some embodiments, a subject with rumination disorder swallows again the regurgitated food. In some embodiments, a subject with rumination disorder spits out the regurgitated food. In some embodiments, a subject with rumination disorder chews the regurgitated food. In some embodiments, a subject with rumination disorder chews and swallows the regurgitated food. In some embodiments, rumination disorder may cause unhealthy weight loss, malnutrition, dental erosion, bad breath, embarrassment, and/or social isolation.

In some embodiments, after treating according to the methods of the disclosure, the frequency of rumination decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, signs and symptoms of rumination disorder improve for at least 1 day, at least 2 days, at least 3 days, at least 4 days, at least 5 days, at least 6 days, at least 7 days, at least 2 weeks, at least 3 weeks, at least 4 weeks, at least 5 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years, or more.

In some embodiments, after treating according to the methods of the disclosure, signs and symptoms of rumination disorder improve within about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days.

In some embodiments, a method for treating avoidant/restrictive food intake disorder (ARFID) in a subject in need thereof comprising administering to the subject an effective amount of psilocybin or an active metabolite thereof is disclosed herein. ARFID is an eating or feeding disturbance characterized by one or more of apparent lack of interest in eating or food; avoidance based on the sensory characteristics of the food; and concern about aversive consequences of eating). ARFID manifests as persistent failure to meet appropriate nutritional and/or energy needs, nutritional deficiency, dependence on enteral feeding or oral nutritional supplements, or marked interference with psychosocial functioning. In some embodiments, subjects with ARFID have ASD, ADH, or intellectual disabilities.

In some embodiments, after treating according to the methods of the disclosure, one or more signs, symptoms, or consequences of ARFID improve. In some embodiments, the improvement is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the subject with an eating disorder has one or more comorbidities. Non-limiting examples of comorbidities include endocrine and/or metabolic diseases, gastrointestinal diseases, cardiovascular diseases, psychiatric disorders, or a neuroses. In some embodiments, the comorbidity is anxiety disorder, depressive disorder, psychotic disorder, developmental disorder, eating disorder, attention-deficit hyperactivity disorder (ADHD), attention deficit disorder (ADD), autism spectrum disorder (ASD), tic disorder, bipolar disorder, conduct disorder, mental retardation, or a combination thereof. In some embodiments, the comorbidity is a mood disorder, major depressive disorder, bipolar disorder, schizophrenia, an eating disorder, attention deficit/hyperactivity disorder, epilepsy, cardiovascular disease, migraine, irritable bowel syndrome, dementia, Alzheimer's disease, Parkinson's disease, or combinations thereof. In some embodiments, the comorbidity is depression, generalized anxiety, agoraphobia, or panic disorder. In some embodiments, the comorbidity is an anxiety disorder, a mood disorder, an impulse control disorder, a substance use disorder, or any disorder. In some embodiments, the comorbidity is hypertension, dyslipidemias, sleep problems/disorders, pain, functional gastrointestinal symptoms/disorders, menstrual dysfunction, pregnancy complications, intracranial hypertension, polycystic ovary syndrome, or combinations thereof. Table 7 depicts the lifetime comorbidity of eating disorders with other core disorders.

TABLE 7

Lifetime Co-morbidity of Eating Disorders with
Other Core Disorders Among U.S. Adults Data from
National Comorbidity Survey-Replication (NCS-R)

| | Anorexia Nervosa (%) | Bulimia Nervosa (%) | Binge-eating disorder (%) |
|---|---|---|---|
| Any anxiety disorder | 47.9 | 80.6 | 65.1 |
| Any mood disorder | 42.1 | 70.7 | 46.4 |
| Any impulse control disorder | 30.8 | 63.8 | 43.3 |
| Any substance use disorder | 27.0 | 36.8 | 23.3 |
| Any disorder | 56.2 | 94.5 | 78.9 |

In some embodiments, the comorbidity is another eating disorder. In some embodiments, the subject in need has at least two eating disorders. In some embodiments, the subject in need has at least three eating disorders. In some embodiments, the subject in need has at least four eating disorders.

In some embodiments, the comorbidity is a psychiatric disorder selected from schizophrenia, schizoaffective disorder, bipolar disorder, major depressive disorder, anxiety disorder, obsessive compulsive disorder, post-traumatic stress disorder, attention deficit hyperactivity disorder, autism, alcohol use disorder, drug use disorder, or suicide attempt.

In some embodiments, the comorbidity is major depression. In some embodiments, the comorbidity is an eating disorder. In some embodiments, the comorbidity is obesity, one or more conditions related to obesity, or both. In some embodiments, the one or more conditions related to obesity are one or more of metabolic syndrome, diabetes, hypertension, dyslipidaemias, sleep problems or disorders, or pain. In some embodiments, the comorbidity is ADHD. In some embodiments, the comorbidity is ASD. In some embodiments, the comorbidity is major depressive disorder, bipolar disorder, irritable bowel disease, or irritable bowel syndrome. In some embodiments, the one or more comorbidities is reproductive dysfunction, polycystic ovary syndrome, or menstrual dysfunction. In some embodiments, the comorbidity is a psychiatric disorder selected from schizophrenia, schizoaffective disorder, bipolar disorder, major depressive disorder, anxiety disorder, obsessive compulsive disorder, post-traumatic stress disorder, attention deficit hyperactivity disorder, autism, alcohol use disorder, drug use disorder, or suicide attempt.

In some embodiments, no other treatment is administered to the subject to treat eating disorder after administration of psilocybin.

In some embodiments, the subject with anxiety disorder is administered at least one additional therapy and/or therapeutic. In some embodiments, administration of an additional therapy and/or therapeutic is prior to administration of psilocybin. In some embodiments, administration of an additional therapy and/or therapeutic is after administration of psilocybin. In some embodiments, administration of an additional therapy and/or therapeutic is concurrent with administration of psilocybin.

In some embodiments, the additional therapy is an antidepressant, an anticonvulsant, lisdexamfetamine dimesylate, an antipsychotic, an anxiolytic, an anti-inflammatory drug, a benzodiazepine, an analgesic drug, a cardiovascular drug, an opioid antagonist, or combinations thereof.

In some embodiments, the additional therapy is a benzodiazepine. In some embodiments, the benzodiazepine is diazepam or alprazolam.

In some embodiments, the additional therapy is a N-methyl-D-aspartate (NMDA) receptor antagonist. In some embodiments, the NMDA receptor antagonist is ketamine.

In some embodiments, the additional therapy is an antidepressant. In some embodiments, an antidepressant indirectly affects a neurotransmitter receptor, e.g., via interactions affecting the reactivity of other molecules at a neurotransmitter receptor. In some embodiments, an antidepressant is an agonist. In one embodiment, an antidepressant is an antagonist. In some embodiments, an antidepressant acts (either directly or indirectly) at more than one type of neurotransmitter receptor. In some embodiments, an antidepressant is chosen from buproprion, citalopram, duloxetine, escitalopram, fluoxetine, fluvoxamine, milnacipran, mirtazapine, paroxetine, reboxetine, sertraline, and venlafaxine.

In some embodiments, the antidepressant is a tricyclic antidepressant ("TCA"), selective serotonin reuptake inhibitor ("SSRI"), serotonin and noradrenaline reuptake inhibitor ("SNRI"), dopamine reuptake inhibitor ("DRI"), noradrenaline reuptake Monoamine oxidase inhibitor ("MAOI"), including inhibitor ("NRU"), dopamine, serotonin and noradrenaline reuptake inhibitor ("DSNRI"), a reversible inhibitor of monoamine oxidase type A (RIMA), or combination thereof. In some embodiments, the antidepressant is a TCA. In some embodiments, the TCA is imipramine or clomipramine. In some embodiments, the anti-depressant is an SRI. In some embodiments, the SSRI is escitalopram, paroxetine, sertraline, fluvoxamine, fluoxetine, or combinations thereof. In some embodiments, the SNRI is venlafaxine. In some embodiments, the additional therapy is pregabalin.

In some embodiments, the additional therapy is an anticonvulsant. In some embodiments, the anticonvulsant is gabapentin, carbamazepine, ethosuximide, lamotrigin, felbamate, topiramate, zonisamide, tiagabine, oxcarbazepine, levetiracetam, divalproex sodium, phenytoin, fos-phyenytoin. In some embodiments, the anticonvulsant is topiramate.

In some embodiments, the additional therapy is an anti-psychotic. In some embodiments, the antipsychotic is a phenothiazine, butryophenone, thioxanthene, clozapine, risperidone, olanzapine, or sertindole, quetiapine, aripiprazole, zotepine, perospirone, a neurokinin-3 antagonist, such as osanetant and talnetant, rimonabant, or a combination thereof.

In some embodiments, the additional therapy is an anti-inflammatory drug. In some embodiments, the anti-inflammatory drug is a nonsteroidal antiinflammatory drugs (NSAIDS), steroid, acetaminophen (cyclooxygenase-3 (COX-3) inhibitors), 5-lipoxygenase inhibitor, leukotriene receptor antagonist, leukotriene A4 hydrolase inhibitor, angiotensin converting enzyme antagonist, beta blocker, antihistaminic, histamine 2 receptor antagonist, phosphodi-esterase-4 antagonist, cytokine antagonist, CD44 antagonist, antineoplastic agent, 3-hydroxy-3-methylglutaryl coenzyme A inhibitor (statins), estrogen, androgen, antiplatelet agent, antidepressant, *Helicobacter pylori* inhibitors, proton pump inhibitor, thiazolidinedione, dual-action compounds, or combination thereof.

In some embodiments, the additional therapy is an anti-anxiolytic. In one embodiment, an anxiolytic is chosen from alprazolam, an alpha blocker, an antihistamine, a barbiturate, a beta blocker, bromazepam, a carbamate, chlordiazepoxide, clonazepam, clorazepate, diazepam, flurazepam, lorazepam, an opioid, oxazepam, temazepam, or triazolam.

In some embodiments, the additional therapy is a opioid antagonist. Non-limiting examples of opioid antagonists include naloxone, naltrexone, nalmefene, nalorphine, nalrphine dinicotinate, levallrphan, samidorphan, nalodeine, alvimopan, methylnaltrexone, naloxegol, 6β-naltrexol, axelopran, bevenopran, methylsamidorphan, naldemedine, buprenorphine, decozine, butorphanol, levorphanol, nalbuphine, pentazocine, and phenazocine.

In some embodiments, the additional therapy is a cardio-vascular drug. Non-limiting examples of cardiovascular drugs include digoxin or (3β, 5β, 12β)-3-[(O-2,6-dideoxy-β-D-ribo-hexopyranosyl)-(1,4)-O-2,6-dideoxy-β-D-ribo-hexopyranosyl)-(1,4)-O-2,6-dideoxy-β-D-ribo-hexopyrano-syl) oxy]12,14-dihydroxy-card-20 (22)-Enolide, lisinopril, captopril, ramipril, trandolapril, benazepril, cilazapril, enalapril, moexipril, perindopril, quinapril, fludrocortisone, enalaprilate, quinapril, perindopril, apixaban, dabigatran, edoxaban, heparin, rivaroxaban, warfarin, aspirin, clopidogrel, dipyridamole, prasugrel, ticagrelor, azilsartan, candesartan, eprosartan, irbesartan, losartan, olmesartan, telmisartan, valsartanscaubitril, acebutolol, atenolol, betaxolol, bisoprolol, metoprolol, nadolol, propranolol, sotalol, amlodipine, diltiazem, felodipine, nifedipine, nimodipine, nisolidipine, verapamil, statins, nicotinic acids, diuretics, vaso-dilators, and combinations thereof.

In some embodiments, the subject with an eating disorder is administered at least one therapy. Non-limiting examples of therapies include transcranial magnetic stimulation, cognitive behavioral therapy, interpersonal psychotherapy, dialectical behaviour therapy, weight loss therapy, mindfulness techniques, acceptance and commitment therapy, and combinations thereof.

In some embodiments, at least one sign or symptom of an eating disorder is improved following the administration of the psilocybin or active metabolite thereof. In some embodiments, a sign or symptom of an anxiety disorder is measured according to a diary assessment, an assessment by a clinician or caregiver, or a clinical scale. Non-limiting examples of clinical scales, diary assessments, and assessments by a clinician or caregiver include: the Mini International Neuropsychiatric Interview (MINI), the McLean Screening Instrument for Borderline Personality Disorder (MSI-BPD), the Eating Disorder Examination (EDE), the Eating Disorder Questionnaire (EDE-Q), the Eating Disorder Examination Questionnaire Short Form (EDE-QS), the Physical Appearance State and Trait Anxiety Scale—State and Trait version (PASTAS), Spielberger State-Trait Anxiety Inventory (STAI), Eating Disorder Readiness Ruler (ED-RR), Visual Analogue Rating Scales (VAS), the Montgomery-Asberg Depression Rating Scale (MADRS), Yale-Brown Cornell Eating Disorder Scale (YBC-EDS), Yale-Brown Cornell Eating Disorder Scale Self Report (YBC-EDS-SRQ), the Body Image State Scale (BISS), Clinical impairment assessment (CIA) questionnaire, the Eating Disorder Inventory (EDI) (e.g. version 3: EDI-3), the Five Dimension Altered States of Consciousness Questionnaire (5D-ASC), the Columbia-Suicide Severity Rating Scale (C-SSRS), the Life Changes Inventory (LCI), and combinations thereof.

In some embodiments, the Mini International Neuropsychiatric Interview (MINI) (for example, version 7.0.2) is a diagnostic interview instrument for psychiatric disorders in the Diagnostic and Statistical Manual of Mental Disorders (DSM-5) and the International Classification of Diseases-10.

In some embodiments, the McLean Screening Instrument for Borderline Personality Disorder (MSI-BPD) is utilized to diagnose borderline personality disorder (BPD). The MSI-BPD contains 10 items based on the DSM-5 BPD criteria; the first 8 items represent the first eight criteria in the DSM-5 for BPD diagnosis, while the last two questions assess the paranoia and dissociation criteria for BPD. Scores for the MSI-BPD range from 0 to 10, with each item rated as "1" if present and "0" if absent. A score of 7 or higher indicates a likelihood for a subject to meet criteria for BPD. In some embodiments, after treating according to the methods of the disclosure, a subject's MSI-BPD score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, one or more of the Eating Disorder Examination (EDE), the Eating Disorder Questionnaire (EDE-Q), or the Eating Disorder Examination Questionnaire Short Form (EDE-QS) are utilized to assess the range and severity of eating disorders. The EDE is a structured clinical interview (investigator rated), whereas the EDE-Q and EDE-QS are self-report questionnaires. The EDE is a standardized interview used to measure the severity of the characteristic psychopathology of eating disorders. In some embodiments, after treatment according to the methods of the disclosure, a subject's EDE score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

The EDE-Q is a self-reported interview, which assesses a subject's eating disorder severity over 28 days. In some embodiments, after treatment according to the methods of the disclosure, a subject's EDE-Q score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

The EDE-QS is a self-reported interview of eating disorder severity, which assesses the severity of a subject's eating disorder symptoms over seven days. The EDE-QS assesses the frequency of different forms of problematic overeating behaviors, including binge eating (labeled objective bulimic episodes (OBEs) and different forms of inappropriate weight compensatory behaviors (e.g., purging methods). In some embodiments, after treatment according to the methods of the disclosure, a subject's EDE-QS score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Physical Appearance State and Trait Anxiety Scale—State and Trait version (PASTAS) is utilized to evaluate the safety and efficacy of psilocybin for the treatment of eating disorders. The PASTAS is a self-reported 16-item measure that assesses anxiety about physical appearance. Subjects rate how often they experience anxiety about sites of their body on a Likert scale from 0 to 4. A score of 0 is "never," and a score of 4 is "almost always." In some embodiments, PASTAS is used to evaluate anxiety that is associated with eating disorders. In some embodiments, after treatment according to the methods of the disclosure, a subject's PASTAS score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Spielberger State-Trait Anxiety Inventory (STAI) is utilized to evaluate the safety and efficacy of psilocybin for the treatment of eating disorders. The STAI is a widely used instrument that contains separate self-report scales for measuring "state" and "trait" anxiety. "State" anxiety is transient anxiety due to a stressful stimulus, whereas "trait" anxiety is the predisposition of a subject to react with anxiety to stressful situations. is the STAI is self-reported and contains 40 items scored by a 4 point Likert scale with semantic guides taking approximately 10 minutes. The STAI contains 20 questions related to state anxiety and 20 questions related to trait anxiety. Each section is scored between 20 and 80.

In some embodiments, the Eating Disorder Readiness Ruler (ED-RR) is utilized to evaluate the safety and efficacy of psilocybin for the treatment of eating disorders. The ED-RR is a self-reported, two-part 18-item questionnaire that examines readiness to change in nine dimensions of eating disorder behavior (restriction, weight-shape over evaluation, binge eating, vomiting, laxative use, fasting, diuretic use, weight-gain phobia, exercise). The first part of the ED-RR the subjective readiness of a subject to change on a Likert scale from 1-10. The second part of the ED-RR measures whether the motivation to change is for others or the self. The second part of the ED-RR is scored on a scale from 0% to 100%, where a score closer to 0% indicates that the motivation to change is for others, and a score closer to 100% indicates that the motivation to change is for self. Higher readiness to change has shown a correlation with a decrease in eating disorder symptoms over time. In some embodiments, after treating according to the methods of the disclosure, a subject's readiness to change improves by about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, or more, compared to prior to said treatment. In some embodiments, a subject's ED-RR score increases by about 1 point, about 2 points, about 3 points, about 4 points, about 5 points, about 6 points, about 7 points, about 8 points, about 9 points, or about 10 points after treating according to the methods of the disclosure.

In some embodiments, the Visual Analogue Rating Scales (VAS) are utilized to evaluate the safety and efficacy of psilocybin for the treatment of eating disorders. The VAS is self-reported ratings of hunger, fullness and desire to eat. Subjects mark the degree of their experience in relation to the anchors along a 100 mm continuum. In some embodiments, after treating according to the methods of the disclosure a subject's VAS score improves by about 5%, about 10%, about 15%, about 20%, about 25%, about 30%, about 35%, about 40%, about 45%, about 50%, about 55%, about 60%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, or more compared to prior to said treating.

In some embodiments, the Montgomery-Asberg Depression Rating Scale (MADRS) is utilized to evaluate the safety and efficacy of psilocybin for the treatment of eating disorders. The MADRS is a clinician rated scale that measures depression severity, which contains 10 items, each scored from 0 (normal) to 6 (severe), for a total possible score of 60. A higher score denote greater severity of depression. In some embodiments, after treating according to the methods of the disclosure, the subject's MADRS score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Yale-Brown Cornell Eating Disorder Scale (YBC-EDS) and/or Yale-Brown Cornell Eating Disorder Scale Self Report (YBC-EDS-SRQ) are utilized to assess the severity and type of symptoms observed to be present in subject with eating disorders. The YBC-EDS is an interview administered by a physician, whereas the YBC-EDS-SRQ is a self-reported questionnaire. The YBC-EDS-SRQ assesses the current severity of a subject's eating disorder and the worst severity of a subject's eating disorder.

In some embodiments, the Body Image State Scale (BISS) is utilized to evaluate the safety and efficacy of psilocybin for the treatment of eating disorders. The BISS is a 6 item self-reported scale that measures a subject's affective/evaluative body image states. The BISS is used to investigate the momentary affective experience of body image in response to a variety of hypothetical situations. The six items are: 1) dissatisfaction with physical appearance, 2) dissatisfaction with body size and shape, 3) dissatisfaction with weight, 4) feelings of physical unattractiveness, 5) current feeling about one's look relative to how one usually feels, and 6) evaluation of one's appearance relative to how the average person looks. Each item is evaluated on a 9-point bipolar Likert like scale. The scale can be administered in a natural context as well as in a range of positive or negative hypothetical situations. A higher BISS score indicates better body image. In some embodiments, after a subject is treated according to the methods of the disclosure, the subject's BISS score increases by between about 5% and about 300%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 145%, about 150%, about 160%, about 170%, about 180%, about 190%, about 200%, about 210%, about 220%, about 230%, about 240%, about 250%, about 260%, about 270%, about 280%, about 290%, or about 300%.

In some embodiments, a subject's body mass index is evaluated to determine the safety and efficacy of psilocybin for the treatment of eating disorders.

In some embodiments, the Clinical impairment assessment (CIA) questionnaire is utilized to evaluate the safety and efficacy of psilocybin for the treatment of eating disorders. The CIA is a self-reported 16-item scale of the level of social and psychological impairment caused by an eating disorder in the past 28 days. The subscales are in mood, self-perception, cognitive functioning, interpersonal functioning and work preference. The items are rated on a four point Likert scale. In some embodiments, a score of 16 or greater suggests that a subject has an eating disorder. In some embodiments, after treating according to the methods of the disclosure, a subject's CIA score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to treatment.

In some embodiments, the Eating Disorder Inventory (EDI), for example version 3 (EDI-3), is utilized to evaluate the safety and efficacy of psilocybin for the treatment of eating disorders. The EDI-3 is a self-reported questionnaire ranked on a Likert scale from 0-4. The EDI-3 contains 12 subscales, three of which are specific to eating disorders (drive for thinness, bulimia, body dissatisfaction), and nine of which measure general psychological traits (low self-esteem, personal alienation, interpersonal security, interpersonal alienation, interceptive deficits, emotional dysregulation, perfectionism, asceticism, and maturity fear). In some embodiments, after treating according to the methods of the disclosure, a subject's EDI-3 composite decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to treatment.

In some embodiments, the Five Dimension Altered States of Consciousness Questionnaire (5D-ASC) is utilized to evaluate the safety and efficacy of psilocybin for the treatment of eating disorders. The 5D-ASC measures the acute drug effects using five primary dimensions and respective subdimensions to assess alterations in mood, perception, and experience of self in relation to environment and thought disorder. The 5 dimensions include: oceanic boundlessness, anxious ego dissolution, visionary restructuralization, auditory alterations, and reduction of vigilance.

In some embodiments, the Columbia-Suicide Severity Rating Scale (C-SSRS) is utilized to evaluate the safety and efficacy of psilocybin for the treatment of eating disorders. The C-SSRS is used to assess suicide potential or tendency as a study entry criteria and monitored throughout the study. In some embodiments, after treatment according to the methods of the disclosure, a subject's C-SSRS score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to treatment.

In some embodiments, a qualitative interview is utilized to evaluate the safety and efficacy of psilocybin for the treatment of eating disorders.

In some embodiments, electrocardiogram (ECG) is utilized to evaluate the safety and efficacy of psilocybin for the treatment of eating disorders. In some embodiments, the ECG is a standard 12-lead ECG.

In some embodiments, vital signs are utilized to evaluate the safety and efficacy of psilocybin for the treatment of eating disorders. Non-limiting examples of vital signs include weight, blood pressure, respiratory rate, body temperature, and pulse rate.

In some embodiments, clinical laboratory tests are utilized to evaluate the safety and efficacy of psilocybin for the treatment of eating disorders. In some embodiments, the clinical laboratory tests include liver function tests. In some embodiments, the clinical laboratory tests employ blood samples and/or urine samples. In some embodiments, blood is tested for levels of hemoglobin, hematocrit, red blood cell count, mean corpuscular haemoglobin, mean corpuscular volume, mean corpuscular haemoglobin concentration, white blood cell count (with differential), and platelets. In some embodiments, blood is tested for levels of albumin, alkaline phosphatase, alanine aminotransferase (ALT), amylase, aspartate aminotransferase (AST), bicarbonate, bilirubin (direct, indirect, and total), calcium, chloride, creatine kinase, creatinine, gamma-glutamyltransferase, glucose, lactate dehydrogenase, lipase, magnesium, phosphate, potassium, protein-total, sodium, urea (blood urea nitrogen), and uric acid. In some embodiments, urine samples are tested for pregnancy, illicit drugs, blood, glucose, ketones, protein, pH, specific gravity, nitrite, leukocytes, bilirubin, and urobilinogen.

In some embodiments, adverse events (AEs) are measured to determine the safety and efficacy of psilocybin for the treatment of eating disorder. In some embodiments, the adverse events are classified as mild, moderate, or serious. A mild AE does not interfere in a significant manner with the subject's normal level of functioning. A moderate AE produces some impairment of functioning, but is not hazardous to the subject's health. A severe AE produces significant impairment of functioning or incapacitation and is a definite hazard to the subject's health. Non-limiting examples of adverse events include euphoric mood, Euphoric mood, Dissociative disorder, Hallucination, Psychotic disorder, Cognitive disorder, Disturbance in attention, Mood alterations, impaired psychomotor skills, inappropriate affect, overdose, intentional product misuse. Serious adverse events include death, life-threatening events, insubject hospitalization or prolongation of existing hospitalization, Persistent or significant disability/incapacity, congenital anomaly/birth defect in the offspring of a subject who received psilocybin. An event is life threatening if the subject was at immediate risk of death from the event as it occurred; i.e., it does not include a reaction that if it had occurred in a more serious form might have caused death. For example, drug-induced hepatitis that resolved without evidence of hepatic failure would not be considered life threatening even though drug-induced hepatitis can be fatal. Important medical events that may not result in death, be life-threatening, or require hospitalization, may be considered a serious adverse event when, based upon appropriate medical judgment, they may jeopardize the subject and may require medical or surgical intervention to prevent one of the outcomes listed in this definition. Such events include, but are not limited to: intensive treatment in an emergency room or at home for allergic bronchospasm, blood dyscrasias or convulsions that do not result in in subject hospitalization, and development of drug dependency or drug abuse.

In some embodiments, treating according to the methods of the disclosure results in an improvement in an eating disorder compared to pre-treatment of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, according to any one of the diary assessments, assessments by a clinical or caregiver, or clinical scales, described herein.

In some embodiments, after treating according to the methods of the disclosure, the subject in need thereof has a decreased eating disorder examination short form (EDE-QS) score compared to prior to said treating. In some embodiments, after treating according to the methods of the disclosure, the subject in need thereof has a decreased Physical Appearance State and Trait Anxiety Scale (PASTAS) score compared to prior to said treating. In some embodiments, after treating according to the methods of the disclosure, the subject in need thereof has a higher willingness to change compared to prior to said treating as evaluated by the Eating Disorder Readiness Ruler (ED-RR). In some embodiments, after treating according to the methods of the disclosure, the subject in need thereof has a decreased Montgomery-Asberg Depression Rating Scale (MADRS) score compared to prior to said treating. In some embodiments, after treating according to the methods of the disclosure, the subject in need thereof has an increased Body Image State Scale (BISS) compared to prior to said treating.

In some embodiments, after administration of the psilocybin or active metabolite thereof, a subject with an eating disorder has improved cognition, information processing, stress levels, immune system, or combinations thereof.

In some embodiments, after administration of psilocybin or active metabolite thereof, the eating disorder or at least one symptom thereof is alleviated for a period of at least about 5 minutes to at least about 1 year, for example, at least one symptom of anxiety is alleviated for a period of at least about 5 minutes, at least about 15 minutes, at least about 30 minutes, at least about 45 minutes, at least about 1 hour, at least about 2 hours, at least 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the eating disorder or at least one symptom thereof is alleviated for a period of at least 1 month after administration of psilocybin. In some embodiments the eating disorder or at least one symptom thereof is alleviated for a period of at least 3 months after administration of psilocybin. In some embodiments, the eating disorder or at least one symptom thereof is alleviated for a period of at least 1 year after administration of psilocybin.

In some embodiments, after administration of psilocybin or active metabolite thereof, the eating disorder or at least one symptom thereof is alleviated within about 5 minutes to about 1 week, for example, about 5 minutes, about 15 minutes, about 30 minutes, about 45 minutes, about 1 hour, about 2 hours, at least 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days. In some embodiments, the eating disorder or at least one symptom thereof is alleviated within 24 hours of administration of the psilocybin. In some embodiments, the eating disorder or at least one symptom thereof is alleviated within 1 week of administration of the psilocybin.

Headache Disorders

In some embodiments, a method for treating one or more headache disorders in a subject in need thereof comprising administering to the subject an effective amount of psilocybin or an active metabolite thereof is disclosed herein. In some embodiments, the active metabolite is psilocin.

As used herein, the term "headache disorder" refers to a disorder characterized by recurrent headaches. Headache disorders are among the most common disorders of the nervous system. Headache disorders include migraine, tension-type headache, cluster headache, and chronic daily headache syndrome.

In some embodiments, a method for treating cluster headaches in a subject in need thereof comprising administering to the subject an effective amount of psilocybin or an active metabolite thereof is disclosed herein. In some embodiments, at least one sign or symptom of cluster headache is improved following administration of psilocybin or a metabolite thereof. In some embodiments, the sign or symptom of cluster headache is measured according to a diary assessment, a physical or psychological assessment by clinician, an imaging test, or a neurological examination.

Cluster headache is a primary headache disorder and belongs to the trigeminal autonomic cephalalgias. The definition of cluster headaches is a unilateral headache with at least one autonomic symptom ipsilateral to the headache. Attacks are characterized by severe unilateral pain predominantly in the first division of the trigeminal nerve—the fifth cranial nerve whose primary function is to provide sensory and motor innervation to the face. Attacks are also associated with prominent unilateral cranial autonomic symptoms and subjects often experience agitation and restlessness during attacks.

In some embodiments, a subject with cluster headaches has cluster headache attacks that last from 15 to 180 minutes and occur up to eight times a day. They usually occur at approximately the same time each day and often occur at night. In some embodiments, the cluster headaches are episodic. Episodic cluster headaches (ECH) are experienced by 85-90% of subjects and are when subjects experience daily attacks for weeks to months and then have remission for months to years. Subjects often have one to two episodes a year and these are often in spring or autumn. In some embodiments, the cluster headaches are chronic cluster headaches (CCH). An individual that has CCH experiences attacks lasting more than a year without remission, or remission that lasts less than a month. CCH is experienced by 15-20% of subjects that experience cluster headaches.

Approximately 0.1% of the population suffer from cluster headaches. The disorder has historically been considered to have a male preponderance with a high male-to-female ratio, which differs between ECH and CCH. This ratio is highest in subjects where the age of onset is between 20 to 49 years old; 7.2:1 in ECH and 11.0:1 in CCH. The ratio is lowest when the age of onset is after 50; 2.3:1 in ECH and 0.6:1 in CCH. These ratios were determined by observations of 554 cluster headache patients examined between 1963 and 1997. The authors suggested that these ratios could be related to sex hormone regulation and environmental factors. Recent studies have reported a decreasing male predominance with a ratio of 2:1.

In some embodiments, a subject with cluster headaches also experiences nausea and/or vomiting. In some embodiments, a subject with cluster headaches experiences unilateral pain, excessive tearing, facial flushing, a droopy eyelid, a constricted pupil, eye redness, swelling under or around one or both eyes, sensitivity to light, nausea, agitation, and restlessness.

In some embodiments, after treating according to the methods of the disclosure, the frequency of cluster headaches decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, after treating according to the methods of the disclosure, the length of a cluster headache attack decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, after treating according to the methods of the disclosure a sign or symptom of cluster headache decreases compared to prior to said treatment. In some embodiments, the sign or symptom of migraine is measured according to a diary assessment, a physical or psychological assessment by clinician, an imaging test, an electroencephalogram, a blood test, a neurological examination, or combination thereof. In some embodiments, the blood test evaluates blood chemistry and/or vitamins.

In some embodiments, a method for treating migraines in a subject in need thereof comprising administering to the subject an effective amount of psilocybin or an active metabolite thereof is disclosed herein. A migraine is a moderate to severe headache that affects one half or both sides of the head, is pulsating in nature, and last from 2 to 72 hours. Symptoms of migraine include headache, nausea, sensitivity to light, sensitivity to sound, sensitivity to smell, dizziness, difficulty speaking, vertigo, vomiting, seizure, distorted vision, fatigue, or loss of appetite. Some subjects also experience a prodromal phase, occurring hours or days before the headache, and/or a postdromal phase following headache resolution. Prodromal and postdromal symptoms include hyperactivity, hypoactivity, depression, cravings for particular foods, repetitive yawning, fatigue and neck stiffness and/or pain.

In some embodiments, the migraine is a migraine without aura, a migraine with aura, a chronic migraine, an abdominal migraine, a basilar migraine, a menstrual migraine, an ophthalmoplegic migraine, an ocular migraine, an ophthalmic migraine, or a hemiplegic migraine. In some embodiments, the migraine is a migraine without aura. A migraine without aura involves a migraine headache that is not accompanied by a headache. In some embodiments, the migraine is a migraine with aura. A migraine with aura is primarily characterized by the transient focal neurological symptoms that usually precede or sometimes accompany the headache. Less commonly, an aura can occur without a headache, or with a non-migraine headache. In some embodiments, the migraine is a hemiplegic migraine. A hemiplegic migraine is a migraine with aura and accompanying motor weakness. In some embodiments, the hemiplegic migraine is a familial hemiplegic migraine or a sporadic hemiplegic migraine. In some embodiments, the migraine is a basilar migraine. A subject with a basilar migraine has a migraine headache and an aura accompanied by difficulty speaking, world spinning, ringing in ears, or a number of other brainstem-related symptoms, not including motor weakness. In some embodiments, the migraine is a menstrual migraine. A menstrual migraine occurs just before and during menstruation. In some embodiments, the subject has an abdominal migraine. Abdominal migraines are often experienced by children. Abdominal migraines are not headaches, but instead stomach aches. In some embodiments, a subject with abdominal migraines develops migraine headaches. In some embodiments, the subject has an ophthalmic migraine also called an "ocular migraine". Subjects with ocular migraines experience vision or blindness in one eye for a short time with or after a migraine headache. In some embodiments, a subject has an ophthalmoplegic migraine. Ophthalmoplegic migraines are recurrent attacks of migraine headaches associated with paresis of one or more ocular cranial nerves.

In some embodiments, the subject in need experiences chronic migraines. As defined herein, a subject with chronic migraines has more than fifteen headache days per month. In some embodiments, the subject in need experiences episodic migraines. As defined herein, a subject with chronic migraines has less than fifteen headache days per month.

In some embodiments, after treating according to the methods of the disclosure, the frequency of migraine decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, after treating according to the methods of the disclosure, the length of a migraine headache decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, after treating according to the methods of the disclosure a sign or symptom of migraine decreases compared to prior to said treatment. In some embodiments, the sign or symptom of migraine is measured according to a diary assessment, a physical or psychological assessment by clinician, an imaging test, or a neurological examination.

In some embodiments, a method for treating chronic daily headache syndrome (CDHS) in a subject in need thereof comprising administering to the subject an effective amount of psilocybin or an active metabolite thereof is disclosed herein. A subject with CDHS has a headache for more than four hours on more than 15 days per month. Some subjects experience these headaches for a period of six months or longer. CHDS affects 4% of the general population. Chronic migraine, chronic tension-type headaches, new daily persistent headache, and medication overuse headaches account for the vast majority of chronic daily headaches.

In some embodiments, after treating according to the methods of the disclosure, a chronic daily headache experienced by the subject in need is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, after treating according to the methods of the disclosure, the number of chronic daily headaches experienced by the subject in need per month is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, after treating according to the methods of the disclosure, the number of chronic daily headaches experienced by the subject in need per month is reduced by about 1 headache per month, about 2 headaches per month, about 3 headaches per month, about 4 headaches per month, about 5 headaches per month, about 6 headaches per month, about 7 headaches per month, about 8 headaches per month, about 9 headaches per month, about 10 headaches per month, about 11 headaches per month, about 12 headaches per month, about 13 headaches per month, about 14 headaches per month, about 15 headaches per month, or more.

In some embodiments, the subject with a headache disorder has one or more comorbidities. Non-limiting examples of comorbidities include endocrine and/or metabolic diseases, gastrointestinal diseases, cardiovascular diseases, psychiatric disorders, or a neuroses. In some embodiments, the comorbidity is anxiety disorder, depressive disorder, psychotic disorder, developmental disorder, eating disorder, attention-deficit hyperactivity disorder (ADHD), attention deficit disorder (ADD), autism spectrum disorder (ASD), tic disorder, bipolar disorder, conduct disorder, mental retardation, or a combination thereof. In some embodiments, the comorbidity is a mood disorder, major depressive disorder, bipolar disorder, schizophrenia, an eating disorder, attention deficit/hyperactivity disorder, epilepsy, cardiovascular disease, migraine, irritable bowel syndrome, dementia, Alzheimer's disease, Parkinson's disease, or combinations thereof. In some embodiments, the comorbidity is depression, generalized anxiety, agoraphobia, or panic disorder. In some embodiments, the comorbidity is major depression. In some embodiments, the comorbidity is an eating disorder. In some embodiments, the comorbidity is ADHD. In some embodiments, the comorbidity is ASD. In some embodiments, the comorbidity is major depressive disorder, bipolar disorder, irritable bowel disease, or irritable bowel syndrome.

In some embodiments, the comorbidity is sleep apnea, depression, anxiety, aggressive behavior, suicidal ideation, or bipolar disorder. In some embodiments, the comorbidity is tobacco use, sleep apnea, depression, anxiety, aggressive behavior, suicidal ideation, or bipolar disorder. In some embodiments, the comorbidity is stroke, vascular brain lesions, coronary heart disease, patent foramen ovale, hypertension, depression, anxiety, bipolar disorder, panic disorder, suicide, restless leg syndrome, epilepsy, inflammatory bowel disease, or asthma.

In some embodiments, the subject in need thereof is a male. In some embodiments, the subject in need thereof is a female. In some embodiments, the subject in need thereof is a pregnant woman. In some embodiments, the subject in need thereof is a post-partum woman. In some embodiments, the subject in need thereof is psilocybin-naïve. In some embodiments, the subject in need thereof has prior psilocybin experience.

In some embodiments, no other treatment is administered to the subject to treat headache disorder after administration of psilocybin.

In some embodiments, the subject with headache disorder is administered at least one additional therapy and/or therapeutic. In some embodiments, administration of an additional therapy and/or therapeutic is prior to administration of psilocybin. In some embodiments, administration of an additional therapy and/or therapeutic is after administration of psilocybin. In some embodiments, administration of an additional therapy and/or therapeutic is concurrent with administration of psilocybin.

In some embodiments, the additional therapy is oxygen therapy, triptans, ergotamine, lidocaine, somatostatin and somatostatin analogues, corticosteroids, methysergide, verapamil, lithium, topiramate, valproic acid, botulinum toxin, clomiphene, lysergic acid diethylamide, prednisolone, dihydroergotamine, a beta blocker, a vitamin, an antidepressant, an anticonvulsant, lisdexamfetamine dimesylate, an antipsychotic, an anxiolytic, an anti-inflammatory drug, a benzodiazepine, an analgesic drug, a cardiovascular drug, or combinations thereof.

In some embodiments, the additional therapy is an antidepressant. In some embodiments, the antidepressant is amitriptyline. In some embodiments, an antidepressant indirectly affects a neurotransmitter receptor, e.g., via interactions affecting the reactivity of other molecules at a neurotransmitter receptor. In some embodiments, an antidepressant is an agonist. In one embodiment, an antidepressant is an antagonist. In some embodiments, an antidepressant acts (either directly or indirectly) at more than one type of neurotransmitter receptor. In some embodiments, an antidepressant is chosen from buproprion, citalopram, duloxetine, escitalopram, fluoxetine, fluvoxamine, milnacipran, mirtazapine, paroxetine, reboxetine, sertraline, and venlafaxine.

In some embodiments, the antidepressant is a tricyclic antidepressant ("TCA"), selective serotonin reuptake inhibitor ("SSRI"), serotonin and noradrenaline reuptake inhibitor ("SNRI"), dopamine reuptake inhibitor ("DRI"), noradrenaline reuptake monoamine oxidase inhibitor ("MAOI"), including inhibitor ("NRU"), dopamine, serotonin and noradrenaline reuptake inhibitor ("DSNRI"), a reversible inhibitor of monoamine oxidase type A (RIMA), or combination thereof. In some embodiments, the antidepressant is a TCA. In some embodiments, the TCA is imipramine or clomipramine. In some embodiments, the anti-depressant is an SRI. In some embodiments, the SSRI is escitalopram, paroxetine, sertraline, fluvoxamine, fluoxetine, or combinations thereof. In some embodiments, the SNRI is venlafaxine. In some embodiments, the additional therapy is pregabalin.

In some embodiments, the antidepressant is amitriptyline.

In some embodiments, the additional therapeutic is an anticonvulsant. In some embodiments, the anticonvulsant is gabapentin, carbamazepine, ethosuximide, lamotrigine, felbamate, topiramate, zonisamide, tiagabine, oxcarbazepine, levetiracetam, divalproex sodium, phenytoin, fos-phenytoin. In some embodiments, the anticonvulsant is topiramate.

In some embodiments, the additional therapeutic is a beta blocker. Non-limiting examples of beta blockers include acebutolol, atenolol, betaxolol, bisoprolol, carteolol, carvedilol, labetalol, metoprolol, nadolol, nebivolol, penbutolol, pindolol, propranolol, sotalol, or timolol. In some embodiments, the beta blocker is propranolol.

In some embodiments, the additional therapeutic is a non-steroidal anti-inflammatory drug, acetaminophen, caffeine, a triptan, a dihydroergotamine, an opioid, an anti-nausea drug, a blood pressure-lowering medication, an anti-depressant, an anti-seizure drug, a botox injection, a monoclonal antibody directed to calcitonin gene-related peptide, acupuncture, black room, change of diet, hot/cold therapy, magnesium intake, massages, riboflavin/B2 intake, transcranial magnetic stimulation, or any combination thereof.

In some embodiments, at least one sign or symptom of headache disorder is improved following administration of psilocybin or a metabolite thereof. In some embodiments, a sign or symptom of a headache disorder is measured according to a diary assessment, an assessment by a clinician or caregiver, or a clinical scale. In some embodiments, psilocybin treatment causes a demonstrated improvement in one or more of the following: the Visual Analog Scale, Numeric Rating Scale, the Short Form Health Survey, Profile of Mood States, the Pittsburgh Sleep Quality Index, the Major Depression Inventory, the Perceived Stress Scale, the 5-Level EuroQoL-5D, the Headache Impact Test; the ID-migraine; the 3-item screener; the Minnesota Multiphasic Personality Inventory; the Hospital Anxiety and Depression Scale (HADS), the 50 Beck Depression Inventory (BDI; both the original BDI51 and the second edition, BDI-II52), the 9-item Patient Health Questionnaire (PHQ-9), the Migraine Disability Assessment Questionnaire (MIDAS), the Migraine-Specific Quality of Life Questionnaire version 2.1 (MSQ v2.1), the European Quality of Life-5 Dimensions (EQ-5D), the Short-form 36 (SF-36), or a combination thereof.

In some embodiments, treating according to the methods of the disclosure results in an improvement in a headache disorder compared to pre-treatment of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, according to any one of the diary assessments, assessments by a clinical or caregiver, or clinical scales, described herein.

In some embodiments, treating according to the methods of the disclosure results in an improvement in migraine compared to pre-treatment of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, according to any one of the diary assessments, assessments by a clinical or caregiver, or clinical scales, described herein. In some embodiments, the assessment is the Visual Aura Rating Scale or the ID Migraine questionnaire.

In some embodiments, treating according to the methods of the disclosure results in an improvement in cluster headaches compared to pre-treatment of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, according to any one of the diary assessments, assessments by a clinical or caregiver, or clinical scales, described herein. In some embodiments, the assessment is the Visual Analog Scale, the Numeric Rating Scale, the Short Form Health Survey, the Profile of Mood States, the Pittsburgh Sleep Quality Index, the Major Depression Inventory, the Perceived Stress Scale, the 5-Level EuroQoL-5D, the Headache Impact Test, or combinations thereof.

In some embodiments, after administration of psilocybin or active metabolite thereof, at least one symptom of headache disorder is alleviated for a period of at least about 5 minutes to at least about 1 year, for example, at least one symptom of anxiety is alleviated for a period of at least about 5 minutes, at least about 15 minutes, at least about 30 minutes, at least about 45 minutes, at least about 1 hour, at least about 2 hours, at least 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, at least one symptom of headache disorder is alleviated for a period of at least 1 month after administration of psilocybin. In some embodiments, at least one symptom of headache disorder is alleviated for a period of at least 3 months after administration of psilocybin. In some embodiments, at least one symptom of headache disorder is alleviated for a period of at least 1 year after administration of psilocybin.

In some embodiments, the administration of psilocybin prevents the occurrence of the headache disorder for at least about 1 week or more, for example, about 1 week, about 2 weeks, about 3 weeks, about 4 weeks, about 5 weeks, about 1 month, about 6 weeks, about 2 months, about 3 months, about 4 months, about 5 months, about 6 months, about 7 months, about 8 months, about 9 months, about 10 months, about 11 months, about 1 year, or more. In some embodiments, the administration of psilocybin prevents the occurrence of the headache disorder for at least about 1 month. In some embodiments, the administration of psilocybin prevents the occurrence of the headache disorder for at least about 3 months. In some embodiments, the administration of psilocybin prevents the occurrence of the headache disorder for at least about 6 months. In some embodiments, the administration of psilocybin prevents the occurrence of the headache disorder for at least about 12 months.

In some embodiments, after administration of psilocybin or active metabolite thereof, at least one symptom of headache disorder is alleviated within about 5 minutes to about 1 week, for example, about 5 minutes, about 15 minutes, about 30 minutes, about 45 minutes, about 1 hour, about 2 hours, at least 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, or about 7 days. In some embodiments, at least one symptom of headache disorder is alleviated or improved within 15 minutes of administration of the psilocybin. In some embodiments, at least one symptom of headache disorder is alleviated or improved within 30 minutes of administration of the psilocybin. In some embodiments, at least one symptom of headache disorder is alleviated or improved within 1 hour of administration of the psilocybin. In some embodiments, at least one symptom of headache disorder is alleviated or improved within 3 hours of administration of the psilocybin. In some embodiments, at least one symptom of headache disorder is alleviated or improved within 6 hours of administration of the psilocybin.

Pre-Treatments and Combination Therapies

In some embodiments, the methods of treatment comprising administering psilocybin to a subject in need thereof further comprise pretreating the subject with magnesium before administration of the psilocybin. Sometimes, magnesium is administered daily for a least 1 day, at least 2 days, at least 3 days, at least 4 days, at least 5 days, at least 6 days, at least 1 week, at least 2 weeks, at least 3 weeks, at least 4 weeks, at least 5 weeks, or at least 6 weeks before administration of the psilocybin. In some embodiments, about 10 mg to about 500 mg of magnesium are administered to the subject per day. In some embodiments, about 30 mg, about 75 mg, about 80 mg, about 130 mg, about 240 mg, about 310 mg, about 320 mg, about 360 mg, about 410 mg, about 400 mg, or about 420 mg are administered to the subject per day. In some embodiments the magnesium is administered to the subject on the same day as the psilocybin. In some embodiments, the magnesium is administered to the subject immediately before, concurrently with, or immediately after administration of the psilocybin. In some embodiments, magnesium supplements are administered to the subject until the subject's blood level for magnesium is about 1.5 to about 2.5 mEq/L. In some embodiments, psilocybin is not administered to the subject if the subject's blood level of magnesium is less than about 1.5 to about 2.5 mEq/L.

In some embodiments, the methods of treatment comprising administering psilocybin to a subject in need thereof further comprise pretreating the subject with niacin before administration of the psilocybin. Sometimes, niacin is administered daily for a least 1 day, at least 2 days, at least 3 days, at least 4 days, at least 5 days, at least 6 days, at least 1 week, at least 2 weeks, at least 3 weeks, at least 4 weeks, at least 5 weeks, or at least 6 weeks before administration of the psilocybin. In some embodiments, about 1 mg to about 5,000 mg of niacin are administered to the subject per day, for example about 1 mg to about 50 mg, about 10 mg to about 100 mg, about 100 mg to about 200 mg, about 1 mg to about 200 mg, about 100 mg to about 200 mg, about 10 mg to about 50 mg, about 10 to about 35 mg, about 100 mg to about 500 mg, or about 1,000 mg to about 3,000 mg. In some embodiments, about 10 mg, about 14 mg, about 15 mg, about 16 mg, about 20 mg, about 30 mg, about 35 mg, about 50 mg, about 60 mg, about 75 mg, about 100 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1500 mg, about 2000 mg, about 2500 mg, or about 3000 mg of niacin are administered to the subject per day (while avoiding any toxic exposure from excess niacin). In some embodiments, niacin is included as an ingredient/component, for example, to reduce risk of abuse and/or to improve efficacy. In some embodiments the niacin is administered to the subject on the same day as the psilocybin. In some embodiments, the niacin is administered to the subject immediately before, concurrently with, or immediately after administration of the psilocybin.

In some embodiments, psilocybin is administered to the subject in combination with one or more additional therapies. In some embodiments, psilocybin is administered to the subject in combination with one or more anti-depressant or anti-anxiety drugs, such as SSRIs, tricyclic antidepressants (TCAs), monoamine oxidase inhibitors (MAOIs), or serotonin norepinephrine reuptake inhibitors (SNRIs).

In some embodiments, the disclosure provides a method of reducing anxiety in a subject undergoing treatment with psilocybin, the method comprising administering to the subject: i) psilocybin or a precursor or derivative thereof, and ii) one or more benzodiazepines.

In some embodiments, the one or more benzodiazepines are administered to the subject at or around the same time as the psilocybin or precursor or derivative thereof. In some embodiments, the one or more benzodiazepines are administered to the subject prior to administration of the psilocybin or precursor or derivative thereof, such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof. In some embodiments, the one or more benzodiazepines are administered to the subject after the psilocybin or precursor or derivative thereof, such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

In some embodiments, the one or more benzodiazepines are administered at a dose that is lower than doses typically used to treat anxiety, such as about 10%, 20%, 25%, 30%, 40%, 50%, or 75% of a typical dose. In some embodiments, the one or more benzodiazepines are administered at a dose that is approximately equivalent to doses typically used to treat anxiety. In some embodiments, the one or more benzodiazepines are administered at a dose that is higher than doses typically used to treat anxiety, such as about 125%, 150%, 175%, 200%, 250%, or 300% of a typical dose. In some embodiments, the one or more benzodiazepine is administered orally to the subject.

In some embodiments, the benzodiazepine is selected from adinazolam, alprazolam, bentazepam, bretazenil, bromazepam, bromazolam, brotizolam, camazepam, chlordiazepoxide, cinazepam, cinolazepam, clobazam, clonazepam, clonazolam, clorazepate, clotiazepam, cloxazolam, delorazepam, deschloroetizolam, diazepam, diclazepam, estazolam, ethyl carfluzepate, ethyl loflazepate, etizolam, flualprazolam, flubromazepam, flubromazolam, fluclotizolam, flunitrazepam, flunitrazolam, flurazepam, flutazolam, flutoprazepam, halazepam, ketazolam, loprazolam, lorazepam, lormetazepam, meclonazepam, medazepam, metizolam, mexazolam, midazolam, nifoxipam, nimetazepam, nitemazepam, nitrazepam, nitrazolam, nordiazepam, norflurazepam, oxazepam, phenazepam, pinazepam, prazepam, premazepam, pyrazolam, quazepam, rilmazafone, temazepam, tetrazepam, or triazolam.

In certain embodiments, a patient is administered psilocybin or a precursor or derivative thereof as described herein along with one or more 5-HT$_{2A}$ specific antagonists and/or inverse agonists. In some embodiments, the subject is administered psilocybin or a precursor or derivative thereof and the one or more 5-HT$_{2A}$ specific antagonists and/or inverse agonists at the same time. In other embodiments, the subject is administered one or more 5-HT$_{2A}$ specific antagonists and/or inverse agonists prior to psilocybin administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before psilocybin administration. In some embodiments, the subject is administered one or more 5-HT$_{2A}$ specific antagonists and/or inverse agonists after psilocybin administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after psilocybin administration.

In certain embodiments, the one or more 5-HT$_{2A}$ specific antagonists and/or inverse agonists are administered at doses that are lower than doses typically used, e.g., about 10%, about 20%, about 25%, about 30%, about 40%, about 50%, or about 75% of a typical dose. In other embodiments, the one or more 5-HT$_{2A}$ specific antagonists and/or inverse agonists are administered at doses that are equivalent to doses typically used. In yet other embodiments, the one or more 5-HT$_{2A}$ specific antagonists and/or inverse agonists are administered at doses that are higher than doses typically used, e.g., about 125%, about 150%, about 175%, about 200%, about 250%, or about 300% of a typical dose.

Suitable 5-HT$_{2A}$ antagonists include but are not limited to, trazodone, mirtazapine, metergoline, ketanserin, ritanserin, nefazodone, clozapine, olanzapine, quetiapine, risperidone, asenapine, MDL-100907, cyproheptadine, pizotifen, LY-367,265, 2-alkyl-4-aryl-tetrahydro-pyrimido-azepine, 9-aminomethyl-9,10-dihydroanthracene (AMDA), haloperidol, chlorpromazine, hydroxyzine (atarax), 5-MeO-NBpBrT, niaprazine, altanserin, aripiprazole, etoperidone, setoperone, chlorprothixene, cinaserin, adatanserin, medifoxamine, rauwolscine, phenoxybenzamine, pruvanserin, deramciclane, nelotanserin, lubazodone, mepiprazole, xylamidine, R-(+)-alpha-(2,3-dimethoxyphenyl)-1-[2-(4-fluorophenethyl)]-4-piperidinemethanol (M100907), mianserin, AT 1015, DV 7028, eplivanserin, 4F 4PP, fanaserin, alpha-phenyl-1-(2-phenylethyl)-4-piperidinemethanol (MDL 11,939), melperone, mesulergine, paliperidone, 1-[2-(3,4-Dihydro-1H-2-benzopyran-1-yl)ethyl]-4-(4-fluorophenyl) piperazine dihydrochloride (PNU 96415E), (2R,4R)-5-[2-[2-[2-(3-methoxyphenyl)ethyl]phenoxy]ethyl]-1-methyl-3-pyrrolidinol (R-96544), sarpogrelate, spiperone, ziprasidone, zotepine, and 7-[[4-[2-(4-fluorophenyl)ethyl]-1-piperazinyl]carbonyl]-1H-indole-3-carbonitrile (EMD 281014).

Suitable 5-HT$_{2A}$ reverse agonists include but are not limited to, AC-90179, nelotanserin (APD-125), eplivanserin, pimavanserin (ACP-103), and volinaserin.

In certain embodiments, the 5-HT$_{2A}$ antagonist is selected from the compounds of Table 8:

TABLE 8

| 5-HT$_{2A}$ antagonists |
| --- |
| Acepromazine |
| Agomelatine |
| Amitriptyline |
| Amoxapine |

TABLE 8-continued

| 5-HT$_{2A}$ antagonists |
| --- |
| Amperozide |
| APD791 |
| Aripiprazole |
| Aripiprazole lauroxil |
| Blonanserin |
| Brexpiprazole |
| Butriptyline |
| Captodiame |
| Cariprazine |
| Chlorpromazine |
| Chlorprothixene |
| Cimtapride |
| Citalopram |
| Clomipramine |
| Clozapine |
| Cyclobenzaprine |
| Cyproheptadine |
| Deramciclane |
| Desipramine |
| Dosulepin |
| Doxepin |
| Epinastine |
| Esmirtazapine |
| Etoperidone |
| Flibanserin |
| Fluoxetine |
| Flupentixol |
| Fluspirilene |
| Iloperidone |
| Imipramine |
| Lisuride |
| Loxapine |
| Lurasidone |
| Mesoridazine |
| Methotrimeprazine |
| Methysergide |
| Mianserin |
| Mirtazapine |
| Nefazodone |
| Nortriptyline |
| Olanzapine |
| Paliperidone |
| Pimavanserin |
| Pizotifen |
| Promazine |
| Propiomazine |
| PRX-08066 |
| Quetiapine |
| Risperidone |
| Sertindole |
| Thioproperazine |
| Thioridazine |
| Tramadol |
| Trazodone |
| Triflupromazine |
| Trimipramine |
| YKP-1358 |
| Yohimbine |
| Ziprasidone |
| Zotepine |
| Zuclopenthixol |

In some embodiments, the disclosure provides a method of reducing the negative side effects associated with a traumatic psychedelic experience in a subject undergoing treatment with psilocybin, the method comprising administering to the subject: i) psilocybin or a precursor or derivative thereof, and ii) one or more cannabinoids or cannabinoid derivatives.

In some embodiments, the cannabinoid is selected from THC (tetrahydrocannabinol), THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin);

CBCV (cannabichromevarin); CBGV (cannabigerovarin); CBGM (cannabigerol monomethyl ether); CBE (cannabielsoin); or CBT (cannabicitran). In particular embodiments, the cannabinoid is CBD (cannabidiol).

In some embodiments, at least one symptom of a disease, disorder, or condition described herein is alleviated within 24 hours of administering psilocybin. In some embodiments, at least one symptom of the disease, disorder, or condition is alleviated within 1 week of the administering. In some embodiments, at least one symptom of the disease, disorder, or condition is alleviated within 1 month of the administering. In some embodiments, at least one symptom of the disease, disorder, or condition is alleviated within 6 months of the administering. In some embodiments, at least one symptom of the disease, disorder, or condition is alleviated within 12 months of the administering.

In some embodiments, at least one symptom of the disease, disorder, or condition is alleviated for a period of at least 1 month after administering psilocybin. In some embodiments, at least one symptom of the disease, disorder, or condition is alleviated for a period of at least 3 months after the administering. In some embodiments, at least one symptom of the disease, disorder, or condition is alleviated for a period of at least 6 months after the administering. In some embodiments, at least one symptom of the disease, disorder, or condition is alleviated for a period of at least 12 months after the administering.

In some embodiments, no other treatment is administered to the subject to treat the disease, disorder, or condition before administration of the psilocybin. In some embodiments, no other treatment is administered to the subject to treat the disease, disorder, or condition after administration of the psilocybin.

Safety and Efficacy of Psilocybin

The present disclosure also relates to the safety and efficacy of the use of psilocybin as disclosed herein. The following is a non-exhaustive list of tests that can be used to determine the effects of psilocybin, and in particular the psilocybin formulations as disclosed herein administered as disclosed herein.

In some embodiments, the Spatial Working Memory (SWM) test is utilized to evaluate the safety and efficacy of psilocybin as disclosed herein. SWM requires retention and manipulation of visuospatial information. Study subjects are required to find the blue tokens in the on-screen 'boxes'. Boxes are searched by touching them to determine whether they contain a token. Once a token has been located it is 'stacked' in a column on the right of the screen. Study subjects then search for further tokens until they have all been located. The remaining tokens will thereafter only be found in boxes that have not so far yielded a token. Study subjects are explicitly told this is the case and it they revisit a box in which a token has been found they commit a 'between error', the usual primary metric for this test. Occasions on which the subject revisits a box in the same search are scored as a 'within' error. Many study subjects will adopt a search strategy via which they systematically search the array of boxes. This is also scored by the Cambridge Neuropsychological Test Automated Battery system and yields a 'strategy' score. SWM performance is impaired by damage to the prefrontal cortex, especially the dorsolateral prefrontal cortex. Similarly, in neuroimaging studies in healthy volunteers, SWM performance is associated with activations in the dorsolateral and mid-ventrolateral prefrontal cortex. This test takes approximately 4 min to complete.

In some embodiments, the efficacy of psilocybin is evaluated using the spatial working memory between errors (SWMBE) score. In some embodiments, after treating according to the methods of the disclosure, a subject's SWMBE score decreases by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the efficacy of psilocybin is evaluated using the spatial working memory strategy (SWMS) score. In some embodiments, after treating according to the methods of the disclosure, a subject's SWMS score decreases by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the Rapid Visual Information Processing (RVP) test is utilized to evaluate the safety and efficacy of psilocybin. The RVP is a measure of sustained attention outputting measures of response accuracy, target sensitivity and reaction times. In this test, the study subject is required to monitor a stream of digits from 2 to 9 for specific sequences (e.g., 3-5-7) and to acknowledge detection of the sequence by touching the on-screen response button as quickly as possible after presentation of the third digit. Digits are presented pseudorandomly to create the possibility of 'false alarm' responses in which the first 2 digits of a sequence are not followed by a true target, e.g., when 3 is followed by a 5, but not then by a 7. In order to complete the task successfully study subjects must sustain attention to the white box in which the digits appear. Performance on this task is measured by the speed of response to the presentation of the final digit of a target, as well as the study subject's ability to detect specified sequences. This test takes approximately 7 min to complete.

In some embodiments, performance on the Rapid Visual Information Processing test is reported using a RVP A Prime (RPVA) score. Higher scores RVPA scores indicated better performance. In some embodiments, after treating according to the methods of the disclosure, a subject's RVPA score increases by between about 5% and about 300%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Paired Associates Learning (PAL) test is utilized to evaluate safety and/or efficacy of psilocybin. The PAL task is a measure of visuo-spatial memory in which study subjects are required to remember locations at which visual stimuli are located. Boxes are displayed on the screen and are "opened" in a randomized order. One or more of them will contain a pattern. The patterns are then displayed in the middle of the screen, one at a time and the subject must select the box in which the pattern was originally located. If the subject makes an error, the boxes are opened in sequence again to remind the subject of the locations of the patterns. Increased difficulty levels can be used to test high-functioning, healthy individuals. The primary metric for this test is the number of errors made. This test takes approximately 8 min to complete. Successful performance of the PAL test is dependent on functional integrity of the temporal lobe, particularly the entorhinal cortex. In some embodiments, the Paired Associates Learning total errors adjusted (PALTEA) score is used to assess the efficacy of psilocybin. In some embodiments, after treating according to the methods of the disclosure, a subject's PALTEA score decreases by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the efficacy and/or safety of psilocybin is evaluated using the cognitive flexibility panel test.

In some embodiments, the Emotion Recognition Task (ERT) test is utilized to evaluate the safety and/or efficacy of psilocybin. The ERT measures the ability to identify 6 basic emotions in facial expressions along a continuum of expression magnitude. In some embodiments, the ERT is performed according to the following protocol: Subjects are shown computer morphed images derived from the facial features of real individuals each showing a specific emotion, on a screen, one at a time. Each face is displayed for 200 ms and then immediately covered up, and the subject must select which emotion the face displayed from the six options (happy, sad, anger, fear, surprise, disgust). The ERT percent correct (ERTPC) of correct responses (emotion selection) the subject made is assessed. A higher score indicates better performance. In some embodiments, after treating according to the methods of the disclosure, a subject's ERTPC increases by between about 5% and about 300%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Intra-Extra Dimensional Set Shift (IED) test is used to evaluate the safety and/or efficacy of psilocybin. The IED consists of four 7-item subscales, each of which taps a separate aspect of the global concept "empathy." In some embodiments, the Intra-Extra Dimensional Set Shift total errors (IEDYERT) score is used to assess the efficacy of psilocybin. In some embodiments, after treating according to the methods of the disclosure, a subject's IEDYERT score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the One Touch Stockings (OTS) of Cambridge test is used to evaluate the safety and/or efficacy of psilocybin. The OTS is a test of executive function, based upon the Tower of Hanoi test. It assesses both the spatial planning and the working memory subdomains. This test takes approximately 10 min to perform. The OTS test reports an one touch stockings of Cambridge problems solved on first choice (OTSPSFC) score. A higher OTSPSFC score is associated with better executive function. In some embodiments, after treatment according to the methods of the disclosure, a subject's OTSPSFC score increases by between about 5% and about 300%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, as compared to prior to treatment.

In some embodiments, verbal fluency is used to evaluate the safety and/or efficacy of psilocybin. In the verbal fluency test, the study subject is asked to name as many different category exemplars (e.g., 'animals') as they can in 1 min, subject to certain scoring rules, such as repetition. Successful performance on this test is reliant on the integrity of a number of cognitive abilities and especially those traditionally viewed as executive functions, such as planning and working memory. The primary metric for this test is the total number of acceptable words generated. In some embodiments, after treatment with psilocybin, a subject's verbal fluency category score improves by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, as compared to prior to treatment.

In some embodiments, the Digit Span Forward (DSF) test is used to evaluate the safety and/or efficacy of psilocybin. DSF is used to measure number storage capacity. Subjects hear a sequence of digits and are tasked to recall the sequence correctly, with increasingly longer sequences being tested in each trial. The subject's span is the longest number of sequential digits that can accurately be remembered. Digit span tasks can be given forwards or backwards, meaning that once the sequence is presented, the subject is asked to either recall the sequence in normal or reverse order. For this study, subjects will be asked to recall the sequence in the order presented, i.e., Digit Span Forward. The primary metric for this test is the number of digit sequences successfully recalled. In some embodiments, after treatment with psilocybin, a subject's Digit Span Forward score improves by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, as compared to prior to treatment.

In some embodiments, the Five Dimension Altered States of Consciousness questionnaire (5D-ASC) is utilized to evaluate the safety and/or efficacy of psilocybin. The 5D-ASC measures the acute drug effects using 5 primary dimensions and 11 lower-order scales to assess alterations in mood, perception and experience of self in relation to environment and thought disorder. The 5 dimensions include oceanic boundlessness, anxious ego dissolution, visionary restructuralization, auditory alterations and reduction of vigilance. In some embodiments, after treatment according to the methods of the disclosure, a subject experiences an increase on a dimension or a subscale compared to prior to treatment. The lower-order scales include "experience of unity," "spiritual experience," "blissful state," "insightfulness," "disembodiment," "impaired control of cognition," "anxiety," "complex imagery," "elementary imagery," "audio-visual synesthesia," and "changed meaning of percepts." In some embodiments, the increase is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Positive and Negative Affect Schedule (PANAS) is used to evaluate the safety and/or efficacy of psilocybin. The PANAS measures the acute emotional drug effects and comprises 2 mood scales that measure positive and negative affect. Positive affect refers to the propensity to experience positive emotions and interact with others positively. Negative affect involves experiencing the world in a more negative way. Subjects respond to 10 questions associated with negative affect and 10 questions associated with positive affect. The questions are scaled using a 5-point scale that ranges from "slightly or not at all (1)" to "extremely (5)". A total higher score on the positive affect questions indicates more of a positive effect while a lower score on the negative affect questions indicates less of a negative affect. In some embodiments, after treating according to the methods of the disclosure, a subject experiences a decrease in negative affect score of the PANAS, between about 5% and about 100%, for example about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to treatment. In some embodiments, after treating according to the methods of the disclosure, a subject experiences an increase in positive affect score of the PANAS, between about 5% and about 100%, for example about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the NEO-Five Factor Inventory (NEO-FFI) test is used to evaluate the safety and/or efficacy of psilocybin. The NEO-FFI evaluates 5 broad domains of personality—Neuroticism, Extroversion, Openness, Agreeableness and Conscientiousness.

In some embodiments, the Symptom Checklist-90 item (SCL-90) questionnaire is used to evaluate the safety and/or efficacy of psilocybin. The SCL-90 is a relatively brief self-report psychometric instrument designed to evaluate a broad range of psychological problems and symptoms of psychopathology. In some embodiments, the SCL-90 is used to assess somatization, obsessive-compulsive behaviors, interpersonal sensitivity, depression, anxiety, hostility, phobic anxiety, paranoid ideation, and psychoticism of a subject treated according to the methods of the disclosure. The 90 items in the questionnaire are scored on a 5-point Likert scale, indicating the rate of occurrence of the symptom during the time reference. In some embodiments, after treating according to the methods of the disclosure, a subject's SCL-90 score decreases by about 5% to about 100%, for example, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Life Changes Inventory (LCI) questionnaire is utilized to evaluate the safety and/or efficacy of psilocybin. The LCI is designed as a questionnaire to investigate those variables present in the day-to-day experience of adults that might relate either to stability or decline of intellectual ability.

In some embodiments, Social Cognition Panel scales are utilized to evaluate the safety and/or efficacy of psilocybin. The social cognition panel scales comprise the pictorial empathy test (PET), reading the mind in the eyes test (RMET), social value orientation (SVO) test, the Toronto Empathy Questionnaire (TEQ), and the scale of social responsibility (SSR).

In some embodiments, the Pictorial Empathy Test (PET) is utilized to evaluate the effect of psilocybin on affective empathy.

In some embodiments, Reading the Mind in the Eyes Test (RMET) is utilized to evaluate the safety and/or efficacy of psilocybin. The RMET has 36 items, in which subjects are presented with a photograph of the eyes region of the face and must choose 1 of 4 adjectives or phrases to describe the mental state of the person pictured. A definition handout is provided at the beginning of the task and a practice item precedes the first trial.

In some embodiments, the Social Value Orientation (SVO) test is utilized to evaluate the safety and/or efficacy of psilocybin. The SVO Slider Measure has 6 primary items with 9 secondary (and optional) items. All of the items have the same general form. Each item is a resource allocation choice over a well-defined continuum of joint payoffs.

In some embodiments, after treating according to the methods of the disclosure, one or more of the subject's Social Cognition Panel Scales Score, i.e., PET, RMET, SVO, TEQ, and/or SSR score), improves by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Toronto Empathy Questionnaire (TEQ) is utilized to evaluate the safety and/or efficacy of psilocybin. The TEQ represents empathy as a primarily emotional process. The TEQ has exhibited good internal consistency and high test-retest reliability. The TEQ is a brief, reliable and valid instrument for the assessment of empathy. In some embodiments, after treating according to the methods of the disclosure, a subject's TEQ score increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Scale of Social Responsibility (SSR) is utilized to evaluate the safety and/or efficacy of psilocybin. The SSR measures perceptions regarding the importance of ethics and social responsibility.

In some embodiments, the Sheehan Suicidality Tracking Scale (SSTS) is utilized to evaluate the safety and/or efficacy of psilocybin. The SSTS is a 16-item scale that assesses the seriousness of suicidality phenomena on a Likert-type scale (0-4) ranging from "not at all" (0) to "extremely". The SSTS assesses the frequency of key phenomena and the overall time spent in suicidality.

In some embodiments, the Mini International Neuropsychiatric Interview (MINI) (version 7.0.2) is utilized to evaluate the safety and efficacy of psilocybin. The MINI is a brief structured interview for the major Axis I psychiatric disorders in DSM-5 and International Classification of Diseases-10. In some embodiments, the MINI is used to diagnose a subject with a disorder.

In some embodiments, the McLean Screening Instrument for Borderline Personality Disorder (MSIBPD) is utilized for evaluating the safety and/or efficacy of psilocybin. The MSIBPD is a useful screening tool for identifying the presence of DMS-IV borderline personality disorder.

In some embodiments, the Tellegen Absorption Scale is utilized for evaluating the safety and/or efficacy of psilocybin. The Tellegen Absorption Scale is a 34-item multidimensional measure that assesses imaginative involvement and the tendency to become mentally absorbed in everyday activities.

In some embodiments, the safety and/or efficacy of psilocybin is evaluated by physical examination. A physical examination, includes, but is not limited to, an examination of the subject's general appearance, including an examination of the skin, neck, eyes, ears, nose, throat, heart, lungs, abdomen, lymph nodes, extremities and musculoskeletal system.

In some embodiments, body weight and height of a subject are assessed. In some embodiments, body mass index is used to assess the safety and/or efficacy of psilocybin.

In some embodiments, an electrocardiogram (ECG) is utilized to evaluate the safety and/or efficacy of psilocybin. In some embodiments, a Standard 12-lead ECG is obtained.

In some embodiments, vital signs of a subject are used to evaluate safety and/or efficacy of psilocybin. Vital signs include, but are not limited to, blood pressure (BP), respiratory rate, oral body temperature and pulse. In some embodiments, blood pressure is taken after a subject has been sitting down for at least three minutes.

In some embodiments, clinical laboratory tests are utilized to evaluate the safety and/or efficacy of psilocybin. In some embodiments, the clinical laboratory tests include blood samples and/or urine samples. In some embodiments, hemoglobin, hematocrit, red blood cell count, mean corpuscular hemoglobin, mean corpuscular volume, mean corpuscular hemoglobin concentration, white blood cell count (with differential) and platelet count are measured to evaluate safety and/or efficacy of psilocybin. In some embodiments, albumin, alkaline phosphatase, alanine aminotransferase (ALT), amylase, aspartate aminotransferase (AST), bicarbonate, bilirubin (direct, indirect and total), calcium, chloride, creatine kinase, creatinine, γ-glutamyl transferase, glucose, lactate dehydrogenase, lipase, magnesium, phosphate, potassium, protein-total, sodium, blood urea nitrogen and/or uric acid are measured to evaluate the safety and/or efficacy of psilocybin.

In some embodiments, urine is tested for pregnancy and/or illicit drugs.

In some embodiments, the safety and/or efficacy of psilocybin are evaluated by measuring adverse events. Adverse events are classified as mild, moderate, or severe. A mild adverse event does not interfere in a significant manner with the subject's normal level of functioning. A moderate adverse event produces some impairment of functioning, but is not hazardous to the subject's health. A serious adverse event produces significant impairment of functioning or incapacitation and is a definite hazard to the subject's health. Adverse events may include, for example, euphoric mood, dissociative disorder, hallucination, psychotic disorder, cognitive disorder, disturbances in attention, mood alterations, psychomotor skill impairments, inappropriate affects, overdoses, and intentional product misuse. In some embodiments, serious adverse events include death, life-threatening adverse events, inpatient hospitalization or prolongation of existing hospitalization, persistent or significant disability/incapacity, and congenital anomaly/birth defect in the offspring of a subject who received psilocybin. In some embodiments, serious adverse events include intensive treatment in an emergency room or at home for allergic bronchospasm, blood dyscrasias or convulsions that do not result in inpatient hospitalization, or the development of drug dependency or drug abuse.

Numbered Embodiments of the Disclosure

In addition to the disclosure above, the Examples below, and the appended claims, the disclosure sets forth the following numbered embodiments.

Numbered Embodiments for Treatment of Anxiety Disorders with Psilocybin

1. A method of treating an anxiety disorder in a subject in need thereof, the method comprising administering to the subject a therapeutically effective amount of psilocybin or an active metabolite thereof.

2. The method of embodiment 1, wherein the active metabolite is psilocin.

3. The method of any one of embodiments 1-2, wherein the anxiety disorder is a generalized anxiety disorder.

4. The method of any one of embodiments 1-2, wherein the anxiety disorder is a panic disorder.

5. The method of any one of embodiments 1-2, wherein the anxiety disorder is a post-traumatic stress disorder.

6. The method of any one of embodiments 1-2 wherein the anxiety disorder is a social anxiety disorder.

7. The method of any one of embodiments 1-2, wherein the anxiety disorder is an obsessive-compulsive and related disorder.

8. The method of embodiment 7, wherein the obsessive-compulsive and related disorder is obsessive compulsive disorder, body dysmorphic disorder, hoarding disorder, trichotillomania, excoriation, substance-induced obsessive compulsive and related disorder, or an obsessive-compulsive disorder due to another medical condition.

9. The method of any one of embodiments 1-2, wherein the anxiety disorder is a specific phobia and/or agoraphobia.

10. The method of embodiment 9, wherein the specific phobia is an animal phobia, natural environment phobia, blood-injection-injury phobia, or situational phobia.

11. The method of any one of embodiments 1-10, wherein the subject has at least one comorbidity 12. The method of embodiment 11, wherein the comorbidity is a mood disorder, major depressive disorder, bipolar disorder, schizophrenia, an eating disorder, attention deficit/hyperactivity disorder, epilepsy, cardiovascular disease, migraine, irritable bowel syndrome, dementia, Alzheimer's disease, Parkinson's disease, or combinations thereof.

13. The method of any one of embodiments 1-12, wherein no other treatment is administered to the subject to treat anxiety disorder after administration of the psilocybin.

14. The method of any one of embodiments 1-13, wherein the subject is administered a therapy and wherein the therapy is transcranial magnetic stimulation, cognitive behavioral therapy, interpersonal psychotherapy, dialectical behavior therapy, mindfulness techniques, or acceptance and commitment therapy, commitment therapy, or combinations thereof.

15. The method of any one of embodiments 1-14, wherein the subject is administered at least one additional therapeutic, and wherein the additional therapeutic is an antidepressant, an anticonvulsant, lisdexamfetamine dimesylate, an antipsychotic, an anti-inflammatory drug, an analgesic drug, a cardiovascular drug, a triptan, a cardiovascular drug, or combinations thereof.

16. The method of embodiment 15, wherein the administration of the additional therapeutic is prior to administration of psilocybin.

17. The method of embodiment 15, wherein the administration of the additional therapeutic is after administration of psilocybin.

18. The method of embodiment 15, wherein the administration of the additional therapeutic is concurrent with administration of psilocybin.

19. The method of embodiment 14, wherein the administration of a therapy is prior to administration of psilocybin.

20. The method of embodiment 14, wherein the administration of a therapy is after administration of psilocybin.

21. The method of embodiment 14, wherein the administration of a therapy is concurrent with administration of psilocybin.

22. The method of any one of embodiments 1-21, wherein at least one sign or symptom of anxiety is improved following the administration of the psilocybin or active metabolite thereof.

23. The method of any one of embodiments 1-21, wherein the sign or symptom of anxiety is tachycardia, tremor, fatigue, worry, irritability, obsession, compulsion, disturbed sleep, or combinations thereof.

24. The method of embodiment 23, wherein the sign or symptom of anxiety is measured according to a diary assessment, an assessment by clinician or caregiver, or a clinical scale.

25. The method according to embodiment 24, wherein the clinical scale is Spielberger's Trait and Anxiety Scale or a Generalized Anxiety Disorder 7-Item Scale.

26. The method of any one of embodiments 1-25, wherein the subject has improved cognition, information processing, stress levels, immune system, or combinations thereof following the administration of the psilocybin or active metabolite thereof.

27. The method of any one of embodiments 1-26, wherein at least one symptom of anxiety is alleviated within 24 hours of administration of the psilocybin.

28. The method of any one of embodiments 1-26, wherein at least one symptom of anxiety is alleviated within 1 week of administration of the psilocybin.

29. The method of any one of embodiments 1-26, wherein at least one symptom of anxiety is alleviated for a period of at least 1 month after administration of the psilocybin.

30. The method of any one of embodiments 1-26, wherein at least one symptom of anxiety is alleviated for a period of at least 3 months after administration of the psilocybin.

31. The method of any one of embodiments 1-26, wherein at least one symptom of anxiety is alleviated for a period of at least 12 months after administration of the psilocybin.

32. The method of any one of embodiments 1-31, wherein the subject has no prior psilocybin exposure.

33. The method of any one of embodiments 1-31, wherein the subject has prior psilocybin exposure.

34. The method of any one of embodiments 1-33 wherein the subject is a mammal.

35. The method of embodiment 34, wherein the subject is a human.

36. The method of any of embodiments 1-35, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

37. The method of embodiment 36, wherein the crystalline psilocybin comprises at least 95% by weight of Polymorph A.

38. The method of embodiment 36 or 37, wherein the crystalline psilocybin has a chemical purity of greater than 97% by HPLC, and no single impurity of greater than 1%.

39. The method of any of embodiments 1-38, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

40. The method of embodiment 39, wherein the highly pure crystalline psilocybin comprises at least 90% by weight of Polymorph A.

41. The method of embodiment 40, wherein the highly pure crystalline psilocybin comprises at least 95% by weight of Polymorph A.

42. The method of any one of embodiments 36-41, wherein the highly pure crystalline psilocybin is further characterized having either: (i) a water content of <0.5% w/w; or (ii) <0.5% w/w loss in the TGA thermogram between 25° C. and 200° C.

43. The method of any of embodiments 36-42, wherein the highly pure crystalline psilocybin is further characterized by an endothermic event in a DSC thermogram having a first onset temperature of between 145° C. and 155° C. and a second onset temperature of between 205 and 220° C.

44. The method of any one of embodiments 36-43, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

45. The method of any of embodiments 36-44, wherein the highly pure crystalline psilocybin has no single impurity of greater than 0.5%.

46. The method of any of embodiments 36-45, wherein the dosage form further comprises about 5 to 40 mg of the highly pure crystalline psilocybin.

47. The method of embodiment 46, wherein the dosage form comprises 5 mg of highly pure crystalline psilocybin.

48. The method of embodiment 46, wherein the dosage form comprises about 10 mg of highly pure crystalline psilocybin.

49. The method of embodiment 46, wherein the dosage form comprises about 35 mg of highly pure crystalline psilocybin.

50. The method of any of embodiments 36-49, wherein the dosage form comprises silicified microcrystalline cellulose.

51. The method of embodiment 50, wherein the silicified microcrystalline cellulose has a particle size range from about 45 to 150 microns.

52. The method of any of embodiments 36-51, further comprising a mixture of two silicified microcrystalline cellulose variants wherein the first variant has a particle size from about 45 to 80 microns and the second variant has a particle size of about 90 to 150 microns.

53. The method of embodiment 52, wherein about 30% or less of the microcrystalline cellulose is the first variant having a particle size from about 45 to 80 microns and about 70% or more of the microcrystalline cellulose is the second variant having a particle size of about 90 to 150 microns.

54. The method of embodiment 52, wherein about 20% or less of the microcrystalline cellulose is the first variant having a particle size from about 45 to 80 microns and about 80% or more of the microcrystalline cellulose is the second variant having a particle size of about 90 to 150 microns.

55. The method of embodiment 52, wherein about 15% or less of the microcrystalline cellulose is the first variant having a particle size from about 45 to 80 microns and about 85% or more of the microcrystalline cellulose is the second variant having a particle size of about 90 to 150 microns.

56. The method of embodiment 52, wherein about 15% or less of the microcrystalline cellulose is the first variant having a particle size from about 45 to 80 microns and about 85% or more of the microcrystalline cellulose is the second variant having a particle size of about 90 to 150 microns.

57. The method of embodiment 56, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

58. The method of embodiment 56, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

59. The method any one of embodiments 36-58, wherein the dosage form is an oral dosage form.

60. The method embodiment 59, wherein the dosage form is a capsule.

61. The method embodiment 59, wherein the dosage form is a tablet.

62. The method of any one of embodiments 1-61, wherein at least one dose of psilocybin is administered to the subject.

63. The method of embodiment 62, wherein the at least dose of psilocybin is in the range of about 0.1 mg to about 100 mg.

64. The method of embodiment 63, wherein the dose of psilocybin is about 1 mg.

65. The method of embodiment 63, wherein the dose of psilocybin is about 10 mg.

66. The method of embodiment 63, wherein the dose of psilocybin is about 25 mg.

67. The method of any one of embodiments 1-66, wherein more than one dose of psilocybin is administered to the subject.

68. The method of embodiment 67, wherein at least two doses of psilocybin are administered to the subject.

69. The method of any one of embodiments 67-68, wherein the psilocybin is administered once per day.

70. The method of any one of embodiments 67-68, wherein the psilocybin is administered at least once per week.

71. The method of any one of embodiments 67-68, wherein the psilocybin is administered at least twice per week.

72. The method of any one of embodiments 67-68, wherein the psilocybin is administered at least once per month.

73. The method of any one of embodiments 67-68, wherein the psilocybin is administered at least twice per month.

74. The method of any one of embodiments 67-68, wherein the psilocybin is administered at least once every three months.

75. The method of any one of embodiments 67-68, wherein the psilocybin is administered at least once every six months.

76. The method of any one of embodiments 67-68, wherein the psilocybin is administered at least once every 12 months.

77. The method of any one of embodiments 67-76, wherein each dose of psilocybin administered is in the range of about 0.1 mg to about 100 mg.

78. The method of embodiment 77, wherein each dose of psilocybin administered is about 1 mg.

79. The method of embodiment 77, wherein each dose of psilocybin administered is about 10 mg.

80. The method of embodiment 77, wherein each dose of psilocybin administered is about 25 mg.

81. The method of any one of embodiments 62-80, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

82. The method of embodiment 81, wherein the psilocybin is administered orally.

83. The method of any one of embodiments 1-82, wherein the subject participates in at least one psychological support session before administration of the psilocybin.

84. The method of embodiment 83, wherein the subject participates in at least three psychological support sessions before administration of the psilocybin.

85. The method of any one of embodiments 83-84, wherein the at least one therapeutic intention is discussed during the psychological support session.

86. The method of any one of embodiments 83-85, wherein self-directed inquiry and experiential processing are practiced during the psychological support session.

87. The method of any one of embodiments 83-86, wherein the subject participates in at least one psychological support session after administration of the psilocybin.

88. The method of embodiment 87, wherein the subject participates in at least three psychological support sessions after administration of the psilocybin.

89. The method of any one of embodiments 83-88, wherein the psilocybin is administered to the subject in a room with a substantially non-clinical appearance.

90. The method of embodiment 89, wherein the room comprises soft furniture.

91. The method of embodiment 89, wherein the room is decorated using muted colors.

92. The method of embodiment 89, wherein the room comprises a high-resolution sound system.

93. The method of any one of embodiments 89-92, wherein the room comprises a bed or a couch.

94. The method of embodiment 93, wherein the subject lies in the bed or on the couch for approximately 4-8 hours, or a substantial fraction thereof, after administration of the psilocybin.

95. The method of any one of embodiments 89-94, wherein the subject listens to music for approximately 4-8 hours, or a substantial fraction thereof, after administration of the psilocybin.

96. The method of any one of embodiments 89-95, wherein the subject wears an eye mask for approximately 4-8 hours, or a substantial fraction thereof, after administration of the psilocybin.

97. The method of any one of embodiments 89-96, wherein a therapist provides psychological support to the subject for approximately 4-8 hours after administration of the psilocybin.

98. The method of embodiment 97, wherein the therapist uses guided imagery to calm the subject and/or focus the subject's attention.

99. The method of embodiment 97, wherein the therapist provides reassuring physical contact with the subject.

100. The method of embodiment 99, wherein the therapist holds the hand, arm, or shoulder of the subject.

101. The method of embodiment 97, wherein the therapist encourages the subject to perform self-directed inquiry and experiential processing.

102. The method of embodiment 97, wherein the therapist reminds the subject of at least one therapeutic intention.

103. The method of embodiment 97, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

104. The method of embodiment 97, wherein the therapist does not initiate conversation with the subject.

105. The method of embodiment 97, wherein the therapist responds to the subject if the subject initiates conversation.

106. The method of any one of embodiments 1-105, wherein the subject participates in at least one psychological support session before administration of the psilocybin.

107. The method of any one of embodiments 1-105, wherein the subject participates in at least one psychological support session after administration of the psilocybin.

108. The method of any one of embodiments 1-105, wherein a therapist provides psychological support to the subject for approximately 4-8 hours after administration of the psilocybin.

109. The method of any one of embodiments 106-108, wherein the psychological support is provided remotely to the subject.

110. The method of embodiment 109, wherein the psychological support is provided via a digital or electronic system.

111. The method of embodiment 110, wherein the digital or electronic system is a mobile phone app.

112. The method of embodiment 110, wherein the digital or electronic system is a website.

Numbered Embodiments for Treatment of Eating Disorders with Psilocybin

1. A method for treating an eating disorder in a subject in need thereof, the method comprising administering to the subject a therapeutically effective amount of psilocybin or an active metabolite thereof.

2. The method of embodiment 1, wherein the active metabolite is psilocin.

3. The method of embodiment 1 or 2, wherein at least one sign or symptom of an eating disorder is improved following administration of psilocybin or a metabolite thereof.

4. The method of any one of embodiments 1-3, wherein the subject in need thereof has at least two eating disorders.

5. The method of any one of embodiments 1-4, wherein the subject in need thereof has at least three eating disorders.

6. The method of any one of embodiments 1-5, wherein the eating disorder is pica, anorexia nervosa, bulimia nervosa, rumination disorder, avoidant/restrictive food intake disorder, binge-eating disorder, or combinations thereof.

7. The method of embodiment 6, wherein the eating disorder is anorexia nervosa.

8. The method of embodiment 6, wherein the eating disorder is binge-eating disorder.

9. The method of any one of embodiments 1-8, wherein the subject has one or more comorbidities.

10. The method of embodiment 9, wherein the one or more comorbidities is obesity, one or more conditions related to obesity, or both.

11. The method of embodiment 10, wherein the one or more condition related to obesity is a metabolic syndrome, diabetes, hypertension, dyslipidaemias, sleep problems or disorders, or pain.

12. The method of embodiment 9, wherein the one or more comorbidities is reproductive dysfunction, polycystic ovary syndrome, or menstrual dysfunction.

13. The method of embodiment 9, wherein the comorbidity is a psychiatric disorder selected from schizophrenia, schizoaffective disorder, bipolar disorder, major depressive disorder, anxiety disorder, obsessive compulsive disorder, post-traumatic stress disorder, attention deficit hyperactivity disorder, autism, alcohol use disorder, drug use disorder, or suicide attempt.

14. The method of any one of embodiments 9-13, wherein administration of the psilocybin ameliorates at least one sign or symptom of the at least one disease, disorder, or condition which is comorbid with an eating disorder.

15. The method of any one of embodiments 1-14, wherein the subject is administered one or more additional therapeutics.

16. The method of any one of embodiments 1-15, wherein the one or more additional therapeutics is an antidepressant, anticonvulsant, lisdexamfetramine dimesylate, opioid antagonist, or combinations thereof.

17. The method of any one of embodiments 1-14, wherein the subject is administered one or more additional therapies 18. The method of any one of embodiments 1-16, wherein the additional therapy is transcranial magnetic stimulation, cognitive behavioral therapy, interpersonal psychotherapy, dialectical behaviour therapy, weight loss therapy, mindfulness techniques, or acceptance and commitment therapy.

19. The method of embodiment 15 or 16, wherein the administering of one or more additional therapeutics is prior to administration of psilocybin.

20. The method of embodiment 15 or 16, wherein the administering of one or more therapeutics is after administration of psilocybin.

21. The method of embodiment 15 or 16, wherein the administering of one or more therapeutics is concurrent with administration of psilocybin.

22. The method of embodiment 17 or 18, wherein the administering of a therapy is prior to administration of psilocybin.

23. The method of embodiment 17 or 18, wherein the administering of a therapy is after administration of psilocybin.

24. The method of embodiment 17 or 18, wherein the administering of a therapy is concurrent with administration of psilocybin.

25. The method of anyone one of embodiments 1-24, wherein after treating the subject in need thereof has a decreased eating disorder examination short form (EDE-QS) score compared to prior to said treating.

26. The method of anyone one of embodiments 1-25, wherein after treating the subject in need thereof has a decreased Physical Appearance State and Trait Anxiety Scale (PASTAS) score compared to prior to said treating.

27. The method of anyone one of embodiments 1-26, wherein after treating the subject in need thereof has a higher willingness to change compared to prior to said treating as evaluated by the Eating Disorder Readiness Ruler (ED-RR).

28. The method of any one of embodiments 1-27, wherein after treating the subject in need thereof has a decreased Montgomery-Asberg Depression Rating Scale (MADRS) score compared to prior to said treating.

29. The method of any one of embodiments 1-28, wherein after treating the subject in need thereof has an increased Body Image State Scale (BISS) compared to prior to said treating.

30. The method of any one of embodiments 1-37, wherein the subject has no prior psilocybin exposure.

31. The method of any one of embodiments 1-37, wherein the subject has prior psilocybin exposure.

32. The method of any one of embodiments 1-31, wherein the subject is a mammal.

33. The method of embodiment 32, wherein the subject is a human.

34. The method of any of embodiments 1-33, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

35. The method of embodiment 34, wherein the crystalline psilocybin comprises at least 95% by weight of Polymorph A.

36. The method of embodiment 34 or 35, wherein the crystalline psilocybin has a chemical purity of greater than 97% by HPLC, and no single impurity of greater than 1%.

37. The method of any of embodiments 1-33, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

38. The method of embodiment 37, wherein the highly pure crystalline psilocybin comprises at least 90% by weight of Polymorph A.

39. The method of embodiment 38, wherein the highly pure crystalline psilocybin comprises at least 95% by weight of Polymorph A.

40. The method of any one of embodiments 34-38, wherein the highly pure crystalline psilocybin is further characterized having either: (i) a water content of <0.5% w/w; or (ii) <0.5% w/w loss in the TGA thermogram between 25° C. and 200° C.

41. The method of any of embodiments 34-39, wherein the highly pure crystalline psilocybin is further characterized by an endothermic event in a DSC thermogram having a first onset temperature of between 145° C. and 155° C. and a second onset temperature of between 205 and 220° C.

42. The method of any one of embodiments 34-41, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

43. The method of any of embodiments 34-42, wherein the highly pure crystalline psilocybin has no single impurity of greater than 0.5%.

44. The method of any of embodiments 34-43, wherein the dosage form further comprises about 5 to 40 mg of the highly pure crystalline psilocybin.

45. The method of embodiment 44, wherein the dosage form comprises 5 mg of highly pure crystalline psilocybin.

46. The method of embodiment 44, wherein the dosage form comprises about 10 mg of highly pure crystalline psilocybin.

47. The method of embodiment 44, wherein the dosage form comprises about 35 mg of highly pure crystalline psilocybin.

48. The method of any of embodiments 34-47, wherein the dosage form comprises silicified microcrystalline cellulose.

49. The method of embodiment 48, wherein the silicified microcrystalline cellulose has a particle size range from about 45 to 150 microns.

50. The method of any of embodiments 34-49, further comprising a mixture of two silicified microcrystalline cellulose variants wherein the first variant has a particle size from about 45 to 80 microns and the second variant has a particle size of about 90 to 150 microns.

51. The method of embodiment 50, wherein about 30% or less of the microcrystalline cellulose is the first variant having a particle size from about 45 to 80 microns and about 70% or more of the microcrystalline cellulose is the second variant having a particle size of about 90 to 150 microns.

52. The method of embodiment 50, wherein about 20% or less of the microcrystalline cellulose is the first variant having a particle size from about 45 to 80 microns and about 80% or more of the microcrystalline cellulose is the second variant having a particle size of about 90 to 150 microns.

53. The method of embodiment 50, wherein about 15% or less of the microcrystalline cellulose is the first variant having a particle size from about 45 to 80 microns and about 85% or more of the microcrystalline cellulose is the second variant having a particle size of about 90 to 150 microns.

54. The method of embodiment 50, wherein about 15% or less of the microcrystalline cellulose is the first variant having a particle size from about 45 to 80 microns and about 85% or more of the microcrystalline cellulose is the second variant having a particle size of about 90 to 150 microns.

55. The method of embodiment 54, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

56. The method of embodiment 54, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

57. The method any one of embodiments 34-56, wherein the dosage form is an oral dosage form.

58. The method embodiment 57, wherein the dosage form is a capsule.

59. The method embodiment 57, wherein the dosage form is a tablet.

60. The method of any one of embodiments 1-59, wherein at least one dose of psilocybin is administered to the subject.

61. The method of embodiment 60, wherein the at least dose of psilocybin is in the range of about 0.1 mg to about 100 mg.

62. The method of embodiment 61, wherein the dose of psilocybin is about 1 mg.

63. The method of embodiment 61, wherein the dose of psilocybin is about 10 mg.

64. The method of embodiment 61, wherein the dose of psilocybin is about 25 mg.

65. The method of any one of embodiments 1-59, wherein more than one dose of psilocybin is administered to the subject.

66. The method of embodiment 65, wherein at least two doses of psilocybin are administered to the subject.

67. The method of any one of embodiments 65-66, wherein the psilocybin is administered once per day.

68. The method of any one of embodiments 65-66, wherein the psilocybin is administered at least once per week.

69. The method of any one of embodiments 65-66, wherein the psilocybin is administered at least twice per week.

70. The method of any one of embodiments 65-66, wherein the psilocybin is administered at least once per month.

71. The method of any one of embodiments 65-66, wherein the psilocybin is administered at least twice per month.

72. The method of any one of embodiments 65-66, wherein the psilocybin is administered at least once every three months.

73. The method of any one of embodiments 65-66, wherein the psilocybin is administered at least once every six months.

74. The method of any one of embodiments 65-66, wherein the psilocybin is administered at least once every 12 months.

75. The method of any one of embodiments 65-74, wherein each dose of psilocybin administered is in the range of about 0.1 mg to about 100 mg.

76. The method of embodiment 75, wherein each dose of psilocybin administered is about 1 mg.

77. The method of embodiment 75, wherein each dose of psilocybin administered is about 10 mg.

78. The method of embodiment 75, wherein each dose of psilocybin administered is about 25 mg.

79. The method of any one of embodiments 60-78, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

80. The method of embodiment 79, wherein the psilocybin is administered orally.

81. The method of any one of embodiments 1-80, wherein the subject participates in at least one psychological support session before administration of the psilocybin.

82. The method of embodiment 81, wherein the subject participates in at least three psychological support sessions before administration of the psilocybin.

83. The method of any one of embodiments 81-82, wherein the at least one therapeutic intention is discussed during the psychological support session.

84. The method of any one of embodiments 81-83, wherein self-directed inquiry and experiential processing are practiced during the psychological support session.

85. The method of any one of embodiments 81-84, wherein the subject participates in at least one psychological support session after administration of the psilocybin.

86. The method of embodiment 85, wherein the subject participates in at least three psychological support sessions after administration of the psilocybin.

87. The method of any one of embodiments 81-86, wherein the psilocybin is administered to the subject in a room with a substantially non-clinical appearance.

88. The method of embodiment 87, wherein the room comprises soft furniture.

89. The method of embodiment 87, wherein the room is decorated using muted colors.

90. The method of embodiment 87, wherein the room comprises a high-resolution sound system.

91. The method of any one of embodiments 87-90, wherein the room comprises a bed or a couch.

92. The method of embodiment 91, wherein the subject lies in the bed or on the couch for approximately 4-8 hours, or a substantial fraction thereof, after administration of the psilocybin.

93. The method of any one of embodiments 87-92, wherein the subject listens to music for approximately 4-8 hours, or a substantial fraction thereof, after administration of the psilocybin.

94. The method of any one of embodiments 87-93, wherein the subject wears an eye mask for approximately 4-8 hours, or a substantial fraction thereof, after administration of the psilocybin.

95. The method of any one of embodiments 87-94, wherein a therapist provides psychological support to the subject for approximately 4-8 hours after administration of the psilocybin.

96. The method of embodiment 95, wherein the therapist uses guided imagery to calm the subject and/or focus the subject's attention.

97. The method of embodiment 95, wherein the therapist provides reassuring physical contact with the subject.

98. The method of embodiment 97, wherein the therapist holds the hand, arm, or shoulder of the subject.

99. The method of embodiment 95, wherein the therapist encourages the subject to perform self-directed inquiry and experiential processing.

100. The method of embodiment 95, wherein the therapist reminds the subject of at least one therapeutic intention.

101. The method of embodiment 95, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

102. The method of embodiment 95, wherein the therapist does not initiate conversation with the subject.

103. The method of embodiment 95, wherein the therapist responds to the subject if the subject initiates conversation.

104. The method of any one of embodiments 1-103, wherein the subject participates in at least one psychological support session before administration of the psilocybin.

105. The method of any one of embodiments 1-103, wherein the subject participates in at least one psychological support session after administration of the psilocybin.

106. The method of any one of embodiments 1-103, wherein a therapist provides psychological support to the subject for approximately 4-8 hours after administration of the psilocybin.

107. The method of any one of embodiments 104-106, wherein the psychological support is provided remotely to the subject.

108. The method of embodiment 107, wherein the psychological support is provided via a digital or electronic system.

109. The method of embodiment 108, wherein the digital or electronic system is a mobile phone app.

110. The method of embodiment 108, wherein the digital or electronic system is a website.

Numbered Embodiments for Treatment of Migraine with Psilocybin

1. A method of preventing or treating migraine in a subject in need thereof, the method comprising administering to the subject a therapeutically effective amount of psilocybin or an active metabolite thereof.

2. The method of embodiment 1, wherein the migraine is a migraine without aura, a migraine with aura, a chronic migraine, an abdominal migraine, a basilar migraine, a menstrual migraine, an ophthalmoplegic migraine, ophthalmic migraine, or a hemiplegic migraine.

3. The method of embodiment 1 or 2, wherein at least one sign or symptom of migraine is improved following administration of psilocybin or a metabolite thereof.

4. The method of embodiment 3, wherein the sign or symptom of migraine is headache, nausea, sensitivity to light, sensitivity to sound, sensitivity to smell, dizziness, difficulty speaking, vertigo, vomiting, seizure, distorted vision, fatigue, or loss of appetite.

5. The method of embodiment 4, wherein the sign or symptom of migraine is measured according to a diary assessment, a physical or psychological assessment by clinician, an imaging test, an electroencephalogram, or a blood test.

6. The method of embodiment 5, wherein the assessment is the Visual Aura Rating Scale or the ID Migraine questionnaire.

7. The method of any one of embodiments 1-6, wherein at least one sign or symptom of migraine is improved within 15 minutes of administration of the psilocybin.

8. The method of any one of embodiments 1-6, wherein at least one sign or symptom of migraine is improved within about 30 minutes of administration of the psilocybin.

9. The method of any one of embodiments 1-6, wherein at least one sign or symptom of migraine is improved within about 1 hour of administration of the psilocybin.

10. The method of any one of embodiments 1-6, wherein at least one sign or symptom of migraine is improved within about 3 hours of administration of the psilocybin.

11. The method of any one of embodiments 1-6, wherein at least one sign or symptom of migraine is improved within about 6 hours of administration of the psilocybin.

12. The method of any one of embodiments 1-2, wherein administration of psilocybin prevents the occurrence of the migraine for at least about 1 month.

13. The method of any one of embodiments 1-2, wherein administration of psilocybin prevents the occurrence of the migraine for at least about 3 months.

14. The method of any one of embodiments 1-2, wherein administration of psilocybin prevents the occurrence of the migraine for at least about 6 months.

15. The method of any one of embodiments 1-2, wherein administration of psilocybin prevents the occurrence of the migraine for at least about 12 months.

16. The method of any one of embodiments 1-15, wherein no other treatment is administered to the subject to prevent or treat migraine after administration of the psilocybin.

17. The method of any one of embodiments 1-15, wherein the method further comprises administering to the subject at least one additional therapeutic to prevent or treat migraine.

18. The method of embodiment 17, wherein the at least one additional therapeutic comprises a non-steroid anti-inflammatory drug, acetaminophen, caffeine, a triptan, a dihydroergotamine, an opioid, an anti-nausea drug, a blood pressure-lowering medication, an anti-depressant, an anti-seizure drug, a botox injection, a monoclonal antibody directed to calcitonin gene-related peptide, acupuncture, black room, change of diet, hot/cold therapy, magnesium intake, massages, riboflavin/B2 intake, transcranial magnetic stimulation, or any combination thereof.

19. The method of any one of embodiments 1-18, wherein the subject has at least one disease, disorder, or condition which is comorbid with migraine.

20. The method of embodiment 19, wherein the at least one disease, disorder, or condition is stroke, vascular brain lesions, coronary heart disease, patent foramen ovale, hypertension, depression, anxiety, bipolar disorder, panic disorder, suicide, restless leg syndrome, epilepsy, inflammatory bowel disease, or asthma.

21. The method of embodiment 19 or 20, wherein administration of the psilocybin ameliorates at least one sign or symptom of the at least one disease, disorder, or condition which is comorbid with migraines.

22. The method of any one of embodiments 1-21, wherein the active metabolite is psilocin.

23. The method of any one of embodiments 1-22, wherein the subject has no prior psilocybin exposure.

24. The method of any one of embodiments 1-22, wherein the subject has prior psilocybin exposure.

25. The method of any one of embodiments 1-24, wherein the subject is a mammal.

26. The method of embodiment 25, wherein the subject is a human.

27. The method of any of embodiments 1-26, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

28. The method of embodiment 27, wherein the crystalline psilocybin comprises at least 95% by weight of Polymorph A.

29. The method of embodiment 27 or 28, wherein the crystalline psilocybin has a chemical purity of greater than 97% by HPLC, and no single impurity of greater than 1%.

30. The method of any of embodiments 1-29, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

31. The method of embodiment 30, wherein the highly pure crystalline psilocybin comprises at least 90% by weight of Polymorph A.

32. The method of embodiment 31, wherein the highly pure crystalline psilocybin comprises at least 95% by weight of Polymorph A.

33. The method of any one of embodiments 27-32, wherein the highly pure crystalline psilocybin is further characterized having either: (i) a water content of <0.5% w/w; or (ii) <0.5% w/w loss in the TGA thermogram between 25° C. and 200° C.

34. The method of any of embodiments 27-33, wherein the highly pure crystalline psilocybin is further characterized by an endothermic event in a DSC thermogram having a first onset temperature of between 145° C. and 155° C. and a second onset temperature of between 205 and 220° C.

35. The method of any one of embodiments 27-34, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

36. The method of any of embodiments 33-35, wherein the highly pure crystalline psilocybin has no single impurity of greater than 0.5%.

37. The method of any of embodiments 27-36, wherein the dosage form further comprises about 5 to 40 mg of the highly pure crystalline psilocybin.

38. The method of embodiment 37, wherein the dosage form comprises 5 mg of highly pure crystalline psilocybin.

39. The method of embodiment 37, wherein the dosage form comprises about 10 mg of highly pure crystalline psilocybin.

40. The method of embodiment 37, wherein the dosage form comprises about 35 mg of highly pure crystalline psilocybin.

41. The method of any of embodiments 27-40, wherein the dosage form comprises silicified microcrystalline cellulose.

42. The method of embodiment 41, wherein the silicified microcrystalline cellulose has a particle size range from about 45 to 150 microns.

43. The method of any of embodiments 27-42, further comprising a mixture of two silicified microcrystalline cellulose variants wherein the first variant has a particle size from about 45 to 80 microns and the second variant has a particle size of about 90 to 150 microns.

44. The method of embodiment 43, wherein about 30% or less of the microcrystalline cellulose is the first variant having a particle size from about 45 to 80 microns and about 70% or more of the microcrystalline cellulose is the second variant having a particle size of about 90 to 150 microns.

45. The method of embodiment 43, wherein about 20% or less of the microcrystalline cellulose is the first variant having a particle size from about 45 to 80 microns and about 80% or more of the microcrystalline cellulose is the second variant having a particle size of about 90 to 150 microns.

46. The method of embodiment 43, wherein about 15% or less of the microcrystalline cellulose is the first variant having a particle size from about 45 to 80 microns and about 85% or more of the microcrystalline cellulose is the second variant having a particle size of about 90 to 150 microns.

47. The method of embodiment 43, wherein about 15% or less of the microcrystalline cellulose is the first variant having a particle size from about 45 to 80 microns and about 85% or more of the microcrystalline cellulose is the second variant having a particle size of about 90 to 150 microns.

48. The method of embodiment 47, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

49. The method of embodiment 47, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

50. The method any one of embodiments 27-49, wherein the dosage form is an oral dosage form.

51. The method embodiment 50, wherein the dosage form is a capsule.

52. The method embodiment 50, wherein the dosage form is a tablet.

53. The method of any one of embodiments 1-52, wherein at least one dose of psilocybin is administered to the subject.

54. The method of embodiment 53, wherein the at least dose of psilocybin is in the range of about 0.1 mg to about 100 mg.

55. The method of embodiment 54, wherein the dose of psilocybin is about 1 mg.

56. The method of embodiment 54, wherein the dose of psilocybin is about 10 mg.

57. The method of embodiment 54, wherein the dose of psilocybin is about 25 mg.

58. The method of any one of embodiments 1-52, wherein more than one dose of psilocybin is administered to the subject.

59. The method of embodiment 58, wherein at least two doses of psilocybin are administered to the subject.

60. The method of any one of embodiments 58-59, wherein the psilocybin is administered once per day.

61. The method of any one of embodiments 58-59, wherein the psilocybin is administered at least once per week.

62. The method of any one of embodiments 58-59, wherein the psilocybin is administered at least twice per week.

63. The method of any one of embodiments 58-59, wherein the psilocybin is administered at least once per month.

64. The method of any one of embodiments 58-59, wherein the psilocybin is administered at least twice per month.

65. The method of any one of embodiments 58-59, wherein the psilocybin is administered at least once every three months.

66. The method of any one of embodiments 58-59, wherein the psilocybin is administered at least once every six months.

67. The method of any one of embodiments 58-59, wherein the psilocybin is administered at least once every 12 months.

68. The method of any one of embodiments 58-67, wherein each dose of psilocybin administered is in the range of about 0.1 mg to about 100 mg.

69. The method of embodiment 68, wherein each dose of psilocybin administered is about 1 mg.

70. The method of embodiment 68, wherein each dose of psilocybin administered is about 10 mg.

71. The method of embodiment 68, wherein each dose of psilocybin administered is about 25 mg.

72. The method of any one of embodiments 53-71, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

73. The method of embodiment 72, wherein the psilocybin is administered orally.

74. The method of any one of embodiments 1-73, wherein the subject participates in at least one psychological support session before administration of the psilocybin.

75. The method of embodiment 74, wherein the subject participates in at least three psychological support sessions before administration of the psilocybin.

76. The method of any one of embodiments 74-75, wherein the at least one therapeutic intention is discussed during the psychological support session.

77. The method of any one of embodiments 74-76, wherein self-directed inquiry and experiential processing are practiced during the psychological support session.

78. The method of any one of embodiments 74-77, wherein the subject participates in at least one psychological support session after administration of the psilocybin.

79. The method of embodiment 78, wherein the subject participates in at least three psychological support sessions after administration of the psilocybin.

80. The method of any one of embodiments 74-79, wherein the psilocybin is administered to the subject in a room with a substantially non-clinical appearance.

81. The method of embodiment 80, wherein the room comprises soft furniture.

82. The method of embodiment 80, wherein the room is decorated using muted colors.

83. The method of embodiment 80, wherein the room comprises a high-resolution sound system.

84. The method of any one of embodiments 80-83, wherein the room comprises a bed or a couch.

85. The method of embodiment 84, wherein the subject lies in the bed or on the couch for approximately 4-8 hours, or a substantial fraction thereof, after administration of the psilocybin.

86. The method of any one of embodiments 80-85, wherein the subject listens to music for approximately 4-8 hours, or a substantial fraction thereof, after administration of the psilocybin.

87. The method of any one of embodiments 80-86, wherein the subject wears an eye mask for approximately 4-8 hours, or a substantial fraction thereof, after administration of the psilocybin.

88. The method of any one of embodiments 80-87, wherein a therapist provides psychological support to the subject for approximately 4-8 hours after administration of the psilocybin.

89. The method of embodiment 88, wherein the therapist uses guided imagery to calm the subject and/or focus the subject's attention.

90. The method of embodiment 88, wherein the therapist provides reassuring physical contact with the subject.

91. The method of embodiment 90, wherein the therapist holds the hand, arm, or shoulder of the subject.

92. The method of embodiment 88, wherein the therapist encourages the subject to perform self-directed inquiry and experiential processing.

93. The method of embodiment 88, wherein the therapist reminds the subject of at least one therapeutic intention.

94. The method of embodiment 88, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

95. The method of embodiment 88, wherein the therapist does not initiate conversation with the subject.

96. The method of embodiment 88, wherein the therapist responds to the subject if the subject initiates conversation.

97. The method of any one of embodiments 1-96, wherein the subject participates in at least one psychological support session before administration of the psilocybin.

98. The method of any one of embodiments 1-96, wherein the subject participates in at least one psychological support session after administration of the psilocybin.

99. The method of any one of embodiments 1-96, wherein a therapist provides psychological support to the subject for approximately 4-8 hours after administration of the psilocybin.

100. The method of any one of embodiments 97-99, wherein the psychological support is provided remotely to the subject.

101. The method of embodiment 100, wherein the psychological support is provided via a digital or electronic system.

102. The method of embodiment 101, wherein the digital or electronic system is a mobile phone app.

103. The method of embodiment 101, wherein the digital or electronic system is a website.

Numbered Embodiments for Treatment of Cluster Headaches with Psilocybin

1. A method of preventing or treating a cluster headache in a subject in need thereof, the method comprising administering to the subject a therapeutically effective amount of psilocybin or an active metabolite thereof.

2. The method of embodiment 1, wherein the cluster headache is chronic or episodic.

3. The method of embodiment 1 or 2, wherein at least one sign or symptom of cluster headache is improved following administration of psilocybin or a metabolite thereof.

4. The method of embodiment 3, wherein the sign or symptom of cluster headache is unilateral pain, excessive tearing, facial flushing, a droopy eyelid, a constricted pupil, eye redness, swelling under or around one or both eyes, sensitivity to light, nausea, agitation, or restlessness.

5. The method of embodiment 3, wherein the sign or symptom of cluster headache is measured according to a diary assessment, a physical or psychological assessment by clinician, an imaging test, or a neurological examination.

6. The method of embodiment 5, wherein the assessment is the Visual Analog Scale, the Numeric Rating Scale, the Short Form Health Survey, the Profile of Mood States, the Pittsburgh Sleep Quality Index, the Major Depression Inventory, the Perceived Stress Scale, the 5-Level EuroQoL-5D, the Headache Impact Test, or combinations thereof.

7. The method of any one of embodiments 1-6, wherein at least one sign or symptom of cluster headache is improved within 15 minutes of administration of the psilocybin.

8. The method of any one of embodiments 1-6, wherein at least one sign or symptom of cluster headache is improved within about 30 minutes of administration of the psilocybin.

9. The method of any one of embodiments 1-6, wherein at least one sign or symptom of cluster headache is improved within about 1 hour of administration of the psilocybin.

10. The method of any one of embodiments 1-6, wherein at least one sign or symptom of cluster headache is improved within about 3 hours of administration of the psilocybin.

11. The method of any one of embodiments 1-6, wherein at least one sign or symptom of cluster headache is improved within about 6 hours of administration of the psilocybin.

12. The method of any one of embodiments 1-11, wherein administration of psilocybin prevents the occurrence of the cluster headache for at least about 1 month.

13. The method of any one of embodiments 1-11, wherein administration of psilocybin prevents the occurrence of the cluster headache for at least about 3 months.

14. The method of any one of embodiments 1-11, wherein administration of psilocybin prevents the occurrence of the cluster headache for at least about 6 months.

15. The method of any one of embodiments 1, wherein administration of psilocybin prevents the occurrence of the cluster headache for at least about 12 months.

16. The method of any one of embodiments 1-15, wherein no other treatment is administered to the subject to prevent or treat the cluster headache after administration of the psilocybin.

17. The method of any one of embodiments 1-15, wherein the method further comprises administering to the subject at least one additional therapeutic to prevent or treat the cluster headache.

18. The method of embodiment 17, wherein the at least one additional therapeutic comprises a dihydroergotamine, an anti-nausea drug, oxygen therapy, a triptan, a local anesthetic, somatostatin or a somatostatin analogue, octreotide, a corticosteroid, methysergide, verapamil, lithium, topiramate, valproic acid, botulinum toxin, clomiphene, lysergic acid diethylamide, or combinations thereof.

19. The method of any one of embodiments 1-18, wherein the subject has at least one disease, disorder, or condition which is comorbid with cluster headaches.

20. The method of embodiment 19, wherein the at least one disease, disorder, or condition is sleep apnea, depression, anxiety, aggressive behavior, suicidal ideation, or bipolar disorder.

21. The method of embodiment 19 or 20, wherein administration of the psilocybin ameliorates at least one sign or symptom of the at least one disease, disorder, or condition which is comorbid with cluster headaches.

22. The method of any one of embodiments 1-21, wherein the active metabolite is psilocin.

23. The method of any one of embodiments 1-22, wherein the subject has no prior psilocybin exposure.

24. The method of any one of embodiments 1-22, wherein the subject has prior psilocybin exposure.

25. The method of any one of embodiments 1-24, wherein the subject is a mammal.

26. The method of embodiment 25, wherein the subject is a human.

27. The method of any of embodiments 1-26, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

28. The method of embodiment 27, wherein the crystalline psilocybin comprises at least 95% by weight of Polymorph A.

29. The method of embodiment 27 or 28, wherein the crystalline psilocybin has a chemical purity of greater than 97% by HPLC, and no single impurity of greater than 1%.

30. The method of any of embodiments 1-29, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

31. The method of embodiment 30, wherein the highly pure crystalline psilocybin comprises at least 90% by weight of Polymorph A.

32. The method of embodiment 31, wherein the highly pure crystalline psilocybin comprises at least 95% by weight of Polymorph A.

33. The method of any one of embodiments 27-32, wherein the highly pure crystalline psilocybin is further characterized having either: (i) a water content of <0.5% w/w; or (ii) <0.5% w/w loss in the TGA thermogram between 25° C. and 200° C.

34. The method of any of embodiments 27-33, wherein the highly pure crystalline psilocybin is further characterized by an endothermic event in a DSC thermogram having a first onset temperature of between 145° C. and 155° C. and a second onset temperature of between 205 and 220° C.

35. The method of any one of embodiments 27-34, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

36. The method of any of embodiments 33-35, wherein the highly pure crystalline psilocybin has no single impurity of greater than 0.5%.

37. The method of any of embodiments 27-36, wherein the dosage form further comprises about 5 to 40 mg of the highly pure crystalline psilocybin.

38. The method of embodiment 37, wherein the dosage form comprises 5 mg of highly pure crystalline psilocybin.

39. The method of embodiment 37, wherein the dosage form comprises about 10 mg of highly pure crystalline psilocybin.

40. The method of embodiment 37, wherein the dosage form comprises about 35 mg of highly pure crystalline psilocybin.

41. The method of any of embodiments 27-40, wherein the dosage form comprises silicified microcrystalline cellulose.

42. The method of embodiment 41, wherein the silicified microcrystalline cellulose has a particle size range from about 45 to 150 microns.

43. The method of any of embodiments 27-42, further comprising a mixture of two silicified microcrystalline cellulose variants wherein the first variant has a particle size from about 45 to 80 microns and the second variant has a particle size of about 90 to 150 microns.

44. The method of embodiment 43, wherein about 30% or less of the microcrystalline cellulose is the first variant having a particle size from about 45 to 80 microns and about 70% or more of the microcrystalline cellulose is the second variant having a particle size of about 90 to 150 microns.

45. The method of embodiment 43, wherein about 20% or less of the microcrystalline cellulose is the first variant having a particle size from about 45 to 80 microns and about 80% or more of the microcrystalline cellulose is the second variant having a particle size of about 90 to 150 microns.

46. The method of embodiment 43, wherein about 15% or less of the microcrystalline cellulose is the first variant having a particle size from about 45 to 80 microns and about 85% or more of the microcrystalline cellulose is the second variant having a particle size of about 90 to 150 microns.

47. The method of embodiment 43, wherein about 15% or less of the microcrystalline cellulose is the first variant having a particle size from about 45 to 80 microns and about 85% or more of the microcrystalline cellulose is the second variant having a particle size of about 90 to 150 microns.

48. The method of embodiment 47, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

49. The method of embodiment 47, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

50. The method any one of embodiments 27-49, wherein the dosage form is an oral dosage form.

51. The method embodiment 50, wherein the dosage form is a capsule.

52. The method embodiment 50, wherein the dosage form is a tablet.

53. The method of any one of embodiments 1-52, wherein at least one dose of psilocybin is administered to the subject.

54. The method of embodiment 53, wherein the at least dose of psilocybin is in the range of about 0.1 mg to about 100 mg.

55. The method of embodiment 54, wherein the dose of psilocybin is about 1 mg.

56. The method of embodiment 54, wherein the dose of psilocybin is about 10 mg.

57. The method of embodiment 54, wherein the dose of psilocybin is about 25 mg.

58. The method of any one of embodiments 1-52, wherein more than one dose of psilocybin is administered to the subject.

59. The method of embodiment 58, wherein at least two doses of psilocybin are administered to the subject.

60. The method of any one of embodiments 58-59, wherein the psilocybin is administered once per day.

61. The method of any one of embodiments 58-59, wherein the psilocybin is administered at least once per week.

62. The method of any one of embodiments 58-59, wherein the psilocybin is administered at least twice per week.

63. The method of any one of embodiments 58-59, wherein the psilocybin is administered at least once per month.

64. The method of any one of embodiments 58-59, wherein the psilocybin is administered at least twice per month.

65. The method of any one of embodiments 58-59, wherein the psilocybin is administered at least once every three months.

66. The method of any one of embodiments 58-59, wherein the psilocybin is administered at least once every six months.

67. The method of any one of embodiments 58-59, wherein the psilocybin is administered at least once every 12 months.

68. The method of any one of embodiments 58-67, wherein each dose of psilocybin administered is in the range of about 0.1 mg to about 100 mg.

69. The method of embodiment 68, wherein each dose of psilocybin administered is about 1 mg.

70. The method of embodiment 68, wherein each dose of psilocybin administered is about 10 mg.

71. The method of embodiment 68, wherein each dose of psilocybin administered is about 25 mg.

72. The method of any one of embodiments 53-71, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

73. The method of embodiment 72, wherein the psilocybin is administered orally.

74. The method of any one of embodiments 1-73, wherein the subject participates in at least one psychological support session before administration of the psilocybin.

75. The method of embodiment 74, wherein the subject participates in at least three psychological support sessions before administration of the psilocybin.

76. The method of any one of embodiments 74-75, wherein the at least one therapeutic intention is discussed during the psychological support session.

77. The method of any one of embodiments 74-76, wherein self-directed inquiry and experiential processing are practiced during the psychological support session.

78. The method of any one of embodiments 74-77, wherein the subject participates in at least one psychological support session after administration of the psilocybin.

79. The method of embodiment 78, wherein the subject participates in at least three psychological support sessions after administration of the psilocybin.

80. The method of any one of embodiments 74-79, wherein the psilocybin is administered to the subject in a room with a substantially non-clinical appearance.

81. The method of embodiment 80, wherein the room comprises soft furniture.

82. The method of embodiment 80, wherein the room is decorated using muted colors.

83. The method of embodiment 80, wherein the room comprises a high-resolution sound system.

84. The method of any one of embodiments 80-83, wherein the room comprises a bed or a couch.

85. The method of embodiment 84, wherein the subject lies in the bed or on the couch for approximately 4-8 hours, or a substantial fraction thereof, after administration of the psilocybin.

86. The method of any one of embodiments 80-85, wherein the subject listens to music for approximately 4-8 hours, or a substantial fraction thereof, after administration of the psilocybin.

87. The method of any one of embodiments 80-86, wherein the subject wears an eye mask for approximately 4-8 hours, or a substantial fraction thereof, after administration of the psilocybin.

88. The method of any one of embodiments 80-87, wherein a therapist provides psychological support to the subject for approximately 4-8 hours after administration of the psilocybin.

89. The method of embodiment 88, wherein the therapist uses guided imagery to calm the subject and/or focus the subject's attention.

90. The method of embodiment 88, wherein the therapist provides reassuring physical contact with the subject.

91. The method of embodiment 90, wherein the therapist holds the hand, arm, or shoulder of the subject.

92. The method of embodiment 88, wherein the therapist encourages the subject to perform self-directed inquiry and experiential processing.

93. The method of embodiment 88, wherein the therapist reminds the subject of at least one therapeutic intention.

94. The method of embodiment 88, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

95. The method of embodiment 88, wherein the therapist does not initiate conversation with the subject.

96. The method of embodiment 88, wherein the therapist responds to the subject if the subject initiates conversation.

97. The method of any one of embodiments 1-96, wherein the subject participates in at least one psychological support session before administration of the psilocybin.

98. The method of any one of embodiments 1-96, wherein the subject participates in at least one psychological support session after administration of the psilocybin.

99. The method of any one of embodiments 1-96, wherein a therapist provides psychological support to the subject for approximately 4-8 hours after administration of the psilocybin.

100. The method of any one of embodiments 98-100, wherein the psychological support is provided remotely to the subject.

101. The method of embodiment 100, wherein the psychological support is provided via a digital or electronic system.

102. The method of embodiment 101, wherein the digital or electronic system is a mobile phone app.

103. The method of embodiment 101, wherein the digital or electronic system is a website.

Numbered Embodiments for Co-Administration of Psilocybin and Benzodiazepines

1. A method of reducing anxiety in a subject undergoing treatment with psilocybin, the method comprising administering to the subject:
   i) psilocybin or a precursor or derivative thereof, and
   ii) one or more benzodiazepines.

2. The method of embodiment 1, wherein the subject suffers from a disease, disorder, or condition selected from Disruptive Mood Dysregulation Disorder, Major Depressive Disorder (MDD), Treatment Resistant Depression, Persistent Depressive Disorder (Dysthymia), Premenstrual Dysphoric Disorder, Substance/Medication-Induced Depressive Disorder, Post-Partum depression, or Depressive Disorder due to Another Medical Condition, Separation Anxiety Disorder, Selective Mutism, Specific Phobia, Social Anxiety Disorder (Social Phobia), Panic Disorder, Panic Attack, Agoraphobia, Generalized Anxiety Disorder, Substance-Medication-Induced Anxiety Disorder, Anxiety Disorder Due to Another Medical Condition, Somatic Symptom Disorder, Illness Anxiety Disorder (hypochondriac), Conversion Disorder (Functional Neurological Symptom Disorder), Factitious Disorder, Post-Traumatic Stress Disorder (PTSD), Adjustment Disorders, Acute Distress Disorder, Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, Obsessive-Compulsive and Related Disorder due to Another Medical Condition, Substance-Related Disorders, Alcohol-Related Disorders, Cannabis-Related Disorders, Hallucinogen-Related Disorders, Inhalant-Related Disorders, Cocaine-Related Disorders, Opioid-Related Disorders, Sedative-, Hypnotic-, or Anxiolytic-Related Disorders, Stimulant-Related Disorders, Tobacco-Related Disorders, Non-Substance-Related Disorders (Gambling or Gaming Disorder), Migraines, Cluster Headaches such as Chronic Cluster Headaches, Cyclical Vomiting, Tension-Type Headache, Dysphasia, Pica, Anorexia Nervosa, Bulimia Nervosa, Binge-Eating Disorder, Oppositional Defiant Disorder, Intermittent Explosive Disorder, Conduct Disorder, Antisocial Personality Disorder, Psychopathy, Pyromania, and Kleptomania.

3. The method of embodiment 1 or 2, wherein the one or more benzodiazepines are administered to the subject at or around the same time as the psilocybin or precursor or derivative thereof.

4. The method of embodiment 1 or 2, wherein the one or more benzodiazepines are administered to the subject prior to administration of the psilocybin or precursor or derivative thereof.

5. The method of embodiment 4, wherein the one or more benzodiazepines are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof.

6. The method of embodiment 1 or 2, wherein the one or more benzodiazepines are administered to the subject after the psilocybin or precursor or derivative thereof.

7. The method of embodiment 6, wherein the one or more benzodiazepines are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

8. The method of any one of embodiments 1-7, wherein the psilocybin or precursor or derivative thereof, is administered to the subject at a dose of between about 0.1 mg to about 100 mg.

9. The method of embodiment 8, wherein the psilocybin or precursor or derivative thereof is administered to the subject at a dose of between about 1 mg to about 50 mg.

10. The method of embodiment 9, wherein the psilocybin or precursor or derivative thereof is administered to the subject at a dose of about 1 mg, about 10 mg, or about 25 mg.

11. The method of any one of embodiments 1-10, wherein the one or more benzodiazepines are administered at a dose that is lower than doses typically used to treat anxiety.

12. The method of embodiment 11, wherein the dose is about 10%, 20%, 25%, 30%, 40%, 50%, or 75% of a typical dose.

13. The method of any one of embodiments 1-10, wherein the one or more benzodiazepines are administered at a dose that is approximately equivalent to doses typically used to treat anxiety.

14. The method of any one of embodiments 1-10, wherein the one or more benzodiazepines are administered at a dose that is higher than doses typically used to treat anxiety.

15. The method of embodiment 14, wherein the dose is about 125%, 150%, 175%, 200%, 250%, or 300% of a typical dose.

16. The method of any one of embodiments 1-15, wherein the benzodiazepine is selected from adinazolam, alprazolam, bentazepam, bretazenil, bromazepam, bromazolam, brotizolam, camazepam, chlordiazepoxide, cinazepam, cinolazepam, clobazam, clonazepam, clonazolam, clorazepate, clotiazepam, cloxazolam, delorazepam, deschloroetizolam, diazepam, diclazepam, estazolam, ethyl carfluzepate, ethyl loflazepate, etizolam, flualprazolam, flubromazepam, flubromazolam, fluclotizolam, flunitrazepam, flunitrazolam, flurazepam, flutazolam, flutoprazepam, halazepam, ketazolam, loprazolam, lorazepam, lormetazepam, meclonazepam, medazepam, metizolam, mexazolam, midazolam, nifoxipam, nimetazepam, nitemazepam, nitrazepam, nitrazolam, nordiazepam, norflurazepam, oxazepam, phenazepam, pinazepam, prazepam, premazepam, pyrazolam, quazepam, rilmazafone, temazepam, tetrazepam, or triazolam.

17. The method of embodiment 16, wherein the benzodiazepine is alprazolam.

18. The method of embodiment 16, wherein the benzodiazepine is diazepam.

19. The method of any one of embodiments 1-18, wherein the psilocybin is a crystalline psilocybin in the form of Polymorph A, Polymorph A', Polymorph B, or Hydrate A.

20. The method of embodiment 19, wherein the crystalline psilocybin is Polymorph A, characterised by one or more of:
   a. peaks in an XRPD diffractogram at 11.5, 12.0, 14.5, and 17.5, °2θ±0.1°2θ;
   b. peaks in an XRPD diffractogram at 11.5, 12.0, 14.5 and 17.5, °2θ±0.1°2θ, further characterised by at least one further peak at 19.7, 20.4, 22.2, 24.3 or 25.7°2θ±0.1°2θ;
   c. an XRPD diffractogram as substantially illustrated in FIG. 2A; and/or
   d. an endothermic event in a DSC thermogram having a first onset temperature of between 145° C. and 165° C. and a second onset temperature of between 205° C. and 220° C. substantially as illustrated in FIG. 3A.

21. The method of embodiment 19, wherein the crystalline psilocybin is Polymorph A', characterised by one or more of:
   a. peaks in an XRPD diffractogram at 11.5, 12.0 and 14.5°2θ±0.1°2θ, but absent or substantially absent of a peak at 17.5°2θ±0.1°2θ;
   b. peaks in an XRPD diffractogram at 11.5, 12.0 and 14.5°2θ±0.1°2θ, but absent or substantially absent of a peak at 17.5°2θ±0.1°2θ, further characterised by at least one further peak at 19.7, 20.4, 22.2, 24.3 or 25.7°2θ±0.1°2θ;
   c. an XRPD diffractogram as substantially illustrated in FIG. 2B; and/or
   d. an endothermic event in a DSC thermogram having a first onset temperature of between 145° C. and 165° C. and a second onset temperature of between 205° C. and 220° C. substantially as illustrated in FIG. 3B.

22. The method of any one of embodiments 1-21, wherein the psilocybin or precursor or derivative thereof is administered orally to the subject.

23. The method of any one of embodiments 1-22, wherein the one or more benzodiazepine is administered orally to the subject.

24. The method of any one of embodiments 1-23, wherein the psilocybin or precursor or derivative thereof is administered at least once to the subject.

25. The method of embodiment 24, wherein the psilocybin is administered at least twice to the subject, at therapeutically effective intervals.

26. The method of embodiment 25, wherein the therapeutically effective intervals are about 2 weeks, about 3 weeks, about 4 weeks, about 5 weeks, about 6 weeks, about 7 weeks, about 8 weeks, about 9 weeks, about 10 weeks, about 11 weeks, or about 12 weeks.

27. The method of any one of embodiments 1-16, wherein the subject has never taken psilocybin before.

28. The method of any one of embodiments 1-26, wherein the subject has taken psilocybin before.

29. The method of any one of embodiments 1-28, wherein the subject is supervised during the administration and for at least 4 to 12 hours thereafter.

30. The method of any one of embodiments 1-29, wherein the subject receives psychological support during the administration, and for at least 4 to 12 hours thereafter.

31. The method of any one of embodiments 1-30, wherein the subject has not taken any serotonergic antidepressant for at least 2 weeks, at least 4 weeks, or at least 6 weeks prior.

32. The method of any one of embodiments 1-31, wherein the subject receives counseling with regard to the expected effects of the psilocybin.

33. The method of any one of embodiments 1-32, wherein the subject is a male.

34. The method of any one of embodiments 1-32, wherein the subject is a female.

35. A combination therapy for treating or preventing a disease, disorder, or condition selected from Disruptive Mood Dysregulation Disorder, Major Depressive Disorder (MDD), Treatment Resistant Depression, Persistent Depressive Disorder (Dysthymia), Premenstrual Dysphoric Disorder, Substance/Medication-Induced Depressive Disorder, Post-Partum depression, or Depressive Disorder due to Another Medical Condition, Separation Anxiety Disorder, Selective Mutism, Specific Phobia, Social Anxiety Disorder (Social Phobia), Panic Disorder, Panic Attack, Agoraphobia, Generalized Anxiety Disorder, Substance-Medication-Induced Anxiety Disorder, Anxiety Disorder Due to Another Medical Condition, Somatic Symptom Disorder, Illness Anxiety Disorder (hypochondriac), Conversion Disorder (Functional Neurological Symptom Disorder), Factitious Disorder, Post-Traumatic Stress Disorder (PTSD), Adjustment Disorders, Acute Distress Disorder, Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, Obsessive-Compulsive and Related Disorder due to Another Medical Condition, Substance-Related Disorders, Alcohol-Related Disorders, Cannabis-Related Disorders, Hallucinogen-Related Disorders, Inhalant-Related Disorders, Cocaine-Related Disorders, Opioid-Related Disorders, Sedative-, Hypnotic-, or Anxiolytic-Related Disorders, Stimulant-Related Disorders, Tobacco-Related Disorders, Non-Substance-Related Disorders (Gambling or Gaming Disorder), Migraines, Cluster Headaches such as Chronic Cluster Headaches, Cyclical Vomiting, Tension-Type Headache, Dysphasia, Pica, Anorexia Nervosa, Bulimia Nervosa, Binge-Eating Disorder, Oppositional Defiant Disorder, Intermittent Explosive Disorder, Conduct Disorder, Antisocial Personality Disorder, Psychopathy, Pyromania, and Kleptomania, the combination therapy comprising administering to the subject:

i) psilocybin or a precursor or derivative thereof, and ii) one or more benzodiazepines.

36. A kit for treating a subject in need thereof, the kit comprising:

a first pharmaceutical composition comprising psilocybin, or a precursor or derivative thereof, and a second pharmaceutical composition comprising one or more benzodiazepines.

37. The kit of embodiment 36, wherein the kit further comprises instructions for administering the first and the second pharmaceutical composition to the subject.

Numbered Embodiments for Co-Administration of Psilocybin and 5-HT$_{2A}$ Specific Antagonists and/or Inverse Agonists.

1. A method of reducing the negative side effects associated with a traumatic psychedelic experience in a subject undergoing treatment with psilocybin, the method comprising administering to the subject:

i) psilocybin or a precursor or derivative thereof, and ii) one or more 5-HT$_{2A}$ specific antagonists and/or inverse agonists.

2. The method of embodiment 1, wherein the subject suffers from a disease, disorder, or condition selected from Disruptive Mood Dysregulation Disorder, Major Depressive Disorder (MDD), Treatment Resistant Depression, Persistent Depressive Disorder (Dysthymia), Premenstrual Dysphoric Disorder, Substance/Medication-Induced Depressive Disorder, Post-Partum depression, or Depressive Disorder due to Another Medical Condition, Separation Anxiety Disorder, Selective Mutism, Specific Phobia, Social Anxiety Disorder (Social Phobia), Panic Disorder, Panic Attack, Agoraphobia, Generalized Anxiety Disorder, Substance-Medication-Induced Anxiety Disorder, Anxiety Disorder Due to Another Medical Condition, Somatic Symptom Disorder, Illness Anxiety Disorder (hypochondriac), Conversion Disorder (Functional Neurological Symptom Disorder), Factitious Disorder, Post-Traumatic Stress Disorder (PTSD), Adjustment Disorders, Acute Distress Disorder, Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, Obsessive-Compulsive and Related Disorder due to Another Medical Condition, Substance-Related Disorders, Alcohol-Related Disorders, Cannabis-Related Disorders, Hallucinogen-Related Disorders, Inhalant-Related Disorders, Cocaine-Related Disorders, Opioid-Related Disorders, Sedative-, Hypnotic-, or Anxiolytic-Related Disorders, Stimulant-Related Disorders, Tobacco-Related Disorders, Non-Substance-Related Disorders (Gambling or Gaming Disorder), Migraines, Cluster Headaches such as Chronic Cluster Headaches, Cyclical Vomiting, Tension-Type Headache, Dysphasia, Pica, Anorexia Nervosa, Bulimia Nervosa, Binge-Eating Disorder, Oppositional Defiant Disorder, Intermittent Explosive Disorder, Conduct Disorder, Antisocial Personality Disorder, Psychopathy, Pyromania, Kleptomania, and burnout, vegetative states, and asthma (and other inflammatory diseases).

3. The method of embodiment 1 or 2, wherein the one or more 5-HT$_{2A}$ specific antagonists and/or inverse agonists are administered to the subject at or around the same time as the psilocybin or precursor or derivative thereof.

4. The method of embodiment 1 or 2, wherein the one or more 5-HT$_{2A}$ specific antagonists and/or inverse agonists are administered to the subject prior to administration of the psilocybin or precursor or derivative thereof.

5. The method of embodiment 4, wherein the one or more 5-HT$_{2A}$ specific antagonists and/or inverse agonists are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof.

6. The method of embodiment 1 or 2, wherein the one or more 5-HT$_{2A}$ specific antagonists and/or inverse agonists are administered to the subject after the psilocybin or precursor or derivative thereof.

7. The method of embodiment 6, wherein the one or more 5-HT$_{2A}$ specific antagonists and/or inverse agonists are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

8. The method of any one of embodiments 1-7, wherein the psilocybin or precursor or derivative thereof, is administered to the subject at a dose of between about 0.1 mg to about 100 mg.

9. The method of embodiment 8, wherein the psilocybin or precursor or derivative thereof is administered to the subject at a dose of between about 1 mg to about 50 mg.

10. The method of embodiment 9, wherein the psilocybin or precursor or derivative thereof is administered to the subject at a dose of about 1 mg, about 10 mg, or about 25 mg.

11. The method of any one of embodiments 1-10, wherein the one or more 5-HT$_{2A}$ specific antagonists and/or inverse agonists are administered at a dose that is lower than a typical dose.

12. The method of embodiment 11, wherein the dose is about 10%, 20%, 25%, 30%, 40%, 50%, or 75% of a typical dose.

13. The method of any one of embodiments 1-10, wherein the one or more 5-HT$_{2A}$ specific antagonists and/or inverse agonists are administered at a dose that is approximately equivalent to a typical dose.

14. The method of any one of embodiments 1-10, wherein the one or more 5-HT$_{2A}$ specific antagonists and/or inverse agonists are administered at a dose that is higher than a typical dose.

15. The method of embodiment 14, wherein the dose is about 125%, 150%, 175%, 200%, 250%, or 300% of a typical dose.

16. The method of any one of embodiments 1-15, wherein the 5-HT$_{2A}$ specific antagonist is trazodone, mirtazapine, metergoline, ketanserin, ritanserin, nefazodone, clozapine, olanzapine, quetiapine, risperidone, asenapine, MDL-100907, cyproheptadine, pizotifen, LY-367,265, 2-alkyl-4-aryl-tetrahydro-pyrimido-azepine, 9-aminomethyl-9,10-dihydroanthracene (AMDA), haloperidol, chlorpromazine, hydroxyzine (atarax), 5-MeO-NBpBrT, niaprazine, altanserin, aripiprazole, etoperidone, setoperone, chlorprothixene, cinaserin, adatanserin, medifoxamine, rauwolscine, phenoxybenzamine, pruvanserin, deramciclane, nelotanserin, lubazodone, mepiprazole, xylamidine, R-(+)-alpha-(2,3-dimethoxyphenyl)-1-[2-(4-fluorophenethyl)]-4-
piperidinemethanol (M100907), mianserin, AT 1015,
DV 7028, eplivanserin, 4F 4PP, fanaserin, alpha-phe-
nyl-1-(2-phenylethyl)-4-piperidinemethanol (MDL
11,939), melperone, mesulergine, paliperidone, 1-[2-
(3,4-Dihydro-1H-2-benzopyran-1-yl)ethyl]-4-(4-fluo-
rophenyl)piperazine dihydrochloride (PNU 96415E),
(2R,4R)-5-[2-[2-[2-(3-methoxyphenyl)ethyl]phenoxy]
ethyl]-1-methyl-3-pyrrolidinol (R-96544), sarpogrel-
ate, spiperone, ziprasidone, zotepine, or 7-[[4-[2-(4-
fluorophenyl)ethyl]-1-piperazinyl]carbonyl]-1H-
indole-3-carbonitrile (EMD 281014).

17. The method of embodiment 16, wherein the 5-HT$_{2A}$
specific antagonist is ketanserin.

18. The method of any one of embodiments 1-15, wherein
the 5-HT$_{2A}$ inverse antagonist is AC-90179, nelotan-
serin (APD-125), eplivanserin, pimavanserin (ACP-
103), or volinaserin.

19. The method of embodiment 18, wherein the 5-HT$_{2A}$
inverse antagonist is pimavanserin.

20. The method of any one of embodiments 1-19, wherein
the psilocybin is a crystalline psilocybin in the form of
Polymorph A, Polymorph A', Polymorph B, or Hydrate
A.

21. The method of embodiment 20, wherein the crystal-
line psilocybin is Polymorph A, characterised by one or
more of:
e. peaks in an XRPD diffractogram at 11.5, 12.0, 14.5,
and 17.5, °2θ±0.1°2θ;
f. peaks in an XRPD diffractogram at 11.5, 12.0, 14.5
and 17.5, °2θ±0.1°2θ, further characterised by at
least one further peak at 19.7, 20.4, 22.2, 24.3 or
25.7°2θ±0.1°2θ;
g. an XRPD diffractogram as substantially illustrated in
FIG. 2A; and/or
h. an endothermic event in a DSC thermogram having
a first onset temperature of between 145° C. and
165° C. and a second onset temperature of between
205° C. and 220° C. substantially as illustrated in
FIG. 3A.

22. The method of embodiment 20, wherein the crystal-
line psilocybin is Polymorph A', characterised by one
or more of:
e. peaks in an XRPD diffractogram at 11.5, 12.0 and
14.5°2θ±0.1°2θ, but absent or substantially absent of
a peak at 17.5°2θ±0.1°2θ;
f. peaks in an XRPD diffractogram at 11.5, 12.0 and
14.5°2θ±0.1°2θ, but absent or substantially absent of
a peak at 17.5°2θ±0.1°2θ, further characterised by at
least one further peak at 19.7, 20.4, 22.2, 24.3 or
25.7°2θ±0.1°2θ;
g. an XRPD diffractogram as substantially illustrated in
FIG. 2B; and/or
h. an endothermic event in a DSC thermogram having
a first onset temperature of between 145° C. and
165° C. and a second onset temperature of between
205° C. and 220° C. substantially as illustrated in
FIG. 3B.

23. The method of any one of embodiments 1-22, wherein
the psilocybin or precursor or derivative thereof is
administered orally to the subject.

24. The method of any one of embodiments 1-23, wherein
the one or more 5-HT$_{2A}$ specific antagonists and/or
inverse agonists is administered orally to the subject.

25. The method of any one of embodiments 1-24, wherein
the psilocybin or precursor or derivative thereof is
administered at least once to the subject.

26. The method of embodiment 25, wherein the psilocy-
bin is administered at least twice to the subject, at
therapeutically effective intervals.

27. The method of embodiment 26, wherein the thera-
peutically effective intervals are about 2 weeks, about
3 weeks, about 4 weeks, about 5 weeks, about 6 weeks,
about 7 weeks, about 8 weeks, about 9 weeks, about 10
weeks, about 11 weeks, or about 12 weeks.

28. The method of any one of embodiments 1-27, wherein
the subject has never taken psilocybin before.

29. The method of any one of embodiments 1-27, wherein
the subject has taken psilocybin before.

30. The method of any one of embodiments 1-29, wherein
the subject is supervised during the administration and
for at least 4 to 12 hours thereafter.

31. The method of any one of embodiments 1-30, wherein
the subject receives psychological support during the
administration, and for at least 4 to 12 hours thereafter.

32. The method of any one of embodiments 1-31, wherein
the subject has not taken any serotonergic antidepres-
sant for at least 2 weeks, at least 4 weeks, or at least 6
weeks prior.

33. The method of any one of embodiments 1-32, wherein
the subject receives counseling with regard to the
expected effects of the psilocybin.

34. The method of any one of embodiments 1-33, wherein
the subject is a male.

35. The method of any one of embodiments 1-33, wherein
the subject is a female.

36. A combination therapy for treating or preventing a
disease, disorder, or condition selected from Disruptive
Mood Dysregulation Disorder, Major Depressive Dis-
order (MDD), Treatment Resistant Depression, Persis-
tent Depressive Disorder (Dysthymia), Premenstrual
Dysphoric Disorder, Substance/Medication-Induced
Depressive Disorder, Post-Partum depression, or
Depressive Disorder due to Another Medical Condi-
tion, Separation Anxiety Disorder, Selective Mutism,
Specific Phobia, Social Anxiety Disorder (Social Pho-
bia), Panic Disorder, Panic Attack, Agoraphobia, Gen-
eralized Anxiety Disorder, Substance-Medication-In-
duced Anxiety Disorder, Anxiety Disorder Due to
Another Medical Condition, Somatic Symptom Disor-
der, Illness Anxiety Disorder (hypochondriac), Conver-
sion Disorder (Functional Neurological Symptom Dis-
order), Factitious Disorder, Post-Traumatic Stress
Disorder (PTSD), Adjustment Disorders, Acute Dis-
tress Disorder, Obsessive-Compulsive Disorder, Body
Dysmorphic Disorder, Hoarding Disorder, Trichotillo-
mania (Hair-Pulling Disorder), Excoriation (Skin-Pick-
ing) Disorder, Substance/Medication-Induced Obses-
sive-Compulsive and Related Disorder, Obsessive-
Compulsive and Related Disorder due to Another
Medical Condition, Substance-Related Disorders,
Alcohol-Related Disorders, Cannabis-Related Disor-
ders, Hallucinogen-Related Disorders, Inhalant-Re-
lated Disorders, Cocaine-Related Disorders, Opioid-
Related Disorders, Sedative-, Hypnotic-, or Anxiolytic-
Related Disorders, Stimulant-Related Disorders,
Tobacco-Related Disorders, Non-Substance-Related
Disorders (Gambling or Gaming Disorder), Migraines,
Cluster Headaches such as Chronic Cluster Headaches,
Cyclical Vomiting, Tension-Type Headache, Dyspha-
sia, Pica, Anorexia Nervosa, Bulimia Nervosa, Binge-
Eating Disorder, Oppositional Defiant Disorder, Inter-
mittent Explosive Disorder, Conduct Disorder,
Antisocial Personality Disorder, Psychopathy, Pyromania, Kleptomania, and burnout, vegetative states, and asthma (and other inflammatory diseases), the combination therapy comprising administering to the subject:
i) psilocybin or a precursor or derivative thereof, and
ii) one or more 5-HT$_{2A}$ specific antagonists and/or inverse agonists.

37. A kit for treating a subject in need thereof, the kit comprising:
a first pharmaceutical composition comprising psilocybin, or a precursor or derivative thereof, and
a second pharmaceutical composition comprising one or more 5-HT$_{2A}$ specific antagonists and/or inverse agonists.

38. The kit of embodiment 37, wherein the kit further comprises instructions for administering the first and the second pharmaceutical composition to the subject.

39. A method of reducing the negative side effects associated with a traumatic psychedelic experience in a subject undergoing treatment with psilocybin, the method comprising administering to the subject:
i) psilocybin or a precursor or derivative thereof, and
ii) one or more cannabinoids or cannabinoid derivatives.

Numbered Embodiments Related to Polymorph A and Use Thereof

1. Crystalline psilocybin Polymorph A or Polymorph A', characterised by one or more of:
a) peaks in an XRPD diffractogram at 11.5, 12.0 and 14.5°2θ±0.1°2θ; and/or
b) an endothermic event in a DSC thermogram having a first onset temperature of between 145° C. and 155° C. and a second onset temperature of between 210° C. and 220° C.
for use in the treatment of: Alzheimer's, Autism spectrum disorder, Attention deficit hyperactivity disorder (ADHD), Downs, Epilepsy (though not seizures), Multiple Sclerosis, Parkinson's disease, Schizophrenia, Huntington's, Stroke and other cerebrovascular conditions, Traumatic brain injury, Major depressive disorder, chronic cluster headaches, antisocial personality disorder and psychopathy.

2. A method for the treatment of Alzheimer's, Autism spectrum disorder, Attention deficit hyperactivity disorder (ADHD), Downs, Epilepsy (though not seizures), Multiple Sclerosis, Parkinson's disease, Schizophrenia, Huntington's, Stroke and other cerebrovascular conditions, Traumatic brain injury, Major depressive disorder, chronic cluster headaches, antisocial personality disorder and psychopathy comprising administering to a subject in need thereof an effective amount of crystalline psilocybin Polymorph A or Polymorph A', characterised by one or more of
a) peaks in an XRPD diffractogram at 11.5, 12.0 and 14.5°2θ±0.1°2θ; and/or
b) an endothermic event in a DSC thermogram having a first onset temperature of between 145° C. and 155° C. and a second onset temperature of between 210° C. and 220° C.

3 Crystalline psilocybin Polymorph A or Polymorph A', characterised by one or more of:
a) peaks in an XRPD diffractogram at 11.5, 12.0 and 14.5°2θ±0.1°2θ; and/or
b) an endothermic event in a DSC thermogram having a first onset temperature of between 145° C. and 155° C. and a second onset temperature of between 210° C. and 220° C.

for use in the treatment of a central nervous disorder together with psychotherapy wherein the psychotherapy is a transdiagnostic therapy.

4. Crystalline psilocybin Polymorph A or Polymorph A' for use as claimed in claim 3 wherein the transdiagnostic therapy is a Method of Levels (MOL) therapy.

5. Crystalline psilocybin Polymorph A or Polymorph A' for use as claimed in claim 4 wherein the Method of Levels (MOL) therapy comprises Self-directed enquiry and Experiential processing.

6. A method for the treatment of a central nervous disorder together with psychotherapy wherein the psychotherapy is a transdiagnostic therapy.

7. A method as claimed in claim 6 wherein the transdiagnostic therapy is a Method of Levels (MOL) therapy.

8. A method as claimed in claim 7 wherein the Method of Levels (MOL) therapy comprises Self-directed enquiry and Experiential processing.

9. A digital biomarker, as a diagnostic and/or prognostic tool for patient management pre, during and/or post treatment of a central nervous system disorder with psilocybin wherein the digital biomarker is one or more biomarkers associated with executive function, cognitive control, working memory, processing speed, and emotional valence.

10. A digital biomarker as claimed in claim 9 wherein the biomarker is identified from patterns in smartphone use such as swipes, taps, and other touchscreen activities, and are scientifically validated to provide measurements of cognition and mood.

11. A digital biomarker as claimed in claim 10 wherein the pattern is identified using one or more:
Number of and/or time of phone calls/e-mails/texts;
Gestures used (taps, swipes, or other);
Gyroscope derived information e.g. orientation of the phone;
Acceleration of the phone;
Keystroke patterns;
Location derived information from GPS; and/or
Specific words or emojis used or not used;
and the central nervous system disorder treated is treatment resistant depression.

12. A method of assessing a subject pre, during and/or post treatment of a central nervous system disorder to determine whether to provide a psilocybin treatment or a further psilocybin treatment comprising monitoring one or more biomarkers associated with executive function, cognitive control, working memory, processing speed, and emotional valence, and determining the treatment based on an outcome.

13. A method as claimed in claim 12 further comprising administering psilocybin for a first or a subsequent time.

14. A method as claimed in claim 13 wherein the psilocybin is administered together with psychotherapy.

Numbered Embodiment for Formulations of Psilocybin

1. A pharmaceutic formulation comprising psilocybin, one or more fillers, and one or more disintegrants.

2. The pharmaceutical formulation of embodiment 1 wherein one or more of the fillers is a silicified filler.

3. The pharmaceutical formulation of embodiment 2 wherein one or more silicified filler is silicified microcrystalline cellulose.

4. The pharmaceutical formulation of embodiment 3 comprising silicified microcrystalline cellulose with a particle size range of from about 45 to 80 microns (SMCC 50), silicified microcrystalline cellulose with a particle size range of from about 90 to 150 microns (SMCC 90), or mixtures thereof.

5. The pharmaceutical formulation of embodiment 4 comprising SMCC 50 and SMCC 90.

6. The pharmaceutical formulation of embodiment 5 wherein the ratio of SMCC 50 to SMCC 90 is 1:5 to 1:8 (SMCC 50:SMCC 90) wt %.

7. The pharmaceutical formulation of embodiment 6 wherein the ratio of SMCC 50 to SMCC 90 is 1:6 to 1:7 (SMCC 50:SMCC 90) wt %.

8. The pharmaceutical formulation of embodiment 7 wherein the ratio of SMCC 50 to SMCC 90 is 1:6.4 (SMCC 50:SMCC 90) wt %.

9. The pharmaceutical formulation of any of embodiment 1-8 wherein the disintegrant is present in an amount of less than 3% by weight.

10. The pharmaceutical formulation of embodiment 9 wherein the disintegrant is present in an amount of less than 2% by weight.

11. The pharmaceutical formulation of embodiment 10 wherein the disintegrant is present in an amount of 1% or less by weight.

12. The pharmaceutical formulation of any of embodiment 1-11 wherein the disintegrant is sodium starch glycolate, croscarmellose sodium, or mixtures thereof.

13. The pharmaceutical formulation of embodiment 12 wherein the disintegrant is sodium starch glycolate.

14. The pharmaceutical formulation of any of embodiment 1-13 wherein the psilocybin is crystalline psilocybin in the form of Polymorph A, Polymorph A', Polymorph B, or Hydrate A.

15. The pharmaceutical formulation of embodiment 14 wherein the psilocybin is crystalline psilocybin in the form of Polymorph A, characterized by one or more of:
   a. peaks in an XRPD diffractogram at 11.5, 12.0, 14.5, and 17.5, °2θ±0.1°2θ;
   b. peaks in an XRPD diffractogram at 11.5, 12.0, 14.5 and 17.5, °2θ±0.1°2θ, further characterized by at least one further peak at 19.7, 20.4, 22.2, 24.3 or 25.7°2θ±0.1°2θ;
   c. an XRPD diffractogram as substantially illustrated in FIG. 7A; and/or
   d. an endothermic event in a DSC thermogram having a first onset temperature of between 145° C. and 165° C. and a second onset temperature of between 205° C. and 220° C. substantially as illustrated in FIG. 8A.

16. The pharmaceutical formulation of embodiment 14 wherein the psilocybin is crystalline psilocybin in the form of Polymorph A', according to embodiment 1 or 2 characterized by one or more of:
   a. peaks in an XRPD diffractogram at 11.5, 12.0 and 14.5°2θ±0.1°2θ, but absent or substantially absent of a peak at 17.5°2θ±0.1°2θ;
   b. peaks in an XRPD diffractogram at 11.5, 12.0 and 14.5°2θ±0.1°2θ, but absent or substantially absent of a peak at 17.5°2θ±0.1°2θ, further characterized by at least one further peak at 19.7, 20.4, 22.2, 24.3 or 25.7°2θ±0.1°2θ;
   c. an XRPD diffractogram as substantially illustrated in FIG. 7B; and/or
   d. an endothermic event in a DSC thermogram having a first onset temperature of between 145° C. and 165° C. and a second onset temperature of between 205° C. and 220° C. substantially as illustrated in FIG. 8B.

17. The pharmaceutical formulation of any of embodiment 1-16 comprising about 1 mg to about 50 mg psilocybin.

18. The pharmaceutical formulation of embodiment 17 comprising about 1 mg, 5 mg, 10 mg, 15 mg, 20 mg, 25 mg, 30 mg, 35 mg, 40 mg, 45 mg, or 50 mg psilocybin.

19. A method for large scale manufacture of psilocybin in the form Polymorph A or Polymorph A', characterised by one or more of
   a) peaks in an XRPD diffractogram at 11.5, 12.0 and 14.5°2θ±0.1°2θ; and/or
   b) an endothermic event in a DSC thermogram having a first onset temperature of between 145° C. and 165° C. and a second onset temperature of between 205° C. and 220° C.
wherein the method comprises water crystallization wherein psilocybin is solubilized in water at a temperature below 90° C. to provide an aqueous solution of psilocybin.

20. The method of embodiment 19 wherein psilocybin is solubilized in water at a temperature below 85° C. to provide an aqueous solution of psilocybin.

21. The method of embodiment 19 or 20 wherein the temperature of the aqueous solution of psilocybin is lowered at a rate of about 5° C.-15° C. an hour to provide crystalline psilocybin 22. The method of embodiment 21 wherein the temperature of the aqueous solution of psilocybin is lowered at a rate of about 10° C. an hour to provide crystalline psilocybin.

23. The method of any one of embodiments 19-22 further comprising stirring the solution during solubilization.

EXAMPLES

The following examples, which are included herein for illustration purposes only, are not intended to be limiting.

Example 1—Formulation Development

The five formulations (Ex 1A, 1B, 1C, 1D, and 1E) described in Table 9 were assessed for powder flow, blend uniformity, content uniformity and dissolution.

TABLE 9

| Material Name | % w/w | | | | |
| --- | --- | --- | --- | --- | --- |
| | Ex 1A | Ex 1B | Ex 1C | Ex 1D | Ex 1E |
| Psilocybin | 1.0 | 1.0 | 1.0 | 1.0 | 1.0 |
| Prosolv SMCC 50* | 15.5 | 20.5 | 10.5 | 20.5 | 10.5 |
| Prosolv SMCC 90* | 79.0 | 74.0 | 83.5 | 73.5 | 84.25 |
| Ratio | 1:5.1 | 1:3.6 | 1:8 | 1:3.6 | 1:8 |
| Sodium Starch glycolate | 3.0 | 3.0 | 3.0 | 3.0 | 3.0 |
| Colloidal Silicon Dioxide (Aerosil 200) | 0.5 | 0.25 | 1.0 | 1.0 | 0.25 |
| Sodium Stearyl Fumarate | 1.0 | 1.0 | 1.0 | 1.0 | 1.0 |
| TOTAL weight of tablet | 100.0 | 100.0 | 100.0 | 100.0 | 100.0 |
| Powder flow (Hausner ratio) | 22.4 | 26.5 | 21.8 | 21.3 | 19.5 |
| Blend Uniformity | | | | | |
| TOP | 107.6 | 103.0 | 96.0 | 97.0 | 96.0 |
| MIDDLE | 114.3 | 106.9 | 100.0 | 99.0 | 99.0 |
| BOTTOM | 125.6 | 109.3 | 108.0 | 104.0 | 103.0 |
| MEAN | 115.8 | 106.4 | 101.0 | 100.0 | 99.0 |
| % RSD | 7.8 | 3.7 | 5.5 | 3.3 | 3.1 |

TABLE 9-continued

| Material Name | Ex 1A | Ex 1B | Ex 1C | Ex 1D | Ex 1E |
|---|---|---|---|---|---|
| | | | % w/w | | |
| Content Uniformity | | | | | |
| % label Claim | 97.0 | 96.0 | 95.0 | 98.0 | 96.0 |
| AV | 4.3 | 4.5 | 5.5 | 2.0 | 4.8 |
| Dissolution Time (min) | | | % release | | |
| 5 | 94 | 93 | 92 | 94 | 94 |
| 10 | 96 | 96 | 95 | 97 | 96 |
| 15 | 96 | 96 | 95 | 97 | 95 |
| 30 | 95 | 96 | 95 | 96 | 95 |
| Infinity | 95 | 95 | 94 | 96 | 94 |
| Assay (%) | 97.0 | 95.0 | 95.0 | 98.0 | 96.0 |

*The quantity of fillers adjusted to account for glidant quantity and total tablet weight.

Ex. 1D was used as a base formulation for the optimization of an exemplary higher dose tablet (5 mg). Tablets tested for dissolution from all five examples were found be unaffected by change in the fillers ratio and quantity of glidant. Hence, it was decided to study the level of disintegrate in the final formulation. Two batches of Psilocybin tablet 5 mg were manufactured using high (3% w/w) and low (1% w/w) levels of a disintegrant in the formulation composition.

The additional studies were conducted to justify the amount of disintegrant in the formulation. These studies were performed on the higher strength product (5 mg).

A quantity of filler was replaced with psilocybin, the active pharmaceutical ingredient (API) in order to accommodate the additional amount API. The formulation composition and results for powder flow, blend uniformity, content uniformity and dissolution for Ex. 1F and 1G are summarized in Table 10.

TABLE 10

| Material Name | Ex. 1F | Ex. 1G |
|---|---|---|
| | % w/w | |
| Psilocybin | 5.0 | 5.0 |
| Prosolv SMCC 50 | 14.5 | 12.5 |
| Prosolv SMCC 90 | 75.5 | 79.5 |
| Ratio | 1:5.2 | 1:6.4 |
| Sodium Starch glycolate | 3.0 | 1.0 |
| Colloidal Silicon Dioxide (Aerosil 200) | 1.0 | 1.0 |
| Sodium Stearyl Fumarate | 1.0 | 1.0 |
| TOTAL weight of tablet | 100.0 | 100.0 |
| Powder flow (Hausner ratio) | 22.6 | 20.9 |
| Blend Uniformity | | |
| TOP | 98.0 | 98.0 |
| MIDDLE | 99.0 | 99.0 |
| BOTTOM | 102.0 | 100.0 |
| MEAN | 100.0 | 99.0 |
| % RSD | 1.7 | 1.9 |
| Content Uniformity | | |
| % label Claim | 96.0 | 97.0 |
| AV | 9.2 | 3.7 |
| Dissolution Time (min) | % release | |
| 5 | 98.0 | 90.0 |
| 10 | 101.0 | 102.0 |
| 15 | 100.0 | 102.0 |

TABLE 10-continued

| Material Name | Ex. 1F | Ex. 1G |
|---|---|---|
| | % w/w | |
| 30 | 100.0 | 101.0 |
| Infinity | 99.0 | 101.0 |
| Assay (%) | 96.0 | 97.0 |

Both examples met pre-defined criteria for blend uniformity, content uniformity, assay and dissolution. The material flow property was measured using Hausner ratio and no significant difference was found between the two formulations. However, the content uniformity results for Ex. 1G (AV=3.7) was found better in comparison to Ex. 1F (AV=9.2).

Tablets from both batches (Ex. 1F and Ex. 1G) were tested for dissolution. The results showed no significant difference between two formulations.

Psilocybin tablet formulations comprising 1 mg and 5 mg of API are presented in Table 11.

TABLE 11

| Excipient/material Name | Psilocybin 1 mg Tablet | | Psilocybin 5 mg Tablet | |
|---|---|---|---|---|
| | Percent Formula (% w/w) | Quantity (mg/tablet) | Percent Formula (% w/w) | Quantity (mg/tablet) |
| Psilocybin | 1.0 | 1.0 | 5.0 | 5.0 |
| Silicified Microcrystaline Cellulose SMCC 50 | 20.5 | 20.5 | 12.5 | 12.5 |
| Silicified Microcrystaline Cellulose SMCC 90 | 75.5 | 75.5 | 79.5 | 79.5 |
| Ratio | 1:3.7 | | 1:6.4 | |
| Sodium Starch Glycolate (disintegrant) | 1.0 | 1.0 | 1.0 | 1.0 |
| Colloidal silicon Dioxide (Aerosil) (glidant) | 1.0 | 1.0 | 1.0 | 1.0 |
| Sodium Stearyl Fumarate (Pruv) (lubricant) | 1.0 | 1.0 | 1.0 | 1.0 |
| TOTAL | 100.0 | 100.0 | 100.0 | 100.0 |

It will be noted that alternative disintegrants, glidants and lubricants to those exemplified may be used.

Example 2: Treating a Subject with High Dose Psilocybin

Initially, a subject is counseled as to the expected effects of psilocybin by a professional who is trained to administer psilocybin therapy. One or more tablets or capsules comprising psilocybin are administered to the subject, in an environment where the subject is made to feel safe and comfortable. The total dose of psilocybin administered to the subject is between about 1 mg to about 25 mg.

The subject is supervised by the professional during administration of the psilocybin, and for a period of time thereafter (e.g., from about 4 hours to about 12 hours) until the psychoactive effects of the psilocybin have worn off. Optionally, the subject may receive psychological support during administration of the psilocybin, and for a period of time thereafter (e.g., from about 4 hours to about 12 hours).

Example 3: Safety and Efficacy of Psilocybin in Healthy Subjects

Aim of Study:

A Phase 1 randomized, double-blind, placebo-controlled study to evaluate the effect of psilocybin on cognitive and emotional processing as compared to placebo in healthy volunteers was conducted. The study investigated the short-term (Day 7) and long-term (Day 28) effects of moderate (10 mg) and high doses (25 mg) of psilocybin on key domains of cognition, such as episodic memory, attention, working and spatial memory, social cognition and elements of executive function, including cognitive flexibility.

Study Design:

Subjects 90 healthy subjects were studied. Approximately 50% of the subjects were psilocybin-naïve. For subjects with prior psilocybin experience, the last exposure was at least 1 year prior to the signing of the Informed Consent Form (ICF). Approximately 50% of the subjects were female. Subjects were stratified by sex and age (18-35 years old; >35 years old).

Dosing Procedure:

Each subject was assigned 1 treatment bottle containing 5 capsules packaged in a double-blind fashion, depending on the randomized treatment arm, the bottle contained one of the following:

a. Psilocybin 10 mg: 2×5-mg oral psilocybin capsules plus 3×placebo capsules b. Psilocybin 25 mg: 5×5-mg oral psilocybin capsules c. Placebo: 5×placebo capsules Each 5-mg oral psilocybin capsule comprised 5 mg crystalline psilocybin in the form of Polymorph A, 12.5 mg of SMCC 50, 79.5 mg of SMCC 90, 1 mg sodium starch glycolate, 1 mg colloidal silicon dioxide, and 1 mg sodium stearyl fumarate The dose was swallowed with at least a full glass of water.

Outcome Measures:

The following list of outcome measures are non-exhaustive.

a. The short-term change from Baseline (Day −1 [Visit 2]) to Day 7 (Visit 5) in cognitive measures of attention, spatial and working memory and executive function was measured by a composite score of the CANTAB Panel (Spatial Working Memory [SWM], Rapid Visual Information Processing [RVP], Paired Associates Learning [PAL]).

b. The short-term change from Baseline (Day −1 [Visit 2]) to Day 7 (Visit 5) in Social Cognition Panel scales (Pictorial Empathy Test [PET], Reading the Mind in the Eyes Test [RMET], Toronto Empathy Questionnaire [TEQ], Social Value Orientation [SVO], Scale of Social Responsibility [SSR]).

c. The change from Baseline (Day −1 [Visit 2]) to Day 28 (Visit 6) in cognitive measures of attention, spatial and working memory and executive function as measured by a composite score of the CANTAB Panel (SWM, RVP, PAL).

d. The long-term change from Baseline (Day −1 [Visit 2]) to Day 84 (Visit 7) in Social Cognition Panel scales (PET, RMET, TEQ, SVO, SSR).

e. Dose-related differences between cognitive effects of psilocybin at Baseline (Day −1 [Visit 2]), Day 7 (Visit 5) and Day 28 (Visit 6), as measured by a composite score of the CANTAB Panel (SWM, RVP, PAL).

f. Dose-related differences between psychological effects of psilocybin at Baseline (Day −1 [Visit 2]), Day 7 (Visit 5) and Day 84 (Visit 7), as measured by Social Cognition Panel scales (PET, RMET, TEQ, SVO, SSR).

g. Differences in cognitive effects of psilocybin between psilocybin-naïve and experienced subjects at Baseline (Day −1 [Visit 2]), Day 7 (Visit 5) and Day 28 (Visit 6), as measured by a composite score of the CANTAB Panel (SWM, RVP, PAL).

h. Differences in Positive and Negative Affect Schedule (PANAS) after study drug administration on Day 0 (Visit 3).

i. Differences between psilocybin and placebo in the Emotion Recognition Test (ERT), Intra-Extra Dimensional Set Shift (IED), One Touch Stockings (OTS), Verbal Fluency and Digit Span Forward at Day 7 (Visit 5).

j. A composite score of the CANTAB Panel, including the following tests:

i. Spatial Working Memory (SWM) (performed at Visit 2, Visit 5, and Visit 6).

ii. Rapid Visual Information Processing (RVP) (performed at Visit 2, Visit 5, and Visit 6).

iii. Paired Associates Learning (PAL) (performed at Visit 2, Visit 5, and Visit 6).

k. Cognitive Flexibility Panel i. Emotion Recognition Task (ERT) (performed at Visit 5).

ii. Intra-Extra Dimensional Set Shift (IED) (performed at Visit 5).

iii. One Touch Stockings (OTS) (performed at Visit 5).

iv. Verbal Fluency (performed at Visit 5).

v. Digit Span Forward (performed at Visit 5).

l. Five Dimension Altered States of Consciousness questionnaire (5D-ASC) (performed at Visit 3).

m. PANAS (performed at Visit 2 and Visit 3).

n. NEO-Five Factor Inventory (NEO-FFI) (performed at Visit 2, Visit 5, and Visit 7).

o. Symptom Checklist-90 item (SCL-90) (performed at Visit 2, Visit 5, and Visit 7).

p. Life Changes Inventory (LCI): The LCI measures changes in attitudes and values after near-death experiences often used to evaluate personal transformation following spiritually oriented experiences and practices. (performed at Visit 5 and Visit 7).

q. Social Cognition Panel scales i. Pictorial Empathy Test (PET) (performed at Visit 2, Visit 5, and Visit 7).

ii. Reading the Mind in the Eyes Test (RMET) (performed at Visit 2, Visit 5, and Visit 7).

iii. Social Value Orientation (SVO) (performed at Visit 2, Visit 5, and Visit 7).

iv. Toronto Empathy Questionnaire (TEQ) (performed at Visit 2, Visit 5, and Visit 7).

v. Scale of Social Responsibility (SSR) (performed at Visit 2, Visit 5, and Visit 7).

r. Sheehan Suicidality Tracking Scale (SSTS)

s. Mini International Neuropsychiatric Interview (MINI).

t. McLean Screening Instrument for Borderline Personality Disorder (MSIBPD) (performed at Visit 1).

u. Tellegen Absorption Scale (performed at Visit 2).

v. Physical Examination (performed at Visit 1).

w. Electrocardiogram (ECG) (performed at Visit 1, Visit 2, Visit 3 and Visit 4).

Clinical Laboratory Tests: Blood samples were obtained at Screening (Visit 1) and Day 1 (Visit 4) for the following:

i. Hematology: hemoglobin, hematocrit, red blood cell count, mean corpuscular hemoglobin, mean corpuscular volume, mean corpuscular hemoglobin concentration, white blood cell count (with differential) and platelet count.

ii. Chemistry: albumin, alkaline phosphatase, alanine aminotransferase (ALT), amylase, aspartate aminotransferase (AST), bicarbonate, bilirubin (direct, indirect and total), calcium, chloride, creatine kinase, creatinine, γ-glutamyl transferase, glucose, lactate dehydrogenase, lipase, magnesium, phosphate, potassium, protein-total, sodium, blood urea nitrogen and uric acid.

Urine samples were obtained at Screening (Visit 1) and Baseline (Visit 2) for the following:

i. Urine Drug Screen: for illicit drugs or drugs of abuse at Screening (Visit 1) and Baseline (Visit 2). Results of a positive drug screen will be reviewed by the study clinician for pattern of use.

ii. Urine Pregnancy Test: a dipstick test in females of childbearing potential at Screening (Visit 1) and Baseline (Visit 2).

Adverse events: Throughout the course of the study, all AEs were monitored and recorded. Each AE was classified according to the following criteria:

i. Mild: The AE does not interfere in a significant manner with the subject's normal level of functioning.

ii. Moderate: The AE produces some impairment of functioning, but is not hazardous to the subject's health.

iii. Severe: The AE produces significant impairment of functioning or incapacitation and is a definite hazard to the subject's health.

Selected Adverse Events of included:

(a) Euphoric mood (b) Dissociative disorder (c) Hallucination (d) Psychotic disorder (e) Cognitive disorder (f) Disturbance in attention (g) Altered mood (h) Impairment of psychomotor skills (i) Inappropriate affect (j) Overdose (k) Intentional product misuse (l) Illusion Serious adverse events included:

(a) Death.

(b) Life-threatening: An AE is life-threatening if the subject was at immediate risk of death from the event as it occurred; i.e., it did not include a reaction that if it had occurred in a more serious form might have caused death. For example, drug-induced hepatitis that resolved without evidence of hepatic failure would not be considered life threatening even though drug-induced hepatitis can be fatal.

(c) Inpatient hospitalization or prolongation of existing hospitalization.

(d) Persistent or significant disability/incapacity.

(e) Congenital anomaly/birth defect in the offspring of a subject who received psilocybin.

(f) Other: Important medical events that may not result in death, be life-threatening, or require hospitalization, may be considered an SAE when, based upon appropriate medical judgment, they may jeopardize the subject and may require medical or surgical intervention to prevent one of the outcomes listed in this definition. Examples of such events are:

(i) Intensive treatment in an emergency room or at home for allergic bronchospasm.

(ii) Blood dyscrasias or convulsions that do not result in inpatient hospitalization.

(iii) Development of drug dependency or drug abuse.

Visits:

Visit 1 (V1): Eligibility Screening (Days −56 to Day −2): All subjects were screened for eligibility in the 8 weeks (i.e., Day −56 to Day −2) prior to Baseline: including medical and psychiatric history, the Mini International Neuropsychiatric Interview (MINI, English version, 7.0.2), McLean Screening Instrument for Borderline Personality Disorder (MSIBPD), SSTS, physical examination, vital signs, body weight, height, body mass index (BMI), 12-lead electrocardiogram (ECG), clinical laboratory tests, urine drug screen, urine pregnancy test, documentation of contraceptive method, review of prior and concomitant medications and recording of AEs.

Visit 2 (V2): Baseline Assessments (Day −1): Subjects completed the Baseline assessments (Day −1 [V2]) 1 day prior to study drug administration including: Tellegen Absorption Scale (TAS), NEO-FFI, SCL-90, PANAS, PET, RMET, SVO, TEQ, SSR, SWM, RVP, SSTS, Paired Associates Learning (PAL), vital signs, urine drug screen, review of prior and concomitant medications and recording of AEs. During this visit, subjects joined in a 2 hour group session with the study psychiatrist, lead therapist, chaperones, and all subjects to be dosed the following day. The subject was informed about what to expect during the session. All questions were answered. Subjects who had additional questions or concerns were able to have a 1:1 preparatory session with the assigned chaperone.

Visit 3 (V3): Drug Administration (Day 0): The subject was asked to eat a light breakfast at least two hours prior to coming to the clinic for study drug administration. On Day 0 (V3), the subject underwent the SSTS, had vital signs obtained, medications reviewed, AEs recorded and eligibility reviewed prior to being randomized to study drug. The study drug was administered to up to six subjects simultaneously in individual beds separated by a curtain. The subject was invited to put on eyeshades and headphones, lie down and listen to calming music for the rest of the session (six hours). The subject was supported 1:1 with a chaperone and supervised by the study psychiatrist and lead therapist.

The effects of psilocybin usually started about 20 to 30 min after administration, becoming most intense in the first 90 to 120 min and gradually subsiding in about 5 to 6 hours. The subjects were asked to remain in the room for the duration of the session regardless of the intensity of the effects, preferably lying down and mostly silent unless they have a concern or need to communicate a discomfort or seek reassurance from the therapist, or use the restroom. A light meal and fruit was available for the subject after the session. After the acute effects of study drug administration had subsided, all subjects were assessed for safety and asked to complete the following assessments: PANAS and 5D-ASC. Medications used, if any, during study drug administration session, and adverse events were recorded. The subjects also discussed their psilocybin experience with their therapist. The subject was discharged 6 to 8 hours post dose when, in the opinion of the investigator, the acute effects of psilocybin were resolved. After the acute effects of study drug administration subsided, subjects returned home accompanied by a family member, friend, or chaperone. The therapists checked with the subjects by phone at the end of the day to ensure that the subject arrived home safely.

Visit 4 (V4): Safety Assessments (Day 1): Subjects returned to the clinic the next morning (Day 1 [V4]) for safety assessments, including but not limited to: SSTS, vital signs, clinical laboratory tests, review of concomitant medications and AEs and a one-on-one discussion about the subject's experience with the subject's assigned therapist.

Visit 5 (V5): Follow up visit (Day 7 or at Early Termination): Psychometric assessments were completed remotely on Day 7 (V5) or at Early Termination (ET): NEO-FFI, SCL-90, LCI, PET, RMET, SVO, TEQ, SSR, SSTS, SWM, RVP, PAL, review of concomitant medication and recording of AEs. Additionally, at Day 7 (V5) the ERT, IED, OTS, Verbal Fluency and Digit Span Forward tests were conducted.

Visit 6: Follow up visit (Day 28): The SSTS, SWM, RVP, PAL, review of concomitant medication and recording of AEs were obtained at Day 28 (V6).

Visit 7: Follow up Visit (Day 84): The NEO-FFI, SCL-90, LCI, PET, RMET, SVO, TEQ and SSR was obtained remotely at Day 84 (V7). If the subject discontinued the study early, this visit was performed early.

Recording of adverse events and prior/concomitant medication was performed at each visit.

Table 12 summarizes the assessments and procedures that were performed at each visit.

TABLE 12

| | | | | | | | |
|---|---|---|---|---|---|---|---|
| Schedule of Visits | | | | | | | |
| | Screening | Baseline | | | Treatment Period | | |
| | | | | | Visit | | |
| | V1 | V2 | V3 | V4 | V5 | V6 | V7 (EOS/ET) |
| | | | | Day | | | |
| | −56 to −2 | −1 | 0 | 1 | 7 | 28 | 84 |
| | | | | Allowed Window | | | |
| | | | | | ± 1 Day | ± 3 Days | ± 7 Days |
| | | | | Place of Testing | | | |
| | Clinic | Clinic | Clinic | Clinic | Remote[1] | Remote[1] | Remote[1] |
| Assessments and Procedures | | | | | | | |
| ICF | | | | | | | |
| Medical and Psychiatric History | X | | | | | | |
| MINI | X | | | | | | |
| MSIBPD | X | | | | | | |
| TAS[2] | | X | | | | | |
| NEO-FFI[2] | | X | | | X | | X |
| SCL-90[2] | | X | | | X | | X |
| LCI[2] | | | | | X | | X |
| Eligibility Review | X | X | X[3] | | | | |
| Randomization | | | X[3] | | | | |
| Preparatory Session[4] | | X | X | X[5] | | | |
| Study Drug Administration | | | X | | | | |
| PANAS[2] | | X | X[6] | | | | |
| 5D-ASC[2] | | | X[6] | | | | |
| Social Cognition Panel[2] | | | | | | | |
| PET | | X | | | X | | X |
| RMET | | X | | | X | | X |
| SVO | | X | | | X | | X |
| TEQ | | X | | | X | | X |
| SSR | | X | | | X | | X |
| Exploratory Assessments | | | | | | | |
| ERT[7] | | | | | X | | |
| IED[7] | | | | | X | | |
| OTS[7] | | | | | X | | |
| Verbal Fluency[8] | | | | | X | | |
| Digit Span Forward[8] | | | | | X | | |
| Safety Assessments | | | | | | | |
| SSTS[2] | X | X | X[3] | X | X | X | |
| SWM[9] | | X | | | X | X | |
| RVP[9] | | X | | | X | X | |
| PAL[9] | | X | | | X | X | |
| Physical Examination | X | | | | | | |
| Vital Signs[10] | X | X | X[3] | X | | | |
| Body Weight, Height and BMI | X | | | | | | |
| 12-lead ECG | X | | | | | | |
| Clinical Laboratory Tests[11] | X | | | X | | | |
| Urine Drug Screen | X | X | | | | | |
| Urine Pregnancy Test[12] | X | X | | | | | |
| Documentation of Contraceptive Method[13] | X | | | | | | |

TABLE 12-continued

| | | | | | | | | |
|---|---|---|---|---|---|---|---|---|
| Schedule of Visits | | | | | | | | |
| | Screening | Baseline | Treatment Period | | | | | |
| | | | Visit | | | | | |
| | V1 | V2 | V3 | V4 | V5 | V6 | V7 (EOS/ET) | |
| | | | | Day | | | | |
| | −56 to −2 | −1 | 0 | 1 | 7 | 28 | 84 | |
| | | | | Allowed Window | | | | |
| | | | | | ± 1 Day | ± 3 Days | ± 7 Days | |
| | | | | Place of Testing | | | | |
| | Clinic | Clinic | Clinic | Clinic | Remote[1] | Remote[1] | Remote[1] | |
| Prior/Concomitant Medications[14] | X | X | X | X | X | X | X | |
| AE[15] | X | X | X | X | X | X | X | |

[1]This session may be done remotely by telephone or in the clinic.
[2]Paper and pencil test.
[3]Obtained prior to study drug administration.
[4]A preparatory session will be conducted in a group session at Baseline (Day −1, V2) and prior to dosing on Day 0 (V3). An individual session will also be conducted at Baseline (Day −1, V2).
[5]A group discussion will be held about the study drug administration experience.
[6]Obtained immediately after study drug administration.
[7]Part of the Cambridge Cognition Panel; to be recorded on the digital platform.
[8]Part of the Cambridge Cognition Panel; to be recorded during the telephone interview.
[9]To be done electronically, V1, subjects will carry out a practice session of the computerized tests, but the data will not be used.
[10]Vital signs (sitting BP, pulse, oral body temperature and respiratory rate) are to be obtained after the subject has been seated for at least 3 min.
[11]Chemistry: albumin, alkaline phosphatase, ALT, amylase, AST, bicarbonate, bilirubin (direct, indirect and total), calcium, chloride, creatine kinase, creatinine, GGT, glucose, LDH, lipase, magnesium, phosphate, potassium, protein-total, sodium, BUN and uric acid. Haematology: haemoglobin, haematocrit, red blood cell count, mean corpuscular haemoglobin, mean corpuscular volume, mean corpuscular haemoglobin concentration, white blood cell count (with differential) and platelet count.
[12]All females.
[13]For females of childbearing potential and all males; site is to document method of contraception agreed to be used by each subject.
[14]Prior medications will be obtained until dosing of study drug, thereafter, concomitant medications will be recorded.
[15]All AEs occurring after the subject signs the ICF and up to the last study event will be recorded. Any AEs occurring before the start of treatment (i.e., before the administration of the study drug on Day 0 [V3]) will be recorded in the medical history.

Results

The phase I, randomized, double-blind, placebo-controlled study to evaluate the effects of 10 mg and 25 mg COMP360 (psilocybin) compared with placebo in healthy subjects was performed. FIG. 9A shows a timeline of the study.

A total of 89 subjects were enrolled in the study. Of these, 30 participants were randomized to receive 25 mg psilocybin, 30 to 10 mg psilocybin, and 29 to placebo. All subjects randomized to both psilocybin arms completed the study; four (13.8%) placebo-treated subjects did not complete all study visits (three were lost to follow-up and one subject discontinued due to a protocol violation). Some subjects that completed the study did not complete certain cognition and/or emotional processing assessments at all timepoints. In these instances, analyses only included the available data and missing data were not imputed. Table 13 shows the number of subjects from each treatment arm that completed the study.

TABLE 13

| Number of Subjects that Completed the Phase 1 Clinical Study | | | | | |
|---|---|---|---|---|---|
| Parameter | Statistic | Psilocybin (25 mg) (N = 30) | Psilocybin (10 mg) (N = 30) | Placebo (N = 29) | Overall (N = 89) |
| Number of randomized population | N | 30 | 30 | 29 | 89 |

TABLE 13-continued

| Number of Subjects that Completed the Phase 1 Clinical Study | | | | | |
|---|---|---|---|---|---|
| Parameter | Statistic | Psilocybin (25 mg) (N = 30) | Psilocybin (10 mg) (N = 30) | Placebo (N = 29) | Overall (N = 89) |
| Number of completions | N (%) | 30 (100.0) | 30 (100.0) | 25 (86.2) | 85 (95.5) |
| Number of early terminations | N (%) | 0 | 0 | 4 (13.8) | 4 (4.5) |
| Reason for early terminations | | | | | |
| Lost to follow-up | N (%) | 0 | 0 | 3 (10.3) | 3 (3.4) |
| Protocol violation | N (%) | 0 | 0 | 1 (3.4) | 1 (1.1) |

Abbreviation: N = number of subjects.

During administration of psilocybin, each subject received one on one support from a trained assisting therapist and each dosing session was supervised by a study psychiatrist and a lead therapist. The study drug was administered simultaneously to up to six participants as a single 5-capsule oral dose (10 mg psilocybin: 2×5-mg psilocybin capsules plus 3×placebo capsules; 25 mg psilocybin: 5×5-mg psilocybin capsules; placebo: 5×placebo capsules). Twenty-five dosing sessions were completed, with up to six participants dosed simultaneously per session. Each session lasted approximately 6 to 8 hours with subjects encouraged to relax and engage in introspection for the duration. After the acute effects of the study drug had subsided, subjects were discharged.

A diagram of the study is presented in FIG. 9B, which shows the number of subjects that completed screening (Visit 1), baseline measurements (Visit 2), and drug administration (Visit 3).

The mean (SD) age of the subjects was 36.1 (9.06) years with the range of 20 to 59 years. The majority of the subjects were white (72 [80.9%]). Forty-eight (53.9%) of subjects were male and 41 (46.1%) were female. The mean (SD) BMI of the subjects was 23.2 (3.37) $kg/m^2$ with the range of 18 to 35 $kg/m^2$. Thirty-three (37.1%) subjects had prior psilocybin experience. For subjects with prior psilocybin experience, the last experience was at least one year prior to the signing of the informed consent form. The subjects were highly educated with approximately 97% having an education level over Undergraduate/Higher National Diploma. The average age and gender of the subjects was consistent across the treatment arms.

The demographics of the subjects are revealed in Table 14.

TABLE 14

| Demographics of Subjects in Healthy Volunteer Study | | | |
|---|---|---|---|
| Parameter | 25 mg psilocybin (n = 30) | 10 mg psilocybin (n = 30) | Placebo (n = 29) | Overall (n = 89) |
| Sex, n (%) | | | | |
| Male | 16 (53.3) | 16 (53.3) | 16 (55.2) | 48 (53.9) |
| Female | 14 (46.7) | 14 (46.7) | 13 (44.8) | 41 (46.1) |
| Ethnicity, n (%) | | | | |
| White | 25 (83.3) | 27 (90.0) | 20 (69.0) | 72 (80.9) |
| Asian | 2 (6.7) | 1 (3.3) | 3 (10.3) | 6 (6.7) |
| Mixed | 2 (6.7) | 1 (3.3) | 1 (3.4) | 4 (4.5) |
| Black | — | — | 1 (3.4) | 1 (1.1) |
| Other | 1 (3.3) | 1 (3.3) | 4 (13.8) | 6 (6.7) |
| Age at screening, years | | | | |
| Mean (SD) | 36.6 (10.29) | 36.1 (9.25) | 35.6 (7.69) | 36.1 (9.06) |
| BMI, $kg/m^2$ | | | | |
| Mean (SD) | 23.0 (3.74) | 23.0 (2.89) | 23.7 (3.49) | 23.2 (3.37) |
| Prior psilocybin experience n (%) | | | | |
| Yes | 11 (36.7) | 15 (50.0) | 7 (24.1) | 33 (37.1) |
| No | 19 (63.3) | 15 (50.0) | 22 (75.9) | 56 (62.9) |
| Educational level n (%) | | | | |
| A level/NVQ | 2 (6.7) | 1 (3.3) | 0 | 3 (3.4) |
| Undergrad/Higher National Diploma | 9 (30.0) | 11 (36.7) | 10 (34.5) | 30 (33.7) |
| Masters or postgraduate diploma | 16 (53.3) | 16 (53.3) | 15 (51.7) | 47 (52.8) |
| PhD | 3 (10.0) | 2 (6.7) | 4 (13.8) | 9 (10.1) |

89 subjects were administered psilocybin or placebo in a dosing session, which contained between 1 and 6 subjects. FIG. 9C shows the group size of the dosing sessions.

All subjects that were administered psilocybin (groups 1 and 2) completed the study.

511 adverse events (AEs) were reported throughout the 12-week duration of the study: 217 in the 25 mg psilocybin arm (reported by 96.7% of subjects); 203 in the 10 mg psilocybin arm (reported by 96.7% of subjects); and 91 in the placebo arm (reported by 89.7% of subjects). Of these, 473 (92.6%) AEs were deemed by the investigators to potentially be related to study treatment, including 208

(95.9%) in the 25 mg psilocybin arm, 188 (92.6%) in the 10 mg psilocybin arm, and 77 (84.6%) in the placebo arm. There were no serious adverse events or adverse events that led to withdrawal.

Overall, the most common treatment-emergent adverse events (TEAEs) by system organ class were Psychiatric disorders, Nervous system disorders, General disorders and administration site conditions, Gastrointestinal disorders and Infections and infestations. The most frequent TEAEs were (number of events in parentheses): Illusion (56), Mood altered (54), Hallucination visual (44), Headache (33), Fatigue (21), Somatic hallucination (19), Euphoric mood (14), Paraesthesia (12), Tension headache (12), Time perception altered (11), Hallucination, auditory (9), Affect lability (9), Feeling of relaxation (8), Emotional disorder (8), Hypoaesthesia (7).

Table 15 shows a summary of treatment-emergent adverse events.

TABLE 15

Summary of Treatment-Emergent Adverse Events

| | Psilocybin 25 mg (N = 30) | | Psilocybin 10 mg (N = 30) | | Placebo (N = 29) | |
|---|---|---|---|---|---|---|
| | N (%) | Events | N (%) | Events | N (%) | Events |
| Any TEAE | 29 (96.7) | 217 | 29 (96.7) | 203 | 26 (89.7) | 91 |
| Any serious TEAE | 0 | 0 | 0 | 0 | 0 | 0 |
| Any TEAE related to study treatment | 29 (96.7) | 208 | 29 (96.7) | 188 | 23 (79.3) | 77 |
| Any serious TEAE related to study treatment | 0 | 0 | 0 | 0 | 0 | 0 |
| Any severe TEAE | 10 (33.3) | 29 | 10 (33.3) | 22 | 1 (3.4) | 2 |
| Any Selected TEAE | 27 (90.0) | 106 | 27 (90.0) | 106 | 11 (37.9) | 24 |
| Any TEAE leading to study discontinuation | 0 | 0 | 0 | 0 | 0 | 0 |
| Any TEAE leading to death | 0 | 0 | 0 | 0 | 0 | 0 |

Percentages are based on the number of subjects in each treatment group.
Adverse events are coded using MedDRA.
Abbreviations:
N = Number of subjects;
MedDRA = Medical Dictionary for Regulatory Activities;
TEAE = Treatment-emergent adverse event.

A summary of TEAEs by Medical Dictionary for Regulatory Activities (MedDRA) SOC and PTs is presented in Table 16 and FIG. 9D.

TABLE 16

Summary of Treatment-Emergent Adverse Events by MedDRA Primary SOC and PT With ≥10% Subjects in Each Treatment Arm (Safety Population)

| System Organ Class | Psilocybin 25 mg (N = 30) | | Psilocybin 10 mg (N = 30) | | Placebo (N = 29) | |
|---|---|---|---|---|---|---|
| Preferred Term | N (%) | Events | N (%) | Events | N (%) | Events |
| Any TEAE | 29 (96.7) | 217 | 29 (96.7) | 203 | 26 (89.7) | 91 |
| Gastrointestinal disorders | 5 (16.7) | 5 | 4 (13.3) | 4 | 5 (17.2) | 5 |
| Nausea | 3 (10.0) | 3 | 1 (3.3) | 1 | 1 (3.4) | 1 |
| General disorders and administration site conditions | 15 (50.0) | 18 | 17 (56.7) | 27 | 7 (24.1) | 7 |
| Fatigue | 8 (26.7) | 8 | 9 (30.0) | 10 | 3 (10.3) | 3 |
| Feeling abnormal | 0 | 0 | 4 (13.3) | 4 | 0 | 0 |
| Feeling of relaxation | 1 (3.3) | 1 | 3 (10.0) | 5 | 2 (6.9) | 2 |
| Infections and infestations | 4 (13.3) | 4 | 4 (13.3) | 4 | 5 (17.2) | 5 |
| Investigations | 1 (3.3) | 1 | 2 (6.7) | 2 | 4 (13.8) | 5 |
| Musculoskeletal and connective tissue disorders | 3 (10.0) | 4 | 1 (3.3) | 1 | 3 (10.3) | 3 |
| Nervous system disorders | 25 (83.3) | 43 | 21 (70.0) | 35 | 12 (41.4) | 16 |
| Headache | 15 (50.0) | 16 | 9 (30.0) | 12 | 5 (17.2) | 5 |
| Hypoaesthesia | 3 (10.0) | 4 | 2 (6.7) | 2 | 1 (3.4) | 1 |

TABLE 16-continued

Summary of Treatment-Emergent Adverse Events by MedDRA Primary
SOC and PT With ≥10% Subjects in Each Treatment Arm (Safety Population)

| System Organ Class | Psilocybin 25 mg (N = 30) | | Psilocybin 10 mg (N = 30) | | Placebo (N = 29) | |
|---|---|---|---|---|---|---|
| Preferred Term | N (%) | Events | N (%) | Events | N (%) | Events |
| Paraesthesia | 4 (13.3) | 4 | 4 (13.3) | 4 | 4 (13.8) | 4 |
| Tension headache | 6 (20.0) | 6 | 3 (10.0) | 3 | 3 (10.3) | 3 |
| Psychiatric disorders | 29 (96.7) | 135 | 27 (90.0) | 121 | 16 (55.2) | 44 |
| Affect lability | 3 (10.0) | 3 | 5 (16.7) | 5 | 1 (3.4) | 1 |
| Emotional disorder | 5 (16.7) | 6 | 2 (6.7) | 2 | 0 | 0 |
| Euphoric mood | 7 (23.3) | 8 | 7 (23.3) | 7 | 0 | 0 |
| Hallucination | 2 (6.7) | 2 | 3 (10.0) | 3 | 0 | 0 |
| Hallucination, auditory | 4 (13.3) | 4 | 4 (13.3) | 4 | 1 (3.4) | 1 |
| Hallucination, tactile | 4 (13.3) | 4 | 2 (6.7) | 2 | 0 | 0 |
| Hallucination, visual | 21 (70.0) | 22 | 18 (60.0) | 20 | 2 (6.9) | 2 |
| Illusion | 18 (60.0) | 26 | 19 (63.3) | 25 | 4 (13.8) | 5 |
| Mental fatigue | 3 (10.0) | 3 | 0 | 0 | 0 | 0 |
| Mood altered | 15 (50.0) | 25 | 13 (43.3) | 23 | 6 (20.7) | 9 |
| Somatic hallucination | 5 (16.7) | 6 | 8 (26.7) | 8 | 4 (13.8) | 5 |
| Time perception altered | 6 (20.0) | 6 | 2 (6.7) | 2 | 3 (10.3) | 3 |
| Respiratory, thoracic and mediastinal disorders | 3 (10.0) | 3 | 0 | 0 | 2 (6.9) | 2 |

Percentages are based on the number of subjects in each treatment group.
Adverse events are coded using MedDRA.
Abbreviations:
N = Number of subjects;
MedDRA = Medical Dictionary for Regulatory Activities;
PT = Preferred term;
SOC = System organ class;
TEAE = Treatment-emergent adverse event.

The majority of TEAEs were of mild to moderate severity (Table 17). The incidence of severe TEAEs was higher in the subjects receiving psilocybin (both 10 mg and 25 mg) compared to placebo (29 in the psilocybin 25 mg arm, 22 in the psilocybin 10 mg arm, and two in the placebo arm).

The majority of the severe TEAEs were psychiatric disorders for both the psilocybin 10 mg and 25 mg arms. The incidence of Illusion, Hallucination (visual), Mood altered, Headache, Fatigue and Euphoric mood were higher in the subjects receiving psilocybin (both 10 and 25 mg) compared to placebo.

TABLE 17

Summary of TEAES by MedDRA Primary System Organ Class (SOC)
and preferred term (PT) with ≥10% Subjects in Each Treatment Arm by Worst
Severity (Safety Population)

| System Organ Class Preferred Term | Worst Severity | Psilocybin 25 mg (N = 30) | | Psilocybin 10 mg (N = 30) | | Placebo (N = 29) | |
|---|---|---|---|---|---|---|---|
| | | N (%) | Events | N (%) | Events | N (%) | Events |
| Any TEAE | Mild | 3 (10.0) | 14 | 6 (20.0) | 12 | 16 (55.2) | 40 |
| | Moderate | 16 (53.3) | 52 | 13 (43.3) | 38 | 9 (31.0) | 23 |
| | Severe | 10 (33.3) | 29 | 10 (33.3) | 22 | 1 (3.4) | 2 |
| Gastrointestinal disorders | Mild | 4 (13.3) | 4 | 3 (10.0) | 3 | 3 (10.3) | 3 |
| | Moderate | 1 (3.3) | 1 | 1 (3.3) | 1 | 2 (6.9) | 2 |
| | Severe | 0 | 0 | 0 | 0 | 0 | 0 |
| General disorders and administration site conditions | Mild | 8 (26.7) | 8 | 13 (43.3) | 17 | 3 (10.3) | 3 |
| | Moderate | 6 (20.0) | 7 | 3 (10.0) | 6 | 3 (10.3) | 3 |
| | Severe | 1 (3.3) | 1 | 1 (3.3) | 1 | 1 (3.4) | 1 |
| Fatigue | Mild | 3 (10.0) | 3 | 6 (20.0) | 6 | 2 (6.9) | 2 |
| | Moderate | 5 (16.7) | 5 | 2 (6.7) | 3 | 1 (3.4) | 1 |
| | Severe | 0 | 0 | 1 (3.3) | 1 | 0 | 0 |
| Feeling abnormal | Mild | 0 | 0 | 3 (10.0) | 3 | 0 | 0 |
| | Moderate | 0 | 0 | 1 (3.3) | 1 | 0 | 0 |
| | Severe | 0 | 0 | 0 | 0 | 0 | 0 |
| Infections and infestations | Mild | 4 (13.3) | 4 | 2 (6.7) | 2 | 4 (13.8) | 4 |
| | Moderate | 0 | 0 | 2 (6.7) | 2 | 1 (3.4) | 1 |
| | Severe | 0 | 0 | 0 | 0 | 0 | 0 |
| Investigations | Mild | 1 (3.3) | 1 | 2 (6.7) | 2 | 3 (10.3) | 4 |
| | Moderate | 0 | 0 | 0 | 0 | 1 (3.4) | 1 |
| | Severe | 0 | 0 | 0 | 0 | 0 | 0 |

TABLE 17-continued

Summary of TEAES by MedDRA Primary System Organ Class (SOC)
and preferred term (PT) with ≥10% Subjects in Each Treatment Arm by Worst
Severity (Safety Population)

| System Organ Class Preferred Term | Worst Severity | Psilocybin 25 mg (N = 30) | | Psilocybin 10 mg (N = 30) | | Placebo (N = 29) | |
|---|---|---|---|---|---|---|---|
| | | N (%) | Events | N (%) | Events | N (%) | Events |
| Musculoskeletal | Mild | 2 (6.7) | 3 | 0 | 0 | 3 (10.3) | 3 |
| and connective | Moderate | 1 (3.3) | 1 | 1 (3.3) | 1 | 0 | 0 |
| tissue disorders | Severe | 0 | 0 | 0 | 0 | 0 | 0 |
| Nervous system | Mild | 16 (53.3) | 24 | 15 (50.0) | 23 | 11 (37.9) | 15 |
| disorders | Moderate | 8 (26.7) | 10 | 6 (20.0) | 8 | 1 (3.4) | 1 |
| | Severe | 1 (3.3) | 1 | 0 | 0 | 0 | 0 |
| Headache | Mild | 10 (33.3) | 10 | 9 (30.0) | 12 | 4 (13.8) | 4 |
| | Moderate | 5 (16.7) | 5 | 0 | 0 | 1 (3.4) | 1 |
| | Severe | 0 | 0 | 0 | 0 | 0 | 0 |
| Hypoaesthesia | Mild | 3 (10.0) | 4 | 2 (6.7) | 2 | 1 (3.4) | 1 |
| | Moderate | 0 | 0 | 0 | 0 | 0 | 0 |
| | Severe | 0 | 0 | 0 | 0 | 0 | 0 |
| Paraesthesia | Mild | 3 (10.0) | 3 | 4 (13.3) | 4 | 4 (13.8) | 4 |
| | Moderate | 1 (3.3) | 1 | 0 | 0 | 0 | 0 |
| | Severe | 0 | 0 | 0 | 0 | 0 | 0 |
| Tension | Mild | 4 (13.3) | 4 | 1 (3.3) | 1 | 3 (10.3) | 3 |
| headache | Moderate | 2 (6.7) | 2 | 2 (6.7) | 2 | 0 | 0 |
| | Severe | 0 | 0 | 0 | 0 | 0 | 0 |
| Psychiatric | Mild | 4 (13.3) | 5 | 4 (13.3) | 6 | 8 (27.6) | 13 |
| disorders | Moderate | 16 (53.3) | 45 | 13 (43.3) | 29 | 7 (24.1) | 15 |
| | Severe | 9 (30.0) | 27 | 10 (33.3) | 21 | 1 (3.4) | 1 |
| Affect lability | Mild | 2 (6.7) | 2 | 3 (10.0) | 3 | 0 | 0 |
| | Moderate | 1 (3.3) | 1 | 2 (6.7) | 2 | 1 (3.4) | 1 |
| | Severe | 0 | 0 | 0 | 0 | 0 | 0 |
| Emotional | Mild | 1 (3.3) | 1 | 1 (3.3) | 1 | 0 | 0 |
| disorder | Moderate | 4 (13.3) | 5 | 1 (3.3) | 1 | 0 | 0 |
| | Severe | 0 | 0 | 0 | 0 | 0 | 0 |
| Euphoric | Mild | 3 (10.0) | 3 | 0 | 0 | 0 | 0 |
| mood | Moderate | 4 (13.3) | 4 | 6 (20.0) | 6 | 0 | 0 |
| | Severe | 0 | 0 | 1 (3.3) | 1 | 0 | 0 |
| Hallucination | Mild | 0 | 0 | 0 | 0 | 0 | 0 |
| | Moderate | 2 (6.7) | 2 | 3 (10.0) | 3 | 0 | 0 |
| | Severe | 0 | 0 | 0 | 0 | 0 | 0 |
| Hallucination, | Mild | 1 (3.3) | 1 | 1 (3.3) | 1 | 0 | 0 |
| auditory | Moderate | 3 (10.0) | 3 | 1 (3.3) | 1 | 1 (3.4) | 1 |
| | Severe | 0 | 0 | 2 (6.7) | 2 | 0 | 0 |
| Hallucination, | Mild | 3 (10.0) | 3 | 3 (10.0) | 3 | 1 (3.4) | 1 |
| visual | Moderate | 13 (43.3) | 13 | 8 (26.7) | 8 | 1 (3.4) | 1 |
| | Severe | 5 (16.7) | 5 | 7 (23.3) | 7 | 0 | 0 |
| Illusion | Mild | 3 (10.0) | 4 | 7 (23.3) | 7 | 3 (10.3) | 4 |
| | Moderate | 10 (33.3) | 12 | 12 (40.0) | 16 | 0 | 0 |
| | Severe | 5 (16.7) | 7 | 0 | 0 | 1 (3.4) | 1 |
| Mood altered | Mild | 2 (6.7) | 3 | 2 (6.7) | 2 | 0 | 0 |
| | Moderate | 6 (20.0) | 7 | 5 (16.7) | 8 | 6 (20.7) | 6 |
| | Severe | 7 (23.3) | 9 | 6 (20.0) | 9 | 0 | 0 |
| Somatic | Mild | 2 (6.7) | 2 | 1 (3.3) | 1 | 4 (13.8) | 5 |
| hallucination | Moderate | 2 (6.7) | 2 | 7 (23.3) | 7 | 0 | 0 |
| | Severe | 1 (3.3) | 2 | 0 | 0 | 0 | 0 |
| Time | Mild | 2 (6.7) | 2 | 1 (3.3) | 1 | 3 (10.3) | 3 |
| perception | Moderate | 4 (13.3) | 4 | 1 (3.3) | 1 | 0 | 0 |
| altered | Severe | 0 | 0 | 0 | 0 | 0 | 0 |

Percentages are based on the number of subjects in each treatment group.
Adverse events are coded using MedDRA.
Abbreviations:
N = Number of subjects;
MedDRA = Medical Dictionary for Regulatory Activities;
PT = Preferred term;
SOC = System organ class;
TEAE = Treatment-emergent adverse event.

Selected adverse events are displayed in Table 18. The most frequent of these adverse events were Mood altered (n=57), Illusion (n=56), Hallucination visual (n=44), Somatic hallucination (n=19) and Euphoric mood (n=15).

TABLE 18

Summary of selected TEAEs of by MedDRA primary system organ class and preferred term

| System Organ Class Preferred Term | Psilocybin 25 mg (N = 30) | | Psilocybin 10 mg (N = 30) | | Placebo (N = 29) | |
|---|---|---|---|---|---|---|
| | N (%) | Events | N (%) | Events | N (%) | Events |
| Selected TEAE | 27 (90.0) | 106 | 27 (90.0) | 106 | 11 (37.9) | 24 |
| Nervous system disorders | 0 | 0 | 2 (6.7) | 2 | 0 | 0 |
| Memory impairment | 0 | 0 | 1 (3.3) | 1 | 0 | 0 |
| Psychomotor skills impaired | 0 | 0 | 1 (3.3) | 1 | 0 | 0 |
| Psychiatric disorders | 27 (90.0) | 106 | 27 (90.0) | 104 | 11 (37.9) | 24 |
| Affect lability | 3 (10.0) | 3 | 5 (16.7) | 5 | 1 (3.4) | 1 |
| Change in sustained attention | 0 | 0 | 2 (6.7) | 2 | 0 | 0 |
| Depressed mood | 2 (6.7) | 2 | 1 (3.3) | 1 | 1 (3.4) | 1 |
| Dissociative identity disorder | 2 (6.7) | 2 | 1 (3.3) | 2 | 0 | 0 |
| Euphoric mood | 7 (23.3) | 8 | 7 (23.3) | 7 | 0 | 0 |
| Hallucination | 2 (6.7) | 2 | 3 (10.0) | 3 | 0 | 0 |
| Hallucination, auditory | 4 (13.3) | 4 | 4 (13.3) | 4 | 1 (3.4) | 1 |
| Hallucination, gustatory | 0 | 0 | 1 (3.3) | 1 | 0 | 0 |
| Hallucination, olfactory | 1 (3.3) | 1 | 1 (3.3) | 1 | 0 | 0 |
| Hallucination, tactile | 4 (13.3) | 4 | 2 (6.7) | 2 | 0 | 0 |
| Hallucination, visual | 21 (70.0) | 22 | 18 (60.0) | 20 | 2 (6.9) | 2 |
| Somatic hallucination | 5 (16.7) | 6 | 8 (26.7) | 8 | 4 (13.8) | 5 |
| Illusion | 18 (60.0) | 26 | 19 (63.3) | 25 | 4 (13.8) | 5 |
| Mood altered | 15 (50.0) | 25 | 13 (43.3) | 23 | 6 (20.7) | 9 |
| Substance-induced psychotic disorder[b] | 1 (3.3) | 1 | 0 | 0 | 0 | 0 |

Percentages are based on the number of subjects in each treatment group.
Adverse events are coded using MedDRA.
Abbreviations: N = Number of subjects; MedDRA = Medical Dictionary for Regulatory Activities; PT = Preferred term; SOC = System organ class; TEAE = Treatment-emergent adverse event.
[b]This subject became behaviorally disinhibited during the acute drug experience. After a medical assessment, 2.5 mg oromucosal midazolam was administered. The subject recovered with no sequelae and was discharged 11 hours after receiving the study intervention. This event was not considered to be an SAE, and no clinically significant ongoing effects were noted at follow-up.

Mood alteration (MedDRA term is 'mood altered') was one of the most frequently reported adverse events. 57 AEs of mood alteration were reported (grouped according to regulatory requirements in MedDRA terms).

Table 19 shows the frequency of specific 'mood altered' AEs. Most 'mood altered' AEs were positive or neutral in nature (96%).

TABLE 19

Reported Mood Altered Events (ranked by incidence in the 25 mg psilocybin group)

| Description of 'Mood altered' Event | 25 mg psilocybin (n = 30) | 10 mg psilocybin (n = 30) | Placebo (n = 29) | Overall (n = 89) |
|---|---|---|---|---|
| Introspection | 8 | 5 | 2 | 15 |
| Reflections | 4 | 3 | 2 | 9 |
| Sense of oneness | 2 | 4 | 0 | 6 |
| Increased empathy | 2 | 2 | 0 | 4 |
| Contemplative state | 1 | 1 | 0 | 2 |
| Laughter | 1 | 1 | 0 | 2 |
| Clarity of thought | 1 | 0 | 0 | 1 |
| Increased compassion | 1 | 0 | 0 | 1 |
| Increased creativity | 1 | 0 | 0 | 1 |
| Increased sense of connectedness | 1 | 0 | 0 | 1 |
| More socially upbeat | 1 | 0 | 0 | 1 |
| Saw themselves from a new perspective | 1 | 0 | 0 | 1 |
| Being less judgmental | 0 | 1 | 0 | 1 |
| Feeling more moody/sensitive | 0 | 1 | 0 | 1 |
| Feeling rested | 0 | 1 | 0 | 1 |
| Increased wit | 0 | 1 | 0 | 1 |

TABLE 19-continued

Reported Mood Altered Events (ranked by incidence in the 25 mg psilocybin group)

| Description of 'Mood altered' Event | 25 mg psilocybin (n = 30) | 10 mg psilocybin (n = 30) | Placebo (n = 29) | Overall (n = 89) |
|---|---|---|---|---|
| Sense of openness | 0 | 1 | 0 | 1 |
| Unusual appreciation of music | 0 | 0 | 1 | 1 |
| Calm | 0 | 0 | 1 | 1 |
| Feeling of adrenaline release | 0 | 0 | 1 | 1 |
| Negative mood | 0 | 0 | 1 | 1 |

The median duration of adverse events in all treatment arms across the 12-week trial was one day, as shown in FIG. 9E. 67% of all adverse events appeared and resolved on day 0 (day of dosing). 92% of adverse events likely to be psychedelic in nature were resolved on the day of onset or within a day of onset The efficacy of psilocybin was assessed using the Cambridge Neuropsychological Test Automated Battery (CANTAB). The CANTAB variables analysed are shown in Table 20.

TABLE 20

| CANTAB Variables Analyzed During Phase 1 Study | | | |
|---|---|---|---|
| Test | Domain Tested | Outcome Variable | Variable Code |
| Primary and secondary efficacy and safety | | | |
| PAL, SWM, RVP (Safety) | Global cognition | CANTAB global functioning composite | CANTAB composite (+ve) |
| PAL | Episodic memory | Total errors adjusted | PALTEA (−ve) |
| SWM | Working memory | Between errors | SWMBE (−ve) |
| SWM | Executive function | Strategy | SWMS (−ve) |
| RVP | Sustained attention | A′ (A prime) | RVPA (+ve) |
| Exploratory efficacy | | | |
| ERT | Emotion perception | Percent correct | ERTPC (+ve) |
| OTS | Planning | Problems solved on first choice | OTSPSFC (+ve) |
| IED | Cognitive flexibility | Total errors | IEDYERT (−ve) |

Abbreviations: CANTAB = Cambridge Neuropsychological Test Automated Battery; ERT = Emotion Recognition Test; ERTPC = Emotion Recognition Test percent correct; IED = Intra-Extra Dimensional Set Shift; IEDYERT = Intra-Extra Dimensional Set Shift total errors; OTS = One Touch Stockings of Cambridge; OTSPSFC = One Touch Stockings of Cambridge problems solved on first choice; PAL = Paired Associates Learning; PALTEA = Paired Associates Learning total errors adjusted; RVP = Rapid Visual Information Processing; RVPA = Rapid Visual Information Processing A′ prime; SWM = Spatial Working Memory; SWMBE = Spatial Working Memory between errors; SWMS = Spatial Working Memory strategy.
−ve lower scores indicate better performance
+ve higher scores indicate better performance The Paired Associates Learning (PAL) test of the CANTAB was used to assess the effect of psilocybin on memory. The result of the PAL was reported as PAL Total Errors Adjusted (PALTEA). A lower score on the PALTEA indicated better performance (lower error count) and a positive change from baseline indicated worse performance (higher error count). On average, there was a numeric improvement in performance for the 10 mg and 25 mg psilocybin groups from Baseline to Day 28 whereas the placebo group showed a decrease in performance from Baseline to Day 28 as shown in FIG. 9F. Both the 10 mg psilocybin and 25 mg psilocybin groups showed on average of about a 2-point improvement in performance compared to the placebo group (LS mean difference from placebo) at Day 28 as shown in FIG. 9G.

The Spatial Working Memory (SWM) of CANTAB was also used to assess the effect of psilocybin on memory. The result of the SWM was reported as Spatial Working Memory between errors (SWMBE). A lower SWMBE score indicated better performance. Therefore, a negative change from baseline indicates better performance (lower error count), and a positive change from baseline indicates worse performance (higher error count). On average, performance improved numerically across psilocybin-treated and placebo treated groups from Baseline to Day 28, with the 25 mg psilocybin group showing a similar performance to that of placebo. The 10 mg group improved less, on average, with a higher error score at Day 28 than placebo as shown in FIG. 9H. The least squares (LS) mean difference indicated the 10 mg group performed less well on average than the placebo group at both Day 7 and Day 28, whilst the 25 mg group performs similarly to the placebo group at Day 28 (FIG. 9I). However, for these effects there was insufficient evidence of change.

The spatial working memory strategy score (SWMS) of CANTAB was also assessed. Lower SWMS scores indicated better performance. On average, there was a small numeric improvement in performance from Baseline to Day 28 across 10 mg and 25 mg psilocybin groups and placebo (FIG. 9J). The least squares mean difference indicated that the 25 mg psilocybin group and 10 mg psilocybin group performed similar to placebo at Day 7. However, the 25 mg group performed on average slightly better than the placebo, whilst the 10 mg group performed on average slightly worse than placebo at Day 28 (FIG. 9K).

The rapid visual information processing test of CANTAB, RVP A Prime (RPVA) was also assessed. Higher scores on the RVPA indicated better performance. As shown in FIG. 9L, there was an average numeric improvement in performance across all groups. The ANOVA suggested there was no evidence of an overall change in RVPA as a result of exposure to intervention. For both the 10 mg group and 25 mg group, the LS mean difference from placebo at Day 28 was different from placebo (FIG. 9M). This suggested a separation in performance at Day 28 between the psilocybin dose groups and the placebo group.

No main effect for psilocybin status or interaction (psilocybin status by visit by dose) was observed for the CANTAB composite measure in the subjects who completed the assessments without a major protocol deviation as part of the analysis of covariance (ANCOVA) analysis (p-values >0.05), suggesting no consistent differential performance due to previous exposure to psilocybin.

Least square means estimates indicated an improvement from Baseline to Day 7 and Day 28 in those psilocybin-naïve subjects in the placebo group. Conversely, least square means estimates indicated improvement from Baseline to Day 28 for those from the 10 mg psilocybin dose group who were previously exposed to psilocybin only. This improvement from baseline to Day 28 in the psilocybin experienced subjects was also an improvement relative to placebo. FIG. 9V shows the CANTAB composite score for psilocybin-naïve subjects (0) and psilocybin-experienced subjects (1).

However, for the 25 mg group, an improvement to Day 28 was observed irrespective of previous psilocybin exposure. This improvement was also higher relative to placebo.

The Emotional Recognition Task (ERT) test of the CANTAB was used to assess the effect of psilocybin. The result of the ERT was reported as the ERT percent correct (ERTPC). Higher ERTPC scores indicated better performance. No evidence of a difference was observed between the 25 mg and 10 mg psilocybin groups and placebo nor between the 25 mg and 10 mg psilocybin groups at Day 7 (FIG. 9N).

The One Touch Stockings of CANTAB was used to assess the effect of psilocybin on executive function. A higher OTS Problems Solved on First Choice indicated better performance. There was insufficient evidence of a difference observed between the 25 mg and 10 mg psilocybin groups or difference of these groups from placebo for performance on OTSPSFC at Day 7 (FIG. 9O).

The Intra-Extra Dimensional Set Shift of CANTAB was used to assess the effect of psilocybin on executive function. A lower IED Total Errors (IEDYERT) score indicated better performance. No difference in performance on IEDYERT was observed between psilocybin-treated groups or between placebo and psilocybin-treated groups at Day 7 (FIG. 9P).

The composite score of the CANTAB was assessed. The composite score was derived from Z scores for each CANTAB outcomes measure (PALTEA, SWMBE, SWMS, RVPA). A higher global composite score indicated a better performance. Both psilocybin-treated groups and placebo showed an improvement in performance over time from Baseline to Day 28 (FIG. 9O).

The LS mean difference from placebo was different from 0 for the 10 mg group at Day 7 (FIG. 9R, LS mean difference=−0.18320, p value ~0.04460, effect size 0.53;). For the 10 mg group, performance increased again at Day 28 suggesting no adverse effects of the 10 mg dose compared with placebo.

The verbal fluency test was completed at Visit 5 via phone. This task was reliant on the integrity of a range of cognitive abilities including executive functions such as planning and working memory. Subjects were asked to name different category exemplars (e.g. animals) in one minute. No statistically significant difference in the verbal fluency score was observed compared to placebo for both the psilocybin 10 mg (p-value 0.7635) and 25 mg arm (p-value 0.8412) (FIG. 9S).

The digit span forward test was completed at Visit 5 via phone. This task was a measure of number storage capacity, a common measure of short-term memory. No statistically significant difference in digit span scores was observed compared to placebo for both the psilocybin 10 mg (p value 0.6432) and 25 mg arm (p value 0.1147) (FIG. 9T).

The Five-Dimensional Altered States of Consciousness (5D-ASC) Questionnaire was administered, as summarized in Table 21. FIG. 9U summarizes the results of the Five Dimensional-Altered States of Consciousness (5D-ASC).

TABLE 21

| Analysis of variance (ANOVA) Model F-Tests for the 5D-ASC | | | | | | |
|---|---|---|---|---|---|---|
| Parameter | Source | DF | SS | MS | F-value | Pvalue |
| Oceanic | Treatment | 2 | 47562.11748 | 23781.05874 | 62.66 | <0.0001 |
| boundlessness | FPE | 1 | 406.80610 | 406.80610 | 1.07 | 0.3035 |
| Dread of ego | Treatment | 2 | 13243.54504 | 6621.77252 | 21.81 | <0.0001 |
| dissolution | FPE | 1 | 398.65320 | 398.65320 | 1.31 | 0.2552 |
| Visual | Treatment | 2 | 55584.85537 | 27792.42768 | 113.68 | <0.0001 |
| restructuralisation | FPE | 1 | 31.46543 | 31.46543 | 0.13 | 0.7207 |
| Auditory | Treatment | 2 | 11807.54615 | 5903.77308 | 26.51 | <0.0001 |
| alteration | FPE | 1 | 171.64561 | 171.64561 | 0.77 | 0.3825 |
| Vigilance | Treatment | 2 | 12983.11807 | 6491.55904 | 14.43 | <0.0001 |
| reduction | FPE | 1 | 1669.03601 | 1669.03601 | 3.71 | 0.0576 |
| Experience of | Treatment | 2 | 45746.16992 | 22873.08496 | 38.52 | <0.0001 |
| unity | FPE | 1 | 419.21831 | 419.21831 | 0.71 | 0.4033 |
| Spiritual | Treatment | 2 | 44295.01759 | 22147.50880 | 33.47 | <0.0001 |
| experience | FPE | 1 | 106.12236 | 106.12236 | 0.16 | 0.6899 |
| Blissful state | Treatment | 2 | 48144.44507 | 24072.22254 | 39.91 | <0.0001 |
| | FPE | 1 | 21.22999 | 21.22999 | 0.04 | 0.8517 |
| Insightfulness | Treatment | 2 | 51518.58287 | 25759.29144 | 45.01 | <0.0001 |
| | FPE | 1 | 82.51431 | 82.51431 | 0.14 | 0.7051 |
| Disembodiment | Treatment | 2 | 38024.97280 | 19012.48640 | 39.19 | <0.0001 |
| | FPE | 1 | 432.56944 | 432.56944 | 0.89 | 0.3478 |
| Impaired control | Treatment | 2 | 14847.05053 | 7423.52526 | 18.90 | <0.0001 |
| and cognition | FPE | 1 | 367.97317 | 367.97317 | 0.94 | 0.3359 |
| Anxiety | Treatment | 2 | 13654.18304 | 6827.09152 | 19.43 | <0.0001 |
| | FPE | 1 | 90.95683 | 90.95683 | 0.26 | 0.6122 |
| Complex imagery | Treatment | 2 | 55098.80129 | 27549.40064 | 103.59 | <0.0001 |
| | FPE | 1 | 148.07986 | 148.07986 | 0.56 | 0.4577 |
| Elementary | Treatment | 2 | 72036.48627 | 36018.24314 | 61.13 | <0.0001 |
| imagery | FPE | 1 | 411.61569 | 411.61569 | 0.70 | 0.4057 |
| Audio-visual | Treatment | 2 | 79483.55646 | 39741.77823 | 79.53 | <0.0001 |
| synaesthesia | FPE | 1 | 421.45066 | 421.45066 | 0.84 | 0.3611 |
| Changed | Treatment | 2 | 34476.31342 | 17238.15671 | 24.58 | <0.0001 |
| meaning of | FPE | 1 | 319.13449 | 319.13449 | 0.46 | 0.5018 |
| percepts | | | | | | |

Note:

F-test from ANOVA model with fixed effect for treatment and FPE.

Abbreviations: 5D-ASC = Five-Dimensional Altered States of Consciousness questionnaire; ANOVA = Analysis of variance; DF = Degrees of freedom; FPE = Former psilocybin experience; MS = Mean sum of squares; SS = Sum of squares; TAS = Tellegen absorption scale.

There were differences detected among treatment groups for each domain of the 5D-ASC. Prior exposure to psilocybin had no apparent effect on this scale. Differences between the placebo and psilocybin groups in each of the primary domains of the 5D-ASC scale were observed. The Dread of Ego Dissolution and Auditory Alteration subscales also showed a difference between psilocybin doses (10 mg and 25 mg; p≤0.05), with the 25 mg psilocybin group showing higher scores than the 10 mg psilocybin group on both domains, as shown in Table 22.

TABLE 22

Differences between placebo and psilocybin-treated groups in the
primary dimensions of the 5D-ASC

| Parameter | | Psilocybin 25 mg (N = 30) | Psilocybin 10 mg (N = 30) | Placebo (N = 29) | Psilocybin 25 mg- Placebo | Psilocybin 10 mg- Placebo | Psilocybin 25 mg- 10 mg |
|---|---|---|---|---|---|---|---|
| | | Oceanic boundlessness | | | | | |
| Post- | n | 30 | 30 | 29 | — | — | — |
| Treatment | Mean | 62.9 | 55.7 | 8.0 | 54.9 | 47.7 | 7.2 |
| Day 0 | 95% CI | — | — | — | 44.48, 65.32 | 37.11, 58.26 | −2.86, 17.29 |
| | pvalue | — | — | — | <0.0001 | <0.0001 | 0.1581 |
| | | Dread of ego dissolution | | | | | |
| Post- | n | 30 | 30 | 26 | — | — | — |
| Treatment | Mean | 31.9 | 21.7 | 1.2 | 30.6 | 20.5 | 10.1 |
| Day 0 | 95% CI | — | — | — | 21.32, 39.95 | 11.03, 29.95 | 1.13, 19.16 |
| | pvalue | — | — | — | <0.0001 | <0.0001 | 0.0278 |
| | | Visual restructuralisation | | | | | |
| Post- | n | 30 | 30 | 26 | — | — | — |
| Treatment | Mean | 65.2 | 59.1 | 6.5 | 58.7 | 52.6 | 6.1 |
| Day 0 | 95% CI | — | — | — | 50.35, 67.07 | 44.11, 61.09 | −1.98, 14.20 |
| | pvalue | — | — | — | <0.0001 | <0.0001 | 0.1366 |
| | | Auditory alteration | | | | | |
| Post- | n | 30 | 30 | 26 | — | — | — |
| Treatment | Mean | 30.7 | 20.3 | 1.7 | 29.1 | 18.6 | 10.5 |
| Day 0 | 95% CI | — | — | — | 21.07, 37.03 | 10.46, 26.66 | 2.77, 18.21 |
| | pvalue | — | — | — | <0.0001 | <0.0001 | 0.0083 |
| | | Vigilance reduction | | | | | |
| Post- | n | 30 | 30 | 26 | — | — | — |
| Treatment | Mean | 45.7 | 35.3 | 15.3 | 30.4 | 20.0 | 10.3 |
| Day 0 | 95% CI | — | — | — | 19.03, 41.72 | 8.51, 31.55 | −0.62, 21.31 |
| | pvalue | — | — | — | <0.0001 | 0.0009 | 0.0642 |

Note:
LS means and p-values from ANOVA model with fixed effects for treatment and FPE.
Abbreviations: 5D-ASC = Five-Dimensional Altered States of Consciousness questionnaire; ANOVA = Analysis of variance; CI = Confidence interval; FPE = Former psilocybin experience; LS = Least squares; N = All subjects randomized; n = Subjects with post-treatment assessments.

As shown in Table 23 below, differences between each of the psilocybin dose groups and placebo were observed for the 11 sub-scores of the 5D-ASC ($p \leq 0.0001$). There was insufficient evidence for differences between the psilocybin doses except for the anxiety and complex imagery subscales which showed a higher mean value in the psilocybin 25 mg dose group compared to psilocybin 10 mg ($p \leq 0.001$).

TABLE 23

Differences between placebo and psilocybin-treated groups in the 11
sub-dimensions of the 5D-ASC

| Parameter | | Psilocybin 25 mg (N = 30) | Psilocybin 10 mg (N = 30) | Placebo (N = 29) | Psilocybin 25 mg- Placebo | Psilocybin 10 mg- Placebo | Psilocybin 25 mg- 10 mg |
|---|---|---|---|---|---|---|---|
| | | Experience of unity | | | | | |
| Post- | N | 30 | 30 | 26 | — | — | — |
| Treatment | Mean | 60.9 | 54.4 | 7.2 | 53.6 | 47.1 | 6.5 |
| Day 0 | 95% CI | — | — | — | 40.60, 66.66 | 33.89, 60.35 | −6.09, 19.11 |
| | p-value | — | — | — | <0.0001 | <0.0001 | 0.3070 |
| | | Spiritual experience | | | | | |
| Post- | n | 30 | 30 | 26 | — | — | — |
| Treatment | Mean | 57.9 | 48.7 | 4.2 | 53.7 | 44.6 | 9.2 |
| Day 0 | 95% CI | — | — | — | 39.98, 67.50 | 30.61, 58.55 | −4.14, 22.46 |
| | p-value | — | — | — | <0.0001 | <0.0001 | 0.1745 |

TABLE 23-continued

| | | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25 mg-10 mg |
|---|---|---|---|---|---|---|---|
| Parameter | | | | | | | |

Differences between placebo and psilocybin-treated groups in the 11 sub-dimensions of the 5D-ASC

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25 mg-10 mg |
|---|---|---|---|---|---|---|---|
| *Blissful state* | | | | | | | |
| Post-Treatment Day 0 | n | 29 | 30 | 26 | — | — | — |
| | Mean | 61.9 | 59.1 | 8.2 | 53.6 | 50.9 | 2.8 |
| | 95% CI | — | — | — | 40.39, 66.90 | 37.54, 64.22 | −10.03, 15.56 |
| | p-value | — | — | — | <0.0001 | <0.0001 | 0.6683 |
| *Insightfulness* | | | | | | | |
| Post-Treatment Day 0 | n | 30 | 30 | 26 | — | — | — |
| | Mean | 64.4 | 53.9 | 6.3 | 58.2 | 47.6 | 10.5 |
| | 95% CI | — | — | — | 45.38, 70.97 | 34.64, 60.62 | −1.83, 22.92 |
| | p-value | — | — | — | <0.0001 | <0.0001 | 0.0937 |
| *Disembodiment* | | | | | | | |
| Post-Treatment Day 0 | n | 30 | 30 | 26 | — | — | — |
| | Mean | 53.8 | 52.7 | 6.9 | 46.9 | 45.8 | 1.1 |
| | 95% CI | — | — | — | 35.08, 58.64 | 33.81, 57.73 | −10.30, 12.48 |
| | p-value | — | — | — | <0.0001 | <0.0001 | 0.8490 |
| *Impaired control and cognition* | | | | | | | |
| Post-Treatment Day 0 | n | 30 | 30 | 26 | — | — | — |
| | Mean | 32.7 | 27.9 | 1.8 | 30.9 | 26.2 | 4.7 |
| | 95% CI | — | — | — | 20.33, 41.53 | 15.42, 36.94 | −5.50, 15.00 |
| | p-value | — | — | — | <0.0001 | <0.0001 | 0.3593 |
| *Anxiety* | | | | | | | |
| Post-Treatment Day 0 | n | 30 | 30 | 26 | — | — | — |
| | Mean | 32.4 | 15.7 | 1.1 | 31.3 | 14.6 | 16.7 |
| | 95% CI | — | — | — | 21.25, 41.30 | 4.39, 24.75 | 7.01, 26.39 |
| | p-value | — | — | — | <0.0001 | 0.0056 | 0.0010 |
| *Complex imagery* | | | | | | | |
| Post-Treatment Day 0 | n | 30 | 30 | 26 | — | — | — |
| | Mean | 64.9 | 53.0 | 4.4 | 60.5 | 48.6 | 11.9 |
| | 95% CI | — | — | — | 51.76, 69.20 | 39.70, 57.41 | 3.49, 20.36 |
| | p-value | — | — | — | <0.0001 | <0.0001 | 0.0061 |
| *Elementary imagery* | | | | | | | |
| Post-Treatment Day 0 | n | 30 | 30 | 26 | — | — | — |
| | Mean | 76.9 | 76.5 | 13.0 | 64.0 | 63.6 | 0.4 |
| | 95% CI | — | — | — | 51.00, 76.97 | 50.40, 76.76 | −12.15, 12.96 |
| | p-value | — | — | — | <0.0001 | <0.0001 | 0.9489 |
| *Audio-visual synaesthesia* | | | | | | | |
| Post-Treatment Day 0 | n | 30 | 30 | 26 | — | — | — |
| | Mean | 75.4 | 74.7 | 8.1 | 67.3 | 66.6 | 0.7 |
| | 95% CI | — | — | — | 55.38, 79.29 | 54.51, 78.79 | −10.87, 12.24 |
| | p-value | — | — | — | <0.0001 | <0.0001 | 0.9064 |
| *Changed meaning of percepts* | | | | | | | |
| Post-Treatment Day 0 | n | 30 | 30 | 26 | — | — | — |
| | Mean | 46.1 | 46.6 | 2.2 | 43.9 | 44.4 | −0.5 |
| | 95% CI | — | — | — | 29.73, 58.05 | 30.00, 58.76 | −14.19, 13.20 |
| | p-value | — | — | — | <0.0001 | <0.0001 | 0.9430 |

Note:
LS means and p-values from ANOVA model with fixed effects for treatment and FPE.

Abbreviations: 5D-ASC = Five-Dimensional Altered States of Consciousness questionnaire; ANOVA = Analysis of variance; CI = confidence interval; FPE = Former psilocybin experience; LS = least squares; N = All subjects randomized; n = Subjects with post-treatment assessments.

The Positive and Negative Affects Schedule (PANAS) score was also evaluated to measure the effect of psilocybin. For the change in PANAS score (from pre- to post-treatment), an effect of treatment was observed for positive affect (p=0.02) but not for negative affect (p=0.0604). The ANCOVA model components are shown in Table 24.

TABLE 24

| | F-tests from Analysis of Covariance Model: PANAS | | | | | |
|---|---|---|---|---|---|---|
| Parameter | Source | DF | SS | MS | F-value | P-value |
| PANAS- | Treatment | 2 | 54.3731933 | 27.1865967 | 2.90 | 0.0604 |
| Negative | FPE | 1 | 0.0197343 | 0.0197343 | 0.00 | 0.9635 |
| | Baseline score | 1 | 298.2929518 | 298.2929518 | 31.86 | <0.0001 |
| PANAS- | Treatment | 2 | 507.1469094 | 253.5734547 | 4.10 | 0.0200 |
| Positive | FPE | 1 | 174.4461646 | 174.4461646 | 2.82 | 0.0968 |
| | Baseline score | 1 | 710.6961764 | 710.6961764 | 11.49 | 0.0011 |

Source: Emotional Processing Table 14.8.1.12
Abbreviations: ANOVA = Analysis of covariance; DF = Degrees of freedom; MS = Mean sum of squares; PANAS = Positive and negative Affect Schedule; SS = Sum of squares.

Prior psilocybin experience did not have a significant impact on the change in PANAS score, but the baseline value was highly predictive, with higher pre-treatment scores predicting a greater increase after dosing.

As shown in Table 25 below, the placebo group showed a reduction in positive affect from baseline to the day of dosing which was not observed in the psilocybin groups (p<0.03). By contrast, the 25 mg psilocybin group had a mean increase in negative affect of 1.3, compared to a slight decrease observed in the 10 mg group (p=0.0218) and the placebo group (p=0.0989).

TABLE 25

| | | Summary of PANAS-Change from Baseline After Treatment on Day 0 | | | | | |
|---|---|---|---|---|---|---|---|
| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25 mg-10mg |
| | | | | PANAS-Negative | | | |
| Post- | n | 29 | 30 | 29 | — | — | — |
| treatment | Mean | 1.3 | −0.6 | −0.1 | 1.4 | −0.5 | 1.9 |
| Day 0 | 95% CI | — | — | — | −0.26, 2.99 | −2.16, 1.09 | 0.28, 3.51 |
| | Pvalue | — | — | — | 0.0989 | 0.5164 | 0.0218 |
| | | | | PANAS-Positive | | | |
| | n | 29 | 30 | 29 | — | — | — |
| Post- | Mean | −0.4 | 0.7 | −5.0 | 4.6 | 5.7 | −1.0 |
| treatment | 95% CI | — | — | — | 0.48, 8.79 | 1.49, 9.87 | −5.14, 3.05 |
| Day 0 | pvalue | — | — | — | 0.0293 | 0.0085 | 0.6126 |

Note:
LS means and p-values from ANOVA model with fixed effects for treatment and FPE, and baseline score as covariate.
Abbreviations: ANCOVA = Analysis of covariance; CI = confidence interval; FPE = Former psilocybin experience; LS = least squares; N = All subjects randomized; n = Subjects with post-treatment assessments; PANAS = Positive and Negative Affect Schedule.

The Pictorial Empathy Test (PET), Reading the Mind in the Eyes Test (RMET), Scale of Social Responsibility (SSR), Social Value Orientation (SVO), and Toronto Empathy Questionnaire (TEQ) were performed. Table 26 summarizes the results of the mixed model for repeated measures (MMRM) analysis for each of the aforementioned social cognition panel scales measured on Day 7 and Day 84 after study drug administration.

TABLE 26

| | F-Tests from MMRM Model: PET, RMET, SSR, SVO, and TEQ | | | | | |
|---|---|---|---|---|---|---|
| Parameter | Source | DF | Denominator DF | F-value | Pvalue |
| PET | Baseline score | 1 | 82.753690 | 0.33 | 0.5690 |
| | FPE | 1 | 82.739811 | 1.64 | 0.2035 |
| | Treatment | 2 | 81.827569 | 2.66 | 0.0761 |

TABLE 26-continued

| | F-Tests from MMRM Model: PET, RMET, SSR, SVO, and TEQ | | | | | |
|---|---|---|---|---|---|---|
| Parameter | Source | DF | Denominator DF | F-value | Pvalue |
| RMET | Visit | 1 | 80.165106 | 3.16 | 0.0794 |
| | Treatment × Visit | 2 | 80.123570 | 0.01 | 0.9889 |
| | Baseline score | 1 | 79.642446 | 13.11 | 0.0005 |
| | FPE | 1 | 81.293995 | 0.30 | 0.5841 |
| | Treatment | 2 | 81.089435 | 0.09 | 0.9109 |

TABLE 26-continued

| | F-Tests from MMRM Model: PET, RMET, SSR, SVO, and TEQ | | | | | |
|---|---|---|---|---|---|---|
| Parameter | Source | DF | Denominator DF | F-value | Pvalue |
| SSR global | Visit | 1 | 78.718169 | 0.58 | 0.4502 |
| | Treatment × Visit | 2 | 78.697428 | 0.11 | 0.8983 |
| | Baseline score | 1 | 78.029198 | 1.76 | 0.1890 |
| | FPE | 1 | 77.981354 | 2.57 | 0.1130 |
| | Treatment | 2 | 77.535686 | 1.73 | 0.1846 |
| SSR fulfilling expectation | Visit | 1 | 74.336261 | 0.69 | 0.4076 |
| | Treatment × Visit | 2 | 74.149063 | 0.17 | 0.8465 |
| | Baseline score | 1 | 79.708607 | 7.43 | 0.0079 |
| | FPE | 1 | 80.530339 | 1.10 | 0.2965 |
| | Treatment | 2 | 79.898753 | 1.17 | 0.3164 |
| SSR compliance social rules | Visit | 1 | 77.391208 | 0.16 | 0.6881 |
| | Treatment × Visit | 2 | 77.356175 | 1.82 | 0.1682 |
| | Baseline score | 1 | 81.040786 | 15.30 | 0.0002 |
| | FPE | 1 | 79.293376 | 0.10 | 0.7527 |
| | Treatment | 2 | 78.731740 | 1.44 | 0.2440 |

TABLE 26-continued

F-Tests from MMRM Model: PET, RMET, SSR, SVO, and TEQ

| Parameter | Source | DF | Denominator DF | F-value | Pvalue |
|---|---|---|---|---|---|
| | Visit | 1 | 75.158892 | 0.00 | 0.9739 |
| | Treatment × Visit | 2 | 74.971352 | 0.02 | 0.9843 |
| SVO angle | Baseline score | 1 | 84.293719 | 2.33 | 0.1305 |
| | FPE | 1 | 81.152189 | 0.02 | 0.8978 |
| | Treatment | 2 | 80.655666 | 2.81 | 0.0661 |
| | Visit | 1 | 80.233253 | 3.68 | 0.0588 |
| | Treatment × Visit | 2 | 80.245032 | 0.02 | 0.9821 |
| SVO type | Baseline score | 1 | 83.474000 | 14.15 | 0.0003 |
| | FPE | 1 | 80.219127 | 0.05 | 0.8176 |
| | Treatment | 2 | 79.202003 | 0.99 | 0.3770 |
| | Visit | 1 | 78.469668 | 1.19 | 0.2783 |
| | Treatment × Visit | 2 | 78.517417 | 0.00 | 0.9975 |
| TEQ | Baseline score | 1 | 78.310229 | 10.05 | 0.0022 |
| | FPE | 1 | 80.793937 | 0.07 | 0.7882 |
| | Treatment | 2 | 79.633057 | 0.83 | 0.4381 |

TABLE 26-continued

F-Tests from MMRM Model: PET, RMET, SSR, SVO, and TEQ

| Parameter | Source | DF | Denominator DF | F-value | Pvalue |
|---|---|---|---|---|---|
| | Visit | 1 | 77.965918 | 0.08 | 0.7725 |
| | Treatment × Visit | 2 | 77.943131 | 0.13 | 0.8800 |

Note:

F-tests from a MMRM analysis with change from baseline score as the dependent variable. Model has fixed effects for treatment, visit, FPE, and treatment by visit interaction, visit as the repeating factor, subject as a random effect, and baseline score as a covariate. Abbreviations: DF = Degrees of freedom; FPE = Former psilocybin experience; MMRM = Mixed model for repeated measures; PET = Pictorial Empathy Test; RMET = Reading the Eyes in the Mind Test; SSR = Scale of Social Responsibility; SVO = Social Value Orientation; TEQ = Tellegen Absorption Questionnaire.

No differences among treatment groups for change from baseline values of RMET, SSR, SVO Type, or TEQ were found ($p > 0.05$ in all cases). P-values were approaching the $<0.05$ level for PET and SVO Angle. In each statistical model, the baseline score was typically the best independent predictor of change, with higher pre-treatment scores predicting a greater increase after dosing.

Table 27 shows tests of pairwise differences between treatment groups in the MMRM model for each of the parameters at Day 7 and Day 84.

TABLE 27

Summary of PET, RMET, SSR, SVO, and TEQ Results-Change from Baseline on Day 7 and Day 84

| | | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25 mg-10 mg |
|---|---|---|---|---|---|---|---|
| | | | | PET | | | |
| Day 7 | n | 29 | 30 | 26 | — | — | — |
| | Mean | 0.0 | −0.3 | −0.1 | 0.2 | −0.1 | 0.3 |
| | 95% CI | — | — | — | 0.11, 0.42 | −0.39, 0.15 | 0.02, 0.54 |
| | P-value | — | — | — | 0.2429 | 0.3659 | 0.0360 |
| Day 84 | n | 27 | 30 | 23 | — | — | — |
| | Mean | −0.1 | −0.3 | −0.2 | 0.1 | −0.1 | 0.3 |
| | 95% CI | — | — | — | −0.12, 0.41 | −0.39, 0.15 | 0.00, 0.52 |
| | P-value | — | — | — | 0.2851 | 0.3807 | 0.0464 |
| | | | | RMET | | | |
| Day 7 | n | 29 | 30 | 26 | — | — | — |
| | Mean | 0.4 | 0.4 | 0.3 | 0.2 | 0.1 | 0.0 |
| | 95% CI | — | — | — | −1.44, 1.74 | −1.43, 1.69 | −1.50, 1.55 |
| | p-value | — | — | — | 0.8505 | 0.8719 | 0.9748 |
| Day 84 | n | 27 | 30 | 23 | — | — | — |
| | Mean | 0.4 | 0.1 | −0.1 | 0.5 | 0.2 | 0.3 |
| | 95% CI | — | — | — | −1.29, 2.28 | −1.53, 1.95 | −1.39, 1.97 |
| | p-value | — | — | — | 0.5806 | 0.8103 | 0.7339 |
| | | | | SSR global | | | |
| Day 7 | n | 26 | 29 | 25 | — | — | — |
| | Mean | −0.3 | −2.0 | −3.2 | 2.8 | 1.2 | 1.6 |
| | 95% CI | — | — | — | 0.50, 6.18 | −2.16, 4.56 | −1.58, 4.86 |
| | P-value | — | — | — | 0.0941 | 0.4783 | 0.3141 |
| Day 84 | n | 26 | 28 | 20 | — | — | — |
| | Mean | 0.1 | −1.8 | −2.1 | 2.2 | 0.3 | 1.8 |
| | 95% CI | — | — | — | −0.94, 5.29 | −2.83, 3.49 | −1.04, 4.71 |
| | P-value | — | — | — | 0.1687 | 0.8338 | 0.2068 |
| | | | | SSR fufilling expectations | | | |
| Day 7 | n | 28 | 29 | 26 | — | — | — |
| | Mean | −0.0 | −0.1 | −0.2 | 0.2 | 0.1 | 0.1 |
| | 95% CI | — | — | — | −0.04, 0.35 | −0.14, 0.26 | −0.10, 0.28 |
| | p-value | — | — | — | 0.1233 | 0.5468 | 0.3461 |
| Day 84 | n | 26 | 29 | 22 | — | — | — |
| | Mean | −0.0 | −0.2 | −0.1 | 0.0 | −0.1 | 0.2 |
| | 95% CI | — | — | — | 0.16, 0.23 | −0.32, 0.08 | −0.04, 0.34 |
| | p-value | — | — | — | 0.7238 | 0.2461 | 0.1114 |

TABLE 27-continued

Summary of PET, RMET, SSR, SVO, and TEQ Results-Change from
Baseline on Day 7 and Day 84

| | | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25 mg-10 mg |
|---|---|---|---|---|---|---|---|
| | | | | SSR compliance social rules | | | |
| Day 7 | n | 27 | 30 | 25 | — | — | — |
| | Mean | 0.0 | −0.1 | −0.1 | 0.1 | 0.0 | 0.1 |
| | 95% CI | — | — | — | −0.07, 0.34 | −0.19, 0.22 | −0.08, 0.32 |
| | p-value | — | — | — | 0.1983 | 0.8831 | 0.2331 |
| Day 84 | n | 26 | 29 | 20 | — | — | — |
| | Mean | 0.0 | −0.1 | −0.1 | 0.1 | −0.0 | 0.1 |
| | 95% CI | — | — | — | −0.08, 0.35 | −0.22, 0.22 | −0.06, 0.33 |
| | p-value | — | — | — | 0.2242 | 0.9949 | 0.1827 |
| | | | | SVO angle | | | |
| Day 7 | n | 29 | 30 | 26 | — | — | — |
| | Mean | 0.5 | 1.8 | −1.6 | 2.1 | 3.4 | −1.3 |
| | 95% CI | — | — | — | −1.32, 5.58 | −0.05, 6.85 | −4.60, 2.04 |
| | p-value | — | — | — | 0.2233 | 0.0531 | 0.4466 |
| Day 84 | n | 27 | 30 | 23 | — | — | — |
| | Mean | −0.9 | 0.1 | −3.3 | 2.4 | 3.4 | −1.0 |
| | 95% CI | — | — | — | −1.16, 6.06 | −0.16, 6.97 | −4.34, 2.44 |
| | P-value | — | — | — | 0.1803 | 0.0613 | 0.5785 |
| | | | | SVO type | | | |
| Day 7 | n | 29 | 30 | 26 | — | — | — |
| | Mean | 0.1 | 0.1 | −0.0 | 0.1 | 0.1 | −0.0 |
| | 95% CI | — | — | — | −0.11, 0.24 | −0.07, 0.28 | −0.21, 0.13 |
| | P-value | — | — | — | 0.4551 | 0.2460 | 0.6630 |
| Day 84 | n | 27 | 30 | 23 | — | — | — |
| | Mean | 0.0 | 0.1 | −0.0 | 0.1 | 0.1 | −0.0 |
| | 95% CI | — | — | — | −0.10, 0.24 | −0.06, 0.28 | −0.20, 0.12 |
| | p-value | — | — | — | 0.4321 | 0.1993 | 0.5994 |
| | | | | TEQ | | | |
| Day 7 | n | 29 | 30 | 26 | — | — | — |
| | Mean | 0.0 | −0.1 | −0.1 | 0.2 | 0.1 | 0.1 |
| | 95% CI | — | — | — | −0.08, 0.38 | −0.16, 0.31 | −0.14, 0.30 |
| | p-value | — | — | — | 0.2004 | 0.5425 | 0.4846 |
| Day 84 | n | 26 | 30 | 23 | — | — | — |
| | Mean | −0.0 | −0.1 | −0.2 | 0.1 | 0.1 | 0.0 |
| | 95% CI | — | — | — | 0.13, 0.36 | −0.15, 0.34 | −0.21, 0.25 |
| | p-value | — | — | — | 0.3420 | 0.4403 | 0.8454 |

Note:
LS means and p-values from a MMRM analysis with change from baseline score as the dependent variable. Model has fixed effects for treatment, visit, FPE, and treatment by visit interaction, visit as the repeating factor, subject as a random effect, and baseline score as a covariate.
Abbreviations: CI = Confidence interval; FPE = Former psilocybin experience; LS = Least squares; MMRM = Mixed model for repeated measures; N = All subjects randomized; n = Subjects with post-treatment assessments; PET = Pictorial Empathy Test; RMET = Reading the Eyes in the Mind Test; SSR = Scale of Social Responsibility; SVO = Social Value Orientation; TEQ = Tellegen Absorption Questionnaire.

There was no difference between either psilocybin group and placebo on PET, RMET, SSR, SVO, or TEQ at either timepoint. The reduction in PET score was greater with 10 mg than 25 mg psilocybin at both Day 7 and Day 84, but no differences were detected between psilocybin groups and placebo (for all p>0.05).

The Neuroticism Extraversion Openness-Five Factor Inventory (NEO-FFI) and Symptom Checklist-90 Item (SCL-90) were administered. Details of the MMRM applied to the change from baseline scores for the NEO-FFI and SCL-90 are provided below in Table 28.

TABLE 28

F-Tests from MMRM Model: NEO-FFI and SCL-90

| Parameter | Source | DF | Denominator DF | F-value | P-value |
|---|---|---|---|---|---|
| NEO-neuroticism | Baseline score | 1 | 76.979208 | 5.74 | 0.0190 |
| | FPE | 1 | 77.840113 | 0.93 | 0.3383 |

TABLE 28-continued

F-Tests from MMRM Model: NEO-FFI and SCL-90

| Parameter | Source | DF | Denominator DF | F-value | P-value |
|---|---|---|---|---|---|
| | Treatment | 2 | 77.617527 | 0.25 | 0.7790 |
| | Visit | 1 | 73.682482 | 7.74 | 0.0068 |
| | Treatment × Visit | 2 | 73.686883 | 0.68 | 0.5082 |
| NEO-extraversion | Baseline score | 1 | 78.374755 | 14.95 | 0.0002 |
| | FPE | 1 | 78.343718 | 0.96 | 0.3292 |
| | Treatment | 2 | 78.626820 | 0.02 | 0.9845 |
| | Visit | 1 | 73.855914 | 4.63 | 0.0348 |
| | Treatment × Visit | 2 | 73.862965 | 0.81 | 0.4477 |
| NEO-openness | Baseline score | 1 | 74.806595 | 6.32 | 0.0141 |
| | FPE | 1 | 77.275373 | 0.00 | 0.9549 |
| | Treatment | 2 | 76.498330 | 1.41 | 0.2503 |
| | Visit | 1 | 74.250319 | 0.24 | 0.6261 |
| | Treatment × Visit | 2 | 74.270107 | 0.61 | 0.5446 |
| NEO agreeableness | Baseline score | 1 | 78.147167 | 5.13 | 0.0263 |
| | FPE | 1 | 78.408944 | 0.40 | 0.5292 |
| | Treatment | 2 | 78.501462 | 0.37 | 0.6886 |

TABLE 28-continued

F-Tests from MMRM Model: NEO-FFI and SCL-90

| Parameter | Source | DF | Denominator DF | F-value | P-value |
|---|---|---|---|---|---|
| | Visit | 1 | 73.826719 | 5.46 | 0.0221 |
| | Treatment × Visit | 2 | 73.845054 | 0.29 | 0.7497 |
| NEO conscientiousness | Baseline score | 1 | 77.124423 | 4.82 | 0.0312 |
| | FPE | 1 | 77.786049 | 1.86 | 0.1764 |
| | Treatment | 2 | 76.183832 | 1.12 | 0.3301 |
| | Visit | 1 | 74.486641 | 4.14 | 0.0454 |
| | Treatment × Visit | 2 | 74.477293 | 0.56 | 0.5741 |
| SCL-90-somatisation | Baseline score | 1 | 79.868863 | 0.55 | 0.4613 |
| | FPE | 1 | 80.705565 | 1.49 | 0.2256 |
| | Treatment | 2 | 81.464446 | 0.34 | 0.7150 |
| | Visit | 1 | 78.071807 | 0.94 | 0.3357 |
| | Treatment × Visit | 2 | 78.070370 | 0.42 | 0.6559 |
| SCL-90 obsessive compulsive | Baseline score | 1 | 80.547228 | 14.11 | 0.0003 |
| | FPE | 1 | 82.484967 | 3.28 | 0.0736 |
| | Treatment | 2 | 81.559194 | 0.59 | 0.5556 |
| | Visit | 1 | 80.073966 | 0.33 | 0.5691 |
| | Treatment × Visit | 2 | 80.064909 | 0.42 | 0.6554 |
| SCL-90 interpersonal sensitivity | Baseline score | 1 | 80.121543 | 3.70 | 0.0580 |
| | FPE | 1 | 80.874433 | 3.13 | 0.0807 |
| | Treatment | 2 | 82.579702 | 0.30 | 0.7403 |
| | Visit | 1 | 77.993603 | 1.43 | 0.2350 |
| | Treatment × Visit | 2 | 77.991778 | 0.28 | 0.7566 |
| SCL-90 depression | Baseline score | 1 | 80.197894 | 2.91 | 0.0918 |
| | FPE | 1 | 80.342361 | 1.84 | 0.1784 |
| | Treatment | 2 | 81.303470 | 0.07 | 0.9345 |
| | Visit | 1 | 77.391519 | 0.31 | 0.5802 |
| | Treatment × Visit | 2 | 77.389587 | 0.06 | 0.9420 |
| SCL-90 anxiety | Baseline score | 1 | 80.428114 | 12.64 | 0.0006 |
| | FPE | 1 | 81.212552 | 0.15 | 0.7015 |
| | Treatment | 2 | 82.662941 | 0.18 | 0.8352 |
| | Visit | 1 | 78.366882 | 0.13 | 0.7161 |
| | Treatment × Visit | 2 | 78.359701 | 0.13 | 0.8758 |
| SCL-90 anger | Baseline score | 1 | 79.979660 | 54.73 | <0.0001 |

TABLE 28-continued

F-Tests from MMRM Model: NEO-FFI and SCL-90

| Parameter | Source | DF | Denominator DF | F-value | P-value |
|---|---|---|---|---|---|
| hostility | FPE | 1 | 79.997333 | 0.83 | 0.3636 |
| | Treatment | 2 | 76.243037 | 0.22 | 0.8001 |
| | Visit | 1 | 76.998093 | 3.73 | 0.0571 |
| | Treatment × Visit | 2 | 76.998109 | 0.66 | 0.5194 |
| SCL-90 phobic anxiety | Baseline score | 1 | 80.002443 | 72.72 | <0.0001 |
| | FPE | 1 | 80.012526 | 1.66 | 0.2014 |
| | Treatment | 2 | 83.392134 | 0.25 | 0.7801 |
| | Visit | 1 | 77.011834 | 0.35 | 0.5541 |
| | Treatment × Visit | 2 | 77.011930 | 0.11 | 0.9001 |
| SCL-90 paranoid ideation | Baseline score | 1 | 82.462798 | 2.09 | 0.1525 |
| | FPE | 1 | 81.511417 | 3.38 | 0.0695 |
| | Treatment | 2 | 80.282457 | 1.35 | 0.2658 |
| | Visit | 1 | 79.911612 | 1.70 | 0.1954 |
| | Treatment × Visit | 2 | 79.848142 | 0.59 | 0.5550 |
| SCL-90 psychoticism | Baseline score | 1 | 79.993358 | 0.75 | 0.3887 |
| | FPE | 1 | 81.786131 | 0.93 | 0.3379 |
| | Treatment | 2 | 81.672000 | 0.18 | 0.8367 |
| | Visit | 1 | 79.185707 | 0.18 | 0.6729 |
| | Treatment × Visit | 2 | 79.178467 | 0.67 | 0.5153 |

Note:

F-tests from a MMRM analysis with change from baseline score as the dependent variable. Model has fixed effects for treatment, visit, FPE, and treatment by visit interaction, visit as the repeating factor, subject as a random effect, and baseline score as a covariate. Abbreviations: DF = Degrees of freedom; FPE = Former psilocybin experience; MMRM = Mixed model for repeated measures; NEO-FFI = Neuroticism Extraversion Openness-Five Factor Inventory; SCL-90 = Symptom Checklist-90 Item.

The strongest predictor of change in each scale was the baseline value itself, which was positively correlated with the change after dosing, whereas prior exposure to psilocybin had no detectable effect.

Table 29 presents the LS means and pairwise treatment comparisons based on the change from baseline scores for NEO-FFI and SCL-90.

TABLE 29

Summary of NEO-FFI and SCL-90 Results-Change from Baseline on Day 7 and Day 84

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| | | | NEO neuroticism | | | | |
| Day 7 | n | 28 | 28 | 26 | — | — | — |
| | Mean | 0.2 | 0.2 | 0.4 | 0.2 | −0.2 | −0.0 |
| | 95% CI | — | — | — | −2.31, 1.96 | −2.28, 1.93 | −2.04, 2.04 |
| | p value | — | — | — | 0.8714 | 0.8701 | 0.9997 |
| Day 84 | n | 26 | 27 | 22 | — | — | — |
| | Mean | 0.8 | 2.1 | 1.8 | −1.0 | 0.3 | −1.3 |
| | 95% CI | — | — | — | −3.56, 1.60 | −2.24, 2.83 | −3.70, 1.14 |
| | pvalue | — | — | — | 0.4512 | 0.8152 | 0.2957 |
| | | | NEO extraversion | | | | |
| Day 7 | n | 28 | 28 | 26 | — | — | — |
| | Mean | 0.3 | 0.3 | −0.1 | 0.5 | 0.4 | 0.1 |
| | 95% CI | — | — | — | −1.19, 2.10 | −1.28, 2.06 | −1.56, 1.68 |
| | pvalue | — | — | — | 0.5848 | 0.6411 | 0.9399 |
| Day 84 | n | 26 | 27 | 22 | — | — | — |
| | Mean | −0.7 | −0.9 | −0.2 | −0.5 | −0.7 | 0.2 |
| | 95% CI | — | — | — | −2.52, 1.55 | −2.70, 1.39 | −1.78, 2.13 |
| | pvalue | — | — | — | 0.6383 | 0.5255 | 0.8617 |
| | | | NEO openness | | | | |
| Day 7 | n | 28 | 28 | 26 | — | — | — |
| | Mean | 0.4 | 0.3 | −0.8 | 1.2 | 1.1 | 0.1 |
| | 95% CI | — | — | — | −0.25, 2.71 | −0.37, 2.59 | −1.34, 1.58 |
| | pvalue | — | — | — | 0.1030 | 0.1405 | 0.8717 |
| Day 84 | n | 26 | 27 | 22 | — | — | — |
| | Mean | 0.3 | 0.4 | −0.7 | 0.4 | 1.1 | −0.7 |
| | 95% CI | — | — | — | −1.28, 2.14 | −0.60, 2.79 | −2.31, 0.97 |
| | pvalue | — | — | — | 0.6190 | 0.2026 | 0.4202 |

TABLE 29-continued

Summary of NEO-FFI and SCL-90 Results-Change from Baseline on
Day 7 and Day 84

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| NEO agreeableness | | | | | | | |
| Day 7 | n | 28 | 30 | 26 | — | — | — |
| | Mean | 0.1 | −0.2 | 0.2 | −0.1 | −0.4 | 0.4 |
| | 95% CI | — | — | — | −1.50, 1.31 | −1.89, 0.99 | −1.04, 1.75 |
| | pvalue | — | — | — | 0.8963 | 0.5355 | 0.6115 |
| Day 84 | n | 26 | 27 | 22 | — | — | — |
| | Mean | −0.9 | −0.9 | −0.2 | −0.7 | −0.8 | 0.1 |
| | 95% CI | — | — | — | −2.37, 1.03 | −2.47, 0.97 | −1.56, 1.72 |
| | pvalue | — | — | — | 0.4339 | 0.3873 | 0.9242 |
| NEO conscientiousness | | | | | | | |
| Day 7 | n | 28 | 28 | 26 | — | — | — |
| | Mean | 0.1 | −0.1 | −0.6 | 0.7 | 0.4 | 0.3 |
| | 95% CI | — | — | — | −0.91,2.34 | −1.20, 2.10 | −1.34, 1.86 |
| | pvalue | — | — | — | 0.3855 | 0.5892 | 0.7446 |
| Day 84 | n | 26 | 27 | 22 | — | — | — |
| | Mean | −0.1 | −1.3 | −1.5 | 1.4 | 0.2 | 1.2 |
| | 95% CI | — | — | — | −0.40, 3.20 | −1.56, 2.05 | −0.56, 2.88 |
| | pvalue | — | — | — | 0.1243 | 0.7873 | 0.1844 |
| SCL-90-somatisation | | | | | | | |
| Day 7 | n | 29 | 30 | 26 | — | — | — |
| | Mean | 0.1 | 0.1 | −0.0 | 0.1 | 0.1 | −0.0 |
| | 95% CI | — | — | — | −0.06, 0.17 | −0.06, 0.18 | −0.12, 0.11 |
| | pvalue | — | — | — | 0.3299 | 0.3277 | 0.9794 |
| Day 84 | n | 27 | 30 | 23 | — | — | — |
| | Mean | 0.0 | 0.0 | 0.0 | 0.0 | 0.0 | 0.0 |
| | 95% CI | — | — | — | −0.10, 0.18 | −0.13, 0.15 | −0.11,0.16 |
| | pvalue | — | — | — | 0.6109 | 0.9229 | 0.6672 |
| SCL-90 obsessive compulsive | | | | | | | |
| Day 7 | n | 29 | 30 | 26 | — | — | — |
| | Mean | −0.1 | −0.1 | −0.2 | 0.1 | 0.1 | −0.0 |
| | 95% CI | — | — | — | −0.09, 0.28 | −0.09, 0.29 | −0.18, 0.18 |
| | pvalue | — | — | — | 0.3052 | 0.3049 | 0.9908 |
| Day 84 | n | 27 | 30 | 23 | — | — | — |
| | Mean | −0.1 | −0.0 | −0.1 | 0.0 | 0.1 | −0.1 |
| | 95% CI | — | — | — | −0.17, 0.21 | −0.11, 0.28 | −0.25, 0.12 |
| | pvalue | — | — | — | 0.8118 | 0.3756 | 0.4944 |
| SCL-90 interpersonal sensitivity | | | | | | | |
| Day 7 | n | 29 | 30 | 26 | — | — | — |
| | Mean | 0.0 | −0.0 | 0.0 | 0.0 | −0.0 | 0.1 |
| | 95% CI | — | — | — | −0.11, 0.15 | −0.17, 0.09 | −0.07, 0.18 |
| | pvalue | — | — | — | 0.8110 | 0.5479 | 0.3802 |
| Day 84 | n | 27 | 30 | 23 | — | — | — |
| | Mean | 0.0 | 0.0 | 0.1 | −0.0 | −0.1 | 0.0 |
| | 95% CI | — | — | — | −0.21, 0.13 | −0.23, 0.11 | −0.14, 0.18 |
| | pvalue | — | — | — | 0.6592 | 0.4992 | 0.8067 |
| SCL-90 depression | | | | | | | |
| Day 7 | n | 29 | 30 | 26 | — | — | — |
| | Mean | 0.0 | 0.0 | 0.0 | 0.0 | 0.0 | −0.0 |
| | 95% CI | — | — | — | −0.17, 0.21 | −0.17, 0.22 | −0.19, 0.18 |
| | pvalue | — | — | — | 0.8566 | 0.7878 | 0.9259 |
| Day 84 | n | 27 | 30 | 23 | — | — | — |
| | Mean | 0.1 | 0.1 | 0.0 | 0.0 | 0.0 | 0.0 |
| | 95% CI | — | — | — | 0.18, 0.28 | −0.19, 0.27 | −0.21,0.23 |
| | pvalue | — | — | — | 0.6964 | 0.7395 | 0.9501 |
| SCL-90 anxiety | | | | | | | |
| Day 7 | n | 29 | 30 | 26 | — | — | — |
| | Mean | −0.0 | −0.0 | −0.0 | 0.0 | −0.0 | 0.0 |
| | 95% CI | — | — | — | −0.12, 0.11 | −0.14, 0.10 | −0.10, 0.13 |
| | pvalue | — | — | — | 0.9312 | 0.7178 | 0.7739 |
| Day 84 | n | 27 | 30 | 23 | — | — | — |
| | Mean | −0.0 | −0.0 | 0.0 | −0.0 | −0.1 | 0.0 |
| | 95% CI | — | — | — | −0.23, 0.13 | −0.23, 0.13 | −0.17, 0.17 |
| | pvalue | — | — | — | 0.5904 | 0.5588 | 0.9674 |

TABLE 29-continued

Summary of NEO-FFI and SCL-90 Results-Change from Baseline on Day 7 and Day 84

| Parameter | | Psilocybin 25 mg (N = 30) | Psilocybin 10 mg (N = 30) | Placebo (N = 29) | Psilocybin 25 mg- Placebo | Psilocybin 10 mg- Placebo | Psilocybin (25 mg- 10 mg) |
|---|---|---|---|---|---|---|---|
| | | SCL-90 anger hostility | | | | | |
| Day 7 | n | 29 | 30 | 26 | — | — | — |
| | Mean | −0.0 | −0.0 | 0.0 | −0.0 | −0.0 | 0.0 |
| | 95% CI | — | — | — | −0.09, 0.07 | −0.13, 0.03 | −0.04, 0.11 |
| | pvalue | — | — | — | 0.7591 | 0.2564 | 0.3847 |
| Day 84 | n | 27 | 30 | 23 | — | — | — |
| | Mean | 0.0 | 0.0 | 0.0 | −0.0 | −0.0 | −0.0 |
| | 95% CI | — | — | — | −0.16, 0.09 | −0.14, 0.11 | −0.14, 0.10 |
| | p value | — | — | — | 0.5890 | 0.8112 | 0.7495 |
| | | SCL-90 phobic anxiety | | | | | |
| Day 7 | n | 29 | 30 | 26 | — | — | — |
| | Mean | 0.0 | −0.0 | 0.0 | 0.0 | −0.0 | 0.0 |
| | 95% CI | — | — | — | −0.03, 0.04 | −0.05, 0.03 | −0.02, 0.05 |
| | pvalue | — | — | — | 0.7815 | 0.5556 | 0.3647 |
| Day 84 | n | 27 | 30 | 23 | — | — | — |
| | Mean | 0.0 | 0.0 | 0.0 | 0.0 | −0.0 | 0.0 |
| | 95% CI | — | — | — | 0.04, 0.07 | −0.06, 0.05 | −0.04, 0.06 |
| | pvalue | — | — | — | 0.7081 | 0.9499 | 0.6450 |
| | | SCL-90 paranoid ideation | | | | | |
| Day 7 | n | 29 | 30 | 26 | — | — | — |
| | Mean | 0.1 | −0.0 | −0.0 | 0.1 | 0.0 | 0.1 |
| | 95% CI | — | — | — | −0.02, 0.23 | −0.09, 0.17 | −0.06, 0.19 |
| | p-value | — | — | — | 0.1016 | 0.5489 | 0.2800 |
| Day 84 | n | 27 | 30 | 23 | — | — | — |
| | Mean | 0.1 | 0.1 | −0.0 | 0.1 | 0.1 | 0.0 |
| | 95% CI | — | — | — | −0.05, 0.18 | −0.05, 0.18 | −0.11, 0.11 |
| | p-value | — | — | — | 0.2543 | 0.2863 | 0.9363 |
| | | SCL-90 psychoticism | | | | | |
| Day 7 | n | 29 | 30 | 26 | — | — | — |
| | Mean | 0.0 | 0.0 | 0.0 | 0.0 | 0.0 | 0.0 |
| | 95% CI | — | — | — | −0.07, 0.08 | −0.07, 0.07 | −0.06, 0.08 |
| | p-value | — | — | — | 0.8196 | 0.9812 | 0.8302 |
| Day 84 | n | 27 | 30 | 23 | — | — | — |
| | Mean | 0.0 | −0.0 | 0.0 | −0.0 | −0.0 | 0.0 |
| | 95% CI | — | — | — | −0.08, 0.07 | −0.11, 0.04 | −0.05, 0.10 |
| | p-value | — | — | — | 0.8823 | 0.3851 | 0.4476 |

Note:

LS means and p-value from a MMRM with fixed effects for treatment, visit, FPE, and treatment by visit interaction term, with visit as the repeating factor, subject as a random effect, and baseline score as a covariate.

Abbreviations: CI = Confidence interval; DF = Degrees of freedom; FPE = Former psilocybin experience; LS = Least squares; MMRM = Mixed model for repeated measures; N = All subjects randomized; n = Subjects with post-treatment assessments; NEO-FFI = Neuroticism Extraversion Openness-Five Factor Inventory; SCL-90 = Symptom Checklist-90 Item.

Table 30 summarizes the results of the MMRM model applied to LCI parameters measured on Day 7 and Day 84 after study drug administration.

TABLE 30

F-Tests from MMRM Model: LCI Measures

| Parameter | Source | DF | Denominator DF | F-value | P-value |
|---|---|---|---|---|---|
| LCI-absolute change | FPE | 1 | 82.799713 | 0.04 | 0.8352 |
| | Treatment | 2 | 82.605786 | 12.69 | <0.0001 |
| | Visit | 1 | 78.162909 | 0.31 | 0.5765 |
| | Treatment × Visit | 2 | 78.054268 | 0.40 | 0.6740 |
| LCI appreciation for life | FPE | 1 | 82.909504 | 0.33 | 0.5661 |
| | Treatment | 2 | 82.198916 | 12.35 | <0.0001 |
| | Visit | 1 | 79.332039 | 0.02 | 0.8767 |
| | Treatment × Visit | 2 | 79.170548 | 0.17 | 0.8464 |
| LCI self- acceptance | FPE | 1 | 83.843514 | 0.03 | 0.8521 |
| | Treatment | 2 | 83.332333 | 23.73 | <0.0001 |
| | Visit | 1 | 81.020342 | 0.66 | 0.4199 |
| | Treatment × Visit | 2 | 80.834117 | 0.98 | 0.3791 |

TABLE 30-continued

F-Tests from MMRM Model: LCI Measures

| Parameter | Source | DF | Denominator DF | F-value | P-value |
|---|---|---|---|---|---|
| LCI concern for others | FPE | 1 | 83.730773 | 0.01 | 0.9302 |
| | Treatment | 2 | 82.680005 | 7.95 | 0.0007 |
| | Visit | 1 | 80.322544 | 0.33 | 0.5660 |
| | Treatment × Visit | 2 | 80.155567 | 0.42 | 0.6578 |
| LCI concern for worldly achievement | FPE | 1 | 82.629869 | 1.17 | 0.2826 |
| | Treatment | 2 | 83.456184 | 3.78 | 0.0269 |
| | Visit | 1 | 77.542669 | 0.67 | 0.4161 |
| | Treatment × Visit | 2 | 77.464305 | 0.75 | 0.4750 |
| LCI concern social | FPE | 1 | 82.874879 | 0.63 | 0.4297 |
| | Treatment | 2 | 83.174991 | 2.06 | 0.1334 |
| | Visit | 1 | 78.231885 | 1.02 | 0.3167 |
| | Treatment × Visit | 2 | 78.123691 | 0.21 | 0.8137 |
| LCI quest for meaning | FPE | 1 | 81.846606 | 0.04 | 0.8448 |
| | Treatment | 2 | 82.365281 | 6.71 | 0.0020 |
| | Visit | 1 | 76.551800 | 0.36 | 0.5495 |
| | Treatment × Visit | 2 | 76.488228 | 0.11 | 0.8952 |

TABLE 30-continued

| F-Tests from MMRM Model: LCI Measures | | | | | |
|---|---|---|---|---|---|
| Parameter | Source | DF | Denominator DF | F-value | P-value |
| LCI spirituality | FPE | 1 | 83.145868 | 0.09 | 0.7617 |
| | Treatment | 2 | 82.820446 | 5.08 | 0.0083 |
| | Visit | 1 | 79.406353 | 0.03 | 0.8635 |
| | Treatment × Visit | 2 | 79.252439 | 0.44 | 0.6459 |
| LCI religiousness | FPE | 1 | 83.221381 | 0.00 | 0.9560 |
| | Treatment | 2 | 81.343523 | 0.71 | 0.4966 |
| | Visit | 1 | 79.127237 | 0.01 | 0.9113 |
| | Treatment × Visit | 2 | 78.990086 | 0.01 | 0.9922 |
| LCI appreciation of death | FPE | 1 | 83.009544 | 0.24 | 0.6288 |
| | Treatment | 2 | 83.554368 | 2.48 | 0.0897 |

TABLE 30-continued

| F-Tests from MMRM Model: LCI Measures | | | | | |
|---|---|---|---|---|---|
| Parameter | Source | DF | Denominator DF | F-value | P-value |
| | Visit | 1 | 78.314013 | 3.04 | 0.0853 |
| | Treatment × Visit | 2 | 78.209655 | 0.54 | 0.5853 |

Source: Emotional Processing Table 14.8.2.8
Note:
F-tests from a MMRM with outcome score as the dependent variable. The model has fixed effects for treatment, visit, FPE, and treatment by visit interaction, visit as the repeating factor, and subject as a random effect.
Abbreviations: DF = Degrees of freedom; FPE = Former psilocybin experience; MMRM = Mixed model for repeated measures; LCI = Line Changes Inventory.

An overall effect of treatment was found for all LCI domains except Concern Social, Religiousness, and Appreciation of Death. No treatment by visit interaction was found in any case, indicating that the treatment effect was consistent over time. Time and prior psilocybin use had no apparent impact on this scale.

LS means and pairwise treatment comparisons for each domain of the LCI scale are summarized in Table 31 below.

TABLE 31

| | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| | | | | Summary of LCI Results on Day 7 and Day 84 | | | |
| | | | | LCI-absolute change | | | |
| Day 7 | n | 29 | 30 | 26 | — | — | — |
| | Mean | 0.4 | 0.5 | 0.1 | 0.3 | 0.4 | −0.1 |
| | 95% CI | — | — | — | 0.14, 0.48 | 0.20, 0.55 | −0.23, 0.11 |
| | pvalue | — | — | — | 0.0007 | <0.0001 | 0.4723 |
| Day 84 | n | 27 | 30 | 21 | — | — | — |
| | Mean | 0.5 | 0.5 | 0.1 | 0.4 | 0.4 | −0.0 |
| | 95% CI | — | — | — | 0.19, 0.55 | 0.21, 0.56 | −0.19, 0.15 |
| | pvalue | — | — | — | <0.0001 | <0.0001 | 0.8393 |
| | | | | LCI appreciation for life | | | |
| Day 7 | n | 29 | 30 | 26 | — | — | — |
| | Mean | 0.6 | 0.8 | 0.2 | 0.5 | 0.6 | −0.2 |
| | 95% CI | — | — | — | 0.16, 0.74 | 0.31, 0.90 | −0.44, 0.13 |
| | pvalue | — | — | — | 0.0028 | <0.0001 | 0.2762 |
| Day 84 | N | 27 | 30 | 21 | — | — | — |
| | Mean | 0.7 | 0.8 | 0.2 | 0.5 | 0.6 | −0.1 |
| | 95% CI | — | — | — | 0.24, 0.79 | 0.35, 0.90 | −0.37, 0.15 |
| | pvalue | — | — | — | 0.0003 | <0.0001 | 0.4037 |
| | | | | LCI self-acceptance | | | |
| Day 7 | N | 29 | 30 | 26 | — | — | — |
| | Mean | 0.6 | 0.8 | 0.1 | 0.5 | 0.7 | −0.1 |
| | 95% CI | — | — | — | 0.32, 0.75 | 0.45, 0.88 | −0.35, 0.07 |
| | pvalue | — | — | — | <0.0001 | <0.0001 | 0.1938 |
| Day 84 | N | 27 | 30 | 21 | — | — | — |
| | Mean | 0.6 | 0.6 | 0.1 | 0.5 | 0.5 | 0.0 |
| | 95% CI | — | — | — | 0.28, 0.76 | 0.26, 0.75 | −0.21, 0.24 |
| | pvalue | — | — | — | <0.0001 | <0.0001 | 0.8961 |
| | | | | LCI concern for others | | | |
| Day 7 | n | 29 | 30 | 26 | — | — | — |
| | Mean | 0.6 | 0.5 | 0.1 | 0.4 | 0.4 | 0.0 |
| | 95% CI | — | — | — | 0.15, 0.71 | 0.11, 0.67 | −0.23, 0.31 |
| | pvalue | — | — | — | 0.0034 | 0.0075 | 0.7864 |
| Day 84 | n | 27 | 30 | 21 | — | — | — |
| | Mean | 0.7 | 0.5 | 0.1 | 0.5 | 0.4 | 0.1 |
| | 95% CI | — | — | — | 0.25, 0.77 | 0.12, 0.64 | −0.12, 0.37 |
| | pvalue | — | — | — | 0.0002 | 0.0046 | 0.3046 |
| | | | | LCI concern for worldly achievement | | | |
| Day 7 | n | 29 | 30 | 26 | — | — | — |
| | Mean | −0.2 | −0.2 | −0.0 | −0.1 | −0.2 | 0.1 |
| | 95% CI | — | — | — | −0.31, 0.02 | −0.37, −0.03 | −0.11, 0.22 |
| | pvalue | — | — | — | 0.0908 | 0.0197 | 0.4818 |

TABLE 31-continued

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| | | | | Summary of LCI Results on Day 7 and Day 84 | | | |
| Day 84 | n | 27 | 30 | 21 | — | — | — |
| | Mean | -0.1 | -0.2 | 0.0 | -0.1 | -0.2 | 0.1 |
| | 95% CI | — | — | — | -0.29, 0.09 | -0.44, -0.06 | -0.03, 0.33 |
| | pvalue | — | — | — | 0.3069 | 0.0118 | 0.1050 |
| | | | | LCI concern social | | | |
| Day 7 | n | 29 | 30 | 26 | — | — | — |
| | Mean | 0.2 | 0.2 | 0.1 | 0.2 | 0.1 | 0.1 |
| | 95% CI | — | — | — | 0.01, 0.33 | -0.05, 0.27 | -0.10, 0.22 |
| | pvalue | — | — | — | 0.0412 | 0.1915 | 0.4428 |
| Day 84 | n | 27 | 30 | 21 | — | — | — |
| | Mean | 0.2 | 0.2 | 0.1 | 0.1 | 0.1 | 0.0 |
| | 95% CI | — | — | — | -0.06, 0.32 | -0.07, 0.32 | -0.17, 0.19 |
| | pvalue | — | — | — | 0.1741 | 0.1952 | 0.9365 |
| | | | | LCI quest for meaning | | | |
| Day 7 | n | 29 | 30 | 26 | | | |
| | Mean | 0.5 | 0.5 | 0.1 | 0.4 | 0.4 | 0.0 |
| | 95% CI | — | — | — | 0.16, 0.64 | 0.15, 0.64 | -0.23, 0.24 |
| | pvalue | — | — | — | 0.0015 | 0.0018 | 0.9737 |
| Day 84 | n | 27 | 30 | 21 | | | |
| | Mean | 0.5 | 0.5 | 0.1 | 0.4 | 0.4 | -0.0 |
| | 95% CI | — | — | — | 0.07, 0.63 | 0.11, 0.66 | -0.30, 0.23 |
| | pvalue | — | — | — | 0.0139 | 0.0070 | 0.7956 |
| | | | | LCI spirituality | | | |
| Day 7 | n | 29 | 30 | 26 | — | — | — |
| | Mean | 0.4 | 0.5 | 0.2 | 0.2 | 0.3 | -0.1 |
| | 95% CI | — | — | — | -0.03, 0.51 | 0.05, 0.59 | -0.34, 0.18 |
| | pvalue | — | — | — | 0.0789 | 0.0204 | 0.5318 |
| Day 84 | n | 27 | 30 | 21 | — | — | — |
| | Mean | 0.5 | 0.5 | 0.1 | 0.4 | 0.4 | -0.0 |
| | 95% CI | — | — | — | 0.09, 0.65 | 0.12, 0.68 | -0.29, 0.23 |
| | pvalue | — | — | — | 0.0105 | 0.0052 | 0.7985 |
| | | | | LCI religiousness | | | |
| Day 7 | n | 29 | 30 | 26 | — | — | — |
| | Mean | 0.0 | -0.0 | 0.0 | 0.0 | -0.1 | 0.1 |
| | 95% CI | — | — | — | -0.09, 0.15 | -0.17, 0.07 | -0.04, 0.19 |
| | pvalue | — | — | — | 0.6789 | 0.4061 | 0.1991 |
| Day 84 | n | 27 | 30 | 21 | — | — | — |
| | Mean | 0.0 | -0.0 | -0.0 | 0.0 | -0.0 | 0.1 |
| | 95% CI | — | — | — | -0.19, 0.24 | -0.25, 0.17 | -0.13, 0.26 |
| | pvalue | — | — | — | 0.8056 | 0.7212 | 0.5143 |
| | | | | LCI appreciation of death | | | |
| Day 7 | n | 27 | 30 | 21 | — | — | — |
| | Mean | 0.1 | 0.2 | 0.0 | 0.1 | 0.1 | -0.0 |
| | 95% CI | — | — | — | -0.06, 0.25 | -0.03, 0.28 | -0.17, 0.13 |
| | pvalue | — | — | — | 0.2163 | 0.1265 | 0.7511 |
| Day 84 | n | 27 | 30 | 21 | — | — | — |
| | Mean | 0.3 | 0.2 | 0.1 | 0.2 | 0.2 | 0.0 |
| | 95% CI | — | — | — | -0.01, 0.45 | -0.05, 0.40 | -0.17, 0.25 |
| | pvalue | — | — | — | 0.0597 | 0.1190 | 0.7010 |

Note:

LS means and p-values from the MMRM with outcome score as the dependent variable. The model has fixed effects for treatment, visit, FPE, and treatment by visit interaction, visit as the repeating factor, and subject as a random effect. Abbreviations: CI = Confidence interval; FPE = Former psilocybin experience; LCI = Line Changes Inventory; LS = least squares; MMRM = Mixed model for repeated measures; N = All subjects randomized; n = Subjects with post-treatment assessments.

Each psilocybin dose group showed a higher absolute change in LCI compared to the placebo group at both Day 7 and Day 84 after drug administration (p<0.05). The effect of each psilocybin dose compared to placebo was <0.05 for nearly all LCI domains at both timepoints, notably Appreciation for Life, Self-Acceptance, Concern for Others, and Quest for Meaning. Positive trends were also observed for Spirituality, Concern for Worldly Achievement, and Concern Social. However, Religiousness and Appreciation of Death appeared to be unaffected.

The differences between psilocybin dose effects (10 mg versus 25 mg) were not statistically significant for any LCI domain at either timepoint.

Psilocybin had an effect on each of the five primary dimensions of the 5D-ASC scale compared to placebo assessed immediately post-treatment (p≤0.0001).

Differences between doses were observed (p≤0.05) in two cases (Dread of Ego Dissolution and Auditory Alteration), with the 25 mg psilocybin group showing higher scores than the 10 mg psilocybin group on each of these domains. The 11 sub-scores of the 5D-ASC scale also showed differences between each of the psilocybin dose groups and placebo (p≤0.0001). Only two of the subscales showed a dose relationship: the mean scores for Anxiety and Complex Imagery were higher in the 25 mg dose group than in the 10 mg dose group.

At both the 25 mg and 10 mg doses, subjects treated with psilocybin showed an increase in the LCI absolute change (p≤0.0007) and in LCI domain scores measuring Appreciation for Life (p≤0.0028), Self-Acceptance (p<0.0001), Concern for Others (P≤0.0075), and Quest for Meaning (p<0.0139). These effects were evident regardless of the psilocybin dose administered.

PANAS scores, measured immediately post-treatment, showed a reduction in Positive Affect for placebo-treated subjects, which was not observed in the psilocybin groups (p<0.03). PANAS Negative Affect was increased in the 25 mg psilocybin group, compared to a slight decrease in the 10 mg group (p=0.0218) and the placebo group (p=0.0989).

There were no consistent or noteworthy trends to suggest that either dose of psilocybin had a short- or long-term effect on PET, RMET, SSR, SVO, or TEQ. Likewise, psilocybin had no detectable effect on changes in NEO-FFI or SCL 90 scales at either Day 7 or Day 84.

There was no evidence of improvement or deterioration in performance on CANTAB tasks as a result of the psilocybin exposure over this 28-day study in this study population of healthy volunteers (inclusion criteria ranging from 20 to 59 years of age). No pro-cognitive effect was detected at Day 7 on the exploratory efficacy outcomes.

On the CANTAB Global Composite score, performance was worse than placebo for the 10 mg psilocybin group at Day 7 (p<0.05). However, this result is due in part to the larger improvement in performance from Baseline by the placebo group at Day 7. For the 10 mg group, performance increases again at Day 28 to a level similar to placebo suggesting no adverse effects of the 10 mg dose compared with placebo. The CANTAB cognitive performance results support the safety and tolerability of the administration of a single 10 mg or 25 mg dose of psilocybin.

There was no Visit-Dose effect observed on any of the cognitive outcome measures; PALTEA (episodic memory), SWMBE (working memory), SWMS (executive function and planning), RVPA (sustained attention) and Global Cognitive Composite, suggesting there was no consistent and differential performance changes between the placebo and the 10 mg and 25 mg psilocybin dose groups.

Despite no overall main effect of dose group on RVPA performance (cognitive domain of sustained attention), there was a LS mean difference from placebo for both the 10 mg and 25 mg groups at Day 28 (p<0.05), suggesting better performance of subjects in the psilocybin dose groups relative to placebo at Day 28.

PANAS scores, measured immediately post-treatment, showed a reduction in Positive Affect for placebo-treated subjects, which was not observed in the psilocybin groups (p<0.03). PANAS Negative Affect was increased in the 25 mg psilocybin group, compared to a slight decrease in the 10 mg group (p=0.0218) and the placebo group (p=0.0989).

No significant difference in performance was observed between 10 mg psilocybin, 25 mg psilocybin and placebo groups at Day 7 for the exploratory efficacy outcome measures ERTPC (Emotion recognition), OTSPSFC (executive function, planning and working memory) or IEDYERT (rule acquisition and reversal, flexibility of attention).

Example 4: Co-Administration of Psilocybin and a Benzodiazepine

The following example provides details of a study to determine the effects of low and high dose of the benzodiazepine alprazolam on the acute psilocybin experience in healthy volunteers, and to provide an evidence base for the use of benzodiazepines to control anxiety, which may be used to inform future dose and drug selection. This study also seeks to show the dimension of the psychedelic experience affected by GABAergic manipulation, including subjective (11D-ASC) and neurological (fMRA), to help develop an understanding of which aspects are important therapeutically.

In a first dosing session, at t=0; 315 μg/kg psilocybin (PSI) will be administered to a healthy, psychedelic naïve subject (i.e., the subject has no prior experience taking psychedelic drugs). Approximately 4 weeks later, the subject will participate in a second dosing session. In the second dosing session, 315 μg/kg psilocybin will be co-administered to the subject with either (a) a placebo (PSI+PLA), (2) 0.25 mg alprazolam (PSI+0.25 mg), or (3) 1 mg alprazolam (PSI+1 mg) at t=0.

In both dosing sessions, after the subject begins to have a psychedelic experience, the subject will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) & blood cortisol will be evaluated. Longer term effects on wellbeing will also be evaluated after the psychological experience has ended.

Functional mMRI (fMRI) will also be used to measure the effects of low and high dose alprazolam in these subjects. Individuals in each group (PSI+PLA, PSA+0.25 mg, PSI+1 mg) will be randomized for resting state fMRI scanning at the peak of the experience. Brain regions associated with fear, panic, and anxiety will be examined. The following comparisons will be performed: (PSI+PLA) vs (PSI+0.25) mg vs (PSI+1 mg). It is hypothesized that activation in fear regions will decrease disproportionately to other neural correlates of the psychedelic state.

Example 5: Co-Administration of Psilocybin and a Benzodiazepine

The following examples 5A and 5B provide details of studies that will be used to determine the effects of low and high dose benzodiazepine (e.g., alprazolam or diazepam) on the acute psilocybin experience in healthy volunteers. The purpose of these studies is to provide an evidence base for the use of benzodiazepines to control psychedelic anxiety, which may be used to inform future dose and drug selection. This study also seeks to show the dimension of the psychedelic experience affected by GABAergic manipulation, including subjective (11D-ASC) and neurological (fMRI), to help develop an understanding of which aspects are important therapeutically.

Example 5A: Alprazolam

In a first dosing session, at t=0:315 μg/kg psilocybin (PSI) will be administered to a healthy, psychedelic naïve subject (i.e., the subject has no prior experience taking psychedelic drugs) in an open-label manner.

Approximately 4 weeks later, the subject will participate in a second dosing session. In the second dosing session, 315 μg/kg psilocybin will be co-administered to the subject with either (a) a placebo (PSI+PLA), (2) 0.25 mg alprazolam (PSI+0.25 mg), or (3) 1 mg alprazolam (PSI+1 mg) at t=0.

In both dosing sessions, after the subject begins to have a psychedelic experience, the subject will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) and blood cortisol will be evaluated. Longer term effects on well being will also be evaluated after the psychological experience has ended.

Functional mMRI (fMRI) will also be used to measure the effects of low and high dose alprazolam in these subjects. Individuals in each group (PSI+PLA, PSA+0.25 mg, PSI+1 mg) will be randomized for resting state fMRI scanning at the peak of the experience. Brain regions associated with fear, panic, and anxiety will be examined. The following comparisons will be performed: (PSI+PLA) vs (PSI+0.25) mg vs (PSI+1 mg). It is hypothesized that activation in fear regions will decrease disproportionately to other neural correlates of the psychedelic state due to co-administration of alprazolam.

Example 5B: Diazepam

In a first dosing session, at t=0:25 mg psilocybin (PSI) will be administered to a healthy, psychedelic naïve subject in an open-label manner.

Approximately 4 weeks later, the subject will participate in a second dosing session. In the second dosing session, 25 mg psilocybin will be administered to the subject. Additionally, the subject will also be administered (a) a placebo (PSI+PLA), (2) 2 mg diazepam (PSI+2 mg), (3) 5 mg diazepam (PSI+5 mg), (4) or 10 mg diazepam (PSI+10 mg) at the same time as the psilocybin or at the peak of the psychedelic experience.

In both dosing sessions, after the subject begins to have a psychedelic experience, the subject will be asked to provide a subjective rating approximately every 15 minutes of his or her experience intensity, blissfulness, and anxiety. Heart rate, blood pressure and galvanic skin reaction will also be measured. After each session, 5D-ADC, PANAS, and blood cortisol will be measured. Additionally, a standardized interview will be performed, to discuss the quality of the experience and to get any comments that may be overlooked in the surveys.

Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) & blood cortisol will be evaluated. Longer term effects on wellbeing will also be evaluated after the psychological experience has ended.

Functional mMRI (fMRI) will also be used to measure the effects of low and high dose diazepam in these subjects. Individuals in each group (PSI+PLA, PSA+2 mg, PSI+5 mg, PSI+10 mg) will be randomized for resting state fMRI scanning at the peak of the experience. Brain regions associated with fear, panic, and anxiety will be examined.

The following comparisons will be performed: (PSI+PLA) vs (PSI+2 mg) vs (PSI+5 mg) vs. (PSI+10 mg). It is hypothesized that activation in fear regions will decrease disproportionately to other neural correlates of the psychedelic state due to co-administration of diazepam.

Example 6: Effect of Alprazolam on 5-HT$_{2A}$ Receptor Binding by Psilocybin The following example provides details of a study used to determine whether alprazolam-induced changes in subjective experience during psilocybin therapy are due to changes in 5-HT$_{2A}$ occupancy. If not, downstream molecular and cellular effects that may be important in psilocybin's therapeutic effects may be preserved after co-treatment with a benzodiazepine.

In this study, [$^{11}$C]CIMBI-36 (a selective 5-HT$_{2A}$ receptor agonist positron emission tomography (PET) radioligand) will be used to investigate whether 5-HT$_{2A}$ binding is affected by placebo vs. alprazolam.

At time t=0, subjects will be administered 25 mg psilocybin (PSI) in combination with either a placebo, or alprazolam. At t=2 hours, subjects will be given a tracer dose of [$^{11}$C]CIMBI-36. At t=2-3 hours, a PET scan will be performed, to determine whether 5-HT$_{2A}$ binding is affected by either dose of alprazolam.

This study may optionally be performed using diazepam instead of alprazolam.

Example 7: Co-Administration of Psilocybin and a 5-HT$_{2A}$ Specific Antagonist The following example provides details of a study used to determine the effects of low and high dose of ketanserin, a 5-HT$_{2A}$ specific antagonist on the acute psilocybin experience in healthy volunteers. The purpose of this study is to provide an evidence base for the use of 5-HT$_{2A}$ specific antagonists to control the negative side effects associated with a traumatic psychedelic experience, which may be used to inform future dose and drug selection. This study also seeks to show the dimension of the psychedelic experience affected by GABAergic manipulation, including subjective (11D-ASC) and neurological (fMRI), to help develop an understanding of which aspects are important therapeutically.

In a first dosing session, at t=0:315 µg/kg psilocybin (PSI) will be administered to a healthy, psychedelic naïve subject (i.e., the subject has no prior experience taking psychedelic drugs). Approximately 4 weeks later, the subject will participate in a second dosing session. In the second dosing session, 315 µg/kg psilocybin will be co-administered to the subject with either (1) a placebo (PSI+PLA), (2) low dose ketanserin (PSI+LD), or (3) high dose ketanserin (PSI+HD) at t=0.

In both dosing sessions, after the subject begins to have a psychedelic experience, the subject will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) & blood cortisol will be evaluated. Longer term effects on well being will also be evaluated after the psychological experience has ended.

Functional mMRI (fMRI) will also be used to measure the effects of low and high dose ketanserin in these subjects. Individuals in each group (PSI+PLA, PSA+LD, PSI+HD) will be randomized for resting state fMRI scanning at the peak of the experience. Brain regions associated with fear, panic, and anxiety will be examined. The following comparisons will be performed: (PSI+PLA) vs (PSI+LD) vs (PSI+HD). It is hypothesized that activation in fear regions will decrease disproportionately to other neural correlates of the psychedelic state due to co-administration of ketanserin.

Example 8: Co-Administration of Psilocybin and a 5-HT$_{2A}$ Inverse Agonist The following example provides details of a study used to determine the effects of low and high dose of pimavanserin, a 5-HT$_{2A}$ inverse agonist on the acute psilocybin experience in healthy volunteers. The purpose of this study is to provide an evidence base for the use of 5-HT$_{2A}$ inverse agonists to control the negative side effects associated with a traumatic psychedelic experience, which may be used to inform future dose and drug selection. This study also seeks to show the dimension of the psychedelic experience affected by GABAergic manipulation, including subjective (11D-ASC) and neurological (fMRIA), to help develop an understanding of which aspects are important therapeutically.

In a first dosing session, at t=0, 315 μg/kg psilocybin (PSI) will be administered to a healthy, psychedelic naïve subject (i.e., the subject has no prior experience taking psychedelic drugs). Approximately 4 weeks later, the subject will participate in a second dosing session. In the second dosing session, 315 μg/kg psilocybin will be co-administered to the subject with either (1) a placebo (PSI+PLA), (2) low dose pimavanserin (PSI+LD), or (3) high dose pimavanserin (PSI+HD) at t=0.

In both dosing sessions, after the subject begins to have a psychedelic experience, the subject will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) & blood cortisol will be evaluated. Longer term effects on well being will also be evaluated after the psychological experience has ended.

Functional mMRI (fMRI) will also be used to measure the effects of low and high dose pimavanserin in these subjects. Individuals in each group (PSI+PLA, PSA+LD, PSI+HD) will be randomized for resting state fMRI scanning at the peak of the experience. Brain regions associated with fear, panic, and anxiety will be examined. The following comparisons will be performed: (PSI+PLA) vs (PSI+LD) vs (PSI+HD). It is hypothesized that activation in fear regions will decrease disproportionately to other neural correlates of the psychedelic state due to co-administration of pimavanserin.

Example 9: Effect of Pimavanserin or Ketanserin on 5-HT$_{2A}$ Receptor Binding by Psilocybin The following example provides details of a study used to determine whether pimavanserin or ketanserin induced changes in subjective experience during psilocybin therapy are due to changes in 5-HT$_{2A}$ occupancy. If not, downstream molecular and cellular effects that may be important in psilocybin's therapeutic effects may be preserved after co-treatment with a 5-HT$_{2A}$ specific antagonist and/or inverse agonist.

In this study, [$^{11}$C]CIMBI-36 (a selective 5-HT$_{2A}$ receptor agonist positron emission tomography (PET radioligand) will be used to investigate whether 5-HT$_{2A}$ binding is affected by placebo vs. pimavanserin or ketanserin At time t=0, subjects will be administered 25 mg psilocybin (PSI) in combination with either a placebo, or a low or high dose of pimavanserin or ketanserin. At t=2 hours, subjects will be given a tracer dose of [$^{11}$C]CIMBI-36. At t=2-3 hours, a PET scan will be performed, to determine whether 5-HT$_{2A}$ binding is affected by either dose of pimavanserin or ketanserin.

Example 10: In Vivo Study Investigating Changes in Mouse Protein Expression Levels Associated with the Pathophysiology of Anxiety, Obsessive Compulsive Disorder, Eating Disorders, and Migraines Experimental Design:

The objective of this study was to outline the analysis of 92 proteins in mouse plasma samples by Olink® Proteomics after a single administration of psilocybin. Relative quantification of the proteins in mouse samples were conducted using Olink® Mouse Exploratory Panel, consisting of 92 biomarker assays known to be detectable in human serum and plasma. The 92 proteins in the panel encompass a broad range of biological functions and pathways.

In this study, 3 doses of psilocybin (1, 3, and 10 mg/kg) and vehicle (0.9% NaCl solution) were administered. Data was collected at 3 time points post-administration of psilocybin and/or vehicle (1 hr, 24 hr & 8 days). There were 10 mice per group (n=10, 120 total samples). Blood samples were taken from mice. More than 40 μL of each sample were supplied in temperature-resistant, non-protein binding plastics. Samples were shipped on dry ice. Samples were randomized by Olink® before the analysis.

The first step in the analysis of the samples was the immunology reaction. This step was performed by preparation of an Incubation mix (containing A- and B-probes, buffer & internal controls) and distribution of three μL of this to the wells of a 96-well PCR (polymerase chain reaction) plate. One microliter of each sample; a duplicate of a pooled plasma sample; triplicate wells of interplate control and the negative control, were transferred to the plate in this sequence. The plate was then sealed, centrifuged and incubated at 4° C. overnight.

On the following day, an extension- and pre-amplification PCR reaction took place. A proximity extension assay mix was added directly to the samples in the overnight incubation plate and a classical PCR reaction generating a unique PCR target sequence for each biomarker was performed. The resulting DNA sequences were subsequently detected and quantified in a singleplex readout format using the microfluidic real-time PCR instrument (Biomark HD, Fluidigm). Briefly, integrated fluid circuits (IFCs) from Fluidigm were loaded with primers on the left side and samples (DNA sequences) on the right side. An HX Controller instrument distributed samples and primers to the central part of the IFC before the IFC was transferred to the Fluidigm Biomark for protein quantification using qPCR.

The resulting data was quality controlled using RT-PCR Software. Generated Ct (cycle threshold)-values were exported from the software and imported to Olink® NPX Manager for additional quality control and generation of normalized protein expression (NPX) values.

Assay performance was assessed by measurements of internal and external controls included in all Olink® Panels. The four internal controls (two Incubation controls, one Detection control and one Extension control) were spiked into every sample at an equal level and were used to monitor each step of the reaction. The two external controls (Interplate control and Negative control) were added in triplicate reactions in a separate column of the reaction plate; they were used to minimize plate variation (interplate control) and generate limit of detection (LOD) for each assay (negative control).

Each assay run was accepted when QCs were within the run acceptance criteria (see Table 32).

TABLE 32

| Attribute | Acceptance level |
| --- | --- |
| No. of samples that does not pass QC | $<\frac{1}{6}$ of total no. of samples on a plate |
| Incubation control 1 | Standard deviation <0.2 NPX |
| Incubation control 2 | Standard deviation <0.2 NPX |
| Detection control | Standard deviation <0.2 NPX |

A sample did not pass quality control if either the Incubation control 2 or Detection control for that specific sample deviated more than ±0.3 NPX from the plate median of the respective internal control.

Results from Olink® panels were generated as Ct values from the Fluidigm Biomark. Ct values were then re-calculated to normalized protein expression (NPX) values using Olink® NPX Manager. Results of protein expression levels were reported in normalized protein expression (NPX), an arbitrary unit on a log 2 scale.

NPX was calculated according to the following scheme:
1. Each sample was normalized against the Extension control.

$$Ct_{Analyte} - Ct_{Extension\ Control} = dCt_{Analyte}$$

2. Each assay was normalized against its corresponding interplate control.

$$dCt_{Analyte} - dCt_{Inter-plate\ Control} = ddCt_{Analyte}$$

3. Each assay was adjusted using a pre-determined correction factor, which inverts the values with respect to Ct, so that a high NPX value corresponds to a high protein expression level.

$$Correction\ factor - ddCt_{Analyte} = NPX_{Analyte}$$

Psilocybin induced changes in various plasma proteins known to be involved in the pathophysiology of anxiety. Clnstn2 expression levels were significantly decreased 24 hours following a single administration of 10 mg/kg psilocybin in naïve mice (FIG. 10). Twenty four hours after administration of 10 mg/kg psilocybin, protein expression of Erbb4 increased (FIG. 11).

Psilocybin induced changes in various plasma proteins known to be involved in the pathophysiology of OCD. One hour after administration of 10 mg/kg psilocybin, protein expression of glucagon (Gcg) was increased (FIG. 12).

Psilocybin induced changes in a plasma protein known to be involved in the pathophysiology of eating disorder. One hour after administration of 10 mg/kg psilocybin, protein expression of glucagon (Gcg) was increased (FIG. 12). Cxcl1 expression levels were significantly decreased 8 days following a single administration of 10 mg/kg psilocybin in naïve mice (FIG. 13).

Psilocybin induced changes in plasma proteins known to be involved in the pathophysiology of migraines. Cxcl1 expression levels were significantly decreased 8 days following a single administration of 10 mg/kg psilocybin in naïve mice (FIG. 13). ACVRL1 expression levels were significantly increased 1 hour following a single administration of 10 mg/kg psilocybin in naïve mice (FIG. 14).

Example 11. Effect of Psilocybin on Marble Burying (MB) Test in an In Vivo Model This example examines the effects of psilocybin treatment on repetitive or compulsive behaviors associated with anxiety, obsessive compulsive disorder, and eating disorders using the Marble Burying (MB) test.

The Marble Burying (MB) test is a minimally invasive animal model that represents the compulsive behavior associated with anxiety. The innate stereotypic behavior in rodents is to bury as many marbles as possible. This behavior occurs without pharmacological manipulation or behavioral training. A greater number of buried marbles represents a higher degree of compulsivity. Mice also do not avoid marbles, indicating that the marbles themselves do not have aversive or fear-provoking properties for the animal. Thus, MB behavior in mice can be used for testing compounds with anti-compulsive properties.

Adult C57BL/6 mice (5-7 weeks-old, male, n=81) were acclimatized for 10 days in standard caging and laboratory conditions in groups of 4 or 5 per cage. Mice had free access to food and water and were housed on a 12/12 light/dark cycle. Mice were weighed: 1) after the acclimatization period to obtain a baseline weight; 2) on days of dosing to calculate dose volumes; and 3) after completing the MB test.

Animals were placed individually in a clear cage containing 5 cm of wood chip bedding upon which glass marbles (n=20) were arranged in even rows on the bedding (FIG. 15). Each animal was allowed a period of 30 min in the cage, after which it was removed, and the number of marbles buried was recorded. A marble is considered "buried" if it is covered >75% by bedding. Two blinded experimenters counted the marbles and data represents an average score of the two counts. Data were expressed as mean±standard error of the mean (SEM).

Mice were intraperitoneally administered either vehicle for fluoxetine (vehicle FL, 0.9% NaCl at 10 ml/kg), fluoxetine (10 mg/kg), vehicle for psilocybin (vehicle PS, 0.9% NaCl at 10 ml/kg) or psilocybin (1 mg/kg, 3 mg/kg, 10 mg/kg IP). Mice underwent the MB test either 30 minutes (vehicle FL and fluoxetine) or 1 hour (vehicle PS and psilocybin) after drug administration. Once the marble assessment was completed, mice were culled. Data were analyzed by comparing treatment groups to control groups (n=9 mice per group). The data from the vehicle FL and fluoxetine groups were statistically analyzed using an unpaired t-test, while data from the vehicle PS and psilocybin groups were statistically analyzed using a one-way ANOVA and Tukey's correction test.

As shown in FIG. 16, the highest dose of psilocybin (10 mg/kg) significantly reduced the number of marbles buried by mice compared to the vehicle PS control (##p<0.001) 1 hour post-treatment. The effects of the highest dose of psilocybin on marble burying were similar to that of fluoxetine, a selective serotonin reuptake inhibitor (***p<0.0001).

Example 12: In Vivo Study Testing the Effect of Psilocybin on Wakefulness, NREM, and/or REM Sleep To determine whether psilocybin may treat sleep disorders associated with anxiety and obsessive compulsive disorder, various doses of psilocybin were tested in an animal model to determine if psilocybin had an effect on wakefulness, NREM and/or REM sleep, as well as on common electroencephalogram (EEG) frequency bands.

Wistar-Kyoto (WKY) rats exhibit abnormal behavioural, hormonal, neurochemical as well as sleep-wake characteristics that are often associated with depression. Since WKY rats show decreased sensitivity to conventional monoamine-based antidepressant treatment, they are used as a model of TRD. WKY rats are known to exhibit enhanced REM sleep, a common feature in depressed subjects.

Male WKY rats (200-250 g) were implanted with electroencephalography (EEG) and electromyography (EMG) electrodes and telemetry transmitters under general anaesthesia (2-5% isoflurane in Oxygen). A telemetry transmitter (HD-S02, Data Sciences International) was placed in the peritoneal cavity, and the wires of the transmitter were passed through the muscle wall and then sub-dermally to the scalp to act as EEG/EMG electrodes. Two bore holes were made in the skull (Fronto-parietal coordinates; Bregma +2 mm anterior, midline +1.0 mm lateral and Lambda 0 mm, +1.5 mm lateral). The positive EEG electrode was attached to the anterior bore hole and the negative EEG electrode to the posterior bore hole. Both electrodes were secured in place using a suitable adhesive agent (Cyanoacrylate gel, RS components). A second set of electrodes were sutured into the nuchal muscle to act as EMG electrodes. During the post-surgical recovery period (minimum 7 days), the rats received standard post-operative care and no experimental procedures were performed until the pre-operative body weight was regained.

The animals were not drug-naïve at the beginning of the study as they were used in a previous study. The length of the washout period between the two studies was more than 3 months.

Animals were maintained on a 12/12 hour light dark cycle. On study days, the animals were placed in recording boxes and EEG/EMG, locomotor activity, as well as body temperature were recorded for 0.5 h before and 24 h after each dosing. All animals were dosed with saline vehicle first, followed by one of the drug treatments 24 h later. Drug treatments included ketamine (5 and 10 mg/kg) administered subcutaneously (s.c.), and psilocybin (1, 3 and 10 mg/kg); administered intraperitoneally (i.p.). All treatments were administered 2 h after light onset. All animals received all treatment conditions by escalating the doses on a weekly basis, and with a 6 days washout period between a drug treatment and the subsequent vehicle treatment.

EEG, EMG, locomotor activity and body temperature data were acquired for 0.5 hours before and 24 hours after each treatment with Spike2 software (CED, Cambridge UK). EEG/EMG signals were amplified, analogue filtered (0.5-100 Hz), digitized (256 Hz), and then digitally filtered (EEG: 0.5-100 Hz and EMG: 5-100 Hz).

The subsequent EEG/EMG recordings were automatically scored as wake, non-REM (NREM) sleep, or REM sleep in 10 second epochs using SleepSign (Kissei Comtec, Japan).

Power spectral analysis was performed on EEG data recorded over the 0-1 hr, 1-7 hours and 11-19 hours periods post-treatment. EEG power spectra were computed for consecutive 2 second epochs by fast Fourier transformation (Hanning window, 0.5 Hz resolution) between 0.5-100 Hz. Epochs with artefacts (5×STD of RMS) were discarded. Data were presented in 1 Hz bins, and the bins were marked by their upper limits.

Statistical analysis: Repeated measures ANOVA followed by Dunnett post-test was used to compare the different treatment groups (GraphPad, Prism 8).

In this study, both psilocybin (1, 3 and 10 mg/kg, i.p.) and ketamine (5 and 10 mg/kg) decreased the amount of REM sleep in a dose-dependent manner (FIG. 17 and FIG. 18).

Psilocybin also caused a dose-dependent increase in wake amount and a slight decrease in NREM sleep amount during the light period (FIG. 17 and FIG. 18). This was followed by a slight but significant increase in the amount of NREM sleep at the expense of wakefulness in psilocybin-treated rats during the dark period most likely caused by a rebound effect (FIG. 17 and FIG. 19).

Psilocybin suppressed high-frequency gamma (30-100 Hz) oscillations in the EEG of WKY rats in the 1st hour post-treatment (FIG. 20). In the subsequent part of the light period, psilocybin (1, 3 and 10 mg/kg, i.p.) increased both EEG theta (4-10 Hz) and beta (10-30 Hz) oscillations and suppressed EEG gamma oscillations in WKY rats (FIG. 21).

Example 13: In Vivo Study of the Effect of Psilocybin on CCK-4 Induced Panic Anxiety This example examines the effects of psilocybin on induced panic anxiety. The elevated plus maze (EPM) is a widely used behavioral assay for rodents to assess anti-panic or anti-anxiety effects of pharmacological agents. Briefly, rodents are placed at the junction of the four arms of the maze, facing an open arm, and entries/duration in each arm are recorded over a period of time. An increase in open arm activity reflects anti-anxiety behavior (Waif et al., Nature Protocols, 2007).

Panic anxiety can be induced in rodents through administration of panicogenic drugs such as cholecystokinin tetrapeptide (CCK-4). Peripheral administration of CCK-4 leads to an anxiogenic-like action in the EPM model of anxiety in rats. The anxiogenic effect of CCK-4 can be antagonized by benzodiazepine (e.g., diazepam) treatment.

The aim of this study is to investigate the anti-panic or anti-anxiolytic effect of psilocybin on rats after inducing panic anxiety using CCK-4.

Animal handling was performed on a daily basis starting 1 week before the EPM assay. CCK-4 was prepared in saline at the dosage volume of 1 mL/kg and was intraperitoneally administered to the rats 30 min before implementation of the EPM test resulting in a CCK-4 dose of 0.2 mg/kg. CCK-4 was administered to all treatment groups except for the vehicle control (saline). Treatment groups for this study are shown below in Table 33. The EPM assay was performed 2 hours, and 24 hours following administration of psilocybin, and 1 hour after administration of diazepam.

TABLE 33

| Group number | Description/Dose | n | Test route | Dosage volume |
|---|---|---|---|---|
| 1 | Saline (0.9% NaCl)/Vehicle | 12 | IP | 1 mL/kg |
| 2 | CCK-4/Vehicle | 12 | IP | 1 mL/kg |
| 3 | CCK-4/Positive Control (Diazepam 1 mg/kg) | 12 | PO | 1 mL/kg |
| 4 | CCK-4/Psilocybin (1 mg/kg) | 12 | IP | 1 mL/kg |
| 5 | CCK-4/Psilocybin (3 mg/kg) | 12 | IP | 1 mL/kg |
| 6 | CCK-4/ Psilocybin (10 mg/kg) | 12 | IP | 1 mL/kg |

IP: intraperitoneal;
PO: peroral

The apparatus used in the EPM assay was a PVC maze covered with Plexiglas and subdivided into four equal exploratory arms (21×8 cm). All arms were interconnected by a small platform (8×8 cm). The apparatus was placed 59 cm above the floor. Two arms were open and two arms were closed with walls (height: 21 cm).

After the appropriate pre-treatment time, the rat was placed on the platform opposite a closed arm. The number of entries and the time spent in each arm were recorded during a 5 min period. The animal was considered as entered in an arm when it placed four paws in the arm. During the trial, animal handling and the visibility of the operator was minimized as much as possible.

The apparatus was cleaned between each animal using 70% ethanol. Urine and feces were removed from the maze.

The results were analyzed by analysis of variance (ANOVA). Fisher's PLSD was used for pairwise comparisons and p value ≤0.05 were considered significant.

Administration of CCK-4 significantly reduced the number of entries into and time spent in the open arm compared to rats treated with saline alone (FIGS. 22-23), suggesting that CCK-4 treatment induced panic anxiety. As shown in FIG. 22, 2 hours following administration of 1, 3 and 10 mg/kg psilocybin (acute dose) in CCK-4-treated rats, the number of entries into and the time spent in the open arms was significantly increased compared to vehicle control treated with CCK-4 alone. As shown in FIG. 23, 24 hours following administration of 3 and 10 mg/kg psilocybin (chronic dose) in CCK-4-treated rats, the number of entries into and the time spent in the open arms was significantly increased compared to vehicle control treated with CCK-4 alone.

Diazepam, a benzodiazepine, was used as a positive control and showed a significant increase in the number of entries into and the time spent in the open arms compared to vehicle control treated with CCK-4 alone (FIGS. 22-23).

Example 14: Effect of Psilocybin on Acute and Long-Term Effects of Psilocybin on Social Cognition and Behavior Study Design:

To determine whether psilocybin may have a beneficial effect on social cognition and behaviour in subjects with anxiety or post-traumatic stress disorder, a healthy volunteer study was conducted. The study measured various psychological and brain measures both acutely and long-term following psilocybin administration. A total of 17 healthy psychedelic-naïve participants were included. All participants underwent two dosing sessions, four weeks apart with doses of 1 mg (first session) and 25 mg psilocybin (second session), each session was followed one day later by an integration therapy session. Three neuroimaging fMRI sessions were conducted: one day before the 1 mg psilocybin session; four weeks after the 1 mg session/one day prior to 25 mg psilocybin session & four weeks after the 25 mg session (key endpoint). Psychological measures including an emotional processing battery (including the facial expression recognition task; emotional categorisation task and emotional recall task) and social connectedness scale were completed by participants at baseline, 2 weeks and 4 weeks following the 1 mg and 25 mg psilocybin dosing sessions.

Social connectedness is the measure of how individuals come together and the experience of feeling close and connected to other people, including feeling cared for, valued, loved, and forms the basis of interpersonal relationships. The social connectedness scale is a well-validated and established, self-administered scale.

The facial expression recognition task (FERT) assessed the interpretation of various facial expressions including those displaying happiness, surprise, sadness, fear, anger and disgust. Examples of each expression with varying intensity are presented to participants and reaction times for correct responses are measured.

Each of the aforementioned scans were 90 minutes and incorporated the following:

1. A high resolution anatomical scan (e.g. for measuring cortical thickness and for registering functional scans)
2. A diffusion tensor imaging (DTI) scan (e.g. for measuring fractional anisotropy of white matter)
3. An eyes-closed resting state blood-oxygen-level-dependent (BOLD) scan (e.g. for measuring resting-state functional connectivity, RSFC)
4. An eyes-closed resting state BOLD scan with music listening
5. An emotional faces paradigm (BOLD)

Different versions of the faces were used for each scan, order of their presentation was counterbalanced across the conditions.

Social connectedness, as assessed by the social connectedness scale scores, was significantly increased 2 weeks following the administration of 25 mg psilocybin compared to baseline, this was sustained (at trend level) at week 4 (FIG. 24). Analysis was performed using repeated measures (RM) ANOVA (with Bonferroni correction), with p values <0.05 deemed significant.

Participants were significantly faster at recognising the expression of "disgust", as assessed by increased reaction time to faces displaying this expression, in the facial expression recognition test 4 weeks following the administration of 25 mg of psilocybin when compared to baseline, this was also significantly reduced in 25 mg dose groups at 4 weeks when compared to the very low 1 mg dose. (FIG. 25). Analysis was performed using repeated measures (RM) ANOVA, with p values <0.05 deemed significant.

In the emotional faces task in the fMRI scanner, a significantly decreased (p<0.01 ) left amygdala responsivity to fearful faces was observed compared to baseline (trend level) and this was also significantly reduced (p<0.01 ) compared to 4 weeks following a very low dose 1 mg psilocybin administration (FIG. 26). Significantly increased (p<0.01 **) left amygdala responsivity to happy faces 4 weeks after both 1 mg and 25 mg psilocybin administration, when compared to baseline (FIG. 26). Analysis was performed using repeated measures (RM) ANOVA, with p values <0.05 deemed significant.

Example 15: The Effect of Psilocybin in Subjects with Chronic Cluster Headaches This study determined the effect of psilocybin in subjects with chronic cluster headaches (CCH).

The study took place over a 10 week period which consisted of a baseline observation period, 3 psilocybin sessions, and a follow-up period in subjects with CCH (FIG. 27). Throughout the course of the study, subjects completed questionnaires and headache logs in order to access headache frequency, duration, and severity.

Before the beginning of the study, subjects taking prophylactic medication underwent a 2 week wash-out period to eliminate medication. Subjects then began a baseline observation period lasting 4 weeks during which the subjects received a functional MRI (magnetic resonance imaging) scan. After the observation period, subjects were perorally administered their first dose of 0.14 mg/kg psilocybin. Blood samples were collected during the initial dosing session to establish psilocin plasma concentrations. Over the next two weeks, subjects were administered two additional doses of psilocybin with each dose administered one week apart. The last psilocybin dose was followed by 4 weeks of observation that included a functional MRI scan one week after the last psilocybin dose. Subjects were also contacted 6 and 12 months after the last psilocybin dose to gain information about the duration of potential remission periods. All regular acute treatments were permitted during the study period and recorded in the headache diary. Subjects were allowed to resume prophylactic medication after the 4 week follow-up period.

All subjects treated with psilocybin experienced psychedelic effects. Following psilocybin treatment, one subject experienced less painful headaches, as well as a decrease in the frequency of headaches. The subject also reported at least one very painful cluster headache where the pain was greater than normal.

Example 16: In Vitro Model to Examine Psilocybin as a Treatment for Migraine An in vitro model is used to examine whether psilocyin, the active metabolite of psilocybin, is effective for the treatment of migraine. In this study, levels of calcitonin-gene related peptide (CGRP) secretion are examined in KCl-treated rat neuronal cells in culture. High doses of KCl (e.g., 60 mM) result in toxic over-activation of trigeminal neurons and subsequent CGRP secretion. CGRP plays an integral role in migraine pathology by causing vasodilation and inflammation, which results in pain.

Briefly, trigeminal ganglion (TG) cells are isolated from rats and seeded in tissue culture flasks according to a standard protocol. Cells are maintained at 37° C. in a 5% C02 atmosphere.

After the TG cells have adhered, they are washed and treated with 60 mM KCl and either vehicle control or psilocin (0.1 $\mu$M, 0.3 $\mu$M, 1 $\mu$M, 3 $\mu$M or 10 $\mu$M) for 24 hours. Cells and supernatants are harvested according to standard techniques, and CGRP protein levels are measured.

Example 17: Phase II Clinical Study Examining Psilocybin for the Treatment of Anorexia The aim of this Phase II, single-center, single-dose, open-label trial of psilocybin (25 mg) is to explore the safety, tolerability and feasibility of 25 mg psilocybin in adult subjects with anorexia (AN). The therapeutic goals of psilocybin are:

Ensure psychological safety essential for optimal clinical efficacy

Allow the subject's subjective experience to unfold naturally within the boundaries of the therapeutic intention set at the preparation Maintain the subject's attention and awareness on the experience of the present moment thus allowing exposure and processing of the challenging emotional states and personal memories Generate insights and solutions for the resolution of challenging personal situations, conflicts and traumatic experiences To explore the safety and tolerability of a 25 mg dose of psilocybin in subjects with AN based on adverse events (AEs), changes in vital signs, electrocardiograms (ECGs), clinical laboratory tests, and suicidality.

To explore the efficacy of 25 mg psilocybin on eating disorder symptoms and behaviors, body image, anxiety, food related obsessions and rituals, and body weight.

To explore the effects of 25 mg psilocybin on psychosocial impairment, depressive symptoms, motivational states and appetitive states including hunger and fullness and desire to eat.

Links between psychedelic intensity and changes in efficacy variables are also be explored, as well as subject experience and acceptability of the treatment.

Up to 20 subjects are enrolled in the study. Non-limiting examples of inclusion criteria which subjects should satisfy for inclusion into the study are: signed informed consent form; 18 to 40 years of age at Screening [Visit 1]; current or past diagnosis of anorexia nervosa (informed by DSM 5) based on medical records, clinical assessment, weight, and documented completion of the version 7.0.2 MINI; agreed for the study team to maintain contact with their primary care team for the duration of the study; not have taken antidepressants, antipsychotics or other serotonergic medications for at least 2 weeks prior to Baseline [Visit 2]; able to complete all protocol required assessment tools without any assistance or alteration to the copyrighted assessments, and to comply with all study visits; and, has capacity to consent (assessed via investigator judgment).

Non-limiting examples of exclusion criteria which prohibit subjects from enrolling in the study are detailed below:

BMI<16 kg/m$^2$*

Medical instability as indicated by significant (>3 kg) weight loss the screening period, orthostatic heart rate and blood pressure *

Women who are pregnant, nursing, or planning a pregnancy. Male and female subjects who are sexually active must agree to use a highly effective contraceptive method throughout their participation in the study. Women of child bearing potential must have a negative urine pregnancy test at Screening visits [Visit 1 and Visit 1a] and Baseline [Visit 2], and psilocybin dosing session days *

Cardiovascular conditions: recent stroke (<1 year from signing of ICF), recent myocardial infarction (<1 year from signing of ICF), uncontrolled hypertension (blood pressure >140/90 mmHg) or clinically significant arrhythmia within 1 year of signing the ICF Uncontrolled or insulin-dependent diabetes Seizure disorder Use of psychedelics, including psilocybin, within one year prior to Screening [Visit 1] assessment Positive urine drug screen for illicit drugs or drugs of abuse in the Screening Period [Visit 1 and Visit 1a] and Baseline [Visit 2] and psilocybin dosing days. Any positive urine drug test is reviewed with subjects to determine the pattern of use and eligibility is determined at the investigator's discretion *

Current enrolment in any investigational drug or device study or participation in such within 30 days prior to Screening [Visit 1]

Abnormal and clinically significant results on the physical examination, vital signs, ECG, or laboratory tests at Screening (Visit 1), such as liver function tests (LFTs) three times greater than the upper limit of normal, reduced glomerular filtration rate (GFR) and elevated creatinin two times of upper limit of normal Any other clinically significant cardiovascular, pulmonary, gastrointestinal, hepatic, renal or any other major concurrent illness that, in the opinion of the investigator, may interfere with the interpretation of the study results or constitute a health risk for the subject if he/she takes part in the study.

Current or past history of schizophrenia, psychotic disorder, bipolar disorder, significant history of mania, delusional disorder, paranoid personality disorder, schizoaffective disorder, or borderline personality disorder as assessed by medical history and a structured clinical interview (version 7.0.2 MINI)

McLean Screening Instrument for Borderline Personality Disorder >7 at Screening [Visit 1]

Current (within the last year) alcohol or substance use disorder as informed by DSM 5 at Screening [Visit 1]

Significant suicide risk as defined by (1) suicidal ideation as endorsed on items 4 or 5 on the Columbia-Suicide Severity Rating Scale (C-SSRS) within the past year, at Screening [Visit 1] or at Baseline [Visit 2], or; (2) suicidal behaviors within the past year, or; (3) clinical assessment of significant suicidal risk during subject interview (pre-treatment VISIT 2 sessions).

Other personal circumstances and behavior judged to be incompatible with establishment of rapport or safe exposure to psilocybin, including exposure to psilocybin within the past year and use of psychedelics, such as ayahuasca, during the current episode.

Dosing Procedure:

Each subject is be assigned 1 treatment bottle containing 5 capsules of 5 mg psilocybin. After an optional light breakfast taken at least 2 hours prior to dosing and under observation of study staff, the 5-capsule dose is to be swallowed with a full glass of water; due to the number of capsules in a dose, additional water is be provided as necessary to swallow the dose. Study staff ensure the entire 5-capsule dose has been swallowed.

To prepare for the drug experience, the subject takes the investigational product (IP) (e.g. the psilocybin) and lies down on a couch or bed in a room with dim lights and a standard playlist of relaxing music playing quietly. The trained therapist is present with the subject at all times.

The effects of psilocybin usually start about 20 to 30 minutes after administration, becoming most intense in the first 90 minutes to 120 minutes, and gradually subside in 5 hours to 6 hours. The subjects is asked to remain in the room for the duration of the session regardless of the intensity of the effects, preferably lying down and mostly silent unless they have a concern or need to communicate a discomfort or seek reassurance from the therapist, or use the restroom.

About 5 hours to 6 hours after dosing, a trained therapist discusses the IP administration experience with the subject. The subject is to be discharged 8 hours postdosing when, in the opinion of the investigator, the acute effects of psilocybin are resolved and the subject is assessed for safety. The subject is then be accompanied home. The site is to be notified that the subject has returned home safely, and in the absence of receiving a phone call, site staff directly contacts the subject.

The main objective of the psychological support during psilocybin session is to ensure subjects' psychological safety, as effective management of anxiety is essential to safety, tolerability and efficacy of psilocybin.

Therapists may actively guide subjects, for example, by saying:

Remember you enrolled in this research study of psilocybin for treatment of your anorexia. As psilocybin takes effect, some anxiety and fear are expected. It is part of the process. Remember we practice relaxation and breathing experiences for situations like this?

Let's take deep breaths together and focus on the sensations of the breath throughout the body. As you do this, pay attention to the rhythm of your breath and watch it becoming deeper and slower. Let go of muscle tension with every exhalation.

Therapists are asked to validate the feeling of anxiety without providing interpretations of perceptual disturbances or guiding subjects towards a particular image or memory, other than encouraging them to stay relaxed and open to the emergent experiences.

In preparation for the psilocybin session, therapists demonstrate and practice skills of self-directed inquiry and experiential processing with subjects. Subjects are encouraged to face and explore their experience, including the challenging ones. During the peak and later stages of the session, self-directed inquiry and experiential processing become essential for subjects to develop a different perspective on their personal challenges and conflicts, and to generate their own solutions. Such self-generated insights are not only therapeutic because of the emotional resolution, but also empowering to subjects.

The psilocybin session is supported by a lead therapist and an assisting therapist, selected and trained according to the FDA-approved training model in conjunction with the current IND for psilocybin. The study psychiatrist is in the immediate vicinity of the session to respond to any emergencies. On the day of the session, subjects come in early in the morning with the goal to take psilocybin around 9 am.

Prior to dose administration, a team of therapists reviews the rules and structure of the session with the subject again. Once all the questions are answered, and the subject reconfirms their consent for the session, they administer the psilocybin (25 mg or capsules that are each 5 mg) with a full glass of water.

The treatment rooms in all trial sites are furnished in soft furniture in muted colors to create a non-clinical calming feel. All treatment rooms are equipped with a high-resolution sound system that allows for simultaneous ambient and earphone listening. The playlist is designed to provide nonverbal guidance.

Subjects are then be encouraged to lie down, practice relaxation and breathing exercises, and listen to calming music. Therapists might want to revisit the intention for the treatment session with the subject. Such revisions immediately prior to the session provide an implicit direction for the subjective experience during the psilocybin session.

Once the effects of psilocybin become noticeable, subjects are encouraged to put on Mindfold eyeshades and earphones and focus on their internal experience.

Patients and/or psychotherapists are discouraged from reading, using laptops or phones at all times, and eating or drinking other than water, during the first 2-3 hours of the session.

Most subjects should tolerate the onset well using the skills practiced during preparation period. Therapists offer support in the form of reminders, encouragement, grounding hand holding, or active guiding, should challenging experiences arise. The best ways for support, and boundaries of physical touch are discussed and practiced during the preparation. In general, therapists are instructed to provide therapeutic grounding above shoulder level only. In case of subjects with a history of physical and sexual abuse, therapeutic touch should be limited to hand and forearm areas only, or to the form of physical support that was agreed during preparation.

As the drug effects start to subside, subjects again might become engaged with emergent narratives. In case of prolonged anxiety or distress, therapists may choose to actively guide subjects through such experiences without interpreting or judging the experiences or giving advice. Once subjects are comfortable, they are encouraged again to engage in introspection.

At the end of the session and after the effects of the psilocybin are no longer evident, subjects become more talkative and interactive. The role of the therapists now is to ensure that experiential processing is complete with some emotional resolution. In those cases where there is still anxiety or despair at the end of the session, subjects are encouraged to relax and reflect for a longer period of time. The provisions are made for therapists to stay with the subject until the effects of the drug have fully subsided, and subject is assessed to be comfortable and fully sober. This is assessed through engaging in 'small talk' about non-contentious topics unrelated to the content of the session.

Subjects and therapists are discouraged to discuss the content of the session until the next day to avoid premature consolidation of the insights.

After the safety assessments, subjects are discharged in the care of a family member or a friend.

On the day of the psilocybin session, the subject arrives at the clinical center between 8 AM and 9 AM. Since subjects are likely to be at least mildly anxious, it is important to validate their anxiety and assure them it is common to be anxious prior to a new experience. The time following arrival and prior to entering the treatment room should be as minimal as possible, as "waiting outside" (even if reading a book) tends to increase anxiety. The behavioral rules are reviewed again. The subject should reconfirm that he/she:

Will stay in the room for the duration of the session.

Will follow the therapist's instructions as all directions are given entirely to ensure their safety.

Have an accurate mutual understanding of ways the therapist can provide support during the session, including interpersonal grounding, guided imagery and breathing exercises.

Once all the agreements are reconfirmed and the subject is settled in the treatment room, the study investigator or designee offers 25 mg of psilocybin with a full glass of water. After the subject takes the capsules and drinks all the water, he/she should settle back on the couch, listen to the music, focus on his/her breathing and relax.

Before the drug's effects begin, the therapist re-establishes the subject's stated goals for the treatment and to revisit the question: "What does feeling better or recovery feel like?" The subject is reminded that their primary task during this session is to simply collect new and interesting experiences which can then be discussed with the therapist during the integration phase.

The therapist can remind the subject of the purpose of the psilocybin therapy and the role of experiential processing, namely allowing the subject to be open and curious to whatever arises and encountering thoughts and feelings previously unknown to them.

It should be emphasized that this process inherently requires letting go and a willing passivity to the psychedelic experience; the willingness to let go is correlated with better outcomes in psilocybin therapy. The therapist should remind the subject that the therapeutic team will be supporting them at all times.

Setting and Music: A standardized playlist is employed in all sessions. The playlist follows the pharmacodynamics of psilocybin and provides helpful content to facilitate emergence of memories and emotions as a material for experiential processing and subsequent emotional resolution.

The subject is instructed to accept and explore the music as the day progresses, irrespective of their usual personal preferences or current emotional responses. Criticizing and trying to control the music has often been found to be a symptom of resistance to unfolding content. Therapists may choose to deviate from the playlist in highly unusual situations but allowing the standardized playlist to unfold generally proves effective and frees the therapist to focus on the subject.

Managing Anxiety: Transient anxiety is often reported as subjects encounter changing psychological content. Such anxiety might be viewed as natural and even necessary. It can manifest in different ways, ranging from mild intractability and avoidance of the emerging experiences to extreme paranoia. In most cases, anxiety resolves on its own accord and can be minimized with skillful interpersonal support. Psilocybin provides a unique opportunity for a subject to normalize anxiety and view it as excitement and experience the encounter with honest ambivalence.

During the acute onset of action, the subject might experience perceptual changes in visual, auditory or olfactory modes, and a range of unusual physical sensations. These experiences could be anxiety-provoking. If the subject manifests anxiety and emotional distress, the therapist may offer therapeutic touch or interpersonal grounding, if that is something the subject has agreed to during preparation and has been rehearsed. "I want to state again my commitment to be here for you. I will do whatever is necessary to make this a safe place for you so that you can fully experience whatever comes up. If what comes up is difficult, I'd like you to try and stay with it and explore it as much as you can. Please ask me for whatever you need."

If the subject is agitated and/or frightened, simple reminders could be helpful: "You remember that you are participating in a clinical trial of a new medication for your anorexia. During preparation, we talked about possible anxiety, unusual sensations and intense emotions. This is simply the drug taking effect. It is safe; you will not be harmed. These challenging experiences pass by very quickly if you relax and just watch them. You will return to everyday reality as the effect of psilocybin wanes."

The therapist encourages the subject to focus inwards and fully immerse him/herself in all aspects of the experience. The subject may want to practice guided imagery or breathing relaxation techniques in preparation.

Managing Distractions and Avoidance: Occasionally, the subject tries to avoid emerging experiences or distract him/herself while trying to regain cognitive control over the unusual state of their mind. The therapist must recognize that such distractions could take different forms. The subject might want to engage in a conversation or prematurely describe in detail their experience, visions or insights. When this occurs, the therapist and assistant aim to remain as silent as possible, thereby enabling the subject and his/her inner experience to direct the course of the psilocybin session. Active listening skills may be required if the subject engages the therapist in conversation; this should be paired with prompts to encourage the subject to continue focusing attention on present experiences.

Sometimes a subject might ask to go to the bathroom or have a drink of water. The sudden and urgent character of such requests might suggest that they are really trying to avoid emerging material. In such cases, the therapist should encourage subjects to stay with the experience by simply redirecting their attention.

Outcome Measures:

The study investigates several outcome measurements, including, but not limited to:

Incidence and occurrence of adverse events (AEs) from Baseline (Day −1 [VISIT 2]) to Day 28 (VISIT 6), and from Day 1 [VISIT 4] to Day 28 [VISIT 6].

Incidence of clinically important changes in ECG parameters from Baseline [VISIT 2] to Day 1 [VISIT 4], Day 7 [VISIT 5] and Day 28 [VISIT 6].

Incidence of clinically important changes in laboratory tests from Baseline (Day −1 [VISIT 2]) to Day 1 [VISIT 4], Day 7 [VISIT 5] and Day 28 [VISIT 6].

Incidence of clinically significant changes in vital signs from Baseline (Day −1 [VISIT 2]) to Day 1 [VISIT 4], Day 7 [VISIT 5] and Day 28 [VISIT 6].

Incidence of changes in the C-SSRS at each post-Baseline visit

Change in EDE scores for Dietary Restraint, Eating Concern, Weight Concern, and Shape Concern from Baseline (Day −1 [VISIT 2]) to Day 28 [VISIT 6]

Change in weight (kg) from Baseline (Day −1 [VISIT 2]) to Day 7 [VISIT 5], and Day 28 [VISIT 6]

Change in trait anxiety total score on the STAI from Baseline (Day −1 [VISIT 2]) to Day 1 [VISIT 4], Day 7 [VISIT 5], and Day 28 [VISIT 6]

Change in state anxiety total score on the STAI from Baseline (Day −1 [VISIT 2]) to Day 1 [VISIT 4], Day 7 [VISIT 5], and Day 28 [VISIT 6]

Change in PASTAS trait score from Baseline (Day −1 [VISIT 2]) to Day 1 [VISIT 4], Day 7 [VISIT 5], and Day 28 [VISIT 6]

Change in PASTAS state score from Baseline (Day −1 [VISIT 2]) to Day 1 [VISIT 4], Day 7 [VISIT 5], and Day 28 [VISIT 6]

Change in BISS total score from Baseline (Day −1 [VISIT 2]) to Day 28 [VISIT 6]

Change in YBC-EDS total score from Baseline (Day −1 [VISIT 2]) to Day 1 [VISIT 4], Day 7 [VISIT 5], and Day 28 [VISIT 6]

Change in EDI total score from Baseline (Day −1 [VISIT 2]) to Day 1 [VISIT 4], Day 7 [VISIT 5], and Day 28 [VISIT 6]

Change in EDE-QS total scores from Baseline (Day−1 [VISIT 2]) to Day 1 [VISIT 4], Day 7 [VISIT 5], and Day 28 [VISIT 6]

The study also investigates other metrics, including, but not limited to:

Change in MADRS total scores from Baseline (Day −1 [VISIT 2]) to Day 1 [VISIT 4], Day 7 [VISIT 5] and Day 28 [VISIT 6]

Change in CIA total scores from Baseline (Day −1 [VISIT 2]) to Day 1 [VISIT 4], Day 7 [VISIT 5] and Day 28 [VISIT 6]

Change in VAS measures from Baseline (Day −1 [VISIT 2]) to Day 1 [VISIT 4], Day 7 [VISIT 5] and Day 28 [VISIT 6]

Change in ED-RR readiness to change and motivation for change from Baseline (Day −1 [VISIT 2]) to Day 1 [VISIT 4], Day 7 [VISIT 5] and Day 28 [VISIT 6]

Summary of the 5D-ASC on the day of the psilocybin dosing [VISIT 3]

Links between psychedelic intensity and experience (via the 5D-ASC) and eating disorder outcomes will also be explored and subject experience and acceptability of the treatment summarised at Visit 3, Visit 4 and Visit 6.

Mini International Neuropsychiatric Interview (MINI) (version 7.0.2) (performed at Visit 1)

Assessment for anorexia, as documented by DSM-5 criteria (VISIT 1)

McLean Screening Instrument for Borderline Personality Disorder (MSI-BPD) (assessed at Visit 1)

Eating Disorder Examination (EDE) and/or Eating Disorder Examination Questionnaire Short Form (EDE-QS) (assessed at Visit 2 and Visit 6)

Physical Appearance State and Trait Anxiety Scale—State and Trait version (PASTAS) (Assessed at Visit 2, Visit 4, Visit 5, and Visit 6)

Spielberger State-Trait Anxiety Inventory (STAI) (assessed at Visit 2, Visit 4, Visit 5, and Visit 6).

Eating Disorder Readiness Ruler (ED-RR) (assessed at Visit 2, Visit 4, Visit 5, and Visit 6)

Visual Analogue Rating Scales (VAS) (assessed at Visit 2, Visit 4, Visit 5, and Visit 6)

Montgomery-Asberg Depression Rating Scale (MADRS) (assessed at Visit 2, Visit 4, Visit 5, an Visit 6)

Yale-Brown Cornell Eating Disorder Scale (YBC-EDS) and/or Yale-Brown Cornell Eating Disorder Scale Self Report (YBC-EDS-SRQ) (assessed at Visit 2, Visit 4, Visit 5, and Visit 6)

Body Image State Scale (BISS) (assessed at Visit 2, Visit 4, Visit 5, and Visit 6)

Clinical impairment assessment (CIA) questionnaire (assessed at Visit 2, Visit 4, VISIT 5, and Visit 6).

Eating Disorder Inventory (EDI)

Five Dimension Altered States of Consciousness Questionnaire (5D-ASC) (assessed at Visit 3

Columbia-Suicide Severity Rating Scale (C-SSRS): The C-SSRS is used to assess suicide potential or tendency as a study entry criteria and monitored throughout the study.

Qualitative interview: (assessed at Visit 4): A semi-structured qualitative interview is asked on Day 1 [Visit 4] regarding the subject's views on their psilocybin experience and acceptability of treatment.

Electrocardiogram (ECG) (Visit 1, Visit 4, Visit 5, Visit 6)

Vital signs including weight, blood pressure, respiratory rate, body temperature, and pulse rate. Blood pressure is measured supine, after at least 5 min at rest. Three measurements are recorded 1 to 2 min apart, and the results averaged to inform eligibility.

Clinical laboratory tests including liver function tests: Blood samples are obtained at Visit 1, Visit 4, Visit 5, and Visit 6:

Hematology: hemoglobin, hematocrit, red blood cell count, mean corpuscular haemoglobin, mean corpuscular volume, mean corpuscular hemoglobin concentration, white blood cell count (with differential), and platelet count.

Chemistry:albumin, alkaline phosphatase, alanine aminotransferase (ALT), amylase, aspartate aminotransferase (AST), bicarbonate, bilirubin (direct, indirect, and total), calcium, chloride, creatine kinase, creatinine, gamma-glutamyltransferase, glucose, lactate dehydrogenase, lipase, magnesium, phosphate, potassium, protein-total, sodium, urea (blood urea nitrogen), and uric acid.

Urine samples are obtained at Screening (Visit 1), Baseline (Visit 2) and Day 1 (Visit 4) for the following:

Urinalysis: A dipstick urinalysis is performed for blood, glucose, ketone, protein, pH, specific gravity, nitrite, leukocytes, bilirubin, and urobilinogen at Visit 1, Visit 2 and Visit 4.

Urine Drug Screen: for illicit drugs or drugs of abuse at
Screening (Visit 1) and Baseline [Visit 2]. Results of a
positive drug screen are reviewed by the study clinician
for pattern of use.

Urine Pregnancy Test: a dipstick test in women of child-
bearing potential at Screening [Visit 1] and Baseline
[Visit 2].

Adverse events: Throughout the course of the study, all
AEs are monitored and recorded. Each AE is classified
according to the following criteria:

Mild: The AE does not interfere in a significant manner
with the subject's normal level of functioning.

Moderate: The AE produces some impairment of func-
tioning, but is not hazardous to the subject's health.

Severe: The AE produces significant impairment of func-
tioning or incapacitation and is a definite hazard to the
subject's health.

Adverse events may include, but are not limited to, for
example, euphoric mood, dissociative disorder, hallucina-
tion, psychotic disorder, cognitive disorder, disturbance in
attention, mood altered, psychomotor skills impaired, inap-
propriate affect, overdose, intentional product misuse, death,
life-threatening events, inpatient hospitalization or prolon-
gation of existing hospitalization, persistent or significant
disability/incapacity, congenital anomaly/birth defect in the
offspring of a subject who received psilocybin. important
medical events that may not result in death, be life-threat-
ening, or require hospitalization, may be considered a severe
adverse event (SAE) when, based upon appropriate medical
judgment, they may jeopardize the subject and may require
medical or surgical intervention to prevent one of the
outcomes listed in this definition. Examples of such events
include Intensive treatment in an emergency room or at
home for allergic bronchospasm, blood dyscrasias or con-
vulsions that do not result in inpatient hospitalization, or
development of drug dependency or drug abuse.

Visits

Visit 1: Eligibility Screening: After signing the informed
consent form, all subjects are screened for eligibility using
screening assessments: Medical history, Prior and current
medications and therapies, Review of inclusion/exclusion
criteria, Mini International Neuropsychiatric Interview
(MINI version 7.0.2), C-SSRS (last 12 Months), MSI-BPD,
Vital signs (i.e., sitting blood pressure, pulse, body tempera-
ture, and respiratory rate), Physical Examination, 12-lead
electrocardiogram (ECG), blood and urine samples for:
clinical laboratory tests, urinalysis, urine drug screen, urine
pregnancy test for all women of childbearing potential,
documented contraceptive method to be used by the subject,
adverse events (AEs) and serious adverse events (SAEs)
AEs and SAEs (Sections 9 and 10). Once a subject com-
pletes all Visit 1 assessments the clinical team reviews
information and issues approval, if the subject is eligible. At
the conclusion of the Visit 1, the subject meets with the study
therapist who supports them during the session. Subjects
then are given access to an online preparatory material with
information about psilocybin safety and effects, videos of
subjects from the previous studies sharing their experiences,
and guided relaxation and breathing exercises.

Visit 1a: First preparatory session to discuss safety and
effects of psilocybin, personal and medical history, and
current symptoms. Once a medically qualified study clini-
cian confirms subject eligibility, the subject is seen by the
study therapist for preparation between the Screening [Visit
1] and Baseline visit [Visit 2]. During Visit 1a preparatory
session, the therapist and subject discuss the subject's his-
tory and current symptoms, expectations for the therapeutic session effects and safety profile of psilocybin, and what to
expect during the session, and answer any questions the
subject may have. The goal of the preparatory session is to
start building trust and therapeutic alliance. If at the end of
the Visit 1a preparatory session, if either a therapist or a
subject feel that sufficient trust and therapeutic alliance
could not be formed, the subject does not progress to
Baseline visit.

Visit 2 (Visit 2): Baseline visit to discuss safety and effects
of psilocybin, personal and medical history, and current
symptoms. The day before the psilocybin session (≥24 hours
(h) after Screening [Visit 1]; Visit 1a, Day −7; Visit 2, Day
−1), the subjects undergo a baseline assessment that contains
the Spielberger State-Trait Anxiety Inventory (STAI;), the
Eating Disorder Examination (EDE), the Eating Disorder
Examination-Questionnaire Short Form (EDE-QS), the
Montgomery Asberg Depression Rating Scale (MADRS),
the Clinical Impairment Assessment Questionnaire (CIA),
Eating Disorder readiness ruler (ED-RR), the Eating Disor-
der Inventory (EDI), the Physical Appearance State and
Trait Anxiety Scale—State and Trait Versions (PASTAS),
the C-SSRS, the Body Image State Scale (BISS), food
related rituals and obsessions using the Yale-Brown-Cornell
Eating Disorder Scale-Self-Report (YBC-EDS-SRQ), visual
analogue scales (VAS) to rate hunger, fullness and desire to
eat, vital signs including weight (measured by a health
professional), urinalysis, urine drug screen, and urine preg-
nancy test (only for women of childbearing potential), blood
test, and ECG. After baseline data is collected, the team
completes a final review to ensure the subject's continued
eligibility [Visit 2]. Subjects cannot be progressed to the
psilocybin dosing session [Visit 3] until eligibility is con-
firmed and approval is received.

Visit 3 (day 0): The 25 mg psilocybin administration
session ([Visit 3]) lasts approximately 4-6 h and is supported
by the lead therapist and an assisting therapist. Subjects are
required to remain in the study facility for a total of eight
hours post ingestion. After the acute effects of the psilocybin
pass, subjects are evaluated for safety by the study psychia-
trist and accompanied home by a previously agreed upon
support person. On the day of psilocybin administration, the
following tests are administered: vital signs (i.e., sitting
blood pressure, pulse, body temperature, and respiratory
rate), Columbia-Suicide Severity Rating Scale (C-SSRS),
and 5-Dimensional Altered States of Consciousness Rating
Scale (5D ASC). Medicines that are taken and changes in
medications and/or therapy since the previous visit are
recorded. Adverse events and serious adverse events from
psilocybin are recorded.

Visit 4 (Visit 4): On Day 1 [Visit 4], the day following
psilocybin administration, subjects are seen in person for the
post-treatment/integration session. This session includes a
safety check, completion of all questionnaires completed at
baseline, a qualitative post-dosing interview, and a discus-
sion regarding the subject's experience during the psilocybin
session. All subjects participate in two integration sessions.
In addition to the above stated objectives of Visit 4 sessions,
sessions focus on the therapist assisting subjects in attending
to and processing therapeutic content relevant to their
illness(es). At visit 4, the following tests are conducted:
STAI, MADRS, CIA, EDE-QS, ED-RR, EDI, C-SSRS,
PASTAS, BISS, YBC-ES, VAS measures, C-SSRS, Vital
signs (ie, sitting blood pressure, pulse, body temperature,
and respiratory rate) and weight, and 12 lead ECG. Blood
samples for clinical laboratory tests are taken, and urine
samples are taken for urinalysis. Medicines that are taken
and changes in medications and/or therapy since the previous visit are recorded. Adverse events and serious adverse events from psilocybin are recorded.

Visit 5 (Visit 5): On visit 5, the following tests are conducted: STAI, EDE-QS, MADRS, CIA, ED-RR, EDI, PASTAS, BISS, YBC-ES, C-SSRS, VAS measures, Weight, Blood samples for clinical laboratory tests, Vital signs, and a 12 lead ECG. Medications that are taken and changes in medications and/or therapy since the previous visit are recorded. Adverse events and serious adverse events from psilocybin are recorded.

Visit 6: Follow-up visit: Subjects are followed up at 7 (+/−2) days, Visit 5 (Visit 5), and again at 28 (+/−3) days, Visit 6 (Visit 6). At the end of the Day 28 [Visit 6]) assessment, subjects are asked how they would feel about receiving subsequent doses of psilocybin to explore perceived acceptability of multiple losings. On visit 6, the following tests are conducted: STAI, EDE, EDE-QS, MADRS, CIA, ED-RR, EDI, PASTAS, BISS, YBC-ES, C-SSRS, VAS measures, Weight, Blood samples for clinical laboratory tests, Vital signs, and 12 lead ECG.

A schematic of the visits is shown in FIG. 28. A table of the visit procedures is found in Table 34.

TABLE 34

| | | | | | Time Since Psilocybin | | |
| | | | | Psilocybin | Treatment | | |
| Visit | Screening[1] 1 | Dosing preparation 1a | Baseline (Day −1) 2 | Session (Day 0) 3 | Day 1 4 | Day 7 5 | Day 28 (EOS/ET) 6 |
| Allowable Window | — | | + < 7 days | None | None | ±2 days | ±3 days |
| Clinician Assessments and Procedures | | | | | | | |
| Informed Consent | ✓ | | | | | | |
| Medical History | ✓ | | ✓ | | | | |
| Inclusion/ exclusion Criteria | ✓ | | ✓ | ✓ | | | |
| MINI 7.0.2 | ✓ | | | | | | |
| MADRS | | | ✓ | | ✓ | ✓ | ✓ |
| C-SSRS | ✓ | | ✓ | ✓ | ✓ | ✓ | ✓ |
| MSI-BPD | ✓ | | | | | | |
| EDE | | | ✓ | | | | ✓ |
| Qualitative assessment | | | | | ✓ | | |
| Vital signs | ✓ | | ✓ | ✓ | ✓ | ✓ | ✓ |
| Physical examination including weight | ✓ | | ✓ | ✓ | ✓ | ✓ | ✓ |
| 12-Lead ECG | ✓ | | | | ✓ | ✓ | ✓ |
| Clinical laboratory tests | ✓ | | | | ✓ | ✓ | ✓ |
| Urinalysis | ✓ | | ✓ | ✓ | ✓ | | |
| Urine drug screem | ✓ | | ✓ | ✓ | | | |
| Urine pregnancy test[2] | ✓ | | ✓ | ✓ | | | |
| Documentation of contraceptive method to be used[3] | ✓ | | | | | | |
| Preparation | | ✓ | ✓ | | | | |
| Psiolcybin dose | | | | ✓ | | | ✓ |
| Integration | | | | | ✓ | ✓ | |
| prior/Concomitant Medications | ✓ | ✓ | ✓ | ✓ | ✓ | ✓ | ✓ |
| AE/SAEs | ✓ | ✓ | ✓ | ✓ | ✓ | ✓ | ✓ |
| Subject Completed Assessments | | | | | | | |
| STAI | | | ✓ | | ✓ | ✓ | ✓ |
| EDE-QS | | | ✓ | | ✓ | ✓ | ✓ |
| CIA | | | ✓ | | ✓ | ✓ | ✓ |
| BISS | | | ✓ | | ✓ | ✓ | ✓ |
| ED-RR | | | ✓ | | ✓ | ✓ | ✓ |
| PASTAS | | | ✓ | | ✓ | ✓ | ✓ |
| EDI | | | ✓ | | ✓ | ✓ | ✓ |
| YBC-EDS | | | ✓ | | ✓ | ✓ | ✓ |
| VAS measures | | | ✓ | | | ✓ | ✓ |
| 5D-ASC | | | | ✓[4] | | | |

Abbreviations: 5D-ASC, Five Dimension Altered States of Consciousness; AE, adverse event; BISS, Body Image State Scale; CIA, Clinical Impairment Assessment; C-SSRS;
Notes:
Columbia-Suicide Severity Rating Scale; ECG, electrocardiogram; EDE, Eating Disorder Examination; EDE-QS, Eating Disorder Examination Questionnaire Short Form; EDI, Eating Disorder Inventory; EDR-RR, Eating Disorder readiness ruler; EOS, End of Study; ET, early termination; MINI 7.0.2, Mini International Neuropsychiatric Interview; MADRS, Montgomery-Asberg Depression Scale; MSI-BPD, Mclean Screening Instrument for Boarderline Personality Disorder; PASTAS, Physical Appearance State and Trait Anxiety Scale; SAE, serious adverse event; STAI, Speilbergers State Trait Anxiety Inventory; VAS, Visual Analogue Scale; YBC-EDS, Young-Brown Cornell Eating Disorder Scale.
[1]Screening (VISIT 1) will be performed at least 24 h prior to the Baseline visit (VISIT 2).
[2]For women of child-bearing potential only.
[3]For females of childbearing potential and all males; site is to document method of contraception agreed to be used by each subject.
[4]To be administrered immediately after the psilocybin session.

Example 18: In Vivo Study Examining Psilocybin for the Treatment of Binge Eating The aim of this in vivo study is to explore the efficacy of psilocybin for the treatment of binge eating. 65 female Wistar rats were obtained from Charles River Laboratories and individually-housed in polypropylene cages with sawdust bedding and environmental enrichment. Animals were maintained on a reverse phase light-dark cycle and had access to standard powdered diet at all times and free access to water.

56 animals were trained to binge-eat using 2-hour exposure to preferred fatty food (chocolate) according to an irregular access schedule on days 1, 2, 4, 6, 7, 9, 12, 14, 15, 18, 23, and 28, while a separate control cohort of 9 animals was exposed to an empty pot for 2 hours on the same irregular access schedule. Once trained to binge-eat, animals were treated with vehicle (saline, negative control), psilocybin (1 mg/kg, 3 mg/kg, or 10 mg/kg IP), or lisdexamfetamine (LDX, 0.8 mg/kg, daily PO) (positive control). A timeline of the study is presented in FIG. 29.

Binging behavior was assessed one hour after administration of treatment (e.g. psilocybin, vehicle, or LDX as described above). The weight of the chocolate pot was recorded before and after each binging session. Body weight, food intake (using the food energy values, kJ/g) and water intake were recorded.

In order to assess an longer term timepoint but also avoid performing two binging sessions in quick succession, 8 days following treatment each animal was administered with a single injection of the same treatment given previously and then tested for binging behavior 24 hours later, as described above.

Body weight was analyzed by analysis of covariance with Day 1 body weight as a covariate. Body weight change from Day 1 to 10 of dosing (Day 30 to 39) was analyzed similarly. On binge days, chow intake, chocolate intake, and total food intake during the 2 hour binge session (expressed as kJ) and 24 hour food (kJ) intake were analyzed by analysis of covariance with the equivalent measure, averaged over the previous 2 binge days (Day 23 and 28 of the training phase), as a covariate. Average intake for the 3 post-dose binge days was analyzed similarly. On non-binge days, 24-hour food (kJ) was analyzed by analysis of covariance with average food/water intake from non-binge days from −5 to 0 (training days 24 to 27 and 29) as a covariate. Average food intake for all post-dose non-binge days was analyzed similarly. Comparisons to the binge eating vehicle group were by Williams' test for psilocybin and the multiple t test for LDX. All tests were carried out as two-sided tests.

All data from the vehicle/no chocolate group are presented as mean±standard error of the mean (SEM). For the other treatment groups, food intake data collected on post-treatment binge days (Day 30 and/or Day 38) were adjusted for differences between the groups at baseline (average of Days 23 and 28 of the training phase) and food intake data collected on post-treatment non-binge days (Day 31 to Day 37, and Day 39) were adjusted for differences between the groups at the appropriate baseline (Days 24 to 27 and Day 29 of the training phase). Accordingly, data from groups other than the vehicle/no chocolate group are presented as adjusted mean±SEM. Mean body weight changes were adjusted for differences between the treatment groups in Day 1 body weight and are presented as adjusted mean±SEM.

Chocolate and total food (i.e. sum of chocolate and chow intake) were significantly decreased during the binging session 1 hour following administration of 1 mg/kg psilocybin, 3 mg/kg psilocybin, and 10 mg/kg psilocybin, as compared to the vehicle treated group that were trained to binge eat (FIG. 30). The positive control (LDX) also significantly reduced chocolate eating.

Chocolate and total food (i.e. sum of chocolate and chow intake) were also significantly decreased during the binging session 24 hour following administration of 1 mg/kg psilocybin, 3 mg/kg psilocybin, and 10 mg/kg psilocybin, as compared to the vehicle treated group that were trained to binge eat (FIG. 31).

FIG. 32 shows the effect of psilocybin on 24 hour food intake across the whole study. The food intake over a 24 hour period is significantly reduced on Day 1 in all psilocybin groups and in the LDX positive control group. The food intake over the 24 hour period is not significantly altered in the psilocybin group, suggesting that psilocybin does not affect normal feeding behaviour. FIG. 33 shows the effect of psilocybin on average 24 hour food intake on binge days versus non-binge days. FIG. 34 shows that overall body weight is not affected by administration of psilocybin.

Example 19: In Vivo Study Examining Psilocybin's Effect on the Life Changes Inventory (LCI)—Self-Acceptance Score To determine whether psilocybin may have a beneficial effect on self acceptance in subjects with eating disorders, a healthy volunteer study was conducted. The study measured various psychological and brain measures both acutely and long-term following psilocybin administration. Healthy volunteers were administered 10 mg psilocybin, 25 mg psilocybin, or placebo. Data were analysed using a mixed model for repeated measures with outcome score as the dependent variable. The model had fixed effects for treatment, visit, former psilocybin experience, and treatment by visit interaction, visit as the repeating factor, and subject as a random effect. Least squares (LS) means were calculated from the model and used for pairwise comparisons between the groups.

The Life Changes Inventory (LCI) was administered 7 days and 84 days after psilocybin administration. FIG. 35 shows the effect of psilocybin on the LCI self-acceptance score. Treatment with both 10 mg (p<0.001) and 25 mg (p<0.001) psilocybin resulted in an improved LCI self-acceptance score compared to placebo. Table 35 shows the LCI Changes in self-acceptance.

TABLE 35

| Group | Visit | LCI Self-Acceptance Scores | Standard Error | P-value (comparison with placebo) | Number of participants, n |
|---|---|---|---|---|---|
| 10 mg | Day 7 | 0.8 | 0.07 | <0.001 | 30 |
| 25 mg | Day 7 | 0.6 | 0.08 | <0.001 | 29 |
| 10 mg | Day 84 | 0.6 | 0.08 | <0.001 | 30 |
| 25 mg | Day 84 | 0.6 | 0.08 | <0.001 | 27 |

Note:
Life Changes Inventory (LCI) Self-Acceptance Scores represent least squares (LS) mean of the treatment groups. P-values calculated using pairwise comparison of with placebo.

Without being bound by any particular mechanism of action, one of skill in the art would understand that the models used to study the efficacy of an active agent in a particular indication, and data obtained using the same, can also be applied to other indications. As such, Table 36 indicates which models and examples are potentially relevant for the listed indications. This is non-exhaustive, and one of skill in the art would understand that the various examples discussed herein can be used to support the activity of psilocybin, active metabolites of psilocybin, prodrugs of psilocybin, and prodrugs of active metabolites of psilocybin in a variety of indications.

TABLE 36

| Example | Relevant indication(s) |
|---|---|
| Example 10<br>In vivo study investigating changes in mouse protein:<br>Increase in receptor protein kinase erbB4 (Erbb4) expression | Anxiety |
| Example 10<br>In vivo study investigating changes in mouse protein:<br>Decrease in calsyntenin 2 (Clstn2) expression | Anxiety |
| Example 10<br>In vivo study investigating changes in mouse protein:<br>Increase in glucagon (Gcg) expression | Eating disorders<br>OCD |
| Example 11<br>Effect of Psilocybin on Marble Burying (MB) Test in an in vivo model | OCD<br>Anxiety<br>Eating disorders |
| Example 12:<br>In vivo study testing the effect of psilocybin on wakefulness, NREM, and/or REM sleep | Anxiety<br>OCD |
| Example 13<br>In vivo study of the effect of Psilocybin on CCK-4 induced panic anxiety | Anxiety<br>Panic anxiety<br>PTSD |
| Example 14<br>Effect of psilocybin on acute and long-term effects of psilocybin on social cognition and behavior | Anxiety |
| Example 14<br>Effect of psilocybin on acute and long-term effects of psilocybin on social cognition and behaviour (RVP (rapid visual information processing task) | Anxiety |
| Example 18<br>In vivo study examining Psilocybin for the Treatment of Binge Eating | Eating disorders |
| Example 19<br>In vivo study examining Psilocybin's Effect on the Life Changes Inventory (LCI)-Self-Acceptance Score | Anxiety |

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The foregoing is illustrative of the present invention, and is not to be construed as limiting thereof. The invention is defined by the following claims, with equivalents of the claims to be included therein.

The invention claimed is:

1. A method of treating a bipolar disorder in a subject in need thereof, the method comprising administering to the subject a therapeutically effective amount of crystalline psilocybin comprising Polymorph A characterized by XRPD peaks at $11.5\pm0.1$, $12.0\pm0.1$, $14.5\pm0.1$, $17.5\pm0.1$, and $19.7\pm0.1°2\theta$, wherein the crystalline psilocybin has a chemical purity of greater than 97% as determined by HPLC analysis.

2. The method of claim 1, wherein the subject has bipolar disorder I.

3. The method of claim 1, wherein the subject has bipolar disorder II.

4. The method of claim 1, wherein the crystalline psilocybin has no single impurity of greater than 1% as determined by HPLC analysis.

5. The method of claim 1, wherein the crystalline psilocybin is administered in an oral dosage form.

6. The method of claim 5, wherein the oral dosage form is a capsule.

7. The method of claim 5, wherein the oral dosage form is a tablet.

8. The method of claim 1, wherein about 1 mg to about 40 mg of crystalline psilocybin is administered.

9. The method of claim 1, wherein about 1 mg of crystalline psilocybin is administered.

10. The method of claim 1, wherein about 10 mg of crystalline psilocybin is administered.

11. The method of claim 1, wherein about 25 mg of crystalline psilocybin is administered.

12. The method of claim 1, wherein the subject participates in at least one psychological support session before administration of the crystalline psilocybin.

13. The method of claim 1, wherein the subject participates in at least one psychological support session after administration of the crystalline psilocybin.

14. The method of claim 1, wherein about 10 mg to about 30 mg of crystalline psilocybin is administered.

15. The method of claim 1, wherein about 5 mg of crystalline psilocybin is administered.

16. The method of claim 1, wherein the crystalline psilocybin of polymorph A is further characterized by at least one peak selected from the group consisting of $20.4\pm0.1$, $22.2\pm0.1$, $24.3\pm0.1$, and $25.7\pm0.1°2\theta$.

* * * * *